(12) United States Patent
Noel et al.

(10) Patent No.: US 7,286,973 B1
(45) Date of Patent: Oct. 23, 2007

(54) METHOD OF SCREENING INHIBITORS OF MEVALONATE-INDEPENDENT ISOPRENOID BIOSYNTHETIC PATHWAY

(75) Inventors: Joseph P. Noel, San Diego, CA (US); Marianne E. Bowman, San Diego, CA (US); Stephane Richard, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 354 days.

(21) Appl. No.: 10/240,636

(22) PCT Filed: May 3, 2001

(86) PCT No.: PCT/US01/14371

§ 371 (c)(1),
(2), (4) Date: May 5, 2003

(87) PCT Pub. No.: WO01/83769

PCT Pub. Date: Nov. 8, 2001

Related U.S. Application Data

(60) Provisional application No. 60/201,589, filed on May 3, 2000, provisional application No. 60/255,088, filed on Dec. 12, 2000.

(51) Int. Cl.
G06G 7/58 (2006.01)
C12N 9/00 (2006.01)
(52) U.S. Cl. .......................................... 703/11; 435/183
(58) Field of Classification Search ................ 435/183
See application file for complete search history.

(56) References Cited

U.S. PATENT DOCUMENTS 5,579,250 A * 11/1996 Balaji et al. .................. 702/19
5,642,292 A *  6/1997 Itai et al. ...................... 702/27

OTHER PUBLICATIONS

H. Jomaa et al. (1999) "Inhibitors of the nonmevalonate pathway of isoprenoid biosynthesis as antimalarial drugs," Science vol. 285, pp. 1573-1576.*
Eisenreich et al.Cell Mol Life Sci. Jun. 2004;61(12):1401-26.*
Sprenger et al., Proc. Natl. Acad. Sci. USA vol. 94, pp. 12857-12862, 1997.*
Takahashi et al., Prroc. Natl. Acad. Sci. USA, vol. 95, pp. 9879-9884, 1998.*
Seeman et al. Angew. Chem. Int. Ed. vol. 41, pp. 4337-4339, 2002.*
Rohdich et al. Proc. Natl. Acad. Sci. USA, vol. 100, pp. 1586-1591, 2003.*
"Encyclopedia of Molecular Biology" (Creighton, T., John Wiley and Sons, Inc. New York, 1999).*
Kierzek et al., Biophys. Chem., vol. 91, pp. 1-20, 2001.*
Wiencek, Annu. Rev. Biomed. Eng., vol. 1, pp. 505-534, 1999.*
Ke & Doudna, Methods, vol. 34, pp. 408-414, 2004.*
Derewenda et al. Acta Crystallogr. D., vol. 62, pp. 116-124, 2006.*
Buts et al. (Acta Crystallogr. D., vol. 61, pp. 1149-1159, 2005).*
Skarzynski et al. (Acta Crystallogr. D., vol. 62, pp. 102-107, 2006.*
Ridley, Science, vol. 285, pp. 1502-1503, 1999.*
McPherson, A. Current Approaches to Macromolecular Crystallization. European Journal of Biochemistry. 1990. vol. 189, pp. 1-23.*
International Search Report for PCT Application No. PCT/US01/14371.
Bork, et al., "The cytidylyltransferase superfamily: Identification of the nucleotide-binding site and fold prediction." *Proteins*, 22:259-266, (1995).
Herz, et al., "Biosynthesis of terpenoids: YgbB protein converts 4-diphosphocytidyl-2C-methyl-$_D$-erythritol 2-phosphate to 2C-methyl-$_D$-erythritol 2,4-cyclodiphosphate," *PNAS*, 97:2486-2490, (2000).
Jelakovic, et al., "The three-dimensional structure of capsule-specific CMP: 2-keto-3-deoxy-*manno*-octonic acid synthetase from *Escherichia coli*," *FEBS Lett.*, 391:157-161, (1996).
Jomaa et al., "Inhibitors of the nonmevalonate pathway of isoprenoid biosynthesis as antimalarial drugs." *Science*, 285:1573-1576, (1999).
Koppisch, et al., "Synthesis of 2-C-Methyl-$_D$-erythritol 4-phosphate: The first pathway-specific intermediate in the methylerythritol phosphate route to isoprenoids." *Org. Lett.*, 2:215-17, (2000).
Kuzuyama, et al., "Formation of 4-(cytidine 5'-diphospho)-2-C-methyl-$_D$-erythritol from 2-C-methyl-*D*-erythritol 4-phosphate cytidylyltransferase, a new enzyme in the nonmevalonate pathway." *Tet. Lett.*, 41:703-6, (2000).
Kuzuyama et al., "Fosmidomycin, a specific inhibnitor of 1-Deoxy-D-Xylulose 5-phosphate reductoisomerase in the nonmevalonate pathway for terpenoid biosynthesis." Tetrahedron Letters, 39: 7913-7916, (1998).

(Continued)

*Primary Examiner*—David J. Steadman
*Assistant Examiner*—Suzanne M. Noakes
(74) *Attorney, Agent, or Firm*—Foley & Lardner LLP; Stephen E. Reiter

(57) ABSTRACT

The present invention provides the structure of the enzyme 4-diphosphocytidyl-2-C-methylerythritol (CDP-ME) synthase, a member of the cytidyltransferase family of enzymes from *Escherichia coli*. CDP-ME is a critical intermediate in the mevalonate-independent pathway for isoprenoid biosynthesis in a number of prokaryotic organisms, in algae, in the plastids of plants, and in the malaria parasite. Since vertebrates synthesize isoprenoid precursors using a mevalonate pathway, CDP-ME synthase and other enzymes of the mevalonate-independent pathway for isoprenoid production represent attractive targets for the structure-based design of selective antibacterial, herbicidal, and antimalarial drugs. Accordingly, the present invention provides methods for screening for compounds that inhibit enzymes of the mevalonate-independent pathway and pharmaceutical compositions and antibacterial formulations thereof. Further provided are methods of inhibiting the enzymes of the pathway and bacterial terpenoid synthesis and methods for treating a subject suffering from a bacterial infection.

8 Claims, 10 Drawing Sheets

OTHER PUBLICATIONS

Luttgen, et al., "Biosynthesis of terpenoids, YchB protein of *Escherichia coli* phosphorylates the 2-hydroxy group of 4-diphosphocytidyl-2C-methyl-$_D$-erythritol." *PNSA*, 97:1062-7, (2000).

Park, et al., "Identification of functional conserved residues of CTP:glycerol-3-phosphate Cytidylyltransferase." *J. Biol. Chem.*, 272:15161-6, (1997).

Rohdich, et al., Cytidine 5'-triphosphate-dependent biosynthesis of isoprenoids: YgbP protein of *Escherichia coli* catalyzes the formation of 4-diphosphocytidyl-2-*C*-methylerythritol. *PNSA*, 96:11758-63, (1999).

Rohdich, et al., "Biosynthesis of terpenoids: 4-Diphosphocytidyl-2-*C*-methyl-*D*-erythritol kinase from tomato." *PNAS*, 97:8251-6, (2000).

Takagi, et al., "Studies on the nonmevalonate pathway: formation of 2-*C*-methyl-$_D$-erythritol 2,4-cyclodiphosphate from 2-phospho-4-(cytidine 5'-diphospho)-2-*C*-methyl-D-erythritol." *Tetr. Lett.*, 41:3395-8, (2000).

Veitch, et al. "The role of histidine residues in the HXGH site of CTP:phosphocholine cytidylyltransferase in CTP binding and catalysis." *Eur. J. Biochem.*, 255:227-34, (1998).

Veitch, et al., "Substitution of serine for glycine-91 in the HXGH motif of CTP: Phosphocholine cytidylyltransferase implicates this motif in CTP binding." *Biochemistry*, 35: 10743-10750, (1996).

Weber, et al., "A prototypical cytidylyltransferase: CTP:glycerol-3-phosphate cytidylyltransferase from *Bacillus subtilis*." *Structure. Fold. Des.*, 7:1113-24, (1999).

\* cited by examiner

"Apo" form

CTP·Mg2+ complex

MEP·CTP·Mg2+ complex (model)

CDP-ME·Mg2+·PPi complex (model)

CDP-ME·Mg2+ complex

SEQUENCE LISTING

<160> NUMBER OF SEQ ID NOS: 12

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccgtatgcca tggcatggca accactcatt tggatg                               36

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgccggaat tcttatgtat tctcctgatg gatgg                                35

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgaaacac caccaccacc ac                                              22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caccaccacg gtggtctg                                                   18

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 5
gttccgcgtg gttcccatgg cg                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatccgccat gggaaccacg                                                 20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cggaaccaga ccaccgtg                                                   18

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtgctggtgg tggtggtggt gttt                                            24

<210> SEQ ID NO 9
<211> LENGTH: 11
<212> TYPE: PRT
<213> ORGANISM: Escherichia coli

<400> SEQUENCE: 9

His Leu Asp Val Cys Ala Val Val Pro Ala Ala
  1               5                  10

<210> SEQ ID NO 10
<211> LENGTH: 202
<212> TYPE: PRT
<213> ORGANISM: Escherichia coli

<400> SEQUENCE: 10

Lys Gln Tyr Leu Ser Ile Gly Asn Gln Thr Ile Leu Glu His Ser Val
  1               5                  10                  15

His Ala Leu Leu Ala His Pro Arg Val Lys Arg Val Val Ile Ala Ile
                 20                  25                  30

Ser Pro Gly Asp Ser Arg Phe Ala Gln Leu Pro Leu Ala Asn His Pro
             35                  40                  45

Gln Ile Thr Val Val Asp Gly Gly Asp Glu Arg Ala Asp Ser Val Leu
         50                  55                  60

Ala Gly Leu Lys Ala Ala Gly Asp Ala Gln Trp Val Leu Val His Asp
 65                  70                  75                  80

Ala Ala Arg Pro Cys Leu His Gln Asp Asp Leu Ala Arg Leu Leu Ala
```

```
                    85                  90                  95
Leu Ser Glu Thr Ser Arg Thr Gly Gly Ile Leu Ala Ala Pro Val Arg
            100                 105                 110
Asp Thr Met Lys Arg Ala Glu Pro Gly Lys Asn Ala Ile Ala His Thr
            115                 120                 125
Val Asp Arg Asn Gly Leu Trp His Ala Leu Thr Pro Gln Phe Phe Pro
            130                 135                 140
Arg Glu Leu Leu His Asp Cys Leu Thr Arg Ala Leu Asn Glu Gly Ala
145                 150                 155                 160
Thr Ile Thr Asp Glu Ala Ser Ala Leu Glu Tyr Cys Gly Phe His Pro
                165                 170                 175
Gln Leu Val Glu Gly Arg Ala Asp Asn Ile Lys Val Thr Arg Pro Glu
            180                 185                 190
Asp Leu Ala Leu Ala Glu Phe Tyr Leu Ala
            195                 200
```

<210> SEQ ID NO 11
<211> LENGTH: 225
<212> TYPE: PRT
<213> ORGANISM: Escherichia coli

<400> SEQUENCE: 11

```
His Leu Asp Val Cys Ala Val Val Pro Ala Ala Gly Phe Gly Arg Arg
1               5                   10                  15
Met Ala Thr Glu Cys Pro Lys Gln Tyr Leu Ser Ile Gly Asn Gln Thr
            20                  25                  30
Ile Leu Glu His Ser Val His Ala Leu Leu Ala His Pro Arg Val Lys
        35                  40                  45
Arg Val Val Ile Ala Ile Ser Pro Gly Asp Ser Arg Phe Ala Gln Leu
    50                  55                  60
Pro Leu Ala Asn His Pro Gln Ile Thr Val Val Asp Gly Gly Asp Glu
65                  70                  75                  80
Arg Ala Asp Ser Val Leu Ala Gly Leu Lys Ala Ala Gly Asp Ala Gln
                85                  90                  95
Trp Val Leu Val His Asp Ala Ala Arg Pro Cys Leu His Gln Asp Asp
            100                 105                 110
Leu Ala Arg Leu Leu Ala Leu Ser Glu Thr Ser Arg Thr Gly Gly Ile
            115                 120                 125
Leu Ala Ala Pro Val Arg Asp Thr Met Lys Arg Ala Glu Pro Gly Lys
            130                 135                 140
Asn Ala Ile Ala His Thr Val Asp Arg Asn Gly Leu Trp His Ala Leu
145                 150                 155                 160
Thr Pro Gln Phe Phe Pro Arg Glu Leu Leu His Asp Cys Leu Thr Arg
                165                 170                 175
Ala Leu Asn Glu Gly Ala Thr Ile Thr Asp Glu Ala Ser Ala Leu Glu
            180                 185                 190
Tyr Cys Gly Phe His Pro Gln Leu Val Glu Gly Arg Ala Asp Asn Ile
            195                 200                 205
Lys Val Thr Arg Pro Glu Asp Leu Ala Leu Ala Glu Phe Tyr Leu Ala
    210                 215                 220
Arg
225
```

<210> SEQ ID NO 12
<211> LENGTH: 225

-continued

```
<212> TYPE: PRT
<213> ORGANISM: Escherichia coli

<400> SEQUENCE: 12

Thr His Leu Asp Val Cys Ala Val Val Pro Ala Ala Gly Phe Gly Arg
 1               5                  10                  15

Arg Met Ala Thr Glu Cys Pro Lys Gln Tyr Leu Ser Ile Gly Asn Gln
                20                  25                  30

Thr Ile Leu Glu His Ser Val His Ala Leu Leu Ala His Pro Arg Val
            35                  40                  45

Lys Arg Val Val Ile Ala Ile Ser Pro Gly Asp Ser Arg Phe Ala Gln
    50                  55                  60

Leu Pro Leu Ala Asn His Pro Gln Ile Thr Val Val Asp Gly Gly Asp
65                  70                  75                  80

Glu Arg Ala Asp Ser Val Leu Ala Gly Leu Lys Ala Ala Gly Asp Ala
                85                  90                  95

Gln Trp Val Leu Val His Asp Ala Ala Arg Pro Cys Leu His Gln Asp
                100                 105                 110

Asp Leu Ala Arg Leu Leu Ala Leu Ser Glu Thr Ser Arg Thr Gly Gly
            115                 120                 125

Ile Leu Ala Ala Pro Val Arg Asp Thr Met Lys Arg Ala Glu Pro Gly
        130                 135                 140

Lys Asn Ala Ile Ala His Thr Val Asp Arg Asn Gly Leu Trp His Ala
145                 150                 155                 160

Leu Thr Pro Gln Phe Phe Pro Arg Glu Leu Leu His Asp Cys Leu Thr
                165                 170                 175

Arg Ala Leu Asn Glu Gly Ala Thr Ile Thr Asp Glu Ala Ser Ala Leu
            180                 185                 190

Glu Tyr Cys Gly Phe His Pro Gln Leu Val Glu Gly Arg Ala Asp Asn
        195                 200                 205

Ile Lys Val Thr Arg Pro Glu Asp Leu Ala Leu Ala Glu Phe Tyr Leu
    210                 215                 220

Thr
225
```

US 7,286,973 B1

METHOD OF SCREENING INHIBITORS OF MEVALONATE-INDEPENDENT ISOPRENOID BIOSYNTHETIC PATHWAY

RELATED APPLICATIONS

This application claims the benefit of U.S. Provisional Application No. 60/201,589, filed May 3, 2000, and U.S. Provisional Application No. 60/255,088, filed Dec. 12, 2000, the contents of both of which are hereby incorporated by reference herein in their entirety.

ACKNOWLEDGMENT

This invention was made with United States Government support under Grant No. GM-54029, awarded by the National Institutes of Health. The Government has certain rights in the invention.

FIELD OF THE INVENTION

The present invention relates to the structures of crystallized enzymes, methods of identifying enzyme inhibitors, and compositions and methods for the use thereof. In a particular aspect, the invention relates to modulation of the mevalonate-independent isoprenoid biosynthetic pathway for the treatment of bacterial infections.

BACKGROUND OF THE INVENTION

Isopentenyl diphosphate (IPP) and the isomeric compound, dimethylallyl diphosphate (DMAPP) are the fundamental building blocks of isoprenoids in all organisms. The isoprenoids include more than 23,000 naturally occurring molecules of both primary and secondary metabolism (Sacchettiii, J. C. & Poulter, C. D., 1997). The chemical diversity of this natural product class reflects their wide-ranging physiological roles in all living systems (Connolly, J. D. & Hill, R. A., 1991). Isoprenoids include hopane triterpenes, ubiquinones and menaquinones in bacteria, carotenoids, plastoquinones, mono-, sesqui-, di-, and tri-terpenes, and the prenyl side chains of chlorophylls in plants, and quinones, dolichols, steroids and retinoids in mammals (Edwards, P. A. & Ericcson, J. 1999).

Until recently it was generally assumed that IPP was derived solely from mevalonate synthesized from the condensation of three molecules of acetyl-CoA (McGarvey, D. J. & Croteau, R., 1995). However, recent independent studies demonstrated the existence of a novel, mevalonate-independent pathway for IPP synthesis known as the 1-deoxy-D-xylulose 5-phosphate/2-C-methyl-D-erythritol 4-phosphate (DXP/MEP) pathway (Rohmer, M. et al., 1993; Rohmer, M., 1999; Schwender, J. et al., 1996; Eisenreich, W. et al., 1998). This latter mevalonate-independent pathway utilizes pyruvate and glyceraldehyde 3-phosphate as starting materials for production of IPP (Rohmer, M. et al., 1996) (FIG. 1).

Since vertebrates synthesize isoprenoid precursors using a mevalonate pathway, enzymes of the mevalonate-independent (DXP/MEP) pathway for isoprenoid production represent attractive targets for the structure-based design of selective pharmaceutical compounds. The DXP/MEP pathway occurs in a variety of eubacteria that includes several pathogenic species such as Mycobacterium tuberculosis, in algae (Rohmer, M., 1999), in the plastids of plant cells (Schwender, J. et al., 1999) and in the apicoplast of Plasmodium falciparum (the parasite that causes malaria) (Jomaa, H. et al., 1999; Vial, H. J., 2000). Given the essential nature of the DXP/MEP pathway in these organisms and the absence of this pathway in mammals, the enzymes comprising the DXP/MEP pathway represent unique targets for the generation of selective antibacterial (Rohmer, M., 1998; Kuzuyama, T. et al., 1998), antimalarial (Jomaa, H. et al., 1999; Vial, H. J., 2000; Ridley, R. G., 1999), and herbicidal (Lichtenthaler, H. K. et al., 2000) molecules.

For example, the YgbP protein of E. coli encodes the enzyme 4 diphosphocytidyl-2-C-methylerythritol (CDP-ME) synthase (Rohdick, F. et al., 1999; Kuzuyama, T. et al., 2000). CDP-ME synthase belongs to the cytidyltransferase family of enzymes but utilizes a distinct architecture and a novel set of active site residues for CDP-ME formation. CDP-ME is a critical intermediate in the mevalonate-independent pathway for isoprenoid biosynthesis in a number of prokaryotic organisms, in algae, in the plastids of plants, and in the malaria parasite, catalyzing the formation of CDP-ME from 2-C-methyl-D-erythritol-4-phosphate (Koppisch, A. T. et al., 2000) and cytidine triphosphate (CTP). Accordingly, there is a need in the art for the three dimensional protein structures of E. coli CDP-ME synthase and related proteins in order to reveal the stereochemical principles underlying substrate recognition and catalysis in CDP-ME synthase.

BRIEF SUMMARY OF THE INVENTION

In accordance with the present invention, the three dimensional atomic resolution structures of E. coli CDP-ME synthase have been solved in the apo form (enzyme alone) and complexed with $CTP.Mg^{2+}$ and $CDP-ME.Mg^{2+}$. These atomic resolution structures reveal active site features responsible for the conformational and stereochemical control of the cytidyltransferase reaction of CDP-ME synthase and serve as three dimensional templates for inhibitor design. The invention reveals the stereochemical principles underlying substrate recognition and catalysis in CDP-ME synthase and provides an understanding of the mechanistic features of this pathway for the design of novel antibacterial and antimalarial agents. Since this pathway does not operate in animal cells, the enzymes which comprise it represent unique and important targets for new medicinal agents identified in accordance with the present invention.

CDP-ME synthase is a functional homodimer in solution (Rohdich, F. et al., 1999) with each polypeptide comprising 237 residues. The E. coli CDP-ME synthase gene was isolated by PCR amplification from total genomic DNA obtained from E. coli K12. The recombinant protein was expressed in E. coli with a thrombin cleavable N-terminal octahistidine tag and purified by $Ni^{2+}$-affinity and gel filtration chromatography. Crystals were readily obtained and the apo structure solved by multiple isomorphous replacement (MIR). Subsequent complexes were obtained using difference Fourier analysis. Mutations of CDP-ME synthase were similarly generated and studied to assess the roles of specific active site residues in the catalytic mechanism of the larger cytidyltransferase family of enzymes.

The present invention provides the first three dimensional view of intermediate formation in the non-mevalonate isoprenoid biosynthesis pathway (DXP/MEP pathway) by solving the three dimensional structures of E. coli CDP-ME synthase complexed with both substrate and product. In another aspect of the present invention, selective mutants have been shown to critically impair the catalytic activity of CDP-ME synthase. In a preferred embodiment of this invention, these structures can be used as structural templates for the identification of effective inhibitors of the DXP/MEP pathway for isoprenoid biosynthesis. Such inhibitors are useful for inhibiting the activity of the target enzyme in a cell-free environment or within a cell, either in vitro or in vivo. In turn, these inhibitors provide novel drugs directed against pathogenic bacteria and the malaria parasite by modulating cell growth via the inhibition of terpenoid synthesis.

DETAILED DESCRIPTION OF THE INVENTION

In accordance with the present invention, there are provided compositions comprising 4-diphosphocytidyl-2-C- methylerythritol synthases (CDP-ME synthase) in crystalline form. In accordance with another embodiment of the present invention, the high resolution structures of CDP-ME synthases complexed with CTP•Mg$^{2+}$ and CDP-ME.Mg$^{2+}$ are described, providing compositions comprising a substrate, substrate mimic or inhibitor of CDP-ME synthase. The discovered structure of a CDP-ME synthase provides the first three dimensional view of the structural basis for intermediate formation in the DXP/MEP pathway for isoprenoid biosynthesis using a mevalonate-independent pathway. The structures of CDP-ME synthase complexed with CTP•Mg$^{2+}$ and CDP-ME•Mg$^{2+}$ respectively, reveal the stereochemical principles underlying both substrate and product recognition as well as catalysis in CDP-ME synthase.

Figure 1:
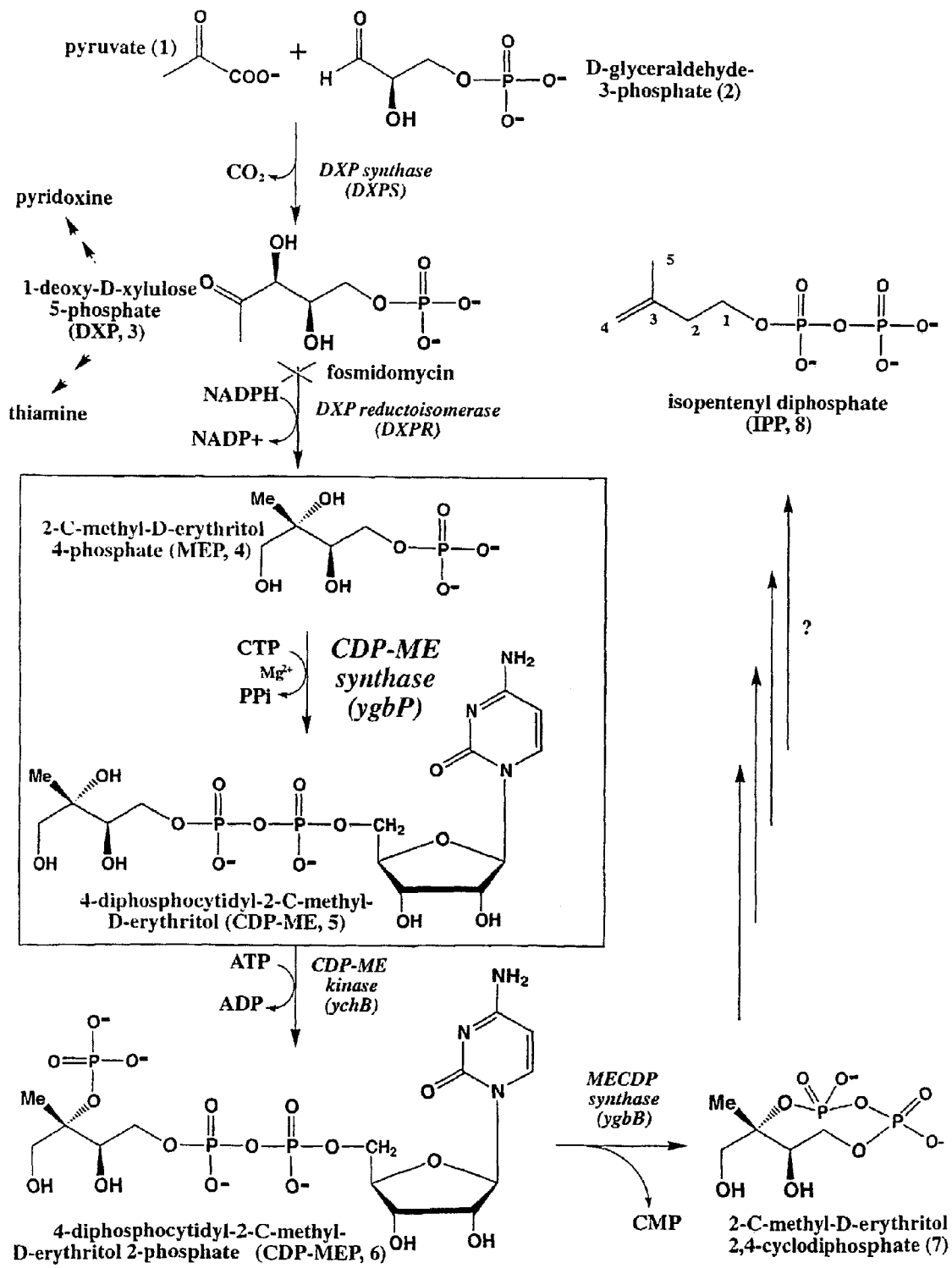
FIG. 1 illustrates the biosynthesis of the isoprenoid precursor IPP via the alternative, non-mevalonate DXP/MEP pathway. The synthesis of the C5 IPP skeleton begins with the condensation of a C2 moiety from the decarboxylation of pyruvate (1) and a C3 moiety from glyceraldehyde 3-phosphate (2), to form 1-deoxy-D-xylulose 5-phosphate (DXP, 3) by the action of DXP synthase (Sprenger, G. A. et al. 1997; Lois, L. M. et al., 1997; Harker, M. & Bramley, P. M., 1999; Lois, L. M. et al., 2000; Kuzuyama, T. et al., 2000) (DXPS; also referred to as DXS). Next DXP is converted into 2-C-methyl-D-erythritol 4-phosphate (MEP, 4) by DXP reductoisomerase (Kuzuyama, T. et al., 1998; Takahashi, S. et al. 1998; Lange B. M. & Croteau, R., 1999; Kuzuyama, T. et al., 2000) (DXPR; sometimes referred to as DXR), and subsequently transformed into 4-diphosphocytidyl-2-C-methyl-D-erythritol (CDP-ME, 5) by CDP-ME synthase (Rohdich, F. et al., 1999; Kuzuyama, T. et al., 2000; Rohdich, F. et al., 2000) (YgbP protein) in a $Mg^{2+}$ and CTP dependent reaction. CDP-ME is phosphorylated on the 2-hydroxy group to form 4-diphosphocytidyl-2-C-methyl-D-erythritol 2-phosphate (CDP-MEP, 6) in an ATP-dependent reaction by the enzyme CDP-ME kinase encoded by the ychB gene of *E. coli* (Luttgen, H. et al., 2000; Kuzuyama, T. et al., 2000). Subsequent formation of 2-C-methyl-D-erythritol 2,4-cyclodiphosphate (7) is catalyzed by the enzyme MECDP synthase encoded by the gene ygbB (Herz, S. et al., 2000; Takagi, M. et al., 2000). Additional steps, which remain to be elucidated, ultimately form isopentenyl diphosphate (IPP, 8).
Figure 2A:
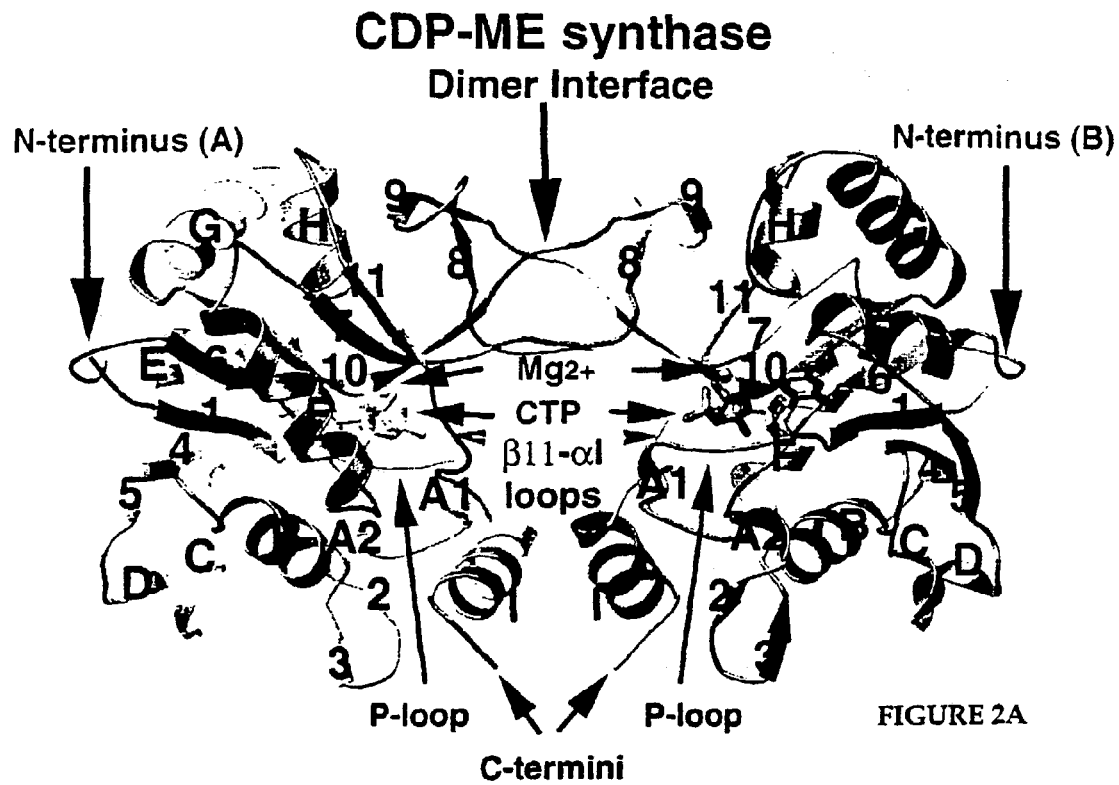
FIGS. 2A and 2B collectively depict the overall architecture of *E. coli* CDP-ME synthase and *Neisseria meningitidis* CMP-NeuAc synthetase (CMP acyl neuraminate synthetase). The molecules are shown as a ribbon representation of the homodimers complexed with $CTP.Mg^{2+}$. The secondary structure is annotated according to the cytidyltransferases nomenclature which is based on the CMP-NeuAc synthetase structure aligned with CDP-ME synthase, depicted in FIG. 2B. A partially disordered CDP acting as a substrate analog is also shown in FIG. 2B.
Figure 2B:
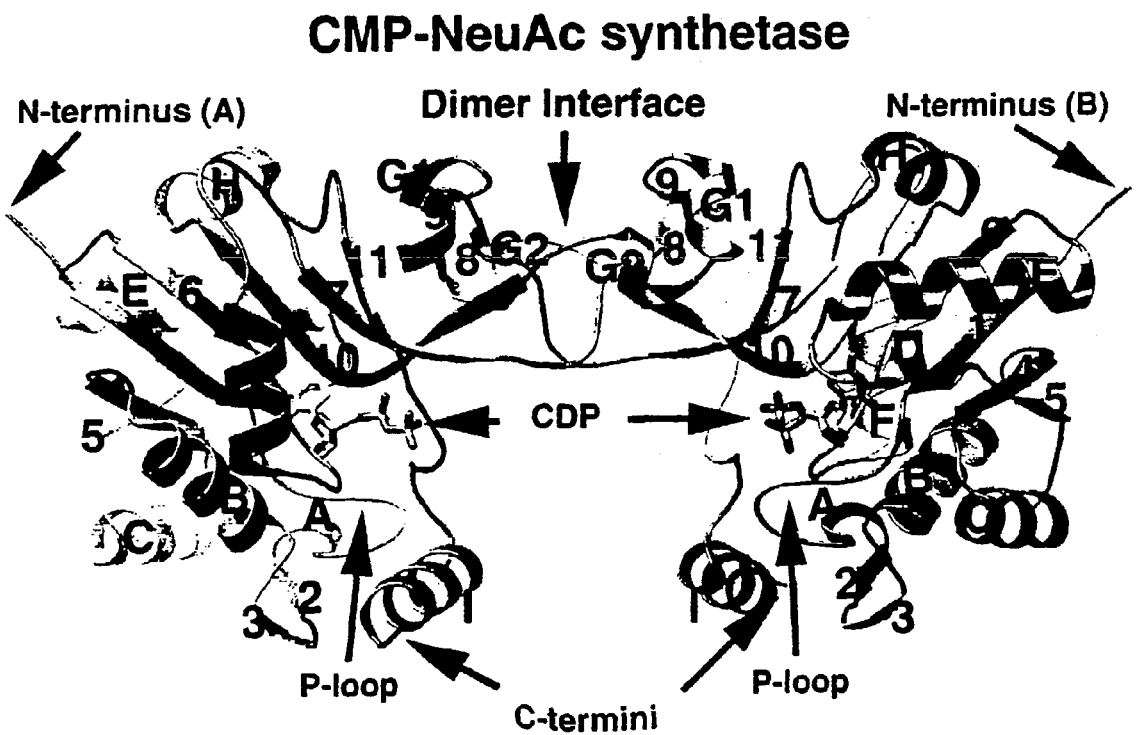
Figure 3:
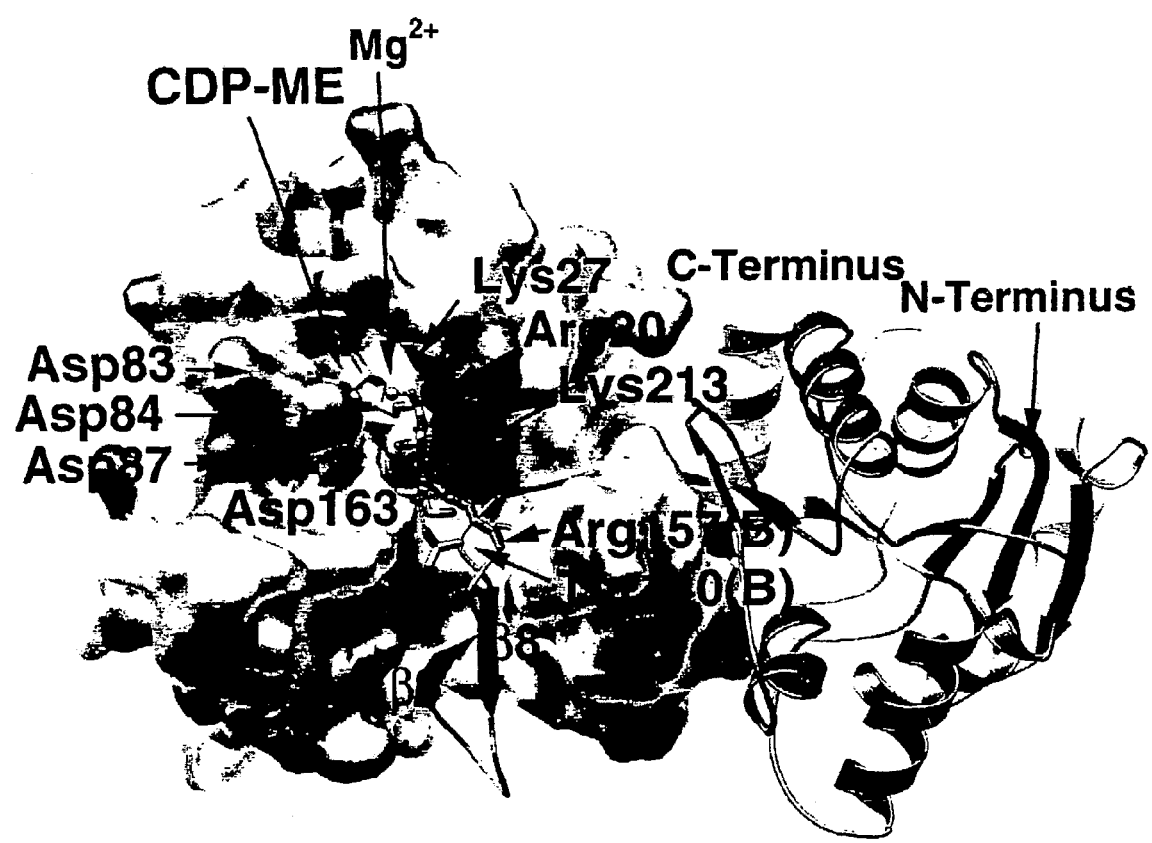
FIG. 3 provides a combined surface and ribbon view of CDP-ME synthase complexed with $CDP-ME.Mg^{2+}$. The molecular surface representation of monomer A (left) was calculated with GRASP (Esnouf, R., 1997). Monomer B (right) is represented in ribbon mode, with the side chains of Thr 140 and Arg 157 shown as rendered sticks. This orientation is derived from the view depicted in FIG. 2 after a 180 degree rotation around the horizontal axis.

In accordance with the present invention, the apo form of CDP-ME synthase has been refined to 1.55 Å resolution, the complex with CTP•Mg$^{2+}$ to 1.5 Å resolution (FIG. 2), and the complex with CDP-ME•Mg$^{2+}$ to 1.81 Å resolution (FIG. 3). YgbP crystals belong to space group C2 with one subunit per asymmetric unit and cell parameters of about a=130.6 Å, b 47.1 Å, c 38.1 Å and β94°. The complete X-ray data coordinates for the apo form of CDP-ME synthase are set forth in Appendix 1; for the complex with CTP•Mg$^{2+}$ in Appendix 2; and for the complex with CDP-ME•Mg$^{2+}$ in Appendix 3.

The crystallographic data for CDP-ME synthase used for phasing and refinement follows in Tables 1 and 2. Diffraction data was collected on a single crystal grown from SeMet containing CDP-ME synthase co-crystallized with CTP, to a resolution of 1.5 Å (Table 1). A single crystal of CDP-ME synthase was co-crystallized with CTP to a resolution of 1.5 Å, co-crystallized with MEP (referred to as the apo form) to a resolution of 1.55 Å, and co-crystallized with CDP-ME to a resolution of 1.81 Å, all on a 180/345 mm MAR imaging plate system detector (Table 2).

TABLE 2

Crystallographic data and refinement statistics

|  | CTP•Mg$^{2+}$ | Apo | CDP-ME•Mg$^{2+}$ |
| --- | --- | --- | --- |
| Wavelength (Å) | 1.08 | 1.08 | 0.773 |
| Resolution (Å) | 90-1.5 Å | 90-1.55 | 90-1.81 |
| Unique reflections[1] | 34216 (1353) | 30652 (880) | 20268 (641) |
| Redundancy | 4.7 (3.9) | 3.2 (2.1) | 2.8 (2.9) |
| Completeness[1] (%) | 92.2 (72.6) | 90.3 (51.8) | 98.6 (98.6) |
| I/σ[1] | 25.6 (1.9) | 32.7 (6) | 26.4 (2.7) |
| $R_{sym}$[1,2] (%) | 4.5 (34.5) | 2.6 (13.4) | 2.6 (30.8) |
| $R_{cryst}$[3]/$R_{free}$[4] (%) | 22.7/24.8 | 24.6/26.8 | 23.0/28.8 |
| Missing residues | [1-4] | [1-4], [16-27] | [1-4] |
|  | [229-236] | [229-236] | [229-236] |
| Protein atoms | 1713 | 1625 |  |
| Water molecules | 328 | 370 | 96 |
| Ions bound | 1 Mg$^{2+}$ | 1 Ca$^{2+}$ | 1 Mg$^{2+}$ |
|  | 1 Ca$^{2+}$ |  |  |
| Ligand atoms[5] | 29 | 0 | 33 |
| R.m.s.d. bonds (Å) | 0.0092 | 0.0051 | 0.0068 |
| R.m.s.d. angles (°) | 1.535 | 1.23 | 1.20 |
| Average B-factor (Å$^2$) |  |  |  |
| Protein | 24.9 | 25.6 | 35.0 |
| Water | 38.3 | 39.8 | 43.5 |
| Ligand | 32.3 |  | 30.0 |

[1]Number in parenthesis is for highest resolution shell.
[2]$R_{sym} = \Sigma_h|I_h - \langle I_h\rangle|/\Sigma_h I_h$, where $\langle I_h\rangle$ is the average intensity over symmetry equivalent reflections.
[3]$R_{cryst} = \Sigma|F_{obs} - F_{calc}|/\Sigma F_{obs}$, where summation is over the data used for refinement.
[4]$R_{free}$ factor is $R_{cryst}$ calculated using 5% of data (test set) excluded from refinement.
[5]Ligand atoms refer to a CTP molecule in the CTP•Mg$^{2+}$ complex and to a CDP-ME molecule in the CDP-ME•Mg$^{2+}$ complex.

TABLE 1

Crystallographic data used for phasing

|  | Native | SeMet, λ1 | SeMet, λ2 | SeMet, λ3 | Hg$_2$(OAc) | KAu(CN$_4$) |
| --- | --- | --- | --- | --- | --- | --- |
| Wavelength (Å) | 0.9848 | 0.9797 | 0.9795 | 0.8952 | 1.5418 | 1.5418 |
| Resolution (Å) | 90-1.24 | 90-1.35 | 90-1.35 | 90-1.35 | 90-1.65 | 90-1.75 |
| Unique reflections[1] | 59518 | 94279 | 93977 | 94976 | 51709 | 41116 |
|  | (1539) | (4556) | (4277) | (4529) | (1714) | (1502) |
| Completeness[1] (%) | 86.4 | 94.5 | 94.2 | 95.2 | 94.6 | 91.7 |
|  | (44.9) | (91.4) | (85.8) | (90.3) | (64.3) | (66.3) |
| I/σI[1] | 22.5 (2.3) | 20.1 (1.8) | 20.8 (1.8) | 19.7 (1.5) | 33 (3) | 27.4 (2.5) |
| $R_{sym}$[1,2] (%) | 3.5 (37.9) | 2.7 (35.6) | 2.6 (35.8) | 2.9 (43.2) | 3.4 (34.0) | 3.1 (31.0) |
| No of sites |  |  |  |  | 4 | 5 |
| Phasing power[3] |  |  |  |  |  |  |
| centric iso |  |  |  |  | 0.626 | 1.466 |
| acentric iso |  |  |  |  | 1.384 | 1.066 |
| acentric ano |  |  |  |  | 1.184 | 0.806 |
| $R_{cullis}$[4] |  |  |  |  |  |  |
| centric iso |  |  |  |  | 0.846 | 0.911 |
| acentric iso |  |  |  |  | 0.815 | 0.917 |
| acentric ano |  |  |  |  | 0.715 | 0.831 |

[1]Number in parenthesis is for highest resolution shell.
[2]$R_{sym} = \Sigma_h|I_h - \langle I_h\rangle|/\Sigma_h(I_h)$, where $\langle I_h\rangle$ is the average intensity over symmetry equivalent reflections.
[3]Phasing power = $\langle|F_{H(calc)}|/E|\rangle$, where $F_{H(calc)}$ is the calculated difference and E is the estimated lack-of-closure error, where iso is isomorphous and ano is anomalous.
[4]$R_{cullis} = \Sigma|E|/\Sigma|F_{PH} - F_P|$.

One aspect of the invention resides in obtaining crystals of an enzyme of the DXP/MEP pathway for isoprenoid biosynthesis of sufficient quality to determine the three dimensional structure of the protein by X-ray diffraction methods. X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated solution of that protein. The process of X-ray crystallography can include the following steps:

(a) synthesizing and isolating a polypeptide;

(b) growing a crystal from a solution comprising the polypeptide with or without a compound, modulator, ligand, or ligand analog; and (c) collecting X-ray diffraction patterns from the crystals, determining unit cell dimensions and symmetry, determining electron density, fitting the amino acid sequence of the polypeptide to the electron density, and refining the structure.

The term "crystalline form" refers to a crystal formed from a solution comprising a purified polypeptide corresponding to all or part of CDP-ME synthase. In preferred embodiments, a crystalline form may also be formed from a purified polypeptide corresponding to all or part of CDP-ME synthase in a complex with one or more substrates, substrate mimics or inhibitors of CDP-ME synthase.

The term "substrate" refers to a compound whose activity is typically enhanced by an enzyme. Enzymes can catalyze a specific reaction on a specific substrate. For example, CDP-ME synthase can catalyze the formation of CDP-ME from 2-C-methyl-D-erythritol-4-phosphate and CTP. The term "substrate mimic" refers to a compound that is structurally similar, but not identical, to a substrate. The term "inhibitor" refers to a compound causes inhibition of one or more biochemical events which the enzyme may catalyze.

The term "X-ray coordinates" or "X-ray data coordinates" as used herein refers to a data set that defines the three dimensional structure of a molecule, for example, as set forth in Appendices 1, 2 and 3. The data sets are derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal cell. Structural coordinates can be slightly modified and still render nearly identical three dimensional structures. A measure of a unique set of structural coordinates is the root-mean-square (r.m.s.) deviation of the resulting structure. Structural coordinates that render three dimensional structures that deviated from one another by a r.m.s. deviation of less than about 1.5 Å may be viewed by a person of ordinary skill in the art as identical since they have little effect on the overall structure, and would not significantly alter the nature of binding associations. Furthermore, those of skill in the art understand that a set of coordinates for an enzyme or complex thereof, is a relative set of points that define the three dimensional shape of said enzyme or enzyme complex. As such, it is possible that an entirely different set of coordinates could define a similar or identical shape. Hence, the structural coordinates set forth in Tables 1 and 2, and Appendices 1, 2 and 3 are not limited to the express values set forth therein.

The use of X-ray crystallography can elucidate the three dimensional structure of crystalline forms according to the invention. Typically, the first characterization of crystalline forms by X-ray crystallography can determine the unit cell shape and its orientation in the crystal. The term "unit cell" refers to the smallest and simplest volume element of a crystal that is completely representative of the unit of pattern of the crystal. The dimensions of the unit cell are defined by six numbers: dimensions a, b and c and angles $\alpha$, $\beta$ and $\gamma$. A crystal can be viewed as an efficiently packed array of multiple unit cells. Detailed descriptions of crystallographic terms are described in Hahn, 1996, *The International Tables for Crystallography, Volume A*, Fourth Edition, Kluwer Academic Publishers; and Shmueli, *The International Tables for Crystallography, Volume B*, First Edition, Kluwer Academic Publishers. The term "space group" refers to the symmetry of a unit cell. In a space group designation (e.g., C2) the capital letter indicates the lattice type and the other symbols represent symmetry operations that can be carried out on the unit cell without changing its appearance.

The knowledge obtained from X-ray diffraction patterns can be used in the determination of the three dimensional structure of the binding sites of other homologous enzymes. This is achieved through the use of commercially available software known in the art that is capable of generating three dimensional graphical representations of molecules or portions thereof from a set of structure coordinates. The binding domain can also be predicted by various computer models. Based on the structural X-ray coordinates of the solved structure, small molecules which mimic the functional binding of an enzyme to its substrate can be designed and synthesized as potential drugs. Another approach to such "rational" drug design is based on a lead compound that is discovered using high throughput screens; the lead compound is further modified based on a crystal structure of the binding regions of the molecule in question using the points of interaction between the compound and target molecule.

Accordingly, in one embodiment of the present invention, there is provided a computer for producing a three-dimensional representation of a molecule or molecular complex or a homologue of said molecule or molecular complex, wherein said molecule or molecular complex or a homologue of said molecule or molecular complex comprises an active site defined by structure coordinates of Appendix 1, 2 or 3, wherein said computer comprises:

(i) a computer-readable data storage medium comprising a data storage material encoded with computer-readable data, wherein said data comprises the structure coordinates of Appendix 1, 2 or 3;

(ii) a working memory for storing instructions for processing said computer-readable data;

(iii) a central-processing unit coupled to said working memory and to said computer-readable data storage medium for processing said computer-machine readable data into said three-dimensional representation; and (iv) a display coupled to said central-processing unit for displaying said three-dimensional representation.

According to an alternative embodiment there is provided a computer for determining at least a portion of the structure coordinates corresponding to X-ray diffraction data obtained from a molecule or molecular complex or a homologue of said molecule or molecular complex, wherein said computer comprises:

(i) a computer-readable data storage medium comprising a data storage material encoded with machine-readable data, wherein said data comprises at least a portion of the structural coordinates of Appendix 1, 2 or 3;

(ii) a computer-readable data storage medium comprising a data storage material encoded with computer-readable data, wherein said data comprises X-ray diffraction data obtained from said molecule or molecular complex or a homologue of said molecule or molecular complex;

(iii) a working memory for storing instructions for processing said computer-readable data of (i) and (ii);

(iv) a central-processing unit coupled to said working memory and to said computer-readable data storage medium of (i) and (ii) for performing a Fourier transform of the machine readable data of (i) and for processing said computer-readable data of (ii) into structure coordinates; and (v) a display coupled to said central-processing unit for displaying said structure coordinates of said molecule or molecular complex.

The term "computer" as used herein can be composed of a central processing unit (for example, the Pentium III from Intel Corporation, or similar processor from Sun, Motorola, Compaq, AMD or International Business Machines, and the like), a working memory which may be random-access memory or core memory, mass storage memory (for example, one or more floppy disk drives, compact disk drives or magnetic tape containing data recorded thereon), at least one display terminal, at least one keyboard and accompanying input and output devices and connections therefor. The computer typically includes a mechanism for processing, accessing and manipulating input data. A skilled artisan can readily appreciate that any one of the currently available computer systems are suitable. It should also be noted that the computer can be linked to other computer systems in a network or wide area network to provide centralized access to the information contained within the computer.

Contemplated input devices for entering machine readable data include, for example, telephone modem lines, cable modems, CD-ROMs, a keyboard or disk drives. The computer may advantageously include or be programmed with appropriate software for reading the data from the data storage component or input device, for example computational programs for use in rational drug design that are described in detail below. Contemplated output devices include conventional systems known in the art, for example, display terminals, printers, or disk drives for further storage of output.

In a further embodiment of the present invention, there are provided methods for screening for compounds that inhibit the mevalonate-independent isoprenoid biosynthesis pathway. These methods comprise determining the points of interaction between any one or more enzymes in this pathway, with a substrate or substrate mimic therefor; selecting compound(s) having similar interaction with said one or more enzymes; and testing the selected compound for the ability to inhibit the activity of any one or more enzymes in the non-mevalonate isoprenoid biosynthesis pathway.

The term "points of interaction" refers to hydrophobic, aromatic, and ionic forces and hydrogen bonds formed between atoms. Such interactions can be "intramolecular," or within the same molecule, or "intermolecular," or between separate molecules. Compounds with similar points of interaction are preferably selected by docking a three dimensional representation of a structure of a compound with a three dimensional representation of the target enzyme in the non-mevalonate isoprenoid biosynthesis pathway, for example, CDP-ME synthase. The computer representation of the target enzyme can be defined in a variety of ways, for example, by atomic X-ray coordinates.

For example, from the crystal structure of CDP-ME synthase it was determined that CTP and CDP-ME are sequestered by a glycine rich loop spanning Pro 13 to Arg 20. Selectivity for the pyrimidine base is achieved through hydrogen bonding interactions and steric constrictions in the base-binding pocket, which do not allow for the sequestration of larger purine bases (Weber, C. H. et al., 1999). This selectivity is specifically achieved through hydrogen bonds formed between the backbone amides of Ala 14 and Ala 15, the carbonyl oxygens of Gly 82 and Asp 83, and the hydroxyl group of Ser 88. The cytosine base is stacked between the flexible loop spanning β1 and β2, and the methylene portion of the Arg 85 side chain projecting outward from the β5-αE catalytic loop. The 2' and 3' hydroxyl groups of the ribose moiety are involved in backbone hydrogen bonding interactions with Pro 13, Gly 16, and Ala 107 (FIGS. 6 and 7).

Furthermore, the main chain monomers of CDP-ME synthase superpose with a root mean square (r.m.s) deviation of 0.264 Å, 0.773 Å, and 0.754 Å between the apo and $CTP.Mg^{2+}$, apo and $CDP-ME.Mg^{2+}$, and $CTP.Mg^{2+}$ and $CDP-ME.Mg^{2+}$ bound forms, respectively. The largest backbone differences occur in the loop linking β1 and β2 supporting the $3_{10}$-helices, A1 and A2. In CMP-NeuAc synthetase, this so-called P-loop (Mossimann, S. C. et al., 2000) responsible for phosphate recognition, together with the residues following β5, enclose the mononucleotide binding pocket. In CDP-ME synthase, the P-loop comprising residues 17-25 is not defined in the apo form and poorly defined in the $CDP-ME.Mg^{2+}$ complex. In both CDP-ME synthase and CMP-NeuAc synthetase, the P-loop undergoes a dramatic ordering upon binding of CDP in CMP-NeuAc synthetase or $CTP.Mg^{2+}$ in CDP-ME synthase. The rest of the nucleotide binding pocket responsible for base recognition and ribose binding are well defined in the electron density maps of the apo form and both the $CTP.Mg^{2+}$ and $CDP-ME.Mg^{2+}$ complexes.

Figure 6:
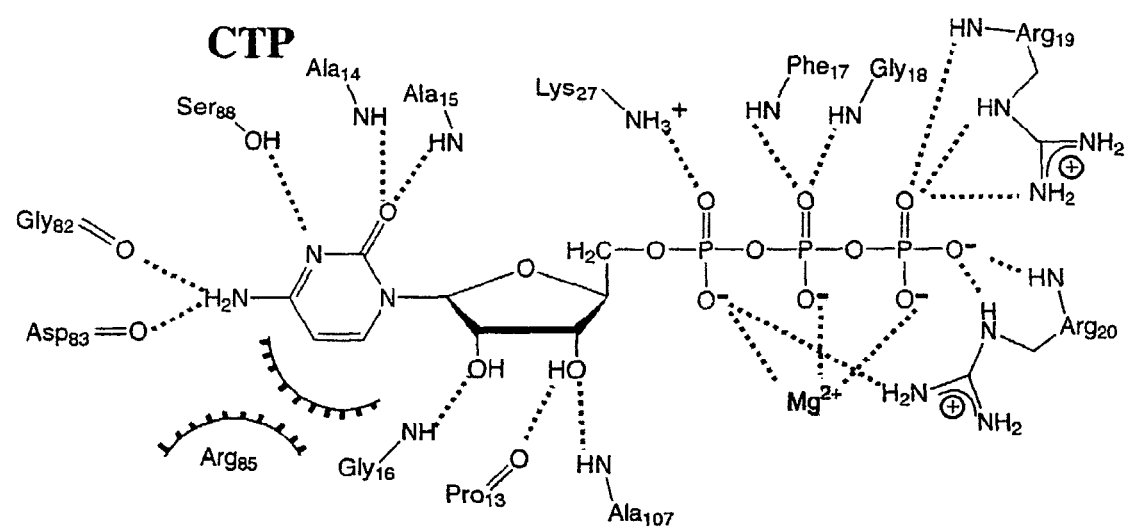
FIG. 6 provides a schematic representation of the $CTP•Mg^{2+}$ binding site of the CDP-ME synthase active site, showing the hydrogen and coordination bonds to CTP and $Mg^{2+}$, respectively.
Figure 7:
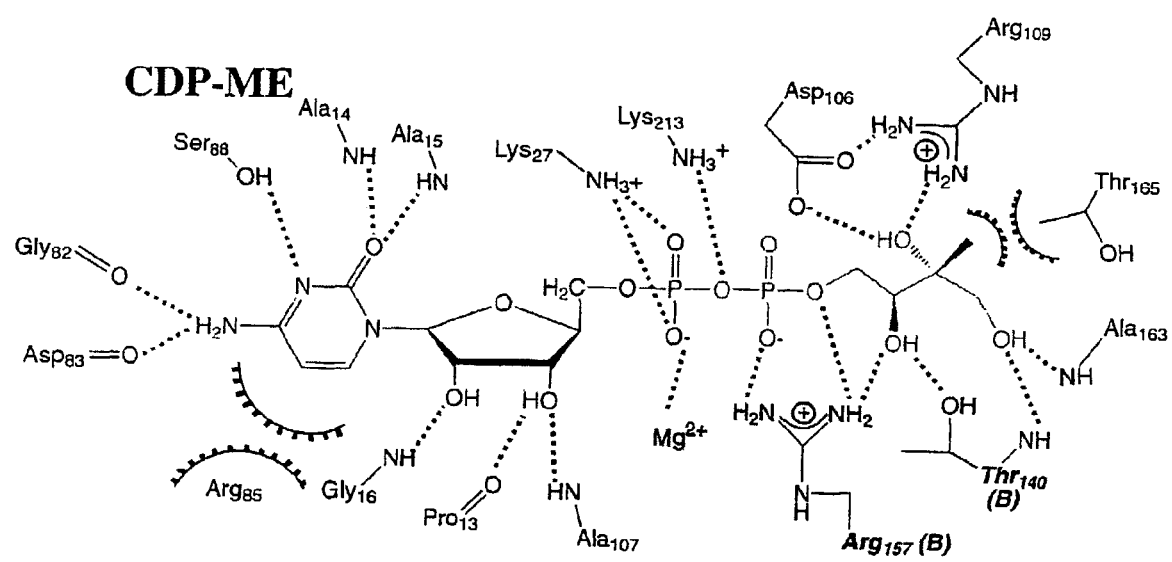
FIG. 7 provides a schematic representation of the CDP-$ME•Mg^{2+}$ binding site of the CDP-ME synthase active site. Recognition of the CDP-ME product is accomplished using an extensive set of hydrogen-bonding interactions that includes residues from both polypeptide chains of the CDP-ME synthase homodimer. This subset of interactions partially maps the putative MEP binding site in CDP-ME synthase. The carboxyl group of Asp 106 forms a hydrogen bond with the C2 hydroxyl group of the MEP portion of CDP-ME, the backbone amide of Thr 140 from the dyad related monomer hydrogen bonds with the C1 hydroxyl group of CDP-ME, and the side chain δ-guanido group of Asp 157 from the dyad related monomer provides hydrogen bonds to both the C3 hydroxyl group and two phosphate oxygens of MEP.
Figure 8A:
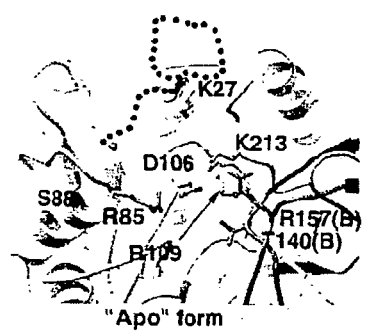
FIGS. 8A-8E collectively provide a rendered view of the ground state complexes of CDP-ME synthase. The apo form of CDP-ME synthase is shown in FIG. 8A, the $CTP•Mg^{2+}$ complex in FIG. 8B and the $CDP-ME•Mg^{2+}$ complex in FIG. 8E. The model for the $MEP.CTP.Mg^{2+}$ complex shown in FIG. 8C is based on the observed positions of CTP and the MEP-derived portion of CDP-ME. The model for the product complex that includes diphosphate (PPi) shown in FIG. 8D is based on the observed position of the β and γ phosphates of CTP. These close-up views are shown in an orientation identical to the views depicted in FIG. 3.
Figure 8B:
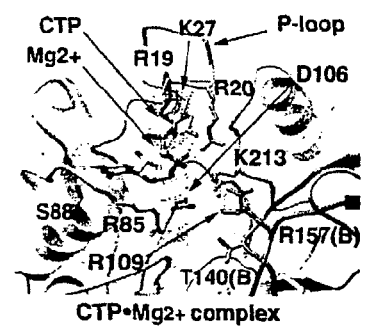
Figure 8C:
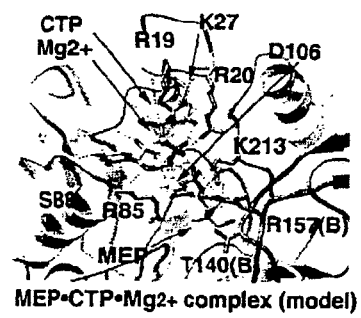
Figure 8D:
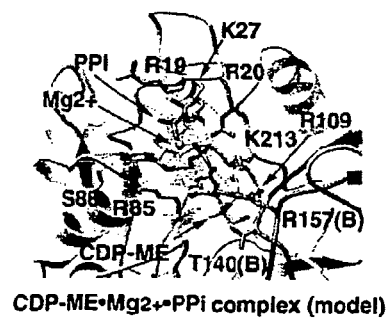
Figure 8E:
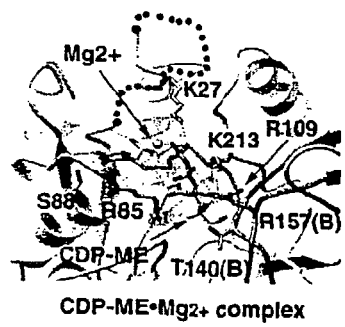

In addition, the side chain amino group of Lys 27 is in direct contact with the α-phosphates of CTP and CDP-ME (FIG. 6). Arg 20 through both its backbone amide and its side chain δ-guanido moiety forms an elaborate series of hydrogen bonding interactions with the α and γ phosphate oxygens (FIG. 6). Given their positions near the α-phosphate of CTP, their absolute conservation in the CDP-ME enzyme family, and the potential accumulation of negative charges in the pentacoordinate transition state for CDP-ME formation, Arg 20 and Lys 27 may play important roles in transition state stabilization during CDP-ME formation.

$Mg^{2+}$, which is essential for cytidyltransferase activity (Rohdich, F. et al., 1999), forms coordination bonds with the α, β, and γ phosphate oxygens of CTP and the α phosphate oxygen of CDP-ME. The $Mg^{2+}$ ion coordinates with regular octahedral geometry to CTP with water molecules occupying the coordination sites not occupied by the phosphate oxygens. No coordination bonds between CDP-ME synthase and $Mg^{2+}$ occur in any of the complexes examined to date. Lys 213, together with Arg 157 from the dyad related subunit, does not participate in hydrogen bonds with CTP, but both are in direct contact with the MEP derived portions of CDP-ME (FIG. 7).

Thus, the structural analysis of the substrate and product complexes suggest that MEP does not bind in the absence of CTP as all attempts to obtain an MEP complex in the absence of CTP failed to reveal any density in the CDP-ME synthase active site. In cytidyltransferases, as in class I aminoacyl-tRNA synthetases, the CTP or ATP substrates bind first followed by the second substrate prior to product formation through a pentacoordinate (associative mechanism) transition state (Veitch, D. P. & Cornell, R. B., 1996; Veitch, D. P. et al., 1998). The MEP-derived portion of the CDP-ME molecule contacts the protein through hydrogen bonds between MEP's three hydroxyl groups and the side chain carboxyl group of Asp 106, the δ-guanido moiety of Arg 109, the main chain amide of Thr 140, and the side chain δ-guanido moiety of Arg 157. Finally, the C4 methyl group of CDP-ME is nestled in a hydrophobic pocket formed by the side chain methyl groups of Thr 165 and Ala 163 (FIG. 7). Notably, it is the polypeptide chain of the dyad related subunit which contains Thr 140 and Arg 157.

Methods of using crystal structure data to design inhibitors of enzyme activity are known in the art. Thus, the crystal structure data provided herein can be used in the design of new or improved enzymatic inhibitors. For example, the CDP-ME synthase binding site X-ray coordinates, provided herein, can be superimposed onto other available coordinates of similar enzymes which have inhibitors bound to them to give an approximation of the way these and related inhibitors might bind to CDP-ME synthase. Alternatively, computer programs employed in the practice of rational drug design can be used to identify compounds that reproduce interaction characteristics similar to those found between the enzyme and its substrate or product. For, example, the CDP-ME synthase coordinates when complexed with $CTP.Mg^{2+}$ and $CDP-ME.Mg^{2+}$, provided herein, can be used to model beneficial points of interaction in a potential drug compound. Furthermore, detailed knowledge of the nature of binding site interactions allows for the modification of compounds to alter or improve solubility, pharmokinetics, etc. without affecting binding activity.

Computer programs are widely available that are capable of carrying out the activities necessary to design compounds using the crystal structure information provided herein. Examples include, but are not limited to, the computer programs listed below:

Catalyst Databases™—an information retrieval program accessing chemical databases such as BioByte Master File, Derwent WDI and ACD;

Catalyst/HYPO™—generates models of compounds and hypotheses to explain variations of activity with the structure of drug candidates;

Ludi™—fits molecules into the active site of a protein by identifying and matching complementary polar and hydrophobic groups;

Leapfrog™—"grows" new ligands using an algorithm with parameters under the control of the user.

In addition, various general purpose machines may be used with programs written in accordance with the teachings herein, or it may be more convenient to construct more specialized apparatus to perform the operations. However, preferably this is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

For the first time, the present invention permits the use of molecular design techniques to design, select and synthesize chemical entities and compounds, including inhibitory compounds, capable of binding to the active site of the enzymes of the mevalonate-independent isoprenoid biosynthetic pathway.

One approach contemplated by this invention is to use the structure coordinates set forth in Appendices 1, 2 and 3 to design compounds that bind to the enzyme and alter the physical properties of the compounds in different ways, e.g., solubility. For example, this invention enables the design of compounds that act as competitive inhibitors of CDP-ME synthase by binding to the identified active site. In another approach, the active site of a crystal of an enzyme is probed with molecules composed of a variety of different chemical entities to determine optimal sites for interaction. For example, these molecules could mimic substrate compounds, or enzyme inhibitors.

In another embodiment, an approach made possible and enabled by this invention is to screen computationally small molecule data bases for chemical entities or compounds that can bind to the active site of a target enzyme. In this screening, the quality of fit of such entities or compounds to the binding site may be judged either by shape complementarity or by estimated interaction energy (Meng, E. C. et al., 1992).

In addition, in accordance with the present invention, enzyme mutants may be crystallized in co-complex with known binding agents, substrates, or inhibitors. The crystal structures of a series of such complexes may then be solved by molecular replacement and compared with that of a wild-type enzyme. Potential sites for modification within the enzyme's active site may thus be identified. This information provides an additional tool for determining the most efficient binding interactions, for example, increased hydrophobic interactions, between an active site residue and a chemical entity or compound.

All of the complexes referred to above may be studied using well-known X-ray diffraction techniques and may be refined versus 2-3 Å resolution X-ray data to an R value of about 0.20 or less using computer software, such as X-PLOR (Yale University, 1992, distributed by Molecular Simulations, Inc.). See, e.g., Methods in Enzymology, 1985). This information may thus be used to optimize known classes of enzyme binding agents (e.g., inhibitors), and to design and synthesize novel classes of active site agents (e.g., inhibitors).

The design of binding agents that bind or otherwise associate with or inhibit the active site of an enzyme according to the invention generally involves consideration of two factors. First, the compound or binding agent must be capable of physically and structurally associating with the target enzyme. Non-covalent molecular interactions important in the association of an enzyme with a substrate include hydrogen bonding, van der Waals and hydrophobic interactions.

Second, the compound or binding agent must be able to assume a conformation that allows it to associate with the active site. Although certain portions of the compound or binding agent will not directly participate in this association, those portions may still influence the overall conformation of the molecule. This, in turn, may have a significant impact on potency. Such conformational requirements include the overall three-dimensional structure and orientation of the chemical entity or compound in relation to all or a portion of the binding site, or the spacing between functional groups of a compound comprising several chemical entities that directly interact with an active site.

The potential inhibitory or binding effect of a chemical compound on an active site may be analyzed prior to its actual synthesis and testing by the use of computer modeling techniques. If the theoretical structure of the given compound suggests insufficient interaction and association between it and the active site, synthesis and testing of the compound may be obviated. However, if computer modeling indicates a strong interaction, the molecule may then be tested in efforts to confirm its ability to bind to the target enzyme. Methods of assaying for enzymatic activity are known in the art. Methods for assaying the effect of a potential binding agent can be performed in the presence of a known binding agent of the target enzyme. For example, the effect of the potential binding agent can be assayed by measuring the ability of the potential binding agent to compete with a known binding agent.

An inhibitory or other binding compound of the target enzyme may be computationally evaluated and designed by means of a series of steps in which chemical entities or fragments are screened and selected for their ability to associate with the individual binding pockets or other areas of the active site of the target enzyme.

One skilled in the art may use one of several methods to screen chemical entities or fragments for their ability to associate with the target active site. This process may begin by visual inspection of, for example, the active site on the computer screen based on the X-ray coordinates of the enzyme. Selected fragments or chemical entities may then be positioned in a variety of orientations, or docked, within an individual binding pocket of an active site. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

1. GRID (Goodford, P. J., 1985). GRID is available from Oxford University, Oxford, UK.

2. MCSS (Miranker, A. and Karplus, M., 1991). MCSS is available from Molecular Simulations, Burlington, Mass.

3. AUTODOCK (Goodsell, D. S. and Olsen, A. J., 1990). AUTODOCK is available from Scripps Research Institute, La Jolla, Calif.

4. DOCK (Kuntz, I. D. et al., 1982). DOCK is available from University of California, San Francisco, Calif.

Once suitable chemical entities or fragments have been selected, they can be assembled into a single compound or binding agent (e.g., an inhibitor). Assembly may be performed by visual inspection of the relationship of the fragments to each other on the three-dimensional image displayed on a computer screen in relation to the structure coordinates of the enzyme. This would be followed by manual model building using software such as Quanta or Sybyl.

Useful programs to aid one of skill in the art in connecting the individual chemical entities or fragments include:

1. CAVEAT (Bartlett, P. A. et al, 1989). CAVEAT is available from the University of California, Berkeley, Calif.

2. 3D Database systems such as MACCS-3D (MDL Information Systems, San Leandro, Calif.). This area is reviewed in Martin, Y. C., 1992).

3. HOOK (available from Molecular Simulations, Burlington, Mass.).

In addition to the method of building or identifying a binding agent in a step-wise fashion one fragment or chemical entity at a time as described above, inhibitory or other active site binding compounds may be designed as a whole or "de novo" using either an empty active site or optionally including some portion(s) of a known inhibitor(s). These methods include:

1. LUDI (Bohm, H.-J., 1992). LUDI is available from Biosym Technologies, San Diego, Calif.

2. LEGEND (Nishibata, Y. and Itai, A., 1991). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., 1990. See also, Navia, M. A. and Murcko, M. A., 1992.

Once a compound or binding agent has been designed or selected by the above methods, the efficiency with which that compound may bind to an enzyme's active site may be tested and optimized by computational evaluation.

A compound designed or selected as an active site binding agent may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and the active site when the binding agent is bound to it, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollan, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified.

Once an active site binding agent has been selected or designed, as described above, substitutions may then be made in some of its atoms or side groups in order to improve or modify its binding properties. Generally, initial substitutions are conservative, e.g., the replacement group will have approximately the same size, shape, hydrophobicity and charge as the original group. Such substituted chemical compounds may then be analyzed for efficiency of fit to an active site by the same computer methods described above.

In accordance with another aspect of the present invention, there are provided methods for inhibiting the activity of any one or more enzymes in the non-mevalonate isoprenoid biosynthesis pathway comprising contacting said one or more enzymes with an effective amount of an inhibitory compound in a cell-free environment or in a cell. Such cellular contact may be in vitro or in vivo. In a preferred embodiment of the invention, the cell's growth is modulated by contact with the inhibitory compound. In another preferred embodiment of the invention, the cell is a bacterial cell.

The term "growth of the cell" refers to the rate at which a cell divides. A compound can modulate growth by either increasing or decreasing cell division rates. Cell division rates can be readily measured by methods known in the art.

In accordance with another embodiment of the present invention there are provided compounds identified as inhibitors of the mevalonate-independent isoprenoid biosynthesis pathway and pharmaceutical compositions thereof in a pharmaceutically acceptable carrier. In a preferred embodiment of the invention there is provided an antibacterial formulation containing at least one inhibitory compound in a suitable carrier.

In accordance with yet another aspect of the present invention, there are provided methods for inhibiting bacterial terpenoid synthesis comprising contacting bacteria with an effective amount of at least one inhibitory compound.

The term "effective amount" as used herein refers to the amount of inhibitor required to biologically inhibit terpenoid synthesis via inhibition of any enzyme involved along the mevalonate-independent isoprenoid biosynthetic pathway.

In accordance with yet another aspect of the present invention, there are provided methods for treating a subject suffering from a bacterial infection. These methods comprise administering to the subject an effective amount of at least one inhibitory compound. In a preferred embodiment of the present invention, the subject is suffering from an E. coli infection or a streptococcal infection.

Bacterial infections contemplated for treatment using invention compounds and methods include infections caused by both gram-positive and gram-negative bacteria, including infections caused by Staphylococcus, Clostridium, Streptococcus, Enterococcus, Diplococcus, Hemophilus, Neisseria, Erysipelothricosis, Listeria, Bacillus, Salmonella, Shigella, Escherichia, Klebsiella, Enterobacter, Serratia, Proteus, Morganella, Providencia, Yersinia, Camphylobacter, Mycobacteria, and the like. Infection by such organisms causes a wide variety of disorders including pneumonia, diarrhea and dysentery, anthrax, rheumatic fever, toxic shock syndrome, mastoiditis, meningitis, gonorrhea, typhoid fever, gastroenteritis, brucellosis, cholera, bubonic plague, tetanus, tuberculosis, Lyme disease, and the like.

The particular invention compound(s) selected for therapeutic use as taught herein can be administered to a subject either alone or in a pharmaceutical composition where the compound(s) is mixed with suitable carriers or excipient(s). In treating a subject, a therapeutically effective dose of compound (i.e., active ingredient) is administered. A therapeutically effective dose refers to that amount of the active ingredient that produces amelioration of symptoms or a prolongation of survival of a subject.

Toxicity and therapeutic efficacy of a compound can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages suitable for use in humans. The dosage of such compounds lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

For any compound used in the method of the invention, the therapeutically effective dose can be estimated initially from cell culture assays by determining an $IC_{50}$ (i.e., the concentration of the test substance which achieves a half-maximal inhibition of PPIase activity). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975).

It should be noted that the attending physician would know how to and when to terminate, interrupt, or adjust administration due to toxicity, to organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient. Typically, the dose will be between about 1-10 mg/kg of body weight. About 1 mg to about 50 mg will be administered to a child, and between about 25 mg and about 1000 mg will be administered to an adult. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for oral administration. Such carriers enable the compounds of the invention to be formulated as tablets, pills, capsules, dragees, liquids, gels, syrups, slurries, suspensions, and the like, for oral ingestion by a subject to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Delivery systems involving liposomes are discussed in International Patent Publication No. WO 91/02805 and International Patent Publication No. WO 91/19501, as well as U.S. Pat. No. 4,880,635 to Janoff et al. These publications and patents provide useful descriptions of techniques for liposome drug delivery and are incorporated by reference herein in their entirety.

Pharmaceutical compositions contemplated for use in the present invention include compositions wherein the active ingredients are contained in an amount effective to achieve the intended purpose. Determination of an effective amount is well within the capability of those skilled in the art, especially in light of the detailed disclosure provided herein.

In addition to the active ingredients, these pharmaceutical compositions may contain suitable pharmaceutically acceptable excipients and auxiliaries which facilitate processing of the active compounds into preparations which can be used pharmaceutically.

The pharmaceutical compositions of the present invention may be manufactured in a manner that is itself known, e.g., by means of conventional mixing, dissolving, granulating, dragee-making, levigating, emulsifying, encapsulating, entrapping, lyophilizing processes, or the like.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations such as, for example, maize starch, wheat starch, rice starch, potato starch, gelatin, gum tragacanth, methyl cellulose, hydroxypropylmethylcellulose, sodium carboxymethylcellulose, polyvinylpyrrolidone (PVP), and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

A detailed description of CDP-ME synthase structure is provided below as a preferred embodiment of the invention.

The present invention may suitably be practice in the absence of any element or limitation not specifically disclosed herein. The terms and expressions employed herein have been used as terms of description to facilitate enablement and not of limitation, and there is no intention in the use of such terms and expressions of excluding any equivalents of the features shown and described or portions thereof, but it is recognized that various modifications are possible within the scope of the invention claimed. Thus it should be understood that although the present invention has been specifically disclosed by preferred embodiments and optional features, modification and variation of the inventions embodied herein disclosed may be resorted to by those skilled in the art, and that such modifications and variations are considered to be within the scope of this invention.

CDP-ME synthase packs as a homodimer in the crystalline state with each monomer related by a crystallographic two-fold axis, in accordance with its hydrodynamic characterization. The dimeric arrangement is believed to represent the physiologically relevant dimeric arrangement for two reasons. Firstly, oligomerization buries 3750 $Å^2$ of surface area, a value typical of dimeric proteins. Secondly, the polypeptide chain of each monomer contributes residues to the active site of the dyad related monomer, lending mechanistic relevance to this oligomeric arrangement (FIG. 3).

Each monomer is comprised of two structurally distinct domains. The larger core-domain (residues 1 to 136 and 160 to 236) is globular in shape and maintains an $\alpha/\beta$ structure that resembles a Rossman fold (Rossman, M. G. et al., 1975), but which displays a distinct $\alpha/\beta$ connectivity pattern including an insertion of two $\beta$-strands, $\beta7$ and $\beta10$, into a canonical 3-2-1-5 type of parallel $\beta$-sheet topology (strands $\beta5$, $\beta4$, $\beta1$, $\beta6$ and $\beta11$ in FIG. 4). The second much smaller lobe or subdomain (residues 137 to 159) resembles a curved arm that interlocks in traits with its symmetry related arm to mediate dimer formation. Moreover, the interlocking arms form a significant fraction of the MEP binding site, and organize portions of the catalytic surface responsible for cytidyltransferase activity (FIG. 3). In CDP-ME synthase, the connecting loops, $\beta1$-$\beta2$ and $\beta11$-$\alpha I$, become ordered upon CTP binding and form the upper section of the catalytic pocket responsible for CTP recognition (FIG. 2). The lower half of this catalytic crevice is extended across the dimer interface through a conserved network of salt bridges.

A PSI-BLAST (Altschul, S. F. et al., 1997) search of the non-redundant sequence database with E. coli CDP-ME synthase retrieved a large number of similar sequences from a variety of organisms. These sequences exhibit several highly conserved regions that, when viewed with reference to the structure of the E. coli enzyme, support their role as vital active site residues utilized for substrate recognition and catalysis in CDP-ME synthase. A search for related three dimensional structures in the Protein Data Bank (Berman, H. M. et al., 2000) using the DALI (Holm, L. & Sander C., 1993) server retrieved a number of enzyme cores containing a mononucleotide binding fold. Currently, three cytidyltransferase structures have been described and include capsule specific CMP:2-keto-3-deoxy-manno-octonic acid synthetase (Jelakovic, S. et al., 1996) (K-CKS), CTP:glycerol-3-phosphate cytidyltransferase (GCT)(Weber, C. H. et al., 1999), and most recently CMP acylneuraminate synthetase (CMP-NeuAc synthetase) (Mossimann, S. C. et al., 2000).

Figure 4:
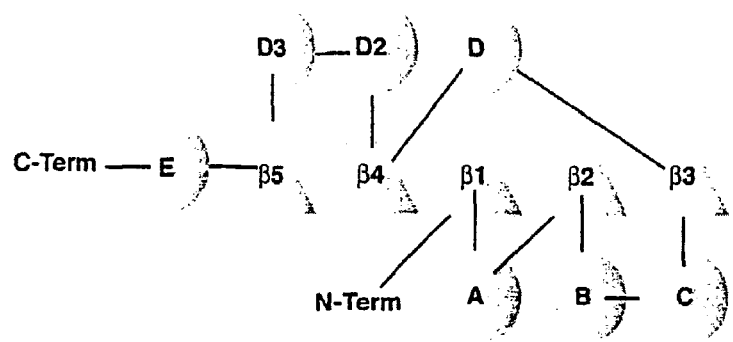
FIG. 4 depicts a family of cytidyltransferases as a topology diagram for GCT (CTP:glycerol-3-phosphate cytidyltransferase), CDP-ME synthase (ygbP) and CMP-NeuAc synthetase monomers. The diagram was generated with TOPS (Westhead, D. R. et al., 1999); helices are represented as circles and strands as triangles.
Figure 4:
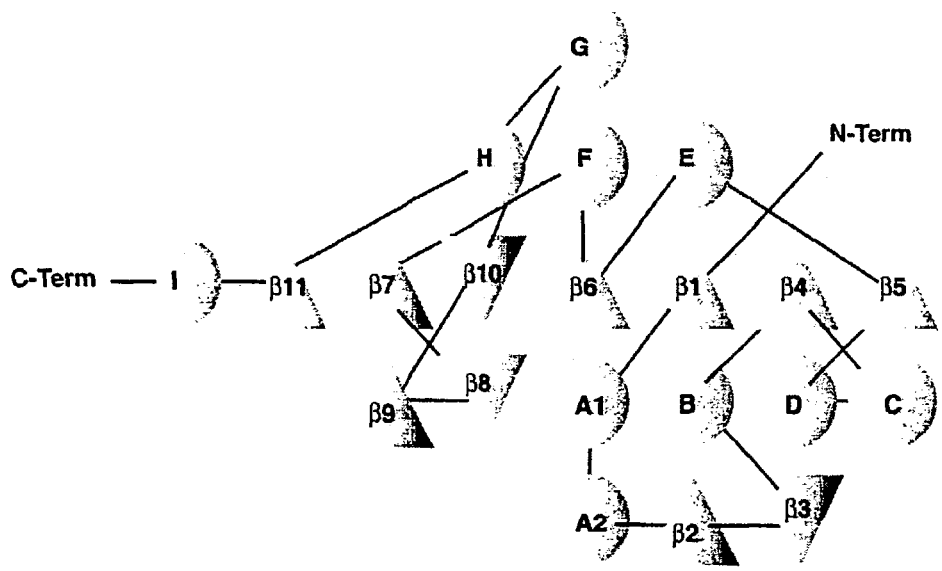
Figure 4:
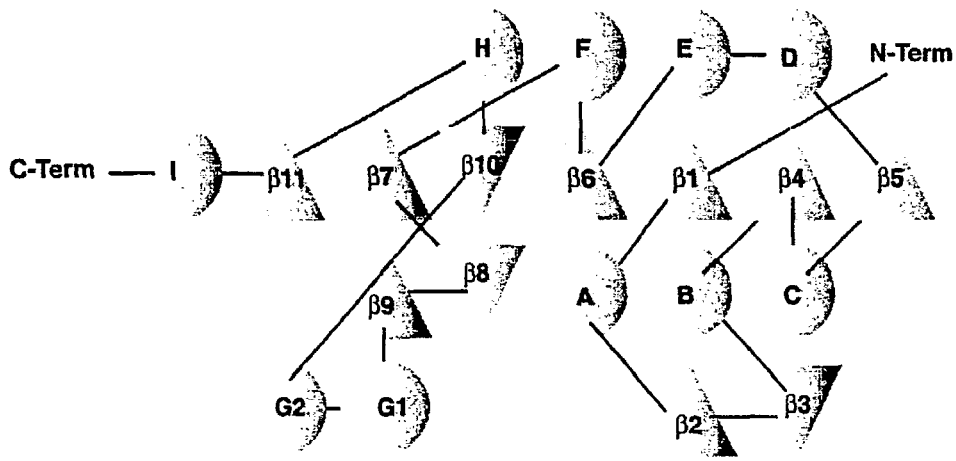
Figure 5:
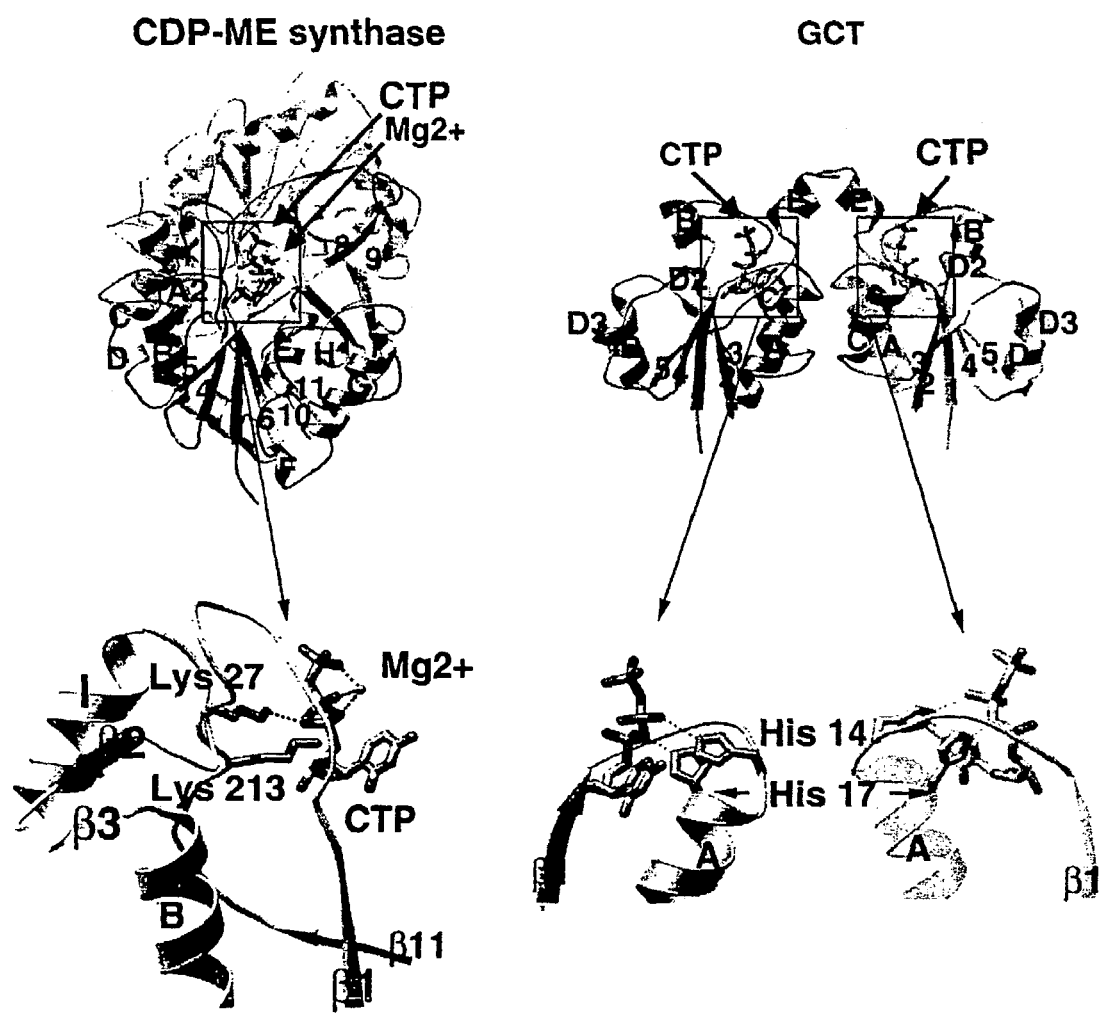
FIG. 5 presents evidence of contrasting CTP binding modes in GCT and CDP-ME synthase. In CDP-ME synthase, CTP binds on the top of β1 with the triphosphate arm resting against the P-loop and the cytosine base residing against the β5-αE loop. In GCT, CTP binds on the top of β4 with the triphosphate moiety contacting the β5-αE loop and the cytosine base in contact with the β5-αE loop. The overall orientation of CDP-ME synthase depicted is derived from the view shown in FIG. 2A following a 90 degree clockwise rotation in the plane of the figure and a 45 degree rotation around the horizontal axis. In GCT, H is 14 and H is 17 form hydrogen bonds with the α- and β-phosphate oxygens, respectively (Weber, C. H. et al., 1999). Lys 27 and Lys 213 of CDP-ME synthase are spatially equivalent to H is 14 and H is 17 of GCT.

CDP-ME synthase, CMP-NeuAc synthetase, and GCT share similarly folded cores (FIGS. 2 and 5). However, the five parallel P-strands of GCT, which maintain a 3-2-1-4-5 topology, are interrupted in CDP-ME synthase and CMP-NunAc synthetase by the insertion of two antiparallel β-strands (β7 and β10) between strands 4 and 5 (β6 and β11) of the core β-sheet (FIG. 4). This insertion extends the central β-sheet leading to a structural alteration of the nucleotide binding region and subsequent formation of a distinct and spatially non-overlapping CTP binding motif in CDP-ME synthase, CMP-NeuAc synthetase, and presumably K-CKS. While all earlier cytidyltransferase structures described to date have lacked bound product, the currently described CDP-ME synthase structures with $Mg^{2+}$, substrates, and products bound accurately map the complete cytidyltransferase active site. Notably, the inserted β-strands, β7 and β10, position the extended arm lobe of CDP-ME synthase that modulates formation of the MEP binding site in trans through dimerization.

By superimposing GCT and CDP-ME synthase to constrain the connectivity pattern of the central β-sheets and the surrounding α-helices, the GCT and CDP-ME synthase active sites reside on the same C-terminal side of the central β-sheets, but the orientations of the bound CTP molecules in each enzyme are arranged in opposite fashions (FIG. 5). In contrast, alignments of the two structures using the bound CTP molecules as a guide reveals an internal pseudosymmetry in the core α/β fold of both GCT and CDP-ME synthase (FIG. 5). Indeed, it appears that this pseudosymmetric folding pattern can be utilized for two distinct modes of binding the CTP substrate partially dictated by the extension of the parallel 3-2-1-4-5 β-strand topology in CDP-ME synthase by two antiparallel β-strands.

While the cytidine base and ribose exhibit nearly identical orientations in GCT and CDP-ME synthase, the curved triphosphate ends of the bound CTP molecules pucker in opposite directions. These alternative orientations of the triphosphate tail of CTP position each of the α-phosphates of the CTP substrates for nucleophilic attack by MEP in CDP-ME synthase and glycerol 3-phosphate in GCT. The structure of CMP-NeuAc synthetase was solved in the apo form and complexed to a partially disordered CDP molecule which serves as a mimic of the true CTP substrate. Structural alignments of E. coli CDP-ME synthase or Neisseria meningitidis CMP-NeuAc synthetase with GCT reveal that the catalytic machinery of CDP-ME synthase and CMP-NeuAc synthetase are spatially conserved but not shared with the GCT family of CTP-dependent cytidyltransferases (Bork, P. et al., 1995; Park, Y. S. et al., 1997; Veitch, D. P. & Cornell, R. B., 1996; Veitch, D. P. et al., 1998). While there are similarities between the two sub-families including spatial correspondence of the putative catalytic residues H is 14/H is 17 of GCT with Lys 27/Lys 213 of CDP-ME synthase and Lys 21/Asp 209 of CMP-NeuAc synthetase, there is very little correspondence at the primary amino acid level.

Two catalytic mechanisms are likely in the cytidyltransferase family of enzymes. The first encompasses a dissociative pathway that results in the transient formation of a reactive metaphosphate intermediate at the α-phosphate position of CTP. Subsequent capture of the reactive metaphosphate intermediate by the 4-phosphate group of MEP would form CDP-ME. The second mechanism mirrors the associative pathway described for a number of GTPases and ATPases. This pathway forms a negatively charged pentacoordinate transition state upon nucleophilic attack on the α-phosphate of CTP by the 4-phosphate of MEP. Collapse of this charged state would lead to pyrophosphate release and CDP-ME formation. The large number of positive charges surrounding the active site cavity suggest that CDP-ME synthase is organized to stabilize the negatively charged pentacoordinate transition state characteristic of associative type mechanisms. The substrate and product bound structures that include $Mg^{2+}$ ions provide a useful model to assess the roles of specific residues in the catalytic mechanism of the larger cytidyltransferase family of enzymes which includes CDP-ME synthase and CMP-NeuAc synthetase.

The roles of both Lys 27 and Lys 213 have been examined by mutating Lys 27 to Ala and Ser, respectively, and Lys 213 has been mutated to Ser. Assays conducted on these mutants and compared to the wild type protein indicate that Lys 27 plays an essential role in catalysis. This observation supports the absolute conservation of this residue in the active sites of CDP-ME family members and Lys 27's postulated role in stabilization of the negatively charged pentacoordinate transition state. While the activity of the K213S mutant is severely compromised, it retains the ability to form the CDP-ME product albeit with significantly reduced efficiency.

Figure 9:
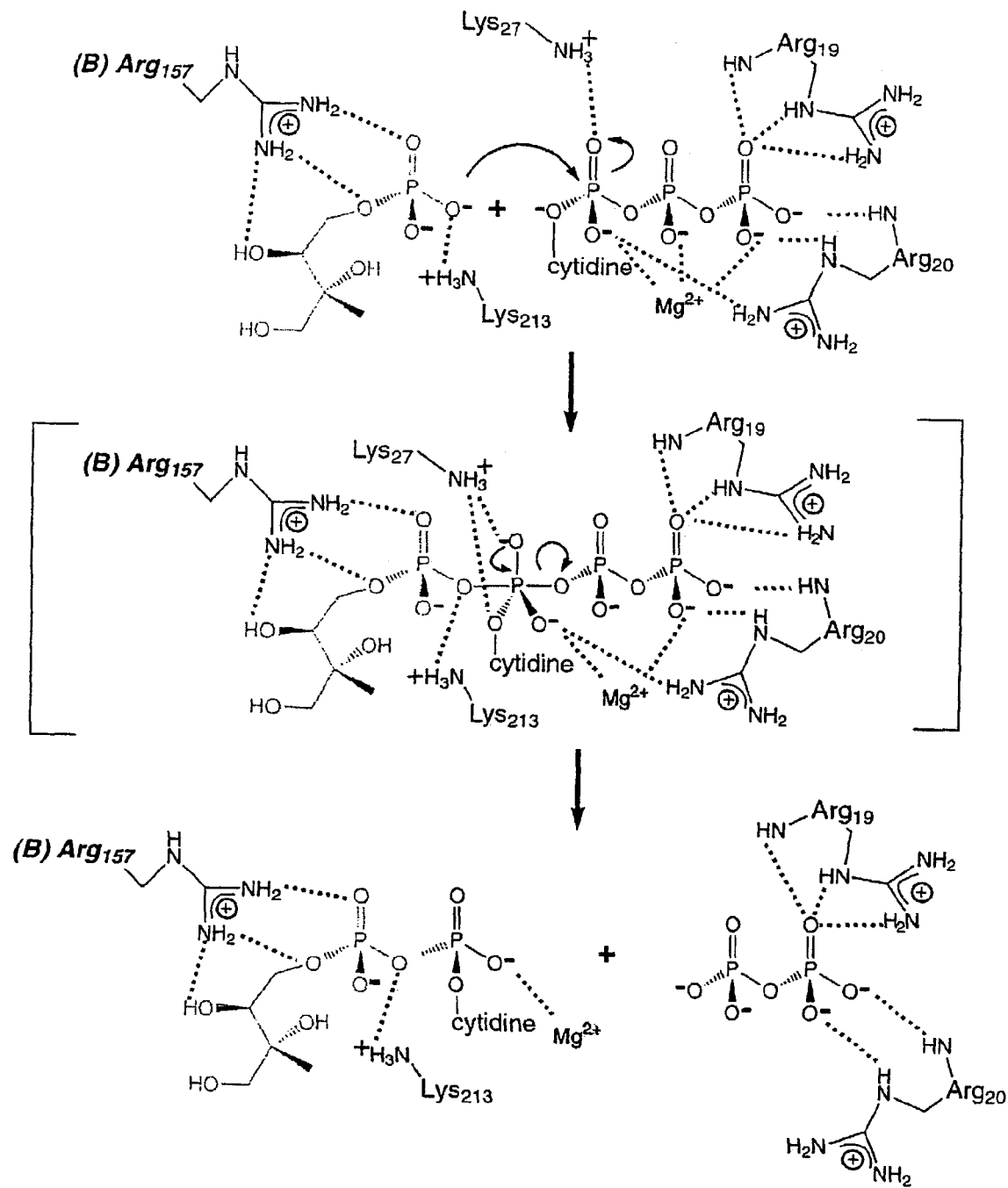
FIG. 9 illustrates a putative role of side chains in the catalytic mechanism of CDP-ME synthase. The curved black arrows represent hypothetical electron flow during both the nucleophilic attack on the CTP α-phosphate as well as the breakdown of the putative pentacoordinate transition state.
Figure 10:
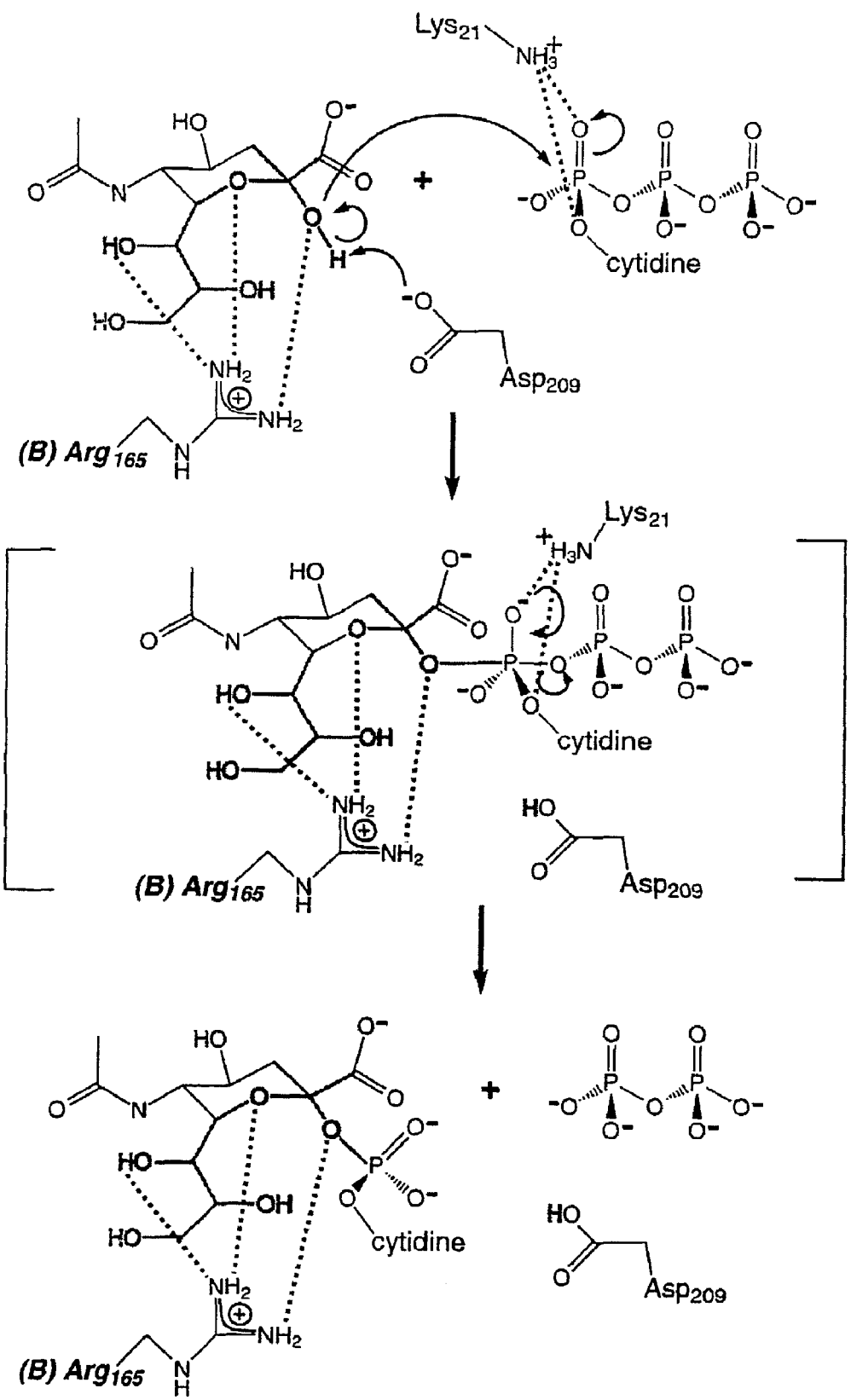
FIG. 10 provides a model for the same reaction pathway as shown in FIG. 9, in CMP-NeuAc synthetase based upon the chemical equivalence of portions of the MEP substrate of CDP-ME synthase and the acylneuraminate substrate of CMP-NeuAc synthetase. Notably, Asp 209, which is equivalent to Lys 213 in CDP-ME synthase, is ideally positioned to act as a general base next to the 2-OH group of acylneuraminate in CMP-NeuAc synthetase.

In addition to the utility of the substrate and product complexes in assessing the role of specific residues of CDP-ME synthase in substrate recognition and catalysis (FIGS. 8 and 9), comparison of these structures with the previously described structure of CMP-NeuAc synthetase (Mossimann, S. C. et al., 2000) lends further support to the role of specific residues in cytidyltransferase activity. Arg 20, Lys 27, Arg 157, and Lys 213 in CDP-ME synthase are spatially equivalent to Arg 12, Lys 21, Arg 165, and Asp 209, respectively, in CMP-NeuAc synthetase (FIGS. 9 and 10). Arg 20 (Arg 12 in CMP-NeuAc synthetase) interacts with the α and β-phosphates of CTP, positioning the α-phosphate for nucleophilic attack, and together with Lys 27 (Lys 21 in CMP-NeuAc synthetase) and $Mg^{2+}$, serve as complementary charges for the negatively charged pentacoordinate transition state during CMP transfer. Arg 157 (Arg 165 in CMP-NeuAc synthetase) positioned on the dyad-related subunits most likely position the attacking nucleophiles near the α-phosphates of the respective CTP substrates in CDP-ME synthase and CMP-NeuAc synthetase. Lys 213 (Asp 209 in CMP-NeuAc synthetase) may act as an electrostatic guide for the MEP phosphate prior to nucleophilic attack on CTP (FIGS. 8 and 9).

Notably, in CMP-NeuAc synthetase, Asp 209, which is spatially equivalent to Lys 213 in CDP-ME synthase, is ideally positioned to act as a general base during activation of the 2-OH of the acylneuraminate substrate in CMP-NeuAc synthetase (FIG. 10). The close resemblance between the MEP derived portions of CDP-ME and the acylneuraminate substrate of CMP-NeuAc synthetase provided a starting point for the modeling of the ground state complex of CMP-NeuAc synthetase (FIG. 10). This model, based upon the close chemical similarity of MEP and acylneuraminate, assigns distinct roles to Asp 209 than an earlier proposal where Asp 209 was thought to act as a $Mg^{2+}$ binding site while the identity of the general base responsible for proton abstraction from the 2-OH group of acylneuraminate was attributed to an ordered water molecule (Mossimann, S. C. et al., 2000). It is clear in all of the CDP-ME synthase structures determined to date that the $Mg^{2+}$ ion does not contact any side chain in the active site of CDP-ME synthase.

The invention will now be described in greater detail by reference to the following non-limiting examples.

EXAMPLE 1

Subcloning of the *E. coli* ygbP Gene Encoding CDP-ME Synthase and Mutations Thereof The *E. coli* ygbP gene (GenBank accession number AP002562) was cloned by PCR amplification of total genomic DNA isolated from *E. coli* K12 strain, NovaBlue using oligonucleotides designed for ligation into the *E. coli* expression vector pHIS8. The 5' and 3' ends of *E. coli* ygbP were taken from the deposited genome sequence of *E. coli*. The sense oligo, 5'-CC GTA TG<u>CCATGG</u>C ATG GCA ACC ACT CAT TTG GAT G-3', (Nco I site underlined and the translation start site in bold—Sequence I.D. No. 1) and antisense oligo, 5'-ATG CCG <u>GAATTC</u> TTA TGT ATT CTC CTG ATG GAT GG-3', (Bam-H I site underlined and the stop codon in bold—Sequence I.D. No. 2) amplified the coding sequence of ygbP (711 base pairs) which was efficiently ligated into the *E. coli* expression vector pHIS8. The 0.7 kb PCR product was digested with Nco I and BamH I, gel purified, and ligated with Nco I/BamH I digested pHIS8 to generate the expression vector. The pET-28a(+) expression vector and *E. coli* strain BL21(DE3) were purchased from Novagen. All oligonucleotides were ordered from Operon, Inc. NuSieve GTG agarose was obtained from FMC BioProducts. Restriction endonucleases, T4 DNA ligase, and dNTPs were from New England Biolabs. $Ni^{2+}$-NTA was bought from Qiagen. Benzamidine-Sepharose and the Superdex-200 FPLC column were from Pharmacia. Thrombin was purchased from Sigma. The CDP-ME synthase K27S, K27A and K213S mutants were generated with the QuickChange (Stratagene) PCR method.

EXAMPLE 2

Expression and Purification of *E. coli* CDP-ME Synthase

A set of three sense:

5'-dCATGAAACACCACCACCACCAC-3' (Sequence I.D. No. 3),

5'-dCACCACCACGGTGGTCTG-3' (Sequence I.D. No. 4),

5'-dGTTCCGCGTGGTTCCCATGGCG-3' (Sequence I.D. No. 5)

and three antisense:

5'-dGATCCGCCATGGGAACCACG-3' (Sequence I.D. No. 6),

5'-dCGGAACCAGACCACCGTG-3' (Sequence I.D. No. 7),

5'-dGTGCTGGTGGTGGTGGTGGTGTTT-3' (Sequence I.D. No. 8)

overlapping oligonucleotides were used to introduce an Nco I site after the thrombin cleavage site of pET-28a(+) and to extend the N-terminal hexahistidyl-coding sequence to eight histidines. The new sequence uses *E. coli* preferred codons and an AAA codon at the +2 site. The second and third sense and the second and third anti-sense strands were phosphorylated using T4 polynucleotide kinase, followed by incubation of all six oligonucleotides with T4 ligase. The 62 bp fragment was isolated from a 3% NuSieve GTG agarose gel. pET-28a(+) was cut with Nde I and BamH I and the resulting 5279 bp product gel purified. The synthetic 62 bp fragment was then ligated into the Nde I/BamH I digested pET-28a(+). Automated nucleotide sequencing (Salk Institute DNA sequencing facility) verified the sequence of the pHIS8 construct.

Constructs of pHIS8-ygbP were transformed into *E. coli* BL21(DE3). Transformed *E. coli* were grown at 37° C. in Terrific broth containing 50 μg/ml kanamycin until $A_{600nm}$=1.2. After induction with 0.5 mM isopropyl 1-thio-β-D-galactopyranoside, the cultures were grown at 20° C. for four hours. Cells were pelleted, harvested, and resuspended in 50 mM Tris —HCO (pH 8.0), 500 mM NaCl, 20 mM imidazole (pH 8.0), 20 mM β-mercaptoethanol, 10% (v/v) glycerol, and 1% (v/v) Tween-20. After sonication and centrifugation, the supernatant was passed over a $Ni^{2+}$-NTA column, the column washed with 10 bed volumes of lysis buffer, 10 bed volumes of lysis buffer minus Tween-20, then the His8-tagged protein was eluted with lysis buffer minus Tween-20 but containing 250 mM imidazole (pH 8.0). Incubation with thrombin during dialysis for 24 hours at 4° C. against the lysis buffer without Tween-20 removed the amino-terminal His8-tag. Dialyzed protein was re-loaded on a $Ni^{2+}$-NTA column and the flow-through depleted of thrombin using a benzamidine-Sepharose column. Gel filtration on a Superdex-200 FPLC column equilibrated with 25 mM HEPES (pH 7.5), 100 mM NaCl, and 5 mM dithiothreitol (DTT) was the final step. Fractions containing ygbP were pooled, concentrated to 35 mg/ml, and stored at −80° C. in 12.5 mM HEPES (pH 7.5), 50 mM NaCl, 10 mM $MgCl_2$, 1 mM CTP, and 2 mM DTT after buffer exchange. The CDP-ME synthase K27S, K27A and K213S mutants were similarly expressed and purified as His8-tagged proteins.

EXAMPLE 3

Synthesis of methyl-D-erythritol-4-phosphate (MEP)

MEP was prepared on a 2 mmol scale by a one-pot, coupled enzymatic synthesis using malate as source of pyruvate, fructose-1,6-diphosphate as the source of glyceraldehyde-3-phosphate, and a NADPH recycling system involving malic enzyme and deoxyxylulose-5-phosphate reductoisomerase (DXPR). The reaction mixture contained: fructose 1,6-diphosphate (10.0 mmol), malate (20.0 mmol), pyruvate (2 mmol), $NADP^+$ (1.24 mmol), $MgCl_2$ (0.5 mmol), Tris-Cl pH 7.5 (40 mmol), DTT (0.1 mmol), TPP (0.06 mmol), aldolase (570 units), isomerase (9700 units), malic enzyme (50 units), DXPS2 (deoxyxylulose phosphate synthase from *Streptomyces coelicolor* (Cane, D. E. et al., 2001) (50 units) and DXPR (≈50 units from *S. coelicolor* (Cane, D. E. et al., 2001)) in total volume of 100 ml. This solution was incubated for 3 days at 30° C.

The crude reaction mixture was mixed with activated charcoal (10 g) and stirred at room temperature for 10 min, then passed through a 0.45 μm filter to remove the charcoal. The charcoal was then washed with distilled water (50 ml) and the filtrates were combined. This solution (150 ml) was passed through a cation exchange column (DOWEX 50W-X8, 2.5×50 cm) in the $H^+$ form to remove the Tris buffer, which was the major contaminant identified by $^1$H-NMR analysis. The column was eluted until the pH of the eluent was neutral. The eluate was titrated to pH 7 with NaOH, as MEP is unstable at low pH, then concentrated to 20 ml by rotary evaporation under reduced pressure. An aliquot of the concentrated solution (5 ml) was loaded onto a cellulose column (2.5×50 cm) equilibrated with a acetonitrile:water: TFA mixture (90:10:1) and eluted with the same solvent. Fractions containing pure MEP were pooled and concentrated to 50 ml. The material was filtered and applied onto an anion exchange column (DOWEX 1×8-100, formate form, 2.5×16.5 cm) in 10 ml aliquots. The column washed with 150 ml water and eluted with 150 ml of a 1:1 mixture of ammonium formate (1 M) and formic acid. The MEP-containing fractions were combined and lyophilized to dryness. Analysis by $^1$H-NMR showed the yield of MEP to be 11.0 mmol (53% yield based on the fructose-1,6-diphosphate starting material), with a purity of >85%.

EXAMPLE 4

Synthesis of 4-diphosphocytidyl-2-C-methylerythritol (CDP-ME)

CDP-ME was prepared on a 0.1 mmol scale. The reaction mixture contained 104 μmol MEP, (purified as described above), CTP (104 μmol), MgCl$_2$ (16.8 μmol), Tris-HCl pH 7.8 (168 μmol), NaOH (120 μmol), 1.3 mg of *E. coli* CDP-ME synthase, and inorganic phosphatase (20 units) in a total volume of 1.68 ml. This solution was incubated for 3 hr at 37° C. Approximately 80% of the MEP was converted to CDP-ME as determined by TLC analysis (silica plates, n-propanol:ethyl acetate:water/35:10:5 eluant, anysaldehyde:sulphuric acid:ethanol/4:2:94 staining solution). The crude reaction mixture was deproteinized (500 NMWL filter, Millipore), lyophilized, and dissolved in 100 μL of an aqueous solution containing 40% methanol and 0.1 M ammonium formate. Aliquots of 10 μl were loaded onto an ion exchange analytical HPLC column (Nucleosil SB100-10 4.6×250 mm, Macherey Nagel) and eluted with the same solution (Herz, S. et al., 1999). The eluate was monitored by UV spectrophotometry at λ=260 nm. The peak detected at 35 min corresponded to CDP-ME. Upon repeated lyophilizations (to remove the formate), CDP-ME was obtained in 30% overall yield and >85% purity as determined by $^1$H NMR analysis.

EXAMPLE 5

Enzymatic Analysis of CDP-ME Synthase

Assay mixtures at 25° C. contained 30 μg/ml CDP-ME synthase, 600 μM CTP, 600 μM MEP, 5 mM MgCl$_2$ and 0.2 μCi/ml [α-$^{32}$P]CTP (400 Ci/mmol), in 0.1 M Tris-HCl pH 8.0, 2 mM DTT in a final volume of 25 μl. Reactions were initiated by adding CDP-ME synthase at a stock concentration of 2.25 mg/ml. After incubation for 2 hr, the samples were boiled for 5 min, and 5 μl aliquots were spotted on polyethyleneimine (PEI)-cellulose TLC plates previously activated by immersion in 10% (w/v) NaCl for 10 min, dried with cool air, then soaked in deionized water for 10 min and dried again. After application of the samples, the plates were dried with warm air, soaked for 10 min in 500 ml of methanol and dried. Before proceeding with ascending chromatography, the plates were pre-developed for 5 cm in methanol to prevent trailing of the nucleotides. Ascending chromatography was accomplished at 4° C. in rectangular glass tanks containing 100 ml of 0.8 M (NH$_4$)$_2$ SO$_4$ and plates developed to within 1 cm of the top. The plate was dried with hot, exposed for 8 hr with an imaging plate, and scanned with a Molecular Dynamics' PhosphorImager.

Thin layer chromatography assays were used to compare the enzymatic activity of CDP-ME synthase wild type to CDP-ME synthase mutants K27A, K27S, and K213S. Assays were standardized using controls with no enzyme added and either added CTP, or added CTP and MEP. CDP-ME synthase activity was determined using a concentration of 30-60 μg/ml; mutant CDP-ME synthases were added at a concentration of 30 μg/ml. The quantity of CDP-ME produced by the K27S, K213A, and K27A mutants were 1.5%, 25% and 1.5%, respectively, normalized to 100% for wild type CDP-ME synthase formed over 2 hr. The reaction with wild type protein is complete within 1-2 minutes.

EXAMPLE 6

Crystallization of CDP-ME Synthase

Crystals of CDP-ME synthase (800 μm×600 μm×200 μm) were obtained by the vapor diffusion method at 4° C. 2 μl hanging drops containing a 1:1 mixture of the protein solution and crystallization buffer (10% [w/v] PEG 8000, 0.2 M calcium acetate, 2 mM DTT, 0.1 M PIPES pH 6.5) produced well diffracting crystals that grew overnight. Crystallization of CDP-ME synthase was accomplished in the presence of up to 19% (v/v) ethylene glycol used both as a cryoprotectant and as an additive to improve crystal size and morphology. Crystals were stabilized in 15% (w/v) PEG 8000, 15% (v/v) ethylene glycol, 0.2 M calcium acetate, 0.1 M PIPES pH 6.5 (no DTT), and flash frozen in liquid nitrogen prior to data collection. CDP-ME synthase crystals belong to space group C2 with unit cell dimensions of a=130.6 Å, b=47.1 Å, c=38.1 Å, β=94°, with one monomer per asymmetric unit, and a solvent content of 42%. Complexes of CDP-ME synthase with CTP or CDP-ME were obtained as above by crystallization in the presence of 10 mM CTP/10 mM MgCl$_2$ and 10 mM CDP-ME/10 mM MgCl$_2$, respectively.

EXAMPLE 7

Crystallography Data Collection and Analysis

A data set was collected on beamline 9.2 (λ0.9848 Å) of the Stanford Synchrotron Radiation Laboratory (SSRL) equipped with an ADSC Quantum 4 CCD detector on a single crystal co-crystallized with 1 mM CTP, to a resolution of 1.24 Å. A MAD data set with minimal signal was collected on beamline 9-2 (selenium edge with $\lambda_1$=0.9797 Å, $\lambda_2$=0.9795 Å, $\lambda_3$=0.8952 Å) at SSRL on a single crystal grown from Se-met containing CDP-ME synthase (three potential methionines) co-crystallized with 1 mM CTP, to a resolution of 1.5 Å (Table 1). Finally, diffraction data were collected on beamline 7-1 (λ=1.08 Å) at SSRL on a single crystal co-crystallized with 10 mM CTP to a resolution of 1.5 Å, on a crystal co-crystallized with 10 mM MEP (referred to as the apo form) to a resolution of 1.55 Å, and on a crystal co-crystallized with 10 mM CDP-ME to a resolution of 1.8 Å, all on a 180/345 mm MAR imaging plate system detector (Table 2). Heavy atom derivatives were obtained by soaking native crystals for 12-16 hr in the cryopreservation solution in the presence of either 13 mM KAu(CN)$_4$ or a saturated solution of dimercurial acetate (DMA). MIR data sets were collected in-house at 100 K using a DIP 2030 imaging plate system (Mac Science Corporation, Japan) and Cuk$_α$ radiation produced by a rotating anode operated at 45 kV and 100 mA and equipped with double-focusing Pt/Ni coated mirrors (Table 1). All data were indexed and integrated using DENZO (Otwinowski, Z. & Minor, W., 1997) and scaled with the program SCALEPACK (French, G. S. & Wilson, K. S., 1978). Intensities were transformed into amplitudes using TRUN- CATE (CCP4, 1994). The heavy atom derivative data sets were scaled against the 1.24 Å resolution native data set with the program SCALEIT (CCP4, 1994).

All crystallographic calculations were performed using the CCP4 suite of programs (CCP4, 1994) unless stated otherwise. MAD experiments attempting to solve the structure of Se-met containing CDP-ME synthase yielded two potential Se sites and low quality experimental maps that did not permit chain tracing. However, the phases obtained from SHARP (La Fortelle, E. de & Bricogne, G., 1997) were sufficient to identify initial metal-binding sites for the Au and Hg. derivatives by difference Fourier analysis. These initial sites were verified by inspection of difference Patterson maps using XTALVIEW (McRee, D. E., 1992), and initially refined using MLPHARE (Otwinowski, Z., 1991). Final refinement of heavy atom parameters, identification of minor heavy atom binding sites, and phase-angle calculations were performed with the program SHARP (La Fortelle, E. de & Bricogne, G., 1997) using the 1.24 Å resolution native data set. Solvent flipping using the CCP4 program SOLOMON(CCP4, 1994) significantly improved and extended phases to 1.24 Å.

The initial atomic model was generated using wARP (Perrakis, A. et al., 1997). Subsequent model building was carried out with the program O (Jones, T. A. & Kjeldgaard, M. O., 1997), and refinement steps consisting of bulk-solvent correction, positional, torsion angle simulated annealing, and B-factor refinement were carried out with CNS (Brunger, A. T. et al., 1998). However, due to the low occupancy of the CTP binding site and the corresponding partial disorder surrounding this site further refinement using the 1.24 Å data set was halted. Subsequent building and refinement steps were carried out using data obtained from a crystal co-crystallized with 10 mM CTP and 10 mM $MgCl_2$. This data set yielded a well-ordered $CTP.Mg^{2+}$ binding site with full occupancy. This refined model served as the starting model for construction and refinement of the apo form and $CDP-ME.Mg^{2+}$ complex. PROCHECK (Laskowski, R. A. et al., 1993) analysis of all models shows 92% of the main chain torsion angles in the most favored regions, and no residues in the disallowed regions. The current apo model includes residues 5 to 228 with the loop spanning Ala 16 to Phe 26 absent due to disorder. The $CTP.Mg^{2+}$ complex includes residues 5 to 229. The $CDP-ME.Mg^{2+}$ complex includes residues 5 to 228 with the loop spanning Phe 17 to Glu 24 poorly defined in the density due to disorder. Figures were generated using MOLSCRIPT (Kraulis, P. J., 1991) and BOBSCRIPT (Esnouf, R., 1997) and rendered with POV-RAY (Amundsen, S., 1997). The electrostatic surface potential was generated using GRASP (Nicholls, A. & Honig, B. (1991).

While the invention has been described in detail with reference to certain preferred embodiments thereof, it will be understood that modifications and variations are within the spirit and scope of that which is described and claimed.

REFERENCES CITED

Altschul, S. F. et al. Gapped BLAST and PSI-BLAST: a new generation of protein database search programs. *Nucleic Acids Res.* 25, 3389-3402 (1997).

Amundsen, S. X-POV-Team POV-Ray: persistence of vision ray-tracer. Available on the World Wide Web at povray.org (1997).

Bartlett, P. A. et al, CAVEAT: A Program to Facilitate the Structure-Derived Design of Biologically Active Molecules. In Molecular Recognition in Chemical and Biological Problems, Special Pub., *Royal Chem. Soc.* 78, 182-196 (1989).

Berman, H. M., Westbrook, J., Feng, Z., Gilliland, G., Bhat, T. N., Weissig, H., Shindyalov, I. N. & Bourne, P. E. The Protein Data Bank. *Nucleic Acids Res.* 28, 235-242 (2000).

Bohm, H.-J. The Computer Program LUDI: A New Method for the De Novo Design of Enzyme Inhibitors. *J. Comp. Aid. Molec. Design* 6, 61-78 (1992).

Bork, P., Holm, L., Koonin, E. V. & Sander, C. The cytidylyltransferase superfamily: identification of the nucleotide-binding site and fold prediction. *Proteins* 22, 259-66 (1995).

Brunger, A. T. et al. Crystallography and NMR System (CNS): a new software system for macromolecular structure determination. *Acta Crystallog. sect. D* 54, 905-921 (1998).

Cane, D. E., Chow, C., Lillo, A. & Kang, I. *Bioorg. Med. Chem.* 2001 (in press)

Cohen, N. C. et al. Molecular Modeling Software and Methods for Medicinal Chemistry. *J. Med. Chem.* 33, 883-894 (1990).

Collaborative Computational Project Number 4. The CCP4 suite: programs for protein crystallography. *Acta Crystallog. D* 50, 760-763 (1994).

Connolly, J. D. & Hill, R. A. *Dictionary of Terpenoids*. Chapman & Hall., London (1991).

Edwards, P. A. & Ericsson, J. Sterols and isoprenoids: signaling molecules derived from the cholesterol biosynthetic pathway. *Annu. Rev. Biochem.* 68, 157-185 (1999).

Eisenreich, W., Schwarz, M., Cartayrade, A., Arigoni, D., Zenk, M. H. & Bacher, A. The deoxyxylulose phosphate pathway of terpenoid biosynthesis in plants and microorganisms. *Chem. Biol.* 5, 221-233 (1998).

Esnouf, R. An extensively modified version of Molscript that includes greatly enhanced coloring capabilities. *J. Mol. Graph.* 15, 133-138 (1997).

Fingl et al., in "The Pharmacological Basis of Therapeutics", Ch. 1 pl (1975).

French, G. S. & Wilson, K. S. On the treatment of negative intensity observations. *Acta Crystallog. A* 34, 517-525 (1978).

Goodford, P. J., A Computational Procedure for Determining Energetically Favorable Binding Sites on Biologically Important Macromolecules. *J. Med. Chem.* 28, 849-857 (1985).

Goodsell, D. S. and Olsen, A. J. "Automated Docking of Substrates to Proteins by Simulated Annealing", *Proteins: Structure. Function, and Genetics* 8, 195-202 (1990).

Harker, M. & Bramley, P.M. Expression of prokaryotic 1-deoxy-D-xylulose-5-phosphatases in *Escherichia coli* increases carotenoid and ubiquinone biosynthesis. *FEBS Lett.* 448, 115-119 (1999).

Herz S. et al. Biosynthesis of terpenoids: YgbB protein converts 4-diphosphocytidyl-2C-methyl-D-erythritol 2-phosphate to 2C-methyl-D-erythritol 2,4-cyclodiphosphate. *Proc. Nail. Acad. Sci. USA* 97, 2486-90 (2000).

Herz, S., Wungsintaweekul, J., Schuhr, A., Hecht, S. Luttgen, H., Sagner, S., Fellermeier, M., Eisenreich, W., Zenk, M. H., Bacher, A., & Rohdich, F. *Proc. Natl. Acad. Sci. USA* 97, 2486-2490 (1999).

Holm, L. & Sander, C. Protein structure comparison by alignment of distance matrices. *J. Mol. Biol.*, 233, 123-38 (1993).

Jelakovic, S., Jann, K. & Schulz G. E. (1996) The three-dimensional structure of capsule-specific CMP:2-keto-3- deoxy-manno-octonic acid synthetase from *Escherichia coli*. *FEBS Lett.*, 391, 157-161.

Jomaa, H. et al. Inhibitors of the nonmevalonate pathway of isoprenoid biosynthesis as antimalarial drugs. *Science* 285, 1573-1576 (1999).

Jones, T. A. & Kjeldgaard, M. O. Electron-density map interpretation. *Methods Enzymol.* 277, 173-208 (1997).

Koppisch, A. T., Blagg, B. S. & Poulter, C.D. Synthesis of 2-C-methyl-D-erythritol 4-phosphate: the first pathway-specific intermediate in the methylerythritol phosphate route to isoprenoids. *Org. Lett.* 2, 215-217 (2000).

Kraulis, P. J. MOLSCRIPT: a program to produce both detailed and schematic plots of structures. *J. Appl. Crystallog.* 24, 946-950 (1991).

Kuntz, I. D. et al. A Geometric Approach to Macromolecule-Ligand Interactions, *J. Mol. Biol.* 161, 269-288 (1982).

Kuzuyama, T. et al. Studies on the nonmevalonate pathway: conversion of 4-(cytidine 5'-diphospho)-2-C-methyl-erythritol to its 2-phospho derivative by 4-(cytidine 5'-diphospho)-2-C-methyl-erythritol kinase. *Tetrahedron Lett.* 41, 2925-2928 (2000).

Kuzuyama, T., Shimizu, T., Takahashi, S. & Seto, H. Fosmidomycin, a specific inhibitor of 1-deoxy-D-xylulose 5-phosphate reductoisomerase in the non-mevalonate pathway for terpenoid biosynthesis. *Tetrahedron Lett.* 39, 7913-7916 (1998).

Kuzuyama, T., Takagi, M., Kaneda, K., Dairi, T. & Seto, H. Formation of 4-(cytidine 5'-diphospho)-2-C-methyl-erythritol from 2-C-methyl-erythritol 4-phosphate by 2-C-methyl-erythritol 4-phosphate cytidylyltransferase, a new enzyme in the nonmevalonate pathway. *Tetrahedron Lett.* 41, 703-706 (2000).

Kuzuyama, T., Takagi, M., Takahashi, S. & Seto, H. Cloning and characterization of 1-deoxy-D-xylulose 5-phosphate synthase from *Streptomyces* sp. Strain CL190, which uses both the mevalonate and nonmevalonate pathways for isopentenyl diphosphate biosynthesis. *J. Bacteriol.* 182, 891-897 (2000).

Kuzuyama, T., Takahashi, S., Takagi, M. & Seto, H. Characterization of 1-deoxy-D-xylulose 5-phosphate reductoisomerase, an enzyme involved in isopentenyl diphosphate biosynthesis, and identification of its catalytic amino acid residues. *J. Biol. Chem.* 275, 19928-19932 (2000).

Kuzuyama, T., Takahashi, S., Watanabe, H. & Seto, H. Direct formation of 2-C-methyl-D-erythritol 4-phosphate from 1-deoxy-D-xylulose 5-phosphate by 1-deoxy-D-xylulose 5-phosphate reductoisomerase, a new enzyme in the non-mevalonate pathway to isopentenyl diphosphate. *Tetrahedron Lett.* 39, 4509-4512 (1998).

La Fortelle E. de & Bricogne G. Maximum-likelihood heavy-atom parameter refinement for multiple isomorphous replacement and multiwavelength anomalous diffraction methods. *Methods Enzylnol.* 276, 472-494 (1997).

Lange, B. M. & Croteau, R. Isoprenoid biosynthesis via a mevalonate-independent pathway in plants: cloning and heterologous expression of 1-deoxy-D-xylulose-5-phosphate reductoisomerase from peppermint. *Arch. Biochem. Biophys.* 365, 170-174 (1999).

Laskowski, R. A., MacArthur, M. W., Moss, D. S. & Thornton, J. M. PROCHECK: a program to check the stereochemical quality of protein structures. *J. Appl. Crystallog.* 26, 283-291 (1993).

Lichtenthaler, H. K., Zeidler, J., Schwender, J. & Muller, C. The non-mevalonate isoprenoid biosynthesis of plants as a test system for new herbicides and drugs against pathogenic bacteria and the malaria parasite. *Z. Naturforsch.* 55, 305-313 (2000).

Lois, L. M. et al. Cloning and characterization of a gene from Esclerichia coli encoding a transketolase-like enzyme that catalyzes the synthesis of D-1-deoxyxylulose 5-phosphate, a common precursor for isoprenoid, thiamin, and pyridoxol biosynthesis. *Proc. Natl. Acad. Sci. USA* 95, 2105-2110 (1997).

Lois, L. M., Rodriguez-Concepcion, M., Gallego, F., Campos, N. & Boronat, A. Carotenoid biosynthesis during tomato fruit development: regulatory role of 1-deoxy-D-xylulose 5-phosphate synthase. *Plant J.* 22, 503-513 (2000).

Luttgen, H. et al. Biosynthesis of terpenoids: YchB protein of *Escherichia coli* phosphorylates the 2-hydroxy group of 4-diphosphocytidyl-2C-methyl-D-erythritol. *Proc. Natl. Acad. Sci. USA* 97, 1062-1067 (2000).

Martin, Y. C. 3D Database Searching in Drug Design. *J. Med. Chem.* 35, 2145-2154 (1992).

McGarvey, D. J. & Croteau, R. Terpenoid metabolism. *Plant. Cell.* 7, 1015-1026 (1995).

McRee, D. E. A visual protein crystallographic software system for X11/Xview. *J. Mol. Graph.* 10, 4446 (1992).

Methods in Enzymology, vol. 114 and 115, H. W. Wyckoff et al., eds., Academic Press (1985).

Meng, E. C. et al., *J. Comp. Chem.* 13, 505-524 (1992).

Miranker, A. and Karplus, M. Functionality Maps of Binding Sites: A Multiple Copy Simultaneous Search Method. *Proteins: Structure. Function and Genetics* 11, 29-34 (1991).

Mossimann, S. C., Gilbert, M., Dombrowski, D., To, R., Wakarchuk W. & Strynadka N. C. J. Structure of a sialic acid activating synthetase, CMP acylneuraminate synthetase in the presence and absence of CDP. *J. Biol. Chem.* (PMID: 11113120, epub ahead of print) (2000).

Navia, M. A. and Murcko, M. A. The Use of Structural Information in Drug Design. *Current Opinions in Structural Biology* 2, 202-210 (1992).

Nicholls, A. & Honig, B. GRASP. *J. Comput. Chem.* 12, 435-445 (1991).

Nishibata, Y. and Itai, A. *Tetrahedron* 47, 8985 (1991).

Otwinowski, Z. & Minor, W. Processing of X-ray diffraction data collected in oscillation mode. *Methods Enzymol.* 276, 307-326 (1997).

Otwinowski, Z. Maximum likelihood refinement of heavy-atom parameters in isomorphous replacement and anomalous scattering. *Proceedings of CCP4 Study Weekend*, Warrington U K, 307-326 (1991).

Park, Y. S. et al. Identification of functional conserved residues of CTP:glycerol-3-phosphate cytidylyltransferase. Role of histidines in the conserved HXGH in catalysis. *Biol. Chem.* 272, 15161-15166 (1997).

Perrakis, A., Sixma, T. K., Wilson K. S. & Lamzin, V. S. wARP: improvement and extension of crystallographic phases by weighted averaging of multiple refined dummy atomic models. *Acta Crystallogr. D* 53, 448-455 (1997).

Ridley, R. G. Planting the seeds of new antimalarial drugs. *Science* 285, 1502-1503 (1999).

Rohdich, F. et al. Biosynthesis of terpenoids: 4-diphosphocytidyl-2-C-methyl-D-erythritol kinase from tomato. *Proc. Natl. Acad. Sci. USA,* 97(15), 8251-8256 (2000).

Rohdich, F. et al. Cytidine 5'-triphosphate-dependent biosynthesis of isoprenoids: YgbP protein of *Escherichia coli* catalyzes the formation of 4-diphosphocytidyl-2-C-methylerythritol. *Proc. Natl. Acad. Sci. USA* 96, 11758-11763 (1999).

Rohmer, M. Isoprenoid biosynthesis via the mevalonate-independent route, a novel target for antibacterial drugs? *Prog. Drug. Res.* 50, 135-154 (1998).

Rolmer, M. The discovery of a mevalonate-independent pathway for isoprenoid biosynthesis in bacteria, algae and higher plants. *Nat. Prod. Rep.* 16, 565-574 (1999).

Rohmer, M., Knani, M., Simonin, P., Sutter, B. & Sahm, H. Isoprenoid biosynthesis in bacteria: a novel pathway for the early steps leading to isopentenyl diphosphate. *Biochem. J.* 295, 517-524 (1993).

Rohmer, M., Seemann, M., Horbach, S., Bringer-Meyer, S. & Sahm, H. Glyceraldehyde 3-phosphate and pyruvate as precursors of isoprenic units in an alternative non-mevalonate pathway for terpenoid biosynthesis. *J. Am. Chem. Soc.* 118, 2564-2566 (1996).

Rossmann, M. G., Liljas, A., Branden, C.-I. & Banaszak, L. J. Evolutionnary and structural relationship among dehydrogenases, in *The Enzymes*. New York, Academic Press (1975).

Sacchettini, J. C., & Poulter, C.D. Creating isoprenoid diversity. *Science* 277(5333), 1788-1789 (1997).

Schwender, J., Muller, C., Zeidler, J. & Lichtenthaler, H. K. Cloning and heterologous expression of a cDNA encoding 1-deoxy-D-xylulose-5-phosphate reductoisomerase of *Arabidopsis thaliana*. *FEBS Lett.* 455, 140-144 (1999).

Schwender, J., Seemann, M., Lichtenthaler, H. K. & Rohmer, M. Biosynthesis of isoprenoids (carotenoids, sterols, prenyl side-chains of chlorophylls and plastoquinone) via a novel pyruvate/glyceraldehyde 3-phosphate non-mevalonate pathway in the green alga *Scenedesmus obliquus*. *Biochem. J.* 316, 73-80 (1996).

Sprenger G. A. et al. Identification of a thiamin-dependent synthase in *Escherichia coli* required for the formation of the 1-deoxy-D-xylulose 5-phosphate precursor to isoprenoids, thiamin, and pyridoxol. *Proc. Natl. Acad. Sci. USA* 94(24), 12857-12862 (1997).

Takagi, M. et al. Studies on the nonmevalonate pathway: formation of 2-C-methyl-D-erythritol 2,4-cyclodiphosphate from 2-phospho-4(cytidine 5'-diphospho)-2-C-methyl-D-erythritol. *Tetrahedron Lett.* 41, 3395-3398 (2000).

Takahashi, S., Kuzuyama, T., Watanabe, H. & Seto, H. A 1-deoxy-D-xylulose 5-phosphate reductoisomerase catalyzing the formation of 2-C-methyl-D-erythritol 4 phosphate in an alternative nonmevalonate pathway for terpenoid biosynthesis. *Proc. Natl. Acad. Sci. USA* 95, 9879-9884 (1998).

Veitch, D. P. & Cornell, R. B. Substitution of serine for glycine-91 in the HXGH motif of CTP:phosphocholine cytidylyltransferase implicates this motif in CTP binding. *Biochem.* 35, 10743-10750 (1996).

Veitch, D. P., Gilham, D. & Cornell, R. B. The role of histidine residues in the HXGH site of CTP:phosphocholine cytidylyltransferase in CTP binding and catalysis. *Eur. J. Biochem.* 225, 227-234 (1998).

Vial, H. J. Isoprenoid biosynthesis and drug targeting in the Apicomplexa. *Parasitol. Today* 16, 140-141 (2000).

Weber, C. H., Park, Y. S., Sanker, S., Kent, C. & Ludwig, M. L. A prototypical cytidylyltransferase: CTP:glycerol-3-phosphate cytidylyltransferase from *Bacillus subtilis*. *Structure Fold. Des.* 7, 1113-1124 (1999).

Westhead, D. R., Slidel, T. W., Flores, T. P. & Thornton, J.M. Protein structural topology: Automated analysis and diagrammatic representation. *Protein Sci.* 8, 897-904 (1999).

APPENDIX 1

X-RAY DATA COORDINATES FOR THE APO FORM OF CDP-ME SYNTHASE
(SEQ ID NOS: 9 and 10)

```
REMARK coordinates from minimization and B-factor refinement
REMARK refinement resolution: 90 – 1.50 A
REMARK starting r = .3521 free_r = .3557
REMARK final r = .2462 free_r = .2682
REMARK rmsd bonds = .005120 rmsd angles = 1.23322
REMARK B rmsd for bonded mainchain atoms = 1.636 target = 1.5
REMARK B rmsd for bonded sidechain atoms = 2.269 target = 2.0
REMARK B rmsd for angle mainchain atoms = 2.510 target = 2.0
REMARK B rmsd for angle sidechain atoms = 3.370 target = 2.5
REMARK target = mlf final wa = .542348
REMARK final rweight = .0659 (with wa = .542348)
REMARK md-method = torsion annealing schedule = constant
REMARK starting temperature = 2000 total md steps = 1 * 100
REMARK cycles = 2 coordinate steps 20 B-factor steps = 10
REMARK sg = C2 a = 130.297 b = 47.328 c = 38.146 alpha = 90 beta = 94.179 gamma = 90
REMARK topology file 1: CNS_TOPPAR: protein.top
REMARK topology file 2: CNS_TOPPAR: dna-rna.top
REMARK topology file 3: CNS_TOPPAR: water.top
REMARK topology file 4: CNS_TOPPAR: ion.top
REMARK topology file 5: CNSPAR: ctp.top
REMARK parameter file 1: CNS_TOPPAR: protein_rep.param
REMARK parameter file 2: CNS_TOPPAR: dna-rna_rep.param
REMARK parameter file 3: CNS_TOPPAR: water_rep.param
REMARK parameter file 4: CNS_TOPPAR: ion.param
REMARK parameter file 5: CNSPAR: ctp.param
REMARK molecular structure file: generate.mtf
REMARK input coordinates: rigid.pdb
REMARK reflection file = ssrljun.xpl
REMARK ncs = none
REMARK B-correction resolution: 6.0 – 1.50
REMARK initial B-factor correction applied to fobs:
REMARK B11 = 4.766 B22 = –4.733 B33 = –.033
REMARK B12 = .000 B13 = –.644 B23 = .000
REMARK B-factor correction applied to coordinate array B: –2.541
```

APPENDIX 1-continued

X-RAY DATA COORDINATES FOR THE APO FORM OF CDP-ME SYNTHASE
(SEQ ID NOS: 9 and 10)

REMARK bulk solvent: density level = .361117 e/A^3, B-factor = 41.4891 A^2
REMARK reflections with |Fobs|/sigma_F < 0.0 rejected
REMARK reflections with |Fobs| >10000 * rms(Fobs) rejected
REMARK theoretical total number of refl. in resol. range: 37283 (100.0%)
REMARK number of unobserved reflections (no entry or |F| = 0): 5238 (14.0%)
REMARK number of reflections rejected: 0 (.0%)
REMARK total number of reflections used: 32045 (86.0%)
REMARK number of reflections in working set: 30422 (81.6%)
REMARK number of reflections in test set: 1623 (4.4%)
CRYST1 130.297 47.328 38.146 90.00 94.18 90.00 C 2
REMARK FILENAME = "refine.pdb"
REMARK DATE: 24-Jun-00 18:09:09 created by user: richard
REMARK VERSION: 1.0

| ATOM | 1 | CB | HIS A | 5 | 29.232 | −18.834 | 9.984 | 1.00 | 40.47 | A |
|---|---|---|---|---|---|---|---|---|---|---|
| ATOM | 2 | CG | HIS A | 5 | 30.635 | −19.194 | 9.613 | 1.00 | 42.58 | A |
| ATOM | 3 | CD2 | HIS A | 5 | 31.438 | −18.753 | 8.613 | 1.00 | 42.79 | A |
| ATOM | 4 | ND1 | HIS A | 5 | 31.393 | −20.079 | 10.347 | 1.00 | 44.08 | A |
| ATOM | 5 | CE1 | HIS A | 5 | 32.602 | −20.168 | 9.821 | 1.00 | 43.60 | A |
| ATOM | 6 | NE2 | HIS A | 5 | 32.653 | −19.372 | 8.767 | 1.00 | 43.39 | A |
| ATOM | 7 | C | HIS A | 5 | 30.334 | −17.383 | 11.680 | 1.00 | 36.12 | A |
| ATOM | 8 | O | HIS A | 5 | 31.173 | −17.732 | 12.504 | 1.00 | 36.81 | A |
| ATOM | 9 | N | HIS A | 5 | 27.797 | −17.559 | 11.547 | 1.00 | 38.66 | A |
| ATOM | 10 | CA | HIS A | 5 | 29.106 | −18.255 | 11.398 | 1.00 | 37.92 | A |
| ATOM | 11 | N | LEU A | 6 | 30.431 | −16.255 | 10.984 | 1.00 | 33.83 | A |
| ATOM | 12 | CA | LEU A | 6 | 31.565 | −15.346 | 11.109 | 1.00 | 30.96 | A |
| ATOM | 13 | CB | LEU A | 6 | 31.508 | −14.303 | 9.982 | 1.00 | 32.34 | A |
| ATOM | 14 | CG | LEU A | 6 | 31.539 | −14.816 | 8.536 | 1.00 | 34.10 | A |
| ATOM | 15 | CD1 | LEU A | 6 | 31.367 | −13.648 | 7.575 | 1.00 | 33.98 | A |
| ATOM | 16 | CD2 | LEU A | 6 | 32.852 | −15.537 | 8.262 | 1.00 | 34.60 | A |
| ATOM | 17 | C | LEU A | 6 | 31.761 | −14.627 | 12.451 | 1.00 | 27.83 | A |
| ATOM | 18 | O | LEU A | 6 | 32.767 | −13.947 | 12.635 | 1.00 | 24.00 | A |
| ATOM | 19 | N | ASP A | 7 | 30.818 | −14.762 | 13.380 | 1.00 | 25.51 | A |
| ATOM | 20 | CA | ASP A | 7 | 30.936 | −14.101 | 14.682 | 1.00 | 24.34 | A |
| ATOM | 21 | CB | ASP A | 7 | 29.602 | −14.179 | 15.432 | 1.00 | 27.72 | A |
| ATOM | 22 | CG | ASP A | 7 | 28.579 | −13.180 | 14.915 | 1.00 | 30.36 | A |
| ATOM | 23 | OD1 | ASP A | 7 | 28.738 | −12.686 | 13.781 | 1.00 | 29.91 | A |
| ATOM | 24 | OD2 | ASP A | 7 | 27.612 | −12.895 | 15.646 | 1.00 | 33.40 | A |
| ATOM | 25 | C | ASP A | 7 | 32.045 | −14.727 | 15.535 | 1.00 | 20.74 | A |
| ATOM | 26 | O | ASP A | 7 | 32.094 | −15.946 | 15.707 | 1.00 | 23.22 | A |
| ATOM | 27 | N | VAL A | 8 | 32.924 | −13.890 | 16.080 | 1.00 | 16.44 | A |
| ATOM | 28 | CA | VAL A | 8 | 34.037 | −14.384 | 16.896 | 1.00 | 13.60 | A |
| ATOM | 29 | CB | VAL A | 8 | 35.396 | −14.105 | 16.203 | 1.00 | 13.39 | A |
| ATOM | 30 | CG1 | VAL A | 8 | 36.553 | −14.486 | 17.132 | 1.00 | 14.55 | A |
| ATOM | 31 | CG2 | VAL A | 8 | 35.486 | −14.876 | 14.903 | 1.00 | 12.40 | A |
| ATOM | 32 | C | VAL A | 8 | 34.092 | −13.707 | 18.250 | 1.00 | 13.03 | A |
| ATOM | 33 | O | VAL A | 8 | 33.872 | −12.500 | 18.342 | 1.00 | 13.92 | A |
| ATOM | 34 | N | CYS A | 9 | 34.385 | −14.483 | 19.296 | 1.00 | 11.76 | A |
| ATOM | 35 | CA | CYS A | 9 | 34.526 | −13.920 | 20.636 | 1.00 | 13.89 | A |
| ATOM | 36 | CB | CYS A | 9 | 33.658 | −14.654 | 21.661 | 1.00 | 13.63 | A |
| ATOM | 37 | SG | CYS A | 9 | 33.746 | −13.953 | 23.345 | 1.00 | 18.72 | A |
| ATOM | 38 | C | CYS A | 9 | 35.989 | −14.082 | 21.011 | 1.00 | 12.22 | A |
| ATOM | 39 | O | CYS A | 9 | 36.568 | −15.150 | 20.799 | 1.00 | 14.47 | A |
| ATOM | 40 | N | ALA A | 10 | 36.586 | −13.032 | 21.562 | 1.00 | 11.63 | A |
| ATOM | 41 | CA | ALA A | 10 | 37.992 | −13.091 | 21.955 | 1.00 | 9.91 | A |
| ATOM | 42 | CB | ALA A | 10 | 38.729 | −11.816 | 21.504 | 1.00 | 13.37 | A |
| ATOM | 43 | C | ALA A | 10 | 38.067 | −13.251 | 23.467 | 1.00 | 11.15 | A |
| ATOM | 44 | O | ALA A | 10 | 37.177 | −12.804 | 24.194 | 1.00 | 12.46 | A |
| ATOM | 45 | N | VAL A | 11 | 39.109 | −13.935 | 23.929 | 1.00 | 12.85 | A |
| ATOM | 46 | CA | VAL A | 11 | 39.328 | −14.151 | 25.350 | 1.00 | 12.20 | A |
| ATOM | 47 | CB | VAL A | 11 | 39.169 | −15.634 | 25.736 | 1.00 | 10.33 | A |
| ATOM | 48 | CG1 | VAL A | 11 | 39.583 | −15.848 | 27.196 | 1.00 | 13.90 | A |
| ATOM | 49 | CG2 | VAL A | 11 | 37.708 | −16.052 | 25.539 | 1.00 | 14.62 | A |
| ATOM | 50 | C | VAL A | 11 | 40.748 | −13.711 | 25.647 | 1.00 | 11.20 | A |
| ATOM | 51 | O | VAL A | 11 | 41.680 | −14.094 | 24.950 | 1.00 | 11.80 | A |
| ATOM | 52 | N | VAL A | 12 | 40.917 | −12.887 | 26.667 | 1.00 | 11.27 | A |
| ATOM | 53 | CA | VAL A | 12 | 42.241 | −12.424 | 27.018 | 1.00 | 12.65 | A |
| ATOM | 54 | CB | VAL A | 12 | 42.362 | −10.894 | 26.821 | 1.00 | 10.70 | A |
| ATOM | 55 | CG1 | VAL A | 12 | 43.724 | −10.415 | 27.298 | 1.00 | 12.07 | A |
| ATOM | 56 | CG2 | VAL A | 12 | 42.169 | −10.547 | 25.343 | 1.00 | 13.88 | A |
| ATOM | 57 | C | VAL A | 12 | 42.495 | −12.777 | 28.475 | 1.00 | 15.37 | A |
| ATOM | 58 | O | VAL A | 12 | 41.864 | −12.221 | 29.373 | 1.00 | 15.08 | A |
| ATOM | 59 | N | PRO A | 13 | 43.384 | −13.746 | 28.727 | 1.00 | 15.67 | A |
| ATOM | 60 | CD | PRO A | 13 | 44.010 | −14.701 | 27.797 | 1.00 | 16.20 | A |
| ATOM | 61 | CA | PRO A | 13 | 43.660 | −14.100 | 30.121 | 1.00 | 18.92 | A |
| ATOM | 62 | CB | PRO A | 13 | 44.298 | −15.484 | 30.005 | 1.00 | 19.01 | A |
| ATOM | 63 | CG | PRO A | 13 | 44.988 | −15.436 | 28.682 | 1.00 | 20.83 | A |

APPENDIX 1-continued

X-RAY DATA COORDINATES FOR THE APO FORM OF CDP-ME SYNTHASE
(SEQ ID NOS: 9 and 10)

| ATOM | 64 C | PRO A | 13 | 44.595 | −13.038 | 30.700 | 1.00 | 19.22 | A |
|---|---|---|---|---|---|---|---|---|---|
| ATOM | 65 O | PRO A | 13 | 45.765 | −12.967 | 30.331 | 1.00 | 24.43 | A |
| ATOM | 66 N | ALA A | 14 | 44.067 | −12.201 | 31.589 | 1.00 | 22.71 | A |
| ATOM | 67 CA | ALA A | 14 | 44.849 | −11.121 | 32.184 | 1.00 | 22.14 | A |
| ATOM | 68 CB | ALA A | 14 | 44.327 | −9.776 | 31.690 | 1.00 | 23.57 | A |
| ATOM | 69 C | ALA A | 14 | 44.819 | −11.170 | 33.704 | 1.00 | 24.27 | A |
| ATOM | 70 O | ALA A | 14 | 44.759 | −10.131 | 34.365 | 1.00 | 22.98 | A |
| ATOM | 71 N | ALA A | 15 | 44.862 | −12.386 | 34.243 | 1.00 | 25.27 | A |
| ATOM | 72 CA | ALA A | 15 | 44.832 | −12.611 | 35.685 | 1.00 | 28.94 | A |
| ATOM | 73 CB | ALA A | 15 | 43.717 | −13.592 | 36.026 | 1.00 | 28.54 | A |
| ATOM | 74 C | ALA A | 15 | 46.173 | −13.151 | 36.172 | 1.00 | 30.75 | A |
| ATOM | 75 O | ALA A | 15 | 46.237 | −14.229 | 36.768 | 1.00 | 34.10 | A |
| ATOM | 76 N | LYS A | 27 | 52.712 | −6.297 | 34.117 | 1.00 | 33.96 | A |
| ATOM | 77 CA | LYS A | 27 | 53.241 | −5.852 | 32.835 | 1.00 | 32.52 | A |
| ATOM | 78 CB | LYS A | 27 | 53.984 | −7.007 | 32.162 | 1.00 | 34.49 | A |
| ATOM | 79 CG | LYS A | 27 | 53.209 | −8.311 | 32.199 | 1.00 | 35.39 | A |
| ATOM | 80 CD | LYS A | 27 | 54.114 | −9.517 | 32.053 | 1.00 | 36.37 | A |
| ATOM | 81 CE | LYS A | 27 | 53.467 | −10.748 | 32.672 | 1.00 | 36.69 | A |
| ATOM | 82 NZ | LYS A | 27 | 54.372 | −11.935 | 32.698 | 1.00 | 37.00 | A |
| ATOM | 83 C | LYS A | 27 | 52.130 | −5.336 | 31.923 | 1.00 | 30.49 | A |
| ATOM | 84 O | LYS A | 27 | 52.309 | −4.360 | 31.196 | 1.00 | 28.46 | A |
| ATOM | 85 N | GLN A | 28 | 50.978 | −5.996 | 31.973 | 1.00 | 28.92 | A |
| ATOM | 86 CA | GLN A | 28 | 49.836 | −5.610 | 31.156 | 1.00 | 27.87 | A |
| ATOM | 87 CB | GLN A | 28 | 48.687 | −6.593 | 31.377 | 1.00 | 29.40 | A |
| ATOM | 88 CG | GLN A | 28 | 48.245 | −6.675 | 32.830 | 1.00 | 31.65 | A |
| ATOM | 89 CD | GLN A | 28 | 47.270 | −7.798 | 33.097 | 1.00 | 32.55 | A |
| ATOM | 90 OE1 | GLN A | 28 | 47.564 | −8.955 | 32.826 | 1.00 | 33.79 | A |
| ATOM | 91 NE2 | GLN A | 28 | 46.092 | −7.458 | 33.618 | 1.00 | 32.72 | A |
| ATOM | 92 C | GLN A | 28 | 49.364 | −4.202 | 31.493 | 1.00 | 26.39 | A |
| ATOM | 93 O | GLN A | 28 | 48.715 | −3.537 | 30.681 | 1.00 | 22.92 | A |
| ATOM | 94 N | TYR A | 29 | 49.685 | −3.735 | 32.694 | 1.00 | 26.86 | A |
| ATOM | 95 CA | TYR A | 29 | 49.258 | −2.404 | 33.097 | 1.00 | 26.87 | A |
| ATOM | 96 CB | TYR A | 29 | 48.768 | −2.437 | 34.548 | 1.00 | 27.42 | A |
| ATOM | 97 CG | TYR A | 29 | 47.439 | −3.152 | 34.685 | 1.00 | 27.42 | A |
| ATOM | 98 CD1 | TYR A | 29 | 47.291 | −4.242 | 35.537 | 1.00 | 27.12 | A |
| ATOM | 99 CE1 | TYR A | 29 | 46.077 | −4.921 | 35.632 | 1.00 | 27.04 | A |
| ATOM | 100 CD2 | TYR A | 29 | 46.333 | −2.751 | 33.933 | 1.00 | 27.62 | A |
| ATOM | 101 CE2 | TYR A | 29 | 45.116 | −3.421 | 34.020 | 1.00 | 25.89 | A |
| ATOM | 102 CZ | TYR A | 29 | 44.996 | −4.505 | 34.874 | 1.00 | 26.62 | A |
| ATOM | 103 OH | TYR A | 29 | 43.792 | −5.165 | 34.956 | 1.00 | 25.35 | A |
| ATOM | 104 C | TYR A | 29 | 50.294 | −1.311 | 32.887 | 1.00 | 28.28 | A |
| ATOM | 105 O | TYR A | 29 | 50.041 | −.147 | 33.198 | 1.00 | 29.12 | A |
| ATOM | 106 N | LEU A | 30 | 51.460 | −1.685 | 32.368 | 1.00 | 30.06 | A |
| ATOM | 107 CA | LEU A | 30 | 52.497 | −.704 | 32.065 | 1.00 | 31.18 | A |
| ATOM | 108 CB | LEU A | 30 | 53.805 | −1.398 | 31.674 | 1.00 | 32.65 | A |
| ATOM | 109 CG | LEU A | 30 | 54.590 | −2.085 | 32.796 | 1.00 | 33.29 | A |
| ATOM | 110 CD1 | LEU A | 30 | 55.792 | −2.817 | 32.215 | 1.00 | 34.40 | A |
| ATOM | 111 CD2 | LEU A | 30 | 55.035 | −1.041 | 33.805 | 1.00 | 34.54 | A |
| ATOM | 112 C | LEU A | 30 | 51.921 | .046 | 30.868 | 1.00 | 31.86 | A |
| ATOM | 113 O | LEU A | 30 | 51.067 | −.492 | 30.157 | 1.00 | 30.51 | A |
| ATOM | 114 N | SER A | 31 | 52.372 | 1.273 | 30.638 | 1.00 | 31.64 | A |
| ATOM | 115 CA | SER A | 31 | 51.836 | 2.040 | 29.527 | 1.00 | 32.60 | A |
| ATOM | 116 CB | SER A | 31 | 51.154 | 3.310 | 30.043 | 1.00 | 32.26 | A |
| ATOM | 117 OG | SER A | 31 | 49.994 | 2.992 | 30.787 | 1.00 | 33.99 | A |
| ATOM | 118 C | SER A | 31 | 52.822 | 2.408 | 28.431 | 1.00 | 33.15 | A |
| ATOM | 119 O | SER A | 31 | 54.030 | 2.505 | 28.654 | 1.00 | 32.44 | A |
| ATOM | 120 N | ILE A | 32 | 52.275 | 2.612 | 27.238 | 1.00 | 33.49 | A |
| ATOM | 121 CA | ILE A | 32 | 53.052 | 2.980 | 26.067 | 1.00 | 33.65 | A |
| ATOM | 122 CB | ILE A | 32 | 53.303 | 1.755 | 25.159 | 1.00 | 34.90 | A |
| ATOM | 123 CG2 | ILE A | 32 | 54.099 | 2.175 | 23.925 | 1.00 | 35.04 | A |
| ATOM | 124 CG1 | ILE A | 32 | 54.046 | .671 | 25.946 | 1.00 | 35.29 | A |
| ATOM | 125 CD1 | ILE A | 32 | 54.283 | −.605 | 25.165 | 1.00 | 36.39 | A |
| ATOM | 126 C | ILE A | 32 | 52.245 | 4.023 | 25.301 | 1.00 | 34.63 | A |
| ATOM | 127 O | ILE A | 32 | 51.408 | 3.684 | 24.467 | 1.00 | 33.63 | A |
| ATOM | 128 N | GLY A | 33 | 52.482 | 5.294 | 25.606 | 1.00 | 35.97 | A |
| ATOM | 129 CA | GLY A | 33 | 51.766 | 6.359 | 24.928 | 1.00 | 37.07 | A |
| ATOM | 130 C | GLY A | 33 | 50.423 | 6.724 | 25.532 | 1.00 | 38.65 | A |
| ATOM | 131 O | GLY A | 33 | 49.454 | 6.946 | 24.811 | 1.00 | 39.47 | A |
| ATOM | 132 N | ASN A | 34 | 50.370 | 6.789 | 26.857 | 1.00 | 38.53 | A |
| ATOM | 133 CA | ASN A | 34 | 49.149 | 7.145 | 27.578 | 1.00 | 39.06 | A |
| ATOM | 134 CB | ASN A | 34 | 48.610 | 8.495 | 27.069 | 1.00 | 39.04 | A |
| ATOM | 135 CG | ASN A | 34 | 47.283 | 8.369 | 26.335 | 1.00 | 39.17 | A |
| ATOM | 136 OD1 | ASN A | 34 | 47.227 | 7.890 | 25.201 | 1.00 | 40.92 | A |
| ATOM | 137 ND2 | ASN A | 34 | 46.203 | 8.800 | 26.987 | 1.00 | 39.47 | A |
| ATOM | 138 C | ASN A | 34 | 48.069 | 6.065 | 27.507 | 1.00 | 37.59 | A |
| ATOM | 139 O | ASN A | 34 | 46.950 | 6.259 | 27.976 | 1.00 | 38.69 | A |

APPENDIX 1-continued

X-RAY DATA COORDINATES FOR THE APO FORM OF CDP-ME SYNTHASE
(SEQ ID NOS: 9 and 10)

| ATOM | 140 N | GLN A | 35 | 48.414 | 4.925 | 26.920 | 1.00 | 36.07 | A |
|------|-------|-------|-----|--------|--------|--------|------|-------|---|
| ATOM | 141 CA | GLN A | 35 | 47.485 | 3.806 | 26.817 | 1.00 | 33.51 | A |
| ATOM | 142 CB | GLN A | 35 | 47.093 | 3.574 | 25.357 | 1.00 | 37.81 | A |
| ATOM | 143 CG | GLN A | 35 | 45.970 | 2.569 | 25.162 | 1.00 | 40.31 | A |
| ATOM | 144 CD | GLN A | 35 | 45.446 | 2.538 | 23.736 | 1.00 | 42.32 | A |
| ATOM | 145 OE1 | GLN A | 35 | 44.979 | 3.549 | 23.213 | 1.00 | 43.92 | A |
| ATOM | 146 NE2 | GLN A | 35 | 45.524 | 1.374 | 23.100 | 1.00 | 42.96 | A |
| ATOM | 147 C | GLN A | 35 | 48.201 | 2.582 | 27.384 | 1.00 | 29.12 | A |
| ATOM | 148 O | GLN A | 35 | 49.381 | 2.369 | 27.103 | 1.00 | 27.11 | A |
| ATOM | 149 N | THR A | 36 | 47.502 | 1.788 | 28.192 | 1.00 | 25.58 | A |
| ATOM | 150 CA | THR A | 36 | 48.113 | .607 | 28.794 | 1.00 | 21.98 | A |
| ATOM | 151 CB | THR A | 36 | 47.253 | .041 | 29.956 | 1.00 | 23.65 | A |
| ATOM | 152 OG1 | THR A | 36 | 46.058 | -.557 | 29.432 | 1.00 | 19.94 | A |
| ATOM | 153 CG2 | THR A | 36 | 46.877 | 1.153 | 30.937 | 1.00 | 23.71 | A |
| ATOM | 154 C | THR A | 36 | 48.316 | -.506 | 27.771 | 1.00 | 19.97 | A |
| ATOM | 155 O | THR A | 36 | 47.643 | -.541 | 26.740 | 1.00 | 18.41 | A |
| ATOM | 156 N | ILE A | 37 | 49.258 | -1.400 | 28.058 | 1.00 | 18.97 | A |
| ATOM | 157 CA | ILE A | 37 | 49.547 | -2.522 | 27.168 | 1.00 | 18.40 | A |
| ATOM | 158 CB | ILE A | 37 | 50.659 | -3.425 | 27.747 | 1.00 | 20.64 | A |
| ATOM | 159 CG2 | ILE A | 37 | 50.775 | -4.709 | 26.940 | 1.00 | 21.89 | A |
| ATOM | 160 CG1 | ILE A | 37 | 51.995 | -2.671 | 27.728 | 1.00 | 24.96 | A |
| ATOM | 161 CD1 | ILE A | 37 | 53.148 | -3.438 | 28.333 | 1.00 | 26.64 | A |
| ATOM | 162 C | ILE A | 37 | 48.277 | -3.342 | 26.946 | 1.00 | 17.58 | A |
| ATOM | 163 O | ILE A | 37 | 47.981 | -3.758 | 25.823 | 1.00 | 15.85 | A |
| ATOM | 164 N | LEU A | 38 | 47.515 | -3.555 | 28.011 | 1.00 | 16.79 | A |
| ATOM | 165 CA | LEU A | 38 | 46.269 | -4.305 | 27.902 | 1.00 | 15.19 | A |
| ATOM | 166 CB | LEU A | 38 | 45.563 | -4.380 | 29.263 | 1.00 | 16.96 | A |
| ATOM | 167 CG | LEU A | 38 | 44.184 | -5.061 | 29.283 | 1.00 | 18.73 | A |
| ATOM | 168 CD1 | LEU A | 38 | 44.269 | -6.480 | 28.730 | 1.00 | 17.43 | A |
| ATOM | 169 CD2 | LEU A | 38 | 43.660 | -5.082 | 30.708 | 1.00 | 20.08 | A |
| ATOM | 170 C | LEU A | 38 | 45.353 | -3.639 | 26.878 | 1.00 | 16.35 | A |
| ATOM | 171 O | LEU A | 38 | 44.763 | -4.317 | 26.040 | 1.00 | 15.22 | A |
| ATOM | 172 N | GLU A | 39 | 45.242 | -2.313 | 26.935 | 1.00 | 18.16 | A |
| ATOM | 173 CA | GLU A | 39 | 44.389 | -1.601 | 25.992 | 1.00 | 17.53 | A |
| ATOM | 174 CB | GLU A | 39 | 44.252 | -.128 | 26.396 | 1.00 | 19.59 | A |
| ATOM | 175 CG | GLU A | 39 | 43.479 | .047 | 27.690 | 1.00 | 22.26 | A |
| ATOM | 176 CD | GLU A | 39 | 43.546 | 1.454 | 28.231 | 1.00 | 24.79 | A |
| ATOM | 177 OE1 | GLU A | 39 | 42.673 | 2.277 | 27.885 | 1.00 | 27.84 | A |
| ATOM | 178 OE2 | GLU A | 39 | 44.490 | 1.721 | 28.991 | 1.00 | 22.15 | A |
| ATOM | 179 C | GLU A | 39 | 44.906 | -1.726 | 24.561 | 1.00 | 16.62 | A |
| ATOM | 180 O | GLU A | 39 | 44.123 | -1.936 | 23.642 | 1.00 | 16.23 | A |
| ATOM | 181 N | HIS A | 40 | 46.218 | -1.610 | 24.368 | 1.00 | 17.52 | A |
| ATOM | 182 CA | HIS A | 40 | 46.779 | -1.745 | 23.021 | 1.00 | 16.85 | A |
| ATOM | 183 CB | HIS A | 40 | 48.304 | -1.627 | 23.049 | 1.00 | 19.55 | A |
| ATOM | 184 CG | HIS A | 40 | 48.808 | -.225 | 23.194 | 1.00 | 18.43 | A |
| ATOM | 185 CD2 | HIS A | 40 | 49.420 | .397 | 24.227 | 1.00 | 20.94 | A |
| ATOM | 186 ND1 | HIS A | 40 | 48.713 | .709 | 22.184 | 1.00 | 22.67 | A |
| ATOM | 187 CE1 | HIS A | 40 | 49.247 | 1.847 | 22.591 | 1.00 | 20.57 | A |
| ATOM | 188 NE2 | HIS A | 40 | 49.684 | 1.686 | 23.826 | 1.00 | 19.25 | A |
| ATOM | 189 C | HIS A | 40 | 46.410 | -3.131 | 22.502 | 1.00 | 17.48 | A |
| ATOM | 190 O | HIS A | 40 | 46.026 | -3.314 | 21.348 | 1.00 | 17.24 | A |
| ATOM | 191 N | SER A | 41 | 46.553 | -4.107 | 23.386 | 1.00 | 15.78 | A |
| ATOM | 192 CA | SER A | 41 | 46.253 | -5.490 | 23.074 | 1.00 | 14.98 | A |
| ATOM | 193 CB | SER A | 41 | 46.587 | -6.345 | 24.285 | 1.00 | 17.90 | A |
| ATOM | 194 OG | SER A | 41 | 47.987 | -6.506 | 24.398 | 1.00 | 20.39 | A |
| ATOM | 195 C | SER A | 41 | 44.800 | -5.723 | 22.657 | 1.00 | 15.59 | A |
| ATOM | 196 O | SER A | 41 | 44.513 | -6.275 | 21.589 | 1.00 | 15.02 | A |
| ATOM | 197 N | VAL A | 42 | 43.886 | -5.289 | 23.512 | 1.00 | 15.11 | A |
| ATOM | 198 CA | VAL A | 42 | 42.460 | -5.453 | 23.280 | 1.00 | 15.70 | A |
| ATOM | 199 CB | VAL A | 42 | 41.673 | -5.037 | 24.541 | 1.00 | 15.99 | A |
| ATOM | 200 CG1 | VAL A | 42 | 40.173 | -5.005 | 24.254 | 1.00 | 16.82 | A |
| ATOM | 201 CG2 | VAL A | 42 | 41.980 | -6.015 | 25.669 | 1.00 | 18.02 | A |
| ATOM | 202 C | VAL A | 42 | 41.982 | -4.666 | 22.079 | 1.00 | 16.05 | A |
| ATOM | 203 O | VAL A | 42 | 41.160 | -5.148 | 21.298 | 1.00 | 13.89 | A |
| ATOM | 204 N | HIS A | 43 | 42.502 | -3.458 | 21.910 | 1.00 | 14.79 | A |
| ATOM | 205 CA | HIS A | 43 | 42.089 | -2.651 | 20.764 | 1.00 | 17.35 | A |
| ATOM | 206 CB | HIS A | 43 | 42.629 | -1.224 | 20.914 | 1.00 | 22.33 | A |
| ATOM | 207 CG | HIS A | 43 | 41.912 | -.425 | 21.963 | 1.00 | 27.03 | A |
| ATOM | 208 CD2 | HIS A | 43 | 42.378 | .316 | 22.997 | 1.00 | 29.13 | A |
| ATOM | 209 ND1 | HIS A | 43 | 40.537 | -.320 | 22.008 | 1.00 | 28.36 | A |
| ATOM | 210 CE1 | HIS A | 43 | 40.187 | .450 | 23.023 | 1.00 | 30.53 | A |
| ATOM | 211 NE2 | HIS A | 43 | 41.286 | .849 | 23.639 | 1.00 | 30.65 | A |
| ATOM | 212 C | HIS A | 43 | 42.506 | -3.287 | 19.434 | 1.00 | 15.29 | A |
| ATOM | 213 O | HIS A | 43 | 41.822 | -3.117 | 18.425 | 1.00 | 16.83 | A |
| ATOM | 214 N | ALA A | 44 | 43.608 | -4.036 | 19.429 | 1.00 | 13.99 | A |
| ATOM | 215 CA | ALA A | 44 | 44.034 | -4.697 | 18.196 | 1.00 | 13.80 | A |

APPENDIX 1-continued

X-RAY DATA COORDINATES FOR THE APO FORM OF CDP-ME SYNTHASE
(SEQ ID NOS: 9 and 10)

| ATOM | 216 | CB  | ALA | A | 44 | 45.407 | −5.338  | 18.378 | 1.00 | 14.31 | A |
|------|-----|-----|-----|---|----|--------|---------|--------|------|-------|---|
| ATOM | 217 | C   | ALA | A | 44 | 42.998 | −5.762  | 17.803 | 1.00 | 14.04 | A |
| ATOM | 218 | O   | ALA | A | 44 | 42.714 | −5.955  | 16.626 | 1.00 | 15.04 | A |
| ATOM | 219 | N   | LEU | A | 45 | 42.440 | −6.453  | 18.796 | 1.00 | 11.85 | A |
| ATOM | 220 | CA  | LEU | A | 45 | 41.441 | −7.476  | 18.542 | 1.00 | 12.91 | A |
| ATOM | 221 | CB  | LEU | A | 45 | 41.161 | −8.284  | 19.816 | 1.00 | 12.72 | A |
| ATOM | 222 | CG  | LEU | A | 45 | 42.365 | −8.955  | 20.479 | 1.00 | 11.52 | A |
| ATOM | 223 | CD1 | LEU | A | 45 | 41.944 | −9.631  | 21.773 | 1.00 | 15.00 | A |
| ATOM | 224 | CD2 | LEU | A | 45 | 42.963 | −9.952  | 19.518 | 1.00 | 13.77 | A |
| ATOM | 225 | C   | LEU | A | 45 | 40.142 | −6.846  | 18.049 | 1.00 | 14.25 | A |
| ATOM | 226 | O   | LEU | A | 45 | 39.557 | −7.298  | 17.070 | 1.00 | 12.38 | A |
| ATOM | 227 | N   | LEU | A | 46 | 39.700 | −5.788  | 18.722 | 1.00 | 14.49 | A |
| ATOM | 228 | CA  | LEU | A | 46 | 38.449 | −5.132  | 18.362 | 1.00 | 13.26 | A |
| ATOM | 229 | CB  | LEU | A | 46 | 38.044 | −4.135  | 19.458 | 1.00 | 14.66 | A |
| ATOM | 230 | CG  | LEU | A | 46 | 37.545 | −4.736  | 20.780 | 1.00 | 17.75 | A |
| ATOM | 231 | CD1 | LEU | A | 46 | 37.360 | −3.634  | 21.805 | 1.00 | 20.21 | A |
| ATOM | 232 | CD2 | LEU | A | 46 | 36.236 | −5.473  | 20.542 | 1.00 | 17.48 | A |
| ATOM | 233 | C   | LEU | A | 46 | 38.505 | −4.429  | 17.010 | 1.00 | 16.05 | A |
| ATOM | 234 | O   | LEU | A | 46 | 37.463 | −4.052  | 16.467 | 1.00 | 14.62 | A |
| ATOM | 235 | N   | ALA | A | 47 | 39.705 | −4.257  | 16.456 | 1.00 | 16.24 | A |
| ATOM | 236 | CA  | ALA | A | 47 | 39.834 | −3.600  | 15.156 | 1.00 | 16.68 | A |
| ATOM | 237 | CB  | ALA | A | 47 | 41.297 | −3.287  | 14.854 | 1.00 | 15.62 | A |
| ATOM | 238 | C   | ALA | A | 47 | 39.246 | −4.448  | 14.039 | 1.00 | 18.38 | A |
| ATOM | 239 | O   | ALA | A | 47 | 38.759 | −3.918  | 13.040 | 1.00 | 18.79 | A |
| ATOM | 240 | N   | HIS | A | 48 | 39.298 | −5.765  | 14.196 | 1.00 | 15.91 | A |
| ATOM | 241 | CA  | HIS | A | 48 | 38.743 | −6.638  | 13.167 | 1.00 | 16.07 | A |
| ATOM | 242 | CB  | HIS | A | 48 | 39.375 | −8.026  | 13.231 | 1.00 | 16.30 | A |
| ATOM | 243 | CG  | HIS | A | 48 | 39.142 | −8.841  | 11.998 | 1.00 | 19.16 | A |
| ATOM | 244 | CD2 | HIS | A | 48 | 39.985 | −9.209  | 11.003 | 1.00 | 22.54 | A |
| ATOM | 245 | ND1 | HIS | A | 48 | 37.905 | −9.345  | 11.656 | 1.00 | 16.89 | A |
| ATOM | 246 | CE1 | HIS | A | 48 | 37.995 | −9.990  | 10.506 | 1.00 | 21.46 | A |
| ATOM | 247 | NE2 | HIS | A | 48 | 39.247 | −9.922  | 10.089 | 1.00 | 23.03 | A |
| ATOM | 248 | C   | HIS | A | 48 | 37.227 | −6.739  | 13.343 | 1.00 | 16.16 | A |
| ATOM | 249 | O   | HIS | A | 48 | 36.739 | −7.027  | 14.437 | 1.00 | 14.25 | A |
| ATOM | 250 | N   | PRO | A | 49 | 36.464 | −6.504  | 12.264 | 1.00 | 17.59 | A |
| ATOM | 251 | CD  | PRO | A | 49 | 36.956 | −6.131  | 10.927 | 1.00 | 20.42 | A |
| ATOM | 252 | CA  | PRO | A | 49 | 34.999 | −6.552  | 12.276 | 1.00 | 18.90 | A |
| ATOM | 253 | CB  | PRO | A | 49 | 34.635 | −6.369  | 10.803 | 1.00 | 19.01 | A |
| ATOM | 254 | CG  | PRO | A | 49 | 35.716 | −5.516  | 10.297 | 1.00 | 21.90 | A |
| ATOM | 255 | C   | PRO | A | 49 | 34.371 | −7.815  | 12.849 | 1.00 | 16.68 | A |
| ATOM | 256 | O   | PRO | A | 49 | 33.301 | −7.753  | 13.454 | 1.00 | 17.25 | A |
| ATOM | 257 | N   | ARG | A | 50 | 35.020 | −8.960  | 12.649 | 1.00 | 13.28 | A |
| ATOM | 258 | CA  | ARG | A | 50 | 34.473 | −10.223 | 13.128 | 1.00 | 13.07 | A |
| ATOM | 259 | CB  | ARG | A | 50 | 35.205 | −11.401 | 12.486 | 1.00 | 14.41 | A |
| ATOM | 260 | CG  | ARG | A | 50 | 34.816 | −11.641 | 11.030 | 1.00 | 12.99 | A |
| ATOM | 261 | CD  | ARG | A | 50 | 35.516 | −12.872 | 10.463 | 1.00 | 14.15 | A |
| ATOM | 262 | NE  | ARG | A | 50 | 35.131 | −14.100 | 11.168 | 1.00 | 14.34 | A |
| ATOM | 263 | CZ  | ARG | A | 50 | 35.733 | −15.270 | 10.994 | 1.00 | 15.46 | A |
| ATOM | 264 | NH1 | ARG | A | 50 | 36.743 | −15.371 | 10.140 | 1.00 | 15.57 | A |
| ATOM | 265 | NH2 | ARG | A | 50 | 35.330 | −16.332 | 11.671 | 1.00 | 15.84 | A |
| ATOM | 266 | C   | ARG | A | 50 | 34.496 | −10.368 | 14.642 | 1.00 | 13.13 | A |
| ATOM | 267 | O   | ARG | A | 50 | 33.716 | −11.139 | 15.193 | 1.00 | 14.18 | A |
| ATOM | 268 | N   | VAL | A | 51 | 35.382 | −9.645  | 15.319 | 1.00 | 11.76 | A |
| ATOM | 269 | CA  | VAL | A | 51 | 35.439 | −9.741  | 16.774 | 1.00 | 11.60 | A |
| ATOM | 270 | CB  | VAL | A | 51 | 36.795 | −9.222  | 17.302 | 1.00 | 10.24 | A |
| ATOM | 271 | CG1 | VAL | A | 51 | 36.811 | −9.245  | 18.820 | 1.00 | 13.77 | A |
| ATOM | 272 | CG2 | VAL | A | 51 | 37.920 | −10.083 | 16.754 | 1.00 | 13.31 | A |
| ATOM | 273 | C   | VAL | A | 51 | 34.273 | −8.936  | 17.356 | 1.00 | 13.81 | A |
| ATOM | 274 | O   | VAL | A | 51 | 34.309 | −7.712  | 17.392 | 1.00 | 16.63 | A |
| ATOM | 275 | N   | LYS | A | 52 | 33.241 | −9.644  | 17.805 | 1.00 | 14.11 | A |
| ATOM | 276 | CA  | LYS | A | 52 | 32.030 | −9.022  | 18.351 | 1.00 | 14.27 | A |
| ATOM | 277 | CB  | LYS | A | 52 | 30.794 | −9.876  | 18.032 | 1.00 | 15.62 | A |
| ATOM | 278 | CG  | LYS | A | 52 | 30.689 | −10.374 | 16.588 | 1.00 | 14.74 | A |
| ATOM | 279 | CD  | LYS | A | 52 | 30.765 | −9.227  | 15.593 | 1.00 | 17.23 | A |
| ATOM | 280 | CE  | LYS | A | 52 | 30.481 | −9.680  | 14.169 | 1.00 | 17.95 | A |
| ATOM | 281 | NZ  | LYS | A | 52 | 30.622 | −8.531  | 13.231 | 1.00 | 17.92 | A |
| ATOM | 282 | C   | LYS | A | 52 | 32.093 | −8.866  | 19.860 | 1.00 | 14.99 | A |
| ATOM | 283 | O   | LYS | A | 52 | 31.310 | −8.127  | 20.465 | 1.00 | 16.43 | A |
| ATOM | 284 | N   | ARG | A | 53 | 33.015 | −9.586  | 20.474 | 1.00 | 13.53 | A |
| ATOM | 285 | CA  | ARG | A | 53 | 33.135 | −9.538  | 21.917 | 1.00 | 16.50 | A |
| ATOM | 286 | CB  | ARG | A | 53 | 32.102 | −10.472 | 22.538 | 1.00 | 19.39 | A |
| ATOM | 287 | CG  | ARG | A | 53 | 32.162 | −10.536 | 24.046 | 1.00 | 30.17 | A |
| ATOM | 288 | CD  | ARG | A | 53 | 31.320 | −11.684 | 24.543 | 1.00 | 35.75 | A |
| ATOM | 289 | NE  | ARG | A | 53 | 30.210 | −11.241 | 25.369 | 1.00 | 41.81 | A |
| ATOM | 290 | CZ  | ARG | A | 53 | 29.213 | −12.032 | 25.748 | 1.00 | 44.74 | A |
| ATOM | 291 | NH1 | ARG | A | 53 | 29.197 | −13.300 | 25.367 | 1.00 | 44.68 | A |

APPENDIX 1-continued

X-RAY DATA COORDINATES FOR THE APO FORM OF CDP-ME SYNTHASE
(SEQ ID NOS: 9 and 10)

| ATOM | 292 | NH2 | ARG A | 53 | 28.236 | −11.560 | 26.514 | 1.00 | 46.41 | A |
|---|---|---|---|---|---|---|---|---|---|---|
| ATOM | 293 | C | ARG A | 53 | 34.515 | −9.927 | 22.408 | 1.00 | 16.44 | A |
| ATOM | 294 | O | ARG A | 53 | 35.197 | −10.753 | 21.808 | 1.00 | 15.60 | A |
| ATOM | 295 | N | VAL A | 54 | 34.924 | −9.296 | 23.499 | 1.00 | 13.78 | A |
| ATOM | 296 | CA | VAL A | 54 | 36.201 | −9.605 | 24.120 | 1.00 | 11.86 | A |
| ATOM | 297 | CB | VAL A | 54 | 37.228 | −8.458 | 23.978 | 1.00 | 13.19 | A |
| ATOM | 298 | CG1 | VAL A | 54 | 38.543 | −8.843 | 24.669 | 1.00 | 15.00 | A |
| ATOM | 299 | CG2 | VAL A | 54 | 37.469 | −8.161 | 22.507 | 1.00 | 12.35 | A |
| ATOM | 300 | C | VAL A | 54 | 35.924 | −9.846 | 25.595 | 1.00 | 12.49 | A |
| ATOM | 301 | O | VAL A | 54 | 35.371 | −8.984 | 26.284 | 1.00 | 14.55 | A |
| ATOM | 302 | N | VAL A | 55 | 36.282 | −11.037 | 26.061 | 1.00 | 11.41 | A |
| ATOM | 303 | CA | VAL A | 55 | 36.113 | −11.403 | 27.464 | 1.00 | 13.16 | A |
| ATOM | 304 | CB | VAL A | 55 | 35.576 | −12.845 | 27.635 | 1.00 | 12.88 | A |
| ATOM | 305 | OG1 | VAL A | 55 | 35.428 | −13.154 | 29.122 | 1.00 | 14.18 | A |
| ATOM | 306 | CG2 | VAL A | 55 | 34.214 | −13.000 | 26.942 | 1.00 | 16.91 | A |
| ATOM | 307 | C | VAL A | 55 | 37.503 | −11.315 | 28.082 | 1.00 | 12.11 | A |
| ATOM | 308 | O | VAL A | 55 | 38.430 | −11.996 | 27.648 | 1.00 | 12.20 | A |
| ATOM | 309 | N | ILE A | 56 | 37.643 | −10.466 | 29.093 | 1.00 | 12.87 | A |
| ATOM | 310 | CA | ILE A | 56 | 38.922 | −10.286 | 29.761 | 1.00 | 10.55 | A |
| ATOM | 311 | CB | ILE A | 56 | 39.271 | −8.785 | 29.889 | 1.00 | 13.40 | A |
| ATOM | 312 | CG2 | ILE A | 56 | 40.625 | −8.612 | 30.554 | 1.00 | 14.69 | A |
| ATOM | 313 | CG1 | ILE A | 56 | 39.284 | −8.133 | 28.503 | 1.00 | 13.13 | A |
| ATOM | 314 | CD1 | ILE A | 56 | 39.575 | −6.654 | 28.529 | 1.00 | 16.74 | A |
| ATOM | 315 | C | ILE A | 56 | 38.817 | −10.908 | 31.143 | 1.00 | 13.77 | A |
| ATOM | 316 | O | ILE A | 56 | 37.924 | −10.561 | 31.909 | 1.00 | 17.04 | A |
| ATOM | 317 | N | ALA A | 57 | 39.706 | −11.849 | 31.439 | 1.00 | 13.75 | A |
| ATOM | 318 | CA | ALA A | 57 | 39.709 | −12.528 | 32.734 | 1.00 | 14.15 | A |
| ATOM | 319 | CB | ALA A | 57 | 40.064 | −13.993 | 32.553 | 1.00 | 15.75 | A |
| ATOM | 320 | C | ALA A | 57 | 40.746 | −11.841 | 33.608 | 1.00 | 15.77 | A |
| ATOM | 321 | O | ALA A | 57 | 41.922 | −11.788 | 33.257 | 1.00 | 16.85 | A |
| ATOM | 322 | N | ILE A | 58 | 40.311 | −11.299 | 34.738 | 1.00 | 17.31 | A |
| ATOM | 323 | CA | ILE A | 58 | 41.234 | −10.620 | 35.625 | 1.00 | 19.97 | A |
| ATOM | 324 | CB | ILE A | 58 | 40.852 | −9.144 | 35.813 | 1.00 | 21.83 | A |
| ATOM | 325 | CG2 | ILE A | 58 | 40.880 | −8.429 | 34.470 | 1.00 | 21.64 | A |
| ATOM | 326 | CG1 | ILE A | 58 | 39.471 | −9.040 | 36.452 | 1.00 | 23.30 | A |
| ATOM | 327 | CD1 | ILE A | 58 | 39.056 | −7.618 | 36.797 | 1.00 | 24.64 | A |
| ATOM | 328 | C | ILE A | 58 | 41.259 | −11.297 | 36.985 | 1.00 | 20.60 | A |
| ATOM | 329 | O | ILE A | 58 | 40.306 | −11.977 | 37.373 | 1.00 | 20.19 | A |
| ATOM | 330 | N | SER A | 59 | 42.351 | −11.109 | 37.711 | 1.00 | 22.78 | A |
| ATOM | 331 | CA | SER A | 59 | 42.466 | −11.711 | 39.029 | 1.00 | 25.59 | A |
| ATOM | 332 | CB | SER A | 59 | 43.909 | −11.590 | 39.529 | 1.00 | 27.11 | A |
| ATOM | 333 | CG | SER A | 59 | 44.007 | −11.991 | 40.886 | 1.00 | 30.40 | A |
| ATOM | 334 | C | SER A | 59 | 41.525 | −11.010 | 39.998 | 1.00 | 26.65 | A |
| ATOM | 335 | O | SER A | 59 | 41.275 | −9.815 | 39.872 | 1.00 | 26.71 | A |
| ATOM | 336 | N | PRO A | 60 | 40.958 | −11.755 | 40.956 | 1.00 | 26.74 | A |
| ATOM | 337 | CD | PRO A | 60 | 41.023 | −13.208 | 41.184 | 1.00 | 28.96 | A |
| ATOM | 338 | CA | PRO A | 60 | 40.060 | −11.106 | 41.913 | 1.00 | 29.64 | A |
| ATOM | 339 | CB | PRO A | 60 | 39.521 | −12.278 | 42.733 | 1.00 | 29.61 | A |
| ATOM | 340 | CG | PRO A | 60 | 40.615 | −13.307 | 42.633 | 1.00 | 30.49 | A |
| ATOM | 341 | C | PRO A | 60 | 40.912 | −10.141 | 42.733 | 1.00 | 29.86 | A |
| ATOM | 342 | O | PRO A | 60 | 42.033 | −10.471 | 43.113 | 1.00 | 30.44 | A |
| ATOM | 343 | N | GLY A | 61 | 40.398 | −8.946 | 42.987 | 1.00 | 31.62 | A |
| ATOM | 344 | CA | GLY A | 61 | 41.176 | −7.978 | 43.739 | 1.00 | 35.17 | A |
| ATOM | 345 | C | GLY A | 61 | 41.895 | −7.002 | 42.818 | 1.00 | 36.30 | A |
| ATOM | 346 | O | GLY A | 61 | 42.428 | −5.981 | 43.264 | 1.00 | 37.09 | A |
| ATOM | 347 | N | ASP A | 62 | 41.921 | −7.326 | 41.528 | 1.00 | 36.07 | A |
| ATOM | 348 | CA | ASP A | 62 | 42.547 | −6.473 | 40.525 | 1.00 | 36.11 | A |
| ATOM | 349 | CB | ASP A | 62 | 42.561 | −7.193 | 39.169 | 1.00 | 35.94 | A |
| ATOM | 350 | CG | ASP A | 62 | 43.081 | −6.319 | 38.043 | 1.00 | 36.92 | A |
| ATOM | 351 | OD1 | ASP A | 62 | 43.629 | −5.233 | 38.327 | 1.00 | 36.70 | A |
| ATOM | 352 | OD2 | ASP A | 62 | 42.952 | −6.725 | 36.869 | 1.00 | 36.51 | A |
| ATOM | 353 | C | ASP A | 62 | 41.709 | −5.200 | 40.448 | 1.00 | 36.34 | A |
| ATOM | 354 | O | ASP A | 62 | 40.633 | −5.195 | 39.853 | 1.00 | 35.76 | A |
| ATOM | 355 | N | SER A | 63 | 42.206 | −4.126 | 41.054 | 1.00 | 36.41 | A |
| ATOM | 356 | CA | SER A | 63 | 41.485 | −2.858 | 41.081 | 1.00 | 36.94 | A |
| ATOM | 357 | CB | SER A | 63 | 41.635 | −2.212 | 42.461 | 1.00 | 37.51 | A |
| ATOM | 358 | OG | SER A | 63 | 43.001 | −1.981 | 42.767 | 1.00 | 39.09 | A |
| ATOM | 359 | C | SER A | 63 | 41.900 | −1.848 | 40.012 | 1.00 | 36.43 | A |
| ATOM | 360 | O | SER A | 63 | 41.419 | −.715 | 40.012 | 1.00 | 37.48 | A |
| ATOM | 361 | N | ARG A | 64 | 42.781 | −2.252 | 39.104 | 1.00 | 35.61 | A |
| ATOM | 362 | CA | ARG A | 64 | 43.240 | −1.350 | 38.056 | 1.00 | 34.85 | A |
| ATOM | 363 | CB | ARG A | 64 | 44.667 | −1.713 | 37.641 | 1.00 | 35.80 | A |
| ATOM | 364 | CG | ARG A | 64 | 45.671 | −1.604 | 38.779 | 1.00 | 39.19 | A |
| ATOM | 365 | CD | ARG A | 64 | 47.080 | −1.983 | 38.350 | 1.00 | 40.53 | A |
| ATOM | 366 | NE | ARG A | 64 | 48.016 | −1.867 | 39.465 | 1.00 | 43.86 | A |
| ATOM | 367 | CZ | ARG A | 64 | 49.299 | −2.205 | 39.407 | 1.00 | 45.50 | A |

APPENDIX 1-continued

X-RAY DATA COORDINATES FOR THE APO FORM OF CDP-ME SYNTHASE
(SEQ ID NOS: 9 and 10)

| ATOM | 368 | NH1 | ARG A | 64 | 49.811 | −2.688 | 38.281 | 1.00 | 46.56 | A |
|------|-----|-----|-------|----|--------|--------|--------|------|-------|---|
| ATOM | 369 | NH2 | ARG A | 64 | 50.071 | −2.063 | 40.477 | 1.00 | 45.56 | A |
| ATOM | 370 | C | ARG A | 64 | 42.329 | −1.363 | 36.832 | 1.00 | 33.04 | A |
| ATOM | 371 | O | ARG A | 64 | 42.029 | −.316 | 36.261 | 1.00 | 32.70 | A |
| ATOM | 372 | N | PHE A | 65 | 41.886 | −2.552 | 36.438 | 1.00 | 32.15 | A |
| ATOM | 373 | CA | PHE A | 65 | 41.023 | −2.709 | 35.273 | 1.00 | 31.23 | A |
| ATOM | 374 | CB | PHE A | 65 | 40.545 | −4.157 | 35.169 | 1.00 | 29.22 | A |
| ATOM | 375 | CG | PHE A | 65 | 39.684 | −4.420 | 33.970 | 1.00 | 29.52 | A |
| ATOM | 376 | CD1 | PHE A | 65 | 40.256 | −4.607 | 32.716 | 1.00 | 28.67 | A |
| ATOM | 377 | CD2 | PHE A | 65 | 38.298 | −4.427 | 34.083 | 1.00 | 28.69 | A |
| ATOM | 378 | CE1 | PHE A | 65 | 39.460 | −4.806 | 31.593 | 1.00 | 29.30 | A |
| ATOM | 379 | CE2 | PHE A | 65 | 37.492 | −4.623 | 32.966 | 1.00 | 29.54 | A |
| ATOM | 380 | CZ | PHE A | 65 | 38.076 | −4.808 | 31.718 | 1.00 | 28.72 | A |
| ATOM | 381 | C | PHE A | 65 | 39.802 | −1.791 | 35.270 | 1.00 | 31.31 | A |
| ATOM | 382 | O | PHE A | 65 | 39.527 | −1.117 | 34.279 | 1.00 | 29.65 | A |
| ATOM | 383 | N | ALA A | 66 | 39.069 | −1.787 | 36.380 | 1.00 | 32.21 | A |
| ATOM | 384 | CA | ALA A | 66 | 37.859 | −.986 | 36.522 | 1.00 | 33.16 | A |
| ATOM | 385 | CB | ALA A | 66 | 37.280 | −1.173 | 37.918 | 1.00 | 32.79 | A |
| ATOM | 386 | C | ALA A | 66 | 38.077 | .493 | 36.248 | 1.00 | 34.02 | A |
| ATOM | 387 | O | ALA A | 66 | 37.134 | 1.214 | 35.920 | 1.00 | 33.96 | A |
| ATOM | 388 | N | GLN A | 67 | 39.317 | .948 | 36.381 | 1.00 | 34.36 | A |
| ATOM | 389 | CA | GLN A | 67 | 39.630 | 2.352 | 36.143 | 1.00 | 36.22 | A |
| ATOM | 390 | CB | GLN A | 67 | 40.719 | 2.817 | 37.113 | 1.00 | 38.52 | A |
| ATOM | 391 | CG | GLN A | 67 | 40.355 | 2.639 | 38.583 | 1.00 | 42.27 | A |
| ATOM | 392 | CD | GLN A | 67 | 39.039 | 3.306 | 38.958 | 1.00 | 44.93 | A |
| ATOM | 393 | OE1 | GLN A | 67 | 38.857 | 4.508 | 38.752 | 1.00 | 46.46 | A |
| ATOM | 394 | NE2 | GLN A | 67 | 38.109 | 2.524 | 39.504 | 1.00 | 46.05 | A |
| ATOM | 395 | C | GLN A | 67 | 40.057 | 2.618 | 34.698 | 1.00 | 36.36 | A |
| ATOM | 396 | O | GLN A | 67 | 40.520 | 3.714 | 34.374 | 1.00 | 36.17 | A |
| ATOM | 397 | N | LEU A | 68 | 39.903 | 1.612 | 33.837 | 1.00 | 36.05 | A |
| ATOM | 398 | CA | LEU A | 68 | 40.243 | 1.739 | 32.419 | 1.00 | 35.55 | A |
| ATOM | 399 | CB | LEU A | 68 | 40.969 | .481 | 31.917 | 1.00 | 34.55 | A |
| ATOM | 400 | CG | LEU A | 68 | 42.292 | .065 | 32.565 | 1.00 | 34.55 | A |
| ATOM | 401 | CD1 | LEU A | 68 | 42.789 | −1.223 | 31.920 | 1.00 | 33.68 | A |
| ATOM | 402 | CD2 | LEU A | 68 | 43.317 | 1.173 | 32.404 | 1.00 | 33.49 | A |
| ATOM | 403 | C | LEU A | 68 | 38.959 | 1.915 | 31.611 | 1.00 | 35.60 | A |
| ATOM | 404 | O | LEU A | 68 | 37.877 | 1.544 | 32.063 | 1.00 | 35.15 | A |
| ATOM | 405 | N | PRO A | 69 | 39.062 | 2.491 | 30.403 | 1.00 | 36.84 | A |
| ATOM | 406 | CD | PRO A | 69 | 40.232 | 3.190 | 29.845 | 1.00 | 36.87 | A |
| ATOM | 407 | CA | PRO A | 69 | 37.882 | 2.694 | 29.554 | 1.00 | 36.73 | A |
| ATOM | 408 | CB | PRO A | 69 | 38.439 | 3.491 | 28.376 | 1.00 | 37.94 | A |
| ATOM | 409 | CG | PRO A | 69 | 39.583 | 4.248 | 28.991 | 1.00 | 38.08 | A |
| ATOM | 410 | C | PRO A | 69 | 37.264 | 1.368 | 29.111 | 1.00 | 36.14 | A |
| ATOM | 411 | O | PRO A | 69 | 36.081 | 1.297 | 28.785 | 1.00 | 36.69 | A |
| ATOM | 412 | N | LEU A | 70 | 38.079 | .319 | 29.100 | 1.00 | 35.78 | A |
| ATOM | 413 | CA | LEU A | 70 | 37.620 | −1.006 | 28.696 | 1.00 | 35.23 | A |
| ATOM | 414 | CB | LEU A | 70 | 38.783 | −2.000 | 28.732 | 1.00 | 35.52 | A |
| ATOM | 415 | CG | LEU A | 70 | 40.045 | −1.634 | 27.952 | 1.00 | 34.99 | A |
| ATOM | 416 | CD1 | LEU A | 70 | 41.103 | −2.685 | 28.206 | 1.00 | 33.53 | A |
| ATOM | 417 | CD2 | LEU A | 70 | 39.735 | −1.526 | 26.469 | 1.00 | 34.62 | A |
| ATOM | 418 | C | LEU A | 70 | 36.513 | −1.515 | 29.614 | 1.00 | 34.82 | A |
| ATOM | 419 | O | LEU A | 70 | 35.705 | −2.352 | 29.220 | 1.00 | 33.40 | A |
| ATOM | 420 | N | ALA A | 71 | 36.485 | −1.001 | 30.840 | 1.00 | 33.96 | A |
| ATOM | 421 | CA | ALA A | 71 | 35.502 | −1.415 | 31.831 | 1.00 | 34.10 | A |
| ATOM | 422 | CB | ALA A | 71 | 35.847 | −.803 | 33.185 | 1.00 | 34.46 | A |
| ATOM | 423 | C | ALA A | 71 | 34.055 | −1.084 | 31.465 | 1.00 | 33.64 | A |
| ATOM | 424 | O | ALA A | 71 | 33.132 | −1.735 | 31.949 | 1.00 | 34.20 | A |
| ATOM | 425 | N | ASN A | 72 | 33.852 | −.075 | 30.623 | 1.00 | 32.18 | A |
| ATOM | 426 | CA | ASN A | 72 | 32.499 | .308 | 30.237 | 1.00 | 30.99 | A |
| ATOM | 427 | CB | ASN A | 72 | 32.217 | 1.749 | 30.675 | 1.00 | 35.07 | A |
| ATOM | 428 | CG | ASN A | 72 | 32.299 | 1.926 | 32.178 | 1.00 | 38.53 | A |
| ATOM | 429 | OD1 | ASN A | 72 | 33.383 | 2.100 | 32.736 | 1.00 | 41.67 | A |
| ATOM | 430 | ND2 | ASN A | 72 | 31.151 | 1.862 | 32.845 | 1.00 | 39.73 | A |
| ATOM | 431 | C | ASN A | 72 | 32.221 | .158 | 28.745 | 1.00 | 29.14 | A |
| ATOM | 432 | O | ASN A | 72 | 31.247 | .700 | 28.223 | 1.00 | 28.74 | A |
| ATOM | 433 | N | HIS A | 73 | 33.080 | −.588 | 28.064 | 1.00 | 24.55 | A |
| ATOM | 434 | CA | HIS A | 73 | 32.931 | −.819 | 26.633 | 1.00 | 19.09 | A |
| ATOM | 435 | CB | HIS A | 73 | 34.244 | −1.347 | 26.069 | 1.00 | 18.76 | A |
| ATOM | 436 | CG | HIS A | 73 | 34.309 | −1.341 | 24.574 | 1.00 | 18.54 | A |
| ATOM | 437 | CD2 | HIS A | 73 | 35.074 | −.623 | 23.716 | 1.00 | 18.98 | A |
| ATOM | 438 | ND1 | HIS A | 73 | 33.521 | −2.157 | 23.794 | 1.00 | 18.72 | A |
| ATOM | 439 | CE1 | HIS A | 73 | 33.796 | −1.944 | 22.517 | 1.00 | 18.17 | A |
| ATOM | 440 | NE2 | HIS A | 73 | 34.735 | −1.017 | 22.444 | 1.00 | 16.64 | A |
| ATOM | 441 | C | HIS A | 73 | 31.799 | −1.824 | 26.410 | 1.00 | 16.88 | A |
| ATOM | 442 | O | HIS A | 73 | 31.751 | −2.874 | 27.050 | 1.00 | 17.17 | A |
| ATOM | 443 | N | PRO A | 74 | 30.869 | −1.517 | 25.492 | 1.00 | 15.50 | A |

APPENDIX 1-continued

X-RAY DATA COORDINATES FOR THE APO FORM OF CDP-ME SYNTHASE
(SEQ ID NOS: 9 and 10)

| ATOM | 444 CD | PRO A | 74 | 30.798 | −.335 | 24.615 | 1.00 | 16.52 | A |
| --- | --- | --- | --- | --- | --- | --- | --- | --- | --- |
| ATOM | 445 CA | PRO A | 74 | 29.752 | −2.427 | 25.237 | 1.00 | 16.03 | A |
| ATOM | 446 CB | PRO A | 74 | 28.876 | −1.634 | 24.258 | 1.00 | 17.38 | A |
| ATOM | 447 CG | PRO A | 74 | 29.860 | −.802 | 23.515 | 1.00 | 16.74 | A |
| ATOM | 448 C | PRO A | 74 | 30.124 | −3.807 | 24.715 | 1.00 | 15.02 | A |
| ATOM | 449 O | PRO A | 74 | 29.352 | −4.753 | 24.872 | 1.00 | 17.79 | A |
| ATOM | 450 N | GLN A | 75 | 31.306 | −3.937 | 24.114 | 1.00 | 15.57 | A |
| ATOM | 451 CA | GLN A | 75 | 31.722 | −5.228 | 23.564 | 1.00 | 14.87 | A |
| ATOM | 452 CB | GLN A | 75 | 32.374 | −5.045 | 22.190 | 1.00 | 14.55 | A |
| ATOM | 453 CG | GLN A | 75 | 31.425 | −4.520 | 21.107 | 1.00 | 14.95 | A |
| ATOM | 454 CD | GLN A | 75 | 32.155 | −4.175 | 19.827 | 1.00 | 16.12 | A |
| ATOM | 455 OE1 | GLN A | 75 | 33.020 | −3.300 | 19.810 | 1.00 | 18.32 | A |
| ATOM | 456 NE2 | GLN A | 75 | 31.793 | −4.836 | 18.745 | 1.00 | 18.00 | A |
| ATOM | 457 C | GLN A | 75 | 32.686 | −5.964 | 24.472 | 1.00 | 16.57 | A |
| ATOM | 458 O | GLN A | 75 | 33.185 | −7.021 | 24.100 | 1.00 | 18.71 | A |
| ATOM | 459 N | ILE A | 76 | 32.939 | −5.418 | 25.659 | 1.00 | 17.02 | A |
| ATOM | 460 CA | ILE A | 76 | 33.868 | −6.043 | 26.590 | 1.00 | 19.52 | A |
| ATOM | 461 CB | ILE A | 76 | 34.989 | −5.054 | 26.983 | 1.00 | 19.64 | A |
| ATOM | 462 CG2 | ILE A | 76 | 35.946 | −5.709 | 27.971 | 1.00 | 19.62 | A |
| ATOM | 463 CG1 | ILE A | 76 | 35.729 | −4.595 | 25.716 | 1.00 | 20.83 | A |
| ATOM | 464 CD1 | ILE A | 76 | 36.846 | −3.598 | 25.971 | 1.00 | 22.79 | A |
| ATOM | 465 C | ILE A | 76 | 33.173 | −6.546 | 27.844 | 1.00 | 19.71 | A |
| ATOM | 466 O | ILE A | 76 | 32.400 | −5.823 | 28.477 | 1.00 | 19.91 | A |
| ATOM | 467 N | THR A | 77 | 33.450 | −7.799 | 28.185 | 1.00 | 19.66 | A |
| ATOM | 468 CA | THR A | 77 | 32.885 | −8.430 | 29.370 | 1.00 | 19.52 | A |
| ATOM | 469 CB | THR A | 77 | 32.070 | −9.692 | 28.995 | 1.00 | 23.46 | A |
| ATOM | 470 OG1 | THR A | 77 | 30.985 | −9.325 | 28.131 | 1.00 | 23.56 | A |
| ATOM | 471 CG2 | THR A | 77 | 31.514 | −10.362 | 30.248 | 1.00 | 23.02 | A |
| ATOM | 472 C | THR A | 77 | 34.051 | −8.832 | 30.270 | 1.00 | 20.50 | A |
| ATOM | 473 O | THR A | 77 | 35.046 | −9.367 | 29.796 | 1.00 | 16.50 | A |
| ATOM | 474 N | VAL A | 78 | 33.943 | −8.555 | 31.564 | 1.00 | 19.73 | A |
| ATOM | 475 CA | VAL A | 78 | 35.013 | −8.914 | 32.479 | 1.00 | 22.76 | A |
| ATOM | 476 CB | VAL A | 78 | 35.449 | −7.696 | 33.335 | 1.00 | 24.42 | A |
| ATOM | 477 CG1 | VAL A | 78 | 34.281 | −7.221 | 34.188 | 1.00 | 25.84 | A |
| ATOM | 478 CG2 | VAL A | 78 | 36.627 | −8.068 | 34.205 | 1.00 | 25.51 | A |
| ATOM | 479 C | VAL A | 78 | 34.572 | −10.053 | 33.390 | 1.00 | 21.99 | A |
| ATOM | 480 O | VAL A | 78 | 33.422 | −10.092 | 33.836 | 1.00 | 22.76 | A |
| ATOM | 481 N | VAL A | 79 | 35.484 | −10.990 | 33.639 | 1.00 | 22.09 | A |
| ATOM | 482 CA | VAL A | 79 | 35.204 | −12.135 | 34.502 | 1.00 | 22.55 | A |
| ATOM | 483 CB | VAL A | 79 | 34.860 | −13.407 | 33.672 | 1.00 | 23.54 | A |
| ATOM | 484 CG1 | VAL A | 79 | 33.746 | −13.103 | 32.679 | 1.00 | 24.21 | A |
| ATOM | 485 CG2 | VAL A | 79 | 36.096 | −13.922 | 32.945 | 1.00 | 23.72 | A |
| ATOM | 486 C | VAL A | 79 | 36.431 | −12.420 | 35.362 | 1.00 | 22.28 | A |
| ATOM | 487 O | VAL A | 79 | 37.540 | −11.995 | 35.031 | 1.00 | 18.82 | A |
| ATOM | 488 N | ASP A | 80 | 36.237 | −13.120 | 36.476 | 1.00 | 24.78 | A |
| ATOM | 489 CA | ASP A | 80 | 37.363 | −13.452 | 37.345 | 1.00 | 26.08 | A |
| ATOM | 490 CB | ASP A | 80 | 36.887 | −13.843 | 38.749 | 1.00 | 28.75 | A |
| ATOM | 491 CG | ASP A | 80 | 36.275 | −12.681 | 39.507 | 1.00 | 32.43 | A |
| ATOM | 492 OD1 | ASP A | 80 | 36.794 | −11.545 | 39.392 | 1.00 | 32.71 | A |
| ATOM | 493 OD2 | ASP A | 80 | 35.286 | −12.907 | 40.240 | 1.00 | 34.64 | A |
| ATOM | 494 C | ASP A | 80 | 38.149 | −14.611 | 36.747 | 1.00 | 24.74 | A |
| ATOM | 495 O | ASP A | 80 | 37.572 | −15.632 | 36.368 | 1.00 | 23.08 | A |
| ATOM | 496 N | GLY A | 81 | 39.464 | −14.442 | 36.668 | 1.00 | 26.37 | A |
| ATOM | 497 CA | GLY A | 81 | 40.320 | −15.478 | 36.126 | 1.00 | 29.20 | A |
| ATOM | 498 C | GLY A | 81 | 40.706 | −16.488 | 37.190 | 1.00 | 32.90 | A |
| ATOM | 499 O | GLY A | 81 | 40.111 | −16.510 | 38.267 | 1.00 | 32.69 | A |
| ATOM | 500 N | GLY A | 82 | 41.707 | −17.314 | 36.900 | 1.00 | 34.71 | A |
| ATOM | 501 CA | GLY A | 82 | 42.132 | −18.318 | 37.858 | 1.00 | 37.44 | A |
| ATOM | 502 C | GLY A | 82 | 43.603 | −18.273 | 38.213 | 1.00 | 38.81 | A |
| ATOM | 503 O | GLY A | 82 | 44.282 | −17.271 | 37.991 | 1.00 | 38.78 | A |
| ATOM | 504 N | ASP A | 83 | 44.095 | −19.377 | 38.770 | 1.00 | 41.09 | A |
| ATOM | 505 CA | ASP A | 83 | 45.495 | −19.485 | 39.182 | 1.00 | 41.46 | A |
| ATOM | 506 CB | ASP A | 83 | 45.643 | −20.595 | 40.229 | 1.00 | 44.43 | A |
| ATOM | 507 CG | ASP A | 83 | 44.495 | −20.612 | 41.220 | 1.00 | 46.67 | A |
| ATOM | 508 OD1 | ASP A | 83 | 44.130 | −19.527 | 41.731 | 1.00 | 47.68 | A |
| ATOM | 509 OD2 | ASP A | 83 | 43.965 | −21.708 | 41.498 | 1.00 | 47.42 | A |
| ATOM | 510 C | ASP A | 83 | 46.419 | −19.771 | 38.001 | 1.00 | 40.47 | A |
| ATOM | 511 O | ASP A | 83 | 47.537 | −19.257 | 37.935 | 1.00 | 40.46 | A |
| ATOM | 512 N | GLU A | 84 | 45.941 | −20.599 | 37.076 | 1.00 | 39.89 | A |
| ATOM | 513 CA | GLU A | 84 | 46.710 | −20.979 | 35.894 | 1.00 | 37.95 | A |
| ATOM | 514 CB | GLU A | 84 | 46.679 | −22.504 | 35.725 | 1.00 | 40.74 | A |
| ATOM | 515 CG | GLU A | 84 | 47.079 | −23.291 | 36.972 | 1.00 | 44.79 | A |
| ATOM | 516 CD | GLU A | 84 | 48.532 | −23.100 | 37.361 | 1.00 | 46.56 | A |
| ATOM | 517 OE1 | GLU A | 84 | 48.941 | −21.948 | 37.613 | 1.00 | 48.27 | A |
| ATOM | 518 OE2 | GLU A | 84 | 49.275 | −24.107 | 37.393 | 1.00 | 48.94 | A |
| ATOM | 519 C | GLU A | 84 | 46.124 | −20.314 | 34.647 | 1.00 | 35.78 | A |

APPENDIX 1-continued

X-RAY DATA COORDINATES FOR THE APO FORM OF CDP-ME SYNTHASE
(SEQ ID NOS: 9 and 10)

| ATOM | 520 O | GLU A | 84 | 44.976 | −19.861 | 34.656 | 1.00 | 34.26 | A |
|---|---|---|---|---|---|---|---|---|---|
| ATOM | 521 N | ARG A | 85 | 46.906 | −20.271 | 33.572 | 1.00 | 33.23 | A |
| ATOM | 522 CA | ARG A | 85 | 46.445 | −19.658 | 32.330 | 1.00 | 32.01 | A |
| ATOM | 523 CB | ARG A | 85 | 47.542 | −19.702 | 31.260 | 1.00 | 31.90 | A |
| ATOM | 524 CG | ARG A | 85 | 47.170 | −18.952 | 29.984 | 1.00 | 32.74 | A |
| ATOM | 525 CD | ARG A | 85 | 48.125 | −19.250 | 28.839 | 1.00 | 34.27 | A |
| ATOM | 526 NE | ARG A | 85 | 47.629 | −18.689 | 27.583 | 1.00 | 33.13 | A |
| ATOM | 527 CZ | ARG A | 85 | 47.706 | −17.403 | 27.252 | 1.00 | 35.58 | A |
| ATOM | 528 NH1 | ARG A | 85 | 48.268 | −16.534 | 28.080 | 1.00 | 34.76 | A |
| ATOM | 529 NH2 | ARG A | 85 | 47.208 | −16.983 | 26.098 | 1.00 | 34.83 | A |
| ATOM | 530 C | ARG A | 85 | 45.198 | −20.363 | 31.805 | 1.00 | 31.18 | A |
| ATOM | 531 O | ARG A | 85 | 44.194 | −19.720 | 31.498 | 1.00 | 28.04 | A |
| ATOM | 532 N | ALA A | 86 | 45.265 | −21.689 | 31.716 | 1.00 | 29.25 | A |
| ATOM | 533 CA | ALA A | 86 | 44.142 | −22.481 | 31.222 | 1.00 | 28.41 | A |
| ATOM | 534 CB | ALA A | 86 | 44.484 | −23.965 | 31.271 | 1.00 | 28.98 | A |
| ATOM | 535 C | ALA A | 86 | 42.891 | −22.203 | 32.048 | 1.00 | 27.56 | A |
| ATOM | 536 O | ALA A | 86 | 41.775 | −22.221 | 31.529 | 1.00 | 24.46 | A |
| ATOM | 537 N | ASP A | 87 | 43.091 | −21.959 | 33.339 | 1.00 | 27.52 | A |
| ATOM | 538 CA | ASP A | 87 | 41.993 | −21.663 | 34.235 | 1.00 | 28.00 | A |
| ATOM | 539 CB | ASP A | 87 | 42.507 | −21.521 | 35.667 | 1.00 | 32.81 | A |
| ATOM | 540 CG | ASP A | 87 | 42.645 | −22.852 | 36.381 | 1.00 | 36.33 | A |
| ATOM | 541 OD1 | ASP A | 87 | 43.153 | −22.856 | 37.524 | 1.00 | 38.82 | A |
| ATOM | 542 OD2 | ASP A | 87 | 42.245 | −23.885 | 35.813 | 1.00 | 37.71 | A |
| ATOM | 543 C | ASP A | 87 | 41.284 | −20.378 | 33.817 | 1.00 | 25.37 | A |
| ATOM | 544 O | ASP A | 87 | 40.058 | −20.331 | 33.740 | 1.00 | 22.36 | A |
| ATOM | 545 N | SER A | 88 | 42.060 | −19.338 | 33.540 | 1.00 | 22.64 | A |
| ATOM | 546 CA | SER A | 88 | 41.490 | −18.060 | 33.136 | 1.00 | 20.83 | A |
| ATOM | 547 CB | SER A | 88 | 42.571 | −16.976 | 33.118 | 1.00 | 20.52 | A |
| ATOM | 548 OG | SER A | 88 | 43.094 | −16.763 | 34.419 | 1.00 | 21.95 | A |
| ATOM | 549 C | SER A | 88 | 40.823 | −18.150 | 31.767 | 1.00 | 19.20 | A |
| ATOM | 550 O | SER A | 88 | 39.808 | −17.500 | 31.518 | 1.00 | 18.81 | A |
| ATOM | 551 N | VAL A | 89 | 41.388 | −18.953 | 30.876 | 1.00 | 20.32 | A |
| ATOM | 552 CA | VAL A | 89 | 40.793 | −19.098 | 29.559 | 1.00 | 20.47 | A |
| ATOM | 553 CB | VAL A | 89 | 41.733 | −19.841 | 28.597 | 1.00 | 20.38 | A |
| ATOM | 554 CG1 | VAL A | 89 | 41.023 | −20.119 | 27.279 | 1.00 | 21.06 | A |
| ATOM | 555 CG2 | VAL A | 89 | 42.969 | −18.993 | 28.344 | 1.00 | 21.76 | A |
| ATOM | 556 C | VAL A | 89 | 39.458 | −19.827 | 29.652 | 1.00 | 21.97 | A |
| ATOM | 557 O | VAL A | 89 | 38.503 | −19.477 | 28.959 | 1.00 | 20.86 | A |
| ATOM | 558 N | LEU A | 90 | 39.382 | −20.836 | 30.514 | 1.00 | 21.28 | A |
| ATOM | 559 CA | LEU A | 90 | 38.130 | −21.571 | 30.685 | 1.00 | 22.19 | A |
| ATOM | 560 CB | LEU A | 90 | 38.329 | −22.758 | 31.639 | 1.00 | 24.45 | A |
| ATOM | 561 CG | LEU A | 90 | 39.000 | −23.996 | 31.017 | 1.00 | 27.30 | A |
| ATOM | 562 CD1 | LEU A | 90 | 39.320 | −25.028 | 32.085 | 1.00 | 28.23 | A |
| ATOM | 563 CD2 | LEU A | 90 | 38.077 | −24.589 | 29.963 | 1.00 | 28.41 | A |
| ATOM | 564 C | LEU A | 90 | 37.059 | −20.632 | 31.234 | 1.00 | 21.98 | A |
| ATOM | 565 O | LEU A | 90 | 35.904 | −20.684 | 30.813 | 1.00 | 21.69 | A |
| ATOM | 566 N | ALA A | 91 | 37.443 | −19.772 | 32.174 | 1.00 | 20.86 | A |
| ATOM | 567 CA | ALA A | 91 | 36.503 | −18.817 | 32.752 | 1.00 | 22.55 | A |
| ATOM | 568 CD | ALA A | 91 | 37.177 | −18.013 | 33.866 | 1.00 | 23.99 | A |
| ATOM | 569 C | ALA A | 91 | 36.001 | −17.881 | 31.654 | 1.00 | 23.91 | A |
| ATOM | 570 O | ALA A | 91 | 34.822 | −17.536 | 31.609 | 1.00 | 24.34 | A |
| ATOM | 571 N | GLY A | 92 | 36.907 | −17.473 | 30.770 | 1.00 | 23.93 | A |
| ATOM | 572 CA | GLY A | 92 | 36.525 | −16.591 | 29.678 | 1.00 | 23.53 | A |
| ATOM | 573 C | GLY A | 92 | 35.536 | −17.258 | 28.740 | 1.00 | 23.71 | A |
| ATOM | 574 O | GLY A | 92 | 34.570 | −16.637 | 28.304 | 1.00 | 21.27 | A |
| ATOM | 575 N | LEU A | 93 | 35.776 | −18.529 | 28.428 | 1.00 | 23.99 | A |
| ATOM | 576 CA | LEU A | 93 | 34.898 | −19.279 | 27.536 | 1.00 | 26.50 | A |
| ATOM | 577 CB | LEU A | 93 | 35.461 | −20.683 | 27.299 | 1.00 | 27.50 | A |
| ATOM | 578 CG | LEU A | 93 | 36.800 | −20.759 | 26.559 | 1.00 | 28.66 | A |
| ATOM | 579 CD1 | LEU A | 93 | 37.261 | −22.211 | 26.476 | 1.00 | 28.62 | A |
| ATOM | 580 CD2 | LEU A | 93 | 36.646 | −20.169 | 25.163 | 1.00 | 29.21 | A |
| ATOM | 581 C | LEU A | 93 | 33.460 | −19.384 | 28.046 | 1.00 | 29.37 | A |
| ATOM | 582 O | LEU A | 93 | 32.530 | −19.552 | 27.255 | 1.00 | 27.96 | A |
| ATOM | 583 N | LYS A | 94 | 33.277 | −19.290 | 29.362 | 1.00 | 30.59 | A |
| ATOM | 584 CA | LYS A | 94 | 31.940 | −19.374 | 29.945 | 1.00 | 32.14 | A |
| ATOM | 585 CB | LYS A | 94 | 32.032 | −19.562 | 31.463 | 1.00 | 35.43 | A |
| ATOM | 586 CG | LYS A | 94 | 32.427 | −20.969 | 31.890 | 1.00 | 39.25 | A |
| ATOM | 587 CD | LYS A | 94 | 32.481 | −21.109 | 33.410 | 1.00 | 43.48 | A |
| ATOM | 588 CE | LYS A | 94 | 31.180 | −20.634 | 34.060 | 1.00 | 44.76 | A |
| ATOM | 589 NZ | LYS A | 94 | 29.975 | −21.339 | 33.526 | 1.00 | 47.14 | A |
| ATOM | 590 C | LYS A | 94 | 31.086 | −18.152 | 29.623 | 1.00 | 32.08 | A |
| ATOM | 591 O | LYS A | 94 | 29.857 | −18.224 | 29.643 | 1.00 | 32.09 | A |
| ATOM | 592 N | ALA A | 95 | 31.733 | −17.031 | 29.324 | 1.00 | 30.04 | A |
| ATOM | 593 CA | ALA A | 95 | 31.005 | −15.810 | 28.995 | 1.00 | 31.62 | A |
| ATOM | 594 CB | ALA A | 95 | 31.533 | −14.649 | 29.825 | 1.00 | 32.04 | A |
| ATOM | 595 C | ALA A | 95 | 31.136 | −15.495 | 27.510 | 1.00 | 30.34 | A |

APPENDIX 1-continued

X-RAY DATA COORDINATES FOR THE APO FORM OF CDP-ME SYNTHASE
(SEQ ID NOS: 9 and 10)

| ATOM | 596 O   | ALA A | 95  | 30.870 | −14.376 | 27.082 | 1.00 | 30.27 A |
|------|---------|-------|-----|--------|---------|--------|------|---------|
| ATOM | 597 N   | ALA A | 96  | 31.531 | −16.500 | 26.733 | 1.00 | 30.03 A |
| ATOM | 598 CA  | ALA A | 96  | 31.721 | −16.344 | 25.297 | 1.00 | 30.96 A |
| ATOM | 599 CB  | ALA A | 96  | 32.749 | −17.353 | 24.803 | 1.00 | 27.94 A |
| ATOM | 600 C   | ALA A | 96  | 30.429 | −16.492 | 24.505 | 1.00 | 31.70 A |
| ATOM | 601 O   | ALA A | 96  | 30.447 | −16.533 | 23.273 | 1.00 | 31.99 A |
| ATOM | 602 N   | GLY A | 97  | 29.306 | −16.567 | 25.209 | 1.00 | 31.51 A |
| ATOM | 603 CA  | GLY A | 97  | 28.029 | −16.705 | 24.534 | 1.00 | 31.57 A |
| ATOM | 604 C   | GLY A | 97  | 27.970 | −17.909 | 23.613 | 1.00 | 31.63 A |
| ATOM | 605 O   | GLY A | 97  | 28.521 | −18.964 | 23.916 | 1.00 | 30.08 A |
| ATOM | 606 N   | ASP A | 98  | 27.307 | −17.751 | 22.474 | 1.00 | 31.65 A |
| ATOM | 607 CA  | ASP A | 98  | 27.174 | −18.847 | 21.525 | 1.00 | 31.00 A |
| ATOM | 608 CB  | ASP A | 98  | 25.748 | −18.877 | 20.970 | 1.00 | 34.71 A |
| ATOM | 609 CG  | ASP A | 98  | 25.234 | −17.498 | 20.617 | 1.00 | 38.19 A |
| ATOM | 610 OD1 | ASP A | 98  | 25.886 | −16.809 | 19.803 | 1.00 | 40.60 A |
| ATOM | 611 OD2 | ASP A | 98  | 24.178 | −17.101 | 21.159 | 1.00 | 40.66 A |
| ATOM | 612 C   | ASP A | 98  | 28.182 | −18.773 | 20.382 | 1.00 | 28.36 A |
| ATOM | 613 O   | ASP A | 98  | 27.992 | −19.389 | 19.338 | 1.00 | 27.07 A |
| ATOM | 614 N   | ALA A | 99  | 29.255 | −18.017 | 20.588 | 1.00 | 25.77 A |
| ATOM | 615 CA  | ALA A | 99  | 30.294 | −17.874 | 19.575 | 1.00 | 25.01 A |
| ATOM | 616 CB  | ALA A | 99  | 31.440 | −17.037 | 20.117 | 1.00 | 24.89 A |
| ATOM | 617 C   | ALA A | 99  | 30.804 | −19.243 | 19.146 | 1.00 | 21.39 A |
| ATOM | 618 O   | ALA A | 99  | 31.094 | −20.100 | 19.980 | 1.00 | 22.80 A |
| ATOM | 619 N   | GLN A | 100 | 30.911 | −19.443 | 17.839 | 1.00 | 19.59 A |
| ATOM | 620 CA  | GLN A | 100 | 31.378 | −20.712 | 17.293 | 1.00 | 18.74 A |
| ATOM | 621 CB  | GLN A | 100 | 30.834 | −20.890 | 15.881 | 1.00 | 23.69 A |
| ATOM | 622 CG  | GLN A | 100 | 29.354 | −21.239 | 15.812 | 1.00 | 27.57 A |
| ATOM | 623 CD  | GLN A | 100 | 28.845 | −21.221 | 14.385 | 1.00 | 29.17 A |
| ATOM | 624 OE1 | GLN A | 100 | 29.543 | −21.644 | 13.465 | 1.00 | 29.53 A |
| ATOM | 625 NE2 | GLN A | 100 | 27.625 | −20.744 | 14.195 | 1.00 | 32.90 A |
| ATOM | 626 C   | GLN A | 100 | 32.895 | −20.818 | 17.266 | 1.00 | 14.95 A |
| ATOM | 627 O   | GLN A | 100 | 33.434 | −21.921 | 17.319 | 1.00 | 15.67 A |
| ATOM | 628 N   | TRP A | 101 | 33.564 | −19.672 | 17.168 | 1.00 | 15.59 A |
| ATOM | 629 CA  | TRP A | 101 | 35.021 | −19.616 | 17.133 | 1.00 | 14.13 A |
| ATOM | 630 CB  | TRP A | 101 | 35.503 | −19.196 | 15.748 | 1.00 | 9.98 A  |
| ATOM | 631 CG  | TRP A | 101 | 35.472 | −20.296 | 14.731 | 1.00 | 13.76 A |
| ATOM | 632 CD2 | TRP A | 101 | 36.591 | −21.064 | 14.292 | 1.00 | 11.85 A |
| ATOM | 633 CE2 | TRP A | 101 | 36.111 | −22.004 | 13.353 | 1.00 | 13.01 A |
| ATOM | 634 CE3 | TRP A | 101 | 37.950 | −21.064 | 14.616 | 1.00 | 14.42 A |
| ATOM | 635 CD1 | TRP A | 101 | 34.384 | −20.775 | 14.053 | 1.00 | 9.90 A  |
| ATOM | 636 NE1 | TRP A | 101 | 34.765 | −21.802 | 13.220 | 1.00 | 15.17 A |
| ATOM | 637 CZ2 | TRP A | 101 | 36.961 | −22.922 | 12.719 | 1.00 | 15.51 A |
| ATOM | 638 CZ3 | TRP A | 101 | 38.792 | −21.980 | 13.987 | 1.00 | 12.11 A |
| ATOM | 639 CH2 | TRP A | 101 | 38.292 | −22.899 | 13.054 | 1.00 | 14.04 A |
| ATOM | 640 C   | TRP A | 101 | 35.525 | −18.613 | 18.164 | 1.00 | 13.20 A |
| ATOM | 641 O   | TRP A | 101 | 34.943 | −17.540 | 18.325 | 1.00 | 12.54 A |
| ATOM | 642 N   | VAL A | 102 | 36.610 | −18.970 | 18.852 | 1.00 | 12.58 A |
| ATOM | 643 CA  | VAL A | 102 | 37.199 | −18.121 | 19.887 | 1.00 | 10.82 A |
| ATOM | 644 CB  | VAL A | 102 | 37.119 | −18.810 | 21.296 | 1.00 | 13.14 A |
| ATOM | 645 CG1 | VAL A | 102 | 37.809 | −20.170 | 21.263 | 1.00 | 15.75 A |
| ATOM | 646 CG2 | VAL A | 102 | 37.751 | −17.922 | 22.344 | 1.00 | 17.16 A |
| ATOM | 647 C   | VAL A | 102 | 38.650 | −17.776 | 19.566 | 1.00 | 11.95 A |
| ATOM | 648 O   | VAL A | 102 | 39.394 | −18.606 | 19.064 | 1.00 | 8.83 A  |
| ATOM | 649 N   | LEU A | 103 | 39.032 | −16.537 | 19.855 | 1.00 | 11.68 A |
| ATOM | 650 CA  | LEU A | 103 | 40.374 | −16.027 | 19.603 | 1.00 | 13.25 A |
| ATOM | 651 CB  | LEU A | 103 | 40.260 | −14.725 | 18.807 | 1.00 | 16.43 A |
| ATOM | 652 CG  | LEU A | 103 | 41.492 | −14.099 | 18.164 | 1.00 | 20.77 A |
| ATOM | 653 CD1 | LEU A | 103 | 41.968 | −14.963 | 17.003 | 1.00 | 17.90 A |
| ATOM | 654 CD2 | LEU A | 103 | 41.143 | −12.704 | 17.664 | 1.00 | 19.39 A |
| ATOM | 655 C   | LEU A | 103 | 41.013 | −15.740 | 20.955 | 1.00 | 12.79 A |
| ATOM | 656 O   | LEU A | 103 | 40.579 | −14.830 | 21.654 | 1.00 | 18.49 A |
| ATOM | 657 N   | VAL A | 104 | 42.023 | −16.515 | 21.343 | 1.00 | 11.23 A |
| ATOM | 658 CA  | VAL A | 104 | 42.678 | −16.286 | 22.635 | 1.00 | 12.47 A |
| ATOM | 659 CB  | VAL A | 104 | 43.035 | −17.616 | 23.338 | 1.00 | 13.28 A |
| ATOM | 660 CG1 | VAL A | 104 | 43.495 | −17.343 | 24.771 | 1.00 | 12.32 A |
| ATOM | 661 CG2 | VAL A | 104 | 41.831 | −18.539 | 23.328 | 1.00 | 14.21 A |
| ATOM | 662 C   | VAL A | 104 | 43.958 | −15.483 | 22.395 | 1.00 | 11.66 A |
| ATOM | 663 O   | VAL A | 104 | 44.813 | −15.892 | 21.609 | 1.00 | 11.55 A |
| ATOM | 664 N   | HIS A | 105 | 44.084 | −14.341 | 23.068 | 1.00 | 9.57 A  |
| ATOM | 665 CA  | HIS A | 105 | 45.245 | −13.474 | 22.893 | 1.00 | 12.12 A |
| ATOM | 666 CB  | HIS A | 105 | 44.846 | −12.252 | 22.054 | 1.00 | 13.69 A |
| ATOM | 667 CG  | HIS A | 105 | 46.007 | −11.401 | 21.646 | 1.00 | 12.98 A |
| ATOM | 668 CD2 | HIS A | 105 | 47.217 | −11.735 | 21.139 | 1.00 | 11.07 A |
| ATOM | 669 ND1 | HIS A | 105 | 46.009 | −10.030 | 21.775 | 1.00 | 16.81 A |
| ATOM | 670 CE1 | HIS A | 105 | 47.176 | −9.555  | 21.370 | 1.00 | 13.31 A |
| ATOM | 671 NE2 | HIS A | 105 | 47.926 | −10.570 | 20.982 | 1.00 | 16.29 A |

APPENDIX 1-continued

X-RAY DATA COORDINATES FOR THE APO FORM OF CDP-ME SYNTHASE
(SEQ ID NOS: 9 and 10)

| ATOM | 672 C   | HIS A | 105 | 45.868 | −13.004 | 24.210 | 1.00 | 11.88 | A |
| ---- | ------- | ----- | --- | ------ | ------- | ------ | ---- | ----- | - |
| ATOM | 673 O   | HIS A | 105 | 45.157 | −12.657 | 25.146 | 1.00 | 14.50 | A |
| ATOM | 674 N   | ASP A | 106 | 47.199 | −12.997 | 24.260 | 1.00 | 14.51 | A |
| ATOM | 675 CA  | ASP A | 106 | 47.950 | −12.560 | 25.440 | 1.00 | 16.77 | A |
| ATOM | 676 CB  | ASP A | 106 | 49.456 | −12.713 | 25.207 | 1.00 | 19.46 | A |
| ATOM | 677 CG  | ASP A | 106 | 49.930 | −14.148 | 25.305 | 1.00 | 25.68 | A |
| ATOM | 678 OD1 | ASP A | 106 | 51.126 | −14.386 | 25.045 | 1.00 | 27.29 | A |
| ATOM | 679 OD2 | ASP A | 106 | 49.119 | −15.035 | 25.647 | 1.00 | 28.74 | A |
| ATOM | 680 C   | ASP A | 106 | 47.683 | −11.101 | 25.800 | 1.00 | 17.71 | A |
| ATOM | 681 O   | ASP A | 106 | 47.667 | −10.229 | 24.937 | 1.00 | 17.66 | A |
| ATOM | 682 N   | ALA A | 107 | 47.506 | −10.837 | 27.087 | 1.00 | 18.96 | A |
| ATOM | 683 CA  | ALA A | 107 | 47.253 | −9.486  | 27.556 | 1.00 | 16.60 | A |
| ATOM | 684 CB  | ALA A | 107 | 46.922 | −9.513  | 29.044 | 1.00 | 18.05 | A |
| ATOM | 685 C   | ALA A | 107 | 48.469 | −8.590  | 27.309 | 1.00 | 18.01 | A |
| ATOM | 686 O   | ALA A | 107 | 48.325 | −7.382  | 27.121 | 1.00 | 19.04 | A |
| ATOM | 687 N   | ALA A | 108 | 49.653 | −9.194  | 27.293 | 1.00 | 18.15 | A |
| ATOM | 688 CA  | ALA A | 108 | 50.909 | −8.464  | 27.120 | 1.00 | 19.18 | A |
| ATOM | 689 CB  | ALA A | 108 | 51.934 | −8.988  | 28.121 | 1.00 | 18.64 | A |
| ATOM | 690 C   | ALA A | 108 | 51.519 | −8.469  | 25.721 | 1.00 | 18.92 | A |
| ATOM | 691 O   | ALA A | 108 | 52.737 | −8.345  | 25.572 | 1.00 | 20.22 | A |
| ATOM | 692 N   | ARG A | 109 | 50.686 | −8.616  | 24.700 | 1.00 | 17.71 | A |
| ATOM | 693 CA  | ARG A | 109 | 51.155 | −8.602  | 23.319 | 1.00 | 18.18 | A |
| ATOM | 694 CB  | ARG A | 109 | 50.842 | −9.934  | 22.638 | 1.00 | 19.45 | A |
| ATOM | 695 CG  | ARG A | 109 | 51.798 | −11.058 | 22.986 | 1.00 | 19.92 | A |
| ATOM | 696 CD  | ARG A | 109 | 51.473 | −12.301 | 22.174 | 1.00 | 23.69 | A |
| ATOM | 697 NE  | ARG A | 109 | 52.216 | −13.469 | 22.630 | 1.00 | 24.11 | A |
| ATOM | 698 CZ  | ARG A | 109 | 53.478 | −13.739 | 22.309 | 1.00 | 25.77 | A |
| ATOM | 699 NH1 | ARG A | 109 | 54.163 | −12.928 | 21.516 | 1.00 | 26.52 | A |
| ATOM | 700 NH2 | ARG A | 109 | 54.062 | −14.827 | 22.791 | 1.00 | 27.51 | A |
| ATOM | 701 C   | ARG A | 109 | 50.432 | −7.460  | 22.609 | 1.00 | 16.63 | A |
| ATOM | 702 O   | ARG A | 109 | 49.456 | −7.682  | 21.891 | 1.00 | 18.47 | A |
| ATOM | 703 N   | PRO A | 110 | 50.915 | −6.220  | 22.798 | 1.00 | 17.10 | A |
| ATOM | 704 CD  | PRO A | 110 | 52.039 | −5.870  | 23.691 | 1.00 | 18.96 | A |
| ATOM | 705 CA  | PRO A | 110 | 50.333 | −5.018  | 22.207 | 1.00 | 16.23 | A |
| ATOM | 706 CB  | PRO A | 110 | 50.769 | −3.938  | 23.180 | 1.00 | 17.38 | A |
| ATOM | 707 CG  | PRO A | 110 | 52.189 | −4.357  | 23.481 | 1.00 | 18.64 | A |
| ATOM | 708 C   | PRO A | 110 | 50.733 | −4.674  | 20.782 | 1.00 | 17.09 | A |
| ATOM | 709 O   | PRO A | 110 | 50.193 | −3.727  | 20.218 | 1.00 | 19.37 | A |
| ATOM | 710 N   | CYS A | 111 | 51.656 | −5.433  | 20.198 | 1.00 | 14.99 | A |
| ATOM | 711 CA  | CYS A | 111 | 52.128 | −5.125  | 18.849 | 1.00 | 17.77 | A |
| ATOM | 712 CB  | CYS A | 111 | 53.644 | −5.313  | 18.783 | 1.00 | 17.59 | A |
| ATOM | 713 SG  | CYS A | 111 | 54.537 | −4.311  | 19.974 | 1.00 | 18.48 | A |
| ATOM | 714 C   | CYS A | 111 | 51.474 | −5.883  | 17.701 | 1.00 | 15.78 | A |
| ATOM | 715 O   | CYS A | 111 | 51.935 | −5.795  | 16.561 | 1.00 | 20.08 | A |
| ATOM | 716 N   | LEU A | 112 | 50.398 | −6.608  | 17.998 | 1.00 | 16.26 | A |
| ATOM | 717 CA  | LEU A | 112 | 49.667 | −7.377  | 16.990 | 1.00 | 16.16 | A |
| ATOM | 718 CB  | LEU A | 112 | 48.443 | −8.052  | 17.627 | 1.00 | 12.66 | A |
| ATOM | 719 CG  | LEU A | 112 | 47.468 | −8.791  | 16.698 | 1.00 | 16.58 | A |
| ATOM | 720 CD1 | LEU A | 112 | 48.210 | −9.871  | 15.924 | 1.00 | 16.49 | A |
| ATOM | 721 CD2 | LEU A | 112 | 46.325 | −9.395  | 17.513 | 1.00 | 14.62 | A |
| ATOM | 722 C   | LEU A | 112 | 49.211 | −6.495  | 15.833 | 1.00 | 16.47 | A |
| ATOM | 723 O   | LEU A | 112 | 48.654 | −5.417  | 16.051 | 1.00 | 17.96 | A |
| ATOM | 724 N   | HIS A | 113 | 49.443 | −6.965  | 14.608 | 1.00 | 17.36 | A |
| ATOM | 725 CA  | HIS A | 113 | 49.059 | −6.238  | 13.394 | 1.00 | 20.09 | A |
| ATOM | 726 CB  | HIS A | 113 | 50.197 | −6.260  | 12.374 | 1.00 | 25.35 | A |
| ATOM | 727 CG  | HIS A | 113 | 51.254 | −5.232  | 12.631 | 1.00 | 32.50 | A |
| ATOM | 728 CD2 | HIS A | 113 | 51.434 | −4.380  | 13.669 | 1.00 | 34.74 | A |
| ATOM | 729 ND1 | HIS A | 113 | 52.283 | −4.985  | 11.750 | 1.00 | 35.42 | A |
| ATOM | 730 CE1 | HIS A | 113 | 53.052 | −4.024  | 12.232 | 1.00 | 36.57 | A |
| ATOM | 731 NE2 | HIS A | 113 | 52.558 | −3.640  | 13.395 | 1.00 | 36.42 | A |
| ATOM | 732 C   | HIS A | 113 | 47.808 | −6.823  | 12.755 | 1.00 | 19.36 | A |
| ATOM | 733 O   | HIS A | 113 | 47.582 | −8.029  | 12.801 | 1.00 | 16.81 | A |
| ATOM | 734 N   | GLN A | 114 | 47.013 | −5.956  | 12.136 | 1.00 | 18.97 | A |
| ATOM | 735 CA  | GLN A | 114 | 45.773 | −6.347  | 11.490 | 1.00 | 18.43 | A |
| ATOM | 736 CB  | GLN A | 114 | 45.044 | −5.099  | 10.994 | 1.00 | 19.15 | A |
| ATOM | 737 CG  | GLN A | 114 | 44.577 | −4.208  | 12.125 | 1.00 | 19.02 | A |
| ATOM | 738 CD  | GLN A | 114 | 43.711 | −4.972  | 13.114 | 1.00 | 20.79 | A |
| ATOM | 739 OE1 | GLN A | 114 | 42.679 | −5.536  | 12.740 | 1.00 | 18.91 | A |
| ATOM | 740 NE2 | GLN A | 114 | 44.132 | −5.006  | 14.378 | 1.00 | 19.10 | A |
| ATOM | 741 C   | GLN A | 114 | 45.906 | −7.347  | 10.354 | 1.00 | 16.93 | A |
| ATOM | 742 O   | GLN A | 114 | 45.015 | −8.174  | 10.158 | 1.00 | 17.61 | A |
| ATOM | 743 N   | ASP A | 115 | 46.996 | −7.284  | 9.595  | 1.00 | 20.42 | A |
| ATOM | 744 CA  | ASP A | 115 | 47.148 | −8.231  | 8.501  | 1.00 | 19.94 | A |
| ATOM | 745 CB  | ASP A | 115 | 48.328 | −7.857  | 7.595  | 1.00 | 26.74 | A |
| ATOM | 746 CG  | ASP A | 115 | 49.501 | −7.295  | 8.361  | 1.00 | 33.24 | A |
| ATOM | 747 OD1 | ASP A | 115 | 49.731 | −7.729  | 9.509  | 1.00 | 36.12 | A |

APPENDIX 1-continued

X-RAY DATA COORDINATES FOR THE APO FORM OF CDP-ME SYNTHASE
(SEQ ID NOS: 9 and 10)

| ATOM | 748 OD2 | ASP A | 115 | 50.203 | −6.421  | 7.803  | 1.00 | 37.38 A |
|------|---------|-------|-----|--------|---------|--------|------|---------|
| ATOM | 749 C   | ASP A | 115 | 47.316 | −9.650  | 9.038  | 1.00 | 17.93 A |
| ATOM | 750 O   | ASP A | 115 | 46.716 | −10.580 | 8.515  | 1.00 | 18.48 A |
| ATOM | 751 N   | ASP A | 116 | 48.130 | −9.814  | 10.079 | 1.00 | 17.16 A |
| ATOM | 752 CA  | ASP A | 116 | 48.325 | −11.137 | 10.670 | 1.00 | 13.43 A |
| ATOM | 753 CB  | ASP A | 116 | 49.367 | −11.106 | 11.797 | 1.00 | 15.71 A |
| ATOM | 754 CG  | ASP A | 116 | 50.785 | −10.956 | 11.282 | 1.00 | 18.25 A |
| ATOM | 755 OD1 | ASP A | 116 | 51.021 | −11.177 | 10.071 | 1.00 | 22.27 A |
| ATOM | 756 OD2 | ASP A | 116 | 51.672 | −10.644 | 12.102 | 1.00 | 21.50 A |
| ATOM | 757 C   | ASP A | 116 | 46.998 | −11.630 | 11.244 | 1.00 | 13.26 A |
| ATOM | 758 O   | ASP A | 116 | 46.587 | −12.753 | 11.031 | 1.00 | 13.86 A |
| ATOM | 759 N   | LEU A | 117 | 46.317 | −10.753 | 11.972 | 1.00 | 13.44 A |
| ATOM | 760 CA  | LEU A | 117 | 45.046 | −11.119 | 12.574 | 1.00 | 12.31 A |
| ATOM | 761 CB  | LEU A | 117 | 44.467 | −9.940  | 13.361 | 1.00 | 13.58 A |
| ATOM | 762 CG  | LEU A | 117 | 43.093 | −10.181 | 14.006 | 1.00 | 11.80 A |
| ATOM | 763 CD1 | LEU A | 117 | 43.134 | −11.466 | 14.837 | 1.00 | 15.45 A |
| ATOM | 764 CD2 | LEU A | 117 | 42.717 | −8.986  | 14.887 | 1.00 | 13.79 A |
| ATOM | 765 C   | LEU A | 117 | 44.056 | −11.576 | 11.514 | 1.00 | 12.12 A |
| ATOM | 766 O   | LEU A | 117 | 43.411 | −12.599 | 11.681 | 1.00 | 12.32 A |
| ATOM | 767 N   | ALA A | 118 | 43.958 | −10.827 | 10.415 | 1.00 | 13.60 A |
| ATOM | 768 CA  | ALA A | 118 | 43.034 | −11.177 | 9.349  | 1.00 | 11.41 A |
| ATOM | 769 CB  | ALA A | 118 | 43.026 | −10.072 | 8.282  | 1.00 | 12.83 A |
| ATOM | 770 C   | ALA A | 118 | 43.352 | −12.532 | 8.714  | 1.00 | 13.87 A |
| ATOM | 771 O   | ALA A | 118 | 42.445 | −13.302 | 8.390  | 1.00 | 14.88 A |
| ATOM | 772 N   | ARG A | 119 | 44.635 | −12.833 | 8.548  | 1.00 | 13.87 A |
| ATOM | 773 CA  | ARG A | 119 | 45.028 | −14.106 | 7.952  | 1.00 | 15.14 A |
| ATOM | 774 CB  | ARG A | 119 | 46.508 | −14.062 | 7.568  | 1.00 | 15.90 A |
| ATOM | 775 CG  | ARG A | 119 | 46.744 | −13.247 | 6.286  | 1.00 | 20.12 A |
| ATOM | 776 CD  | ARG A | 119 | 48.216 | −13.054 | 5.963  | 1.00 | 22.73 A |
| ATOM | 777 NE  | ARG A | 119 | 48.949 | −14.297 | 6.123  | 1.00 | 27.58 A |
| ATOM | 778 CZ  | ARG A | 119 | 49.855 | −14.510 | 7.070  | 1.00 | 27.85 A |
| ATOM | 779 NH1 | ARG A | 119 | 50.147 | −13.550 | 7.939  | 1.00 | 29.62 A |
| ATOM | 780 NH2 | ARG A | 119 | 50.450 | −15.691 | 7.159  | 1.00 | 27.30 A |
| ATOM | 781 C   | ARG A | 119 | 44.739 | −15.251 | 8.916  | 1.00 | 14.62 A |
| ATOM | 782 O   | ARG A | 119 | 44.417 | −16.363 | 8.495  | 1.00 | 15.97 A |
| ATOM | 783 N   | LEU A | 120 | 44.842 | −14.972 | 10.213 | 1.00 | 13.88 A |
| ATOM | 784 CA  | LEU A | 120 | 44.555 | −15.989 | 11.210 | 1.00 | 12.37 A |
| ATOM | 785 CB  | LEU A | 120 | 44.937 | −15.499 | 12.607 | 1.00 | 11.78 A |
| ATOM | 786 CG  | LEU A | 120 | 44.670 | −16.502 | 13.741 | 1.00 | 8.70 A  |
| ATOM | 787 CD1 | LEU A | 120 | 45.526 | −17.749 | 13.544 | 1.00 | 13.27 A |
| ATOM | 788 CD2 | LEU A | 120 | 44.990 | −15.846 | 15.084 | 1.00 | 10.15 A |
| ATOM | 789 C   | LEU A | 120 | 43.066 | −16.328 | 11.182 | 1.00 | 14.67 A |
| ATOM | 790 O   | LEU A | 120 | 42.683 | −17.503 | 11.169 | 1.00 | 10.18 A |
| ATOM | 791 N   | LEU A | 121 | 42.222 | −15.300 | 11.155 | 1.00 | 13.67 A |
| ATOM | 792 CA  | LEU A | 121 | 40.778 | −15.515 | 11.141 | 1.00 | 13.47 A |
| ATOM | 793 CB  | LEU A | 121 | 40.035 | −14.182 | 11.284 | 1.00 | 14.29 A |
| ATOM | 794 CG  | LEU A | 121 | 40.298 | −13.500 | 12.630 | 1.00 | 17.41 A |
| ATOM | 795 CD1 | LEU A | 121 | 39.610 | −12.153 | 12.646 | 1.00 | 19.73 A |
| ATOM | 796 CD2 | LEU A | 121 | 39.813 | −14.377 | 13.774 | 1.00 | 21.64 A |
| ATOM | 797 C   | LEU A | 121 | 40.276 | −16.257 | 9.911  | 1.00 | 12.02 A |
| ATOM | 798 O   | LEU A | 121 | 39.204 | −16.862 | 9.947  | 1.00 | 12.55 A |
| ATOM | 799 N   | ALA A | 122 | 41.043 | −16.224 | 8.827  | 1.00 | 14.76 A |
| ATOM | 800 CA  | ALA A | 122 | 40.634 | −16.926 | 7.614  | 1.00 | 14.23 A |
| ATOM | 801 CB  | ALA A | 122 | 41.604 | −16.624 | 6.473  | 1.00 | 18.76 A |
| ATOM | 802 C   | ALA A | 122 | 40.548 | −18.438 | 7.845  | 1.00 | 15.49 A |
| ATOM | 803 O   | ALA A | 122 | 39.884 | −19.142 | 7.096  | 1.00 | 15.88 A |
| ATOM | 804 N   | LEU A | 123 | 41.220 | −18.933 | 8.884  | 1.00 | 13.57 A |
| ATOM | 805 CA  | LEU A | 123 | 41.199 | −20.355 | 9.178  | 1.00 | 14.42 A |
| ATOM | 806 CB  | LEU A | 123 | 42.078 | −20.663 | 10.392 | 1.00 | 15.14 A |
| ATOM | 807 CG  | LEU A | 123 | 43.584 | −20.476 | 10.225 | 1.00 | 17.02 A |
| ATOM | 808 CD1 | LEU A | 123 | 44.263 | −20.668 | 11.578 | 1.00 | 18.65 A |
| ATOM | 809 CD2 | LEU A | 123 | 44.131 | −21.471 | 9.208  | 1.00 | 18.23 A |
| ATOM | 810 C   | LEU A | 123 | 39.807 | −20.940 | 9.407  | 1.00 | 15.97 A |
| ATOM | 811 O   | LEU A | 123 | 39.604 | −22.127 | 9.181  | 1.00 | 17.79 A |
| ATOM | 812 N   | SER A | 124 | 38.842 | −20.134 | 9.844  | 1.00 | 14.36 A |
| ATOM | 813 CA  | SER A | 124 | 37.504 | −20.679 | 10.080 | 1.00 | 17.77 A |
| ATOM | 814 CB  | SER A | 124 | 36.617 | −19.670 | 10.840 | 1.00 | 16.39 A |
| ATOM | 815 OG  | SER A | 124 | 36.484 | −18.444 | 10.156 | 1.00 | 17.43 A |
| ATOM | 816 C   | SER A | 124 | 36.814 | −21.135 | 8.800  | 1.00 | 21.52 A |
| ATOM | 817 O   | SER A | 124 | 35.833 | −21.872 | 8.857  | 1.00 | 22.89 A |
| ATOM | 818 N   | GLU A | 125 | 37.331 | −20.720 | 7.648  | 1.00 | 25.43 A |
| ATOM | 819 CA  | GLU A | 125 | 36.728 | −21.098 | 6.371  | 1.00 | 30.20 A |
| ATOM | 820 CB  | GLU A | 125 | 36.746 | −19.906 | 5.413  | 1.00 | 33.50 A |
| ATOM | 821 CG  | GLU A | 125 | 36.392 | −18.583 | 6.076  | 1.00 | 38.90 A |
| ATOM | 822 CD  | GLU A | 125 | 34.984 | −18.560 | 6.637  | 1.00 | 42.32 A |
| ATOM | 823 OE1 | GLU A | 125 | 34.805 | −18.063 | 7.773  | 1.00 | 42.43 A |

APPENDIX 1-continued

X-RAY DATA COORDINATES FOR THE APO FORM OF CDP-ME SYNTHASE
(SEQ ID NOS: 9 and 10)

| ATOM | 824 | OE2 | GLU A | 125 | 34.055 | −19.029 | 5.941  | 1.00 | 42.68 | A |
|------|-----|-----|-------|-----|--------|---------|--------|------|-------|---|
| ATOM | 825 | C   | GLU A | 125 | 37.441 | −22.279 | 5.711  | 1.00 | 32.83 | A |
| ATOM | 826 | O   | GLU A | 125 | 36.950 | −22.835 | 4.723  | 1.00 | 33.97 | A |
| ATOM | 827 | N   | THR A | 126 | 38.596 | −22.663 | 6.251  | 1.00 | 33.85 | A |
| ATOM | 828 | CA  | THR A | 126 | 39.364 | −23.765 | 5.677  | 1.00 | 35.96 | A |
| ATOM | 829 | CB  | THR A | 126 | 40.602 | −23.241 | 4.932  | 1.00 | 37.11 | A |
| ATOM | 830 | CG1 | THR A | 126 | 41.457 | −22.546 | 5.849  | 1.00 | 37.88 | A |
| ATOM | 831 | CG2 | THR A | 126 | 40.193 | −22.299 | 3.817  | 1.00 | 39.26 | A |
| ATOM | 832 | C   | THR A | 126 | 39.846 | −24.802 | 6.688  | 1.00 | 36.26 | A |
| ATOM | 833 | O   | THR A | 126 | 40.568 | −25.732 | 6.326  | 1.00 | 36.88 | A |
| ATOM | 834 | N   | SER A | 127 | 39.455 | −24.651 | 7.948  | 1.00 | 33.28 | A |
| ATOM | 835 | CA  | SER A | 127 | 39.886 | −25.590 | 8.979  | 1.00 | 32.06 | A |
| ATOM | 836 | CB  | SER A | 127 | 41.133 | −25.044 | 9.681  | 1.00 | 31.98 | A |
| ATOM | 837 | CG  | SER A | 127 | 41.516 | −25.867 | 10.768 | 1.00 | 30.61 | A |
| ATOM | 838 | C   | SER A | 127 | 38.810 | −25.882 | 10.020 | 1.00 | 31.11 | A |
| ATOM | 839 | O   | SER A | 127 | 37.950 | −25.048 | 10.290 | 1.00 | 30.07 | A |
| ATOM | 840 | N   | ARG A | 128 | 38.861 | −27.077 | 10.597 | 1.00 | 31.72 | A |
| ATOM | 841 | CA  | ARG A | 128 | 37.909 | −27.462 | 11.632 | 1.00 | 32.38 | A |
| ATOM | 842 | CB  | ARG A | 128 | 37.206 | −28.775 | 11.273 | 1.00 | 35.73 | A |
| ATOM | 843 | CG  | ARG A | 128 | 36.128 | −28.655 | 10.208 | 1.00 | 38.72 | A |
| ATOM | 844 | CD  | ARG A | 128 | 35.500 | −30.010 | 9.925  | 1.00 | 41.24 | A |
| ATOM | 845 | NE  | ARG A | 128 | 34.516 | −29.955 | 8.847  | 1.00 | 42.38 | A |
| ATOM | 846 | CZ  | ARG A | 128 | 33.311 | −29.404 | 8.954  | 1.00 | 42.29 | A |
| ATOM | 847 | NH1 | ARG A | 128 | 32.925 | −28.855 | 10.099 | 1.00 | 40.71 | A |
| ATOM | 848 | NH2 | ARG A | 128 | 32.489 | −29.402 | 7.913  | 1.00 | 41.94 | A |
| ATOM | 849 | C   | ARG A | 128 | 38.646 | −27.630 | 12.953 | 1.00 | 30.99 | A |
| ATOM | 850 | O   | ARG A | 128 | 38.054 | −28.015 | 13.955 | 1.00 | 30.26 | A |
| ATOM | 851 | N   | THR A | 129 | 39.945 | −27.337 | 12.944 | 1.00 | 28.93 | A |
| ATOM | 852 | CA  | THR A | 129 | 40.766 | −27.461 | 14.142 | 1.00 | 27.52 | A |
| ATOM | 853 | CB  | THR A | 129 | 41.988 | −28.365 | 13.872 | 1.00 | 29.50 | A |
| ATOM | 854 | OG1 | THR A | 129 | 41.535 | −29.671 | 13.495 | 1.00 | 30.04 | A |
| ATOM | 855 | CG2 | THR A | 129 | 42.862 | −28.477 | 15.110 | 1.00 | 31.06 | A |
| ATOM | 856 | C   | THR A | 129 | 41.248 | −26.095 | 14.618 | 1.00 | 25.08 | A |
| ATOM | 857 | O   | THR A | 129 | 41.413 | −25.872 | 15.816 | 1.00 | 25.13 | A |
| ATOM | 858 | N   | GLY A | 130 | 41.461 | −25.182 | 13.674 | 1.00 | 20.33 | A |
| ATOM | 859 | CA  | GLY A | 130 | 41.933 | −23.852 | 14.025 | 1.00 | 19.42 | A |
| ATOM | 860 | C   | GLY A | 130 | 43.440 | −23.749 | 13.856 | 1.00 | 15.78 | A |
| ATOM | 861 | O   | GLY A | 130 | 44.050 | −24.609 | 13.234 | 1.00 | 17.44 | A |
| ATOM | 862 | N   | GLY A | 131 | 44.048 | −22.715 | 14.427 | 1.00 | 12.10 | A |
| ATOM | 863 | CA  | GLY A | 131 | 45.483 | −22.538 | 14.287 | 1.00 | 12.38 | A |
| ATOM | 864 | C   | GLY A | 131 | 46.004 | −21.365 | 15.096 | 1.00 | 12.12 | A |
| ATOM | 865 | O   | GLY A | 131 | 45.257 | −20.765 | 15.855 | 1.00 | 10.17 | A |
| ATOM | 866 | N   | ILE A | 132 | 47.280 | −21.035 | 14.936 | 1.00 | 12.54 | A |
| ATOM | 867 | CA  | ILE A | 132 | 47.883 | −19.948 | 15.691 | 1.00 | 13.32 | A |
| ATOM | 868 | CB  | ILE A | 132 | 48.668 | −20.476 | 16.903 | 1.00 | 13.35 | A |
| ATOM | 869 | CG2 | ILE A | 132 | 47.801 | −21.432 | 17.696 | 1.00 | 13.94 | A |
| ATOM | 870 | CG1 | ILE A | 132 | 49.926 | −21.200 | 16.434 | 1.00 | 13.72 | A |
| ATOM | 871 | CD1 | ILE A | 132 | 50.884 | −21.599 | 17.560 | 1.00 | 13.89 | A |
| ATOM | 872 | C   | ILE A | 132 | 48.861 | −19.136 | 14.859 | 1.00 | 13.30 | A |
| ATOM | 873 | O   | ILE A | 132 | 49.316 | −19.573 | 13.793 | 1.00 | 10.62 | A |
| ATOM | 874 | N   | LEU A | 133 | 49.169 | −17.938 | 15.340 | 1.00 | 11.52 | A |
| ATOM | 875 | CA  | LEU A | 133 | 50.168 | −17.107 | 14.681 | 1.00 | 10.97 | A |
| ATOM | 876 | CB  | LEU A | 133 | 49.993 | −15.635 | 15.058 | 1.00 | 14.16 | A |
| ATOM | 877 | CG  | LEU A | 133 | 48.889 | −14.879 | 14.303 | 1.00 | 12.06 | A |
| ATOM | 878 | CD1 | LEU A | 133 | 48.904 | −13.406 | 14.726 | 1.00 | 14.52 | A |
| ATOM | 879 | CD2 | LEU A | 133 | 49.116 | −15.002 | 12.785 | 1.00 | 14.14 | A |
| ATOM | 880 | C   | LEU A | 133 | 51.513 | −17.615 | 15.183 | 1.00 | 13.35 | A |
| ATOM | 881 | O   | LEU A | 133 | 51.670 | −17.937 | 16.360 | 1.00 | 12.40 | A |
| ATOM | 882 | N   | ALA A | 134 | 52.468 | −17.721 | 14.270 | 1.00 | 11.69 | A |
| ATOM | 883 | CA  | ALA A | 134 | 53.807 | −18.198 | 14.607 | 1.00 | 12.80 | A |
| ATOM | 884 | CB  | ALA A | 134 | 53.869 | −19.726 | 14.510 | 1.00 | 14.58 | A |
| ATOM | 885 | C   | ALA A | 134 | 54.853 | −17.578 | 13.693 | 1.00 | 15.81 | A |
| ATOM | 886 | O   | ALA A | 134 | 54.554 | −17.153 | 12.576 | 1.00 | 16.25 | A |
| ATOM | 887 | N   | ALA A | 135 | 56.085 | −17.528 | 14.181 | 1.00 | 15.38 | A |
| ATOM | 888 | CA  | ALA A | 135 | 57.180 | −16.963 | 13.413 | 1.00 | 18.24 | A |
| ATOM | 889 | CB  | ALA A | 135 | 57.779 | −15.782 | 14.152 | 1.00 | 18.05 | A |
| ATOM | 890 | C   | ALA A | 135 | 58.211 | −18.056 | 13.228 | 1.00 | 19.21 | A |
| ATOM | 891 | O   | ALA A | 135 | 58.537 | −18.771 | 14.172 | 1.00 | 17.25 | A |
| ATOM | 892 | N   | PRO A | 136 | 58.716 | −18.225 | 12.000 | 1.00 | 21.79 | A |
| ATOM | 893 | CD  | PRO A | 136 | 58.266 | −17.601 | 10.743 | 1.00 | 24.33 | A |
| ATOM | 894 | CA  | PRO A | 136 | 59.718 | −19.262 | 11.736 | 1.00 | 23.21 | A |
| ATOM | 895 | CB  | PRO A | 136 | 59.898 | −19.192 | 10.219 | 1.00 | 24.80 | A |
| ATOM | 896 | CG  | PRO A | 136 | 58.575 | −18.673 | 9.735  | 1.00 | 26.80 | A |
| ATOM | 897 | C   | PRO A | 136 | 61.031 | −19.010 | 12.480 | 1.00 | 23.50 | A |
| ATOM | 898 | O   | PRO A | 136 | 61.458 | −17.867 | 12.641 | 1.00 | 23.63 | A |
| ATOM | 899 | N   | VAL A | 137 | 61.668 | −20.079 | 12.943 | 1.00 | 23.67 | A |

APPENDIX 1-continued

X-RAY DATA COORDINATES FOR THE APO FORM OF CDP-ME SYNTHASE
(SEQ ID NOS: 9 and 10)

| ATOM | 900 | CA  | VAL A | 137 | 62.935 | −19.943 | 13.648 | 1.00 | 26.07 | A |
|------|-----|-----|-------|-----|--------|---------|--------|------|-------|---|
| ATOM | 901 | CB  | VAL A | 137 | 63.324 | −21.259 | 14.356 | 1.00 | 25.68 | A |
| ATOM | 902 | CG1 | VAL A | 137 | 64.699 | −21.126 | 15.003 | 1.00 | 26.40 | A |
| ATOM | 903 | CG2 | VAL A | 137 | 62.284 | −21.598 | 15.401 | 1.00 | 26.39 | A |
| ATOM | 904 | C   | VAL A | 137 | 64.033 | −19.564 | 12.656 | 1.00 | 26.57 | A |
| ATOM | 905 | O   | VAL A | 137 | 64.162 | −20.172 | 11.592 | 1.00 | 25.54 | A |
| ATOM | 906 | N   | ARG A | 138 | 64.817 | −18.554 | 13.010 | 1.00 | 29.06 | A |
| ATOM | 907 | CA  | ARG A | 138 | 65.900 | −18.079 | 12.158 | 1.00 | 32.25 | A |
| ATOM | 908 | CB  | ARG A | 138 | 65.889 | −16.548 | 12.110 | 1.00 | 35.01 | A |
| ATOM | 909 | CG  | ARG A | 138 | 64.535 | −15.923 | 11.793 | 1.00 | 38.28 | A |
| ATOM | 910 | CD  | ARG A | 138 | 64.017 | −16.329 | 10.422 | 1.00 | 41.58 | A |
| ATOM | 911 | NE  | ARG A | 138 | 62.809 | −15.584 | 10.064 | 1.00 | 44.85 | A |
| ATOM | 912 | CZ  | ARG A | 138 | 62.180 | −15.684 | 8.896  | 1.00 | 45.49 | A |
| ATOM | 913 | NH1 | ARG A | 138 | 62.636 | −16.501 | 7.957  | 1.00 | 45.87 | A |
| ATOM | 914 | NH2 | ARG A | 138 | 61.094 | −14.959 | 8.666  | 1.00 | 46.20 | A |
| ATOM | 915 | C   | ARG A | 138 | 67.258 | −18.560 | 12.669 | 1.00 | 31.97 | A |
| ATOM | 916 | O   | ARG A | 138 | 68.027 | −19.177 | 11.935 | 1.00 | 35.21 | A |
| ATOM | 917 | N   | ASP A | 139 | 67.541 | −18.274 | 13.933 | 1.00 | 32.82 | A |
| ATOM | 918 | CA  | ASP A | 139 | 68.803 | −18.650 | 14.555 | 1.00 | 31.03 | A |
| ATOM | 919 | CB  | ASP A | 139 | 68.837 | −18.127 | 15.991 | 1.00 | 35.68 | A |
| ATOM | 920 | CG  | ASP A | 139 | 68.474 | −16.654 | 16.090 | 1.00 | 39.16 | A |
| ATOM | 921 | OD1 | ASP A | 139 | 69.320 | −15.803 | 15.747 | 1.00 | 41.17 | A |
| ATOM | 922 | OD2 | ASP A | 139 | 67.332 | −16.361 | 16.503 | 1.00 | 43.42 | A |
| ATOM | 923 | C   | ASP A | 139 | 69.046 | −20.154 | 14.590 | 1.00 | 27.87 | A |
| ATOM | 924 | O   | ASP A | 139 | 68.112 | −20.952 | 14.509 | 1.00 | 27.06 | A |
| ATOM | 925 | N   | THR A | 140 | 70.314 | −20.530 | 14.703 | 1.00 | 24.30 | A |
| ATOM | 926 | CA  | THR A | 140 | 70.680 | −21.928 | 14.810 | 1.00 | 21.14 | A |
| ATOM | 927 | CB  | THR A | 140 | 72.187 | −22.139 | 14.561 | 1.00 | 22.23 | A |
| ATOM | 928 | OG1 | THR A | 140 | 72.475 | −21.885 | 13.182 | 1.00 | 21.88 | A |
| ATOM | 929 | CG2 | THR A | 140 | 72.603 | −23.561 | 14.919 | 1.00 | 22.96 | A |
| ATOM | 930 | C   | THR A | 140 | 70.342 | −22.272 | 16.254 | 1.00 | 21.73 | A |
| ATOM | 931 | O   | THR A | 140 | 70.667 | −21.516 | 17.172 | 1.00 | 18.42 | A |
| ATOM | 932 | N   | MET A | 141 | 69.678 | −23.403 | 16.463 | 1.00 | 18.59 | A |
| ATOM | 933 | CA  | MET A | 141 | 69.283 | −23.806 | 17.808 | 1.00 | 19.96 | A |
| ATOM | 934 | CB  | MET A | 141 | 67.811 | −24.230 | 17.811 | 1.00 | 21.51 | A |
| ATOM | 935 | CG  | MET A | 141 | 66.856 | −23.184 | 17.241 | 1.00 | 25.41 | A |
| ATOM | 936 | SD  | MET A | 141 | 66.986 | −21.560 | 18.060 | 1.00 | 17.06 | A |
| ATOM | 937 | CE  | MET A | 141 | 66.221 | −21.915 | 19.563 | 1.00 | 27.99 | A |
| ATOM | 938 | C   | MET A | 141 | 70.133 | −24.937 | 18.352 | 1.00 | 19.10 | A |
| ATOM | 939 | O   | MET A | 141 | 70.534 | −25.833 | 17.612 | 1.00 | 18.10 | A |
| ATOM | 940 | N   | LYS A | 142 | 70.403 | −24.886 | 19.651 | 1.00 | 17.32 | A |
| ATOM | 941 | CA  | LYS A | 142 | 71.192 | −25.915 | 20.313 | 1.00 | 18.18 | A |
| ATOM | 942 | CB  | LYS A | 142 | 72.483 | −25.324 | 20.893 | 1.00 | 19.02 | A |
| ATOM | 943 | CG  | LYS A | 142 | 73.368 | −24.569 | 19.910 | 1.00 | 17.78 | A |
| ATOM | 944 | CD  | LYS A | 142 | 73.942 | −25.472 | 18.833 | 1.00 | 15.70 | A |
| ATOM | 945 | CE  | LYS A | 142 | 74.884 | −24.686 | 17.938 | 1.00 | 15.17 | A |
| ATOM | 946 | NZ  | LYS A | 142 | 75.530 | −25.531 | 16.897 | 1.00 | 15.59 | A |
| ATOM | 947 | C   | LYS A | 142 | 70.407 | −26.533 | 21.468 | 1.00 | 18.62 | A |
| ATOM | 948 | O   | LYS A | 142 | 69.684 | −25.840 | 22.181 | 1.00 | 17.28 | A |
| ATOM | 949 | N   | ARG A | 143 | 70.552 | −27.840 | 21.642 | 1.00 | 22.22 | A |
| ATOM | 950 | CA  | ARG A | 143 | 69.911 | −28.538 | 22.743 | 1.00 | 23.73 | A |
| ATOM | 951 | CB  | ARG A | 143 | 69.330 | −29.877 | 22.286 | 1.00 | 26.64 | A |
| ATOM | 952 | CG  | ARG A | 143 | 68.822 | −30.759 | 23.423 | 1.00 | 31.34 | A |
| ATOM | 953 | CD  | ARG A | 143 | 67.630 | −30.136 | 24.130 | 1.00 | 33.12 | A |
| ATOM | 954 | NE  | ARG A | 143 | 66.473 | −30.049 | 23.242 | 1.00 | 33.98 | A |
| ATOM | 955 | CZ  | ARG A | 143 | 65.340 | −29.427 | 23.548 | 1.00 | 35.27 | A |
| ATOM | 956 | NH1 | ARG A | 143 | 65.206 | −28.832 | 24.724 | 1.00 | 34.19 | A |
| ATOM | 957 | NH2 | ARG A | 143 | 64.341 | −29.402 | 22.675 | 1.00 | 35.32 | A |
| ATOM | 958 | C   | ARG A | 143 | 71.038 | −28.786 | 23.730 | 1.00 | 24.33 | A |
| ATOM | 959 | O   | ARG A | 143 | 72.062 | −29.370 | 23.370 | 1.00 | 22.85 | A |
| ATOM | 960 | N   | ALA A | 144 | 70.864 | −28.331 | 24.964 | 1.00 | 24.49 | A |
| ATOM | 961 | CA  | ALA A | 144 | 71.887 | −28.516 | 25.985 | 1.00 | 27.63 | A |
| ATOM | 962 | CB  | ALA A | 144 | 71.717 | −27.480 | 27.090 | 1.00 | 27.11 | A |
| ATOM | 963 | C   | ALA A | 144 | 71.788 | −29.913 | 26.569 | 1.00 | 30.21 | A |
| ATOM | 964 | O   | ALA A | 144 | 70.735 | −30.549 | 26.505 | 1.00 | 28.83 | A |
| ATOM | 965 | N   | GLU A | 145 | 72.891 | −30.395 | 27.124 | 1.00 | 32.42 | A |
| ATOM | 966 | CA  | GLU A | 145 | 72.888 | −31.710 | 27.736 | 1.00 | 35.15 | A |
| ATOM | 967 | CB  | GLU A | 145 | 74.317 | −32.200 | 27.952 | 1.00 | 36.58 | A |
| ATOM | 968 | CG  | GLU A | 145 | 75.078 | −32.352 | 26.654 | 1.00 | 40.24 | A |
| ATOM | 969 | CD  | GLU A | 145 | 76.378 | −33.105 | 26.817 | 1.00 | 43.79 | A |
| ATOM | 970 | OE1 | GLU A | 145 | 77.244 | −32.643 | 27.591 | 1.00 | 44.06 | A |
| ATOM | 971 | OE2 | GLU A | 145 | 76.527 | −34.167 | 26.174 | 1.00 | 45.67 | A |
| ATOM | 972 | C   | GLU A | 145 | 72.152 | −31.594 | 29.060 | 1.00 | 35.81 | A |
| ATOM | 973 | O   | GLU A | 145 | 72.264 | −30.584 | 29.756 | 1.00 | 35.23 | A |
| ATOM | 974 | N   | PRO A | 146 | 71.383 | −32.629 | 29.423 | 1.00 | 36.57 | A |
| ATOM | 975 | CD  | PRO A | 146 | 71.317 | −33.945 | 28.765 | 1.00 | 37.78 | A |

APPENDIX 1-continued

X-RAY DATA COORDINATES FOR THE APO FORM OF CDP-ME SYNTHASE
(SEQ ID NOS: 9 and 10)

| ATOM | 976 | CA | PRO A | 146 | 70.620 | −32.630 | 30.672 | 1.00 | 38.88 | A |
|---|---|---|---|---|---|---|---|---|---|---|
| ATOM | 977 | CB | PRO A | 146 | 70.002 | −34.029 | 30.694 | 1.00 | 38.91 | A |
| ATOM | 978 | CG | PRO A | 146 | 70.985 | −34.851 | 29.916 | 1.00 | 39.01 | A |
| ATOM | 979 | C | PRO A | 146 | 71.426 | −32.321 | 31.928 | 1.00 | 38.94 | A |
| ATOM | 980 | O | PRO A | 146 | 72.326 | −33.071 | 32.299 | 1.00 | 39.80 | A |
| ATOM | 981 | N | GLY A | 147 | 71.101 | −31.200 | 32.565 | 1.00 | 39.50 | A |
| ATOM | 982 | CA | GLY A | 147 | 71.779 | −30.820 | 33.788 | 1.00 | 40.63 | A |
| ATOM | 983 | C | GLY A | 147 | 72.932 | −29.841 | 33.691 | 1.00 | 41.03 | A |
| ATOM | 984 | O | GLY A | 147 | 73.437 | −29.394 | 34.723 | 1.00 | 41.24 | A |
| ATOM | 985 | N | LYS A | 148 | 73.362 | −29.494 | 32.481 | 1.00 | 40.80 | A |
| ATOM | 986 | CA | LYS A | 148 | 74.478 | −28.559 | 32.350 | 1.00 | 41.09 | A |
| ATOM | 987 | CB | LYS A | 148 | 75.804 | −29.315 | 32.487 | 1.00 | 43.02 | A |
| ATOM | 988 | CG | LYS A | 148 | 75.922 | −30.559 | 31.634 | 1.00 | 44.82 | A |
| ATOM | 989 | CD | LYS A | 148 | 77.203 | −31.304 | 31.973 | 1.00 | 46.04 | A |
| ATOM | 990 | CE | LYS A | 148 | 77.309 | −32.616 | 31.212 | 1.00 | 47.64 | A |
| ATOM | 991 | NZ | LYS A | 148 | 78.531 | −33.375 | 31.613 | 1.00 | 48.80 | A |
| ATOM | 992 | C | LYS A | 148 | 74.485 | −27.718 | 31.080 | 1.00 | 39.86 | A |
| ATOM | 993 | O | LYS A | 148 | 73.754 | −27.997 | 30.133 | 1.00 | 38.94 | A |
| ATOM | 994 | N | ASN A | 149 | 75.322 | −26.684 | 31.079 | 1.00 | 39.20 | A |
| ATOM | 995 | CA | ASN A | 149 | 75.438 | −25.778 | 29.942 | 1.00 | 38.48 | A |
| ATOM | 996 | CB | ASN A | 149 | 75.851 | −24.379 | 30.420 | 1.00 | 40.65 | A |
| ATOM | 997 | CG | ASN A | 149 | 74.692 | −23.591 | 31.007 | 1.00 | 42.32 | A |
| ATOM | 998 | OD1 | ASN A | 149 | 74.838 | −22.413 | 31.339 | 1.00 | 44.71 | A |
| ATOM | 999 | ND2 | ASN A | 149 | 73.535 | −24.233 | 31.133 | 1.00 | 42.35 | A |
| ATOM | 1000 | C | ASN A | 149 | 76.405 | −26.247 | 28.859 | 1.00 | 36.56 | A |
| ATOM | 1001 | O | ASN A | 149 | 77.265 | −25.490 | 28.415 | 1.00 | 35.90 | A |
| ATOM | 1002 | N | ALA A | 150 | 76.265 | −27.500 | 28.443 | 1.00 | 34.82 | A |
| ATOM | 1003 | CA | ALA A | 150 | 77.105 | −28.054 | 27.390 | 1.00 | 31.22 | A |
| ATOM | 1004 | CB | ALA A | 150 | 77.848 | −29.285 | 27.891 | 1.00 | 32.48 | A |
| ATOM | 1005 | C | ALA A | 150 | 76.171 | −28.428 | 26.243 | 1.00 | 30.16 | A |
| ATOM | 1006 | O | ALA A | 150 | 75.058 | −28.904 | 26.474 | 1.00 | 26.62 | A |
| ATOM | 1007 | N | ILE A | 151 | 76.615 | −28.197 | 25.010 | 1.00 | 26.58 | A |
| ATOM | 1008 | CA | ILE A | 151 | 75.805 | −28.504 | 23.837 | 1.00 | 25.41 | A |
| ATOM | 1009 | CB | ILE A | 151 | 76.349 | −27.801 | 22.573 | 1.00 | 26.65 | A |
| ATOM | 1010 | CG2 | ILE A | 151 | 75.533 | −28.219 | 21.356 | 1.00 | 27.05 | A |
| ATOM | 1011 | CG1 | ILE A | 151 | 76.305 | −26.282 | 22.759 | 1.00 | 26.83 | A |
| ATOM | 1012 | CD1 | ILE A | 151 | 76.862 | −25.510 | 21.581 | 1.00 | 26.44 | A |
| ATOM | 1013 | C | ILE A | 151 | 75.738 | −29.998 | 23.544 | 1.00 | 25.85 | A |
| ATOM | 1014 | O | ILE A | 151 | 76.760 | −30.641 | 23.306 | 1.00 | 22.07 | A |
| ATOM | 1015 | N | ALA A | 152 | 74.527 | −30.543 | 23.558 | 1.00 | 24.82 | A |
| ATOM | 1016 | CA | ALA A | 152 | 74.327 | −31.954 | 23.256 | 1.00 | 25.61 | A |
| ATOM | 1017 | CB | ALA A | 152 | 72.971 | −32.419 | 23.793 | 1.00 | 26.97 | A |
| ATOM | 1018 | C | ALA A | 152 | 74.379 | −32.115 | 21.738 | 1.00 | 24.46 | A |
| ATOM | 1019 | O | ALA A | 152 | 75.088 | −32.970 | 21.211 | 1.00 | 23.85 | A |
| ATOM | 1020 | N | HIS A | 153 | 73.617 | −31.283 | 21.036 | 1.00 | 24.67 | A |
| ATOM | 1021 | CA | HIS A | 153 | 73.580 | −31.322 | 19.583 | 1.00 | 24.68 | A |
| ATOM | 1022 | CB | HIS A | 153 | 72.908 | −32.610 | 19.095 | 1.00 | 28.30 | A |
| ATOM | 1023 | CG | HIS A | 153 | 71.510 | −32.790 | 19.599 | 1.00 | 29.87 | A |
| ATOM | 1024 | CD2 | HIS A | 153 | 70.317 | −32.447 | 19.058 | 1.00 | 31.70 | A |
| ATOM | 1025 | ND1 | HIS A | 153 | 71.226 | −33.363 | 20.821 | 1.00 | 31.07 | A |
| ATOM | 1026 | CE1 | HIS A | 153 | 69.918 | −33.365 | 21.010 | 1.00 | 32.69 | A |
| ATOM | 1027 | NE2 | HIS A | 153 | 69.344 | −32.814 | 19.955 | 1.00 | 31.92 | A |
| ATOM | 1028 | C | HIS A | 153 | 72.797 | −30.120 | 19.073 | 1.00 | 23.95 | A |
| ATOM | 1029 | O | HIS A | 153 | 72.210 | −29.374 | 19.860 | 1.00 | 22.59 | A |
| ATOM | 1030 | N | THR A | 154 | 72.800 | −29.932 | 17.759 | 1.00 | 21.70 | A |
| ATOM | 1031 | CA | THR A | 154 | 72.075 | −28.832 | 17.134 | 1.00 | 24.21 | A |
| ATOM | 1032 | CB | THR A | 154 | 72.782 | −28.354 | 15.847 | 1.00 | 24.72 | A |
| ATOM | 1033 | CG1 | THR A | 154 | 74.059 | −27.797 | 16.180 | 1.00 | 21.79 | A |
| ATOM | 1034 | CG2 | THR A | 154 | 71.954 | −27.297 | 15.135 | 1.00 | 24.37 | A |
| ATOM | 1035 | C | THR A | 154 | 70.677 | −29.316 | 16.769 | 1.00 | 24.31 | A |
| ATOM | 1036 | O | THR A | 154 | 70.514 | −30.412 | 16.237 | 1.00 | 25.51 | A |
| ATOM | 1037 | N | VAL A | 155 | 69.671 | −28.501 | 17.068 | 1.00 | 24.64 | A |
| ATOM | 1038 | CA | VAL A | 155 | 68.289 | −28.846 | 16.754 | 1.00 | 26.89 | A |
| ATOM | 1039 | CB | VAL A | 155 | 67.327 | −28.285 | 17.823 | 1.00 | 27.09 | A |
| ATOM | 1040 | CG1 | VAL A | 155 | 65.883 | −28.450 | 17.369 | 1.00 | 26.63 | A |
| ATOM | 1041 | CG2 | VAL A | 155 | 67.548 | −29.009 | 19.150 | 1.00 | 26.37 | A |
| ATOM | 1042 | C | VAL A | 155 | 67.925 | −28.263 | 15.393 | 1.00 | 27.39 | A |
| ATOM | 1043 | O | VAL A | 155 | 68.016 | −27.056 | 15.191 | 1.00 | 28.03 | A |
| ATOM | 1044 | N | ASP A | 156 | 67.517 | −29.123 | 14.463 | 1.00 | 28.13 | A |
| ATOM | 1045 | CA | ASP A | 156 | 67.144 | −28.686 | 13.123 | 1.00 | 30.49 | A |
| ATOM | 1046 | CB | ASP A | 156 | 66.578 | −29.863 | 12.327 | 1.00 | 33.54 | A |
| ATOM | 1047 | CG | ASP A | 156 | 66.654 | −29.644 | 10.828 | 1.00 | 36.97 | A |
| ATOM | 1048 | OD1 | ASP A | 156 | 66.264 | −28.557 | 10.361 | 1.00 | 36.97 | A |
| ATOM | 1049 | OD2 | ASP A | 156 | 67.101 | −30.564 | 10.117 | 1.00 | 40.34 | A |
| ATOM | 1050 | C | ASP A | 156 | 66.087 | −27.592 | 13.231 | 1.00 | 30.33 | A |
| ATOM | 1051 | O | ASP A | 156 | 64.991 | −27.835 | 13.734 | 1.00 | 28.83 | A |

APPENDIX 1-continued

X-RAY DATA COORDINATES FOR THE APO FORM OF CDP-ME SYNTHASE
(SEQ ID NOS: 9 and 10)

| ATOM | 1052 N    | ARG A | 157 | 66.412 | −26.392 | 12.760 | 1.00 | 30.07 | A |
|------|-----------|-------|-----|--------|---------|--------|------|-------|---|
| ATOM | 1053 CA   | ARG A | 157 | 65.469 | −25.282 | 12.835 | 1.00 | 31.99 | A |
| ATOM | 1054 CB   | ARG A | 157 | 66.210 | −23.942 | 12.824 | 1.00 | 32.24 | A |
| ATOM | 1055 CG   | ARG A | 157 | 66.844 | −23.559 | 11.496 | 1.00 | 35.50 | A |
| ATOM | 1056 CD   | ARG A | 157 | 67.567 | −22.225 | 11.623 | 1.00 | 36.83 | A |
| ATOM | 1057 NE   | ARG A | 157 | 68.201 | −21.799 | 10.380 | 1.00 | 39.56 | A |
| ATOM | 1058 CZ   | ARG A | 157 | 67.542 | −21.450 | 9.279  | 1.00 | 41.25 | A |
| ATOM | 1059 NH1  | ARG A | 157 | 66.216 | −21.476 | 9.257  | 1.00 | 41.35 | A |
| ATOM | 1060 NH2  | ARG A | 157 | 68.212 | −21.067 | 8.200  | 1.00 | 41.73 | A |
| ATOM | 1061 C    | ARG A | 157 | 64.443 | −25.307 | 11.711 | 1.00 | 32.45 | A |
| ATOM | 1062 O    | ARG A | 157 | 63.503 | −24.515 | 11.706 | 1.00 | 30.04 | A |
| ATOM | 1063 N    | ASN A | 158 | 64.625 | −26.214 | 10.760 | 1.00 | 32.54 | A |
| ATOM | 1064 CA   | ASN A | 158 | 63.696 | −26.335 | 9.647  | 1.00 | 33.71 | A |
| ATOM | 1065 CB   | ASN A | 158 | 64.305 | −27.205 | 8.546  | 1.00 | 37.98 | A |
| ATOM | 1066 CG   | ASN A | 158 | 63.351 | −27.436 | 7.389  | 1.00 | 41.42 | A |
| ATOM | 1067 OD1  | ASN A | 158 | 62.845 | −26.489 | 6.783  | 1.00 | 43.61 | A |
| ATOM | 1068 ND2  | ASN A | 158 | 63.108 | −28.703 | 7.070  | 1.00 | 43.14 | A |
| ATOM | 1069 C    | ASN A | 158 | 62.393 | −26.950 | 10.152 | 1.00 | 31.21 | A |
| ATOM | 1070 O    | ASN A | 158 | 62.379 | −28.070 | 10.663 | 1.00 | 30.10 | A |
| ATOM | 1071 N    | GLY A | 159 | 61.298 | −26.212 | 10.008 | 1.00 | 28.44 | A |
| ATOM | 1072 CA   | GLY A | 159 | 60.016 | −26.705 | 10.473 | 1.00 | 26.58 | A |
| ATOM | 1073 C    | GLY A | 159 | 59.798 | −26.386 | 11.942 | 1.00 | 24.02 | A |
| ATOM | 1074 O    | GLY A | 159 | 58.865 | −26.886 | 12.564 | 1.00 | 21.02 | A |
| ATOM | 1075 N    | LEU A | 160 | 60.670 | −25.550 | 12.496 | 1.00 | 22.36 | A |
| ATOM | 1076 CA   | LEU A | 160 | 60.573 | −25.149 | 13.896 | 1.00 | 21.71 | A |
| ATOM | 1077 CB   | LEU A | 160 | 61.952 | −25.171 | 14.554 | 1.00 | 22.54 | A |
| ATOM | 1078 CG   | LEU A | 160 | 61.982 | −25.095 | 16.081 | 1.00 | 23.43 | A |
| ATOM | 1079 CD1  | LEU A | 160 | 61.317 | −26.329 | 16.678 | 1.00 | 22.78 | A |
| ATOM | 1080 CD2  | LEU A | 160 | 63.429 | −24.994 | 16.553 | 1.00 | 23.28 | A |
| ATOM | 1081 C    | LEU A | 160 | 60.004 | −23.737 | 13.906 | 1.00 | 20.61 | A |
| ATOM | 1082 O    | LEU A | 160 | 60.465 | −22.867 | 13.164 | 1.00 | 20.82 | A |
| ATOM | 1083 N    | TRP A | 161 | 59.005 | −23.512 | 14.753 | 1.00 | 19.44 | A |
| ATOM | 1084 CA   | TRP A | 161 | 58.342 | −22.216 | 14.818 | 1.00 | 18.39 | A |
| ATOM | 1085 CB   | TRP A | 161 | 56.937 | −22.317 | 14.198 | 1.00 | 18.58 | A |
| ATOM | 1086 CG   | TRP A | 161 | 56.879 | −22.686 | 12.730 | 1.00 | 21.47 | A |
| ATOM | 1087 CD2  | TRP A | 161 | 56.373 | −21.868 | 11.670 | 1.00 | 22.44 | A |
| ATOM | 1088 CE2  | TRP A | 161 | 56.491 | −22.611 | 10.472 | 1.00 | 23.10 | A |
| ATOM | 1089 CE3  | TRP A | 161 | 55.823 | −20.580 | 11.617 | 1.00 | 24.37 | A |
| ATOM | 1090 CD1  | TRP A | 161 | 57.280 | −23.862 | 12.147 | 1.00 | 22.79 | A |
| ATOM | 1091 NE1  | TRP A | 161 | 57.048 | −23.821 | 10.791 | 1.00 | 22.67 | A |
| ATOM | 1092 CZ2  | TRP A | 161 | 56.089 | −22.100 | 9.230  | 1.00 | 26.00 | A |
| ATOM | 1093 CZ3  | TRP A | 161 | 55.423 | −20.073 | 10.387 | 1.00 | 26.39 | A |
| ATOM | 1094 CH2  | TRP A | 161 | 55.555 | −20.835 | 9.209  | 1.00 | 27.16 | A |
| ATOM | 1095 C    | TRP A | 161 | 58.183 | −21.670 | 16.231 | 1.00 | 15.37 | A |
| ATOM | 1096 O    | TRP A | 161 | 58.079 | −22.427 | 17.189 | 1.00 | 15.87 | A |
| ATOM | 1097 N    | HIS A | 162 | 58.173 | −20.344 | 16.343 | 1.00 | 16.40 | A |
| ATOM | 1098 CA   | HIS A | 162 | 57.949 | −19.664 | 17.607 | 1.00 | 17.13 | A |
| ATOM | 1099 CB   | HIS A | 162 | 58.565 | −18.263 | 17.590 | 1.00 | 19.43 | A |
| ATOM | 1100 CG   | HIS A | 162 | 60.046 | −18.243 | 17.775 | 1.00 | 24.18 | A |
| ATOM | 1101 CD2  | HIS A | 162 | 60.797 | −18.004 | 18.873 | 1.00 | 23.64 | A |
| ATOM | 1102 ND1  | HIS A | 162 | 60.932 | −18.472 | 16.744 | 1.00 | 27.34 | A |
| ATOM | 1103 CE1  | HIS A | 162 | 62.167 | −18.372 | 17.202 | 1.00 | 26.03 | A |
| ATOM | 1104 NE2  | HIS A | 162 | 62.113 | −18.088 | 18.490 | 1.00 | 27.35 | A |
| ATOM | 1105 C    | HIS A | 162 | 56.427 | −19.509 | 17.706 | 1.00 | 15.26 | A |
| ATOM | 1106 O    | HIS A | 162 | 55.823 | −18.880 | 16.840 | 1.00 | 17.66 | A |
| ATOM | 1107 N    | ALA A | 163 | 55.809 | −20.073 | 18.738 | 1.00 | 13.97 | A |
| ATOM | 1108 CA   | ALA A | 163 | 54.362 | −19.952 | 18.902 | 1.00 | 13.57 | A |
| ATOM | 1109 CB   | ALA A | 163 | 53.862 | −20.976 | 19.901 | 1.00 | 14.57 | A |
| ATOM | 1110 C    | ALA A | 163 | 54.034 | −18.552 | 19.391 | 1.00 | 14.53 | A |
| ATOM | 1111 O    | ALA A | 163 | 54.675 | −18.042 | 20.314 | 1.00 | 16.45 | A |
| ATOM | 1112 N    | LEU A | 164 | 53.065 | −17.898 | 18.757 | 1.00 | 13.14 | A |
| ATOM | 1113 CA   | LEU A | 164 | 52.670 | −16.553 | 19.204 | 1.00 | 11.47 | A |
| ATOM | 1114 CB   | LEU A | 164 | 52.984 | −15.514 | 18.120 | 1.00 | 13.09 | A |
| ATOM | 1115 CG   | LEU A | 164 | 54.448 | −15.463 | 17.633 | 1.00 | 14.10 | A |
| ATOM | 1116 CD1  | LEU A | 164 | 54.539 | −14.520 | 16.440 | 1.00 | 17.90 | A |
| ATOM | 1117 CD2  | LEU A | 164 | 55.363 | −15.000 | 18.753 | 1.00 | 16.79 | A |
| ATOM | 1118 C    | LEU A | 164 | 51.169 | −16.600 | 19.463 | 1.00 | 12.44 | A |
| ATOM | 1119 O    | LEU A | 164 | 50.603 | −17.681 | 19.589 | 1.00 | 12.56 | A |
| ATOM | 1120 N    | THR A | 165 | 50.534 | −15.445 | 19.620 | 1.00 | 12.78 | A |
| ATOM | 1121 CA   | THR A | 165 | 49.085 | −15.391 | 19.802 | 1.00 | 11.52 | A |
| ATOM | 1122 CB   | THR A | 165 | 48.645 | −15.233 | 21.300 | 1.00 | 11.71 | A |
| ATOM | 1123 OG1  | THR A | 165 | 48.793 | −13.876 | 21.724 | 1.00 | 12.61 | A |
| ATOM | 1124 CG2  | THR A | 165 | 49.488 | −16.113 | 22.200 | 1.00 | 14.85 | A |
| ATOM | 1125 C    | THR A | 165 | 48.659 | −14.175 | 18.981 | 1.00 | 11.86 | A |
| ATOM | 1126 O    | THR A | 165 | 49.478 | −13.303 | 18.681 | 1.00 | 12.37 | A |
| ATOM | 1127 N    | PRO A | 166 | 47.373 | −14.082 | 18.628 | 1.00 | 10.19 | A |

APPENDIX 1-continued

X-RAY DATA COORDINATES FOR THE APO FORM OF CDP-ME SYNTHASE
(SEQ ID NOS: 9 and 10)

| ATOM | 1128CD | PRO A | 166 | 46.851 | −12.904 | 17.917 | 1.00 | 11.81 | A |
|---|---|---|---|---|---|---|---|---|---|
| ATOM | 1129CA | PRO A | 166 | 46.275 | −14.997 | 18.941 | 1.00 | 10.40 | A |
| ATOM | 1130CB | PRO A | 166 | 45.063 | −14.307 | 18.315 | 1.00 | 12.38 | A |
| ATOM | 1131CG | PRO A | 166 | 45.404 | −12.891 | 18.365 | 1.00 | 11.90 | A |
| ATOM | 1132C | PRO A | 166 | 46.364 | −16.441 | 18.469 | 1.00 | 12.81 | A |
| ATOM | 1133O | PRO A | 166 | 47.119 | −16.791 | 17.550 | 1.00 | 10.98 | A |
| ATOM | 1134N | GLN A | 167 | 45.540 | −17.251 | 19.129 | 1.00 | 11.38 | A |
| ATOM | 1135CA | GLN A | 167 | 45.376 | −18.666 | 18.848 | 1.00 | 10.22 | A |
| ATOM | 1136CB | GLN A | 167 | 45.898 | −19.489 | 20.026 | 1.00 | 11.32 | A |
| ATOM | 1137CG | GLN A | 167 | 47.367 | −19.167 | 20.284 | 1.00 | 11.76 | A |
| ATOM | 1138CD | GLN A | 167 | 48.173 | −20.327 | 20.833 | 1.00 | 13.08 | A |
| ATOM | 1139OE1 | GLN A | 167 | 47.624 | −21.332 | 21.292 | 1.00 | 14.71 | A |
| ATOM | 1140NE2 | GLN A | 167 | 49.494 | −20.184 | 20.797 | 1.00 | 13.26 | A |
| ATOM | 1141C | GLN A | 167 | 43.863 | −18.754 | 18.636 | 1.00 | 11.42 | A |
| ATOM | 1142O | GLN A | 167 | 43.078 | −18.354 | 19.490 | 1.00 | 13.10 | A |
| ATOM | 1143N | PHE A | 168 | 43.485 | −19.262 | 17.469 | 1.00 | 10.38 | A |
| ATOM | 1144CA | PHE A | 168 | 42.104 | −19.303 | 16.997 | 1.00 | 9.78 | A |
| ATOM | 1145CB | PHE A | 168 | 42.121 | −18.586 | 15.638 | 1.00 | 9.64 | A |
| ATOM | 1146CG | PHE A | 168 | 40.775 | −18.236 | 15.103 | 1.00 | 9.45 | A |
| ATOM | 1147CD1 | PHE A | 168 | 39.814 | −17.659 | 15.917 | 1.00 | 10.13 | A |
| ATOM | 1148CD2 | PHE A | 168 | 40.469 | −18.471 | 13.770 | 1.00 | 13.27 | A |
| ATOM | 1149CE1 | PHE A | 168 | 38.566 | −17.315 | 15.412 | 1.00 | 11.77 | A |
| ATOM | 1150CE2 | PHE A | 168 | 39.225 | −18.129 | 13.262 | 1.00 | 12.71 | A |
| ATOM | 1151CZ | PHE A | 168 | 38.270 | −17.554 | 14.084 | 1.00 | 13.44 | A |
| ATOM | 1152C | PHE A | 168 | 41.526 | −20.710 | 16.862 | 1.00 | 9.50 | A |
| ATOM | 1153O | PHE A | 168 | 41.988 | −21.484 | 16.030 | 1.00 | 11.15 | A |
| ATOM | 1154N | PHE A | 169 | 40.513 | −21.049 | 17.655 | 1.00 | 11.61 | A |
| ATOM | 1155CA | PHE A | 169 | 39.950 | −22.400 | 17.565 | 1.00 | 11.09 | A |
| ATOM | 1156CB | PHE A | 169 | 40.533 | −23.312 | 18.663 | 1.00 | 13.00 | A |
| ATOM | 1157CG | PHE A | 169 | 42.023 | −23.199 | 18.853 | 1.00 | 15.57 | A |
| ATOM | 1158CD1 | PHE A | 169 | 42.542 | −22.401 | 19.861 | 1.00 | 16.47 | A |
| ATOM | 1159CD2 | PHE A | 169 | 42.897 | −23.947 | 18.074 | 1.00 | 18.54 | A |
| ATOM | 1160CE1 | PHE A | 169 | 43.907 | −22.348 | 20.093 | 1.00 | 18.21 | A |
| ATOM | 1161CE2 | PHE A | 169 | 44.272 | −23.902 | 18.297 | 1.00 | 18.21 | A |
| ATOM | 1162CZ | PHE A | 169 | 44.773 | −23.104 | 19.314 | 1.00 | 16.26 | A |
| ATOM | 1163C | PHE A | 169 | 38.436 | −22.442 | 17.740 | 1.00 | 11.01 | A |
| ATOM | 1164O | PHE A | 169 | 37.827 | −21.490 | 18.205 | 1.00 | 12.13 | A |
| ATOM | 1165N | PRO A | 170 | 37.803 | −23.552 | 17.333 | 1.00 | 13.08 | A |
| ATOM | 1166CD | PRO A | 170 | 38.293 | −24.621 | 16.447 | 1.00 | 13.96 | A |
| ATOM | 1167CA | PRO A | 170 | 36.351 | −23.636 | 17.523 | 1.00 | 13.24 | A |
| ATOM | 1168CB | PRO A | 170 | 36.010 | −25.010 | 16.953 | 1.00 | 13.11 | A |
| ATOM | 1169CG | PRO A | 170 | 36.996 | −25.159 | 15.834 | 1.00 | 13.87 | A |
| ATOM | 1170C | PRO A | 170 | 36.168 | −23.573 | 19.055 | 1.00 | 14.27 | A |
| ATOM | 1171O | PRO A | 170 | 36.904 | −24.223 | 19.793 | 1.00 | 15.64 | A |
| ATOM | 1172N | ARG A | 171 | 35.203 | −22.784 | 19.516 | 1.00 | 15.38 | A |
| ATOM | 1173CA | ARG A | 171 | 34.944 | −22.568 | 20.943 | 1.00 | 16.47 | A |
| ATOM | 1174CB | ARG A | 171 | 33.707 | −21.671 | 21.089 | 1.00 | 19.58 | A |
| ATOM | 1175CG | ARG A | 171 | 33.499 | −21.045 | 22.464 | 1.00 | 24.53 | A |
| ATOM | 1176CD | ARG A | 171 | 32.538 | −21.843 | 23.341 | 1.00 | 32.28 | A |
| ATOM | 1177NE | ARG A | 171 | 31.163 | −21.825 | 22.837 | 1.00 | 39.17 | A |
| ATOM | 1178CZ | ARG A | 171 | 30.141 | −22.433 | 23.433 | 1.00 | 41.43 | A |
| ATOM | 1179NH1 | ARG A | 171 | 30.329 | −23.110 | 24.558 | 1.00 | 43.39 | A |
| ATOM | 1180NH2 | ARG A | 171 | 28.930 | −22.364 | 22.904 | 1.00 | 43.43 | A |
| ATOM | 1181C | ARG A | 171 | 34.773 | −23.823 | 21.798 | 1.00 | 15.64 | A |
| ATOM | 1182O | ARG A | 171 | 35.511 | −24.041 | 22.765 | 1.00 | 15.62 | A |
| ATOM | 1183N | GLU A | 172 | 33.811 | −24.665 | 21.443 | 1.00 | 16.65 | A |
| ATOM | 1184CA | GLU A | 172 | 33.586 | −25.851 | 22.249 | 1.00 | 15.38 | A |
| ATOM | 1185CB | GLU A | 172 | 32.235 | −26.506 | 21.879 | 1.00 | 14.49 | A |
| ATOM | 1186CG | GLU A | 172 | 31.091 | −25.810 | 22.641 | 1.00 | 17.62 | A |
| ATOM | 1187CD | GLU A | 172 | 29.674 | −26.221 | 22.232 | 1.00 | 15.62 | A |
| ATOM | 1188OE1 | GLU A | 172 | 29.455 | −27.379 | 21.803 | 1.00 | 16.63 | A |
| ATOM | 1189OE2 | GLU A | 172 | 28.765 | −25.382 | 22.373 | 1.00 | 16.16 | A |
| ATOM | 1190C | GLU A | 172 | 34.758 | −26.824 | 22.220 | 1.00 | 15.30 | A |
| ATOM | 1191O | GLU A | 172 | 35.094 | −27.426 | 23.244 | 1.00 | 15.03 | A |
| ATOM | 1192N | LEU A | 173 | 35.404 | −26.964 | 21.066 | 1.00 | 15.19 | A |
| ATOM | 1193CA | LEU A | 173 | 36.556 | −27.865 | 20.957 | 1.00 | 15.54 | A |
| ATOM | 1194CB | LEU A | 173 | 37.074 | −27.912 | 19.515 | 1.00 | 16.17 | A |
| ATOM | 1195CG | LEU A | 173 | 38.302 | −28.780 | 19.253 | 1.00 | 19.39 | A |
| ATOM | 1196CD1 | LEU A | 173 | 37.989 | −30.242 | 19.554 | 1.00 | 22.96 | A |
| ATOM | 1197CD2 | LEU A | 173 | 38.736 | −28.613 | 17.800 | 1.00 | 21.76 | A |
| ATOM | 1198C | LEU A | 173 | 37.664 | −27.387 | 21.893 | 1.00 | 16.30 | A |
| ATOM | 1199O | LEU A | 173 | 38.293 | −28.196 | 22.577 | 1.00 | 16.75 | A |
| ATOM | 1200N | LEU A | 174 | 37.902 | −26.076 | 21.923 | 1.00 | 15.80 | A |
| ATOM | 1201CA | LEU A | 174 | 38.935 | −25.526 | 22.802 | 1.00 | 17.81 | A |
| ATOM | 1202CB | LEU A | 174 | 39.064 | −24.007 | 22.613 | 1.00 | 18.63 | A |
| ATOM | 1203CG | LEU A | 174 | 40.204 | −23.353 | 23.424 | 1.00 | 20.38 | A |

APPENDIX 1-continued

X-RAY DATA COORDINATES FOR THE APO FORM OF CDP-ME SYNTHASE
(SEQ ID NOS: 9 and 10)

| ATOM | 1204 | CD1 | LEU A | 174 | 41.551 | −23.921 | 22.968 | 1.00 | 22.36 | A |
|---|---|---|---|---|---|---|---|---|---|---|
| ATOM | 1205 | CD2 | LEU A | 174 | 40.196 | −21.840 | 23.223 | 1.00 | 20.45 | A |
| ATOM | 1206 | C | LEU A | 174 | 38.560 | −25.824 | 24.243 | 1.00 | 18.39 | A |
| ATOM | 1207 | O | LEU A | 174 | 39.398 | −26.230 | 25.041 | 1.00 | 19.22 | A |
| ATOM | 1208 | N | HIS A | 175 | 37.289 | −25.616 | 24.571 | 1.00 | 16.07 | A |
| ATOM | 1209 | CA | HIS A | 175 | 36.804 | −25.875 | 25.922 | 1.00 | 18.44 | A |
| ATOM | 1210 | CB | HIS A | 175 | 35.301 | −25.595 | 26.002 | 1.00 | 20.30 | A |
| ATOM | 1211 | CG | HIS A | 175 | 34.657 | −26.074 | 27.267 | 1.00 | 26.13 | A |
| ATOM | 1212 | CD2 | HIS A | 175 | 34.076 | −27.259 | 27.578 | 1.00 | 24.95 | A |
| ATOM | 1213 | ND1 | HIS A | 175 | 34.573 | −25.299 | 28.403 | 1.00 | 27.10 | A |
| ATOM | 1214 | CE1 | HIS A | 175 | 33.970 | −25.983 | 29.359 | 1.00 | 27.70 | A |
| ATOM | 1215 | NE2 | HIS A | 175 | 33.659 | −27.176 | 28.884 | 1.00 | 28.69 | A |
| ATOM | 1216 | C | HIS A | 175 | 37.060 | −27.326 | 26.325 | 1.00 | 18.42 | A |
| ATOM | 1217 | O | HIS A | 175 | 37.607 | −27.593 | 27.393 | 1.00 | 20.46 | A |
| ATOM | 1218 | N | ASP A | 176 | 36.663 | −28.260 | 25.470 | 1.00 | 20.15 | A |
| ATOM | 1219 | CA | ASP A | 176 | 36.829 | −29.671 | 25.783 | 1.00 | 18.85 | A |
| ATOM | 1220 | CB | ASP A | 176 | 36.087 | −30.524 | 24.757 | 1.00 | 19.63 | A |
| ATOM | 1221 | CG | ASP A | 176 | 34.597 | −30.270 | 24.777 | 1.00 | 20.97 | A |
| ATOM | 1222 | OD1 | ASP A | 176 | 34.129 | −29.693 | 25.777 | 1.00 | 20.22 | A |
| ATOM | 1223 | OD2 | ASP A | 176 | 33.912 | −30.644 | 23.801 | 1.00 | 21.93 | A |
| ATOM | 1224 | C | ASP A | 176 | 38.275 | −30.122 | 25.894 | 1.00 | 19.46 | A |
| ATOM | 1225 | O | ASP A | 176 | 38.631 | −30.880 | 26.799 | 1.00 | 20.15 | A |
| ATOM | 1226 | N | CYS A | 177 | 39.113 | −29.635 | 24.989 | 1.00 | 18.28 | A |
| ATOM | 1227 | CA | CYS A | 177 | 40.522 | −30.003 | 24.996 | 1.00 | 20.61 | A |
| ATOM | 1228 | CB | CYS A | 177 | 41.215 | −29.469 | 23.750 | 1.00 | 19.81 | A |
| ATOM | 1229 | SG | CYS A | 177 | 40.782 | −30.393 | 22.277 | 1.00 | 16.88 | A |
| ATOM | 1230 | C | CYS A | 177 | 41.261 | −29.512 | 26.226 | 1.00 | 22.14 | A |
| ATOM | 1231 | O | CYS A | 177 | 42.071 | −30.236 | 26.802 | 1.00 | 21.55 | A |
| ATOM | 1232 | N | LEU A | 178 | 40.995 | −28.278 | 26.624 | 1.00 | 22.35 | A |
| ATOM | 1233 | CA | LEU A | 178 | 41.663 | −27.743 | 27.795 | 1.00 | 26.07 | A |
| ATOM | 1234 | CB | LEU A | 178 | 41.582 | −26.217 | 27.795 | 1.00 | 28.55 | A |
| ATOM | 1235 | CG | LEU A | 178 | 42.714 | −25.640 | 26.937 | 1.00 | 31.41 | A |
| ATOM | 1236 | CD1 | LEU A | 178 | 42.177 | −24.634 | 25.944 | 1.00 | 35.20 | A |
| ATOM | 1237 | CD2 | LEU A | 178 | 43.759 | −25.012 | 27.835 | 1.00 | 33.45 | A |
| ATOM | 1238 | C | LEU A | 178 | 41.083 | −28.339 | 29.070 | 1.00 | 25.60 | A |
| ATOM | 1239 | O | LEU A | 178 | 41.780 | −28.489 | 30.077 | 1.00 | 25.60 | A |
| ATOM | 1240 | N | THR A | 179 | 39.810 | −28.703 | 29.020 | 1.00 | 24.95 | A |
| ATOM | 1241 | CA | THR A | 179 | 39.165 | −29.306 | 30.177 | 1.00 | 25.40 | A |
| ATOM | 1242 | CB | THR A | 179 | 37.649 | −29.433 | 29.960 | 1.00 | 24.57 | A |
| ATOM | 1243 | OG1 | THR A | 179 | 37.037 | −28.149 | 30.145 | 1.00 | 22.07 | A |
| ATOM | 1244 | CG2 | THR A | 179 | 37.049 | −30.437 | 30.942 | 1.00 | 25.77 | A |
| ATOM | 1245 | C | THR A | 179 | 39.759 | −30.690 | 30.411 | 1.00 | 27.23 | A |
| ATOM | 1246 | O | THR A | 179 | 40.062 | −31.057 | 31.546 | 1.00 | 27.48 | A |
| ATOM | 1247 | N | ARG A | 180 | 39.934 | −31.450 | 29.334 | 1.00 | 28.52 | A |
| ATOM | 1248 | CA | ARG A | 180 | 40.488 | −32.795 | 29.440 | 1.00 | 31.50 | A |
| ATOM | 1249 | CB | ARG A | 180 | 40.269 | −33.566 | 28.136 | 1.00 | 33.72 | A |
| ATOM | 1250 | CG | ARG A | 180 | 40.901 | −34.947 | 28.138 | 1.00 | 36.92 | A |
| ATOM | 1251 | CD | ARG A | 180 | 40.499 | −35.757 | 26.916 | 1.00 | 40.93 | A |
| ATOM | 1252 | NE | ARG A | 180 | 41.208 | −37.032 | 26.861 | 1.00 | 43.91 | A |
| ATOM | 1253 | CZ | ARG A | 180 | 40.912 | −38.022 | 26.026 | 1.00 | 45.94 | A |
| ATOM | 1254 | NH1 | ARG A | 180 | 39.911 | −37.893 | 25.167 | 1.00 | 46.67 | A |
| ATOM | 1255 | NH2 | ARG A | 180 | 41.618 | −39.146 | 26.052 | 1.00 | 47.09 | A |
| ATOM | 1256 | C | ARG A | 180 | 41.974 | −32.777 | 29.786 | 1.00 | 32.83 | A |
| ATOM | 1257 | O | ARG A | 180 | 42.429 | −33.549 | 30.628 | 1.00 | 33.15 | A |
| ATOM | 1258 | N | ALA A | 181 | 42.723 | −31.892 | 29.135 | 1.00 | 33.00 | A |
| ATOM | 1259 | CA | ALA A | 181 | 44.159 | −31.778 | 29.377 | 1.00 | 34.41 | A |
| ATOM | 1260 | CB | ALA A | 181 | 44.744 | −30.651 | 28.523 | 1.00 | 32.92 | A |
| ATOM | 1261 | C | ALA A | 181 | 44.448 | −31.521 | 30.854 | 1.00 | 35.71 | A |
| ATOM | 1262 | O | ALA A | 181 | 45.376 | −32.097 | 31.423 | 1.00 | 34.97 | A |
| ATOM | 1263 | N | LEU A | 182 | 43.649 | −30.654 | 31.467 | 1.00 | 36.77 | A |
| ATOM | 1264 | CA | LEU A | 182 | 43.818 | −30.319 | 32.876 | 1.00 | 39.13 | A |
| ATOM | 1265 | CB | LEU A | 182 | 42.981 | −29.091 | 33.232 | 1.00 | 38.77 | A |
| ATOM | 1266 | CG | LEU A | 182 | 43.462 | −27.746 | 32.688 | 1.00 | 40.00 | A |
| ATOM | 1267 | CD1 | LEU A | 182 | 42.441 | −26.672 | 33.019 | 1.00 | 39.19 | A |
| ATOM | 1268 | CD2 | LEU A | 182 | 44.821 | −27.396 | 33.293 | 1.00 | 39.21 | A |
| ATOM | 1269 | C | LEU A | 182 | 43.435 | −31.470 | 33.800 | 1.00 | 41.08 | A |
| ATOM | 1270 | O | LEU A | 182 | 44.134 | −31.750 | 34.774 | 1.00 | 41.29 | A |
| ATOM | 1271 | N | ASN A | 183 | 42.321 | −32.128 | 33.495 | 1.00 | 42.14 | A |
| ATOM | 1272 | CA | ASN A | 183 | 41.845 | −33.242 | 34.305 | 1.00 | 44.22 | A |
| ATOM | 1273 | CB | ASN A | 183 | 40.520 | −33.776 | 33.755 | 1.00 | 45.30 | A |
| ATOM | 1274 | CG | ASN A | 183 | 39.970 | −34.929 | 34.578 | 1.00 | 47.82 | A |
| ATOM | 1275 | OD1 | ASN A | 183 | 39.182 | −35.739 | 34.086 | 1.00 | 49.08 | A |
| ATOM | 1276 | ND2 | ASN A | 183 | 40.376 | −35.001 | 35.843 | 1.00 | 49.10 | A |
| ATOM | 1277 | C | ASN A | 183 | 42.858 | −34.378 | 34.341 | 1.00 | 44.98 | A |
| ATOM | 1278 | O | ASN A | 183 | 43.010 | −35.057 | 35.358 | 1.00 | 45.78 | A |
| ATOM | 1279 | N | GLU A | 184 | 43.546 | −34.589 | 33.225 | 1.00 | 44.35 | A |

APPENDIX 1-continued

X-RAY DATA COORDINATES FOR THE APO FORM OF CDP-ME SYNTHASE
(SEQ ID NOS: 9 and 10)

| ATOM | 1280 | CA | GLU A | 184 | 44.536 | −35.653 | 33.136 | 1.00 | 44.82 | A |
|---|---|---|---|---|---|---|---|---|---|---|
| ATOM | 1281 | CB | GLU A | 184 | 44.546 | −36.236 | 31.720 | 1.00 | 45.55 | A |
| ATOM | 1282 | CG | GLU A | 184 | 43.309 | −37.058 | 31.391 | 1.00 | 47.02 | A |
| ATOM | 1283 | CD | GLU A | 184 | 43.304 | −37.575 | 29.968 | 1.00 | 47.31 | A |
| ATOM | 1284 | OE1 | GLU A | 184 | 44.341 | −38.103 | 29.517 | 1.00 | 49.13 | A |
| ATOM | 1285 | OE2 | GLU A | 184 | 42.259 | −37.465 | 29.297 | 1.00 | 49.40 | A |
| ATOM | 1286 | C | GLU A | 184 | 45.934 | −35.187 | 33.524 | 1.00 | 44.36 | A |
| ATOM | 1287 | O | GLU A | 184 | 46.915 | −35.898 | 33.307 | 1.00 | 44.23 | A |
| ATOM | 1288 | N | GLY A | 185 | 46.017 | −33.992 | 34.101 | 1.00 | 44.38 | A |
| ATOM | 1289 | CA | GLY A | 185 | 47.299 | −33.454 | 34.524 | 1.00 | 44.47 | A |
| ATOM | 1290 | C | GLY A | 185 | 48.365 | −33.401 | 33.444 | 1.00 | 44.39 | A |
| ATOM | 1291 | O | GLY A | 185 | 49.514 | −33.776 | 33.680 | 1.00 | 44.75 | A |
| ATOM | 1292 | N | ALA A | 186 | 47.994 | −32.929 | 32.259 | 1.00 | 43.68 | A |
| ATOM | 1293 | CA | ALA A | 186 | 48.936 | −32.827 | 31.154 | 1.00 | 42.71 | A |
| ATOM | 1294 | CB | ALA A | 186 | 48.192 | −32.899 | 29.826 | 1.00 | 42.94 | A |
| ATOM | 1295 | C | ALA A | 186 | 49.722 | −31.525 | 31.242 | 1.00 | 41.91 | A |
| ATOM | 1296 | O | ALA A | 186 | 49.251 | −30.545 | 31.818 | 1.00 | 41.89 | A |
| ATOM | 1297 | N | THR A | 187 | 50.925 | −31.526 | 30.678 | 1.00 | 41.92 | A |
| ATOM | 1298 | CA | THR A | 187 | 51.776 | −30.341 | 30.675 | 1.00 | 41.18 | A |
| ATOM | 1299 | CB | THR A | 187 | 53.240 | −30.708 | 30.364 | 1.00 | 42.41 | A |
| ATOM | 1300 | OG1 | THR A | 187 | 53.703 | −31.677 | 31.313 | 1.00 | 44.02 | A |
| ATOM | 1301 | CG2 | THR A | 187 | 54.128 | −29.473 | 30.431 | 1.00 | 43.11 | A |
| ATOM | 1302 | C | THR A | 187 | 51.268 | −29.386 | 29.602 | 1.00 | 39.68 | A |
| ATOM | 1303 | O | THR A | 187 | 51.479 | −29.611 | 28.411 | 1.00 | 40.32 | A |
| ATOM | 1304 | N | ILE A | 188 | 50.602 | −28.320 | 30.031 | 1.00 | 37.50 | A |
| ATOM | 1305 | CA | ILE A | 188 | 50.043 | −27.344 | 29.104 | 1.00 | 35.51 | A |
| ATOM | 1306 | CB | ILE A | 188 | 48.575 | −27.025 | 29.469 | 1.00 | 36.05 | A |
| ATOM | 1307 | CG2 | ILE A | 188 | 47.942 | −26.164 | 28.385 | 1.00 | 36.62 | A |
| ATOM | 1308 | CG1 | ILE A | 188 | 47.789 | −28.325 | 29.624 | 1.00 | 37.60 | A |
| ATOM | 1309 | CD1 | ILE A | 188 | 46.371 | −28.127 | 30.108 | 1.00 | 38.78 | A |
| ATOM | 1310 | C | ILE A | 188 | 50.827 | −26.032 | 29.074 | 1.00 | 32.55 | A |
| ATOM | 1311 | O | ILE A | 188 | 51.164 | −25.472 | 30.119 | 1.00 | 32.59 | A |
| ATOM | 1312 | N | THR A | 189 | 51.115 | −25.554 | 27.867 | 1.00 | 27.88 | A |
| ATOM | 1313 | CA | THR A | 189 | 51.819 | −24.296 | 27.681 | 1.00 | 25.45 | A |
| ATOM | 1314 | CB | THR A | 189 | 53.035 | −24.458 | 26.742 | 1.00 | 24.62 | A |
| ATOM | 1315 | OG1 | THR A | 189 | 52.666 | −25.255 | 25.612 | 1.00 | 22.11 | A |
| ATOM | 1316 | CG2 | THR A | 189 | 54.191 | −25.135 | 27.478 | 1.00 | 25.89 | A |
| ATOM | 1317 | C | THR A | 189 | 50.816 | −23.314 | 27.089 | 1.00 | 23.45 | A |
| ATOM | 1318 | O | THR A | 189 | 50.216 | −22.523 | 27.822 | 1.00 | 24.18 | A |
| ATOM | 1319 | N | ASP A | 190 | 50.614 | −23.365 | 25.775 | 1.00 | 20.98 | A |
| ATOM | 1320 | CA | ASP A | 190 | 49.642 | −22.475 | 25.143 | 1.00 | 17.54 | A |
| ATOM | 1321 | CB | ASP A | 190 | 50.218 | −21.838 | 23.865 | 1.00 | 16.47 | A |
| ATOM | 1322 | CG | ASP A | 190 | 50.681 | −22.854 | 22.830 | 1.00 | 16.26 | A |
| ATOM | 1323 | OD1 | ASP A | 190 | 50.635 | −24.068 | 23.075 | 1.00 | 15.78 | A |
| ATOM | 1324 | OD2 | ASP A | 190 | 51.111 | −22.432 | 21.730 | 1.00 | 15.44 | A |
| ATOM | 1325 | C | ASP A | 190 | 48.357 | −23.257 | 24.833 | 1.00 | 15.97 | A |
| ATOM | 1326 | O | ASP A | 190 | 48.256 | −24.436 | 25.149 | 1.00 | 17.40 | A |
| ATOM | 1327 | N | GLU A | 191 | 47.368 | −22.582 | 24.257 | 1.00 | 16.07 | A |
| ATOM | 1328 | CA | GLU A | 191 | 46.110 | −23.221 | 23.938 | 1.00 | 15.95 | A |
| ATOM | 1329 | CB | GLU A | 191 | 45.088 | −22.205 | 23.413 | 1.00 | 15.82 | A |
| ATOM | 1330 | CG | GLU A | 191 | 44.532 | −21.243 | 24.467 | 1.00 | 20.72 | A |
| ATOM | 1331 | CD | GLU A | 191 | 45.597 | −20.325 | 25.049 | 1.00 | 19.71 | A |
| ATOM | 1332 | OE1 | GLU A | 191 | 46.362 | −19.738 | 24.266 | 1.00 | 19.33 | A |
| ATOM | 1333 | OE2 | GLU A | 191 | 45.658 | −20.176 | 26.281 | 1.00 | 21.42 | A |
| ATOM | 1334 | C | GLU A | 191 | 46.322 | −24.322 | 22.906 | 1.00 | 14.63 | A |
| ATOM | 1335 | O | GLU A | 191 | 45.683 | −25.382 | 22.958 | 1.00 | 16.14 | A |
| ATOM | 1336 | N | ALA A | 192 | 47.230 | −24.094 | 21.968 | 1.00 | 14.56 | A |
| ATOM | 1337 | CA | ALA A | 192 | 47.496 | −25.094 | 20.944 | 1.00 | 13.41 | A |
| ATOM | 1338 | CB | ALA A | 192 | 48.591 | −24.596 | 19.993 | 1.00 | 17.89 | A |
| ATOM | 1339 | C | ALA A | 192 | 47.918 | −26.403 | 21.598 | 1.00 | 16.28 | A |
| ATOM | 1340 | O | ALA A | 192 | 47.444 | −27.463 | 21.217 | 1.00 | 16.63 | A |
| ATOM | 1341 | N | SER A | 193 | 48.782 | −26.323 | 22.606 | 1.00 | 16.39 | A |
| ATOM | 1342 | CA | SER A | 193 | 49.261 | −27.533 | 23.276 | 1.00 | 15.48 | A |
| ATOM | 1343 | CB | SER A | 193 | 50.290 | −27.182 | 24.359 | 1.00 | 13.46 | A |
| ATOM | 1344 | OG | SER A | 193 | 49.689 | −26.585 | 25.484 | 1.00 | 17.16 | A |
| ATOM | 1345 | C | SER A | 193 | 48.129 | −28.357 | 23.885 | 1.00 | 17.93 | A |
| ATOM | 1346 | O | SER A | 193 | 48.295 | −29.548 | 24.115 | 1.00 | 17.02 | A |
| ATOM | 1347 | N | ALA A | 194 | 46.988 | −27.730 | 24.154 | 1.00 | 16.15 | A |
| ATOM | 1348 | CA | ALA A | 194 | 45.861 | −28.464 | 24.716 | 1.00 | 18.81 | A |
| ATOM | 1349 | CB | ALA A | 194 | 44.854 | −27.516 | 25.334 | 1.00 | 19.68 | A |
| ATOM | 1350 | C | ALA A | 194 | 45.219 | −29.287 | 23.602 | 1.00 | 18.96 | A |
| ATOM | 1351 | O | ALA A | 194 | 44.805 | −30.435 | 23.813 | 1.00 | 19.05 | A |
| ATOM | 1352 | N | LEU A | 195 | 45.135 | −28.705 | 22.411 | 1.00 | 18.92 | A |
| ATOM | 1353 | CA | LEU A | 195 | 44.575 | −29.418 | 21.267 | 1.00 | 20.22 | A |
| ATOM | 1354 | CB | LEU A | 195 | 44.428 | −28.474 | 20.066 | 1.00 | 21.80 | A |
| ATOM | 1355 | CG | LEU A | 195 | 43.147 | −27.642 | 19.922 | 1.00 | 26.42 | A |

APPENDIX 1-continued

X-RAY DATA COORDINATES FOR THE APO FORM OF CDP-ME SYNTHASE
(SEQ ID NOS: 9 and 10)

| ATOM | 1356 | CD1 | LEU A | 195 | 42.016 | −28.540 | 19.487 | 1.00 | 29.21 | A |
|---|---|---|---|---|---|---|---|---|---|---|
| ATOM | 1357 | CD2 | LEU A | 195 | 42.828 | −26.935 | 21.226 | 1.00 | 25.36 | A |
| ATOM | 1358 | C | LEU A | 195 | 45.501 | −30.568 | 20.898 | 1.00 | 19.61 | A |
| ATOM | 1359 | O | LEU A | 195 | 45.053 | −31.676 | 20.597 | 1.00 | 19.39 | A |
| ATOM | 1360 | N | GLU A | 196 | 46.801 | −30.295 | 20.928 | 1.00 | 18.68 | A |
| ATOM | 1361 | CA | GLU A | 196 | 47.819 | −31.290 | 20.595 | 1.00 | 19.13 | A |
| ATOM | 1362 | CB | GLU A | 196 | 49.207 | −30.654 | 20.728 | 1.00 | 20.13 | A |
| ATOM | 1363 | CG | GLU A | 196 | 49.504 | −29.573 | 19.687 | 1.00 | 18.83 | A |
| ATOM | 1364 | CD | GLU A | 196 | 50.605 | −28.625 | 20.124 | 1.00 | 20.54 | A |
| ATOM | 1365 | OE1 | GLU A | 196 | 51.591 | −29.092 | 20.733 | 1.00 | 18.89 | A |
| ATOM | 1366 | OE2 | GLU A | 196 | 50.496 | −27.408 | 19.848 | 1.00 | 17.61 | A |
| ATOM | 1367 | C | GLU A | 196 | 47.710 | −32.498 | 21.519 | 1.00 | 21.16 | A |
| ATOM | 1368 | O | GLU A | 196 | 47.795 | −33.635 | 21.070 | 1.00 | 19.34 | A |
| ATOM | 1369 | N | TYR A | 197 | 47.516 | −32.237 | 22.807 | 1.00 | 22.93 | A |
| ATOM | 1370 | CA | TYR A | 197 | 47.400 | −33.301 | 23.796 | 1.00 | 26.31 | A |
| ATOM | 1371 | CB | TYR A | 197 | 47.220 | −32.701 | 25.186 | 1.00 | 28.90 | A |
| ATOM | 1372 | CG | TYR A | 197 | 47.015 | −33.727 | 26.272 | 1.00 | 34.05 | A |
| ATOM | 1373 | CD1 | TYR A | 197 | 48.059 | −34.550 | 26.688 | 1.00 | 36.50 | A |
| ATOM | 1374 | CE1 | TYR A | 197 | 47.866 | −35.506 | 27.683 | 1.00 | 39.04 | A |
| ATOM | 1375 | CD2 | TYR A | 197 | 45.770 | −33.883 | 26.876 | 1.00 | 35.94 | A |
| ATOM | 1376 | CE2 | TYR A | 197 | 45.565 | −34.836 | 27.869 | 1.00 | 38.21 | A |
| ATOM | 1377 | CZ | TYR A | 197 | 46.617 | −35.643 | 28.267 | 1.00 | 38.24 | A |
| ATOM | 1378 | OH | TYR A | 197 | 46.416 | −36.587 | 29.248 | 1.00 | 39.16 | A |
| ATOM | 1379 | C | TYR A | 197 | 46.235 | −34.243 | 23.495 | 1.00 | 26.99 | A |
| ATOM | 1380 | O | TYR A | 197 | 46.293 | −35.436 | 23.795 | 1.00 | 25.99 | A |
| ATOM | 1381 | N | CYS A | 198 | 45.175 | −33.696 | 22.911 | 1.00 | 25.50 | A |
| ATOM | 1382 | CA | CYS A | 198 | 43.990 | −34.470 | 22.571 | 1.00 | 27.08 | A |
| ATOM | 1383 | CB | CYS A | 198 | 42.740 | −33.599 | 22.758 | 1.00 | 26.29 | A |
| ATOM | 1384 | SG | CYS A | 198 | 42.546 | −32.953 | 24.467 | 1.00 | 21.86 | A |
| ATOM | 1385 | C | CYS A | 198 | 44.019 | −35.055 | 21.155 | 1.00 | 26.83 | A |
| ATOM | 1386 | O | CYS A | 198 | 42.986 | −35.482 | 20.631 | 1.00 | 27.50 | A |
| ATOM | 1387 | N | GLY A | 199 | 45.197 | −35.049 | 20.533 | 1.00 | 25.56 | A |
| ATOM | 1388 | CA | GLY A | 199 | 45.352 | −35.623 | 19.207 | 1.00 | 24.91 | A |
| ATOM | 1389 | C | GLY A | 199 | 45.151 | −34.718 | 18.008 | 1.00 | 24.69 | A |
| ATOM | 1390 | O | GLY A | 199 | 45.142 | −35.193 | 16.870 | 1.00 | 22.99 | A |
| ATOM | 1391 | N | PHE A | 200 | 44.992 | −33.421 | 18.247 | 1.00 | 24.89 | A |
| ATOM | 1392 | CA | PHE A | 200 | 44.795 | −32.475 | 17.161 | 1.00 | 26.64 | A |
| ATOM | 1393 | CB | PHE A | 200 | 43.781 | −31.407 | 17.576 | 1.00 | 27.11 | A |
| ATOM | 1394 | CG | PHE A | 200 | 42.405 | −31.949 | 17.824 | 1.00 | 27.64 | A |
| ATOM | 1395 | CD1 | PHE A | 200 | 42.003 | −32.314 | 19.101 | 1.00 | 27.27 | A |
| ATOM | 1396 | CD2 | PHE A | 200 | 41.525 | −32.139 | 16.768 | 1.00 | 28.29 | A |
| ATOM | 1397 | CE1 | PHE A | 200 | 40.741 | −32.865 | 19.324 | 1.00 | 28.86 | A |
| ATOM | 1398 | CE2 | PHE A | 200 | 40.262 | −32.690 | 16.980 | 1.00 | 27.76 | A |
| ATOM | 1399 | CZ | PHE A | 200 | 39.874 | −33.052 | 18.260 | 1.00 | 27.71 | A |
| ATOM | 1400 | C | PHE A | 200 | 46.091 | −31.814 | 16.704 | 1.00 | 26.07 | A |
| ATOM | 1401 | O | PHE A | 200 | 47.083 | −31.786 | 17.435 | 1.00 | 25.11 | A |
| ATOM | 1402 | N | HIS A | 201 | 46.072 | −31.283 | 15.485 | 1.00 | 24.41 | A |
| ATOM | 1403 | CA | HIS A | 201 | 47.238 | −30.621 | 14.915 | 1.00 | 24.83 | A |
| ATOM | 1404 | CB | HIS A | 201 | 47.883 | −31.532 | 13.867 | 1.00 | 26.07 | A |
| ATOM | 1405 | CG | HIS A | 201 | 48.320 | −32.857 | 14.412 | 1.00 | 29.20 | A |
| ATOM | 1406 | CD2 | HIS A | 201 | 49.551 | −33.337 | 14.706 | 1.00 | 29.26 | A |
| ATOM | 1407 | ND1 | HIS A | 201 | 47.430 | −33.850 | 14.760 | 1.00 | 31.82 | A |
| ATOM | 1408 | CE1 | HIS A | 201 | 48.093 | −34.884 | 15.245 | 1.00 | 30.34 | A |
| ATOM | 1409 | NE2 | HIS A | 201 | 49.382 | −34.599 | 15.223 | 1.00 | 31.15 | A |
| ATOM | 1410 | C | HIS A | 201 | 46.855 | −29.278 | 14.288 | 1.00 | 22.68 | A |
| ATOM | 1411 | O | HIS A | 201 | 46.620 | −29.192 | 13.085 | 1.00 | 22.47 | A |
| ATOM | 1412 | N | PRO A | 202 | 46.778 | −28.214 | 15.106 | 1.00 | 21.92 | A |
| ATOM | 1413 | CD | PRO A | 202 | 46.948 | −28.234 | 16.569 | 1.00 | 20.50 | A |
| ATOM | 1414 | CA | PRO A | 202 | 46.421 | −26.866 | 14.649 | 1.00 | 20.93 | A |
| ATOM | 1415 | CB | PRO A | 202 | 46.502 | −26.036 | 15.926 | 1.00 | 21.46 | A |
| ATOM | 1416 | CG | PRO A | 202 | 46.157 | −27.025 | 16.996 | 1.00 | 21.32 | A |
| ATOM | 1417 | C | PRO A | 202 | 47.350 | −26.322 | 13.564 | 1.00 | 19.09 | A |
| ATOM | 1418 | O | PRO A | 202 | 48.537 | −26.664 | 13.504 | 1.00 | 18.10 | A |
| ATOM | 1419 | N | GLN A | 203 | 46.803 | −25.456 | 12.718 | 1.00 | 18.45 | A |
| ATOM | 1420 | CA | GLN A | 203 | 47.574 | −24.859 | 11.640 | 1.00 | 19.50 | A |
| ATOM | 1421 | CB | GLN A | 203 | 46.637 | −24.302 | 10.562 | 1.00 | 23.14 | A |
| ATOM | 1422 | CG | GLN A | 203 | 45.946 | −25.375 | 9.744 | 1.00 | 30.02 | A |
| ATOM | 1423 | CD | GLN A | 203 | 46.934 | −26.212 | 8.953 | 1.00 | 32.83 | A |
| ATOM | 1424 | OE1 | GLN A | 203 | 47.670 | −25.694 | 8.114 | 1.00 | 36.02 | A |
| ATOM | 1425 | NE2 | GLN A | 203 | 46.955 | −27.512 | 9.219 | 1.00 | 36.60 | A |
| ATOM | 1426 | C | GLN A | 203 | 48.500 | −23.753 | 12.125 | 1.00 | 19.54 | A |
| ATOM | 1427 | O | GLN A | 203 | 48.240 | −23.095 | 13.130 | 1.00 | 17.94 | A |
| ATOM | 1428 | N | LEU A | 204 | 49.597 | −23.578 | 11.401 | 1.00 | 16.93 | A |
| ATOM | 1429 | CA | LEU A | 204 | 50.578 | −22.545 | 11.698 | 1.00 | 16.07 | A |
| ATOM | 1430 | CB | LEU A | 204 | 51.990 | −23.132 | 11.612 | 1.00 | 15.88 | A |
| ATOM | 1431 | CG | LEU A | 204 | 52.360 | −24.074 | 12.759 | 1.00 | 15.91 | A |

APPENDIX 1-continued

X-RAY DATA COORDINATES FOR THE APO FORM OF CDP-ME SYNTHASE
(SEQ ID NOS: 9 and 10)

| ATOM | 1432 | CD1 | LEU A | 204 | 53.520 | −24.980 | 12.362 | 1.00 | 16.95 | A |
|---|---|---|---|---|---|---|---|---|---|---|
| ATOM | 1433 | CD2 | LEU A | 204 | 52.715 | −23.234 | 13.974 | 1.00 | 15.31 | A |
| ATOM | 1434 | C | LEU A | 204 | 50.400 | −21.451 | 10.651 | 1.00 | 16.94 | A |
| ATOM | 1435 | O | LEU A | 204 | 50.551 | −21.701 | 9.459 | 1.00 | 20.31 | A |
| ATOM | 1436 | N | VAL A | 205 | 50.050 | −20.251 | 11.097 | 1.00 | 17.13 | A |
| ATOM | 1437 | CA | VAL A | 205 | 49.866 | −19.120 | 10.197 | 1.00 | 16.22 | A |
| ATOM | 1438 | CB | VAL A | 205 | 48.526 | −18.400 | 10.465 | 1.00 | 17.00 | A |
| ATOM | 1439 | CG1 | VAL A | 205 | 48.372 | −17.207 | 9.540 | 1.00 | 17.28 | A |
| ATOM | 1440 | CG2 | VAL A | 205 | 47.373 | −19.374 | 10.264 | 1.00 | 16.18 | A |
| ATOM | 1441 | C | VAL A | 205 | 51.013 | −18.172 | 10.492 | 1.00 | 16.18 | A |
| ATOM | 1442 | O | VAL A | 205 | 51.099 | −17.623 | 11.590 | 1.00 | 15.45 | A |
| ATOM | 1443 | N | GLU A | 206 | 51.901 | −17.984 | 9.523 | 1.00 | 17.10 | A |
| ATOM | 1444 | CA | GLU A | 206 | 53.047 | −17.114 | 9.738 | 1.00 | 17.75 | A |
| ATOM | 1445 | CB | GLU A | 206 | 53.991 | −17.161 | 8.531 | 1.00 | 19.99 | A |
| ATOM | 1446 | CG | GLU A | 206 | 55.038 | −16.060 | 8.553 | 1.00 | 25.62 | A |
| ATOM | 1447 | CD | GLU A | 206 | 56.265 | −16.393 | 7.735 | 1.00 | 27.02 | A |
| ATOM | 1448 | OE1 | GLU A | 206 | 56.125 | −17.075 | 6.701 | 1.00 | 29.15 | A |
| ATOM | 1449 | OE2 | GLU A | 206 | 57.363 | −15.951 | 8.123 | 1.00 | 28.29 | A |
| ATOM | 1450 | C | GLU A | 206 | 52.669 | −15.674 | 10.057 | 1.00 | 19.85 | A |
| ATOM | 1451 | O | GLU A | 206 | 51.857 | −15.056 | 9.366 | 1.00 | 20.61 | A |
| ATOM | 1452 | N | GLY A | 207 | 53.274 | −15.155 | 11.118 | 1.00 | 19.73 | A |
| ATOM | 1453 | CA | GLY A | 207 | 53.014 | −13.794 | 11.536 | 1.00 | 18.34 | A |
| ATOM | 1454 | C | GLY A | 207 | 54.311 | −13.044 | 11.756 | 1.00 | 21.80 | A |
| ATOM | 1455 | O | GLY A | 207 | 55.392 | −13.636 | 11.751 | 1.00 | 20.99 | A |
| ATOM | 1456 | N | ARG A | 208 | 54.206 | −11.736 | 11.945 | 1.00 | 21.05 | A |
| ATOM | 1457 | CA | ARG A | 208 | 55.379 | −10.898 | 12.161 | 1.00 | 22.72 | A |
| ATOM | 1458 | CB | ARG A | 208 | 54.971 | −9.427 | 12.172 | 1.00 | 24.14 | A |
| ATOM | 1459 | CG | ARG A | 208 | 54.277 | −8.934 | 10.918 | 1.00 | 27.47 | A |
| ATOM | 1460 | CD | ARG A | 208 | 53.736 | −7.535 | 11.164 | 1.00 | 31.07 | A |
| ATOM | 1461 | NE | ARG A | 208 | 54.793 | −6.636 | 11.628 | 1.00 | 34.68 | A |
| ATOM | 1462 | CZ | ARG A | 208 | 55.476 | −5.817 | 10.835 | 1.00 | 37.65 | A |
| ATOM | 1463 | NH1 | ARG A | 208 | 55.207 | −5.776 | 9.536 | 1.00 | 38.90 | A |
| ATOM | 1464 | NH2 | ARG A | 208 | 56.436 | −5.051 | 11.336 | 1.00 | 38.25 | A |
| ATOM | 1465 | C | ARG A | 208 | 56.091 | −11.224 | 13.471 | 1.00 | 22.28 | A |
| ATOM | 1466 | O | ARG A | 208 | 55.454 | −11.461 | 14.498 | 1.00 | 19.54 | A |
| ATOM | 1467 | N | ALA A | 209 | 57.419 | −11.207 | 13.435 | 1.00 | 21.98 | A |
| ATOM | 1468 | CA | ALA A | 209 | 58.218 | −11.501 | 14.614 | 1.00 | 22.60 | A |
| ATOM | 1469 | OB | ALA A | 209 | 59.658 | −11.794 | 14.202 | 1.00 | 24.37 | A |
| ATOM | 1470 | C | ALA A | 209 | 58.191 | −10.361 | 15.631 | 1.00 | 23.23 | A |
| ATOM | 1471 | O | ALA A | 209 | 58.589 | −10.548 | 16.778 | 1.00 | 24.96 | A |
| ATOM | 1472 | N | ASP A | 210 | 57.722 | −9.185 | 15.217 | 1.00 | 23.89 | A |
| ATOM | 1473 | CA | ASP A | 210 | 57.664 | −8.033 | 16.117 | 1.00 | 24.37 | A |
| ATOM | 1474 | CB | ASP A | 210 | 57.625 | −6.723 | 15.319 | 1.00 | 27.21 | A |
| ATOM | 1475 | CG | ASP A | 210 | 56.384 | −6.589 | 14.458 | 1.00 | 30.03 | A |
| ATOM | 1476 | OD1 | ASP A | 210 | 55.760 | −7.611 | 14.145 | 1.00 | 29.12 | A |
| ATOM | 1477 | OD2 | ASP A | 210 | 56.042 | −5.447 | 14.085 | 1.00 | 35.48 | A |
| ATOM | 1478 | C | ASP A | 210 | 56.468 | −8.111 | 17.066 | 1.00 | 22.67 | A |
| ATOM | 1479 | O | ASP A | 210 | 56.244 | −7.218 | 17.877 | 1.00 | 20.42 | A |
| ATOM | 1480 | N | ASN A | 211 | 55.710 | −9.198 | 16.964 | 1.00 | 22.16 | A |
| ATOM | 1481 | CA | ASN A | 211 | 54.551 | −9.429 | 17.825 | 1.00 | 19.71 | A |
| ATOM | 1482 | CB | ASN A | 211 | 53.572 | −10.363 | 17.102 | 1.00 | 19.96 | A |
| ATOM | 1483 | CG | ASN A | 211 | 52.345 | −10.706 | 17.929 | 1.00 | 18.74 | A |
| ATOM | 1484 | OD1 | ASN A | 211 | 51.998 | −10.015 | 18.886 | 1.00 | 17.61 | A |
| ATOM | 1485 | ND2 | ASN A | 211 | 51.664 | −11.774 | 17.539 | 1.00 | 14.44 | A |
| ATOM | 1486 | C | ASN A | 211 | 55.100 | −10.064 | 19.102 | 1.00 | 21.24 | A |
| ATOM | 1487 | O | ASN A | 211 | 54.931 | −11.257 | 19.342 | 1.00 | 23.32 | A |
| ATOM | 1488 | N | ILE A | 212 | 55.768 | −9.247 | 19.915 | 1.00 | 20.62 | A |
| ATOM | 1489 | CA | ILE A | 212 | 56.385 | −9.722 | 21.149 | 1.00 | 21.93 | A |
| ATOM | 1490 | CB | ILE A | 212 | 57.712 | −8.977 | 21.413 | 1.00 | 23.60 | A |
| ATOM | 1491 | CG2 | ILE A | 212 | 58.679 | −9.235 | 20.269 | 1.00 | 23.98 | A |
| ATOM | 1492 | CG1 | ILE A | 212 | 57.443 | −7.475 | 21.573 | 1.00 | 24.67 | A |
| ATOM | 1493 | CD1 | ILE A | 212 | 58.609 | −6.690 | 22.159 | 1.00 | 27.58 | A |
| ATOM | 1494 | C | ILE A | 212 | 55.513 | −9.586 | 22.393 | 1.00 | 21.40 | A |
| ATOM | 1495 | O | ILE A | 212 | 54.555 | −8.815 | 22.417 | 1.00 | 19.12 | A |
| ATOM | 1496 | N | LYS A | 213 | 55.860 | −10.345 | 23.429 | 1.00 | 21.31 | A |
| ATOM | 1497 | CA | LYS A | 213 | 55.140 | −10.301 | 24.692 | 1.00 | 22.16 | A |
| ATOM | 1498 | CB | LYS A | 213 | 54.839 | −11.714 | 25.199 | 1.00 | 24.13 | A |
| ATOM | 1499 | CG | LYS A | 213 | 54.059 | −11.730 | 26.507 | 1.00 | 29.39 | A |
| ATOM | 1500 | CD | LYS A | 213 | 53.540 | −13.114 | 26.861 | 1.00 | 32.17 | A |
| ATOM | 1501 | CE | LYS A | 213 | 54.660 | −14.092 | 27.132 | 1.00 | 35.45 | A |
| ATOM | 1502 | NZ | LYS A | 213 | 54.126 | −15.437 | 27.504 | 1.00 | 37.54 | A |
| ATOM | 1503 | C | LYS A | 213 | 56.008 | −9.574 | 25.704 | 1.00 | 24.21 | A |
| ATOM | 1504 | O | LYS A | 213 | 57.155 | −9.954 | 25.933 | 1.00 | 24.13 | A |
| ATOM | 1505 | N | VAL A | 214 | 55.464 | −8.519 | 26.297 | 1.00 | 23.37 | A |
| ATOM | 1506 | CA | VAL A | 214 | 56.204 | −7.746 | 27.284 | 1.00 | 24.37 | A |
| ATOM | 1507 | CB | VAL A | 214 | 55.561 | −6.363 | 27.504 | 1.00 | 24.05 | A |

APPENDIX 1-continued

X-RAY DATA COORDINATES FOR THE APO FORM OF CDP-ME SYNTHASE
(SEQ ID NOS: 9 and 10)

| ATOM | 1508CG1 | VAL A | 214 | 56.376 | −5.561 | 28.506 | 1.00 | 22.70 | A |
|------|---------|-------|-----|--------|--------|--------|------|-------|---|
| ATOM | 1509CG2 | VAL A | 214 | 55.478 | −5.619 | 26.177 | 1.00 | 21.93 | A |
| ATOM | 1510C | VAL A | 214 | 56.239 | −8.510 | 28.601 | 1.00 | 25.84 | A |
| ATOM | 1511O | VAL A | 214 | 55.227 | −8.623 | 29.297 | 1.00 | 26.39 | A |
| ATOM | 1512N | THR A | 215 | 57.413 | −9.037 | 28.936 | 1.00 | 28.69 | A |
| ATOM | 1513CA | THR A | 215 | 57.582 | −9.805 | 30.161 | 1.00 | 30.70 | A |
| ATOM | 1514CB | THR A | 215 | 57.914 | −11.273 | 29.835 | 1.00 | 32.16 | A |
| ATOM | 1515OG1 | THR A | 215 | 56.933 | −11.800 | 28.930 | 1.00 | 34.81 | A |
| ATOM | 1516CG2 | THR A | 215 | 57.915 | −12.108 | 31.103 | 1.00 | 34.57 | A |
| ATOM | 1517C | THR A | 215 | 58.691 | −9.232 | 31.039 | 1.00 | 31.82 | A |
| ATOM | 1518O | THR A | 215 | 58.587 | −9.234 | 32.265 | 1.00 | 31.35 | A |
| ATOM | 1519N | ARG A | 216 | 59.754 | −8.749 | 30.405 | 1.00 | 33.48 | A |
| ATOM | 1520CA | ARG A | 216 | 60.879 | −8.175 | 31.132 | 1.00 | 35.00 | A |
| ATOM | 1521CB | ARG A | 216 | 62.202 | −8.770 | 30.640 | 1.00 | 37.32 | A |
| ATOM | 1522CG | ARG A | 216 | 62.455 | −10.216 | 31.056 | 1.00 | 41.78 | A |
| ATOM | 1523CD | ARG A | 216 | 61.952 | −11.214 | 30.024 | 1.00 | 44.93 | A |
| ATOM | 1524NE | ARG A | 216 | 62.276 | −12.587 | 30.413 | 1.00 | 48.03 | A |
| ATOM | 1525CZ | ARG A | 216 | 62.047 | −13.662 | 29.663 | 1.00 | 49.21 | A |
| ATOM | 1526NH1 | ARG A | 216 | 61.488 | −13.541 | 28.466 | 1.00 | 49.67 | A |
| ATOM | 1527NH2 | ARG A | 216 | 62.384 | −14.864 | 30.113 | 1.00 | 50.23 | A |
| ATOM | 1528C | ARG A | 216 | 60.913 | −6.659 | 30.967 | 1.00 | 35.48 | A |
| ATOM | 1529O | ARG A | 216 | 60.348 | −6.114 | 30.019 | 1.00 | 34.18 | A |
| ATOM | 1530N | PRO A | 217 | 61.587 | −5.956 | 31.891 | 1.00 | 35.81 | A |
| ATOM | 1531CD | PRO A | 217 | 62.304 | −6.517 | 33.051 | 1.00 | 35.99 | A |
| ATOM | 1532CA | PRO A | 217 | 61.708 | −4.496 | 31.868 | 1.00 | 35.89 | A |
| ATOM | 1533CB | PRO A | 217 | 62.783 | −4.233 | 32.918 | 1.00 | 35.87 | A |
| ATOM | 1534CG | PRO A | 217 | 62.509 | −5.299 | 33.925 | 1.00 | 36.63 | A |
| ATOM | 1535C | PRO A | 217 | 62.077 | −3.916 | 30.502 | 1.00 | 35.07 | A |
| ATOM | 1536O | PRO A | 217 | 61.461 | −2.952 | 30.043 | 1.00 | 36.13 | A |
| ATOM | 1537N | GLU A | 218 | 63.074 | −4.509 | 29.851 | 1.00 | 35.38 | A |
| ATOM | 1538CA | GLU A | 218 | 63.526 | −4.031 | 28.549 | 1.00 | 35.94 | A |
| ATOM | 1539CB | GLU A | 218 | 64.802 | −4.764 | 28.121 | 1.00 | 39.06 | A |
| ATOM | 1540CG | GLU A | 218 | 64.606 | −6.250 | 27.848 | 1.00 | 42.32 | A |
| ATOM | 1541CD | GLU A | 218 | 64.882 | −7.114 | 29.063 | 1.00 | 44.84 | A |
| ATOM | 1542OE1 | GLU A | 218 | 64.414 | −6.763 | 30.170 | 1.00 | 45.70 | A |
| ATOM | 1543OE2 | GLU A | 218 | 65.559 | −8.153 | 28.906 | 1.00 | 45.53 | A |
| ATOM | 1544C | GLU A | 218 | 62.477 | −4.194 | 27.458 | 1.00 | 35.05 | A |
| ATOM | 1545O | GLU A | 218 | 62.481 | −3.455 | 26.473 | 1.00 | 34.92 | A |
| ATOM | 1546N | ASP A | 219 | 61.585 | −5.165 | 27.628 | 1.00 | 33.36 | A |
| ATOM | 1547CA | ASP A | 219 | 60.545 | −5.416 | 26.632 | 1.00 | 33.06 | A |
| ATOM | 1548CB | ASP A | 219 | 59.690 | −6.626 | 27.025 | 1.00 | 33.66 | A |
| ATOM | 1549CG | ASP A | 219 | 60.470 | −7.927 | 26.995 | 1.00 | 34.71 | A |
| ATOM | 1550OD1 | ASP A | 219 | 61.406 | −8.047 | 26.173 | 1.00 | 37.33 | A |
| ATOM | 1551OD2 | ASP A | 219 | 60.135 | −8.839 | 27.778 | 1.00 | 34.59 | A |
| ATOM | 1552C | ASP A | 219 | 59.633 | −4.218 | 26.388 | 1.00 | 31.76 | A |
| ATOM | 1553O | ASP A | 219 | 59.133 | −4.038 | 25.280 | 1.00 | 29.92 | A |
| ATOM | 1554N | LEU A | 220 | 59.412 | −3.401 | 27.413 | 1.00 | 31.37 | A |
| ATOM | 1555CA | LEU A | 220 | 58.538 | −2.240 | 27.263 | 1.00 | 30.75 | A |
| ATOM | 1556CB | LEU A | 220 | 58.382 | −1.508 | 28.598 | 1.00 | 32.54 | A |
| ATOM | 1557CG | LEU A | 220 | 57.313 | −.412 | 28.637 | 1.00 | 33.38 | A |
| ATOM | 1558CD1 | LEU A | 220 | 55.932 | −1.037 | 28.462 | 1.00 | 34.72 | A |
| ATOM | 1559CD2 | LEU A | 220 | 57.386 | .329 | 29.961 | 1.00 | 35.06 | A |
| ATOM | 1560C | LEU A | 220 | 59.078 | −1.276 | 26.214 | 1.00 | 29.90 | A |
| ATOM | 1561O | LEU A | 220 | 58.361 | −.871 | 25.297 | 1.00 | 27.81 | A |
| ATOM | 1562N | ALA A | 221 | 60.349 | −.913 | 26.354 | 1.00 | 29.87 | A |
| ATOM | 1563CA | ALA A | 221 | 60.990 | .007 | 25.422 | 1.00 | 30.00 | A |
| ATOM | 1564CB | ALA A | 221 | 62.424 | .276 | 25.863 | 1.00 | 31.39 | A |
| ATOM | 1565C | ALA A | 221 | 60.973 | −.549 | 24.000 | 1.00 | 27.88 | A |
| ATOM | 1566O | ALA A | 221 | 60.763 | .191 | 23.042 | 1.00 | 28.09 | A |
| ATOM | 1567N | LEU A | 222 | 61.194 | −1.854 | 23.871 | 1.00 | 27.19 | A |
| ATOM | 1568CA | LEU A | 222 | 61.196 | −2.499 | 22.565 | 1.00 | 27.07 | A |
| ATOM | 1569CB | LEU A | 222 | 61.704 | −3.941 | 22.679 | 1.00 | 26.82 | A |
| ATOM | 1570CG | LEU A | 222 | 61.769 | −4.762 | 21.386 | 1.00 | 28.14 | A |
| ATOM | 1571CD1 | LEU A | 222 | 62.620 | −4.041 | 20.351 | 1.00 | 28.77 | A |
| ATOM | 1572CD2 | LEU A | 222 | 62.349 | −6.137 | 21.675 | 1.00 | 29.45 | A |
| ATOM | 1573C | LEU A | 222 | 59.797 | −2.492 | 21.956 | 1.00 | 26.03 | A |
| ATOM | 1574O | LEU A | 222 | 59.632 | −2.252 | 20.757 | 1.00 | 23.89 | A |
| ATOM | 1575N | ALA A | 223 | 58.790 | −2.763 | 22.779 | 1.00 | 26.12 | A |
| ATOM | 1576CA | ALA A | 223 | 57.410 | −2.773 | 22.300 | 1.00 | 25.66 | A |
| ATOM | 1577CB | ALA A | 223 | 56.463 | −3.138 | 23.438 | 1.00 | 26.82 | A |
| ATOM | 1578C | ALA A | 223 | 57.058 | −1.396 | 21.747 | 1.00 | 27.62 | A |
| ATOM | 1579O | ALA A | 223 | 56.443 | −1.278 | 20.687 | 1.00 | 25.06 | A |
| ATOM | 1580N | GLU A | 224 | 57.460 | −.355 | 22.469 | 1.00 | 29.02 | A |
| ATOM | 1581CA | GLU A | 224 | 57.191 | 1.010 | 22.038 | 1.00 | 32.44 | A |
| ATOM | 1582CB | GLU A | 224 | 57.702 | 2.002 | 23.081 | 1.00 | 34.38 | A |
| ATOM | 1583CG | GLU A | 224 | 57.622 | 3.447 | 22.633 | 1.00 | 38.78 | A |

APPENDIX 1-continued

X-RAY DATA COORDINATES FOR THE APO FORM OF CDP-ME SYNTHASE
(SEQ ID NOS: 9 and 10)

| ATOM | 1584CD | GLU A | 224 | 57.905 | 4.420 | 23.758 | 1.00 | 41.08 A |
|---|---|---|---|---|---|---|---|---|
| ATOM | 1585OE1 | GLU A | 224 | 58.903 | 4.219 | 24.484 | 1.00 | 42.44 A |
| ATOM | 1586OE2 | GLU A | 224 | 57.135 | 5.389 | 23.908 | 1.00 | 42.70 A |
| ATOM | 1587C | GLU A | 224 | 57.858 | 1.274 | 20.693 | 1.00 | 32.65 A |
| ATOM | 1588O | GLU A | 224 | 57.294 | 1.947 | 19.833 | 1.00 | 32.02 A |
| ATOM | 1589N | PHE A | 225 | 59.061 | .734 | 20.522 | 1.00 | 31.71 A |
| ATOM | 1590CA | PHE A | 225 | 59.802 | .896 | 19.281 | 1.00 | 33.18 A |
| ATOM | 1591CB | PHE A | 225 | 61.172 | .221 | 19.392 | 1.00 | 33.18 A |
| ATOM | 1592CG | PHE A | 225 | 61.914 | .138 | 18.089 | 1.00 | 33.06 A |
| ATOM | 1593CD1 | PHE A | 225 | 62.406 | 1.288 | 17.479 | 1.00 | 32.57 A |
| ATOM | 1594CD2 | PHE A | 225 | 62.082 | −1.086 | 17.448 | 1.00 | 33.06 A |
| ATOM | 1595CE1 | PHE A | 225 | 63.059 | 1.222 | 16.249 | 1.00 | 31.85 A |
| ATOM | 1596CE2 | PHE A | 225 | 62.733 | −1.165 | 16.218 | 1.00 | 32.49 A |
| ATOM | 1597CZ | PHE A | 225 | 63.219 | −.007 | 15.615 | 1.00 | 32.15 A |
| ATOM | 1598C | PHE A | 225 | 59.016 | .276 | 18.130 | 1.00 | 33.56 A |
| ATOM | 1599O | PHE A | 225 | 58.845 | .893 | 17.080 | 1.00 | 33.86 A |
| ATOM | 1600N | TYR A | 226 | 58.539 | −.948 | 18.336 | 1.00 | 33.55 A |
| ATOM | 1601CA | TYR A | 226 | 57.769 | −1.661 | 17.318 | 1.00 | 34.87 A |
| ATOM | 1602CB | TYR A | 226 | 57.500 | −3.097 | 17.777 | 1.00 | 33.17 A |
| ATOM | 1603CG | TYR A | 226 | 58.694 | −4.014 | 17.672 | 1.00 | 31.78 A |
| ATOM | 1604CD1 | TYR A | 226 | 58.857 | −5.074 | 18.557 | 1.00 | 31.15 A |
| ATOM | 1605CE1 | TYR A | 226 | 59.939 | −5.941 | 18.449 | 1.00 | 31.98 A |
| ATOM | 1606CD2 | TYR A | 226 | 59.646 | −3.841 | 16.668 | 1.00 | 32.61 A |
| ATOM | 1607CE2 | TYR A | 226 | 60.732 | −4.702 | 16.549 | 1.00 | 31.90 A |
| ATOM | 1608CZ | TYR A | 226 | 60.872 | −5.749 | 17.440 | 1.00 | 33.04 A |
| ATOM | 1609OH | TYR A | 226 | 61.938 | −6.611 | 17.328 | 1.00 | 32.47 A |
| ATOM | 1610C | TYR A | 226 | 56.445 | −.976 | 17.005 | 1.00 | 36.55 A |
| ATOM | 1611O | TYR A | 226 | 56.068 | −.834 | 15.842 | 1.00 | 36.93 A |
| ATOM | 1612N | LEU A | 227 | 55.744 | −.559 | 18.053 | 1.00 | 37.47 A |
| ATOM | 1613CA | LEU A | 227 | 54.454 | .104 | 17.899 | 1.00 | 39.20 A |
| ATOM | 1614CB | LEU A | 227 | 53.811 | .311 | 19.274 | 1.00 | 38.91 A |
| ATOM | 1615CG | LEU A | 227 | 52.283 | .282 | 19.351 | 1.00 | 39.64 A |
| ATOM | 1616CD1 | LEU A | 227 | 51.778 | −1.076 | 18.887 | 1.00 | 39.00 A |
| ATOM | 1617CD2 | LEU A | 227 | 51.839 | .536 | 20.784 | 1.00 | 39.27 A |
| ATOM | 1618C | LEU A | 227 | 54.639 | 1.446 | 17.193 | 1.00 | 40.78 A |
| ATOM | 1619O | LEU A | 227 | 54.016 | 1.714 | 16.163 | 1.00 | 40.32 A |
| ATOM | 1620N | ALA A | 228 | 55.514 | 2.277 | 17.749 | 1.00 | 41.39 A |
| ATOM | 1621CA | ALA A | 228 | 55.799 | 3.594 | 17.192 | 1.00 | 43.00 A |
| ATOM | 1622CB | ALA A | 228 | 55.149 | 4.677 | 18.050 | 1.00 | 43.48 A |
| ATOM | 1623C | ALA A | 228 | 57.305 | 3.818 | 17.122 | 1.00 | 43.48 A |
| ATOM | 1624O | ALA A | 228 | 57.819 | 4.606 | 17.947 | 1.00 | 42.74 A |
| ATOM | 1625OXT | ALA A | 228 | 57.952 | 3.185 | 16.259 | 1.00 | 43.89 A |
| ATOM | 1626OH2 | WAT W | 1 | 69.246 | −24.960 | 14.039 | 1.00 | 16.05 W |
| ATOM | 1627OH2 | WAT W | 2 | 51.412 | −9.069 | 14.203 | 1.00 | 19.33 W |
| ATOM | 1628OH2 | WAT W | 3 | 35.037 | −2.630 | 18.322 | 1.00 | 13.13 W |
| ATOM | 1629OH2 | WAT W | 4 | 33.748 | −26.657 | 18.710 | 1.00 | 16.51 W |
| ATOM | 1630OH2 | WAT W | 5 | 52.514 | −12.208 | 14.605 | 1.00 | 18.96 W |
| ATOM | 1631OH2 | WAT W | 6 | 52.791 | −8.038 | 20.626 | 1.00 | 17.33 W |
| ATOM | 1632OH2 | WAT W | 7 | 49.029 | −3.382 | 17.928 | 1.00 | 23.46 W |
| ATOM | 1633OH2 | WAT W | 8 | 46.563 | −3.796 | 14.936 | 1.00 | 21.91 W |
| ATOM | 1634OH2 | WAT W | 9 | 44.272 | −9.139 | 36.843 | 1.00 | 21.18 W |
| ATOM | 1635OH2 | WAT W | 10 | 30.303 | −29.396 | 23.277 | 1.00 | 22.44 W |
| ATOM | 1636OH2 | WAT W | 11 | 33.949 | −22.983 | 10.665 | 1.00 | 20.27 W |
| ATOM | 1637OH2 | WAT W | 12 | 53.381 | −7.638 | 15.068 | 1.00 | 21.63 W |
| ATOM | 1638OH2 | WAT W | 13 | 32.469 | −24.357 | 18.629 | 1.00 | 17.27 W |
| ATOM | 1639OH2 | WAT W | 14 | 63.026 | −22.205 | 10.528 | 1.00 | 33.09 W |
| ATOM | 1640OH2 | WAT W | 15 | 64.631 | −17.261 | 15.851 | 1.00 | 27.29 W |
| ATOM | 1641OH2 | WAT W | 16 | 32.049 | −1.046 | 18.852 | 1.00 | 37.69 W |
| ATOM | 1642OH2 | WAT W | 17 | 53.112 | −27.959 | 25.937 | 1.00 | 23.38 W |
| ATOM | 1643OH2 | WAT W | 18 | 58.315 | −12.110 | 23.219 | 1.00 | 26.86 W |
| ATOM | 1644OH2 | WAT W | 19 | 47.971 | −3.165 | 11.920 | 1.00 | 35.46 W |
| ATOM | 1645OH2 | WAT W | 20 | 37.748 | −13.724 | 7.999 | 1.00 | 19.98 W |
| ATOM | 1646OH2 | WAT W | 21 | 52.663 | −31.199 | 22.016 | 1.00 | 21.59 W |
| ATOM | 1647OH2 | WAT W | 22 | 64.593 | −30.935 | 20.354 | 1.00 | 31.09 W |
| ATOM | 1648OH2 | WAT W | 23 | 31.537 | −28.451 | 25.450 | 1.00 | 25.90 W |
| ATOM | 1649OH2 | WAT W | 24 | 56.920 | −25.364 | 8.547 | 1.00 | 28.30 W |
| ATOM | 1650OH2 | WAT W | 25 | 60.221 | −22.855 | 10.260 | 1.00 | 30.69 W |
| ATOM | 1651OH2 | WAT W | 26 | 28.249 | −17.443 | 27.700 | 1.00 | 30.74 W |
| ATOM | 1652OH2 | WAT W | 27 | 35.751 | −9.923 | 37.506 | 1.00 | 38.23 W |
| ATOM | 1653OH2 | WAT W | 28 | 40.037 | −12.109 | 8.097 | 1.00 | 25.74 W |
| ATOM | 1654OH2 | WAT W | 29 | 57.693 | −14.172 | 10.121 | 1.00 | 31.89 W |
| ATOM | 1655OH2 | WAT W | 30 | 56.673 | −10.411 | 33.450 | 1.00 | 38.51 W |
| ATOM | 1656OH2 | WAT W | 31 | 42.642 | −7.374 | 10.869 | 1.00 | 25.99 W |
| ATOM | 1657OH2 | WAT W | 32 | 46.509 | −1.896 | 19.137 | 1.00 | 30.71 W |
| ATOM | 1658OH2 | WAT W | 33 | 31.660 | −6.561 | 32.171 | 1.00 | 39.12 W |
| ATOM | 1659OH2 | WAT W | 34 | 45.041 | −18.191 | 6.632 | 1.00 | 34.41 W |

APPENDIX 1-continued

X-RAY DATA COORDINATES FOR THE APO FORM OF CDP-ME SYNTHASE
(SEQ ID NOS: 9 and 10)

| ATOM | 1660 OH2 | WAT W | 35 | 62.244 | −9.089 | 19.040 | 1.00 | 36.42 W |
|---|---|---|---|---|---|---|---|---|
| ATOM | 1661 OH2 | WAT W | 36 | 39.869 | −1.182 | 17.753 | 1.00 | 24.63 W |
| ATOM | 1662 OH2 | WAT W | 37 | 55.325 | −18.507 | 22.980 | 1.00 | 30.20 W |
| ATOM | 1663 OH2 | WAT W | 38 | 46.156 | −4.753 | 39.342 | 1.00 | 38.96 W |
| ATOM | 1664 OH2 | WAT W | 39 | 46.623 | −9.090 | 37.980 | 1.00 | 36.77 W |
| ATOM | 1665 OH2 | WAT W | 40 | 33.385 | −17.307 | 13.423 | 1.00 | 27.98 W |
| ATOM | 1666 OH2 | WAT W | 41 | 38.813 | −3.666 | 38.631 | 1.00 | 30.14 W |
| ATOM | 1667 OH2 | WAT W | 42 | 61.918 | −.691 | 28.844 | 1.00 | 41.06 W |
| ATOM | 1668 OH2 | WAT W | 43 | 70.827 | −22.840 | 11.042 | 1.00 | 33.42 W |
| ATOM | 1669 OH2 | WAT W | 44 | 48.517 | −22.087 | 7.775 | 1.00 | 41.59 W |
| ATOM | 1670 OH2 | WAT W | 45 | 58.815 | −11.050 | 10.913 | 1.00 | 39.68 W |
| ATOM | 1671 OH2 | WAT W | 46 | 30.062 | −6.577 | 16.316 | 1.00 | 46.22 W |
| ATOM | 1672 OH2 | WAT W | 47 | 33.178 | −16.966 | 33.557 | 1.00 | 39.38 W |
| ATOM | 1673 OH2 | WAT W | 48 | 43.790 | −31.676 | 13.603 | 1.00 | 38.62 W |
| ATOM | 1674 OH2 | WAT W | 49 | 30.057 | −17.713 | 15.587 | 1.00 | 33.32 W |
| ATOM | 1675 OH2 | WAT W | 50 | 64.863 | −3.352 | 24.837 | 1.00 | 38.40 W |
| ATOM | 1676 OH2 | WAT W | 51 | 69.853 | −33.381 | 25.729 | 1.00 | 42.24 W |
| ATOM | 1677 OH2 | WAT W | 52 | 76.383 | −35.990 | 20.525 | 1.00 | 50.00 W |
| ATOM | 1678 OH2 | WAT W | 53 | 34.974 | 2.235 | 26.442 | 1.00 | 44.13 W |
| ATOM | 1679 OH2 | WAT W | 54 | 48.235 | −22.793 | 32.601 | 1.00 | 41.34 W |
| ATOM | 1680 OH2 | WAT W | 55 | 34.621 | −30.605 | 21.183 | 1.00 | 41.63 W |
| ATOM | 1681 OH2 | WAT W | 56 | 51.250 | −18.678 | 6.709 | 1.00 | 33.65 W |
| ATOM | 1682 OH2 | WAT W | 57 | 70.565 | −13.545 | 16.284 | 1.00 | 43.91 W |
| ATOM | 1683 OH2 | WAT W | 58 | 40.644 | 1.975 | 25.990 | 1.00 | 39.90 W |
| ATOM | 1684 OH2 | WAT W | 59 | 41.777 | −36.084 | 16.783 | 1.00 | 42.92 W |
| ATOM | 1685 OH2 | WAT W | 60 | 38.635 | −.149 | 20.191 | 1.00 | 38.28 W |
| ATOM | 1686 OH2 | WAT W | 61 | 48.417 | −34.017 | 18.551 | 1.00 | 27.72 W |
| ATOM | 1687 OH2 | WAT W | 62 | 26.991 | −13.329 | 11.995 | 1.00 | 48.57 W |
| ATOM | 1688 OH2 | WAT W | 63 | 66.842 | −31.824 | 15.221 | 1.00 | 38.52 W |
| ATOM | 1689 OH2 | WAT W | 64 | 36.537 | −28.187 | 32.627 | 1.00 | 49.21 W |
| ATOM | 1690 OH2 | WAT W | 65 | 46.636 | −23.459 | 28.167 | 1.00 | 47.17 W |
| ATOM | 1691 OH2 | WAT W | 66 | 48.616 | −4.648 | 9.478 | 1.00 | 44.89 W |
| ATOM | 1692 OH2 | WAT W | 67 | 62.533 | −30.691 | 10.230 | 1.00 | 49.40 W |
| ATOM | 1693 OH2 | WAT W | 68 | 38.365 | −21.636 | 35.248 | 1.00 | 38.43 W |
| ATOM | 1694 OH2 | WAT W | 69 | 30.506 | −10.319 | 10.891 | 1.00 | 48.05 W |
| ATOM | 1695 OH2 | WAT W | 70 | 61.229 | 2.971 | 23.053 | 1.00 | 33.07 W |
| ATOM | 1696 OH2 | WAT W | 71 | 70.839 | −28.021 | 30.557 | 1.00 | 36.36 W |
| ATOM | 1697 OH2 | WAT W | 72 | 41.046 | −4.390 | 10.686 | 1.00 | 39.11 W |
| ATOM | 1698 OH2 | WAT W | 73 | 60.331 | −4.338 | 13.393 | 1.00 | 42.66 W |
| ATOM | 1699 OH2 | WAT W | 74 | 25.455 | −16.974 | 14.799 | 1.00 | 47.52 W |
| ATOM | 1700 OH2 | WAT W | 75 | 38.240 | −8.792 | 40.148 | 1.00 | 50.64 W |
| ATOM | 1701 OH2 | WAT W | 76 | 35.251 | −25.503 | 10.720 | 1.00 | 40.38 W |
| ATOM | 1702 OH2 | WAT W | 77 | 43.525 | .230 | 44.626 | 1.00 | 50.93 W |
| ATOM | 1703 OH2 | WAT W | 78 | 31.161 | −3.158 | 29.730 | 1.00 | 39.26 W |
| ATOM | 1704 OH2 | WAT W | 79 | 44.692 | 4.129 | 30.103 | 1.00 | 42.10 W |
| ATOM | 1705 OH2 | WAT W | 80 | 47.730 | .629 | 19.833 | 1.00 | 41.81 W |
| ATOM | 1706 OH2 | WAT W | 81 | 28.983 | −6.441 | 19.015 | 1.00 | 37.15 W |
| ATOM | 1707 OH2 | WAT W | 82 | 53.059 | −2.671 | 16.337 | 1.00 | 48.52 W |
| ATOM | 1708 OH2 | WAT W | 83 | 35.652 | −28.960 | 14.519 | 1.00 | 38.10 W |
| ATOM | 1709 OH2 | WAT W | 84 | 40.625 | −36.991 | 20.735 | 1.00 | 40.38 W |
| ATOM | 1710 OH2 | WAT W | 85 | 58.845 | −7.979 | 12.466 | 1.00 | 39.38 W |
| ATOM | 1711 OH2 | WAT W | 86 | 45.002 | −4.273 | 41.882 | 1.00 | 47.19 W |
| ATOM | 1712 OH2 | WAT W | 87 | 33.718 | −26.477 | 8.515 | 1.00 | 50.48 W |
| ATOM | 1713 OH2 | WAT W | 88 | 50.069 | −20.338 | 34.203 | 1.00 | 43.55 W |
| ATOM | 1714 OH2 | WAT W | 89 | 29.960 | −14.517 | 21.721 | 1.00 | 52.73 W |
| ATOM | 1715 OH2 | WAT W | 90 | 43.458 | −20.448 | 5.549 | 1.00 | 45.96 W |
| ATOM | 1716 OH2 | WAT W | 91 | 43.340 | 4.923 | 27.531 | 1.00 | 53.92 W |
| ATOM | 1717 OH2 | WAT W | 92 | 70.329 | −30.549 | 13.073 | 1.00 | 44.38 W |
| ATOM | 1718 OH2 | WAT W | 93 | 60.087 | −10.445 | 24.204 | 1.00 | 57.72 W |
| ATOM | 1719 OH2 | WAT W | 94 | 41.834 | −26.671 | 3.843 | 1.00 | 48.97 W |
| ATOM | 1720 OH2 | WAT W | 95 | 72.976 | −35.458 | 21.556 | 1.00 | 45.34 W |
| ATOM | 1721 OH2 | WAT W | 96 | 50.294 | −30.964 | 24.830 | 1.00 | 40.42 W |
| ATOM | 1722 OH2 | WAT W | 97 | 55.485 | 5.461 | 26.072 | 1.00 | 44.52 W |
| ATOM | 1723 OH2 | WAT W | 98 | 34.294 | .687 | 35.910 | 1.00 | 49.18 W |
| ATOM | 1724 OH2 | WAT W | 99 | 46.604 | −17.402 | 23.217 | 1.00 | 37.43 W |
| ATOM | 1725 OH2 | WAT W | 100 | 26.889 | −14.007 | 27.811 | 1.00 | 51.68 W |
| ATOM | 1726 OH2 | WAT W | 101 | 53.058 | 2.171 | 12.804 | 1.00 | 51.67 W |
| ATOM | 1727 OH2 | WAT W | 102 | 28.899 | .012 | 31.657 | 1.00 | 52.77 W |
| ATOM | 1728 OH2 | WAT W | 103 | 48.126 | 4.685 | 30.317 | 1.00 | 46.21 W |
| ATOM | 1729 OH2 | WAT W | 104 | 37.897 | −1.208 | 12.423 | 1.00 | 52.60 W |
| ATOM | 1730 OH2 | WAT W | 105 | 48.969 | −17.333 | 5.205 | 1.00 | 50.86 W |
| ATOM | 1731 OH2 | WAT W | 106 | 43.189 | −37.139 | 24.550 | 1.00 | 50.37 W |
| ATOM | 1732 OH2 | WAT W | 107 | 29.336 | −21.901 | 27.551 | 1.00 | 57.38 W |
| ATOM | 1733 OH2 | WAT W | 108 | 43.569 | 4.407 | 34.810 | 1.00 | 48.40 W |
| ATOM | 1734 OH2 | WAT W | 109 | 69.798 | −14.989 | 13.364 | 1.00 | 53.72 W |
| ATOM | 1735 OH2 | WAT W | 110 | 42.224 | −16.234 | 42.400 | 1.00 | 51.54 W |

APPENDIX 1-continued

X-RAY DATA COORDINATES FOR THE APO FORM OF CDP-ME SYNTHASE
(SEQ ID NOS: 9 and 10)

| ATOM | 1736 | OH2 | WAT | W | 111 | 44.370 | 1.938 | 36.110 | 1.00 | 48.40 | W |
|------|------|-----|-----|---|-----|--------|-------|--------|------|-------|---|
| ATOM | 1737 | OH2 | WAT | W | 112 | 28.429 | -8.132 | 25.215 | 1.00 | 50.57 | W |
| ATOM | 1738 | OH2 | WAT | W | 113 | 50.216 | -27.285 | 32.630 | 1.00 | 42.37 | W |
| ATOM | 1739 | OH2 | WAT | W | 114 | 72.500 | -26.010 | 33.414 | 1.00 | 49.65 | W |
| ATOM | 1740 | OH2 | WAT | W | 115 | 44.925 | -9.213 | 42.403 | 1.00 | 50.21 | W |
| ATOM | 1741 | OH2 | WAT | W | 116 | 68.600 | -26.791 | 9.097 | 1.00 | 55.95 | W |
| ATOM | 1742 | OH2 | WAT | W | 117 | 33.246 | -4.312 | 32.699 | 1.00 | 49.49 | W |
| ATOM | 1743 | OH2 | WAT | W | 118 | 40.392 | -29.158 | 8.379 | 1.00 | 57.65 | W |
| ATOM | 1744 | OH2 | WAT | W | 119 | 74.338 | -35.936 | 29.115 | 1.00 | 55.95 | W |
| ATOM | 1745 | OH2 | WAT | W | 120 | 34.835 | -23.884 | 33.240 | 1.00 | 50.81 | W |
| ATOM | 1746 | OH2 | WAT | W | 121 | 35.803 | -3.411 | 13.833 | 1.00 | 15.14 | W |
| ATOM | 1747 | OH2 | WAT | W | 122 | 26.307 | -24.145 | 18.144 | 1.00 | 19.74 | W |
| ATOM | 1748 | OH2 | WAT | W | 123 | 35.171 | -5.592 | 15.997 | 1.00 | 15.31 | W |
| ATOM | 1749 | OH2 | WAT | W | 124 | 46.436 | -17.604 | 34.520 | 1.00 | 43.83 | W |
| ATOM | 1750 | OH2 | WAT | W | 125 | 75.516 | -33.855 | 16.538 | 1.00 | 34.44 | W |
| ATOM | 1751 | OH2 | WAT | W | 126 | 34.150 | -2.386 | 11.946 | 1.00 | 27.16 | W |
| ATOM | 1752 | OH2 | WAT | W | 127 | 36.533 | -1.226 | 16.007 | 1.00 | 19.22 | W |
| ATOM | 1753 | OH2 | WAT | W | 128 | 27.964 | -4.648 | 21.057 | 1.00 | 30.15 | W |
| ATOM | 1754 | OH2 | WAT | W | 129 | 45.265 | -1.633 | 16.733 | 1.00 | 38.55 | W |
| ATOM | 1755 | OH2 | WAT | W | 130 | 61.843 | -15.164 | 14.022 | 1.00 | 42.32 | W |
| ATOM | 1756 | OH2 | WAT | W | 131 | 69.549 | -26.025 | 11.790 | 1.00 | 45.61 | W |
| ATOM | 1757 | OH2 | WAT | W | 132 | 35.664 | -2.029 | 9.458 | 1.00 | 46.62 | W |
| ATOM | 1758 | OH2 | WAT | W | 133 | 50.695 | -34.085 | 23.768 | 1.00 | 37.68 | W |
| ATOM | 1759 | OH2 | WAT | W | 134 | 52.795 | -30.334 | 24.553 | 1.00 | 35.10 | W |
| ATOM | 1760 | OH2 | WAT | W | 135 | 32.104 | -22.605 | 29.298 | 1.00 | 39.30 | W |
| ATOM | 1761 | OH2 | WAT | W | 136 | 51.901 | -18.866 | 22.741 | 1.00 | 42.51 | W |
| ATOM | 1762 | OH2 | WAT | W | 137 | 39.919 | -10.349 | 6.223 | 1.00 | 44.77 | W |
| ATOM | 1763 | OH2 | WAT | W | 138 | 41.482 | -6.465 | 8.651 | 1.00 | 40.84 | W |
| ATOM | 1764 | OH2 | WAT | W | 139 | 71.700 | -35.484 | 25.298 | 1.00 | 49.21 | W |
| ATOM | 1765 | OH2 | WAT | W | 140 | 46.543 | 7.381 | 22.804 | 1.00 | 42.24 | W |
| ATOM | 1766 | OH2 | WAT | W | 141 | 52.204 | -16.529 | 24.520 | 1.00 | 44.86 | W |
| ATOM | 1767 | OH2 | WAT | W | 142 | 65.365 | 1.801 | 25.939 | 1.00 | 49.53 | W |
| ATOM | 1768 | OH2 | WAT | W | 143 | 60.813 | 1.922 | 29.123 | 1.00 | 44.60 | W |
| ATOM | 1769 | OH2 | WAT | W | 144 | 33.851 | -31.795 | 17.243 | 1.00 | 46.91 | W |
| ATOM | 1770 | OH2 | WAT | W | 145 | 71.305 | -28.383 | 11.480 | 1.00 | 49.64 | W |
| ATOM | 1771 | OH2 | WAT | W | 146 | 59.135 | -23.485 | 7.953 | 1.00 | 50.51 | W |
| ATOM | 1772 | OH2 | WAT | W | 147 | 46.587 | -7.295 | 39.929 | 1.00 | 44.36 | W |
| ATOM | 1773 | OH2 | WAT | W | 148 | 46.090 | 3.644 | 33.046 | 1.00 | 45.41 | W |
| ATOM | 1774 | OH2 | WAT | W | 149 | 64.392 | -32.060 | 25.629 | 1.00 | 47.04 | W |
| ATOM | 1775 | OH2 | WAT | W | 150 | 42.269 | -39.619 | 18.398 | 1.00 | 51.63 | W |
| ATOM | 1776 | OH2 | WAT | W | 151 | 68.730 | -29.270 | 29.988 | 1.00 | 46.16 | W |
| ATOM | 1777 | OH2 | WAT | W | 152 | 34.281 | -17.141 | 21.416 | 1.00 | 43.61 | W |
| ATOM | 1778 | OH2 | WAT | W | 153 | 34.715 | -17.426 | 37.366 | 1.00 | 51.97 | W |
| ATOM | 1779 | OH2 | WAT | W | 154 | 27.111 | -10.281 | 13.095 | 1.00 | 46.34 | W |
| ATOM | 1780 | OH2 | WAT | W | 155 | 50.360 | -1.990 | 15.586 | 1.00 | 46.73 | W |
| ATOM | 1781 | OH2 | WAT | W | 156 | 36.674 | -4.854 | 37.623 | 1.00 | 43.24 | W |
| ATOM | 1782 | OH2 | WAT | W | 157 | 47.144 | -19.749 | 6.293 | 1.00 | 40.87 | W |
| ATOM | 1783 | OH2 | WAT | W | 158 | 52.276 | -14.076 | 36.660 | 1.00 | 48.83 | W |
| ATOM | 1784 | OH2 | WAT | W | 159 | 38.671 | .366 | 41.137 | 1.00 | 49.19 | W |
| ATOM | 1785 | OH2 | WAT | W | 160 | 36.709 | -9.669 | 4.795 | 1.00 | 50.52 | W |
| ATOM | 1786 | OH2 | WAT | W | 161 | 43.244 | -38.273 | 16.427 | 1.00 | 42.30 | W |
| ATOM | 1787 | OH2 | WAT | W | 162 | 27.735 | -15.226 | 30.946 | 1.00 | 52.66 | W |
| ATOM | 1788 | OH2 | WAT | W | 163 | 51.486 | -18.198 | 29.962 | 1.00 | 40.73 | W |
| ATOM | 1789 | OH2 | WAT | W | 164 | 46.701 | .969 | 36.381 | 1.00 | 44.14 | W |
| ATOM | 1790 | OH2 | WAT | W | 165 | 66.661 | -31.968 | 21.121 | 1.00 | 56.65 | W |
| ATOM | 1791 | OH2 | WAT | W | 166 | 51.184 | -4.445 | 34.952 | 1.00 | 45.62 | W |
| ATOM | 1792 | OH2 | WAT | W | 167 | 34.768 | -3.534 | 36.003 | 1.00 | 48.51 | W |
| ATOM | 1793 | OH2 | WAT | W | 168 | 59.415 | -16.211 | 6.406 | 1.00 | 51.14 | W |
| ATOM | 1794 | OH2 | WAT | W | 169 | 40.259 | -20.791 | 37.003 | 1.00 | 57.12 | W |
| ATOM | 1795 | OH2 | WAT | W | 170 | 46.872 | 7.453 | 32.080 | 1.00 | 60.54 | W |
| ATOM | 1796 | OH2 | WAT | W | 171 | 56.470 | 3.618 | 27.841 | 1.00 | 54.22 | W |
| ATOM | 1797 | OH2 | WAT | W | 172 | 70.936 | -18.836 | 10.804 | 1.00 | 46.77 | W |
| ATOM | 1798 | OH2 | WAT | W | 173 | 36.773 | -15.453 | 41.856 | 1.00 | 46.98 | W |
| ATOM | 1799 | OH2 | WAT | W | 174 | 30.603 | -7.262 | 10.669 | 1.00 | 44.40 | W |
| ATOM | 1800 | OH2 | WAT | W | 175 | 36.480 | -36.175 | 34.173 | 1.00 | 53.09 | W |
| ATOM | 1801 | OH2 | WAT | W | 176 | 49.148 | -37.067 | 21.108 | 1.00 | 50.34 | W |
| ATOM | 1802 | OH2 | WAT | W | 177 | 70.687 | -23.652 | 35.226 | 1.00 | 53.19 | W |
| ATOM | 1803 | OH2 | WAT | W | 178 | 36.694 | -15.622 | 6.575 | 1.00 | 48.97 | W |
| ATOM | 1804 | OH2 | WAT | W | 179 | 54.045 | -18.467 | 5.276 | 1.00 | 46.62 | W |
| ATOM | 1805 | OH2 | WAT | W | 180 | 30.765 | -11.541 | 33.596 | 1.00 | 46.71 | W |
| ATOM | 1806 | OH2 | WAT | W | 181 | 61.475 | -10.906 | 17.507 | 1.00 | 44.41 | W |
| ATOM | 1807 | OH2 | WAT | W | 182 | 50.659 | 2.850 | 33.354 | 1.00 | 54.62 | W |
| ATOM | 1808 | OH2 | WAT | W | 183 | 56.116 | 2.097 | 12.131 | 1.00 | 54.36 | W |
| ATOM | 1809 | OH2 | WAT | W | 184 | 44.396 | -15.035 | 41.417 | 1.00 | 52.33 | W |
| ATOM | 1810 | OH2 | WAT | W | 185 | 50.049 | -10.978 | 7.022 | 1.00 | 46.47 | W |
| ATOM | 1811 | OH2 | WAT | W | 186 | 43.833 | -23.761 | 1.923 | 1.00 | 61.71 | W |

APPENDIX 1-continued

X-RAY DATA COORDINATES FOR THE APO FORM OF CDP-ME SYNTHASE
(SEQ ID NOS: 9 and 10)

| | | | | | | | | | |
|---|---|---|---|---|---|---|---|---|---|
| ATOM | 1812OH2 | WAT | W | 187 | 79.402 | −34.752 | 27.411 | 1.00 | 54.01 W |
| ATOM | 1813OH2 | WAT | W | 188 | 37.293 | −31.403 | 14.941 | 1.00 | 49.95 W |
| ATOM | 1814OH2 | WAT | W | 189 | 70.203 | −17.062 | 18.317 | 1.00 | 54.79 W |
| ATOM | 1815OH2 | WAT | W | 190 | 65.151 | −5.728 | 23.873 | 1.00 | 61.57 W |
| ATOM | 1816OH2 | WAT | W | 191 | 37.853 | −33.800 | 25.789 | 1.00 | 46.69 W |
| ATOM | 1817OH2 | WAT | W | 192 | 39.680 | −18.112 | .455 | 1.00 | 58.93 W |
| ATOM | 1818OH2 | WAT | W | 193 | 54.731 | 6.739 | 14.744 | 1.00 | 51.68 W |
| ATOM | 1819OH2 | WAT | W | 194 | 53.212 | −36.559 | 31.398 | 1.00 | 50.96 W |
| ATOM | 1820OH2 | WAT | W | 195 | 36.525 | −20.445 | 1.537 | 1.00 | 51.26 W |
| ATOM | 1821OH2 | WAT | W | 196 | 49.123 | −7.885 | 41.693 | 1.00 | 63.54 W |
| ATOM | 1822OH2 | WAT | W | 197 | 66.656 | −10.031 | 31.191 | 1.00 | 52.70 W |
| ATOM | 1823OH2 | WAT | W | 198 | 61.761 | −8.146 | 13.688 | 1.00 | 53.54 W |
| ATOM | 1824OH2 | WAT | W | 199 | 48.878 | −18.750 | 24.972 | 1.00 | 50.02 W |
| ATOM | 1825OH2 | WAT | W | 200 | 28.047 | −16.163 | 13.561 | 1.00 | 29.63 W |
| ATOM | 1826OH2 | WAT | W | 201 | 38.951 | −33.622 | 21.898 | 1.00 | 39.34 W |
| ATOM | 1827OH2 | WAT | W | 202 | 33.058 | −22.788 | 26.401 | 1.00 | 36.35 W |
| ATOM | 1828OH2 | WAT | W | 203 | 26.220 | −20.034 | 17.663 | 1.00 | 32.93 W |
| ATOM | 1829OH2 | WAT | W | 204 | 42.937 | .449 | 17.390 | 1.00 | 36.78 W |
| ATOM | 1830OH2 | WAT | W | 205 | 73.381 | −35.387 | 31.582 | 1.00 | 36.40 W |
| ATOM | 1831OH2 | WAT | W | 206 | 68.297 | −33.469 | 11.365 | 1.00 | 39.32 W |
| ATOM | 1832OH2 | WAT | W | 207 | 27.299 | −15.490 | 17.962 | 1.00 | 39.35 W |
| ATOM | 1833OH2 | WAT | W | 208 | 38.576 | −22.452 | 1.220 | 1.00 | 37.72 W |
| ATOM | 1834OH2 | WAT | W | 209 | 68.126 | −28.624 | 32.747 | 1.00 | 37.95 W |
| ATOM | 1835OH2 | WAT | W | 210 | 55.448 | −37.767 | 30.587 | 1.00 | 38.91 W |
| ATOM | 1836OH2 | WAT | W | 211 | 75.053 | −33.823 | 34.010 | 1.00 | 38.15 W |
| ATOM | 1837OH2 | WAT | W | 212 | 52.212 | −33.920 | 32.727 | 1.00 | 37.10 W |
| ATOM | 1838OH2 | WAT | W | 213 | 51.093 | −21.328 | 30.470 | 1.00 | 36.93 W |
| ATOM | 1839OH2 | WAT | W | 214 | 81.957 | −34.963 | 28.344 | 1.00 | 38.58 W |
| ATOM | 1840OH2 | WAT | W | 215 | 45.291 | 3.543 | 19.935 | 1.00 | 35.30 W |
| ATOM | 1841OH2 | WAT | W | 216 | 62.130 | −33.797 | 26.548 | 1.00 | 39.66 W |
| ATOM | 1842OH2 | WAT | W | 217 | 45.208 | −28.641 | 10.874 | 1.00 | 33.55 W |
| ATOM | 1843OH2 | WAT | W | 218 | 39.604 | −16.728 | 40.866 | 1.00 | 31.75 W |
| ATOM | 1844OH2 | WAT | W | 219 | 60.602 | −15.681 | 11.964 | 1.00 | 39.59 W |
| ATOM | 1845OH2 | WAT | W | 220 | 36.103 | −22.302 | 34.761 | 1.00 | 37.39 W |
| ATOM | 1846OH2 | WAT | W | 221 | 76.463 | −33.946 | 18.868 | 1.00 | 30.75 W |
| ATOM | 1847OH2 | WAT | W | 222 | 50.498 | −31.970 | 27.034 | 1.00 | 36.59 W |
| ATOM | 1848OH2 | WAT | W | 223 | 58.236 | −13.487 | 19.226 | 1.00 | 40.48 W |
| ATOM | 1849OH2 | WAT | W | 224 | 32.488 | −8.773 | 9.666 | 1.00 | 35.60 W |
| ATOM | 1850OH2 | WAT | W | 225 | 51.230 | −4.501 | 9.393 | 1.00 | 36.04 W |
| ATOM | 1851OH2 | WAT | W | 226 | 35.085 | −7.502 | 38.101 | 1.00 | 36.81 W |
| ATOM | 1852OH2 | WAT | W | 227 | 34.519 | −23.055 | 30.435 | 1.00 | 26.83 W |
| ATOM | 1853OH2 | WAT | W | 228 | 42.459 | −40.490 | 20.916 | 1.00 | 38.83 W |
| ATOM | 1854OH2 | WAT | W | 229 | 35.846 | −11.183 | 7.433 | 1.00 | 38.58 W |
| ATOM | 1855OH2 | WAT | W | 230 | 61.749 | −10.100 | 21.568 | 1.00 | 35.63 W |
| ATOM | 1856OH2 | WAT | W | 231 | 48.088 | 2.114 | 34.545 | 1.00 | 38.92 W |
| ATOM | 1857OH2 | WAT | W | 232 | 51.384 | .229 | 12.259 | 1.00 | 40.35 W |
| ATOM | 1858OH2 | WAT | W | 233 | 39.510 | −23.976 | 35.730 | 1.00 | 39.65 W |
| ATOM | 1859OH2 | WAT | W | 234 | 67.706 | −18.336 | 9.774 | 1.00 | 38.00 W |
| ATOM | 1860OH2 | WAT | W | 235 | 61.049 | −12.499 | 21.206 | 1.00 | 36.84 W |
| ATOM | 1861OH2 | WAT | W | 236 | 43.438 | −27.522 | 9.385 | 1.00 | 33.00 W |
| ATOM | 1862OH2 | WAT | W | 237 | 43.402 | −24.214 | 6.938 | 1.00 | 27.53 W |
| ATOM | 1863OH2 | WAT | W | 238 | 41.835 | −1.867 | 11.137 | 1.00 | 39.67 W |
| ATOM | 1864OH2 | WAT | W | 239 | 51.610 | −34.621 | 28.404 | 1.00 | 36.38 W |
| ATOM | 1865OH2 | WAT | W | 240 | 28.732 | −13.038 | 29.510 | 1.00 | 37.25 W |
| ATOM | 1866OH2 | WAT | W | 241 | 30.870 | −15.792 | 34.118 | 1.00 | 37.46 W |
| ATOM | 1867OH2 | WAT | W | 242 | 34.612 | 3.886 | 31.054 | 1.00 | 37.30 W |
| ATOM | 1868OH2 | WAT | W | 243 | 45.928 | −13.903 | 39.327 | 1.00 | 40.97 W |
| ATOM | 1869OH2 | WAT | W | 244 | 40.562 | −36.401 | 23.262 | 1.00 | 37.22 W |
| ATOM | 1870OH2 | WAT | W | 245 | 54.642 | −1.209 | 10.634 | 1.00 | 38.84 W |
| ATOM | 1871OH2 | WAT | W | 246 | 47.537 | −29.261 | 33.487 | 1.00 | 35.12 W |
| ATOM | 1872OH2 | WAT | W | 247 | 65.770 | −33.743 | 24.370 | 1.00 | 35.53 W |
| ATOM | 1873OH2 | WAT | W | 248 | 71.323 | −27.195 | 8.289 | 1.00 | 34.44 W |
| ATOM | 1874OH2 | WAT | W | 249 | 38.691 | −7.996 | 7.691 | 1.00 | 37.45 W |
| ATOM | 1875OH2 | WAT | W | 250 | 26.635 | −21.801 | 19.402 | 1.00 | 40.94 W |
| ATOM | 1876OH2 | WAT | W | 251 | 59.792 | −4.179 | 9.401 | 1.00 | 39.95 W |
| ATOM | 1877OH2 | WAT | W | 252 | 34.266 | −30.995 | 28.659 | 1.00 | 33.29 W |
| ATOM | 1878OH2 | WAT | W | 253 | 45.488 | −39.518 | 19.690 | 1.00 | 38.10 W |
| ATOM | 1879OH2 | WAT | W | 254 | 50.380 | −38.178 | 29.545 | 1.00 | 38.65 W |
| ATOM | 1880OH2 | WAT | W | 255 | 49.055 | 5.530 | 22.440 | 1.00 | 36.29 W |
| ATOM | 1881OH2 | WAT | W | 256 | 25.993 | −14.592 | 22.542 | 1.00 | 36.63 W |
| ATOM | 1882OH2 | WAT | W | 257 | 37.021 | −3.914 | 8.037 | 1.00 | 39.14 W |
| ATOM | 1883OH2 | WAT | W | 258 | 46.433 | −30.547 | 9.040 | 1.00 | 40.62 W |
| ATOM | 1884OH2 | WAT | W | 259 | 61.922 | −11.812 | 26.540 | 1.00 | 38.87 W |
| ATOM | 1885OH2 | WAT | W | 260 | 67.352 | −28.635 | 35.330 | 1.00 | 38.57 W |
| ATOM | 1886OH2 | WAT | W | 261 | 33.327 | −1.623 | 36.746 | 1.00 | 35.17 W |
| ATOM | 1887OH2 | WAT | W | 262 | 67.245 | −15.018 | 21.815 | 1.00 | 38.13 W |

APPENDIX 1-continued

X-RAY DATA COORDINATES FOR THE APO FORM OF CDP-ME SYNTHASE
(SEQ ID NOS: 9 and 10)

| ATOM | 1888 OH2 | WAT W | 263 | 63.140 | −10.794 | 15.625 | 1.00 | 37.48 | W |
|---|---|---|---|---|---|---|---|---|---|
| ATOM | 1889 OH2 | WAT W | 264 | 44.444 | 6.021 | 36.984 | 1.00 | 37.46 | W |
| ATOM | 1890 OH2 | WAT W | 265 | 48.915 | −36.830 | 23.991 | 1.00 | 34.41 | W |
| ATOM | 1891 OH2 | WAT W | 266 | 53.177 | 6.584 | 28.788 | 1.00 | 37.55 | W |
| ATOM | 1892 OH2 | WAT W | 267 | 70.033 | −6.803 | 29.472 | 1.00 | 41.07 | W |
| ATOM | 1893 OH2 | WAT W | 268 | 31.037 | −24.101 | 27.627 | 1.00 | 35.03 | W |
| ATOM | 1894 OH2 | WAT W | 269 | 22.643 | −16.819 | 15.031 | 1.00 | 35.15 | W |
| ATOM | 1895 OH2 | WAT W | 270 | 60.672 | −32.913 | 10.688 | 1.00 | 37.73 | W |
| ATOM | 1896 OH2 | WAT W | 271 | 71.897 | −33.555 | 14.885 | 1.00 | 37.96 | W |
| ATOM | 1897 OH2 | WAT W | 272 | 32.489 | −5.999 | 36.729 | 1.00 | 38.27 | W |
| ATOM | 1898 OH2 | WAT W | 273 | 51.397 | −14.486 | 39.300 | 1.00 | 40.75 | W |
| ATOM | 1899 OH2 | WAT W | 274 | 73.215 | −35.263 | 16.494 | 1.00 | 35.26 | W |
| ATOM | 1900 OH2 | WAT W | 275 | 43.450 | −27.121 | 6.183 | 1.00 | 42.76 | W |
| ATOM | 1901 OH2 | WAT W | 276 | 42.886 | −20.713 | 1.544 | 1.00 | 36.42 | W |
| ATOM | 1902 OH2 | WAT W | 277 | 57.540 | −7.214 | 45.424 | 1.00 | 44.20 | W |
| ATOM | 1903 OH2 | WAT W | 278 | 33.091 | −10.337 | 36.900 | 1.00 | 39.10 | W |
| ATOM | 1904 OH2 | WAT W | 279 | 66.306 | −14.561 | 18.687 | 1.00 | 41.44 | W |
| ATOM | 1905 OH2 | WAT W | 280 | 63.990 | −15.269 | 18.044 | 1.00 | 38.04 | W |
| ATOM | 1906 OH2 | WAT W | 281 | 76.897 | −37.735 | 23.633 | 1.00 | 41.53 | W |
| ATOM | 1907 OH2 | WAT W | 282 | 80.276 | −32.365 | 34.015 | 1.00 | 39.33 | W |
| ATOM | 1908 OH2 | WAT W | 283 | 54.173 | −11.914 | 8.067 | 1.00 | 26.94 | W |
| ATOM | 1909 OH2 | WAT W | 284 | 47.730 | −13.279 | 28.873 | 1.00 | 21.23 | W |
| ATOM | 1910 OH2 | WAT W | 285 | 46.244 | −8.593 | 23.770 | 1.00 | 32.34 | W |
| ATOM | 1911 OH2 | WAT W | 286 | 34.478 | −15.466 | 35.653 | 1.00 | 47.84 | W |
| ATOM | 1912 OH2 | WAT W | 287 | 68.461 | −30.111 | 27.640 | 1.00 | 31.10 | W |
| ATOM | 1913 OH2 | WAT W | 288 | 29.982 | −8.197 | 23.061 | 1.00 | 32.62 | W |
| ATOM | 1914 OH2 | WAT W | 289 | 50.221 | −11.963 | 28.572 | 1.00 | 32.60 | W |
| ATOM | 1915 OH2 | WAT W | 290 | 31.124 | −26.176 | 26.158 | 1.00 | 36.05 | W |
| ATOM | 1916 OH2 | WAT W | 291 | 52.051 | −20.208 | 28.464 | 1.00 | 31.51 | W |
| ATOM | 1917 OH2 | WAT W | 292 | 31.899 | −5.559 | 8.582 | 1.00 | 37.99 | W |
| ATOM | 1918 OH2 | WAT W | 293 | 38.422 | −34.999 | 23.754 | 1.00 | 46.66 | W |
| ATOM | 1919 OH2 | WAT W | 294 | 31.113 | −13.932 | 35.960 | 1.00 | 30.82 | W |
| ATOM | 1920 OH2 | WAT W | 295 | 60.269 | −13.415 | 11.203 | 1.00 | 36.12 | W |
| ATOM | 1921 OH2 | WAT W | 296 | 53.027 | −20.763 | 26.247 | 1.00 | 35.30 | W |
| ATOM | 1922 OH2 | WAT W | 297 | 44.908 | 1.001 | 20.320 | 1.00 | 38.21 | W |
| ATOM | 1923 OH2 | WAT W | 298 | 40.914 | −23.590 | .763 | 1.00 | 38.18 | W |
| ATOM | 1924 OH2 | WAT W | 299 | 45.909 | −15.058 | 33.218 | 1.00 | 32.70 | W |
| ATOM | 1925 OH2 | WAT W | 300 | 39.131 | −11.896 | 4.216 | 1.00 | 42.04 | W |
| ATOM | 1926 OH2 | WAT W | 301 | 30.715 | −7.770 | 26.017 | 1.00 | 32.31 | W |
| ATOM | 1927 OH2 | WAT W | 302 | 42.143 | −5.186 | 45.743 | 1.00 | 33.54 | W |
| ATOM | 1928 OH2 | WAT W | 303 | 54.825 | −3.349 | 14.625 | 1.00 | 34.04 | W |
| ATOM | 1929 OH2 | WAT W | 304 | 36.344 | −32.589 | 28.083 | 1.00 | 40.75 | W |
| ATOM | 1930 OH2 | WAT W | 305 | 58.825 | −4.134 | 30.659 | 1.00 | 37.98 | W |
| ATOM | 1931 OH2 | WAT W | 306 | 29.365 | −13.663 | 33.162 | 1.00 | 46.20 | W |
| ATOM | 1932 OH2 | WAT W | 307 | 37.798 | 1.648 | 25.154 | 1.00 | 34.01 | W |
| ATOM | 1933 OH2 | WAT W | 308 | 29.169 | 2.302 | 30.871 | 1.00 | 38.60 | W |
| ATOM | 1934 OH2 | WAT W | 309 | 39.113 | −30.014 | 34.574 | 1.00 | 40.12 | W |
| ATOM | 1935 OH2 | WAT W | 310 | 28.202 | −15.234 | 11.198 | 1.00 | 35.80 | W |
| ATOM | 1936 OH2 | WAT W | 311 | 34.013 | −12.223 | 5.796 | 1.00 | 36.73 | W |
| ATOM | 1937 OH2 | WAT W | 312 | 65.135 | −12.527 | 30.842 | 1.00 | 36.35 | W |
| ATOM | 1938 OH2 | WAT W | 313 | 61.610 | −13.358 | 24.438 | 1.00 | 42.16 | W |
| ATOM | 1939 OH2 | WAT W | 314 | 51.277 | −38.295 | 22.003 | 1.00 | 39.14 | W |
| ATOM | 1940 OH2 | WAT W | 315 | 44.367 | 8.114 | 25.280 | 1.00 | 41.86 | W |
| ATOM | 1941 OH2 | WAT W | 316 | 33.263 | −13.718 | 37.313 | 1.00 | 40.67 | W |
| ATOM | 1942 OH2 | WAT W | 317 | 75.035 | −36.306 | 22.610 | 1.00 | 36.93 | W |
| ATOM | 1943 OH2 | WAT W | 318 | 54.307 | 2.638 | 32.199 | 1.00 | 36.42 | W |
| ATOM | 1944 OH2 | WAT W | 319 | 29.958 | −2.096 | 33.043 | 1.00 | 46.25 | W |
| ATOM | 1945 OH2 | WAT W | 320 | 53.620 | −19.427 | 24.395 | 1.00 | 42.64 | W |
| ATOM | 1946 OH2 | WAT W | 321 | 30.025 | −20.253 | 25.528 | 1.00 | 32.25 | W |
| ATOM | 1947 OH2 | WAT W | 322 | 44.310 | −21.503 | 27.957 | 1.00 | 42.09 | W |
| ATOM | 1948 OH2 | WAT W | 323 | 62.771 | −13.033 | 17.232 | 1.00 | 41.08 | W |
| ATOM | 1949 OH2 | WAT W | 324 | 51.001 | −10.704 | 31.086 | 1.00 | 39.54 | W |
| ATOM | 1950 OH2 | WAT W | 325 | 59.319 | −6.706 | 35.798 | 1.00 | 41.35 | W |
| ATOM | 1951 OH2 | WAT W | 326 | 52.805 | −6.529 | 8.419 | 1.00 | 41.00 | W |
| ATOM | 1952 OH2 | WAT W | 327 | 38.766 | 2.762 | 19.345 | 1.00 | 34.39 | W |
| ATOM | 1953 OH2 | WAT W | 328 | 37.103 | −5.581 | 42.654 | 1.00 | 42.22 | W |
| ATOM | 1954 OH2 | WAT W | 329 | 34.817 | −31.236 | 15.066 | 1.00 | 42.18 | W |
| ATOM | 1955 OH2 | WAT W | 330 | 71.453 | −21.515 | 32.130 | 1.00 | 40.73 | W |
| ATOM | 1956 OH2 | WAT W | 331 | 41.272 | −23.472 | 28.333 | 1.00 | 43.59 | W |
| ATOM | 1957 OH2 | WAT W | 332 | 33.573 | −3.860 | 30.030 | 1.00 | 41.68 | W |
| ATOM | 1958 OH2 | WAT W | 333 | 67.262 | −28.470 | 7.896 | 1.00 | 43.23 | W |
| ATOM | 1959 OH2 | WAT W | 334 | 55.197 | −3.726 | 36.467 | 1.00 | 43.19 | W |
| ATOM | 1960 OH2 | WAT W | 335 | 55.295 | −7.671 | 6.528 | 1.00 | 37.53 | W |
| ATOM | 1961 OH2 | WAT W | 336 | 48.832 | −8.496 | 39.036 | 1.00 | 41.02 | W |
| ATOM | 1962 OH2 | WAT W | 337 | 35.234 | −26.229 | 32.390 | 1.00 | 39.19 | W |
| ATOM | 1963 OH2 | WAT W | 338 | 47.493 | −16.818 | 36.560 | 1.00 | 47.08 | W |

APPENDIX 1-continued

X-RAY DATA COORDINATES FOR THE APO FORM OF CDP-ME SYNTHASE
(SEQ ID NOS: 9 and 10)

| ATOM | 1964OH2 | WAT W | 339 | 48.819 | −12.951 | 41.747 | 1.00 | 42.03 W |
|---|---|---|---|---|---|---|---|---|
| ATOM | 1965OH2 | WAT W | 340 | 43.882 | −38.716 | 22.504 | 1.00 | 44.02 W |
| ATOM | 1966OH2 | WAT W | 341 | 46.578 | −1.977 | 43.191 | 1.00 | 42.24 W |
| ATOM | 1967OH2 | WAT W | 342 | 72.531 | −31.605 | 12.468 | 1.00 | 38.62 W |
| ATOM | 1968OH2 | WAT W | 343 | 40.079 | −33.999 | 38.820 | 1.00 | 42.63 W |
| ATOM | 1969OH2 | WAT W | 344 | 58.324 | −6.292 | 33.262 | 1.00 | 46.55 W |
| ATOM | 1970OH2 | WAT W | 345 | 59.594 | −15.109 | 29.299 | 1.00 | 37.79 W |
| ATOM | 1971OH2 | WAT W | 346 | 35.944 | −32.471 | 21.864 | 1.00 | 38.04 W |
| ATOM | 1972OH2 | WAT W | 347 | 38.115 | −27.656 | 34.427 | 1.00 | 36.95 W |
| ATOM | 1973OH2 | WAT W | 348 | 36.574 | 5.056 | 35.584 | 1.00 | 42.65 W |
| ATOM | 1974OH2 | WAT W | 349 | 25.506 | −14.859 | 25.508 | 1.00 | 41.43 W |
| ATOM | 1975OH2 | WAT W | 350 | 50.547 | 2.686 | 18.569 | 1.00 | 44.73 W |
| ATOM | 1976OH2 | WAT W | 351 | 38.816 | −35.639 | 31.130 | 1.00 | 44.62 W |
| ATOM | 1977OH2 | WAT W | 352 | 34.952 | −.329 | 41.304 | 1.00 | 38.63 W |
| ATOM | 1978OH2 | WAT W | 353 | 46.443 | −23.548 | 7.404 | 1.00 | 42.33 W |
| ATOM | 1979OH2 | WAT W | 354 | 47.114 | −6.665 | 42.494 | 1.00 | 41.73 W |
| ATOM | 1980OH2 | WAT W | 355 | 67.809 | −12.662 | 20.880 | 1.00 | 52.33 W |
| ATOM | 1981OH2 | WAT W | 356 | 63.121 | 4.774 | 27.064 | 1.00 | 38.29 W |
| ATOM | 1982OH2 | WAT W | 357 | 39.688 | −31.762 | 10.395 | 1.00 | 37.01 W |
| ATOM | 1983OH2 | WAT W | 358 | 28.870 | −23.345 | 18.011 | 1.00 | 47.78 W |
| ATOM | 1984OH2 | WAT W | 359 | 60.870 | −31.947 | 8.435 | 1.00 | 33.76 W |
| ATOM | 1985OH2 | WAT W | 360 | 37.501 | −35.144 | 36.269 | 1.00 | 37.97 W |
| ATOM | 1986OH2 | WAT W | 361 | 70.220 | −24.991 | 9.266 | 1.00 | 40.70 W |
| ATOM | 1987OH2 | WAT W | 362 | 35.817 | −17.655 | 2.516 | 1.00 | 45.68 W |
| ATOM | 1988OH2 | WAT W | 363 | 68.321 | −33.612 | 16.959 | 1.00 | 43.51 W |
| ATOM | 1989OH2 | WAT W | 364 | 46.092 | −1.435 | 11.021 | 1.00 | 42.43 W |
| ATOM | 1990OH2 | WAT W | 365 | 33.745 | .630 | 17.603 | 1.00 | 51.36 W |
| ATOM | 1991OH2 | WAT W | 366 | 82.055 | −37.490 | 30.372 | 1.00 | 41.66 W |
| ATOM | 1992OH2 | WAT W | 367 | 57.994 | −8.837 | 38.009 | 1.00 | 44.43 W |
| ATOM | 1993OH2 | WAT W | 368 | 33.895 | −2.783 | 39.558 | 1.00 | 39.11 W |
| ATOM | 1994OH2 | WAT W | 369 | 51.828 | −1.923 | 36.682 | 1.00 | 41.88 W |
| ATOM | 1995OH2 | WAT W | 370 | 68.164 | −35.713 | 18.711 | 1.00 | 37.62 W |
| ATOM | 1996CA + 2 | CA2 C | 1 | 35.316 | −3.287 | 16.067 | 1.00 | 65.43 C |

END

APPENDIX 2

X-RAY DATA COORDINATES FOR CDP-ME SYNTHASE COMPLEXED WITH CTP•Mg$^{2+}$
(SEQ ID NO: 11)

REMARK coordinates from minimization and B-factor refinement
REMARK refinement resolution: 90 − 1.5 A
REMARK starting r = .2933 free_r = .2909
REMARK final r = .2270 free_r = .2494
REMARK rmsd bonds = .009964 rmsd angles = 1.59282
REMARK B rmsd for bonded mainchain atoms = 1.428 target = 1.5
REMARK B rmsd for bonded sidechain atoms 2.284 target = 2.0
REMARK B rmsd for angle mainchain atoms = 2.182 target = 2.0
REMARK B rmsd for angle sidechain atoms = 3.167 target = 2.5
REMARK target = mlf final wa = 2.11827
REMARK final rweight = .1856 (with wa = 2.11827)
REMARK md-method = torsion annealing schedule = constant
REMARK starting temperature = 2000 total md steps = 1 * 100
REMARK cycles = 2 coordinate steps = 20 B-factor steps = 10
REMARK sg = C2 a = 130.564 b = 47.074 c = 38.105 alpha = 90 beta = 93.784 gamma = 90
REMARK topology file 1: CNS_TOPPAR:protein.top
REMARK topology file 2: CNS_TOPPAR:dna-rna.top
REMARK topology file 3: CNS_TOPPAR:water.top
REMARK topology file 4: CNS_TOPPAR:ion.top
REMARK topology file 5: CNSPAR:ctp.top
REMARK parameter file 1: CNS_TOPPAR:protein_rep.param
REMARK parameter file 2: CNS_TOPPAR:dna-rna_rep.param
REMARK parameter file 3: CNS_TOPPAR:water_rep.param
REMARK parameter file 4: CNS_TOPPAR:ion.param
REMARK parameter file 5: CNSPAR:ctp.param
REMARK molecular structure file: generate.mtf
REMARK input coordinates: generate.pdb
REMARK reflection file = ygbp2.xpl
REMARK ncs = none
REMARK B-correction resolution: 6.0 − 1.5
REMARK initial B-factor correction applied to fobs:
REMARK B11 = 7.197 B22 = −7.860 B33 = .663

APPENDIX 2-continued

X-RAY DATA COORDINATES FOR CDP-ME SYNTHASE COMPLEXED WITH CTP•Mg$^{2+}$
(SEQ ID NO: 11)

REMARK B12 = .000 B13 = .143 B23 = .000
REMARK B-factor correction applied to coordinate array B: −.741
REMARK bulk solvent: density level = .365386 e/A^3, B-factor = 45.0858 A^2
REMARK reflections with |Fobs|/sigma_F < 0.0 rejected
REMARK reflections with |Fobs| > 10000 * rms(Fobs) rejected
REMARK theoretical total number of refl. in resol. range: 37155 ( 100.0% )
REMARK number of unobserved reflections (no entry or |F| = 0): 2741 ( 7.4% )
REMARK number of reflections rejected:   0 ( .0% )
REMARK total number of reflections used:   34414 ( 92.6% )
REMARK number of reflections in working set:   32682 ( 88.0% )
REMARK number of reflections in test set:   1732 ( 4.7% )
CRYST1 130.564 47.074 38.105 90.00 93.78 90.00 C 2
REMARK FILENAME = "refine.pdb"
REMARK DATE: Oct. 24, 2000 14:14:42 created by user: richard
REMARK VERSION:1.0

| ATOM | 1  | CB  | HIS | A | 5  | 29.154 | −18.768 | 10.052 | 1.00 | 35.33 | A |
|------|----|-----|-----|---|----|--------|---------|--------|------|-------|---|
| ATOM | 2  | CG  | HIS | A | 5  | 30.545 | −19.141 | 9.646  | 1.00 | 38.47 | A |
| ATOM | 3  | CD2 | HIS | A | 5  | 31.312 | −18.732 | 8.608  | 1.00 | 38.22 | A |
| ATOM | 4  | ND1 | HIS | A | 5  | 31.340 | −19.974 | 10.405 | 1.00 | 38.98 | A |
| ATOM | 5  | CE1 | HIS | A | 5  | 32.537 | −20.058 | 9.853  | 1.00 | 39.06 | A |
| ATOM | 6  | NE2 | HIS | A | 5  | 32.547 | −19.314 | 8.764  | 1.00 | 38.86 | A |
| ATOM | 7  | C   | HIS | A | 5  | 30.439 | −17.272 | 11.579 | 1.00 | 32.77 | A |
| ATOM | 8  | O   | HIS | A | 5  | 31.369 | −17.814 | 12.176 | 1.00 | 32.69 | A |
| ATOM | 9  | N   | HIS | A | 5  | 27.910 | −17.076 | 11.383 | 1.00 | 33.62 | A |
| ATOM | 10 | CA  | HIS | A | 5  | 29.097 | −17.994 | 11.377 | 1.00 | 34.27 | A |
| ATOM | 11 | N   | LEU | A | 6  | 30.524 | −16.049 | 11.075 | 1.00 | 30.52 | A |
| ATOM | 12 | CA  | LEU | A | 6  | 31.750 | −15.270 | 11.141 | 1.00 | 27.09 | A |
| ATOM | 13 | CB  | LEU | A | 6  | 31.784 | −14.282 | 9.966  | 1.00 | 29.57 | A |
| ATOM | 14 | CG  | LEU | A | 6  | 31.822 | −14.886 | 8.551  | 1.00 | 30.37 | A |
| ATOM | 15 | CD1 | LEU | A | 6  | 31.767 | −13.761 | 7.509  | 1.00 | 32.24 | A |
| ATOM | 16 | CD2 | LEU | A | 6  | 33.091 | −15.695 | 8.364  | 1.00 | 31.47 | A |
| ATOM | 17 | C   | LEU | A | 6  | 31.980 | −14.530 | 12.456 | 1.00 | 24.41 | A |
| ATOM | 18 | O   | LEU | A | 6  | 32.988 | −13.856 | 12.619 | 1.00 | 21.54 | A |
| ATOM | 19 | N   | ASP | A | 7  | 31.052 | −14.646 | 13.396 | 1.00 | 22.72 | A |
| ATOM | 20 | CA  | ASP | A | 7  | 31.204 | −13.966 | 14.689 | 1.00 | 21.73 | A |
| ATOM | 21 | CB  | ASP | A | 7  | 29.892 | −14.029 | 15.478 | 1.00 | 24.18 | A |
| ATOM | 22 | CG  | ASP | A | 7  | 28.825 | −13.072 | 14.948 | 1.00 | 29.36 | A |
| ATOM | 23 | OD1 | ASP | A | 7  | 28.909 | −12.639 | 13.786 | 1.00 | 28.09 | A |
| ATOM | 24 | OD2 | ASP | A | 7  | 27.898 | −12.775 | 15.722 | 1.00 | 33.58 | A |
| ATOM | 25 | C   | ASP | A | 7  | 32.301 | −14.661 | 15.505 | 1.00 | 21.28 | A |
| ATOM | 26 | O   | ASP | A | 7  | 32.302 | −15.884 | 15.645 | 1.00 | 23.50 | A |
| ATOM | 27 | N   | VAL | A | 8  | 33.237 | −13.876 | 16.023 | 1.00 | 17.05 | A |
| ATOM | 28 | CA  | VAL | A | 8  | 34.340 | −14.399 | 16.837 | 1.00 | 14.95 | A |
| ATOM | 29 | CB  | VAL | A | 8  | 35.711 | −14.038 | 16.185 | 1.00 | 13.56 | A |
| ATOM | 30 | CG1 | VAL | A | 8  | 36.878 | −14.405 | 17.102 | 1.00 | 14.57 | A |
| ATOM | 31 | CG2 | VAL | A | 8  | 35.830 | −14.770 | 14.869 | 1.00 | 15.46 | A |
| ATOM | 32 | C   | VAL | A | 8  | 34.335 | −13.739 | 18.220 | 1.00 | 15.86 | A |
| ATOM | 33 | O   | VAL | A | 8  | 34.042 | −12.537 | 18.343 | 1.00 | 15.09 | A |
| ATOM | 34 | N   | CYS | A | 9  | 34.639 | −14.509 | 19.264 | 1.00 | 14.35 | A |
| ATOM | 35 | CA  | CYS | A | 9  | 34.790 | −13.934 | 20.598 | 1.00 | 15.35 | A |
| ATOM | 36 | CB  | CYS | A | 9  | 33.944 | −14.672 | 21.638 | 1.00 | 14.95 | A |
| ATOM | 37 | SG  | CYS | A | 9  | 34.106 | −13.995 | 23.322 | 1.00 | 22.28 | A |
| ATOM | 38 | C   | CYS | A | 9  | 36.282 | −14.074 | 20.948 | 1.00 | 16.35 | A |
| ATOM | 39 | O   | CYS | A | 9  | 36.871 | −15.098 | 20.682 | 1.00 | 15.32 | A |
| ATOM | 40 | N   | ALA | A | 10 | 36.886 | −13.034 | 21.498 | 1.00 | 14.31 | A |
| ATOM | 41 | CA  | ALA | A | 10 | 38.291 | −13.115 | 21.907 | 1.00 | 13.64 | A |
| ATOM | 42 | CB  | ALA | A | 10 | 39.016 | −11.885 | 21.503 | 1.00 | 14.82 | A |
| ATOM | 43 | C   | ALA | A | 10 | 38.375 | −13.281 | 23.424 | 1.00 | 14.28 | A |
| ATOM | 44 | O   | ALA | A | 10 | 37.501 | −12.803 | 24.161 | 1.00 | 15.32 | A |
| ATOM | 45 | N   | VAL | A | 11 | 39.406 | −14.004 | 23.879 | 1.00 | 13.95 | A |
| ATOM | 46 | CA  | VAL | A | 11 | 39.636 | −14.180 | 25.312 | 1.00 | 13.66 | A |
| ATOM | 47 | CB  | VAL | A | 11 | 39.544 | −15.658 | 25.765 | 1.00 | 13.48 | A |
| ATOM | 48 | CG1 | VAL | A | 11 | 40.004 | −15.761 | 27.237 | 1.00 | 15.44 | A |
| ATOM | 49 | CG2 | VAL | A | 11 | 38.089 | −16.126 | 25.664 | 1.00 | 15.73 | A |
| ATOM | 50 | C   | VAL | A | 11 | 41.078 | −13.710 | 25.544 | 1.00 | 12.91 | A |
| ATOM | 51 | O   | VAL | A | 11 | 42.009 | −14.165 | 24.857 | 1.00 | 13.54 | A |
| ATOM | 52 | N   | VAL | A | 12 | 41.255 | −12.802 | 26.497 | 1.00 | 12.18 | A |
| ATOM | 53 | CA  | VAL | A | 12 | 42.567 | −12.250 | 26.825 | 1.00 | 13.20 | A |
| ATOM | 54 | CB  | VAL | A | 12 | 42.555 | −10.696 | 26.643 | 1.00 | 14.61 | A |
| ATOM | 55 | CG1 | VAL | A | 12 | 43.878 | −10.102 | 27.089 | 1.00 | 16.25 | A |
| ATOM | 56 | CG2 | VAL | A | 12 | 42.319 | −10.343 | 25.163 | 1.00 | 15.42 | A |
| ATOM | 57 | C   | VAL | A | 12 | 42.936 | −12.576 | 28.275 | 1.00 | 15.56 | A |
| ATOM | 58 | O   | VAL | A | 12 | 42.367 | −11.994 | 29.201 | 1.00 | 16.10 | A |
| ATOM | 59 | N   | PRO | A | 13 | 43.818 | −13.565 | 28.488 | 1.00 | 15.73 | A |
| ATOM | 60 | CD  | PRO | A | 13 | 44.352 | −14.568 | 27.549 | 1.00 | 15.57 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 61 | CA | PRO | A | 13 | 44.201 | −13.866 | 29.877 | 1.00 | 17.87 | A |
|---|---|---|---|---|---|---|---|---|---|---|---|
| ATOM | 62 | CB | PRO | A | 13 | 44.963 | −15.183 | 29.765 | 1.00 | 18.98 | A |
| ATOM | 63 | CG | PRO | A | 13 | 45.440 | −15.242 | 28.360 | 1.00 | 19.82 | A |
| ATOM | 64 | C | PRO | A | 13 | 45.087 | −12.704 | 30.351 | 1.00 | 18.36 | A |
| ATOM | 65 | O | PRO | A | 13 | 46.126 | −12.403 | 29.737 | 1.00 | 20.50 | A |
| ATOM | 66 | N | ALA | A | 14 | 44.658 | −12.036 | 31.420 | 1.00 | 18.05 | A |
| ATOM | 67 | CA | ALA | A | 14 | 45.363 | −10.877 | 31.946 | 1.00 | 17.96 | A |
| ATOM | 68 | CB | ALA | A | 14 | 44.705 | −9.599 | 31.422 | 1.00 | 19.55 | A |
| ATOM | 69 | C | ALA | A | 14 | 45.312 | −10.889 | 33.465 | 1.00 | 19.04 | A |
| ATOM | 70 | O | ALA | A | 14 | 45.187 | −9.842 | 34.099 | 1.00 | 17.63 | A |
| ATOM | 71 | N | ALA | A | 15 | 45.438 | −12.080 | 34.032 | 1.00 | 18.99 | A |
| ATOM | 72 | CA | ALA | A | 15 | 45.348 | −12.268 | 35.476 | 1.00 | 21.55 | A |
| ATOM | 73 | CB | ALA | A | 15 | 44.415 | −13.423 | 35.769 | 1.00 | 22.46 | A |
| ATOM | 74 | C | ALA | A | 15 | 46.698 | −12.500 | 36.140 | 1.00 | 24.97 | A |
| ATOM | 75 | O | ALA | A | 15 | 46.767 | −12.730 | 37.349 | 1.00 | 26.39 | A |
| ATOM | 76 | N | GLY | A | 16 | 47.769 | −12.408 | 35.356 | 1.00 | 24.66 | A |
| ATOM | 77 | CA | GLY | A | 16 | 49.104 | −12.592 | 35.900 | 1.00 | 26.91 | A |
| ATOM | 78 | C | GLY | A | 16 | 49.602 | −11.337 | 36.589 | 1.00 | 27.01 | A |
| ATOM | 79 | O | GLY | A | 16 | 48.979 | −10.270 | 36.499 | 1.00 | 26.91 | A |
| ATOM | 80 | N | PHE | A | 17 | 50.745 | −11.472 | 37.263 | 1.00 | 28.01 | A |
| ATOM | 81 | CA | PHE | A | 17 | 51.372 | −10.385 | 38.024 | 1.00 | 28.35 | A |
| ATOM | 82 | CB | PHE | A | 17 | 51.674 | −10.872 | 39.464 | 1.00 | 28.66 | A |
| ATOM | 83 | CG | PHE | A | 17 | 50.485 | −11.477 | 40.190 | 1.00 | 28.93 | A |
| ATOM | 84 | CD1 | PHE | A | 17 | 50.685 | −12.433 | 41.187 | 1.00 | 30.11 | A |
| ATOM | 85 | CD2 | PHE | A | 17 | 49.183 | −11.079 | 39.907 | 1.00 | 27.69 | A |
| ATOM | 86 | CE1 | PHE | A | 17 | 49.612 | −12.985 | 41.882 | 1.00 | 27.93 | A |
| ATOM | 87 | CE2 | PHE | A | 17 | 48.089 | −11.625 | 40.600 | 1.00 | 27.62 | A |
| ATOM | 88 | CZ | PHE | A | 17 | 48.306 | −12.576 | 41.583 | 1.00 | 28.48 | A |
| ATOM | 89 | C | PHE | A | 17 | 52.683 | −9.856 | 37.392 | 1.00 | 28.54 | A |
| ATOM | 90 | O | PHE | A | 17 | 53.252 | −8.868 | 37.869 | 1.00 | 27.85 | A |
| ATOM | 91 | N | GLY | A | 18 | 53.159 | −10.513 | 36.334 | 1.00 | 29.85 | A |
| ATOM | 92 | CA | GLY | A | 18 | 54.386 | −10.074 | 35.683 | 1.00 | 30.89 | A |
| ATOM | 93 | C | GLY | A | 18 | 55.523 | −9.889 | 36.671 | 1.00 | 31.81 | A |
| ATOM | 94 | O | GLY | A | 18 | 56.138 | −8.812 | 36.759 | 1.00 | 31.37 | A |
| ATOM | 95 | N | ARG | A | 19 | 55.804 | −10.949 | 37.418 | 1.00 | 31.59 | A |
| ATOM | 96 | CA | ARG | A | 19 | 56.864 | −10.911 | 38.426 | 1.00 | 33.23 | A |
| ATOM | 97 | CB | ARG | A | 19 | 56.865 | −12.222 | 39.209 | 1.00 | 32.02 | A |
| ATOM | 98 | CG | ARG | A | 19 | 57.897 | −12.314 | 40.328 | 1.00 | 34.02 | A |
| ATOM | 99 | CD | ARG | A | 19 | 58.464 | −13.733 | 40.386 | 1.00 | 33.39 | A |
| ATOM | 100 | NE | ARG | A | 19 | 57.534 | −14.660 | 39.726 | 1.00 | 33.01 | A |
| ATOM | 101 | CZ | ARG | A | 19 | 57.803 | −15.927 | 39.426 | 1.00 | 31.50 | A |
| ATOM | 102 | NH1 | ARG | A | 19 | 58.985 | −16.471 | 39.721 | 1.00 | 33.70 | A |
| ATOM | 103 | NH2 | ARG | A | 19 | 56.882 | −16.655 | 38.821 | 1.00 | 35.56 | A |
| ATOM | 104 | C | ARG | A | 19 | 58.243 | −10.665 | 37.795 | 1.00 | 33.26 | A |
| ATOM | 105 | O | ARG | A | 19 | 59.107 | −10.049 | 38.410 | 1.00 | 34.50 | A |
| ATOM | 106 | N | ARG | A | 20 | 58.445 | −11.142 | 36.567 | 1.00 | 33.73 | A |
| ATOM | 107 | CA | ARG | A | 20 | 59.722 | −10.942 | 35.884 | 1.00 | 33.83 | A |
| ATOM | 108 | CB | ARG | A | 20 | 59.843 | −11.906 | 34.700 | 1.00 | 34.00 | A |
| ATOM | 109 | CG | ARG | A | 20 | 60.001 | −13.375 | 35.108 | 1.00 | 33.35 | A |
| ATOM | 110 | CD | ARG | A | 20 | 60.002 | −14.302 | 33.887 | 1.00 | 34.51 | A |
| ATOM | 111 | NE | ARG | A | 20 | 58.650 | −14.687 | 33.456 | 1.00 | 34.45 | A |
| ATOM | 112 | CZ | ARG | A | 20 | 58.386 | −15.420 | 32.371 | 1.00 | 33.96 | A |
| ATOM | 113 | NH1 | ARG | A | 20 | 59.375 | −15.850 | 31.593 | 1.00 | 33.51 | A |
| ATOM | 114 | NH2 | ARG | A | 20 | 57.131 | −15.739 | 32.067 | 1.00 | 34.23 | A |
| ATOM | 115 | C | ARG | A | 20 | 59.983 | −9.499 | 35.409 | 1.00 | 34.78 | A |
| ATOM | 116 | O | ARG | A | 20 | 61.030 | −9.224 | 34.803 | 1.00 | 34.95 | A |
| ATOM | 117 | N | MET | A | 21 | 59.055 | −8.579 | 35.685 | 1.00 | 34.67 | A |
| ATOM | 118 | CA | MET | A | 21 | 59.228 | −7.179 | 35.274 | 1.00 | 34.61 | A |
| ATOM | 119 | CB | MET | A | 21 | 57.895 | −6.584 | 34.790 | 1.00 | 33.13 | A |
| ATOM | 120 | CG | MET | A | 21 | 57.401 | −7.115 | 33.452 | 1.00 | 30.27 | A |
| ATOM | 121 | SD | MET | A | 21 | 58.443 | −6.679 | 32.046 | 1.00 | 20.98 | A |
| ATOM | 122 | CE | MET | A | 21 | 58.542 | −4.942 | 32.181 | 1.00 | 25.33 | A |
| ATOM | 123 | C | MET | A | 21 | 59.808 | −6.263 | 36.349 | 1.00 | 36.15 | A |
| ATOM | 124 | O | MET | A | 21 | 60.202 | −5.143 | 36.043 | 1.00 | 37.80 | A |
| ATOM | 125 | N | ALA | A | 22 | 59.854 | −6.719 | 37.600 | 1.00 | 37.34 | A |
| ATOM | 126 | CA | ALA | A | 22 | 60.394 | −5.889 | 38.685 | 1.00 | 38.25 | A |
| ATOM | 127 | CB | ALA | A | 22 | 61.671 | −5.171 | 38.232 | 1.00 | 40.10 | A |
| ATOM | 128 | C | ALA | A | 22 | 59.419 | −4.838 | 39.187 | 1.00 | 38.85 | A |
| ATOM | 129 | O | ALA | A | 22 | 59.606 | −4.290 | 40.273 | 1.00 | 40.70 | A |
| ATOM | 130 | N | THR | A | 23 | 58.397 | −4.530 | 38.401 | 1.00 | 39.16 | A |
| ATOM | 131 | CA | THR | A | 23 | 57.440 | −3.516 | 38.818 | 1.00 | 38.94 | A |
| ATOM | 132 | CB | THR | A | 23 | 56.774 | −2.820 | 37.592 | 1.00 | 39.69 | A |
| ATOM | 133 | OG1 | THR | A | 23 | 56.054 | −3.788 | 36.815 | 1.00 | 40.37 | A |
| ATOM | 134 | CG2 | THR | A | 23 | 57.824 | −2.151 | 36.715 | 1.00 | 38.43 | A |
| ATOM | 135 | C | THR | A | 23 | 56.353 | −4.109 | 39.711 | 1.00 | 38.99 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 136 | O | THR | A | 23 | 55.928 | −5.263 | 39.538 | 1.00 | 39.51 | A |
| ATOM | 137 | N | GLU | A | 24 | 55.937 | −3.337 | 40.704 | 1.00 | 38.56 | A |
| ATOM | 138 | CA | GLU | A | 24 | 54.881 | −3.798 | 41.581 | 1.00 | 37.98 | A |
| ATOM | 139 | CB | GLU | A | 24 | 54.820 | −2.933 | 42.841 | 1.00 | 39.72 | A |
| ATOM | 140 | CG | GLU | A | 24 | 53.568 | −3.148 | 43.681 | 1.00 | 41.57 | A |
| ATOM | 141 | CD | GLU | A | 24 | 53.718 | −2.627 | 45.104 | 1.00 | 43.73 | A |
| ATOM | 142 | OE1 | GLU | A | 24 | 54.435 | −1.608 | 45.289 | 1.00 | 43.87 | A |
| ATOM | 143 | OE2 | GLU | A | 24 | 53.109 | −3.229 | 46.030 | 1.00 | 44.04 | A |
| ATOM | 144 | C | GLU | A | 24 | 53.593 | −3.685 | 40.760 | 1.00 | 36.95 | A |
| ATOM | 145 | O | GLU | A | 24 | 52.598 | −4.341 | 41.049 | 1.00 | 38.13 | A |
| ATOM | 146 | N | CYS | A | 25 | 53.623 | −2.843 | 39.733 | 1.00 | 35.90 | A |
| ATOM | 147 | CA | CYS | A | 25 | 52.471 | −2.684 | 38.857 | 1.00 | 33.76 | A |
| ATOM | 148 | CB | CYS | A | 25 | 52.547 | −1.335 | 38.121 | 1.00 | 33.99 | A |
| ATOM | 149 | SG | CYS | A | 25 | 51.294 | −1.072 | 36.811 | 1.00 | 33.82 | A |
| ATOM | 150 | C | CYS | A | 25 | 52.495 | −3.838 | 37.851 | 1.00 | 32.91 | A |
| ATOM | 151 | O | CYS | A | 25 | 53.534 | −4.124 | 37.241 | 1.00 | 31.82 | A |
| ATOM | 152 | N | PRO | A | 26 | 51.364 | −4.551 | 37.696 | 1.00 | 30.12 | A |
| ATOM | 153 | CD | PRO | A | 26 | 50.112 | −4.502 | 38.473 | 1.00 | 30.73 | A |
| ATOM | 154 | CA | PRO | A | 26 | 51.340 | −5.660 | 36.736 | 1.00 | 29.73 | A |
| ATOM | 155 | CB | PRO | A | 26 | 49.899 | −6.158 | 36.816 | 1.00 | 29.49 | A |
| ATOM | 156 | CG | PRO | A | 26 | 49.547 | −5.892 | 38.249 | 1.00 | 31.19 | A |
| ATOM | 157 | C | PRO | A | 26 | 51.706 | −5.104 | 35.360 | 1.00 | 26.87 | A |
| ATOM | 158 | O | PRO | A | 26 | 51.210 | −4.051 | 34.952 | 1.00 | 27.18 | A |
| ATOM | 159 | N | LYS | A | 27 | 52.584 | −5.810 | 34.658 | 1.00 | 26.55 | A |
| ATOM | 160 | CA | LYS | A | 27 | 53.065 | −5.362 | 33.358 | 1.00 | 25.90 | A |
| ATOM | 161 | CB | LYS | A | 27 | 53.979 | −6.420 | 32.756 | 1.00 | 25.18 | A |
| ATOM | 162 | CG | LYS | A | 27 | 53.280 | −7.695 | 32.334 | 1.00 | 23.47 | A |
| ATOM | 163 | CD | LYS | A | 27 | 54.317 | −8.694 | 31.896 | 1.00 | 24.07 | A |
| ATOM | 164 | CE | LYS | A | 27 | 53.709 | −10.025 | 31.580 | 1.00 | 25.87 | A |
| ATOM | 165 | NZ | LYS | A | 27 | 54.758 | −10.930 | 31.026 | 1.00 | 25.14 | A |
| ATOM | 166 | C | LYS | A | 27 | 51.986 | −4.989 | 32.360 | 1.00 | 26.12 | A |
| ATOM | 167 | O | LYS | A | 27 | 52.164 | −4.057 | 31.567 | 1.00 | 25.02 | A |
| ATOM | 168 | N | GLN | A | 28 | 50.868 | −5.712 | 32.383 | 1.00 | 25.08 | A |
| ATOM | 169 | CA | GLN | A | 28 | 49.798 | −5.385 | 31.444 | 1.00 | 24.50 | A |
| ATOM | 170 | CB | GLN | A | 28 | 48.654 | −6.435 | 31.490 | 1.00 | 25.05 | A |
| ATOM | 171 | CG | GLN | A | 28 | 47.919 | −6.597 | 32.824 | 1.00 | 25.83 | A |
| ATOM | 172 | CD | GLN | A | 28 | 48.597 | −7.620 | 33.704 | 1.00 | 25.85 | A |
| ATOM | 173 | OE1 | GLN | A | 28 | 49.816 | −7.645 | 33.775 | 1.00 | 25.91 | A |
| ATOM | 174 | NE2 | GLN | A | 28 | 47.820 | −8.466 | 34.379 | 1.00 | 25.23 | A |
| ATOM | 175 | C | GLN | A | 28 | 49.252 | −3.989 | 31.719 | 1.00 | 25.09 | A |
| ATOM | 176 | O | GLN | A | 28 | 48.536 | −3.430 | 30.897 | 1.00 | 23.92 | A |
| ATOM | 177 | N | TYR | A | 29 | 49.596 | −3.411 | 32.871 | 1.00 | 24.17 | A |
| ATOM | 178 | CA | TYR | A | 29 | 49.106 | −2.083 | 33.187 | 1.00 | 24.33 | A |
| ATOM | 179 | CB | TYR | A | 29 | 48.494 | −2.043 | 34.602 | 1.00 | 25.67 | A |
| ATOM | 180 | CG | TYR | A | 29 | 47.210 | −2.852 | 34.722 | 1.00 | 24.85 | A |
| ATOM | 181 | CD1 | TYR | A | 29 | 47.181 | −4.075 | 35.398 | 1.00 | 24.71 | A |
| ATOM | 182 | CE1 | TYR | A | 29 | 46.013 | −4.846 | 35.447 | 1.00 | 23.38 | A |
| ATOM | 183 | CD2 | TYR | A | 29 | 46.047 | −2.429 | 34.100 | 1.00 | 24.91 | A |
| ATOM | 184 | CE2 | TYR | A | 29 | 44.883 | −3.200 | 34.133 | 1.00 | 25.03 | A |
| ATOM | 185 | CZ | TYR | A | 29 | 44.876 | −4.403 | 34.809 | 1.00 | 24.59 | A |
| ATOM | 186 | OH | TYR | A | 29 | 43.719 | −5.143 | 34.840 | 1.00 | 25.01 | A |
| ATOM | 187 | C | TYR | A | 29 | 50.184 | −1.014 | 33.020 | 1.00 | 24.55 | A |
| ATOM | 188 | O | TYR | A | 29 | 49.963 | .157 | 33.345 | 1.00 | 25.65 | A |
| ATOM | 189 | N | LEU | A | 30 | 51.345 | −1.421 | 32.518 | 1.00 | 24.86 | A |
| ATOM | 190 | CA | LEU | A | 30 | 52.410 | −.474 | 32.240 | 1.00 | 25.87 | A |
| ATOM | 191 | CB | LEU | A | 30 | 53.752 | −1.171 | 32.038 | 1.00 | 25.35 | A |
| ATOM | 192 | CG | LEU | A | 30 | 54.330 | −1.819 | 33.287 | 1.00 | 28.75 | A |
| ATOM | 193 | CD1 | LEU | A | 30 | 55.608 | −2.547 | 32.933 | 1.00 | 28.54 | A |
| ATOM | 194 | CD2 | LEU | A | 30 | 54.584 | −.748 | 34.360 | 1.00 | 28.94 | A |
| ATOM | 195 | C | LEU | A | 30 | 51.974 | .178 | 30.949 | 1.00 | 26.56 | A |
| ATOM | 196 | O | LEU | A | 30 | 51.209 | −.405 | 30.164 | 1.00 | 23.47 | A |
| ATOM | 197 | N | SER | A | 31 | 52.453 | 1.389 | 30.712 | 1.00 | 27.10 | A |
| ATOM | 198 | CA | SER | A | 31 | 52.037 | 2.082 | 29.517 | 1.00 | 28.58 | A |
| ATOM | 199 | CB | SER | A | 31 | 51.427 | 3.428 | 29.896 | 1.00 | 29.76 | A |
| ATOM | 200 | OG | SER | A | 31 | 50.314 | 3.264 | 30.750 | 1.00 | 33.82 | A |
| ATOM | 201 | C | SER | A | 31 | 53.072 | 2.308 | 28.446 | 1.00 | 29.16 | A |
| ATOM | 202 | O | SER | A | 31 | 54.277 | 2.317 | 28.692 | 1.00 | 29.41 | A |
| ATOM | 203 | N | ILE | A | 32 | 52.553 | 2.463 | 27.234 | 1.00 | 28.68 | A |
| ATOM | 204 | CA | ILE | A | 32 | 53.338 | 2.786 | 26.067 | 1.00 | 29.30 | A |
| ATOM | 205 | CB | ILE | A | 32 | 53.482 | 1.628 | 25.101 | 1.00 | 29.81 | A |
| ATOM | 206 | CG2 | ILE | A | 32 | 54.253 | 2.098 | 23.864 | 1.00 | 31.20 | A |
| ATOM | 207 | CG1 | ILE | A | 32 | 54.242 | .493 | 25.796 | 1.00 | 30.08 | A |
| ATOM | 208 | CD1 | ILE | A | 32 | 54.568 | −.661 | 24.889 | 1.00 | 32.54 | A |
| ATOM | 209 | C | ILE | A | 32 | 52.510 | 3.898 | 25.453 | 1.00 | 30.33 | A |
| ATOM | 210 | O | ILE | A | 32 | 51.378 | 3.695 | 24.997 | 1.00 | 25.79 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 211 | N | GLY | A | 33 | 53.078 | 5.099 | 25.471 | 1.00 | 31.92 | A |
| --- | --- | --- | --- | --- | --- | --- | --- | --- | --- | --- | --- |
| ATOM | 212 | CA | GLY | A | 33 | 52.354 | 6.249 | 24.980 | 1.00 | 34.62 | A |
| ATOM | 213 | C | GLY | A | 33 | 51.560 | 6.707 | 26.187 | 1.00 | 36.21 | A |
| ATOM | 214 | O | GLY | A | 33 | 52.117 | 7.287 | 27.129 | 1.00 | 40.13 | A |
| ATOM | 215 | N | ASN | A | 34 | 50.262 | 6.443 | 26.164 | 1.00 | 35.33 | A |
| ATOM | 216 | CA | ASN | A | 34 | 49.368 | 6.794 | 27.265 | 1.00 | 35.76 | A |
| ATOM | 217 | CB | ASN | A | 34 | 48.767 | 8.165 | 27.059 | 1.00 | 36.00 | A |
| ATOM | 218 | CG | ASN | A | 34 | 49.252 | 8.785 | 25.814 | 1.00 | 34.71 | A |
| ATOM | 219 | OD1 | ASN | A | 34 | 50.242 | 9.530 | 25.826 | 1.00 | 37.75 | A |
| ATOM | 220 | ND2 | ASN | A | 34 | 48.600 | 8.447 | 24.690 | 1.00 | 37.02 | A |
| ATOM | 221 | C | ASN | A | 34 | 48.262 | 5.767 | 27.269 | 1.00 | 35.51 | A |
| ATOM | 222 | O | ASN | A | 34 | 47.159 | 6.017 | 27.753 | 1.00 | 36.99 | A |
| ATOM | 223 | N | GLN | A | 35 | 48.565 | 4.623 | 26.678 | 1.00 | 33.00 | A |
| ATOM | 224 | CA | GLN | A | 35 | 47.641 | 3.508 | 26.656 | 1.00 | 30.33 | A |
| ATOM | 225 | CB | GLN | A | 35 | 47.326 | 3.106 | 25.231 | 1.00 | 34.12 | A |
| ATOM | 226 | CG | GLN | A | 35 | 45.874 | 2.836 | 25.015 | 1.00 | 37.20 | A |
| ATOM | 227 | CD | GLN | A | 35 | 45.536 | 2.633 | 23.558 | 1.00 | 39.52 | A |
| ATOM | 228 | OE1 | GLN | A | 35 | 45.514 | 3.582 | 22.773 | 1.00 | 41.95 | A |
| ATOM | 229 | NE2 | GLN | A | 35 | 45.304 | 1.385 | 23.177 | 1.00 | 41.18 | A |
| ATOM | 230 | C | GLN | A | 35 | 48.396 | 2.381 | 27.336 | 1.00 | 26.79 | A |
| ATOM | 231 | O | GLN | A | 35 | 49.606 | 2.279 | 27.173 | 1.00 | 24.51 | A |
| ATOM | 232 | N | THR | A | 36 | 47.696 | 1.545 | 28.104 | 1.00 | 23.04 | A |
| ATOM | 233 | CA | THR | A | 36 | 48.348 | .435 | 28.781 | 1.00 | 21.21 | A |
| ATOM | 234 | CB | THR | A | 36 | 47.459 | -.158 | 29.892 | 1.00 | 21.39 | A |
| ATOM | 235 | OG1 | THR | A | 36 | 46.212 | -.586 | 29.333 | 1.00 | 20.25 | A |
| ATOM | 236 | CG2 | THR | A | 36 | 47.186 | .869 | 30.982 | 1.00 | 23.04 | A |
| ATOM | 237 | C | THR | A | 36 | 48.604 | -.676 | 27.773 | 1.00 | 19.28 | A |
| ATOM | 238 | O | THR | A | 36 | 47.974 | -.710 | 26.707 | 1.00 | 19.13 | A |
| ATOM | 239 | N | ILE | A | 37 | 49.540 | -1.564 | 28.111 | 1.00 | 17.97 | A |
| ATOM | 240 | CA | ILE | A | 37 | 49.856 | -2.713 | 27.265 | 1.00 | 17.40 | A |
| ATOM | 241 | CB | ILE | A | 37 | 50.906 | -3.642 | 27.960 | 1.00 | 18.43 | A |
| ATOM | 242 | CG2 | ILE | A | 37 | 51.067 | -4.944 | 27.202 | 1.00 | 20.24 | A |
| ATOM | 243 | CG1 | ILE | A | 37 | 52.271 | -2.940 | 28.017 | 1.00 | 21.81 | A |
| ATOM | 244 | CD1 | ILE | A | 37 | 52.702 | -2.402 | 26.714 | 1.00 | 25.97 | A |
| ATOM | 245 | C | ILE | A | 37 | 48.546 | -3.486 | 27.022 | 1.00 | 15.83 | A |
| ATOM | 246 | O | ILE | A | 37 | 48.262 | -3.904 | 25.889 | 1.00 | 15.77 | A |
| ATOM | 247 | N | LEU | A | 38 | 47.741 | -3.671 | 28.067 | 1.00 | 15.45 | A |
| ATOM | 248 | CA | LEU | A | 38 | 46.469 | -4.384 | 27.907 | 1.00 | 15.80 | A |
| ATOM | 249 | CB | LEU | A | 38 | 45.740 | -4.463 | 29.256 | 1.00 | 17.12 | A |
| ATOM | 250 | CG | LEU | A | 38 | 44.335 | -5.061 | 29.212 | 1.00 | 17.44 | A |
| ATOM | 251 | CD1 | LEU | A | 38 | 44.397 | -6.499 | 28.683 | 1.00 | 18.18 | A |
| ATOM | 252 | CD2 | LEU | A | 38 | 43.726 | -5.035 | 30.604 | 1.00 | 19.06 | A |
| ATOM | 253 | C | LEU | A | 38 | 45.587 | -3.672 | 26.851 | 1.00 | 15.36 | A |
| ATOM | 254 | O | LEU | A | 38 | 44.980 | -4.316 | 25.989 | 1.00 | 15.75 | A |
| ATOM | 255 | N | GLU | A | 39 | 45.525 | -2.342 | 26.886 | 1.00 | 15.93 | A |
| ATOM | 256 | CA | GLU | A | 39 | 44.707 | -1.625 | 25.912 | 1.00 | 17.21 | A |
| ATOM | 257 | CB | GLU | A | 39 | 44.595 | -.143 | 26.285 | 1.00 | 18.21 | A |
| ATOM | 258 | CG | GLU | A | 39 | 43.635 | .056 | 27.456 | 1.00 | 20.61 | A |
| ATOM | 259 | CD | GLU | A | 39 | 43.759 | 1.412 | 28.105 | 1.00 | 23.58 | A |
| ATOM | 260 | OE1 | GLU | A | 39 | 42.848 | 2.256 | 27.871 | 1.00 | 28.16 | A |
| ATOM | 261 | OE2 | GLU | A | 39 | 44.757 | 1.628 | 28.834 | 1.00 | 22.14 | A |
| ATOM | 262 | C | GLU | A | 39 | 45.229 | -1.789 | 24.489 | 1.00 | 15.58 | A |
| ATOM | 263 | O | GLU | A | 39 | 44.442 | -2.033 | 23.556 | 1.00 | 18.20 | A |
| ATOM | 264 | N | HIS | A | 40 | 46.542 | -1.676 | 24.292 | 1.00 | 17.07 | A |
| ATOM | 265 | CA | HIS | A | 40 | 47.081 | -1.882 | 22.938 | 1.00 | 16.87 | A |
| ATOM | 266 | CB | HIS | A | 40 | 48.608 | -1.831 | 22.939 | 1.00 | 17.54 | A |
| ATOM | 267 | CG | HIS | A | 40 | 49.184 | -.455 | 23.081 | 1.00 | 18.22 | A |
| ATOM | 268 | CD2 | HIS | A | 40 | 49.786 | .146 | 24.130 | 1.00 | 19.94 | A |
| ATOM | 269 | ND1 | HIS | A | 40 | 49.184 | .467 | 22.054 | 1.00 | 21.68 | A |
| ATOM | 270 | CE1 | HIS | A | 40 | 49.763 | 1.581 | 22.470 | 1.00 | 21.75 | A |
| ATOM | 271 | NE2 | HIS | A | 40 | 50.136 | 1.415 | 23.728 | 1.00 | 20.48 | A |
| ATOM | 272 | C | HIS | A | 40 | 46.663 | -3.265 | 22.421 | 1.00 | 15.95 | A |
| ATOM | 273 | O | HIS | A | 40 | 46.213 | -3.419 | 21.280 | 1.00 | 17.34 | A |
| ATOM | 274 | N | SER | A | 41 | 46.819 | -4.283 | 23.271 | 1.00 | 14.78 | A |
| ATOM | 275 | CA | SER | A | 41 | 46.460 | -5.629 | 22.894 | 1.00 | 15.60 | A |
| ATOM | 276 | CB | SER | A | 41 | 46.833 | -6.611 | 24.014 | 1.00 | 16.56 | A |
| ATOM | 277 | OG | SER | A | 41 | 48.215 | -6.590 | 24.205 | 1.00 | 20.21 | A |
| ATOM | 278 | C | SER | A | 41 | 44.987 | -5.796 | 22.542 | 1.00 | 16.38 | A |
| ATOM | 279 | O | SER | A | 41 | 44.636 | -6.355 | 21.496 | 1.00 | 15.32 | A |
| ATOM | 280 | N | VAL | A | 42 | 44.117 | -5.310 | 23.421 | 1.00 | 14.52 | A |
| ATOM | 281 | CA | VAL | A | 42 | 42.684 | -5.430 | 23.231 | 1.00 | 15.98 | A |
| ATOM | 282 | CB | VAL | A | 42 | 41.966 | -4.917 | 24.495 | 1.00 | 14.93 | A |
| ATOM | 283 | CG1 | VAL | A | 42 | 40.478 | -4.764 | 24.257 | 1.00 | 16.23 | A |
| ATOM | 284 | CG2 | VAL | A | 42 | 42.228 | -5.882 | 25.623 | 1.00 | 15.67 | A |
| ATOM | 285 | C | VAL | A | 42 | 42.222 | -4.671 | 22.008 | 1.00 | 15.24 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 286 | O   | VAL | A | 42 | 41.402 | −5.158  | 21.209 | 1.00 | 15.34 | A |
|------|-----|-----|-----|---|----|--------|---------|--------|------|-------|---|
| ATOM | 287 | N   | HIS | A | 43 | 42.749 | −3.470  | 21.835 | 1.00 | 15.87 | A |
| ATOM | 288 | CA  | HIS | A | 43 | 42.321 | −2.704  | 20.680 | 1.00 | 17.76 | A |
| ATOM | 289 | CB  | HIS | A | 43 | 42.759 | −1.252  | 20.840 | 1.00 | 20.59 | A |
| ATOM | 290 | CG  | HIS | A | 43 | 41.973 | −.521   | 21.891 | 1.00 | 25.11 | A |
| ATOM | 291 | CD2 | HIS | A | 43 | 42.368 | .213    | 22.959 | 1.00 | 26.37 | A |
| ATOM | 292 | ND1 | HIS | A | 43 | 40.592 | −.492   | 21.898 | 1.00 | 24.93 | A |
| ATOM | 293 | CE1 | HIS | A | 43 | 40.173 | .230    | 22.924 | 1.00 | 27.12 | A |
| ATOM | 294 | NE2 | HIS | A | 43 | 41.230 | .671    | 23.583 | 1.00 | 26.59 | A |
| ATOM | 295 | C   | HIS | A | 43 | 42.762 | −3.321  | 19.370 | 1.00 | 16.08 | A |
| ATOM | 296 | O   | HIS | A | 43 | 42.074 | −3.159  | 18.348 | 1.00 | 16.83 | A |
| ATOM | 297 | N   | ALA | A | 44 | 43.870 | −4.067  | 19.363 | 1.00 | 15.17 | A |
| ATOM | 298 | CA  | ALA | A | 44 | 44.266 | −4.687  | 18.097 | 1.00 | 15.38 | A |
| ATOM | 299 | CB  | ALA | A | 44 | 45.690 | −5.285  | 18.189 | 1.00 | 16.25 | A |
| ATOM | 300 | C   | ALA | A | 44 | 43.234 | −5.772  | 17.724 | 1.00 | 14.81 | A |
| ATOM | 301 | O   | ALA | A | 44 | 42.915 | −5.951  | 16.562 | 1.00 | 15.91 | A |
| ATOM | 302 | N   | LEU | A | 45 | 42.702 | −6.489  | 18.712 | 1.00 | 13.33 | A |
| ATOM | 303 | CA  | LEU | A | 45 | 41.694 | −7.494  | 18.431 | 1.00 | 14.68 | A |
| ATOM | 304 | CB  | LEU | A | 45 | 41.400 | −8.305  | 19.701 | 1.00 | 14.24 | A |
| ATOM | 305 | CG  | LEU | A | 45 | 42.639 | −8.968  | 20.321 | 1.00 | 13.57 | A |
| ATOM | 306 | CD1 | LEU | A | 45 | 42.273 | −9.555  | 21.675 | 1.00 | 17.66 | A |
| ATOM | 307 | CD2 | LEU | A | 45 | 43.186 | −10.019 | 19.397 | 1.00 | 15.75 | A |
| ATOM | 308 | C   | LEU | A | 45 | 40.387 | −6.840  | 17.946 | 1.00 | 14.57 | A |
| ATOM | 309 | O   | LEU | A | 45 | 39.772 | −7.330  | 17.007 | 1.00 | 14.75 | A |
| ATOM | 310 | N   | LEU | A | 46 | 39.964 | −5.776  | 18.622 | 1.00 | 15.14 | A |
| ATOM | 311 | CA  | LEU | A | 46 | 38.707 | −5.110  | 18.275 | 1.00 | 16.70 | A |
| ATOM | 312 | CB  | LEU | A | 46 | 38.294 | −4.113  | 19.373 | 1.00 | 15.91 | A |
| ATOM | 313 | CG  | LEU | A | 46 | 37.851 | −4.769  | 20.680 | 1.00 | 17.28 | A |
| ATOM | 314 | CD1 | LEU | A | 46 | 37.588 | −3.731  | 21.759 | 1.00 | 19.07 | A |
| ATOM | 315 | CD2 | LEU | A | 46 | 36.615 | −5.612  | 20.409 | 1.00 | 19.67 | A |
| ATOM | 316 | C   | LEU | A | 46 | 38.747 | −4.426  | 16.921 | 1.00 | 18.12 | A |
| ATOM | 317 | O   | LEU | A | 46 | 37.689 | −4.039  | 16.381 | 1.00 | 17.11 | A |
| ATOM | 318 | N   | ALA | A | 47 | 39.944 | −4.256  | 16.362 | 1.00 | 17.31 | A |
| ATOM | 319 | CA  | ALA | A | 47 | 40.040 | −3.612  | 15.054 | 1.00 | 16.97 | A |
| ATOM | 320 | CB  | ALA | A | 47 | 41.490 | −3.210  | 14.750 | 1.00 | 16.64 | A |
| ATOM | 321 | C   | ALA | A | 47 | 39.502 | −4.494  | 13.942 | 1.00 | 18.74 | A |
| ATOM | 322 | O   | ALA | A | 47 | 39.043 | −3.988  | 12.918 | 1.00 | 20.37 | A |
| ATOM | 323 | N   | HIS | A | 48 | 39.548 | −5.810  | 14.112 | 1.00 | 15.77 | A |
| ATOM | 324 | CA  | HIS | A | 48 | 39.035 | −6.676  | 13.060 | 1.00 | 15.79 | A |
| ATOM | 325 | CB  | HIS | A | 48 | 39.679 | −8.064  | 13.127 | 1.00 | 14.19 | A |
| ATOM | 326 | CG  | HIS | A | 48 | 39.359 | −8.899  | 11.934 | 1.00 | 16.96 | A |
| ATOM | 327 | CD2 | HIS | A | 48 | 40.134 | −9.352  | 10.919 | 1.00 | 19.54 | A |
| ATOM | 328 | ND1 | HIS | A | 48 | 38.072 | −9.282  | 11.638 | 1.00 | 15.40 | A |
| ATOM | 329 | CE1 | HIS | A | 48 | 38.060 | −9.936  | 10.488 | 1.00 | 18.80 | A |
| ATOM | 330 | NE2 | HIS | A | 48 | 39.303 | −9.993  | 10.033 | 1.00 | 20.46 | A |
| ATOM | 331 | C   | HIS | A | 48 | 37.516 | −6.788  | 13.207 | 1.00 | 16.85 | A |
| ATOM | 332 | O   | HIS | A | 48 | 37.013 | −7.122  | 14.288 | 1.00 | 15.48 | A |
| ATOM | 333 | N   | PRO | A | 49 | 36.747 | −6.520  | 12.128 | 1.00 | 17.76 | A |
| ATOM | 334 | CD  | PRO | A | 49 | 37.136 | −6.136  | 10.755 | 1.00 | 20.07 | A |
| ATOM | 335 | CA  | PRO | A | 49 | 35.283 | −6.598  | 12.238 | 1.00 | 17.87 | A |
| ATOM | 336 | CB  | PRO | A | 49 | 34.800 | −6.352  | 10.797 | 1.00 | 18.38 | A |
| ATOM | 337 | CG  | PRO | A | 49 | 35.831 | −5.498  | 10.237 | 1.00 | 20.52 | A |
| ATOM | 338 | C   | PRO | A | 49 | 34.644 | −7.849  | 12.799 | 1.00 | 16.63 | A |
| ATOM | 339 | O   | PRO | A | 49 | 33.567 | −7.779  | 13.358 | 1.00 | 17.87 | A |
| ATOM | 340 | N   | ARG | A | 50 | 35.291 | −9.000  | 12.628 | 1.00 | 15.65 | A |
| ATOM | 341 | CA  | ARG | A | 50 | 34.705 | −10.237 | 13.099 | 1.00 | 14.52 | A |
| ATOM | 342 | CB  | ARG | A | 50 | 35.371 | −11.447 | 12.431 | 1.00 | 14.72 | A |
| ATOM | 343 | CG  | ARG | A | 50 | 34.991 | −11.653 | 10.957 | 1.00 | 15.70 | A |
| ATOM | 344 | CD  | ARG | A | 50 | 35.700 | −12.871 | 10.356 | 1.00 | 16.30 | A |
| ATOM | 345 | NE  | ARG | A | 50 | 35.314 | −14.097 | 11.063 | 1.00 | 15.60 | A |
| ATOM | 346 | CZ  | ARG | A | 50 | 35.924 | −15.264 | 10.920 | 1.00 | 15.54 | A |
| ATOM | 347 | NH1 | ARG | A | 50 | 36.960 | −15.400 | 10.075 | 1.00 | 16.64 | A |
| ATOM | 348 | NH2 | ARG | A | 50 | 35.522 | −16.296 | 11.658 | 1.00 | 16.95 | A |
| ATOM | 349 | C   | ARG | A | 50 | 34.762 | −10.379 | 14.622 | 1.00 | 15.56 | A |
| ATOM | 350 | O   | ARG | A | 50 | 34.024 | −11.174 | 15.189 | 1.00 | 15.79 | A |
| ATOM | 351 | N   | VAL | A | 51 | 35.622 | −9.627  | 15.280 | 1.00 | 13.34 | A |
| ATOM | 352 | CA  | VAL | A | 51 | 35.687 | −9.735  | 16.736 | 1.00 | 12.40 | A |
| ATOM | 353 | CB  | VAL | A | 51 | 37.064 | −9.314  | 17.255 | 1.00 | 12.17 | A |
| ATOM | 354 | CG1 | VAL | A | 51 | 37.093 | −9.505  | 18.780 | 1.00 | 15.31 | A |
| ATOM | 355 | CG2 | VAL | A | 51 | 38.133 | −10.139 | 16.603 | 1.00 | 13.45 | A |
| ATOM | 356 | C   | VAL | A | 51 | 34.543 | −8.931  | 17.364 | 1.00 | 14.50 | A |
| ATOM | 357 | O   | VAL | A | 51 | 34.577 | −7.713  | 17.472 | 1.00 | 16.52 | A |
| ATOM | 358 | N   | LYS | A | 52 | 33.526 | −9.655  | 17.797 | 1.00 | 14.51 | A |
| ATOM | 359 | CA  | LYS | A | 52 | 32.327 | −9.029  | 18.361 | 1.00 | 15.31 | A |
| ATOM | 360 | CB  | LYS | A | 52 | 31.080 | −9.870  | 18.039 | 1.00 | 16.47 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 361 | CG | LYS | A | 52 | 30.985 | −10.359 | 16.588 | 1.00 | 16.59 | A |
|---|---|---|---|---|---|---|---|---|---|---|---|
| ATOM | 362 | CD | LYS | A | 52 | 31.072 | −9.195 | 15.594 | 1.00 | 16.24 | A |
| ATOM | 363 | CE | LYS | A | 52 | 30.781 | −9.656 | 14.183 | 1.00 | 18.96 | A |
| ATOM | 364 | NZ | LYS | A | 52 | 30.848 | −8.511 | 13.240 | 1.00 | 21.54 | A |
| ATOM | 365 | C | LYS | A | 52 | 32.365 | −8.862 | 19.870 | 1.00 | 16.57 | A |
| ATOM | 366 | O | LYS | A | 52 | 31.569 | −8.111 | 20.452 | 1.00 | 18.90 | A |
| ATOM | 367 | N | ARG | A | 53 | 33.261 | −9.589 | 20.496 | 1.00 | 15.64 | A |
| ATOM | 368 | CA | ARG | A | 53 | 33.345 | −9.556 | 21.941 | 1.00 | 17.52 | A |
| ATOM | 369 | CB | ARG | A | 53 | 32.425 | −10.616 | 22.511 | 1.00 | 21.74 | A |
| ATOM | 370 | CG | ARG | A | 53 | 32.315 | −10.597 | 24.011 | 1.00 | 29.80 | A |
| ATOM | 371 | CD | ARG | A | 53 | 31.452 | −11.756 | 24.450 | 1.00 | 34.62 | A |
| ATOM | 372 | NE | ARG | A | 53 | 30.917 | −11.551 | 25.783 | 1.00 | 38.19 | A |
| ATOM | 373 | CZ | ARG | A | 53 | 30.005 | −12.341 | 26.340 | 1.00 | 41.59 | A |
| ATOM | 374 | NH1 | ARG | A | 53 | 29.538 | −13.388 | 25.667 | 1.00 | 41.75 | A |
| ATOM | 375 | NH2 | ARG | A | 53 | 29.545 | −12.078 | 27.559 | 1.00 | 42.21 | A |
| ATOM | 376 | C | ARG | A | 53 | 34.734 | −9.874 | 22.414 | 1.00 | 17.34 | A |
| ATOM | 377 | O | ARG | A | 53 | 35.479 | −10.588 | 21.751 | 1.00 | 16.17 | A |
| ATOM | 378 | N | VAL | A | 54 | 35.094 | −9.330 | 23.568 | 1.00 | 15.82 | A |
| ATOM | 379 | CA | VAL | A | 54 | 36.386 | −9.681 | 24.142 | 1.00 | 13.98 | A |
| ATOM | 380 | CB | VAL | A | 54 | 37.427 | −8.580 | 24.020 | 1.00 | 14.23 | A |
| ATOM | 381 | CG1 | VAL | A | 54 | 38.756 | −9.025 | 24.600 | 1.00 | 15.34 | A |
| ATOM | 382 | CG2 | VAL | A | 54 | 37.622 | −8.259 | 22.549 | 1.00 | 13.83 | A |
| ATOM | 383 | C | VAL | A | 54 | 36.129 | −9.909 | 25.622 | 1.00 | 15.48 | A |
| ATOM | 384 | O | VAL | A | 54 | 35.528 | −9.074 | 26.292 | 1.00 | 19.41 | A |
| ATOM | 385 | N | VAL | A | 55 | 36.562 | −11.068 | 26.096 | 1.00 | 13.36 | A |
| ATOM | 386 | CA | VAL | A | 55 | 36.437 | −11.427 | 27.499 | 1.00 | 13.37 | A |
| ATOM | 387 | CB | VAL | A | 55 | 35.913 | −12.866 | 27.674 | 1.00 | 15.78 | A |
| ATOM | 388 | CG1 | VAL | A | 55 | 35.793 | −13.159 | 29.169 | 1.00 | 16.54 | A |
| ATOM | 389 | CG2 | VAL | A | 55 | 34.541 | −13.046 | 27.017 | 1.00 | 15.99 | A |
| ATOM | 390 | C | VAL | A | 55 | 37.852 | −11.345 | 28.073 | 1.00 | 13.11 | A |
| ATOM | 391 | O | VAL | A | 55 | 38.753 | −12.054 | 27.606 | 1.00 | 13.82 | A |
| ATOM | 392 | N | ILE | A | 56 | 38.045 | −10.498 | 29.082 | 1.00 | 13.16 | A |
| ATOM | 393 | CA | ILE | A | 56 | 39.347 | −10.313 | 29.725 | 1.00 | 14.31 | A |
| ATOM | 394 | CB | ILE | A | 56 | 39.671 | −8.831 | 29.838 | 1.00 | 15.14 | A |
| ATOM | 395 | CG2 | ILE | A | 56 | 41.054 | −8.641 | 30.405 | 1.00 | 16.24 | A |
| ATOM | 396 | CG1 | ILE | A | 56 | 39.537 | −8.186 | 28.445 | 1.00 | 15.56 | A |
| ATOM | 397 | CD1 | ILE | A | 56 | 39.853 | −6.692 | 28.442 | 1.00 | 17.36 | A |
| ATOM | 398 | C | ILE | A | 56 | 39.317 | −10.935 | 31.119 | 1.00 | 15.62 | A |
| ATOM | 399 | O | ILE | A | 56 | 38.454 | −10.597 | 31.918 | 1.00 | 16.74 | A |
| ATOM | 400 | N | ALA | A | 57 | 40.238 | −11.854 | 31.395 | 1.00 | 14.35 | A |
| ATOM | 401 | CA | ALA | A | 57 | 40.266 | −12.508 | 32.705 | 1.00 | 16.52 | A |
| ATOM | 402 | CB | ALA | A | 57 | 40.695 | −13.962 | 32.554 | 1.00 | 14.74 | A |
| ATOM | 403 | C | ALA | A | 57 | 41.287 | −11.760 | 33.533 | 1.00 | 17.14 | A |
| ATOM | 404 | O | ALA | A | 57 | 42.436 | −11.640 | 33.109 | 1.00 | 18.16 | A |
| ATOM | 405 | N | ILE | A | 58 | 40.884 | −11.303 | 34.723 | 1.00 | 18.41 | A |
| ATOM | 406 | CA | ILE | A | 58 | 41.789 | −10.568 | 35.582 | 1.00 | 17.97 | A |
| ATOM | 407 | CB | ILE | A | 58 | 41.322 | −9.116 | 35.765 | 1.00 | 19.92 | A |
| ATOM | 408 | CG2 | ILE | A | 58 | 41.287 | −8.413 | 34.404 | 1.00 | 20.37 | A |
| ATOM | 409 | CG1 | ILE | A | 58 | 39.915 | −9.064 | 36.362 | 1.00 | 18.48 | A |
| ATOM | 410 | CD1 | ILE | A | 58 | 39.473 | −7.647 | 36.748 | 1.00 | 21.10 | A |
| ATOM | 411 | C | ILE | A | 58 | 41.884 | −11.263 | 36.943 | 1.00 | 18.45 | A |
| ATOM | 412 | O | ILE | A | 58 | 41.062 | −12.117 | 37.281 | 1.00 | 19.54 | A |
| ATOM | 413 | N | SER | A | 59 | 42.900 | −10.909 | 37.713 | 1.00 | 20.22 | A |
| ATOM | 414 | CA | SER | A | 59 | 43.068 | −11.523 | 39.020 | 1.00 | 21.73 | A |
| ATOM | 415 | CB | SER | A | 59 | 44.435 | −11.144 | 39.591 | 1.00 | 21.16 | A |
| ATOM | 416 | OG | SER | A | 59 | 44.549 | −11.599 | 40.931 | 1.00 | 27.61 | A |
| ATOM | 417 | C | SER | A | 59 | 41.997 | −11.001 | 39.951 | 1.00 | 20.98 | A |
| ATOM | 418 | O | SER | A | 59 | 41.516 | −9.899 | 39.771 | 1.00 | 21.86 | A |
| ATOM | 419 | N | PRO | A | 60 | 41.560 | −11.810 | 40.932 | 1.00 | 22.36 | A |
| ATOM | 420 | CD | PRO | A | 60 | 41.661 | −13.269 | 41.077 | 1.00 | 24.77 | A |
| ATOM | 421 | CA | PRO | A | 60 | 40.544 | −11.244 | 41.825 | 1.00 | 24.69 | A |
| ATOM | 422 | CB | PRO | A | 60 | 40.165 | −12.420 | 42.742 | 1.00 | 26.73 | A |
| ATOM | 423 | CG | PRO | A | 60 | 41.186 | −13.473 | 42.493 | 1.00 | 26.33 | A |
| ATOM | 424 | C | PRO | A | 60 | 41.243 | −10.097 | 42.581 | 1.00 | 26.73 | A |
| ATOM | 425 | O | PRO | A | 60 | 42.444 | −10.149 | 42.819 | 1.00 | 27.75 | A |
| ATOM | 426 | N | GLY | A | 61 | 40.524 | −9.051 | 42.952 | 1.00 | 30.12 | A |
| ATOM | 427 | CA | GLY | A | 61 | 41.215 | −7.962 | 43.634 | 1.00 | 32.79 | A |
| ATOM | 428 | C | GLY | A | 61 | 41.865 | −6.922 | 42.714 | 1.00 | 33.94 | A |
| ATOM | 429 | O | GLY | A | 61 | 42.068 | −5.774 | 43.135 | 1.00 | 34.84 | A |
| ATOM | 430 | N | ASP | A | 62 | 42.219 | −7.321 | 41.483 | 1.00 | 33.01 | A |
| ATOM | 431 | CA | ASP | A | 62 | 42.796 | −6.407 | 40.481 | 1.00 | 32.37 | A |
| ATOM | 432 | CB | ASP | A | 62 | 42.736 | −7.053 | 39.075 | 1.00 | 31.25 | A |
| ATOM | 433 | CG | ASP | A | 62 | 43.210 | −6.113 | 37.955 | 1.00 | 31.73 | A |
| ATOM | 434 | OD1 | ASP | A | 62 | 43.309 | −4.893 | 38.171 | 1.00 | 32.93 | A |
| ATOM | 435 | OD2 | ASP | A | 62 | 43.471 | −6.598 | 36.842 | 1.00 | 28.27 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 436 | C | ASP | A | 62 | 41.919 | −5.157 | 40.494 | 1.00 | 31.28 | A |
| --- | --- | --- | --- | --- | --- | --- | --- | --- | --- | --- | --- |
| ATOM | 437 | O | ASP | A | 62 | 40.794 | −5.183 | 39.989 | 1.00 | 33.15 | A |
| ATOM | 438 | N | SER | A | 63 | 42.429 | −4.070 | 41.074 | 1.00 | 32.19 | A |
| ATOM | 439 | CA | SER | A | 63 | 41.685 | −2.814 | 41.163 | 1.00 | 33.27 | A |
| ATOM | 440 | CB | SER | A | 63 | 41.974 | −2.130 | 42.505 | 1.00 | 34.57 | A |
| ATOM | 441 | OG | SER | A | 63 | 43.370 | −1.985 | 42.702 | 1.00 | 36.92 | A |
| ATOM | 442 | C | SER | A | 63 | 42.009 | −1.836 | 40.037 | 1.00 | 32.43 | A |
| ATOM | 443 | O | SER | A | 63 | 41.453 | −.740 | 39.964 | 1.00 | 34.16 | A |
| ATOM | 444 | N | ARG | A | 64 | 42.911 | −2.222 | 39.155 | 1.00 | 30.86 | A |
| ATOM | 445 | CA | ARG | A | 64 | 43.294 | −1.333 | 38.069 | 1.00 | 29.54 | A |
| ATOM | 446 | CB | ARG | A | 64 | 44.712 | −1.659 | 37.604 | 1.00 | 31.18 | A |
| ATOM | 447 | CG | ARG | A | 64 | 45.786 | −1.330 | 38.635 | 1.00 | 33.85 | A |
| ATOM | 448 | CD | ARG | A | 64 | 47.174 | −1.582 | 38.070 | 1.00 | 34.86 | A |
| ATOM | 449 | NE | ARG | A | 64 | 48.245 | −1.214 | 38.995 | 1.00 | 38.00 | A |
| ATOM | 450 | CZ | ARG | A | 64 | 48.511 | −1.849 | 40.130 | 1.00 | 39.31 | A |
| ATOM | 451 | NH1 | ARG | A | 64 | 47.781 | −2.890 | 40.496 | 1.00 | 40.37 | A |
| ATOM | 452 | NH2 | ARG | A | 64 | 49.527 | −1.454 | 40.890 | 1.00 | 42.22 | A |
| ATOM | 453 | C | ARG | A | 64 | 42.367 | −1.376 | 36.875 | 1.00 | 29.02 | A |
| ATOM | 454 | O | ARG | A | 64 | 42.015 | −.333 | 36.321 | 1.00 | 26.60 | A |
| ATOM | 455 | N | PHE | A | 65 | 41.978 | −2.578 | 36.470 | 1.00 | 26.58 | A |
| ATOM | 456 | CA | PHE | A | 65 | 41.116 | −2.713 | 35.310 | 1.00 | 27.19 | A |
| ATOM | 457 | CB | PHE | A | 65 | 40.584 | −4.140 | 35.189 | 1.00 | 25.73 | A |
| ATOM | 458 | CG | PHE | A | 65 | 39.777 | −4.374 | 33.943 | 1.00 | 25.26 | A |
| ATOM | 459 | CD1 | PHE | A | 65 | 40.415 | −4.543 | 32.711 | 1.00 | 24.66 | A |
| ATOM | 460 | CD2 | PHE | A | 65 | 38.389 | −4.415 | 33.995 | 1.00 | 24.69 | A |
| ATOM | 461 | CE1 | PHE | A | 65 | 39.682 | −4.751 | 31.553 | 1.00 | 26.53 | A |
| ATOM | 462 | CE2 | PHE | A | 65 | 37.638 | −4.624 | 32.840 | 1.00 | 26.25 | A |
| ATOM | 463 | CZ | PHE | A | 65 | 38.292 | −4.792 | 31.610 | 1.00 | 26.41 | A |
| ATOM | 464 | C | PHE | A | 65 | 39.928 | −1.769 | 35.334 | 1.00 | 27.84 | A |
| ATOM | 465 | O | PHE | A | 65 | 39.634 | −1.105 | 34.343 | 1.00 | 27.31 | A |
| ATOM | 466 | N | ALA | A | 66 | 39.237 | −1.718 | 36.469 | 1.00 | 27.80 | A |
| ATOM | 467 | CA | ALA | A | 66 | 38.052 | −.891 | 36.586 | 1.00 | 29.41 | A |
| ATOM | 468 | CB | ALA | A | 66 | 37.468 | −1.003 | 37.992 | 1.00 | 29.97 | A |
| ATOM | 469 | C | ALA | A | 66 | 38.289 | .561 | 36.235 | 1.00 | 30.45 | A |
| ATOM | 470 | O | ALA | A | 66 | 37.352 | 1.256 | 35.849 | 1.00 | 30.58 | A |
| ATOM | 471 | N | GLN | A | 67 | 39.533 | 1.023 | 36.342 | 1.00 | 30.88 | A |
| ATOM | 472 | CA | GLN | A | 67 | 39.827 | 2.425 | 36.037 | 1.00 | 34.01 | A |
| ATOM | 473 | CB | GLN | A | 67 | 40.967 | 2.923 | 36.929 | 1.00 | 35.63 | A |
| ATOM | 474 | CG | GLN | A | 67 | 40.685 | 2.745 | 38.409 | 1.00 | 38.59 | A |
| ATOM | 475 | CD | GLN | A | 67 | 39.308 | 3.256 | 38.792 | 1.00 | 40.38 | A |
| ATOM | 476 | OE1 | GLN | A | 67 | 38.970 | 4.417 | 38.537 | 1.00 | 42.52 | A |
| ATOM | 477 | NE2 | GLN | A | 67 | 38.501 | 2.393 | 39.407 | 1.00 | 40.21 | A |
| ATOM | 478 | C | GLN | A | 67 | 40.161 | 2.725 | 34.567 | 1.00 | 34.08 | A |
| ATOM | 479 | O | GLN | A | 67 | 40.475 | 3.871 | 34.215 | 1.00 | 35.16 | A |
| ATOM | 480 | N | LEU | A | 68 | 40.092 | 1.704 | 33.715 | 1.00 | 33.17 | A |
| ATOM | 481 | CA | LEU | A | 68 | 40.382 | 1.879 | 32.293 | 1.00 | 31.98 | A |
| ATOM | 482 | CB | LEU | A | 68 | 41.154 | .666 | 31.753 | 1.00 | 30.47 | A |
| ATOM | 483 | CG | LEU | A | 68 | 42.464 | .265 | 32.426 | 1.00 | 30.28 | A |
| ATOM | 484 | CD1 | LEU | A | 68 | 42.987 | −1.026 | 31.797 | 1.00 | 29.38 | A |
| ATOM | 485 | CD2 | LEU | A | 68 | 43.479 | 1.392 | 32.286 | 1.00 | 31.14 | A |
| ATOM | 486 | C | LEU | A | 68 | 39.080 | 2.014 | 31.502 | 1.00 | 32.32 | A |
| ATOM | 487 | O | LEU | A | 68 | 38.023 | 1.596 | 31.965 | 1.00 | 32.34 | A |
| ATOM | 488 | N | PRO | A | 69 | 39.146 | 2.593 | 30.289 | 1.00 | 33.02 | A |
| ATOM | 489 | CD | PRO | A | 69 | 40.317 | 3.302 | 29.735 | 1.00 | 33.95 | A |
| ATOM | 490 | CA | PRO | A | 69 | 37.959 | 2.766 | 29.435 | 1.00 | 33.11 | A |
| ATOM | 491 | CB | PRO | A | 69 | 38.511 | 3.528 | 28.233 | 1.00 | 34.68 | A |
| ATOM | 492 | CG | PRO | A | 69 | 39.671 | 4.319 | 28.835 | 1.00 | 35.12 | A |
| ATOM | 493 | C | PRO | A | 69 | 37.357 | 1.407 | 29.044 | 1.00 | 33.26 | A |
| ATOM | 494 | O | PRO | A | 69 | 36.162 | 1.276 | 28.800 | 1.00 | 33.69 | A |
| ATOM | 495 | N | LEU | A | 70 | 38.197 | .388 | 28.989 | 1.00 | 32.17 | A |
| ATOM | 496 | CA | LEU | A | 70 | 37.729 | −.945 | 28.634 | 1.00 | 31.80 | A |
| ATOM | 497 | CB | LEU | A | 70 | 38.885 | −1.923 | 28.678 | 1.00 | 30.79 | A |
| ATOM | 498 | CG | LEU | A | 70 | 40.110 | −1.613 | 27.834 | 1.00 | 30.22 | A |
| ATOM | 499 | CD1 | LEU | A | 70 | 41.099 | −2.734 | 28.068 | 1.00 | 28.58 | A |
| ATOM | 500 | CD2 | LEU | A | 70 | 39.743 | −1.497 | 26.364 | 1.00 | 28.70 | A |
| ATOM | 501 | C | LEU | A | 70 | 36.649 | −1.471 | 29.557 | 1.00 | 31.86 | A |
| ATOM | 502 | O | LEU | A | 70 | 35.858 | −2.332 | 29.174 | 1.00 | 32.33 | A |
| ATOM | 503 | N | ALA | A | 71 | 36.640 | −.963 | 30.786 | 1.00 | 32.20 | A |
| ATOM | 504 | CA | ALA | A | 71 | 35.692 | −1.395 | 31.797 | 1.00 | 31.87 | A |
| ATOM | 505 | CB | ALA | A | 71 | 36.047 | −.754 | 33.139 | 1.00 | 32.57 | A |
| ATOM | 506 | C | ALA | A | 71 | 34.241 | −1.097 | 31.437 | 1.00 | 30.89 | A |
| ATOM | 507 | O | ALA | A | 71 | 33.336 | −1.777 | 31.916 | 1.00 | 31.74 | A |
| ATOM | 508 | N | ASN | A | 72 | 34.019 | −.097 | 30.589 | 1.00 | 28.33 | A |
| ATOM | 509 | CA | ASN | A | 72 | 32.658 | .277 | 30.202 | 1.00 | 27.96 | A |
| ATOM | 510 | CB | ASN | A | 72 | 32.399 | 1.728 | 30.614 | 1.00 | 32.03 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 511 | CG | ASN | A | 72 | 32.427 | 1.916 | 32.123 | 1.00 | 34.86 | A |
|---|---|---|---|---|---|---|---|---|---|---|---|
| ATOM | 512 | OD1 | ASN | A | 72 | 33.043 | 2.856 | 32.638 | 1.00 | 39.66 | A |
| ATOM | 513 | ND2 | ASN | A | 72 | 31.743 | 1.031 | 32.839 | 1.00 | 35.66 | A |
| ATOM | 514 | C | ASN | A | 72 | 32.341 | .095 | 28.716 | 1.00 | 25.17 | A |
| ATOM | 515 | O | ASN | A | 72 | 31.312 | .570 | 28.217 | 1.00 | 24.91 | A |
| ATOM | 516 | N | HIS | A | 73 | 33.218 | −.618 | 28.019 | 1.00 | 21.98 | A |
| ATOM | 517 | CA | HIS | A | 73 | 33.070 | −.866 | 26.593 | 1.00 | 18.90 | A |
| ATOM | 518 | CB | HIS | A | 73 | 34.404 | −1.355 | 26.069 | 1.00 | 18.25 | A |
| ATOM | 519 | CG | HIS | A | 73 | 34.465 | −1.459 | 24.583 | 1.00 | 18.07 | A |
| ATOM | 520 | CD2 | HIS | A | 73 | 33.730 | −2.195 | 23.725 | 1.00 | 16.10 | A |
| ATOM | 521 | ND1 | HIS | A | 73 | 35.361 | −.746 | 23.811 | 1.00 | 18.96 | A |
| ATOM | 522 | CE1 | HIS | A | 73 | 35.163 | −1.039 | 22.538 | 1.00 | 15.21 | A |
| ATOM | 523 | NE2 | HIS | A | 73 | 34.180 | −1.914 | 22.459 | 1.00 | 19.78 | A |
| ATOM | 524 | C | HIS | A | 73 | 31.976 | −1.903 | 26.366 | 1.00 | 17.23 | A |
| ATOM | 525 | O | HIS | A | 73 | 31.986 | −2.967 | 26.975 | 1.00 | 18.97 | A |
| ATOM | 526 | N | PRO | A | 74 | 31.038 | −1.629 | 25.439 | 1.00 | 16.35 | A |
| ATOM | 527 | CD | PRO | A | 74 | 30.960 | −.463 | 24.541 | 1.00 | 17.25 | A |
| ATOM | 528 | CA | PRO | A | 74 | 29.949 | −2.571 | 25.197 | 1.00 | 16.24 | A |
| ATOM | 529 | CB | PRO | A | 74 | 29.007 | −1.793 | 24.251 | 1.00 | 16.50 | A |
| ATOM | 530 | CG | PRO | A | 74 | 29.911 | −.882 | 23.513 | 1.00 | 16.03 | A |
| ATOM | 531 | C | PRO | A | 74 | 30.336 | −3.935 | 24.683 | 1.00 | 16.81 | A |
| ATOM | 532 | O | PRO | A | 74 | 29.564 | −4.898 | 24.831 | 1.00 | 18.71 | A |
| ATOM | 533 | N | GLN | A | 75 | 31.541 | −4.058 | 24.123 | 1.00 | 16.14 | A |
| ATOM | 534 | CA | GLN | A | 75 | 31.968 | −5.355 | 23.590 | 1.00 | 17.00 | A |
| ATOM | 535 | CB | GLN | A | 75 | 32.655 | −5.177 | 22.233 | 1.00 | 14.34 | A |
| ATOM | 536 | CG | GLN | A | 75 | 31.683 | −4.634 | 21.150 | 1.00 | 15.60 | A |
| ATOM | 537 | CD | GLN | A | 75 | 32.390 | −4.254 | 19.842 | 1.00 | 15.43 | A |
| ATOM | 538 | OE1 | GLN | A | 75 | 33.241 | −3.358 | 19.800 | 1.00 | 19.31 | A |
| ATOM | 539 | NE2 | GLN | A | 75 | 32.038 | −4.930 | 18.785 | 1.00 | 18.09 | A |
| ATOM | 540 | C | GLN | A | 75 | 32.920 | −6.095 | 24.526 | 1.00 | 17.88 | A |
| ATOM | 541 | O | GLN | A | 75 | 33.370 | −7.182 | 24.173 | 1.00 | 18.66 | A |
| ATOM | 542 | N | ILE | A | 76 | 33.185 | −5.543 | 25.716 | 1.00 | 17.28 | A |
| ATOM | 543 | CA | ILE | A | 76 | 34.116 | −6.163 | 26.642 | 1.00 | 17.98 | A |
| ATOM | 544 | CB | ILE | A | 76 | 35.257 | −5.193 | 26.956 | 1.00 | 17.24 | A |
| ATOM | 545 | CG2 | ILE | A | 76 | 36.261 | −5.848 | 27.910 | 1.00 | 19.78 | A |
| ATOM | 546 | CG1 | ILE | A | 76 | 35.985 | −4.838 | 25.650 | 1.00 | 19.19 | A |
| ATOM | 547 | CD1 | ILE | A | 76 | 37.026 | −3.762 | 25.826 | 1.00 | 22.62 | A |
| ATOM | 548 | C | ILE | A | 76 | 33.470 | −6.624 | 27.934 | 1.00 | 19.13 | A |
| ATOM | 549 | O | ILE | A | 76 | 32.742 | −5.874 | 28.570 | 1.00 | 20.34 | A |
| ATOM | 550 | N | THR | A | 77 | 33.788 | −7.856 | 28.317 | 1.00 | 18.36 | A |
| ATOM | 551 | CA | THR | A | 77 | 33.261 | −8.498 | 29.515 | 1.00 | 18.73 | A |
| ATOM | 552 | CB | THR | A | 77 | 32.465 | −9.755 | 29.124 | 1.00 | 22.50 | A |
| ATOM | 553 | OG1 | THR | A | 77 | 31.385 | −9.378 | 28.254 | 1.00 | 25.58 | A |
| ATOM | 554 | CG2 | THR | A | 77 | 31.924 | −10.460 | 30.353 | 1.00 | 23.93 | A |
| ATOM | 555 | C | THR | A | 77 | 34.471 | −8.926 | 30.335 | 1.00 | 19.00 | A |
| ATOM | 556 | O | THR | A | 77 | 35.433 | −9.434 | 29.786 | 1.00 | 18.50 | A |
| ATOM | 557 | N | VAL | A | 78 | 34.436 | −8.719 | 31.642 | 1.00 | 19.40 | A |
| ATOM | 558 | CA | VAL | A | 78 | 35.564 | −9.116 | 32.469 | 1.00 | 19.89 | A |
| ATOM | 559 | CB | VAL | A | 78 | 36.031 | −7.928 | 33.337 | 1.00 | 23.75 | A |
| ATOM | 560 | CG1 | VAL | A | 78 | 34.920 | −7.524 | 34.299 | 1.00 | 24.68 | A |
| ATOM | 561 | CG2 | VAL | A | 78 | 37.284 | −8.286 | 34.105 | 1.00 | 25.87 | A |
| ATOM | 562 | C | VAL | A | 78 | 35.140 | −10.268 | 33.374 | 1.00 | 19.37 | A |
| ATOM | 563 | O | VAL | A | 78 | 33.985 | −10.345 | 33.782 | 1.00 | 20.50 | A |
| ATOM | 564 | N | VAL | A | 79 | 36.069 | −11.171 | 33.662 | 1.00 | 18.53 | A |
| ATOM | 565 | CA | VAL | A | 79 | 35.803 | −12.290 | 34.555 | 1.00 | 19.64 | A |
| ATOM | 566 | CB | VAL | A | 79 | 35.526 | −13.592 | 33.787 | 1.00 | 21.64 | A |
| ATOM | 567 | CG1 | VAL | A | 79 | 34.347 | −13.384 | 32.829 | 1.00 | 20.90 | A |
| ATOM | 568 | CG2 | VAL | A | 79 | 36.764 | −14.042 | 33.027 | 1.00 | 21.64 | A |
| ATOM | 569 | C | VAL | A | 79 | 37.053 | −12.484 | 35.388 | 1.00 | 18.59 | A |
| ATOM | 570 | O | VAL | A | 79 | 38.114 | −11.965 | 35.056 | 1.00 | 17.18 | A |
| ATOM | 571 | N | ASP | A | 80 | 36.936 | −13.224 | 36.484 | 1.00 | 20.90 | A |
| ATOM | 572 | CA | ASP | A | 80 | 38.104 | −13.474 | 37.302 | 1.00 | 21.87 | A |
| ATOM | 573 | CB | ASP | A | 80 | 37.728 | −13.836 | 38.753 | 1.00 | 24.61 | A |
| ATOM | 574 | CG | ASP | A | 80 | 37.342 | −12.630 | 39.593 | 1.00 | 28.38 | A |
| ATOM | 575 | OD1 | ASP | A | 80 | 37.433 | −11.477 | 39.113 | 1.00 | 29.26 | A |
| ATOM | 576 | OD2 | ASP | A | 80 | 36.936 | −12.828 | 40.767 | 1.00 | 30.57 | A |
| ATOM | 577 | C | ASP | A | 80 | 38.861 | −14.645 | 36.700 | 1.00 | 20.01 | A |
| ATOM | 578 | O | ASP | A | 80 | 38.271 | −15.665 | 36.330 | 1.00 | 21.81 | A |
| ATOM | 579 | N | GLY | A | 81 | 40.173 | −14.482 | 36.605 | 1.00 | 22.14 | A |
| ATOM | 580 | CA | GLY | A | 81 | 41.024 | −15.536 | 36.091 | 1.00 | 23.88 | A |
| ATOM | 581 | C | GLY | A | 81 | 41.384 | −16.498 | 37.223 | 1.00 | 27.85 | A |
| ATOM | 582 | O | GLY | A | 81 | 40.781 | −16.433 | 38.311 | 1.00 | 26.32 | A |
| ATOM | 583 | N | GLY | A | 82 | 42.365 | −17.367 | 36.979 | 1.00 | 28.98 | A |
| ATOM | 584 | CA | GLY | A | 82 | 42.765 | −18.364 | 37.969 | 1.00 | 32.02 | A |
| ATOM | 585 | C | GLY | A | 82 | 44.245 | −18.422 | 38.301 | 1.00 | 33.56 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 586 | O | GLY | A | 82 | 44.993 | −17.506 | 37.973 | 1.00 | 32.84 | A |
| --- | --- | --- | --- | --- | --- | --- | --- | --- | --- | --- | --- |
| ATOM | 587 | N | ASP | A | 83 | 44.670 | −19.505 | 38.956 | 1.00 | 35.24 | A |
| ATOM | 588 | CA | ASP | A | 83 | 46.069 | −19.673 | 39.360 | 1.00 | 35.35 | A |
| ATOM | 589 | CB | ASP | A | 83 | 46.225 | −20.948 | 40.199 | 1.00 | 39.08 | A |
| ATOM | 590 | CG | ASP | A | 83 | 45.158 | −21.073 | 41.264 | 1.00 | 41.85 | A |
| ATOM | 591 | OD1 | ASP | A | 83 | 44.854 | −20.051 | 41.922 | 1.00 | 44.29 | A |
| ATOM | 592 | OD2 | ASP | A | 83 | 44.633 | −22.194 | 41.454 | 1.00 | 44.06 | A |
| ATOM | 593 | C | ASP | A | 83 | 47.084 | −19.694 | 38.216 | 1.00 | 33.53 | A |
| ATOM | 594 | O | ASP | A | 83 | 48.151 | −19.075 | 38.306 | 1.00 | 32.73 | A |
| ATOM | 595 | N | GLU | A | 84 | 46.755 | −20.425 | 37.157 | 1.00 | 33.17 | A |
| ATOM | 596 | CA | GLU | A | 84 | 47.620 | −20.529 | 35.989 | 1.00 | 32.63 | A |
| ATOM | 597 | CB | GLU | A | 84 | 48.028 | −21.981 | 35.754 | 1.00 | 35.36 | A |
| ATOM | 598 | CG | GLU | A | 84 | 48.925 | −22.522 | 36.838 | 1.00 | 39.82 | A |
| ATOM | 599 | CD | GLU | A | 84 | 49.532 | −23.836 | 36.448 | 1.00 | 42.75 | A |
| ATOM | 600 | OE1 | GLU | A | 84 | 50.117 | −23.908 | 35.340 | 1.00 | 45.64 | A |
| ATOM | 601 | OE2 | GLU | A | 84 | 49.434 | −24.794 | 37.245 | 1.00 | 45.57 | A |
| ATOM | 602 | C | GLU | A | 84 | 46.910 | −19.986 | 34.755 | 1.00 | 30.41 | A |
| ATOM | 603 | O | GLU | A | 84 | 45.684 | −19.822 | 34.745 | 1.00 | 29.29 | A |
| ATOM | 604 | N | ARG | A | 85 | 47.679 | −19.724 | 33.708 | 1.00 | 30.64 | A |
| ATOM | 605 | CA | ARG | A | 85 | 47.111 | −19.171 | 32.484 | 1.00 | 28.58 | A |
| ATOM | 606 | CB | ARG | A | 85 | 48.225 | −19.015 | 31.439 | 1.00 | 28.67 | A |
| ATOM | 607 | CG | ARG | A | 85 | 47.774 | −18.365 | 30.137 | 1.00 | 27.63 | A |
| ATOM | 608 | CD | ARG | A | 85 | 48.977 | −17.966 | 29.299 | 1.00 | 28.41 | A |
| ATOM | 609 | NE | ARG | A | 85 | 48.558 | −17.410 | 28.019 | 1.00 | 28.39 | A |
| ATOM | 610 | CZ | ARG | A | 85 | 47.925 | −18.117 | 27.093 | 1.00 | 28.68 | A |
| ATOM | 611 | NH1 | ARG | A | 85 | 47.659 | −19.389 | 27.311 | 1.00 | 27.16 | A |
| ATOM | 612 | NH2 | ARG | A | 85 | 47.544 | −17.549 | 25.964 | 1.00 | 27.49 | A |
| ATOM | 613 | C | ARG | A | 85 | 45.953 | −20.004 | 31.929 | 1.00 | 27.39 | A |
| ATOM | 614 | O | ARG | A | 85 | 44.926 | −19.468 | 31.522 | 1.00 | 25.90 | A |
| ATOM | 615 | N | ALA | A | 86 | 46.113 | −21.318 | 31.905 | 1.00 | 27.24 | A |
| ATOM | 616 | CA | ALA | A | 86 | 45.064 | −22.185 | 31.385 | 1.00 | 27.02 | A |
| ATOM | 617 | CB | ALA | A | 86 | 45.521 | −23.631 | 31.413 | 1.00 | 28.51 | A |
| ATOM | 618 | C | ALA | A | 86 | 43.751 | −22.034 | 32.152 | 1.00 | 27.35 | A |
| ATOM | 619 | O | ALA | A | 86 | 42.656 | −22.120 | 31.574 | 1.00 | 25.26 | A |
| ATOM | 620 | N | ASP | A | 87 | 43.852 | −21.811 | 33.460 | 1.00 | 28.02 | A |
| ATOM | 621 | CA | ASP | A | 87 | 42.660 | −21.636 | 34.271 | 1.00 | 26.98 | A |
| ATOM | 622 | CB | ASP | A | 87 | 43.036 | −21.583 | 35.746 | 1.00 | 30.14 | A |
| ATOM | 623 | CG | ASP | A | 87 | 43.703 | −22.871 | 36.220 | 1.00 | 32.77 | A |
| ATOM | 624 | OD1 | ASP | A | 87 | 43.020 | −23.912 | 36.237 | 1.00 | 33.68 | A |
| ATOM | 625 | OD2 | ASP | A | 87 | 44.903 | −22.836 | 36.554 | 1.00 | 34.65 | A |
| ATOM | 626 | C | ASP | A | 87 | 41.967 | −20.345 | 33.864 | 1.00 | 26.42 | A |
| ATOM | 627 | O | ASP | A | 87 | 40.740 | −20.274 | 33.766 | 1.00 | 24.39 | A |
| ATOM | 628 | N | SER | A | 88 | 42.765 | −19.319 | 33.611 | 1.00 | 24.13 | A |
| ATOM | 629 | CA | SER | A | 88 | 42.206 | −18.039 | 33.221 | 1.00 | 22.11 | A |
| ATOM | 630 | CB | SER | A | 88 | 43.285 | −16.958 | 33.267 | 1.00 | 20.60 | A |
| ATOM | 631 | OG | SER | A | 88 | 43.785 | −16.795 | 34.587 | 1.00 | 22.43 | A |
| ATOM | 632 | C | SER | A | 88 | 41.572 | −18.125 | 31.837 | 1.00 | 19.85 | A |
| ATOM | 633 | O | SER | A | 88 | 40.532 | −17.521 | 31.590 | 1.00 | 18.26 | A |
| ATOM | 634 | N | VAL | A | 89 | 42.185 | −18.873 | 30.931 | 1.00 | 20.60 | A |
| ATOM | 635 | CA | VAL | A | 89 | 41.693 | −18.993 | 29.607 | 1.00 | 20.90 | A |
| ATOM | 636 | CB | VAL | A | 89 | 42.528 | −19.738 | 28.629 | 1.00 | 22.14 | A |
| ATOM | 637 | CG1 | VAL | A | 89 | 41.826 | −19.951 | 27.305 | 1.00 | 23.04 | A |
| ATOM | 638 | CG2 | VAL | A | 89 | 43.811 | −18.926 | 28.454 | 1.00 | 22.44 | A |
| ATOM | 639 | C | VAL | A | 89 | 40.252 | −19.711 | 29.705 | 1.00 | 22.92 | A |
| ATOM | 640 | O | VAL | A | 89 | 39.279 | −19.306 | 29.070 | 1.00 | 23.26 | A |
| ATOM | 641 | N | LEU | A | 90 | 40.1.83 | −20.769 | 30.515 | 1.00 | 24.29 | A |
| ATOM | 642 | CA | LEU | A | 90 | 38.922 | −21.509 | 30.691 | 1.00 | 24.22 | A |
| ATOM | 643 | CB | LEU | A | 90 | 39.112 | −22.708 | 31.641 | 1.00 | 26.68 | A |
| ATOM | 644 | CG | LEU | A | 90 | 39.373 | −24.077 | 31.006 | 1.00 | 29.09 | A |
| ATOM | 645 | CD1 | LEU | A | 90 | 39.606 | −25.116 | 32.109 | 1.00 | 29.18 | A |
| ATOM | 646 | CD2 | LEU | A | 90 | 38.197 | −24.494 | 30.153 | 1.00 | 27.80 | A |
| ATOM | 647 | C | LEU | A | 90 | 37.816 | −20.622 | 31.231 | 1.00 | 24.32 | A |
| ATOM | 648 | O | LEU | A | 90 | 36.681 | −20.721 | 30.796 | 1.00 | 23.54 | A |
| ATOM | 649 | N | ALA | A | 91 | 38.152 | −19.770 | 32.198 | 1.00 | 22.19 | A |
| ATOM | 650 | CA | ALA | A | 91 | 37.189 | −18.860 | 32.792 | 1.00 | 22.94 | A |
| ATOM | 651 | CB | ALA | A | 91 | 37.833 | −18.058 | 33.914 | 1.00 | 22.32 | A |
| ATOM | 652 | C | ALA | A | 91 | 36.703 | −17.928 | 31.693 | 1.00 | 22.09 | A |
| ATOM | 653 | O | ALA | A | 91 | 35.538 | −17.608 | 31.629 | 1.00 | 22.86 | A |
| ATOM | 654 | N | GLY | A | 92 | 37.615 | −17.481 | 30.834 | 1.00 | 21.50 | A |
| ATOM | 655 | CA | GLY | A | 92 | 37.200 | −16.620 | 29.743 | 1.00 | 20.45 | A |
| ATOM | 656 | C | GLY | A | 92 | 36.310 | −17.375 | 28.766 | 1.00 | 21.11 | A |
| ATOM | 657 | O | GLY | A | 92 | 35.303 | −16.834 | 28.315 | 1.00 | 20.68 | A |
| ATOM | 658 | N | LEU | A | 93 | 36.664 | −18.621 | 28.439 | 1.00 | 21.79 | A |
| ATOM | 659 | CA | LEU | A | 93 | 35.857 | −19.415 | 27.506 | 1.00 | 24.32 | A |
| ATOM | 660 | CB | LEU | A | 93 | 36.518 | −20.772 | 27.238 | 1.00 | 24.66 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 661 | CG  | LEU | A | 93  | 37.863 | −20.723 | 26.505 | 1.00 | 27.53 | A |
|------|-----|-----|-----|---|-----|--------|---------|--------|------|-------|---|
| ATOM | 662 | CD1 | LEU | A | 93  | 38.431 | −22.134 | 26.413 | 1.00 | 28.96 | A |
| ATOM | 663 | CD2 | LEU | A | 93  | 37.676 | −20.157 | 25.086 | 1.00 | 28.17 | A |
| ATOM | 664 | C   | LEU | A | 93  | 34.423 | −19.617 | 28.018 | 1.00 | 26.57 | A |
| ATOM | 665 | O   | LEU | A | 93  | 33.481 | −19.727 | 27.225 | 1.00 | 27.96 | A |
| ATOM | 666 | N   | LYS | A | 94  | 34.256 | −19.674 | 29.341 | 1.00 | 27.71 | A |
| ATOM | 667 | CA  | LYS | A | 94  | 32.933 | −19.820 | 29.949 | 1.00 | 29.06 | A |
| ATOM | 668 | CB  | LYS | A | 94  | 33.041 | −19.993 | 31.475 | 1.00 | 32.51 | A |
| ATOM | 669 | CG  | LYS | A | 94  | 33.760 | −21.241 | 31.966 | 1.00 | 36.19 | A |
| ATOM | 670 | CD  | LYS | A | 94  | 32.776 | −22.303 | 32.449 | 1.00 | 39.18 | A |
| ATOM | 671 | CE  | LYS | A | 94  | 33.477 | −23.388 | 33.292 | 1.00 | 40.84 | A |
| ATOM | 672 | NZ  | LYS | A | 94  | 34.604 | −24.106 | 32.586 | 1.00 | 41.60 | A |
| ATOM | 673 | C   | LYS | A | 94  | 32.033 | −18.618 | 29.672 | 1.00 | 29.36 | A |
| ATOM | 674 | O   | LYS | A | 94  | 30.820 | −18.755 | 29.657 | 1.00 | 29.33 | A |
| ATOM | 675 | N   | ALA | A | 95  | 32.606 | −17.437 | 29.455 | 1.00 | 27.40 | A |
| ATOM | 676 | CA  | ALA | A | 95  | 31.789 | −16.261 | 29.204 | 1.00 | 28.45 | A |
| ATOM | 677 | CB  | ALA | A | 95  | 32.259 | −15.098 | 30.065 | 1.00 | 31.33 | A |
| ATOM | 678 | C   | ALA | A | 95  | 31.772 | −15.834 | 27.745 | 1.00 | 28.46 | A |
| ATOM | 679 | O   | ALA | A | 95  | 31.276 | −14.756 | 27.416 | 1.00 | 28.85 | A |
| ATOM | 680 | N   | ALA | A | 96  | 32.280 | −16.704 | 26.880 | 1.00 | 28.53 | A |
| ATOM | 681 | CA  | ALA | A | 96  | 32.371 | −16.437 | 25.448 | 1.00 | 29.07 | A |
| ATOM | 682 | CB  | ALA | A | 96  | 33.356 | −17.411 | 24.811 | 1.00 | 27.22 | A |
| ATOM | 683 | C   | ALA | A | 96  | 31.065 | −16.477 | 24.679 | 1.00 | 29.41 | A |
| ATOM | 684 | O   | ALA | A | 96  | 31.060 | −16.320 | 23.455 | 1.00 | 30.31 | A |
| ATOM | 685 | N   | GLY | A | 97  | 29.955 | −16.709 | 25.369 | 1.00 | 29.55 | A |
| ATOM | 686 | CA  | GLY | A | 97  | 28.679 | −16.755 | 24.677 | 1.00 | 29.21 | A |
| ATOM | 687 | C   | GLY | A | 97  | 28.538 | −17.940 | 23.737 | 1.00 | 28.92 | A |
| ATOM | 688 | O   | GLY | A | 97  | 29.065 | −19.017 | 24.012 | 1.00 | 29.22 | A |
| ATOM | 689 | N   | ASP | A | 98  | 27.846 | −17.742 | 22.613 | 1.00 | 27.73 | A |
| ATOM | 690 | CA  | ASP | A | 98  | 27.635 | −18.823 | 21.650 | 1.00 | 27.76 | A |
| ATOM | 691 | CB  | ASP | A | 98  | 26.182 | −18.822 | 21.162 | 1.00 | 31.55 | A |
| ATOM | 692 | CG  | ASP | A | 98  | 25.708 | −17.453 | 20.711 | 1.00 | 35.48 | A |
| ATOM | 693 | OD1 | ASP | A | 98  | 26.489 | −16.715 | 20.079 | 1.00 | 36.29 | A |
| ATOM | 694 | OD2 | ASP | A | 98  | 24.533 | −17.111 | 20.981 | 1.00 | 38.12 | A |
| ATOM | 695 | C   | ASP | A | 98  | 28.580 | −18.771 | 20.449 | 1.00 | 25.53 | A |
| ATOM | 696 | O   | ASP | A | 98  | 28.384 | −19.461 | 19.450 | 1.00 | 24.06 | A |
| ATOM | 697 | N   | ALA | A | 99  | 29.622 | −17.959 | 20.563 | 1.00 | 24.35 | A |
| ATOM | 698 | CA  | ALA | A | 99  | 30.600 | −17.831 | 19.496 | 1.00 | 23.88 | A |
| ATOM | 699 | CB  | ALA | A | 99  | 31.789 | −17.020 | 19.992 | 1.00 | 26.04 | A |
| ATOM | 700 | C   | ALA | A | 99  | 31.084 | −19.199 | 19.027 | 1.00 | 21.02 | A |
| ATOM | 701 | O   | ALA | A | 99  | 31.442 | −20.046 | 19.833 | 1.00 | 22.54 | A |
| ATOM | 702 | N   | GLN | A | 100 | 31.116 | −19.425 | 17.726 | 1.00 | 19.11 | A |
| ATOM | 703 | CA  | GLN | A | 100 | 31.594 | −20.725 | 17.257 | 1.00 | 18.49 | A |
| ATOM | 704 | CB  | GLN | A | 100 | 31.113 | −20.987 | 15.833 | 1.00 | 20.50 | A |
| ATOM | 705 | CG  | GLN | A | 100 | 29.620 | −21.301 | 15.743 | 1.00 | 25.56 | A |
| ATOM | 706 | CD  | GLN | A | 100 | 29.106 | −21.210 | 14.329 | 1.00 | 25.31 | A |
| ATOM | 707 | OE1 | GLN | A | 100 | 29.810 | −21.528 | 13.384 | 1.00 | 28.35 | A |
| ATOM | 708 | NE2 | GLN | A | 100 | 27.859 | −20.784 | 14.180 | 1.00 | 29.57 | A |
| ATOM | 709 | C   | GLN | A | 100 | 33.109 | −20.832 | 17.282 | 1.00 | 16.63 | A |
| ATOM | 710 | O   | GLN | A | 100 | 33.651 | −21.933 | 17.426 | 1.00 | 15.49 | A |
| ATOM | 711 | N   | TRP | A | 101 | 33.785 | −19.690 | 17.116 | 1.00 | 15.31 | A |
| ATOM | 712 | CA  | TRP | A | 101 | 35.246 | −19.641 | 17.100 | 1.00 | 15.64 | A |
| ATOM | 713 | CB  | TRP | A | 101 | 35.734 | −19.218 | 15.711 | 1.00 | 14.31 | A |
| ATOM | 714 | CG  | TRP | A | 101 | 35.695 | −20.313 | 14.699 | 1.00 | 16.23 | A |
| ATOM | 715 | CD2 | TRP | A | 101 | 36.808 | −21.089 | 14.262 | 1.00 | 13.03 | A |
| ATOM | 716 | CE2 | TRP | A | 101 | 36.337 | −22.010 | 13.298 | 1.00 | 15.27 | A |
| ATOM | 717 | CE3 | TRP | A | 101 | 38.168 | −21.089 | 14.586 | 1.00 | 13.69 | A |
| ATOM | 718 | CD1 | TRP | A | 101 | 34.603 | −20.784 | 14.005 | 1.00 | 15.41 | A |
| ATOM | 719 | NE1 | TRP | A | 101 | 34.987 | −21.802 | 13.161 | 1.00 | 15.92 | A |
| ATOM | 720 | CZ2 | TRP | A | 101 | 37.190 | −22.932 | 12.671 | 1.00 | 15.19 | A |
| ATOM | 721 | CZ3 | TRP | A | 101 | 39.012 | −21.995 | 13.956 | 1.00 | 14.28 | A |
| ATOM | 722 | CH2 | TRP | A | 101 | 38.525 | −22.902 | 13.009 | 1.00 | 14.21 | A |
| ATOM | 723 | C   | TRP | A | 101 | 35.763 | −18.644 | 18.134 | 1.00 | 15.17 | A |
| ATOM | 724 | O   | TRP | A | 101 | 35.143 | −17.600 | 18.337 | 1.00 | 13.62 | A |
| ATOM | 725 | N   | VAL | A | 102 | 36.884 | −18.975 | 18.779 | 1.00 | 13.64 | A |
| ATOM | 726 | CA  | VAL | A | 102 | 37.470 | −18.094 | 19.787 | 1.00 | 14.03 | A |
| ATOM | 727 | CB  | VAL | A | 102 | 37.368 | −18.730 | 21.192 | 1.00 | 15.13 | A |
| ATOM | 728 | CG1 | VAL | A | 102 | 38.107 | −20.046 | 21.218 | 1.00 | 17.37 | A |
| ATOM | 729 | CG2 | VAL | A | 102 | 37.898 | −17.786 | 22.217 | 1.00 | 18.27 | A |
| ATOM | 730 | C   | VAL | A | 102 | 38.929 | −17.796 | 19.481 | 1.00 | 14.11 | A |
| ATOM | 731 | O   | VAL | A | 102 | 39.664 | −18.647 | 19.002 | 1.00 | 11.94 | A |
| ATOM | 732 | N   | LEU | A | 103 | 39.325 | −16.560 | 19.771 | 1.00 | 13.71 | A |
| ATOM | 733 | CA  | LEU | A | 103 | 40.673 | −16.052 | 19.536 | 1.00 | 16.36 | A |
| ATOM | 734 | CB  | LEU | A | 103 | 40.551 | −14.701 | 18.847 | 1.00 | 17.08 | A |
| ATOM | 735 | CG  | LEU | A | 103 | 41.634 | −13.976 | 18.091 | 1.00 | 22.42 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 736 | CD1 | LEU | A | 103 | 42.073 | −14.827 | 16.888 | 1.00 | 17.83 | A |
|------|-----|-----|-----|---|-----|--------|---------|--------|------|-------|---|
| ATOM | 737 | CD2 | LEU | A | 103 | 41.046 | −12.630 | 17.615 | 1.00 | 18.34 | A |
| ATOM | 738 | C   | LEU | A | 103 | 41.280 | −15.832 | 20.909 | 1.00 | 15.87 | A |
| ATOM | 739 | O   | LEU | A | 103 | 40.765 | −15.024 | 21.650 | 1.00 | 20.10 | A |
| ATOM | 740 | N   | VAL | A | 104 | 42.358 | −16.526 | 21.266 | 1.00 | 14.32 | A |
| ATOM | 741 | CA  | VAL | A | 104 | 42.957 | −16.315 | 22.586 | 1.00 | 14.36 | A |
| ATOM | 742 | CB  | VAL | A | 104 | 43.296 | −17.645 | 23.287 | 1.00 | 15.31 | A |
| ATOM | 743 | CG1 | VAL | A | 104 | 43.832 | −17.344 | 24.687 | 1.00 | 14.73 | A |
| ATOM | 744 | CG2 | VAL | A | 104 | 42.043 | −18.520 | 23.370 | 1.00 | 16.32 | A |
| ATOM | 745 | C   | VAL | A | 104 | 44.248 | −15.521 | 22.368 | 1.00 | 13.00 | A |
| ATOM | 746 | O   | VAL | A | 104 | 45.111 | −15.941 | 21.596 | 1.00 | 13.68 | A |
| ATOM | 747 | N   | HIS | A | 105 | 44.378 | −14.397 | 23.067 | 1.00 | 12.73 | A |
| ATOM | 748 | CA  | HIS | A | 105 | 45.524 | −13.519 | 22.895 | 1.00 | 13.25 | A |
| ATOM | 749 | CB  | HIS | A | 105 | 45.103 | −12.289 | 22.064 | 1.00 | 13.67 | A |
| ATOM | 750 | CG  | HIS | A | 105 | 46.268 | −11.465 | 21.615 | 1.00 | 15.84 | A |
| ATOM | 751 | CD2 | HIS | A | 105 | 47.421 | −11.844 | 21.024 | 1.00 | 12.69 | A |
| ATOM | 752 | ND1 | HIS | A | 105 | 46.380 | −10.110 | 21.847 | 1.00 | 19.95 | A |
| ATOM | 753 | CE1 | HIS | A | 105 | 47.562 | −9.693  | 21.420 | 1.00 | 14.81 | A |
| ATOM | 754 | NE2 | HIS | A | 105 | 48.213 | −10.729 | 20.919 | 1.00 | 18.87 | A |
| ATOM | 755 | C   | HIS | A | 105 | 46.108 | −13.027 | 24.208 | 1.00 | 13.77 | A |
| ATOM | 756 | O   | HIS | A | 105 | 45.380 | −12.535 | 25.059 | 1.00 | 15.58 | A |
| ATOM | 757 | N   | ASP | A | 106 | 47.430 | −13.126 | 24.353 | 1.00 | 15.17 | A |
| ATOM | 758 | CA  | ASP | A | 106 | 48.090 | −12.661 | 25.580 | 1.00 | 18.01 | A |
| ATOM | 759 | CB  | ASP | A | 106 | 49.577 | −12.972 | 25.559 | 1.00 | 21.72 | A |
| ATOM | 760 | CG  | ASP | A | 106 | 49.873 | −14.410 | 25.862 | 1.00 | 27.57 | A |
| ATOM | 761 | OD1 | ASP | A | 106 | 49.010 | −15.097 | 26.445 | 1.00 | 28.66 | A |
| ATOM | 762 | OD2 | ASP | A | 106 | 50.990 | −14.823 | 25.521 | 1.00 | 31.37 | A |
| ATOM | 763 | C   | ASP | A | 106 | 47.960 | −11.161 | 25.787 | 1.00 | 17.91 | A |
| ATOM | 764 | O   | ASP | A | 106 | 48.175 | −10.391 | 24.870 | 1.00 | 17.99 | A |
| ATOM | 765 | N   | ALA | A | 107 | 47.607 | −10.735 | 26.982 | 1.00 | 18.20 | A |
| ATOM | 766 | CA  | ALA | A | 107 | 47.506 | −9.308  | 27.242 | 1.00 | 17.03 | A |
| ATOM | 767 | CB  | ALA | A | 107 | 47.062 | −9.065  | 28.699 | 1.00 | 21.46 | A |
| ATOM | 768 | C   | ALA | A | 107 | 48.892 | −8.657  | 27.006 | 1.00 | 19.42 | A |
| ATOM | 769 | O   | ALA | A | 107 | 48.972 | −7.490  | 26.626 | 1.00 | 23.53 | A |
| ATOM | 770 | N   | ALA | A | 108 | 49.962 | −9.430  | 27.182 | 1.00 | 18.19 | A |
| ATOM | 771 | CA  | ALA | A | 108 | 51.317 | −8.918  | 27.070 | 1.00 | 19.32 | A |
| ATOM | 772 | CB  | ALA | A | 108 | 52.226 | −9.721  | 27.994 | 1.00 | 22.61 | A |
| ATOM | 773 | C   | ALA | A | 108 | 51.935 | −8.840  | 25.685 | 1.00 | 20.72 | A |
| ATOM | 774 | O   | ALA | A | 108 | 53.166 | −8.647  | 25.563 | 1.00 | 20.01 | A |
| ATOM | 775 | N   | ARG | A | 109 | 51.119 | −9.015  | 24.644 | 1.00 | 18.60 | A |
| ATOM | 776 | CA  | ARG | A | 109 | 51.609 | −8.931  | 23.264 | 1.00 | 19.61 | A |
| ATOM | 777 | CB  | ARG | A | 109 | 51.315 | −10.236 | 22.532 | 1.00 | 18.96 | A |
| ATOM | 778 | CG  | ARG | A | 109 | 52.288 | −11.344 | 22.860 | 1.00 | 18.85 | A |
| ATOM | 779 | CD  | ARG | A | 109 | 51.911 | −12.627 | 22.120 | 1.00 | 22.53 | A |
| ATOM | 780 | NE  | ARG | A | 109 | 52.712 | −13.773 | 22.552 | 1.00 | 25.67 | A |
| ATOM | 781 | CZ  | ARG | A | 109 | 53.972 | −14.006 | 22.189 | 1.00 | 25.25 | A |
| ATOM | 782 | NH1 | ARG | A | 109 | 54.606 | −13.181 | 21.370 | 1.00 | 28.44 | A |
| ATOM | 783 | NH2 | ARG | A | 109 | 54.614 | −15.078 | 22.646 | 1.00 | 28.17 | A |
| ATOM | 784 | C   | ARG | A | 109 | 50.879 | −7.763  | 22.603 | 1.00 | 19.28 | A |
| ATOM | 785 | O   | ARG | A | 109 | 49.928 | −7.957  | 21.825 | 1.00 | 21.88 | A |
| ATOM | 786 | N   | PRO | A | 110 | 51.348 | −6.533  | 22.867 | 1.00 | 17.30 | A |
| ATOM | 787 | CD  | PRO | A | 110 | 52.555 | −6.170  | 23.635 | 1.00 | 19.28 | A |
| ATOM | 788 | CA  | PRO | A | 110 | 50.717 | −5.336  | 22.319 | 1.00 | 16.05 | A |
| ATOM | 789 | CB  | PRO | A | 110 | 51.176 | −4.257  | 23.280 | 1.00 | 18.08 | A |
| ATOM | 790 | CG  | PRO | A | 110 | 52.635 | −4.631  | 23.462 | 1.00 | 18.84 | A |
| ATOM | 791 | C   | PRO | A | 110 | 51.055 | −4.951  | 20.899 | 1.00 | 16.91 | A |
| ATOM | 792 | O   | PRO | A | 110 | 50.436 | −4.024  | 20.372 | 1.00 | 18.13 | A |
| ATOM | 793 | N   | CYS | A | 111 | 51.976 | −5.671  | 20.272 | 1.00 | 14.89 | A |
| ATOM | 794 | CA  | CYS | A | 111 | 52.440 | −5.300  | 18.946 | 1.00 | 16.65 | A |
| ATOM | 795 | CB  | CYS | A | 111 | 53.960 | −5.494  | 18.872 | 1.00 | 18.20 | A |
| ATOM | 796 | SG  | CYS | A | 111 | 54.803 | −4.496  | 20.100 | 1.00 | 21.59 | A |
| ATOM | 797 | C   | CYS | A | 111 | 51.777 | −5.994  | 17.786 | 1.00 | 17.24 | A |
| ATOM | 798 | O   | CYS | A | 111 | 52.241 | −5.871  | 16.655 | 1.00 | 19.05 | A |
| ATOM | 799 | N   | LEU | A | 112 | 50.675 | −6.701  | 18.041 | 1.00 | 15.71 | A |
| ATOM | 800 | CA  | LEU | A | 112 | 49.954 | −7.402  | 16.967 | 1.00 | 16.48 | A |
| ATOM | 801 | CB  | LEU | A | 112 | 48.709 | −8.088  | 17.545 | 1.00 | 13.99 | A |
| ATOM | 802 | CG  | LEU | A | 112 | 47.816 | −8.897  | 16.601 | 1.00 | 16.31 | A |
| ATOM | 803 | CD1 | LEU | A | 112 | 48.581 | −10.078 | 16.004 | 1.00 | 16.00 | A |
| ATOM | 804 | CD2 | LEU | A | 112 | 46.590 | −9.401  | 17.400 | 1.00 | 16.60 | A |
| ATOM | 805 | C   | LEU | A | 112 | 49.513 | −6.532  | 15.794 | 1.00 | 15.46 | A |
| ATOM | 806 | O   | LEU | A | 112 | 48.894 | −5.495  | 15.982 | 1.00 | 16.88 | A |
| ATOM | 807 | N   | HIS | A | 113 | 49.817 | −6.988  | 14.585 | 1.00 | 16.60 | A |
| ATOM | 808 | CA  | HIS | A | 113 | 49.437 | −6.287  | 13.364 | 1.00 | 19.95 | A |
| ATOM | 809 | CB  | HIS | A | 113 | 50.538 | −6.392  | 12.321 | 1.00 | 19.94 | A |
| ATOM | 810 | CG  | HIS | A | 113 | 51.686 | −5.468  | 12.569 | 1.00 | 28.23 | A |

APPENDIX 2-continued

X-RAY DATA COORDINATES FOR CDP-ME SYNTHASE COMPLEXED WITH CTP·Mg$^{2+}$
(SEQ ID NO: 11)

| ATOM | 811 | CD2 | HIS | A | 113 | 52.271 | −5.063 | 13.716 | 1.00 | 29.35 | A |
|---|---|---|---|---|---|---|---|---|---|---|---|
| ATOM | 812 | ND1 | HIS | A | 113 | 52.369 | −4.846 | 11.545 | 1.00 | 29.63 | A |
| ATOM | 813 | CE1 | HIS | A | 113 | 53.326 | −4.095 | 12.058 | 1.00 | 31.75 | A |
| ATOM | 814 | NE2 | HIS | A | 113 | 53.289 | −4.208 | 13.374 | 1.00 | 31.40 | A |
| ATOM | 815 | C | HIS | A | 113 | 48.146 | −6.822 | 12.748 | 1.00 | 18.44 | A |
| ATOM | 816 | O | HIS | A | 113 | 47.831 | −8.000 | 12.833 | 1.00 | 17.33 | A |
| ATOM | 817 | N | GLN | A | 114 | 47.402 | −5.940 | 12.096 | 1.00 | 18.12 | A |
| ATOM | 818 | CA | GLN | A | 114 | 46.157 | −6.351 | 11.485 | 1.00 | 17.59 | A |
| ATOM | 819 | CB | GLN | A | 114 | 45.380 | −5.133 | 10.958 | 1.00 | 16.61 | A |
| ATOM | 820 | CG | GLN | A | 114 | 44.918 | −4.179 | 12.061 | 1.00 | 16.97 | A |
| ATOM | 821 | CD | GLN | A | 114 | 44.030 | −4.891 | 13.059 | 1.00 | 18.29 | A |
| ATOM | 822 | OE1 | GLN | A | 114 | 42.947 | −5.372 | 12.709 | 1.00 | 19.05 | A |
| ATOM | 823 | NE2 | GLN | A | 114 | 44.502 | −4.991 | 14.309 | 1.00 | 15.72 | A |
| ATOM | 824 | C | GLN | A | 114 | 46.277 | −7.366 | 10.370 | 1.00 | 17.30 | A |
| ATOM | 825 | O | GLN | A | 114 | 45.386 | −8.200 | 10.179 | 1.00 | 19.13 | A |
| ATOM | 826 | N | ASP | A | 115 | 47.351 | −7.312 | 9.594 | 1.00 | 18.29 | A |
| ATOM | 827 | CA | ASP | A | 115 | 47.466 | −8.274 | 8.510 | 1.00 | 19.16 | A |
| ATOM | 828 | CB | ASP | A | 115 | 48.629 | −7.892 | 7.572 | 1.00 | 23.11 | A |
| ATOM | 829 | CG | ASP | A | 115 | 49.967 | −7.852 | 8.278 | 1.00 | 30.27 | A |
| ATOM | 830 | OD1 | ASP | A | 115 | 50.039 | −7.318 | 9.409 | 1.00 | 32.83 | A |
| ATOM | 831 | OD2 | ASP | A | 115 | 50.961 | −8.339 | 7.690 | 1.00 | 36.96 | A |
| ATOM | 832 | C | ASP | A | 115 | 47.612 | −9.701 | 9.053 | 1.00 | 17.53 | A |
| ATOM | 833 | O | ASP | A | 115 | 46.986 | −10.643 | 8.543 | 1.00 | 18.94 | A |
| ATOM | 834 | N | ASP | A | 116 | 48.411 | −9.871 | 10.104 | 1.00 | 16.45 | A |
| ATOM | 835 | CA | ASP | A | 116 | 48.579 | −11.202 | 10.729 | 1.00 | 15.17 | A |
| ATOM | 836 | CB | ASP | A | 116 | 49.610 | −11.162 | 11.884 | 1.00 | 14.46 | A |
| ATOM | 837 | CG | ASP | A | 116 | 51.054 | −11.109 | 11.411 | 1.00 | 18.54 | A |
| ATOM | 838 | OD1 | ASP | A | 116 | 51.331 | −11.283 | 10.194 | 1.00 | 19.68 | A |
| ATOM | 839 | OD2 | ASP | A | 116 | 51.924 | −10.897 | 12.284 | 1.00 | 19.69 | A |
| ATOM | 840 | C | ASP | A | 116 | 47.239 | −11.671 | 11.315 | 1.00 | 13.56 | A |
| ATOM | 841 | O | ASP | A | 116 | 46.831 | −12.828 | 11.144 | 1.00 | 13.81 | A |
| ATOM | 842 | N | LEU | A | 117 | 46.555 | −10.765 | 12.007 | 1.00 | 13.13 | A |
| ATOM | 843 | CA | LEU | A | 117 | 45.282 | −11.106 | 12.631 | 1.00 | 12.99 | A |
| ATOM | 844 | CB | LEU | A | 117 | 44.709 | −9.918 | 13.399 | 1.00 | 14.37 | A |
| ATOM | 845 | CG | LEU | A | 117 | 43.334 | −10.159 | 14.026 | 1.00 | 14.86 | A |
| ATOM | 846 | CD1 | LEU | A | 117 | 43.388 | −11.441 | 14.887 | 1.00 | 16.99 | A |
| ATOM | 847 | CD2 | LEU | A | 117 | 42.920 | −8.951 | 14.904 | 1.00 | 16.37 | A |
| ATOM | 848 | C | LEU | A | 117 | 44.298 | −11.574 | 11.575 | 1.00 | 13.28 | A |
| ATOM | 849 | O | LEU | A | 117 | 43.629 | −12.606 | 11.728 | 1.00 | 13.19 | A |
| ATOM | 850 | N | ALA | A | 118 | 44.223 | −10.847 | 10.457 | 1.00 | 14.50 | A |
| ATOM | 851 | CA | ALA | A | 118 | 43.297 | −11.228 | 9.392 | 1.00 | 14.59 | A |
| ATOM | 852 | CB | ALA | A | 118 | 43.243 | −10.114 | 8.325 | 1.00 | 14.44 | A |
| ATOM | 853 | C | ALA | A | 118 | 43.631 | −12.566 | 8.745 | 1.00 | 15.13 | A |
| ATOM | 854 | O | ALA | A | 118 | 42.724 | −13.314 | 8.405 | 1.00 | 16.65 | A |
| ATOM | 855 | N | ARG | A | 119 | 44.921 | −12.876 | 8.582 | 1.00 | 15.00 | A |
| ATOM | 856 | CA | ARG | A | 119 | 45.301 | −14.145 | 7.979 | 1.00 | 15.50 | A |
| ATOM | 857 | CB | ARG | A | 119 | 46.775 | −14.122 | 7.623 | 1.00 | 15.31 | A |
| ATOM | 858 | CG | ARG | A | 119 | 46.982 | −13.277 | 6.349 | 1.00 | 19.88 | A |
| ATOM | 859 | CD | ARG | A | 119 | 48.438 | −13.062 | 5.960 | 1.00 | 21.65 | A |
| ATOM | 860 | NE | ARG | A | 119 | 49.198 | −14.273 | 6.139 | 1.00 | 24.65 | A |
| ATOM | 861 | CZ | ARG | A | 119 | 50.129 | −14.432 | 7.067 | 1.00 | 25.09 | A |
| ATOM | 862 | NH1 | ARG | A | 119 | 50.433 | −13.433 | 7.894 | 1.00 | 22.58 | A |
| ATOM | 863 | NH2 | ARG | A | 119 | 50.714 | −15.615 | 7.191 | 1.00 | 25.34 | A |
| ATOM | 864 | C | ARG | A | 119 | 44.976 | −15.283 | 8.940 | 1.00 | 15.31 | A |
| ATOM | 865 | O | ARG | A | 119 | 44.605 | −16.368 | 8.511 | 1.00 | 16.31 | A |
| ATOM | 866 | N | LEU | A | 120 | 45.114 | −15.020 | 10.240 | 1.00 | 15.11 | A |
| ATOM | 867 | CA | LEU | A | 120 | 44.791 | −16.045 | 11.228 | 1.00 | 14.94 | A |
| ATOM | 868 | CB | LEU | A | 120 | 45.170 | −15.573 | 12.638 | 1.00 | 13.19 | A |
| ATOM | 869 | CG | LEU | A | 120 | 44.849 | −16.629 | 13.709 | 1.00 | 13.92 | A |
| ATOM | 870 | CD1 | LEU | A | 120 | 45.621 | −17.909 | 13.444 | 1.00 | 15.86 | A |
| ATOM | 871 | CD2 | LEU | A | 120 | 45.167 | −16.060 | 15.088 | 1.00 | 13.77 | A |
| ATOM | 872 | C | LEU | A | 120 | 43.291 | −16.362 | 11.188 | 1.00 | 14.09 | A |
| ATOM | 873 | O | LEU | A | 120 | 42.886 | −17.538 | 11.206 | 1.00 | 14.24 | A |
| ATOM | 874 | N | LEU | A | 121 | 42.452 | −15.322 | 11.132 | 1.00 | 14.24 | A |
| ATOM | 875 | CA | LEU | A | 121 | 41.001 | −15.521 | 11.098 | 1.00 | 15.32 | A |
| ATOM | 876 | CB | LEU | A | 121 | 40.282 | −14.175 | 11.179 | 1.00 | 15.34 | A |
| ATOM | 877 | CG | LEU | A | 121 | 40.518 | −13.499 | 12.516 | 1.00 | 17.74 | A |
| ATOM | 878 | CD1 | LEU | A | 121 | 39.767 | −12.176 | 12.606 | 1.00 | 20.95 | A |
| ATOM | 879 | CD2 | LEU | A | 121 | 40.085 | −14.457 | 13.605 | 1.00 | 22.13 | A |
| ATOM | 880 | C | LEU | A | 121 | 40.512 | −16.280 | 9.864 | 1.00 | 14.44 | A |
| ATOM | 881 | O | LEU | A | 121 | 39.446 | −16.911 | 9.887 | 1.00 | 14.00 | A |
| ATOM | 882 | N | ALA | A | 122 | 41.247 | −16.197 | 8.774 | 1.00 | 17.61 | A |
| ATOM | 883 | CA | ALA | A | 122 | 40.831 | −16.918 | 7.578 | 1.00 | 18.71 | A |
| ATOM | 884 | CB | ALA | A | 122 | 41.763 | −16.576 | 6.408 | 1.00 | 19.05 | A |
| ATOM | 885 | C | ALA | A | 122 | 40.772 | −18.433 | 7.805 | 1.00 | 19.32 | A |

APPENDIX 2-continued

X-RAY DATA COORDINATES FOR CDP-ME SYNTHASE
COMPLEXED WITH CTP•$Mg^{2+}$
(SEQ ID NO: 11)

| ATOM | 886 | O | ALA | A | 122 | 40.137 | −19.150 | 7.044 | 1.00 | 18.19 | A |
|---|---|---|---|---|---|---|---|---|---|---|---|
| ATOM | 887 | N | LEU | A | 123 | 41.423 | −18.931 | 8.863 | 1.00 | 17.64 | A |
| ATOM | 888 | CA | LEU | A | 123 | 41.402 | −20.356 | 9.146 | 1.00 | 17.24 | A |
| ATOM | 889 | CB | LEU | A | 123 | 42.220 | −20.688 | 10.390 | 1.00 | 18.69 | A |
| ATOM | 890 | CG | LEU | A | 123 | 43.737 | −20.593 | 10.212 | 1.00 | 17.82 | A |
| ATOM | 891 | CD1 | LEU | A | 123 | 44.389 | −20.942 | 11.551 | 1.00 | 20.65 | A |
| ATOM | 892 | CD2 | LEU | A | 123 | 44.227 | −21.539 | 9.099 | 1.00 | 19.95 | A |
| ATOM | 893 | C | LEU | A | 123 | 40.006 | −20.922 | 9.353 | 1.00 | 17.87 | A |
| ATOM | 894 | O | LEU | A | 123 | 39.770 | −22.116 | 9.105 | 1.00 | 20.15 | A |
| ATOM | 895 | N | SER | A | 124 | 39.064 | −20.092 | 9.793 | 1.00 | 16.28 | A |
| ATOM | 896 | CA | SER | A | 124 | 37.729 | −20.638 | 10.020 | 1.00 | 18.28 | A |
| ATOM | 897 | CB | SER | A | 124 | 36.874 | −19.633 | 10.797 | 1.00 | 16.16 | A |
| ATOM | 898 | OG | SER | A | 124 | 36.601 | −18.466 | 10.060 | 1.00 | 18.89 | A |
| ATOM | 899 | C | SER | A | 124 | 37.031 | −21.072 | 8.731 | 1.00 | 20.71 | A |
| ATOM | 900 | O | SER | A | 124 | 36.046 | −21.812 | 8.777 | 1.00 | 22.36 | A |
| ATOM | 901 | N | GLU | A | 125 | 37.545 | −20.628 | 7.590 | 1.00 | 23.42 | A |
| ATOM | 902 | CA | GLU | A | 125 | 36.937 | −20.984 | 6.314 | 1.00 | 27.79 | A |
| ATOM | 903 | CB | GLU | A | 125 | 36.971 | −19.768 | 5.372 | 1.00 | 31.02 | A |
| ATOM | 904 | CG | GLU | A | 125 | 35.635 | −19.042 | 5.164 | 1.00 | 36.90 | A |
| ATOM | 905 | CD | GLU | A | 125 | 34.712 | −19.047 | 6.388 | 1.00 | 39.97 | A |
| ATOM | 906 | OE1 | GLU | A | 125 | 35.121 | −18.643 | 7.512 | 1.00 | 39.39 | A |
| ATOM | 907 | OE2 | GLU | A | 125 | 33.547 | −19.461 | 6.216 | 1.00 | 41.50 | A |
| ATOM | 908 | C | GLU | A | 125 | 37.643 | −22.173 | 5.667 | 1.00 | 31.06 | A |
| ATOM | 909 | O | GLU | A | 125 | 37.181 | −22.709 | 4.651 | 1.00 | 32.43 | A |
| ATOM | 910 | N | THR | A | 126 | 38.748 | −22.607 | 6.263 | 1.00 | 31.62 | A |
| ATOM | 911 | CA | THR | A | 126 | 39.520 | −23.696 | 5.676 | 1.00 | 33.91 | A |
| ATOM | 912 | CB | THR | A | 126 | 40.740 | −23.140 | 4.958 | 1.00 | 35.03 | A |
| ATOM | 913 | OG1 | THR | A | 126 | 41.408 | −24.203 | 4.276 | 1.00 | 39.67 | A |
| ATOM | 914 | CG2 | THR | A | 126 | 41.712 | −22.516 | 5.971 | 1.00 | 34.52 | A |
| ATOM | 915 | C | THR | A | 126 | 40.027 | −24.764 | 6.637 | 1.00 | 33.01 | A |
| ATOM | 916 | O | THR | A | 126 | 40.761 | −25.658 | 6.218 | 1.00 | 35.04 | A |
| ATOM | 917 | N | SER | A | 127 | 39.649 | −24.675 | 7.911 | 1.00 | 30.59 | A |
| ATOM | 918 | CA | SER | A | 127 | 40.101 | −25.634 | 8.919 | 1.00 | 29.20 | A |
| ATOM | 919 | CB | SER | A | 127 | 41.304 | −25.058 | 9.681 | 1.00 | 30.71 | A |
| ATOM | 920 | OG | SER | A | 127 | 41.598 | −25.827 | 10.845 | 1.00 | 30.55 | A |
| ATOM | 921 | C | SER | A | 127 | 39.022 | −25.981 | 9.933 | 1.00 | 29.41 | A |
| ATOM | 922 | O | SER | A | 127 | 38.142 | −25.172 | 10.197 | 1.00 | 29.20 | A |
| ATOM | 923 | N | ARG | A | 128 | 39.086 | −27.182 | 10.499 | 1.00 | 29.24 | A |
| ATOM | 924 | CA | ARG | A | 128 | 38.131 | −27.562 | 11.530 | 1.00 | 30.11 | A |
| ATOM | 925 | CB | ARG | A | 128 | 37.421 | −28.879 | 11.211 | 1.00 | 33.02 | A |
| ATOM | 926 | CG | ARG | A | 128 | 36.149 | −28.704 | 10.402 | 1.00 | 35.30 | A |
| ATOM | 927 | CD | ARG | A | 128 | 35.557 | −30.049 | 10.047 | 1.00 | 37.21 | A |
| ATOM | 928 | NE | ARG | A | 128 | 34.675 | −29.961 | 8.894 | 1.00 | 37.57 | A |
| ATOM | 929 | CZ | ARG | A | 128 | 33.470 | −29.404 | 8.912 | 1.00 | 37.49 | A |
| ATOM | 930 | NH1 | ARG | A | 128 | 33.001 | −28.879 | 10.039 | 1.00 | 36.16 | A |
| ATOM | 931 | NH2 | ARG | A | 128 | 32.727 | −29.388 | 7.806 | 1.00 | 36.56 | A |
| ATOM | 932 | C | ARG | A | 128 | 38.872 | −27.700 | 12.837 | 1.00 | 29.93 | A |
| ATOM | 933 | O | ARG | A | 128 | 38.287 | −28.050 | 13.861 | 1.00 | 30.50 | A |
| ATOM | 934 | N | THR | A | 129 | 40.175 | −27.426 | 12.805 | 1.00 | 28.24 | A |
| ATOM | 935 | CA | THR | A | 129 | 40.988 | −27.527 | 14.013 | 1.00 | 27.39 | A |
| ATOM | 936 | CB | THR | A | 129 | 42.241 | −28.414 | 13.777 | 1.00 | 29.11 | A |
| ATOM | 937 | OG1 | THR | A | 129 | 41.816 | −29.723 | 13.375 | 1.00 | 31.63 | A |
| ATOM | 938 | CG2 | THR | A | 129 | 43.077 | −28.531 | 15.059 | 1.00 | 30.87 | A |
| ATOM | 939 | C | THR | A | 129 | 41.438 | −26.153 | 14.484 | 1.00 | 25.89 | A |
| ATOM | 940 | O | THR | A | 129 | 41.483 | −25.896 | 15.670 | 1.00 | 26.66 | A |
| ATOM | 941 | N | GLY | A | 130 | 41.748 | −25.269 | 13.549 | 1.00 | 21.52 | A |
| ATOM | 942 | CA | GLY | A | 130 | 42.215 | −23.960 | 13.952 | 1.00 | 20.18 | A |
| ATOM | 943 | C | GLY | A | 130 | 43.721 | −23.865 | 13.820 | 1.00 | 17.98 | A |
| ATOM | 944 | O | GLY | A | 130 | 44.350 | −24.687 | 13.153 | 1.00 | 20.03 | A |
| ATOM | 945 | N | GLY | A | 131 | 44.303 | −22.852 | 14.450 | 1.00 | 15.56 | A |
| ATOM | 946 | CA | GLY | A | 131 | 45.743 | −22.682 | 14.363 | 1.00 | 14.28 | A |
| ATOM | 947 | C | GLY | A | 131 | 46.252 | −21.488 | 15.150 | 1.00 | 14.43 | A |
| ATOM | 948 | O | GLY | A | 131 | 45.526 | −20.889 | 15.917 | 1.00 | 14.30 | A |
| ATOM | 949 | N | ILE | A | 132 | 47.512 | −21.136 | 14.919 | 1.00 | 14.15 | A |
| ATOM | 950 | CA | ILE | A | 132 | 48.178 | −20.068 | 15.653 | 1.00 | 15.03 | A |
| ATOM | 951 | CB | ILE | A | 132 | 49.083 | −20.648 | 16.791 | 1.00 | 15.19 | A |
| ATOM | 952 | CG2 | ILE | A | 132 | 48.251 | −21.573 | 17.675 | 1.00 | 16.70 | A |
| ATOM | 953 | CG1 | ILE | A | 132 | 50.275 | −21.412 | 16.215 | 1.00 | 14.76 | A |
| ATOM | 954 | CD1 | ILE | A | 132 | 51.306 | −21.832 | 17.277 | 1.00 | 16.71 | A |
| ATOM | 955 | C | ILE | A | 132 | 49.102 | −19.249 | 14.779 | 1.00 | 14.47 | A |
| ATOM | 956 | O | ILE | A | 132 | 49.509 | −19.694 | 13.693 | 1.00 | 14.56 | A |
| ATOM | 957 | N | LEU | A | 133 | 49.401 | −18.029 | 15.231 | 1.00 | 13.78 | A |
| ATOM | 958 | CA | LEU | A | 133 | 50.409 | −17.229 | 14.540 | 1.00 | 13.97 | A |
| ATOM | 959 | CB | LEU | A | 133 | 50.306 | −15.748 | 14.917 | 1.00 | 15.26 | A |
| ATOM | 960 | CG | LEU | A | 133 | 49.157 | −14.976 | 14.267 | 1.00 | 16.40 | A |

APPENDIX 2-continued

X-RAY DATA COORDINATES FOR CDP-ME SYNTHASE
COMPLEXED WITH CTP·Mg$^{2+}$
(SEQ ID NO: 11)

| ATOM | 961 | CD1 | LEU | A | 133 | 49.173 | −13.543 | 14.788 | 1.00 | 17.99 | A |
|---|---|---|---|---|---|---|---|---|---|---|---|
| ATOM | 962 | CD2 | LEU | A | 133 | 49.319 | −15.013 | 12.747 | 1.00 | 19.04 | A |
| ATOM | 963 | C | LEU | A | 133 | 51.723 | −17.812 | 15.084 | 1.00 | 15.68 | A |
| ATOM | 964 | O | LEU | A | 133 | 51.838 | −18.153 | 16.274 | 1.00 | 13.89 | A |
| ATOM | 965 | N | ALA | A | 134 | 52.702 | −17.894 | 14.205 | 1.00 | 14.52 | A |
| ATOM | 966 | CA | ALA | A | 134 | 53.999 | −18.432 | 14.575 | 1.00 | 14.76 | A |
| ATOM | 967 | CB | ALA | A | 134 | 53.989 | −19.952 | 14.437 | 1.00 | 14.84 | A |
| ATOM | 968 | C | ALA | A | 134 | 55.074 | −17.828 | 13.691 | 1.00 | 16.49 | A |
| ATOM | 969 | O | ALA | A | 134 | 54.796 | −17.424 | 12.551 | 1.00 | 17.53 | A |
| ATOM | 970 | N | ALA | A | 135 | 56.302 | −17.726 | 14.207 | 1.00 | 16.59 | A |
| ATOM | 971 | CA | ALA | A | 135 | 57.391 | −17.164 | 13.407 | 1.00 | 18.51 | A |
| ATOM | 972 | CB | ALA | A | 135 | 57.960 | −15.927 | 14.084 | 1.00 | 18.92 | A |
| ATOM | 973 | C | ALA | A | 135 | 58.447 | −18.241 | 13.262 | 1.00 | 18.74 | A |
| ATOM | 974 | O | ALA | A | 135 | 58.768 | −18.942 | 14.231 | 1.00 | 17.60 | A |
| ATOM | 975 | N | PRO | A | 136 | 58.986 | −18.401 | 12.043 | 1.00 | 21.29 | A |
| ATOM | 976 | CD | PRO | A | 136 | 58.640 | −17.711 | 10.791 | 1.00 | 22.92 | A |
| ATOM | 977 | CA | PRO | A | 136 | 60.004 | −19.421 | 11.814 | 1.00 | 21.33 | A |
| ATOM | 978 | CB | PRO | A | 136 | 60.267 | −19.336 | 10.311 | 1.00 | 22.92 | A |
| ATOM | 979 | CG | PRO | A | 136 | 59.053 | −18.736 | 9.747 | 1.00 | 25.51 | A |
| ATOM | 980 | C | PRO | A | 136 | 61.272 | −19.172 | 12.605 | 1.00 | 21.46 | A |
| ATOM | 981 | O | PRO | A | 136 | 61.688 | −18.033 | 12.815 | 1.00 | 22.13 | A |
| ATOM | 982 | N | VAL | A | 137 | 61.911 | −20.244 | 13.035 | 1.00 | 22.32 | A |
| ATOM | 983 | CA | VAL | A | 137 | 63.164 | −20.091 | 13.752 | 1.00 | 24.03 | A |
| ATOM | 984 | CB | VAL | A | 137 | 63.581 | −21.399 | 14.401 | 1.00 | 24.30 | A |
| ATOM | 985 | CG1 | VAL | A | 137 | 65.031 | −21.284 | 14.890 | 1.00 | 24.89 | A |
| ATOM | 986 | CG2 | VAL | A | 137 | 62.657 | −21.694 | 15.574 | 1.00 | 23.94 | A |
| ATOM | 987 | C | VAL | A | 137 | 64.250 | −19.654 | 12.779 | 1.00 | 24.59 | A |
| ATOM | 988 | O | VAL | A | 137 | 64.377 | −20.211 | 11.685 | 1.00 | 24.89 | A |
| ATOM | 989 | N | ARG | A | 138 | 65.025 | −18.651 | 13.188 | 1.00 | 26.49 | A |
| ATOM | 990 | CA | ARG | A | 138 | 66.116 | −18.117 | 12.377 | 1.00 | 28.95 | A |
| ATOM | 991 | CB | ARG | A | 138 | 66.065 | −16.584 | 12.356 | 1.00 | 31.56 | A |
| ATOM | 992 | CG | ARG | A | 138 | 64.767 | −15.997 | 11.824 | 1.00 | 33.59 | A |
| ATOM | 993 | CD | ARG | A | 138 | 64.388 | −16.611 | 10.483 | 1.00 | 36.03 | A |
| ATOM | 994 | NE | ARG | A | 138 | 63.269 | −15.910 | 9.847 | 1.00 | 39.10 | A |
| ATOM | 995 | CZ | ARG | A | 138 | 62.707 | −16.293 | 8.704 | 1.00 | 39.60 | A |
| ATOM | 996 | NH1 | ARG | A | 138 | 63.155 | −17.376 | 8.079 | 1.00 | 40.83 | A |
| ATOM | 997 | NH2 | ARG | A | 138 | 61.712 | −15.590 | 8.176 | 1.00 | 39.74 | A |
| ATOM | 998 | C | ARG | A | 138 | 67.500 | −18.549 | 12.879 | 1.00 | 28.27 | A |
| ATOM | 999 | O | ARG | A | 138 | 68.356 | −18.904 | 12.087 | 1.00 | 30.47 | A |
| ATOM | 1000 | N | ASP | A | 139 | 67.735 | −18.516 | 14.186 | 1.00 | 28.91 | A |
| ATOM | 1001 | CA | ASP | A | 139 | 69.057 | −18.894 | 14.694 | 1.00 | 27.49 | A |
| ATOM | 1002 | CB | ASP | A | 139 | 69.236 | −18.414 | 16.142 | 1.00 | 31.28 | A |
| ATOM | 1003 | CG | ASP | A | 139 | 69.529 | −16.918 | 16.243 | 1.00 | 35.12 | A |
| ATOM | 1004 | OD1 | ASP | A | 139 | 70.384 | −16.421 | 15.479 | 1.00 | 35.84 | A |
| ATOM | 1005 | OD2 | ASP | A | 139 | 68.921 | −16.253 | 17.108 | 1.00 | 36.04 | A |
| ATOM | 1006 | C | ASP | A | 139 | 69.343 | −20.400 | 14.663 | 1.00 | 24.95 | A |
| ATOM | 1007 | O | ASP | A | 139 | 68.430 | −21.219 | 14.640 | 1.00 | 24.43 | A |
| ATOM | 1008 | N | THR | A | 140 | 70.618 | −20.763 | 14.648 | 1.00 | 22.15 | A |
| ATOM | 1009 | CA | THR | A | 140 | 70.996 | −22.156 | 14.744 | 1.00 | 21.63 | A |
| ATOM | 1010 | CB | THR | A | 140 | 72.501 | −22.329 | 14.454 | 1.00 | 19.03 | A |
| ATOM | 1011 | OG1 | THR | A | 140 | 72.722 | −22.157 | 13.042 | 1.00 | 22.95 | A |
| ATOM | 1012 | CG2 | THR | A | 140 | 72.974 | −23.697 | 14.882 | 1.00 | 21.28 | A |
| ATOM | 1013 | C | THR | A | 140 | 70.652 | −22.461 | 16.209 | 1.00 | 20.48 | A |
| ATOM | 1014 | O | THR | A | 140 | 70.922 | −21.651 | 17.089 | 1.00 | 22.89 | A |
| ATOM | 1015 | N | MET | A | 141 | 70.004 | −23.588 | 16.474 | 1.00 | 20.63 | A |
| ATOM | 1016 | CA | MET | A | 141 | 69.619 | −23.944 | 17.830 | 1.00 | 18.91 | A |
| ATOM | 1017 | CB | MET | A | 141 | 68.129 | −24.298 | 17.882 | 1.00 | 21.88 | A |
| ATOM | 1018 | CG | MET | A | 141 | 67.232 | −23.284 | 17.243 | 1.00 | 22.65 | A |
| ATOM | 1019 | SD | MET | A | 141 | 67.311 | −21.705 | 18.151 | 1.00 | 19.81 | A |
| ATOM | 1020 | CE | MET | A | 141 | 65.446 | −21.341 | 18.409 | 1.00 | 29.38 | A |
| ATOM | 1021 | C | MET | A | 141 | 70.422 | −25.104 | 18.373 | 1.00 | 20.58 | A |
| ATOM | 1022 | O | MET | A | 141 | 70.755 | −26.046 | 17.639 | 1.00 | 20.90 | A |
| ATOM | 1023 | N | LYS | A | 142 | 70.751 | −25.013 | 19.658 | 1.00 | 18.27 | A |
| ATOM | 1024 | CA | LYS | A | 142 | 71.527 | −26.043 | 20.334 | 1.00 | 19.93 | A |
| ATOM | 1025 | CB | LYS | A | 142 | 72.808 | −25.459 | 20.954 | 1.00 | 19.53 | A |
| ATOM | 1026 | CG | LYS | A | 142 | 73.695 | −24.690 | 19.993 | 1.00 | 17.98 | A |
| ATOM | 1027 | CD | LYS | A | 142 | 74.232 | −25.573 | 18.867 | 1.00 | 18.48 | A |
| ATOM | 1028 | CE | LYS | A | 142 | 75.202 | −24.816 | 17.988 | 1.00 | 17.34 | A |
| ATOM | 1029 | NZ | LYS | A | 142 | 75.826 | −25.675 | 16.952 | 1.00 | 19.58 | A |
| ATOM | 1030 | C | LYS | A | 142 | 70.737 | −26.656 | 21.472 | 1.00 | 21.18 | A |
| ATOM | 1031 | O | LYS | A | 142 | 70.035 | −25.963 | 22.200 | 1.00 | 21.57 | A |
| ATOM | 1032 | N | ARG | A | 143 | 70.867 | −27.964 | 21.615 | 1.00 | 22.95 | A |
| ATOM | 1033 | CA | ARG | A | 143 | 70.251 | −28.677 | 22.715 | 1.00 | 23.82 | A |
| ATOM | 1034 | CB | ARG | A | 143 | 69.668 | −30.005 | 22.230 | 1.00 | 26.85 | A |
| ATOM | 1035 | CG | ARG | A | 143 | 69.123 | −30.906 | 23.330 | 1.00 | 29.45 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1036 | CD | ARG | A | 143 | 67.619 | −30.956 | 23.259 | 1.00 | 33.88 | A |
|---|---|---|---|---|---|---|---|---|---|---|---|
| ATOM | 1037 | NE | ARG | A | 143 | 67.006 | −30.009 | 24.166 | 1.00 | 35.29 | A |
| ATOM | 1038 | CZ | ARG | A | 143 | 65.802 | −29.468 | 23.990 | 1.00 | 31.12 | A |
| ATOM | 1039 | NH1 | ARG | A | 143 | 65.054 | −29.764 | 22.928 | 1.00 | 30.99 | A |
| ATOM | 1040 | NH2 | ARG | A | 143 | 65.351 | −28.628 | 24.891 | 1.00 | 32.03 | A |
| ATOM | 1041 | C | ARG | A | 143 | 71.402 | −28.929 | 23.677 | 1.00 | 24.39 | A |
| ATOM | 1042 | O | ARG | A | 143 | 72.472 | −29.391 | 23.258 | 1.00 | 24.74 | A |
| ATOM | 1043 | N | ALA | A | 144 | 71.191 | −28.623 | 24.954 | 1.00 | 24.49 | A |
| ATOM | 1044 | CA | ALA | A | 144 | 72.222 | −28.802 | 25.972 | 1.00 | 26.27 | A |
| ATOM | 1045 | CB | ALA | A | 144 | 72.018 | −27.806 | 27.102 | 1.00 | 26.21 | A |
| ATOM | 1046 | C | ALA | A | 144 | 72.159 | −30.198 | 26.533 | 1.00 | 28.36 | A |
| ATOM | 1047 | O | ALA | A | 144 | 71.119 | −30.855 | 26.467 | 1.00 | 28.32 | A |
| ATOM | 1048 | N | GLU | A | 145 | 73.279 | −30.656 | 27.082 | 1.00 | 29.88 | A |
| ATOM | 1049 | CA | GLU | A | 145 | 73.302 | −31.965 | 27.702 | 1.00 | 32.20 | A |
| ATOM | 1050 | CB | GLU | A | 145 | 74.735 | −32.436 | 27.944 | 1.00 | 33.38 | A |
| ATOM | 1051 | CG | GLU | A | 145 | 75.478 | −32.686 | 26.656 | 1.00 | 36.34 | A |
| ATOM | 1052 | CD | GLU | A | 145 | 76.847 | −33.293 | 26.860 | 1.00 | 40.24 | A |
| ATOM | 1053 | OE1 | GLU | A | 145 | 77.616 | −32.784 | 27.701 | 1.00 | 41.95 | A |
| ATOM | 1054 | OE2 | GLU | A | 145 | 77.162 | −34.278 | 26.165 | 1.00 | 42.63 | A |
| ATOM | 1055 | C | GLU | A | 145 | 72.566 | −31.811 | 29.021 | 1.00 | 32.59 | A |
| ATOM | 1056 | O | GLU | A | 145 | 72.650 | −30.773 | 29.679 | 1.00 | 31.56 | A |
| ATOM | 1057 | N | PRO | A | 146 | 71.807 | −32.840 | 29.412 | 1.00 | 33.23 | A |
| ATOM | 1058 | CD | PRO | A | 146 | 71.654 | −34.112 | 28.686 | 1.00 | 34.06 | A |
| ATOM | 1059 | CA | PRO | A | 146 | 71.033 | −32.843 | 30.653 | 1.00 | 34.96 | A |
| ATOM | 1060 | CB | PRO | A | 146 | 70.656 | −34.317 | 30.812 | 1.00 | 34.85 | A |
| ATOM | 1061 | CG | PRO | A | 146 | 70.481 | −34.761 | 29.402 | 1.00 | 34.53 | A |
| ATOM | 1062 | C | PRO | A | 146 | 71.768 | −32.288 | 31.877 | 1.00 | 35.35 | A |
| ATOM | 1063 | O | PRO | A | 146 | 72.800 | −32.813 | 32.288 | 1.00 | 37.03 | A |
| ATOM | 1064 | N | GLY | A | 147 | 71.225 | −31.212 | 32.435 | 1.00 | 36.02 | A |
| ATOM | 1065 | CA | GLY | A | 147 | 71.790 | −30.598 | 33.622 | 1.00 | 36.61 | A |
| ATOM | 1066 | C | GLY | A | 147 | 73.090 | −29.831 | 33.491 | 1.00 | 37.30 | A |
| ATOM | 1067 | O | GLY | A | 147 | 73.556 | −29.257 | 34.475 | 1.00 | 38.20 | A |
| ATOM | 1068 | N | LYS | A | 148 | 73.674 | −29.803 | 32.296 | 1.00 | 35.74 | A |
| ATOM | 1069 | CA | LYS | A | 148 | 74.933 | −29.097 | 32.087 | 1.00 | 36.67 | A |
| ATOM | 1070 | CB | LYS | A | 148 | 76.045 | −30.096 | 31.782 | 1.00 | 37.18 | A |
| ATOM | 1071 | CG | LYS | A | 148 | 76.436 | −30.936 | 32.977 | 1.00 | 40.35 | A |
| ATOM | 1072 | CD | LYS | A | 148 | 77.755 | −31.654 | 32.751 | 1.00 | 41.13 | A |
| ATOM | 1073 | CE | LYS | A | 148 | 78.857 | −30.708 | 32.253 | 1.00 | 43.39 | A |
| ATOM | 1074 | NZ | LYS | A | 148 | 78.878 | −30.575 | 30.757 | 1.00 | 44.66 | A |
| ATOM | 1075 | C | LYS | A | 148 | 74.856 | −28.082 | 30.961 | 1.00 | 35.85 | A |
| ATOM | 1076 | O | LYS | A | 148 | 74.061 | −28.236 | 30.037 | 1.00 | 36.15 | A |
| ATOM | 1077 | N | ASN | A | 149 | 75.696 | −27.051 | 31.029 | 1.00 | 35.99 | A |
| ATOM | 1078 | CA | ASN | A | 149 | 75.702 | −26.029 | 29.985 | 1.00 | 34.60 | A |
| ATOM | 1079 | CB | ASN | A | 149 | 75.993 | −24.652 | 30.601 | 1.00 | 36.41 | A |
| ATOM | 1080 | CG | ASN | A | 149 | 74.795 | −24.094 | 31.375 | 1.00 | 38.46 | A |
| ATOM | 1081 | OD1 | ASN | A | 149 | 74.941 | −23.572 | 32.479 | 1.00 | 40.11 | A |
| ATOM | 1082 | ND2 | ASN | A | 149 | 73.601 | −24.201 | 30.785 | 1.00 | 37.85 | A |
| ATOM | 1083 | C | ASN | A | 149 | 76.694 | −26.352 | 28.869 | 1.00 | 32.98 | A |
| ATOM | 1084 | O | ASN | A | 149 | 77.489 | −25.512 | 28.466 | 1.00 | 32.18 | A |
| ATOM | 1085 | N | ALA | A | 150 | 76.636 | −27.586 | 28.383 | 1.00 | 32.00 | A |
| ATOM | 1086 | CA | ALA | A | 150 | 77.488 | −28.053 | 27.298 | 1.00 | 29.93 | A |
| ATOM | 1087 | CB | ALA | A | 150 | 78.337 | −29.211 | 27.763 | 1.00 | 31.12 | A |
| ATOM | 1088 | C | ALA | A | 150 | 76.559 | −28.506 | 26.176 | 1.00 | 28.65 | A |
| ATOM | 1089 | O | ALA | A | 150 | 75.491 | −29.056 | 26.438 | 1.00 | 26.31 | A |
| ATOM | 1090 | N | ILE | A | 151 | 76.949 | −28.261 | 24.929 | 1.00 | 25.44 | A |
| ATOM | 1091 | CA | ILE | A | 151 | 76.125 | −28.649 | 23.790 | 1.00 | 24.98 | A |
| ATOM | 1092 | CB | ILE | A | 151 | 76.640 | −28.000 | 22.492 | 1.00 | 24.68 | A |
| ATOM | 1093 | CG2 | ILE | A | 151 | 75.865 | −28.536 | 21.300 | 1.00 | 24.20 | A |
| ATOM | 1094 | CG1 | ILE | A | 151 | 76.486 | −26.481 | 22.582 | 1.00 | 25.06 | A |
| ATOM | 1095 | CD1 | ILE | A | 151 | 77.161 | −25.721 | 21.433 | 1.00 | 24.42 | A |
| ATOM | 1096 | C | ILE | A | 151 | 76.064 | −30.150 | 23.548 | 1.00 | 25.48 | A |
| ATOM | 1097 | O | ILE | A | 151 | 77.092 | −30.795 | 23.426 | 1.00 | 23.92 | A |
| ATOM | 1098 | N | ALA | A | 152 | 74.857 | −30.704 | 23.481 | 1.00 | 24.21 | A |
| ATOM | 1099 | CA | ALA | A | 152 | 74.689 | −32.120 | 23.181 | 1.00 | 26.01 | A |
| ATOM | 1100 | CB | ALA | A | 152 | 73.347 | −32.611 | 23.687 | 1.00 | 26.00 | A |
| ATOM | 1101 | C | ALA | A | 152 | 74.740 | −32.228 | 21.665 | 1.00 | 25.71 | A |
| ATOM | 1102 | O | ALA | A | 152 | 75.495 | −33.014 | 21.112 | 1.00 | 26.57 | A |
| ATOM | 1103 | N | HIS | A | 153 | 73.922 | −31.433 | 20.983 | 1.00 | 25.10 | A |
| ATOM | 1104 | CA | HIS | A | I53 | 73.907 | −31.445 | 19.527 | 1.00 | 24.64 | A |
| ATOM | 1105 | CB | HIS | A | 153 | 73.260 | −32.737 | 19.001 | 1.00 | 26.68 | A |
| ATOM | 1106 | CG | HIS | A | 153 | 71.838 | −32.907 | 19.433 | 1.00 | 28.74 | A |
| ATOM | 1107 | CD2 | HIS | A | 153 | 70.686 | −32.425 | 18.909 | 1.00 | 30.39 | A |
| ATOM | 1108 | ND1 | HIS | A | 153 | 71.482 | −33.586 | 20.580 | 1.00 | 30.13 | A |
| ATOM | 1109 | CE1 | HIS | A | 153 | 70.172 | −33.510 | 20.744 | 1.00 | 31.06 | A |
| ATOM | 1110 | NE2 | HIS | A | 153 | 69.666 | −32.809 | 19.744 | 1.00 | 30.80 | A |

APPENDIX 2-continued

X-RAY DATA COORDINATES FOR CDP-ME SYNTHASE
COMPLEXED WITH CTP·Mg$^{2+}$
(SEQ ID NO: 11)

| ATOM | 1111 | C   | HIS | A | 153 | 73.101 | −30.249 | 19.036 | 1.00 | 22.38 | A |
| ATOM | 1112 | O   | HIS | A | 153 | 72.482 | −29.545 | 19.830 | 1.00 | 23.29 | A |
| ATOM | 1113 | N   | THR | A | 154 | 73.143 | −30.016 | 17.736 | 1.00 | 21.21 | A |
| ATOM | 1114 | CA  | THR | A | 154 | 72.397 | −28.928 | 17.118 | 1.00 | 23.03 | A |
| ATOM | 1115 | CB  | THR | A | 154 | 73.072 | −28.459 | 15.821 | 1.00 | 24.28 | A |
| ATOM | 1116 | OG1 | THR | A | 154 | 74.327 | −27.844 | 16.139 | 1.00 | 23.30 | A |
| ATOM | 1117 | CG2 | THR | A | 154 | 72.219 | −27.446 | 15.096 | 1.00 | 24.75 | A |
| ATOM | 1118 | C   | THR | A | 154 | 71.011 | −29.465 | 16.781 | 1.00 | 24.02 | A |
| ATOM | 1119 | O   | THR | A | 154 | 70.881 | −30.589 | 16.296 | 1.00 | 25.55 | A |
| ATOM | 1120 | N   | VAL | A | 155 | 69.983 | −28.668 | 17.050 | 1.00 | 22.12 | A |
| ATOM | 1121 | CA  | VAL | A | 155 | 68.601 | −29.062 | 16.752 | 1.00 | 24.49 | A |
| ATOM | 1122 | CB  | VAL | A | 155 | 67.642 | −28.516 | 17.853 | 1.00 | 24.92 | A |
| ATOM | 1123 | CG1 | VAL | A | 155 | 66.177 | −28.780 | 17.472 | 1.00 | 25.18 | A |
| ATOM | 1124 | CG2 | VAL | A | 155 | 67.950 | −29.189 | 19.186 | 1.00 | 25.03 | A |
| ATOM | 1125 | C   | VAL | A | 155 | 68.210 | −28.488 | 15.380 | 1.00 | 25.30 | A |
| ATOM | 1126 | O   | VAL | A | 155 | 68.313 | −27.288 | 15.167 | 1.00 | 26.20 | A |
| ATOM | 1127 | N   | ASP | A | 156 | 67.773 | −29.350 | 14.459 | 1.00 | 25.66 | A |
| ATOM | 1128 | CA  | ASP | A | 156 | 67.375 | −28.931 | 13.110 | 1.00 | 27.01 | A |
| ATOM | 1129 | CB  | ASP | A | 156 | 66.771 | −30.112 | 12.344 | 1.00 | 29.76 | A |
| ATOM | 1130 | CG  | ASP | A | 156 | 66.616 | −29.840 | 10.844 | 1.00 | 33.42 | A |
| ATOM | 1131 | OD1 | ASP | A | 156 | 66.601 | −28.671 | 10.415 | 1.00 | 33.74 | A |
| ATOM | 1132 | OD2 | ASP | A | 156 | 66.503 | −30.822 | 10.091 | 1.00 | 37.18 | A |
| ATOM | 1133 | C   | ASP | A | 156 | 66.312 | −27.848 | 13.237 | 1.00 | 26.63 | A |
| ATOM | 1134 | O   | ASP | A | 156 | 65.240 | −28.107 | 13.794 | 1.00 | 24.84 | A |
| ATOM | 1135 | N   | ARG | A | 157 | 66.587 | −26.655 | 12.716 | 1.00 | 26.74 | A |
| ATOM | 1136 | CA  | ARG | A | 157 | 65.615 | −25.569 | 12.805 | 1.00 | 28.26 | A |
| ATOM | 1137 | CB  | ARG | A | 157 | 66.326 | −24.214 | 12.857 | 1.00 | 29.24 | A |
| ATOM | 1138 | CG  | ARG | A | 157 | 66.907 | −23.721 | 11.541 | 1.00 | 31.76 | A |
| ATOM | 1139 | CD  | ARG | A | 157 | 67.639 | −22.400 | 11.754 | 1.00 | 33.25 | A |
| ATOM | 1140 | NE  | ARG | A | 157 | 68.343 | −21.955 | 10.562 | 1.00 | 33.91 | A |
| ATOM | 1141 | CZ  | ARG | A | 157 | 67.753 | −21.491 |  9.467 | 1.00 | 37.71 | A |
| ATOM | 1142 | NH1 | ARG | A | 157 | 66.426 | −21.399 |  9.408 | 1.00 | 37.76 | A |
| ATOM | 1143 | NH2 | ARG | A | 157 | 68.491 | −21.138 |  8.417 | 1.00 | 38.65 | A |
| ATOM | 1144 | C   | ARG | A | 157 | 64.606 | −25.576 | 11.665 | 1.00 | 29.90 | A |
| ATOM | 1145 | O   | ARG | A | 157 | 63.664 | −24.775 | 11.658 | 1.00 | 27.95 | A |
| ATOM | 1146 | N   | ASN | A | 158 | 64.796 | −26.475 | 10.710 | 1.00 | 29.32 | A |
| ATOM | 1147 | CA  | ASN | A | 158 | 63.889 | −26.594 |  9.578 | 1.00 | 31.14 | A |
| ATOM | 1148 | CB  | ASN | A | 158 | 64.519 | −27.513 |  8.535 | 1.00 | 35.18 | A |
| ATOM | 1149 | CG  | ASN | A | 158 | 63.591 | −27.829 |  7.399 | 1.00 | 38.59 | A |
| ATOM | 1150 | OD1 | ASN | A | 158 | 63.145 | −26.936 |  6.669 | 1.00 | 41.93 | A |
| ATOM | 1151 | ND2 | ASN | A | 158 | 63.284 | −29.111 |  7.236 | 1.00 | 40.45 | A |
| ATOM | 1152 | C   | ASN | A | 158 | 62.559 | −27.159 | 10.090 | 1.00 | 29.06 | A |
| ATOM | 1153 | O   | ASN | A | 158 | 62.509 | −28.257 | 10.645 | 1.00 | 28.91 | A |
| ATOM | 1154 | N   | GLY | A | 159 | 61.485 | −26.393 |  9.915 | 1.00 | 26.63 | A |
| ATOM | 1155 | CA  | GLY | A | 159 | 60.183 | −26.827 | 10.389 | 1.00 | 25.19 | A |
| ATOM | 1156 | C   | GLY | A | 159 | 59.989 | −26.516 | 11.872 | 1.00 | 23.97 | A |
| ATOM | 1157 | O   | GLY | A | 159 | 59.081 | −27.042 | 12.509 | 1.00 | 24.61 | A |
| ATOM | 1158 | N   | LEU | A | 160 | 60.840 | −25.662 | 12.426 | 1.00 | 22.10 | A |
| ATOM | 1159 | CA  | LEU | A | 160 | 60.737 | −25.305 | 13.833 | 1.00 | 21.20 | A |
| ATOM | 1160 | CB  | LEU | A | 160 | 62.111 | −25.392 | 14.484 | 1.00 | 20.15 | A |
| ATOM | 1161 | CG  | LEU | A | 160 | 62.133 | −25.249 | 15.999 | 1.00 | 20.47 | A |
| ATOM | 1162 | CD1 | LEU | A | 160 | 61.452 | −26.478 | 16.659 | 1.00 | 19.89 | A |
| ATOM | 1163 | CD2 | LEU | A | 160 | 63.591 | −25.126 | 16.429 | 1.00 | 21.08 | A |
| ATOM | 1164 | C   | LEU | A | 160 | 60.190 | −23.888 | 13.899 | 1.00 | 20.97 | A |
| ATOM | 1165 | O   | LEU | A | 160 | 60.650 | −23.000 | 13.177 | 1.00 | 19.28 | A |
| ATOM | 1166 | N   | TRP | A | 161 | 59.225 | −23.662 | 14.792 | 1.00 | 18.62 | A |
| ATOM | 1167 | CA  | TRP | A | 161 | 58.561 | −22.362 | 14.883 | 1.00 | 17.91 | A |
| ATOM | 1168 | CB  | TRP | A | 161 | 57.146 | −22.480 | 14.287 | 1.00 | 18.07 | A |
| ATOM | 1169 | CG  | TRP | A | 161 | 57.050 | −22.821 | 12.823 | 1.00 | 20.11 | A |
| ATOM | 1170 | CD2 | TRP | A | 161 | 56.663 | −21.938 | 11.763 | 1.00 | 20.69 | A |
| ATOM | 1171 | CE2 | TRP | A | 161 | 56.702 | −22.686 | 10.565 | 1.00 | 21.93 | A |
| ATOM | 1172 | CE3 | TRP | A | 161 | 56.283 | −20.584 | 11.713 | 1.00 | 22.55 | A |
| ATOM | 1173 | CD1 | TRP | A | 161 | 57.305 | −24.036 | 12.237 | 1.00 | 19.91 | A |
| ATOM | 1174 | NE1 | TRP | A | 161 | 57.098 | −23.958 | 10.889 | 1.00 | 22.38 | A |
| ATOM | 1175 | CZ2 | TRP | A | 161 | 56.374 | −22.127 |  9.320 | 1.00 | 24.31 | A |
| ATOM | 1176 | CZ3 | TRP | A | 161 | 55.961 | −20.029 | 10.484 | 1.00 | 23.64 | A |
| ATOM | 1177 | CH2 | TRP | A | 161 | 56.006 | −20.801 |  9.300 | 1.00 | 26.06 | A |
| ATOM | 1178 | C   | TRP | A | 161 | 58.397 | −21.826 | 16.306 | 1.00 | 16.59 | A |
| ATOM | 1179 | O   | TRP | A | 161 | 58.209 | −22.598 | 17.250 | 1.00 | 16.89 | A |
| ATOM | 1180 | N   | HIS | A | 162 | 58.462 | −20.499 | 16.436 | 1.00 | 17.09 | A |
| ATOM | 1181 | CA  | HIS | A | 162 | 58.188 | −19.829 | 17.710 | 1.00 | 16.99 | A |
| ATOM | 1182 | CB  | HIS | A | 162 | 58.743 | −18.399 | 17.715 | 1.00 | 18.89 | A |
| ATOM | 1183 | CG  | HIS | A | 162 | 60.225 | −18.295 | 17.846 | 1.00 | 22.18 | A |
| ATOM | 1184 | CD2 | HIS | A | 162 | 60.996 | −18.063 | 18.932 | 1.00 | 21.07 | A |
| ATOM | 1185 | ND1 | HIS | A | 162 | 61.081 | −18.334 | 16.764 | 1.00 | 25.27 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1186 | CE1 | HIS | A | 162 | 62.317 | −18.125 | 17.182 | 1.00 | 21.66 | A |
|---|---|---|---|---|---|---|---|---|---|---|---|
| ATOM | 1187 | NE2 | HIS | A | 162 | 62.292 | −17.956 | 18.494 | 1.00 | 25.42 | A |
| ATOM | 1188 | C | HIS | A | 162 | 56.644 | −19.669 | 17.765 | 1.00 | 17.23 | A |
| ATOM | 1189 | O | HIS | A | 162 | 56.086 | −19.053 | 16.873 | 1.00 | 17.47 | A |
| ATOM | 1190 | N | ALA | A | 163 | 55.978 | −20.225 | 18.767 | 1.00 | 15.41 | A |
| ATOM | 1191 | CA | ALA | A | 163 | 54.533 | −20.082 | 18.901 | 1.00 | 15.78 | A |
| ATOM | 1192 | CB | ALA | A | 163 | 54.004 | −21.105 | 19.880 | 1.00 | 16.71 | A |
| ATOM | 1193 | C | ALA | A | 163 | 54.231 | −18.681 | 19.402 | 1.00 | 17.87 | A |
| ATOM | 1194 | O | ALA | A | 163 | 54.854 | −18.202 | 20.356 | 1.00 | 19.80 | A |
| ATOM | 1195 | N | LEU | A | 164 | 53.297 | −17.990 | 18.749 | 1.00 | 14.59 | A |
| ATOM | 1196 | CA | LEU | A | 164 | 52.924 | −16.627 | 19.202 | 1.00 | 15.17 | A |
| ATOM | 1197 | CB | LEU | A | 164 | 53.180 | −15.612 | 18.086 | 1.00 | 15.44 | A |
| ATOM | 1198 | CG | LEU | A | 164 | 54.604 | −15.645 | 17.485 | 1.00 | 17.07 | A |
| ATOM | 1199 | CD1 | LEU | A | 164 | 54.675 | −14.727 | 16.264 | 1.00 | 17.59 | A |
| ATOM | 1200 | CD2 | LEU | A | 164 | 55.632 | −15.233 | 18.533 | 1.00 | 18.12 | A |
| ATOM | 1201 | C | LEU | A | 164 | 51.434 | −16.647 | 19.505 | 1.00 | 13.85 | A |
| ATOM | 1202 | O | LEU | A | 164 | 50.823 | −17.707 | 19.582 | 1.00 | 13.66 | A |
| ATOM | 1203 | N | THR | A | 165 | 50.828 | −15.484 | 19.752 | 1.00 | 15.09 | A |
| ATOM | 1204 | CA | THR | A | 165 | 49.378 | −15.439 | 19.888 | 1.00 | 15.28 | A |
| ATOM | 1205 | CB | THR | A | 165 | 48.854 | −15.291 | 21.368 | 1.00 | 17.09 | A |
| ATOM | 1206 | OG1 | THR | A | 165 | 49.004 | −13.940 | 21.814 | 1.00 | 16.05 | A |
| ATOM | 1207 | CG2 | THR | A | 165 | 49.605 | −16.276 | 22.320 | 1.00 | 18.30 | A |
| ATOM | 1208 | C | THR | A | 165 | 48.968 | −14.241 | 19.006 | 1.00 | 14.90 | A |
| ATOM | 1209 | O | THR | A | 165 | 49.798 | −13.372 | 18.698 | 1.00 | 14.74 | A |
| ATOM | 1210 | N | PRO | A | 166 | 47.690 | −14.140 | 18.641 | 1.00 | 12.97 | A |
| ATOM | 1211 | CD | PRO | A | 166 | 47.227 | −13.048 | 17.773 | 1.00 | 14.13 | A |
| ATOM | 1212 | CA | PRO | A | 166 | 46.579 | −15.033 | 18.963 | 1.00 | 13.39 | A |
| ATOM | 1213 | CB | PRO | A | 166 | 45.365 | −14.340 | 18.338 | 1.00 | 13.43 | A |
| ATOM | 1214 | CG | PRO | A | 166 | 45.781 | −12.944 | 18.168 | 1.00 | 14.27 | A |
| ATOM | 1215 | C | PRO | A | 166 | 46.664 | −16.460 | 18.460 | 1.00 | 13.60 | A |
| ATOM | 1216 | O | PRO | A | 166 | 47.418 | −16.776 | 17.531 | 1.00 | 12.79 | A |
| ATOM | 1217 | N | GLN | A | 167 | 45.813 | −17.271 | 19.080 | 1.00 | 12.21 | A |
| ATOM | 1218 | CA | GLN | A | 167 | 45.646 | −18.680 | 18.739 | 1.00 | 13.45 | A |
| ATOM | 1219 | CB | GLN | A | 167 | 46.191 | −19.554 | 19.861 | 1.00 | 14.14 | A |
| ATOM | 1220 | CG | GLN | A | 167 | 47.661 | −19.278 | 20.054 | 1.00 | 12.95 | A |
| ATOM | 1221 | CD | GLN | A | 167 | 48.430 | −20.420 | 20.660 | 1.00 | 15.02 | A |
| ATOM | 1222 | OE1 | GLN | A | 167 | 47.843 | −21.402 | 21.152 | 1.00 | 16.34 | A |
| ATOM | 1223 | NE2 | GLN | A | 167 | 49.759 | −20.302 | 20.638 | 1.00 | 14.86 | A |
| ATOM | 1224 | C | GLN | A | 167 | 44.129 | −18.753 | 18.555 | 1.00 | 13.08 | A |
| ATOM | 1225 | O | GLN | A | 167 | 43.349 | −18.261 | 19.371 | 1.00 | 16.16 | A |
| ATOM | 1226 | N | PHE | A | 168 | 43.729 | −19.334 | 17.428 | 1.00 | 11.35 | A |
| ATOM | 1227 | CA | PHE | A | 168 | 42.334 | −19.351 | 16.988 | 1.00 | 13.22 | A |
| ATOM | 1228 | CB | PHE | A | 168 | 42.346 | −18.609 | 15.652 | 1.00 | 13.34 | A |
| ATOM | 1229 | CG | PHE | A | 168 | 41.018 | −18.318 | 15.082 | 1.00 | 11.46 | A |
| ATOM | 1230 | CD1 | PHE | A | 168 | 40.024 | −17.696 | 15.835 | 1.00 | 11.80 | A |
| ATOM | 1231 | CD2 | PHE | A | 168 | 40.793 | −18.614 | 13.729 | 1.00 | 13.34 | A |
| ATOM | 1232 | CE1 | PHE | A | 168 | 38.789 | −17.347 | 15.245 | 1.00 | 12.04 | A |
| ATOM | 1233 | CE2 | PHE | A | 168 | 39.583 | −18.284 | 13.136 | 1.00 | 14.21 | A |
| ATOM | 1234 | CZ | PHE | A | 168 | 38.575 | −17.652 | 13.871 | 1.00 | 12.79 | A |
| ATOM | 1235 | C | PHE | A | 168 | 41.758 | −20.742 | 16.819 | 1.00 | 13.32 | A |
| ATOM | 1236 | O | PHE | A | 168 | 42.252 | −21.524 | 15.997 | 1.00 | 13.53 | A |
| ATOM | 1237 | N | PHE | A | 169 | 40.707 | −21.039 | 17.572 | 1.00 | 13.68 | A |
| ATOM | 1238 | CA | PHE | A | 169 | 40.141 | −22.400 | 17.512 | 1.00 | 13.48 | A |
| ATOM | 1239 | CB | PHE | A | 169 | 40.656 | −23.229 | 18.687 | 1.00 | 15.51 | A |
| ATOM | 1240 | CG | PHE | A | 169 | 42.127 | −23.307 | 18.772 | 1.00 | 14.70 | A |
| ATOM | 1241 | CD1 | PHE | A | 169 | 42.834 | −22.482 | 19.634 | 1.00 | 18.78 | A |
| ATOM | 1242 | CD2 | PHE | A | 169 | 42.806 | −24.219 | 17.998 | 1.00 | 16.86 | A |
| ATOM | 1243 | CE1 | PHE | A | 169 | 44.217 | −22.569 | 19.719 | 1.00 | 18.31 | A |
| ATOM | 1244 | CE2 | PHE | A | 169 | 44.185 | −24.318 | 18.074 | 1.00 | 20.03 | A |
| ATOM | 1245 | CZ | PHE | A | 169 | 44.876 | −23.478 | 18.944 | 1.00 | 17.40 | A |
| ATOM | 1246 | C | PHE | A | 169 | 38.652 | −22.438 | 17.675 | 1.00 | 14.22 | A |
| ATOM | 1247 | O | PHE | A | 169 | 38.050 | −21.488 | 18.153 | 1.00 | 13.93 | A |
| ATOM | 1248 | N | PRO | A | 170 | 38.015 | −23.551 | 17.246 | 1.00 | 14.23 | A |
| ATOM | 1249 | CD | PRO | A | 170 | 38.512 | −24.610 | 16.352 | 1.00 | 14.76 | A |
| ATOM | 1250 | CA | PRO | A | 170 | 36.565 | −23.649 | 17.444 | 1.00 | 13.15 | A |
| ATOM | 1251 | CB | PRO | A | 170 | 36.236 | −25.043 | 16.900 | 1.00 | 14.44 | A |
| ATOM | 1252 | CG | PRO | A | 170 | 37.229 | −25.216 | 15.809 | 1.00 | 13.86 | A |
| ATOM | 1253 | C | PRO | A | 170 | 36.428 | −23.593 | 18.994 | 1.00 | 14.51 | A |
| ATOM | 1254 | O | PRO | A | 170 | 37.169 | −24.246 | 19.723 | 1.00 | 15.77 | A |
| ATOM | 1255 | N | ARG | A | 171 | 35.477 | −22.815 | 19.475 | 1.00 | 14.72 | A |
| ATOM | 1256 | CA | ARG | A | 171 | 35.256 | −22.568 | 20.895 | 1.00 | 15.83 | A |
| ATOM | 1257 | CB | ARG | A | 171 | 34.022 | −21.680 | 21.047 | 1.00 | 18.65 | A |
| ATOM | 1258 | CG | ARG | A | 171 | 33.937 | −20.866 | 22.355 | 1.00 | 25.90 | A |
| ATOM | 1259 | CD | ARG | A | 171 | 32.704 | −21.179 | 23.181 | 1.00 | 31.83 | A |
| ATOM | 1260 | NE | ARG | A | 171 | 31.488 | −21.219 | 22.377 | 1.00 | 36.10 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1261 | CZ | ARG | A | 171 | 30.424 | −21.953 | 22.681 | 1.00 | 38.37 | A |
| ATOM | 1262 | NH1 | ARG | A | 171 | 30.424 | −22.692 | 23.782 | 1.00 | 40.28 | A |
| ATOM | 1263 | NH2 | ARG | A | 171 | 29.384 | −21.997 | 21.855 | 1.00 | 39.67 | A |
| ATOM | 1264 | C | ARG | A | 171 | 35.082 | −23.813 | 21.766 | 1.00 | 17.37 | A |
| ATOM | 1265 | O | ARG | A | 171 | 35.822 | −24.043 | 22.734 | 1.00 | 18.69 | A |
| ATOM | 1266 | N | GLU | A | 172 | 34.106 | −24.642 | 21.418 | 1.00 | 18.97 | A |
| ATOM | 1267 | CA | GLU | A | 172 | 33.865 | −25.811 | 22.264 | 1.00 | 16.09 | A |
| ATOM | 1268 | CB | GLU | A | 172 | 32.479 | −26.425 | 21.949 | 1.00 | 16.45 | A |
| ATOM | 1269 | CG | GLU | A | 172 | 31.308 | −25.452 | 22.174 | 1.00 | 15.53 | A |
| ATOM | 1270 | CD | GLU | A | 172 | 29.908 | −26.082 | 22.129 | 1.00 | 16.53 | A |
| ATOM | 1271 | OE1 | GLU | A | 172 | 29.747 | −27.219 | 21.651 | 1.00 | 16.05 | A |
| ATOM | 1272 | OE2 | GLU | A | 172 | 28.948 | −25.442 | 22.589 | 1.00 | 18.55 | A |
| ATOM | 1273 | C | GLU | A | 172 | 34.992 | −26.851 | 22.181 | 1.00 | 14.98 | A |
| ATOM | 1274 | O | GLU | A | 172 | 35.335 | −27.509 | 23.189 | 1.00 | 15.75 | A |
| ATOM | 1275 | N | LEU | A | 173 | 35.631 | −26.971 | 21.018 | 1.00 | 15.02 | A |
| ATOM | 1276 | CA | LEU | A | 173 | 36.745 | −27.921 | 20.904 | 1.00 | 14.35 | A |
| ATOM | 1277 | CB | LEU | A | 173 | 37.253 | −28.000 | 19.452 | 1.00 | 17.88 | A |
| ATOM | 1278 | CG | LEU | A | 173 | 38.467 | −28.895 | 19.204 | 1.00 | 19.94 | A |
| ATOM | 1279 | CD1 | LEU | A | 173 | 38.155 | −30.312 | 19.644 | 1.00 | 23.00 | A |
| ATOM | 1280 | CD2 | LEU | A | 173 | 38.860 | −28.891 | 17.718 | 1.00 | 22.40 | A |
| ATOM | 1281 | C | LEU | A | 173 | 37.869 | −27.444 | 21.843 | 1.00 | 16.58 | A |
| ATOM | 1282 | O | LEU | A | 17 | 338.445 | −28.242 | 22.553 | 1.00 | 17.31 | A |
| ATOM | 1283 | N | LEU | A | 174 | 38.153 | −26.138 | 21.859 | 1.00 | 16.39 | A |
| ATOM | 1284 | CA | LEU | A | 174 | 39.209 | −25.622 | 22.725 | 1.00 | 17.86 | A |
| ATOM | 1285 | CB | LEU | A | 174 | 39.422 | −24.121 | 22.547 | 1.00 | 17.46 | A |
| ATOM | 1286 | CG | LEU | A | 174 | 40.490 | −23.579 | 23.527 | 1.00 | 16.50 | A |
| ATOM | 1287 | CD1 | LEU | A | 174 | 41.823 | −24.280 | 23.354 | 1.00 | 16.77 | A |
| ATOM | 1288 | CD2 | LEU | A | 174 | 40.650 | −22.087 | 23.267 | 1.00 | 18.40 | A |
| ATOM | 1289 | C | LEU | A | 174 | 38.858 | −25.857 | 24.174 | 1.00 | 16.75 | A |
| ATOM | 1290 | O | LEU | A | 174 | 39.693 | −26.313 | 24.956 | 1.00 | 19.65 | A |
| ATOM | 1291 | N | HIS | A | 175 | 37.623 | −25.524 | 24.541 | 1.00 | 16.32 | A |
| ATOM | 1292 | CA | HIS | A | 175 | 37.170 | −25.711 | 25.909 | 1.00 | 17.93 | A |
| ATOM | 1293 | CB | HIS | A | 175 | 35.694 | −25.333 | 26.001 | 1.00 | 18.40 | A |
| ATOM | 1294 | CG | HIS | A | 175 | 35.058 | −25.700 | 27.297 | 1.00 | 24.23 | A |
| ATOM | 1295 | CD2 | HIS | A | 175 | 34.753 | −24.952 | 28.381 | 1.00 | 24.69 | A |
| ATOM | 1296 | ND1 | HIS | A | 175 | 34.699 | −26.997 | 27.603 | 1.00 | 22.69 | A |
| ATOM | 1297 | CE1 | HIS | A | 175 | 34.205 | −27.029 | 28.830 | 1.00 | 24.69 | A |
| ATOM | 1298 | NE2 | HIS | A | 175 | 34.228 | −25.802 | 29.323 | 1.00 | 25.90 | A |
| ATOM | 1299 | C | HIS | A | 175 | 37.365 | −27.186 | 26.321 | 1.00 | 18.61 | A |
| ATOM | 1300 | O | HIS | A | 175 | 37.916 | −27.492 | 27.394 | 1.00 | 21.69 | A |
| ATOM | 1301 | N | ASP | A | 176 | 36.926 | −28.110 | 25.474 | 1.00 | 20.32 | A |
| ATOM | 1302 | CA | ASP | A | 176 | 37.040 | −29.528 | 25.793 | 1.00 | 20.36 | A |
| ATOM | 1303 | CB | ASP | A | 176 | 36.307 | −30.384 | 24.756 | 1.00 | 19.54 | A |
| ATOM | 1304 | CG | ASP | A | 176 | 34.811 | −30.203 | 24.827 | 1.00 | 21.78 | A |
| ATOM | 1305 | OD1 | ASP | A | 176 | 34.318 | −29.598 | 25.811 | 1.00 | 19.43 | A |
| ATOM | 1306 | OD2 | ASP | A | 176 | 34.141 | −30.670 | 23.884 | 1.00 | 24.34 | A |
| ATOM | 1307 | C | ASP | A | 176 | 38.468 | −30.019 | 25.931 | 1.00 | 20.70 | A |
| ATOM | 1308 | O | ASP | A | 176 | 38.781 | −30.763 | 26.862 | 1.00 | 21.08 | A |
| ATOM | 1309 | N | CYS | A | 177 | 39.340 | −29.571 | 25.027 | 1.00 | 20.09 | A |
| ATOM | 1310 | CA | CYS | A | 177 | 40.748 | −29.992 | 25.047 | 1.00 | 20.88 | A |
| ATOM | 1311 | CB | CYS | A | 177 | 41.448 | −29.547 | 23.763 | 1.00 | 20.76 | A |
| ATOM | 1312 | SG | CYS | A | 177 | 40.917 | −30.449 | 22.321 | 1.00 | 22.54 | A |
| ATOM | 1313 | C | CYS | A | 177 | 41.490 | −29.440 | 26.273 | 1.00 | 21.77 | A |
| ATOM | 1314 | O | CYS | A | 177 | 42.289 | −30.170 | 26.877 | 1.00 | 22.18 | A |
| ATOM | 1315 | N | LEU | A | 178 | 41.212 | −28.185 | 26.649 | 1.00 | 21.32 | A |
| ATOM | 1316 | CA | LEU | A | 178 | 41.844 | −27.584 | 27.826 | 1.00 | 23.70 | A |
| ATOM | 1317 | CB | LEU | A | 178 | 41.492 | −26.110 | 27.938 | 1.00 | 25.76 | A |
| ATOM | 1318 | CG | LEU | A | 178 | 42.438 | −25.107 | 27.297 | 1.00 | 29.21 | A |
| ATOM | 1319 | CD1 | LEU | A | 178 | 41.779 | −23.728 | 27.235 | 1.00 | 28.84 | A |
| ATOM | 1320 | CD2 | LEU | A | 178 | 43.738 | −25.069 | 28.106 | 1.00 | 29.51 | A |
| ATOM | 1321 | C | LEU | A | 178 | 41.330 | −28.288 | 29.064 | 1.00 | 24.65 | A |
| ATOM | 1322 | O | LEU | A | 178 | 42.067 | −28.517 | 30.032 | 1.00 | 25.16 | A |
| ATOM | 1323 | N | THR | A | 179 | 40.053 | −28.632 | 29.036 | 1.00 | 22.96 | A |
| ATOM | 1324 | CA | THR | A | 179 | 39.464 | −29.287 | 30.187 | 1.00 | 24.69 | A |
| ATOM | 1325 | CB | THR | A | 179 | 37.942 | −29.405 | 30.040 | 1.00 | 23.46 | A |
| ATOM | 1326 | OG1 | THR | A | 179 | 37.344 | −28.106 | 30.165 | 1.00 | 24.30 | A |
| ATOM | 1327 | CG2 | THR | A | 179 | 37.373 | −30.312 | 31.132 | 1.00 | 25.38 | A |
| ATOM | 1328 | C | THR | A | 179 | 40.074 | −30.662 | 30.396 | 1.00 | 25.03 | A |
| ATOM | 1329 | O | THR | A | 179 | 40.410 | −31.018 | 31.523 | 1.00 | 26.66 | A |
| ATOM | 1330 | N | ARG | A | 180 | 40.241 | −31.417 | 29.318 | 1.00 | 26.02 | A |
| ATOM | 1331 | CA | ARG | A | 180 | 40.814 | −32.759 | 29.402 | 1.00 | 28.99 | A |
| ATOM | 1332 | CB | ARG | A | 180 | 40.683 | −33.500 | 28.068 | 1.00 | 31.28 | A |
| ATOM | 1333 | CG | ARG | A | 180 | 41.251 | −34.917 | 28.111 | 1.00 | 35.07 | A |
| ATOM | 1334 | CD | ARG | A | 180 | 41.087 | −35.678 | 26.795 | 1.00 | 38.12 | A |
| ATOM | 1335 | NE | ARG | A | 180 | 41.055 | −37.119 | 27.047 | 1.00 | 40.37 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 1336 | CZ | ARG | A | 180 | 40.946 | −38.062 | 26.113 | 1.00 | 42.33 | A |
|---|---|---|---|---|---|---|---|---|---|---|---|
| ATOM | 1337 | NH1 | ARG | A | 180 | 40.859 | −37.733 | 24.827 | 1.00 | 40.95 | A |
| ATOM | 1338 | NH2 | ARG | A | 180 | 40.906 | −39.345 | 26.473 | 1.00 | 40.62 | A |
| ATOM | 1339 | C | ARG | A | 180 | 42.283 | −32.715 | 29.794 | 1.00 | 30.47 | A |
| ATOM | 1340 | O | ARG | A | 180 | 42.716 | −33.455 | 30.680 | 1.00 | 31.09 | A |
| ATOM | 1341 | N | ALA | A | 181 | 43.041 | −31.845 | 29.131 | 1.00 | 29.77 | A |
| ATOM | 1342 | CA | ALA | A | 181 | 44.469 | −31.716 | 29.401 | 1.00 | 31.21 | A |
| ATOM | 1343 | CB | ALA | A | 181 | 45.076 | −30.608 | 28.525 | 1.00 | 29.92 | A |
| ATOM | 1344 | C | ALA | A | 181 | 44.710 | −31.421 | 30.876 | 1.00 | 32.21 | A |
| ATOM | 1345 | O | ALA | A | 181 | 45.545 | −32.065 | 31.510 | 1.00 | 32.96 | A |
| ATOM | 1346 | N | LEU | A | 182 | 43.971 | −30.462 | 31.418 | 1.00 | 32.52 | A |
| ATOM | 1347 | CA | LEU | A | 182 | 44.107 | −30.090 | 32.817 | 1.00 | 34.94 | A |
| ATOM | 1348 | CB | LEU | A | 182 | 43.259 | −28.861 | 33.122 | 1.00 | 34.14 | A |
| ATOM | 1349 | CG | LEU | A | 182 | 43.839 | −27.495 | 32.730 | 1.00 | 35.40 | A |
| ATOM | 1350 | CD1 | LEU | A | 182 | 42.780 | −26.406 | 32.905 | 1.00 | 34.56 | A |
| ATOM | 1351 | CD2 | LEU | A | 182 | 45.058 | −27.197 | 33.607 | 1.00 | 36.57 | A |
| ATOM | 1352 | C | LEU | A | 182 | 43.714 | −31.219 | 33.763 | 1.00 | 36.85 | A |
| ATOM | 1353 | O | LEU | A | 182 | 44.402 | −31.464 | 34.753 | 1.00 | 38.12 | A |
| ATOM | 1354 | N | ASN | A | 183 | 42.608 | −31.899 | 33.462 | 1.00 | 38.78 | A |
| ATOM | 1355 | CA | ASN | A | 183 | 42.125 | −32.994 | 34.300 | 1.00 | 40.37 | A |
| ATOM | 1356 | CB | ASN | A | 183 | 40.733 | −33.451 | 33.822 | 1.00 | 41.20 | A |
| ATOM | 1357 | CG | ASN | A | 183 | 40.163 | −34.613 | 34.651 | 1.00 | 43.88 | A |
| ATOM | 1358 | OD1 | ASN | A | 183 | 40.477 | −35.784 | 34.406 | 1.00 | 44.85 | A |
| ATOM | 1359 | ND2 | ASN | A | 183 | 39.323 | −34.286 | 35.637 | 1.00 | 44.80 | A |
| ATOM | 1360 | C | ASN | A | 183 | 43.109 | −34.159 | 34.305 | 1.00 | 40.66 | A |
| ATOM | 1361 | O | ASN | A | 183 | 43.280 | −34.825 | 35.328 | 1.00 | 42.26 | A |
| ATOM | 1362 | N | GLU | A | 184 | 43.771 | −34.399 | 33.175 | 1.00 | 40.71 | A |
| ATOM | 1363 | CA | GLU | A | 184 | 44.742 | −35.490 | 33.090 | 1.00 | 40.79 | A |
| ATOM | 1364 | CB | GLU | A | 184 | 44.781 | −36.067 | 31.671 | 1.00 | 41.32 | A |
| ATOM | 1365 | CG | GLU | A | 184 | 43.549 | −36.877 | 31.309 | 1.00 | 42.20 | A |
| ATOM | 1366 | CD | GLU | A | 184 | 43.689 | −37.612 | 29.996 | 1.00 | 43.64 | A |
| ATOM | 1367 | OE1 | GLU | A | 184 | 44.768 | −38.186 | 29.728 | 1.00 | 44.91 | A |
| ATOM | 1368 | OE2 | GLU | A | 184 | 42.705 | −37.646 | 29.233 | 1.00 | 45.31 | A |
| ATOM | 1369 | C | GLU | A | 184 | 46.147 | −35.060 | 33.509 | 1.00 | 40.44 | A |
| ATOM | 1370 | O | GLU | A | 184 | 47.114 | −35.792 | 33.299 | 1.00 | 39.99 | A |
| ATOM | 1371 | N | GLY | A | 185 | 46.254 | −33.876 | 34.101 | 1.00 | 40.16 | A |
| ATOM | 1372 | CA | GLY | A | 185 | 47.550 | −33.379 | 34.540 | 1.00 | 40.35 | A |
| ATOM | 1373 | C | GLY | A | 185 | 48.603 | −33.250 | 33.447 | 1.00 | 40.25 | A |
| ATOM | 1374 | O | GLY | A | 185 | 49.793 | −33.477 | 33.680 | 1.00 | 40.74 | A |
| ATOM | 1375 | N | ALA | A | 186 | 48.186 | −32.876 | 32.245 | 1.00 | 39.05 | A |
| ATOM | 1376 | CA | ALA | A | 186 | 49.147 | −32.719 | 31.163 | 1.00 | 38.44 | A |
| ATOM | 1377 | CB | ALA | A | 186 | 48.435 | −32.768 | 29.810 | 1.00 | 39.17 | A |
| ATOM | 1378 | C | ALA | A | 186 | 49.897 | −31.390 | 31.317 | 1.00 | 37.45 | A |
| ATOM | 1379 | O | ALA | A | 186 | 49.428 | −30.472 | 31.986 | 1.00 | 36.32 | A |
| ATOM | 1380 | N | THR | A | 187 | 51.069 | −31.309 | 30.700 | 1.00 | 37.15 | A |
| ATOM | 1381 | CA | THR | A | 187 | 51.883 | −30.100 | 30.733 | 1.00 | 36.95 | A |
| ATOM | 1382 | CB | THR | A | 187 | 53.362 | −30.444 | 30.489 | 1.00 | 38.24 | A |
| ATOM | 1383 | OG1 | THR | A | 187 | 53.862 | −31.165 | 31.620 | 1.00 | 40.23 | A |
| ATOM | 1384 | CG2 | THR | A | 187 | 54.193 | −29.185 | 30.271 | 1.00 | 39.65 | A |
| ATOM | 1385 | C | THR | A | 187 | 51.379 | −29.167 | 29.642 | 1.00 | 34.75 | A |
| ATOM | 1386 | O | THR | A | 187 | 51.599 | −29.401 | 28.458 | 1.00 | 36.28 | A |
| ATOM | 1387 | N | ILE | A | 188 | 50.702 | −28.106 | 30.052 | 1.00 | 32.87 | A |
| ATOM | 1388 | CA | ILE | A | 188 | 50.138 | −27.146 | 29.112 | 1.00 | 30.65 | A |
| ATOM | 1389 | CB | ILE | A | 188 | 48.708 | −26.768 | 29.541 | 1.00 | 30.86 | A |
| ATOM | 1390 | CG2 | ILE | A | 188 | 48.147 | −25.659 | 28.650 | 1.00 | 33.36 | A |
| ATOM | 1391 | CG1 | ILE | A | 188 | 47.834 | −28.015 | 29.480 | 1.00 | 32.82 | A |
| ATOM | 1392 | CD1 | ILE | A | 188 | 46.464 | −27.796 | 30.017 | 1.00 | 35.08 | A |
| ATOM | 1393 | C | ILE | A | 188 | 50.969 | −25.881 | 29.019 | 1.00 | 28.60 | A |
| ATOM | 1394 | O | ILE | A | 188 | 51.329 | −25.298 | 30.047 | 1.00 | 29.73 | A |
| ATOM | 1395 | N | THR | A | 189 | 51.297 | −25.479 | 27.795 | 1.00 | 24.39 | A |
| ATOM | 1396 | CA | THR | A | 189 | 52.036 | −24.241 | 27.565 | 1.00 | 23.54 | A |
| ATOM | 1397 | CB | THR | A | 189 | 53.261 | −24.464 | 26.653 | 1.00 | 21.74 | A |
| ATOM | 1398 | OG1 | THR | A | 189 | 52.904 | −25.297 | 25.540 | 1.00 | 22.87 | A |
| ATOM | 1399 | CG2 | THR | A | 189 | 54.395 | −25.142 | 27.458 | 1.00 | 24.44 | A |
| ATOM | 1400 | C | THR | A | 189 | 51.033 | −23.280 | 26.933 | 1.00 | 21.79 | A |
| ATOM | 1401 | O | THR | A | 189 | 50.459 | −22.460 | 27.645 | 1.00 | 23.55 | A |
| ATOM | 1402 | N | ASP | A | 190 | 50.768 | −23.410 | 25.630 | 1.00 | 20.46 | A |
| ATOM | 1403 | CA | ASP | A | 190 | 49.792 | −22.531 | 25.000 | 1.00 | 17.65 | A |
| ATOM | 1404 | CB | ASP | A | 190 | 50.354 | −21.902 | 23.707 | 1.00 | 18.83 | A |
| ATOM | 1405 | CG | ASP | A | 190 | 50.819 | −22.928 | 22.698 | 1.00 | 20.10 | A |
| ATOM | 1406 | OD1 | ASP | A | 190 | 50.733 | −24.157 | 22.966 | 1.00 | 18.81 | A |
| ATOM | 1407 | OD2 | ASP | A | 190 | 51.293 | −22.538 | 21.605 | 1.00 | 20.63 | A |
| ATOM | 1408 | C | ASP | A | 190 | 48.494 | −23.280 | 24.706 | 1.00 | 18.73 | A |
| ATOM | 1409 | O | ASP | A | 190 | 48.363 | −24.463 | 25.042 | 1.00 | 18.88 | A |
| ATOM | 1410 | N | GLU | A | 191 | 47.535 | −22.598 | 24.075 | 1.00 | 17.62 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1411 | CA  | GLU | A | 191 | 46.275 | −23.256 | 23.753 | 1.00 | 18.22 | A |
|------|------|-----|-----|---|-----|--------|---------|--------|------|-------|---|
| ATOM | 1412 | CB  | GLU | A | 191 | 45.251 | −22.270 | 23.186 | 1.00 | 17.72 | A |
| ATOM | 1413 | CG  | GLU | A | 191 | 44.624 | −21.336 | 24.234 | 1.00 | 20.18 | A |
| ATOM | 1414 | CD  | GLU | A | 191 | 45.658 | −20.498 | 24.949 | 1.00 | 19.25 | A |
| ATOM | 1415 | OE1 | GLU | A | 191 | 46.405 | −19.749 | 24.284 | 1.00 | 21.27 | A |
| ATOM | 1416 | OE2 | GLU | A | 191 | 45.746 | −20.579 | 26.183 | 1.00 | 24.43 | A |
| ATOM | 1417 | C   | GLU | A | 191 | 46.494 | −24.386 | 22.766 | 1.00 | 17.25 | A |
| ATOM | 1418 | O   | GLU | A | 191 | 45.845 | −25.433 | 22.858 | 1.00 | 17.71 | A |
| ATOM | 1419 | N   | ALA | A | 192 | 47.414 | −24.211 | 21.824 | 1.00 | 17.27 | A |
| ATOM | 1420 | CA  | ALA | A | 192 | 47.667 | −25.262 | 20.863 | 1.00 | 14.57 | A |
| ATOM | 1421 | CB  | ALA | A | 192 | 48.683 | −24.803 | 19.815 | 1.00 | 17.75 | A |
| ATOM | 1422 | C   | ALA | A | 192 | 48.146 | −26.529 | 21.551 | 1.00 | 18.49 | A |
| ATOM | 1423 | O   | ALA | A | 192 | 47.779 | −27.623 | 21.129 | 1.00 | 18.39 | A |
| ATOM | 1424 | N   | SER | A | 193 | 48.931 | −26.403 | 22.623 | 1.00 | 19.16 | A |
| ATOM | 1425 | CA  | SER | A | 193 | 49.425 | −27.607 | 23.295 | 1.00 | 18.15 | A |
| ATOM | 1426 | CB  | SER | A | 193 | 50.432 | −27.275 | 24.407 | 1.00 | 17.82 | A |
| ATOM | 1427 | OG  | SER | A | 193 | 49.854 | −26.676 | 25.523 | 1.00 | 20.35 | A |
| ATOM | 1428 | C   | SER | A | 193 | 48.271 | −28.441 | 23.860 | 1.00 | 18.39 | A |
| ATOM | 1429 | O   | SER | A | 193 | 48.417 | −29.655 | 24.001 | 1.00 | 20.89 | A |
| ATOM | 1430 | N   | ALA | A | 194 | 47.150 | −27.812 | 24.183 | 1.00 | 17.06 | A |
| ATOM | 1431 | CA  | ALA | A | 194 | 45.998 | −28.581 | 24.695 | 1.00 | 19.00 | A |
| ATOM | 1432 | CB  | ALA | A | 194 | 44.961 | −27.665 | 25.316 | 1.00 | 19.48 | A |
| ATOM | 1433 | C   | ALA | A | 194 | 45.392 | −29.387 | 23.548 | 1.00 | 20.61 | A |
| ATOM | 1434 | O   | ALA | A | 194 | 45.004 | −30.552 | 23.723 | 1.00 | 21.17 | A |
| ATOM | 1435 | N   | LEU | A | 195 | 45.267 | −28.776 | 22.372 | 1.00 | 19.88 | A |
| ATOM | 1436 | CA  | LEU | A | 195 | 44.747 | −29.503 | 21.217 | 1.00 | 20.46 | A |
| ATOM | 1437 | CB  | LEU | A | 195 | 44.644 | −28.607 | 19.978 | 1.00 | 20.87 | A |
| ATOM | 1438 | CG  | LEU | A | 195 | 43.408 | −27.733 | 19.733 | 1.00 | 22.89 | A |
| ATOM | 1439 | CD1 | LEU | A | 195 | 42.301 | −28.615 | 19.240 | 1.00 | 25.41 | A |
| ATOM | 1440 | CD2 | LEU | A | 195 | 43.017 | −26.958 | 21.007 | 1.00 | 22.27 | A |
| ATOM | 1441 | C   | LEU | A | 195 | 45.714 | −30.624 | 20.887 | 1.00 | 20.06 | A |
| ATOM | 1442 | O   | LEU | A | 195 | 45.312 | −31.713 | 20.497 | 1.00 | 21.99 | A |
| ATOM | 1443 | N   | GLU | A | 196 | 47.001 | −30.341 | 21.014 | 1.00 | 20.14 | A |
| ATOM | 1444 | CA  | GLU | A | 196 | 48.004 | −31.341 | 20.698 | 1.00 | 21.08 | A |
| ATOM | 1445 | CB  | GLU | A | 196 | 49.401 | −30.746 | 20.838 | 1.00 | 21.85 | A |
| ATOM | 1446 | CG  | GLU | A | 196 | 49.719 | −29.755 | 19.730 | 1.00 | 20.85 | A |
| ATOM | 1447 | CD  | GLU | A | 196 | 50.810 | −28.790 | 20.131 | 1.00 | 23.06 | A |
| ATOM | 1448 | OE1 | GLU | A | 196 | 51.783 | −29.259 | 20.748 | 1.00 | 22.15 | A |
| ATOM | 1449 | OE2 | GLU | A | 196 | 50.689 | −27.569 | 19.839 | 1.00 | 20.84 | A |
| ATOM | 1450 | C   | GLU | A | 196 | 47.865 | −32.533 | 21.593 | 1.00 | 21.44 | A |
| ATOM | 1451 | O   | GLU | A | 196 | 47.936 | −33.664 | 21.125 | 1.00 | 23.67 | A |
| ATOM | 1452 | N   | TYR | A | 197 | 47.651 | −32.283 | 22.873 | 1.00 | 22.86 | A |
| ATOM | 1453 | CA  | TYR | A | 197 | 47.529 | −33.372 | 23.825 | 1.00 | 24.81 | A |
| ATOM | 1454 | CB  | TYR | A | 197 | 47.294 | −32.815 | 25.217 | 1.00 | 26.70 | A |
| ATOM | 1455 | CG  | TYR | A | 197 | 47.145 | −33.876 | 26.272 | 1.00 | 30.94 | A |
| ATOM | 1456 | CD1 | TYR | A | 197 | 48.255 | −34.556 | 26.771 | 1.00 | 34.41 | A |
| ATOM | 1457 | CE1 | TYR | A | 197 | 48.113 | −35.531 | 27.760 | 1.00 | 36.74 | A |
| ATOM | 1458 | CD2 | TYR | A | 197 | 45.892 | −34.200 | 26.776 | 1.00 | 32.36 | A |
| ATOM | 1459 | CE2 | TYR | A | 197 | 45.739 | −35.176 | 27.762 | 1.00 | 35.27 | A |
| ATOM | 1460 | CZ  | TYR | A | 197 | 46.854 | −35.832 | 28.251 | 1.00 | 36.98 | A |
| ATOM | 1461 | OH  | TYR | A | 197 | 46.707 | −36.759 | 29.261 | 1.00 | 38.43 | A |
| ATOM | 1462 | C   | TYR | A | 197 | 46.388 | −34.313 | 23.454 | 1.00 | 26.65 | A |
| ATOM | 1463 | O   | TYR | A | 197 | 46.479 | −35.517 | 23.679 | 1.00 | 28.06 | A |
| ATOM | 1464 | N   | CYS | A | 198 | 45.323 | −33.758 | 22.882 | 1.00 | 25.61 | A |
| ATOM | 1465 | CA  | CYS | A | 198 | 44.137 | −34.534 | 22.494 | 1.00 | 26.39 | A |
| ATOM | 1466 | CB  | CYS | A | 198 | 42.890 | −33.654 | 22.676 | 1.00 | 25.99 | A |
| ATOM | 1467 | SG  | CYS | A | 198 | 42.661 | −33.118 | 24.389 | 1.00 | 25.29 | A |
| ATOM | 1468 | C   | CYS | A | 198 | 44.185 | −35.147 | 21.082 | 1.00 | 27.48 | A |
| ATOM | 1469 | O   | CYS | A | 198 | 43.175 | −35.655 | 20.555 | 1.00 | 28.61 | A |
| ATOM | 1470 | N   | GLY | A | 199 | 45.363 | −35.101 | 20.467 | 1.00 | 25.51 | A |
| ATOM | 1471 | CA  | GLY | A | 199 | 45.522 | −35.692 | 19.154 | 1.00 | 26.35 | A |
| ATOM | 1472 | C   | GLY | A | 199 | 45.333 | −34.790 | 17.960 | 1.00 | 25.23 | A |
| ATOM | 1473 | O   | GLY | A | 199 | 45.368 | −35.251 | 16.826 | 1.00 | 26.02 | A |
| ATOM | 1474 | N   | PHE | A | 200 | 45.131 | −33.496 | 18.192 | 1.00 | 26.46 | A |
| ATOM | 1475 | CA  | PHE | A | 200 | 44.965 | −32.591 | 17.071 | 1.00 | 25.13 | A |
| ATOM | 1476 | CB  | PHE | A | 200 | 43.935 | −31.515 | 17.410 | 1.00 | 25.59 | A |
| ATOM | 1477 | CG  | PHE | A | 200 | 42.571 | −32.073 | 17.663 | 1.00 | 24.68 | A |
| ATOM | 1478 | CD1 | PHE | A | 200 | 42.137 | −32.323 | 18.952 | 1.00 | 25.33 | A |
| ATOM | 1479 | CD2 | PHE | A | 200 | 41.741 | −32.406 | 16.607 | 1.00 | 25.88 | A |
| ATOM | 1480 | CE1 | PHE | A | 200 | 40.892 | −32.903 | 19.193 | 1.00 | 26.86 | A |
| ATOM | 1481 | CE2 | PHE | A | 200 | 40.481 | −32.995 | 16.838 | 1.00 | 24.95 | A |
| ATOM | 1482 | CZ  | PHE | A | 200 | 40.072 | −33.237 | 18.132 | 1.00 | 25.93 | A |
| ATOM | 1483 | C   | PHE | A | 200 | 46.274 | −31.965 | 16.637 | 1.00 | 26.98 | A |
| ATOM | 1484 | O   | PHE | A | 200 | 47.274 | −31.979 | 17.380 | 1.00 | 26.59 | A |
| ATOM | 1485 | N   | HIS | A | 201 | 46.258 | −31.424 | 15.422 | 1.00 | 25.31 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1486 | CA | HIS | A | 201 | 47.422 | −30.789 | 14.834 | 1.00 | 24.70 | A |
|---|---|---|---|---|---|---|---|---|---|---|---|
| ATOM | 1487 | CB | HIS | A | 201 | 48.016 | −31.716 | 13.774 | 1.00 | 25.44 | A |
| ATOM | 1488 | CG | HIS | A | 201 | 48.545 | −33.001 | 14.336 | 1.00 | 28.40 | A |
| ATOM | 1489 | CD2 | HIS | A | 201 | 49.774 | −33.327 | 14.799 | 1.00 | 26.07 | A |
| ATOM | 1490 | ND1 | HIS | A | 201 | 47.756 | −34.117 | 14.528 | 1.00 | 29.46 | A |
| ATOM | 1491 | CE1 | HIS | A | 201 | 48.478 | −35.073 | 15.086 | 1.00 | 28.32 | A |
| ATOM | 1492 | NE2 | HIS | A | 201 | 49.705 | −34.618 | 15.261 | 1.00 | 30.32 | A |
| ATOM | 1493 | C | HIS | A | 201 | 47.049 | −29.437 | 14.233 | 1.00 | 22.38 | A |
| ATOM | 1494 | O | HIS | A | 201 | 46.786 | −29.330 | 13.037 | 1.00 | 23.23 | A |
| ATOM | 1495 | N | PRO | A | 202 | 47.036 | −28.382 | 15.066 | 1.00 | 21.62 | A |
| ATOM | 1496 | CD | PRO | A | 202 | 47.358 | −28.400 | 16.500 | 1.00 | 21.55 | A |
| ATOM | 1497 | CA | PRO | A | 202 | 46.691 | −27.019 | 14.644 | 1.00 | 20.94 | A |
| ATOM | 1498 | CB | PRO | A | 202 | 46.811 | −26.210 | 15.936 | 1.00 | 21.83 | A |
| ATOM | 1499 | CG | PRO | A | 202 | 46.573 | −27.219 | 17.011 | 1.00 | 22.80 | A |
| ATOM | 1500 | C | PRO | A | 202 | 47.603 | −26.460 | 13.555 | 1.00 | 19.04 | A |
| ATOM | 1501 | O | PRO | A | 202 | 48.770 | −26.846 | 13.421 | 1.00 | 19.03 | A |
| ATOM | 1502 | N | GLN | A | 203 | 47.053 | −25.539 | 12.772 | 1.00 | 17.57 | A |
| ATOM | 1503 | CA | GLN | A | 203 | 47.803 | −24.926 | 11.696 | 1.00 | 19.99 | A |
| ATOM | 1504 | CB | GLN | A | 203 | 46.848 | −24.346 | 10.648 | 1.00 | 21.19 | A |
| ATOM | 1505 | CG | GLN | A | 203 | 46.137 | −25.385 | 9.805 | 1.00 | 28.17 | A |
| ATOM | 1506 | CD | GLN | A | 203 | 47.084 | −26.137 | 8.868 | 1.00 | 31.04 | A |
| ATOM | 1507 | OE1 | GLN | A | 203 | 47.813 | −25.532 | 8.075 | 1.00 | 33.76 | A |
| ATOM | 1508 | NE2 | GLN | A | 203 | 47.060 | −27.464 | 8.945 | 1.00 | 35.67 | A |
| ATOM | 1509 | C | GLN | A | 203 | 48.737 | −23.822 | 12.181 | 1.00 | 18.74 | A |
| ATOM | 1510 | O | GLN | A | 2O3 | 48.462 | −23.146 | 13.179 | 1.00 | 20.08 | A |
| ATOM | 1511 | N | LEU | A | 204 | 49.832 | −23.662 | 11.452 | 1.00 | 18.05 | A |
| ATOM | 1512 | CA | LEU | A | 204 | 50.821 | −22.628 | 11.727 | 1.00 | 17.82 | A |
| ATOM | 1513 | CB | LEU | A | 2O4 | 52.236 | −23.213 | 11.603 | 1.00 | 17.49 | A |
| ATOM | 1514 | CG | LEU | A | 204 | 52.599 | −24.184 | 12.732 | 1.00 | 17.60 | A |
| ATOM | 1515 | CD1 | LEU | A | 204 | 53.704 | −25.173 | 12.316 | 1.00 | 20.96 | A |
| ATOM | 1516 | CD2 | LEU | A | 204 | 53.044 | −23.364 | 13.933 | 1.00 | 19.49 | A |
| ATOM | 1517 | C | LEU | A | 204 | 50.597 | −21.550 | 10.665 | 1.00 | 18.49 | A |
| ATOM | 1518 | O | LEU | A | 204 | 50.682 | −21.814 | 9.470 | 1.00 | 21.23 | A |
| ATOM | 1519 | N | VAL | A | 205 | 50.275 | −20.337 | 11.097 | 1.00 | 19.02 | A |
| ATOM | 1520 | CA | VAL | A | 205 | 50.063 | −19.241 | 10.171 | 1.00 | 17.25 | A |
| ATOM | 1521 | CB | VAL | A | 205 | 48.734 | −18.535 | 10.485 | 1.00 | 16.67 | A |
| ATOM | 1522 | CG1 | VAL | A | 205 | 48.608 | −17.262 | 9.690 | 1.00 | 19.67 | A |
| ATOM | 1523 | CG2 | VAL | A | 205 | 47.583 | −19.464 | 10.150 | 1.00 | 16.36 | A |
| ATOM | 1524 | C | VAL | A | 205 | 51.235 | −18.323 | 10.428 | 1.00 | 18.86 | A |
| ATOM | 1525 | O | VAL | A | 205 | 51.377 | −17.792 | 11.527 | 1.00 | 15.99 | A |
| ATOM | 1526 | N | GLU | A | 206 | 52.095 | −18.136 | 9.439 | 1.00 | 16.73 | A |
| ATOM | 1527 | CA | GLU | A | 206 | 53.265 | −17.306 | 9.682 | 1.00 | 17.54 | A |
| ATOM | 1528 | CB | GLU | A | 206 | 54.227 | −17.361 | 8.490 | 1.00 | 18.17 | A |
| ATOM | 1529 | CG | GLU | A | 206 | 55.401 | −16.413 | 8.677 | 1.00 | 20.97 | A |
| ATOM | 1530 | CD | GLU | A | 206 | 56.567 | −16.677 | 7.733 | 1.00 | 24.77 | A |
| ATOM | 1531 | OE1 | GLU | A | 206 | 56.420 | −17.506 | 6.818 | 1.00 | 29.05 | A |
| ATOM | 1532 | OE2 | GLU | A | 206 | 57.625 | −16.044 | 7.926 | 1.00 | 27.53 | A |
| ATOM | 1533 | C | GLU | A | 206 | 52.927 | −15.860 | 10.000 | 1.00 | 19.59 | A |
| ATOM | 1534 | O | GLU | A | 206 | 52.153 | −15.218 | 9.284 | 1.00 | 19.39 | A |
| ATOM | 1535 | N | GLY | A | 207 | 53.519 | −15.357 | 11.079 | 1.00 | 18.50 | A |
| ATOM | 1536 | CA | GLY | A | 207 | 53.296 | −13.985 | 11.501 | 1.00 | 19.21 | A |
| ATOM | 1537 | C | GLY | A | 207 | 54.589 | −13.216 | 11.737 | 1.00 | 19.02 | A |
| ATOM | 1538 | O | GLY | A | 207 | 55.679 | −13.784 | 11.712 | 1.00 | 21.77 | A |
| ATOM | 1539 | N | ARG | A | 208 | 54.465 | −11.911 | 11.927 | 1.00 | 19.15 | A |
| ATOM | 1540 | CA | ARG | A | 208 | 55.630 | −11.051 | 12.140 | 1.00 | 19.87 | A |
| ATOM | 1541 | CB | ARG | A | 208 | 55.194 | −9.589 | 12.173 | 1.00 | 21.67 | A |
| ATOM | 1542 | CG | ARG | A | 208 | 54.474 | −9.119 | 10.943 | 1.00 | 21.90 | A |
| ATOM | 1543 | CD | ARG | A | 208 | 53.919 | −7.747 | 11.214 | 1.00 | 26.13 | A |
| ATOM | 1544 | NE | ARG | A | 208 | 54.981 | −6.822 | 11.567 | 1.00 | 29.70 | A |
| ATOM | 1545 | CZ | ARG | A | 208 | 55.640 | −6.090 | 10.675 | 1.00 | 33.00 | A |
| ATOM | 1546 | NH1 | ARG | A | 208 | 55.321 | −6.177 | 9.388 | 1.00 | 33.75 | A |
| ATOM | 1547 | NH2 | ARG | A | 208 | 56.634 | −5.306 | 11.066 | 1.00 | 33.49 | A |
| ATOM | 1548 | C | ARG | A | 208 | 56.359 | −11.376 | 13.431 | 1.00 | 21.32 | A |
| ATOM | 1549 | O | ARG | A | 208 | 55.743 | −11.581 | 14.486 | 1.00 | 20.27 | A |
| ATOM | 1550 | N | ALA | A | 209 | 57.685 | −11.360 | 13.365 | 1.00 | 20.28 | A |
| ATOM | 1551 | CA | ALA | A | 209 | 58.484 | −11.665 | 14.541 | 1.00 | 22.16 | A |
| ATOM | 1552 | CB | ALA | A | 209 | 59.905 | −12.025 | 14.120 | 1.00 | 22.70 | A |
| ATOM | 1553 | C | ALA | A | 209 | 58.511 | −10.552 | 15.590 | 1.00 | 21.24 | A |
| ATOM | 1554 | O | ALA | A | 209 | 58.946 | −10.785 | 16.713 | 1.00 | 22.67 | A |
| ATOM | 1555 | N | ASP | A | 210 | 58.037 | −9.357 | 15.234 | 1.00 | 21.21 | A |
| ATOM | 1556 | CA | ASP | A | 210 | 58.009 | −8.253 | 16.180 | 1.00 | 22.11 | A |
| ATOM | 1557 | CB | ASP | A | 210 | 58.143 | −6.884 | 15.494 | 1.00 | 23.53 | A |
| ATOM | 1558 | CG | ASP | A | 210 | 57.169 | −6.676 | 14.354 | 1.00 | 27.09 | A |
| ATOM | 1559 | OD1 | ASP | A | 210 | 56.127 | −7.358 | 14.281 | 1.00 | 22.40 | A |
| ATOM | 1560 | OD2 | ASP | A | 210 | 57.470 | −5.791 | 13.524 | 1.00 | 30.11 | A |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 1561 | C | ASP | A | 210 | 56.767 | −8.272 | 17.058 | 1.00 | 20.66 | A |
|---|---|---|---|---|---|---|---|---|---|---|---|
| ATOM | 1562 | O | ASP | A | 210 | 56.526 | −7.357 | 17.828 | 1.00 | 20.26 | A |
| ATOM | 1563 | N | ASN | A | 211 | 55.992 | −9.344 | 16.936 | 1.00 | 20.39 | A |
| ATOM | 1564 | CA | ASN | A | 211 | 54.802 | −9.540 | 17.768 | 1.00 | 18.95 | A |
| ATOM | 1565 | CB | ASN | A | 211 | 53.877 | −10.546 | 17.057 | 1.00 | 17.97 | A |
| ATOM | 1566 | CG | ASN | A | 211 | 52.625 | −10.856 | 17.842 | 1.00 | 17.29 | A |
| ATOM | 1567 | OD1 | ASN | A | 211 | 52.333 | −10.214 | 18.843 | 1.00 | 17.93 | A |
| ATOM | 1568 | ND2 | ASN | A | 211 | 51.877 | −11.849 | 17.382 | 1.00 | 14.78 | A |
| ATOM | 1569 | C | ASN | A | 211 | 55.394 | −10.140 | 19.059 | 1.00 | 19.68 | A |
| ATOM | 1570 | O | ASN | A | 211 | 55.260 | −11.338 | 19.312 | 1.00 | 22.87 | A |
| ATOM | 1571 | N | ILE | A | 212 | 56.063 | −9.321 | 19.870 | 1.00 | 18.72 | A |
| ATOM | 1572 | CA | ILE | A | 212 | 56.716 | −9.809 | 21.095 | 1.00 | 20.21 | A |
| ATOM | 1573 | CB | ILE | A | 212 | 58.016 | −8.997 | 21.383 | 1.00 | 21.90 | A |
| ATOM | 1574 | CG2 | ILE | A | 212 | 58.999 | −9.171 | 20.232 | 1.00 | 24.05 | A |
| ATOM | 1575 | CG1 | ILE | A | 212 | 57.666 | −7.515 | 21.623 | 1.00 | 21.14 | A |
| ATOM | 1576 | CD1 | ILE | A | 212 | 58.801 | −6.708 | 22.291 | 1.00 | 25.97 | A |
| ATOM | 1577 | C | ILE | A | 212 | 55.881 | −9.764 | 22.360 | 1.00 | 20.50 | A |
| ATOM | 1578 | O | ILE | A | 212 | 54.895 | −9.041 | 22.426 | 1.00 | 18.71 | A |
| ATOM | 1579 | N | LYS | A | 213 | 56.295 | −10.545 | 23.368 | 1.00 | 20.71 | A |
| ATOM | 1580 | CA | LYS | A | 213 | 55.629 | −10.582 | 24.655 | 1.00 | 21.21 | A |
| ATOM | 1581 | CB | LYS | A | 213 | 55.459 | −12.012 | 25.163 | 1.00 | 21.58 | A |
| ATOM | 1582 | CG | LYS | A | 213 | 54.520 | −12.120 | 26.351 | 1.00 | 25.52 | A |
| ATOM | 1583 | CD | LYS | A | 213 | 54.131 | −13.563 | 26.609 | 1.00 | 27.46 | A |
| ATOM | 1584 | CE | LYS | A | 213 | 55.364 | −14.429 | 26.712 | 1.00 | 32.41 | A |
| ATOM | 1585 | NZ | LYS | A | 213 | 54.991 | −15.850 | 26.895 | 1.00 | 35.18 | A |
| ATOM | 1586 | C | LYS | A | 213 | 56.524 | −9.823 | 25.614 | 1.00 | 20.88 | A |
| ATOM | 1587 | O | LYS | A | 213 | 57.711 | −10.118 | 25.739 | 1.00 | 23.26 | A |
| ATOM | 1588 | N | VAL | A | 214 | 55.954 | −8.821 | 26.246 | 1.00 | 19.25 | A |
| ATOM | 1589 | CA | VAL | A | 214 | 56.689 | −8.014 | 27.199 | 1.00 | 21.63 | A |
| ATOM | 1590 | CB | VAL | A | 214 | 55.902 | −6.728 | 27.441 | 1.00 | 21.92 | A |
| ATOM | 1591 | CG1 | VAL | A | 214 | 56.568 | −5.878 | 28.501 | 1.00 | 22.59 | A |
| ATOM | 1592 | CG2 | VAL | A | 214 | 55.798 | −5.958 | 26.114 | 1.00 | 19.13 | A |
| ATOM | 1593 | C | VAL | A | 214 | 56.791 | −8.892 | 28.435 | 1.00 | 21.12 | A |
| ATOM | 1594 | O | VAL | A | 214 | 55.777 | −9.236 | 29.043 | 1.00 | 23.74 | A |
| ATOM | 1595 | N | THR | A | 215 | 58.012 | −9.272 | 28.801 | 1.00 | 23.14 | A |
| ATOM | 1596 | CA | THR | A | 215 | 58.233 | −10.172 | 29.927 | 1.00 | 24.52 | A |
| ATOM | 1597 | CB | THR | A | 215 | 58.722 | −11.550 | 29.426 | 1.00 | 25.23 | A |
| ATOM | 1598 | OG1 | THR | A | 215 | 57.842 | −12.029 | 28.391 | 1.00 | 29.30 | A |
| ATOM | 1599 | CG2 | THR | A | 215 | 58.739 | −12.557 | 30.577 | 1.00 | 28.71 | A |
| ATOM | 1600 | C | THR | A | 215 | 59.267 | −9.645 | 30.906 | 1.00 | 25.65 | A |
| ATOM | 1601 | O | THR | A | 215 | 59.132 | −9.835 | 32.118 | 1.00 | 25.68 | A |
| ATOM | 1602 | N | ARG | A | 216 | 60.308 | −9.009 | 30.365 | 1.00 | 26.81 | A |
| ATOM | 1603 | CA | ARG | A | 216 | 61.399 | −8.451 | 31.167 | 1.00 | 28.70 | A |
| ATOM | 1604 | CB | ARG | A | 216 | 62.762 | −9.009 | 30.738 | 1.00 | 31.94 | A |
| ATOM | 1605 | CG | ARG | A | 216 | 63.023 | −10.452 | 31.106 | 1.00 | 36.40 | A |
| ATOM | 1606 | CD | ARG | A | 216 | 62.506 | −11.398 | 30.046 | 1.00 | 41.09 | A |
| ATOM | 1607 | NE | ARG | A | 216 | 62.570 | −12.780 | 30.512 | 1.00 | 43.98 | A |
| ATOM | 1608 | CZ | ARG | A | 216 | 62.201 | −13.841 | 29.800 | 1.00 | 44.60 | A |
| ATOM | 1609 | NH1 | ARG | A | 216 | 61.734 | −13.697 | 28.561 | 1.00 | 44.81 | A |
| ATOM | 1610 | NH2 | ARG | A | 216 | 62.293 | −15.051 | 30.340 | 1.00 | 45.00 | A |
| ATOM | 1611 | C | ARG | A | 216 | 61.441 | −6.946 | 31.018 | 1.00 | 28.78 | A |
| ATOM | 1612 | O | ARG | A | 216 | 60.928 | −6.391 | 30.051 | 1.00 | 27.46 | A |
| ATOM | 1613 | N | PRO | A | 217 | 62.108 | −6.261 | 31.950 | 1.00 | 28.34 | A |
| ATOM | 1614 | CD | PRO | A | 217 | 62.833 | −6.767 | 33.130 | 1.00 | 30.01 | A |
| ATOM | 1615 | CA | PRO | A | 217 | 62.186 | −4.804 | 31.883 | 1.00 | 30.03 | A |
| ATOM | 1616 | CB | PRO | A | 217 | 63.222 | −4.477 | 32.947 | 1.00 | 28.68 | A |
| ATOM | 1617 | CG | PRO | A | 217 | 62.933 | −5.514 | 33.980 | 1.00 | 29.57 | A |
| ATOM | 1618 | C | PRO | A | 217 | 62.535 | −4.201 | 30.530 | 1.00 | 29.07 | A |
| ATOM | 1619 | O | PRO | A | 217 | 61.881 | −3.266 | 30.084 | 1.00 | 31.81 | A |
| ATOM | 1620 | N | GLU | A | 218 | 63.546 | −4.750 | 29.872 | 1.00 | 30.64 | A |
| ATOM | 1621 | CA | GLU | A | 218 | 63.985 | −4.234 | 28.587 | 1.00 | 30.48 | A |
| ATOM | 1622 | CB | GLU | A | 218 | 65.256 | −4.959 | 28.147 | 1.00 | 33.28 | A |
| ATOM | 1623 | CG | GLU | A | 218 | 65.069 | −6.466 | 28.032 | 1.00 | 38.91 | A |
| ATOM | 1624 | CD | GLU | A | 218 | 65.516 | −7.238 | 29.269 | 1.00 | 41.24 | A |
| ATOM | 1625 | OE1 | GLU | A | 218 | 65.181 | −6.830 | 30.410 | 1.00 | 40.90 | A |
| ATOM | 1626 | OE2 | GLU | A | 218 | 66.196 | −8.272 | 29.087 | 1.00 | 42.62 | A |
| ATOM | 1627 | C | GLU | A | 218 | 62.936 | −4.351 | 27.494 | 1.00 | 29.13 | A |
| ATOM | 1628 | O | GLU | A | 218 | 62.960 | −3.598 | 26.510 | 1.00 | 27.03 | A |
| ATOM | 1629 | N | ASP | A | 219 | 62.017 | −5.298 | 27.659 | 1.00 | 26.62 | A |
| ATOM | 1630 | CA | ASP | A | 219 | 60.968 | −5.508 | 26.669 | 1.00 | 25.98 | A |
| ATOM | 1631 | CB | ASP | A | 219 | 60.140 | −6.750 | 27.014 | 1.00 | 26.06 | A |
| ATOM | 1632 | CG | ASP | A | 219 | 60.950 | −8.023 | 26.961 | 1.00 | 26.52 | A |
| ATOM | 1633 | OD1 | ASP | A | 219 | 61.988 | −8.039 | 26.277 | 1.00 | 31.84 | A |
| ATOM | 1634 | OD2 | ASP | A | 219 | 60.550 | −9.028 | 27.581 | 1.00 | 27.31 | A |
| ATOM | 1635 | C | ASP | A | 219 | 60.040 | −4.321 | 26.510 | 1.00 | 25.26 | A |

APPENDIX 2-continued

X-RAY DATA COORDINATES FOR CDP-ME SYNTHASE COMPLEXED WITH CTP·Mg$^{2+}$
(SEQ ID NO: 11)

| | | | | | | | | | | | |
|---|---|---|---|---|---|---|---|---|---|---|---|
| ATOM | 1636 | O | ASP | A | 219 | 59.484 | −4.130 | 25.451 | 1.00 | 22.56 | A |
| ATOM | 1637 | N | LEU | A | 220 | 59.868 | −3.518 | 27.551 | 1.00 | 25.27 | A |
| ATOM | 1638 | CA | LEU | A | 220 | 58.987 | −2.375 | 27.446 | 1.00 | 26.84 | A |
| ATOM | 1639 | CB | LEU | A | 220 | 58.895 | −1.650 | 28.781 | 1.00 | 28.83 | A |
| ATOM | 1640 | CG | LEU | A | 220 | 57.759 | −.631 | 28.884 | 1.00 | 30.20 | A |
| ATOM | 1641 | CD1 | LEU | A | 220 | 56.406 | −1.338 | 28.717 | 1.00 | 30.95 | A |
| ATOM | 1642 | CD2 | LEU | A | 220 | 57.832 | .054 | 30.243 | 1.00 | 31.79 | A |
| ATOM | 1643 | C | LEU | A | 220 | 59.455 | −1.397 | 26.374 | 1.00 | 25.87 | A |
| ATOM | 1644 | O | LEU | A | 220 | 58.678 | −.973 | 25.536 | 1.00 | 25.32 | A |
| ATOM | 1645 | N | ALA | A | 221 | 60.737 | −1.037 | 26.408 | 1.00 | 27.07 | A |
| ATOM | 1646 | CA | ALA | A | 221 | 61.266 | −.101 | 25.435 | 1.00 | 25.56 | A |
| ATOM | 1647 | CB | ALA | A | 221 | 62.656 | .363 | 25.852 | 1.00 | 26.78 | A |
| ATOM | 1648 | C | ALA | A | 221 | 61.289 | −.711 | 24.038 | 1.00 | 23.26 | A |
| ATOM | 1649 | O | ALA | A | 221 | 61.087 | −.013 | 23.058 | 1.00 | 24.63 | A |
| ATOM | 1650 | N | LEU | A | 222 | 61.504 | −2.013 | 23.938 | 1.00 | 23.08 | A |
| ATOM | 1651 | CA | LEU | A | 222 | 61.503 | −2.661 | 22.628 | 1.00 | 23.30 | A |
| ATOM | 1652 | CB | LEU | A | 222 | 62.014 | −4.101 | 22.728 | 1.00 | 21.55 | A |
| ATOM | 1653 | CG | LEU | A | 222 | 62.050 | −4.926 | 21.437 | 1.00 | 23.49 | A |
| ATOM | 1654 | CD1 | LEU | A | 222 | 62.997 | −4.286 | 20.417 | 1.00 | 23.59 | A |
| ATOM | 1655 | CD2 | LEU | A | 222 | 62.533 | −6.326 | 21.761 | 1.00 | 24.91 | A |
| ATOM | 1656 | C | LEU | A | 222 | 60.091 | −2.655 | 22.056 | 1.00 | 23.53 | A |
| ATOM | 1657 | O | LEU | A | 222 | 59.904 | −2.391 | 20.867 | 1.00 | 21.82 | A |
| ATOM | 1658 | N | ALA | A | 223 | 59.100 | −2.951 | 22.896 | 1.00 | 23.35 | A |
| ATOM | 1659 | CA | ALA | A | 223 | 57.718 | −2.947 | 22.420 | 1.00 | 23.76 | A |
| ATOM | 1660 | CB | ALA | A | 223 | 56.778 | −3.378 | 23.528 | 1.00 | 24.49 | A |
| ATOM | 1661 | C | ALA | A | 223 | 57.366 | −1.552 | 21.934 | 1.00 | 24.90 | A |
| ATOM | 1662 | O | ALA | A | 223 | 56.734 | −1.389 | 20.894 | 1.00 | 24.19 | A |
| ATOM | 1663 | N | GLU | A | 224 | 57.801 | −.541 | 22.684 | 1.00 | 26.47 | A |
| ATOM | 1664 | CA | GLU | A | 224 | 57.547 | .847 | 22.314 | 1.00 | 28.65 | A |
| ATOM | 1665 | CB | GLU | A | 224 | 58.106 | 1.779 | 23.388 | 1.00 | 31.36 | A |
| ATOM | 1666 | CG | GLU | A | 224 | 58.017 | 3.242 | 23.027 | 1.00 | 36.03 | A |
| ATOM | 1667 | CD | GLU | A | 224 | 58.625 | 4.139 | 24.097 | 1.00 | 37.40 | A |
| ATOM | 1668 | OE1 | GLU | A | 224 | 59.707 | 3.810 | 24.630 | 1.00 | 40.58 | A |
| ATOM | 1669 | OE2 | GLU | A | 224 | 58.023 | 5.181 | 24.390 | 1.00 | 39.57 | A |
| ATOM | 1670 | C | GLU | A | 224 | 58.182 | 1.162 | 20.955 | 1.00 | 29.18 | A |
| ATOM | 1671 | O | GLU | A | 224 | 57.601 | 1.875 | 20.138 | 1.00 | 27.89 | A |
| ATOM | 1672 | N | PHE | A | 225 | 59.371 | .612 | 20.715 | 1.00 | 28.71 | A |
| ATOM | 1673 | CA | PHE | A | 225 | 60.078 | .815 | 19.451 | 1.00 | 28.52 | A |
| ATOM | 1674 | CB | PHE | A | 225 | 61.475 | .176 | 19.524 | 1.00 | 28.57 | A |
| ATOM | 1675 | CG | PHE | A | 225 | 62.178 | .085 | 18.187 | 1.00 | 27.70 | A |
| ATOM | 1676 | CD1 | PHE | A | 225 | 62.774 | 1.207 | 17.616 | 1.00 | 29.44 | A |
| ATOM | 1677 | CD2 | PHE | A | 225 | 62.211 | −1.122 | 17.480 | 1.00 | 28.27 | A |
| ATOM | 1678 | CE1 | PHE | A | 225 | 63.380 | 1.130 | 16.370 | 1.00 | 27.78 | A |
| ATOM | 1679 | CE2 | PHE | A | 225 | 62.820 | −1.205 | 16.229 | 1.00 | 28.89 | A |
| ATOM | 1680 | CZ | PHE | A | 225 | 63.404 | −.078 | 15.671 | 1.00 | 28.69 | A |
| ATOM | 1681 | C | PHE | A | 225 | 59.281 | .182 | 18.307 | 1.00 | 30.36 | A |
| ATOM | 1682 | O | PHE | A | 225 | 59.064 | .799 | 17.262 | 1.00 | 30.81 | A |
| ATOM | 1683 | N | TYR | A | 226 | 58.836 | −1.056 | 18.493 | 1.00 | 29.52 | A |
| ATOM | 1684 | CA | TYR | A | 226 | 58.079 | −1.730 | 17.440 | 1.00 | 30.72 | A |
| ATOM | 1685 | CB | TYR | A | 226 | 57.796 | −3.188 | 17.824 | 1.00 | 29.06 | A |
| ATOM | 1686 | CG | TYR | A | 226 | 59.000 | −4.098 | 17.729 | 1.00 | 27.52 | A |
| ATOM | 1687 | CD1 | TYR | A | 226 | 59.185 | −5.113 | 18.653 | 1.00 | 28.12 | A |
| ATOM | 1688 | CE1 | TYR | A | 226 | 60.248 | −5.993 | 18.561 | 1.00 | 29.18 | A |
| ATOM | 1689 | CD2 | TYR | A | 226 | 59.928 | −3.983 | 16.686 | 1.00 | 29.15 | A |
| ATOM | 1690 | CE2 | TYR | A | 226 | 61.005 | −4.867 | 16.585 | 1.00 | 28.48 | A |
| ATOM | 1691 | CZ | TYR | A | 226 | 61.158 | −5.866 | 17.520 | 1.00 | 29.84 | A |
| ATOM | 1692 | OH | TYR | A | 226 | 62.203 | −6.761 | 17.462 | 1.00 | 31.49 | A |
| ATOM | 1693 | C | TYR | A | 226 | 56.765 | −1.020 | 17.096 | 1.00 | 32.01 | A |
| ATOM | 1694 | O | TYR | A | 226 | 56.400 | −.924 | 15.918 | 1.00 | 32.48 | A |
| ATOM | 1695 | N | LEU | A | 227 | 56.043 | −.544 | 18.108 | 1.00 | 33.13 | A |
| ATOM | 1696 | CA | LEU | A | 227 | 54.784 | .155 | 17.843 | 1.00 | 35.84 | A |
| ATOM | 1697 | CB | LEU | A | 227 | 54.136 | .606 | 19.162 | 1.00 | 35.21 | A |
| ATOM | 1698 | CG | LEU | A | 227 | 53.498 | −.535 | 19.968 | 1.00 | 34.38 | A |
| ATOM | 1699 | CD1 | LEU | A | 227 | 53.211 | −.093 | 21.393 | 1.00 | 36.57 | A |
| ATOM | 1700 | CD2 | LEU | A | 227 | 62.226 | −.985 | 19.280 | 1.00 | 31.83 | A |
| ATOM | 1701 | C | LEU | A | 227 | 55.075 | 1.352 | 16.918 | 1.00 | 38.28 | A |
| ATOM | 1702 | O | LEU | A | 227 | 54.316 | 1.624 | 15.978 | 1.00 | 38.83 | A |
| ATOM | 1703 | N | ALA | A | 228 | 56.195 | 2.030 | 17.178 | 1.00 | 39.66 | A |
| ATOM | 1704 | CA | ALA | A | 228 | 56.647 | 3.179 | 16.385 | 1.00 | 41.19 | A |
| ATOM | 1705 | CB | ALA | A | 228 | 55.458 | 4.010 | 15.931 | 1.00 | 42.11 | A |
| ATOM | 1706 | C | ALA | A | 228 | 57.617 | 4.063 | 17.165 | 1.00 | 41.86 | A |
| ATOM | 1707 | O | ALA | A | 228 | 57.670 | 3.999 | 18.397 | 1.00 | 43.53 | A |
| ATOM | 1708 | N | ARG | A | 229 | 58.388 | 4.883 | 16.445 | 1.00 | 42.26 | A |
| ATOM | 1709 | CA | ARG | A | 229 | 59.347 | 5.813 | 17.067 | 1.00 | 42.80 | A |
| ATOM | 1710 | CB | ARG | A | 229 | 60.517 | 5.049 | 17.712 | 1.00 | 42.26 | A |

APPENDIX 2-continued

X-RAY DATA COORDINATES FOR CDP-ME SYNTHASE
COMPLEXED WITH CTP•Mg$^{2+}$
(SEQ ID NO: 11)

| ATOM | 1711 | CG | ARG | A | 229 | 61.470 | 4.368 | 16.711 | 1.00 | 41.20 | A |
|------|------|-----|-----|---|-----|--------|--------|--------|------|-------|---|
| ATOM | 1712 | CD | ARG | A | 229 | 62.923 | 4.350 | 17.224 | 1.00 | 40.43 | A |
| ATOM | 1713 | NE | ARG | A | 229 | 63.616 | 5.639 | 17.075 | 1.00 | 41.57 | A |
| ATOM | 1714 | CZ | ARG | A | 229 | 64.884 | 5.861 | 17.439 | 1.00 | 40.59 | A |
| ATOM | 1715 | NH1 | ARG | A | 229 | 65.604 | 4.875 | 17.982 | 1.00 | 39.90 | A |
| ATOM | 1716 | NH2 | ARG | A | 229 | 65.441 | 7.060 | 17.245 | 1.00 | 38.59 | A |
| ATOM | 1717 | C | ARG | A | 229 | 59.927 | 6.835 | 16.076 | 1.00 | 43.60 | A |
| ATOM | 1718 | O | ARG | A | 229 | 61.020 | 7.381 | 16.389 | 1.00 | 44.29 | A |
| ATOM | 1719 | OXT | ARG | A | 229 | 59.290 | 7.088 | 15.018 | 1.00 | 44.84 | A |
| ATOM | 1720 | OH2 | WAT | W | 1 | 69.448 | -25.156 | 14.038 | 1.00 | 19.25 | W |
| ATOM | 1721 | OH2 | WAT | W | 2 | 51.629 | -9.080 | 14.253 | 1.00 | 19.44 | W |
| ATOM | 1722 | OH2 | WAT | W | 3 | 35.094 | -2.771 | 18.279 | 1.00 | 19.45 | W |
| ATOM | 1723 | OH2 | WAT | W | 4 | 33.976 | -26.705 | 18.662 | 1.00 | 17.10 | W |
| ATOM | 1724 | OH2 | WAT | W | 5 | 52.813 | -12.455 | 14.557 | 1.00 | 16.38 | W |
| ATOM | 1725 | OH2 | WAT | W | 6 | 53.187 | -8.229 | 20.463 | 1.00 | 19.20 | W |
| ATOM | 1726 | OH2 | WAT | W | 7 | 49.268 | -3.449 | 17.985 | 1.00 | 22.05 | W |
| ATOM | 1727 | OH2 | WAT | W | 8 | 46.964 | -3.745 | 15.057 | 1.00 | 21.55 | W |
| ATOM | 1728 | OH2 | WAT | W | 9 | 44.646 | -8.817 | 36.606 | 1.00 | 23.99 | W |
| ATOM | 1729 | OH2 | WAT | W | 10 | 30.477 | -29.293 | 23.227 | 1.00 | 23.15 | W |
| ATOM | 1730 | OH2 | WAT | W | 11 | 34.173 | -22.952 | 10.668 | 1.00 | 24.71 | W |
| ATOM | 1731 | OH2 | WAT | W | 12 | 53.670 | -7.692 | 15.168 | 1.00 | 22.43 | W |
| ATOM | 1732 | OH2 | WAT | W | 13 | 32.609 | -24.270 | 18.778 | 1.00 | 21.27 | W |
| ATOM | 1733 | OH2 | WAT | W | 14 | 63.052 | -22.277 | 10.587 | 1.00 | 33.72 | W |
| ATOM | 1734 | OH2 | WAT | W | 15 | 65.031 | -17.416 | 16.052 | 1.00 | 25.01 | W |
| ATOM | 1735 | OH2 | WAT | W | 16 | 32.872 | -.430 | 19.340 | 1.00 | 25.07 | W |
| ATOM | 1736 | OH2 | WAT | W | 17 | 53.296 | -27.934 | 26.071 | 1.00 | 23.84 | W |
| ATOM | 1737 | OH2 | WAT | W | 18 | 58.482 | -12.425 | 22.987 | 1.00 | 28.79 | W |
| ATOM | 1738 | OH2 | WAT | W | 19 | 48.329 | -3.258 | 11.821 | 1.00 | 29.93 | W |
| ATOM | 1739 | OH2 | WAT | W | 20 | 37.906 | -13.579 | 7.975 | 1.00 | 24.45 | W |
| ATOM | 1740 | OH2 | WAT | W | 21 | 52.857 | -31.323 | 22.008 | 1.00 | 26.31 | W |
| ATOM | 1741 | OH2 | WAT | W | 22 | 64.836 | -31.087 | 20.394 | 1.00 | 29.98 | W |
| ATOM | 1742 | OH2 | WAT | W | 23 | 31.920 | -28.284 | 25.506 | 1.00 | 28.02 | W |
| ATOM | 1743 | OH2 | WAT | W | 24 | 57.175 | -25.382 | 8.480 | 1.00 | 30.36 | W |
| ATOM | 1744 | OH2 | WAT | W | 25 | 60.385 | -22.881 | 10.307 | 1.00 | 31.03 | W |
| ATOM | 1745 | OH2 | WAT | W | 26 | 28.837 | -17.540 | 27.739 | 1.00 | 28.41 | W |
| ATOM | 1746 | OH2 | WAT | W | 27 | 36.224 | -10.019 | 37.482 | 1.00 | 33.45 | W |
| ATOM | 1747 | OH2 | WAT | W | 28 | 40.247 | -12.011 | 8.115 | 1.00 | 25.12 | iW |
| ATOM | 1748 | OH2 | WAT | W | 29 | 57.911 | -14.191 | 10.103 | 1.00 | 27.69 | W |
| ATOM | 1749 | OH2 | WAT | W | 30 | 56.765 | -10.849 | 33.082 | 1.00 | 24.56 | W |
| ATOM | 1750 | OH2 | WAT | W | 31 | 42.902 | -7.474 | 10.867 | 1.00 | 26.36 | W |
| ATOM | 1751 | OH2 | WAT | W | 32 | 46.979 | -2.034 | 19.107 | 1.00 | 31.70 | W |
| ATOM | 1752 | OH2 | WAT | W | 33 | 32.230 | -6.221 | 32.176 | 1.00 | 36.61 | W |
| ATOM | 1753 | OH2 | WAT | W | 34 | 45.253 | -18.307 | 6.591 | 1.00 | 32.11 | W |
| ATOM | 1754 | OH2 | WAT | W | 35 | 62.705 | -9.347 | 19.162 | 1.00 | 30.56 | W |
| ATOM | 1755 | OH2 | WAT | W | 36 | 40.108 | -1.214 | 17.645 | 1.00 | 26.43 | W |
| ATOM | 1756 | OH2 | WAT | W | 37 | 55.363 | -18.633 | 23.017 | 1.00 | 28.90 | W |
| ATOM | 1757 | OH2 | WAT | W | 38 | 46.034 | -4.757 | 39.584 | 1.00 | 32.73 | W |
| ATOM | 1758 | OH2 | WAT | W | 39 | 47.165 | -8.807 | 37.988 | 1.00 | 26.93 | W |
| ATOM | 1759 | OH2 | WAT | W | 40 | 33.578 | -17.230 | 13.377 | 1.00 | 24.83 | W |
| ATOM | 1760 | OH2 | WAT | W | 41 | 39.144 | -3.601 | 38.556 | 1.00 | 28.45 | W |
| ATOM | 1761 | OH2 | WAT | W | 42 | 62.456 | -.794 | 28.993 | 1.00 | 34.38 | W |
| ATOM | 1762 | OH2 | WAT | W | 43 | 71.052 | -22.967 | 11.198 | 1.00 | 26.39 | W |
| ATOM | 1763 | OH2 | WAT | W | 44 | 48.533 | -22.257 | 7.819 | 1.00 | 40.61 | W |
| ATOM | 1764 | OH2 | WAT | W | 45 | 58.944 | -11.053 | 10.727 | 1.00 | 33.19 | W |
| ATOM | 1765 | OH2 | WAT | W | 46 | 30.123 | -6.475 | 16.324 | 1.00 | 43.29 | W |
| ATOM | 1766 | OH2 | WAT | W | 47 | 34.004 | -17.324 | 33.764 | 1.00 | 35.82 | W |
| ATOM | 1767 | OH2 | WAT | W | 48 | 44.071 | -31.670 | 13.539 | 1.00 | 35.88 | W |
| ATOM | 1768 | OH2 | WAT | W | 49 | 30.210 | -17.690 | 15.712 | 1.00 | 33.61 | W |
| ATOM | 1769 | OH2 | WAT | W | 50 | 65.239 | -3.633 | 24.753 | 1.00 | 33.85 | W |
| ATOM | 1770 | OH2 | WAT | W | 51 | 70.276 | -33.334 | 25.730 | 1.00 | 40.63 | W |
| ATOM | 1771 | OH2 | WAT | W | 52 | 76.400 | -36.099 | 20.668 | 1.00 | 45.57 | W |
| ATOM | 1772 | OH2 | WAT | W | 53 | 35.088 | 2.210 | 26.432 | 1.00 | 39.60 | W |
| ATOM | 1773 | OH2 | WAT | W | 54 | 48.956 | -22.613 | 32.043 | 1.00 | 33.99 | W |
| ATOM | 1774 | OH2 | WAT | W | 55 | 35.005 | -31.090 | 21.279 | 1.00 | 36.47 | W |
| ATOM | 1775 | OH2 | WAT | W | 56 | 51.619 | -18.908 | 6.646 | 1.00 | 32.67 | W |
| ATOM | 1776 | OH2 | WAT | W | 57 | 70.171 | -13.596 | 17.282 | 1.00 | 37.33 | W |
| ATOM | 1777 | OH2 | WAT | W | 58 | 41.071 | 1.986 | 25.759 | 1.00 | 35.25 | W |
| ATOM | 1778 | OH2 | WAT | W | 59 | 41.954 | -36.091 | 16.951 | 1.00 | 38.23 | W |
| ATOM | 1779 | OH2 | WAT | W | 60 | 38.880 | -.276 | 19.849 | 1.00 | 33.93 | W |
| ATOM | 1780 | OH2 | WAT | W | 61 | 48.770 | -34.232 | 18.536 | 1.00 | 28.36 | W |
| ATOM | 1781 | OH2 | WAT | W | 62 | 27.373 | -13.659 | 11.856 | 1.00 | 44.81 | W |
| ATOM | 1782 | OH2 | WAT | W | 63 | 67.113 | -32.058 | 15.222 | 1.00 | 35.19 | W |
| ATOM | 1783 | OH2 | WAT | W | 64 | 36.028 | -26.826 | 32.399 | 1.00 | 44.47 | W |
| ATOM | 1784 | OH2 | WAT | W | 65 | 27.443 | -22.432 | 24.743 | 1.00 | 45.82 | W |
| ATOM | 1785 | OH2 | WAT | W | 66 | 46.041 | -22.664 | 27.737 | 1.00 | 39.93 | W |

APPENDIX 2-continued

X-RAY DATA COORDINATES FOR CDP-ME SYNTHASE COMPLEXED WITH CTP·Mg$^{2+}$
(SEQ ID NO: 11)

| ATOM | 1786 | OH2 | WAT | W | 67 | 48.911 | −4.662 | 9.464 | 1.00 | 40.99 | W |
|---|---|---|---|---|---|---|---|---|---|---|---|
| ATOM | 1787 | OH2 | WAT | W | 68 | 62.896 | −30.845 | 10.163 | 1.00 | 47.19 | W |
| ATOM | 1788 | OH2 | WAT | W | 69 | 38.979 | −21.653 | 35.297 | 1.00 | 34.19 | W |
| ATOM | 1789 | OH2 | WAT | W | 70 | 30.860 | −10.334 | 10.875 | 1.00 | 45.08 | W |
| ATOM | 1790 | OH2 | WAT | W | 71 | 61.598 | 2.792 | 22.912 | 1.00 | 30.93 | W |
| ATOM | 1791 | OH2 | WAT | W | 72 | 70.989 | −28.099 | 30.502 | 1.00 | 35.60 | W |
| ATOM | 1792 | OH2 | WAT | W | 73 | 41.470 | −4.255 | 10.603 | 1.00 | 38.04 | W |
| ATOM | 1793 | OH2 | WAT | W | 74 | 60.498 | −4.583 | 13.363 | 1.00 | 36.79 | W |
| ATOM | 1794 | OH2 | WAT | W | 75 | 25.770 | −16.859 | 14.722 | 1.00 | 41.59 | W |
| ATOM | 1795 | OH2 | WAT | W | 76 | 38.461 | −8.889 | 40.013 | 1.00 | 45.19 | W |
| ATOM | 1796 | OH2 | WAY | W | 77 | 35.499 | −25.365 | 10.662 | 1.00 | 33.83 | W |
| ATOM | 1797 | OH2 | WAT | W | 78 | 43.480 | .173 | 44.832 | 1.00 | 42.02 | W |
| ATOM | 1798 | OH2 | WAT | W | 79 | 31.524 | −3.075 | 29.751 | 1.00 | 35.54 | W |
| ATOM | 1799 | OH2 | WAT | W | 80 | 45.075 | 4.120 | 30.144 | 1.00 | 38.37 | W |
| ATOM | 1800 | OH2 | WAT | W | 81 | 48.180 | .505 | 19.595 | 1.00 | 35.81 | W |
| ATOM | 1801 | OH2 | WAT | W | 82 | 29.171 | −6.346 | 18.717 | 1.00 | 28.48 | W |
| ATOM | 1802 | OH2 | WAT | W | 83 | 53.483 | −2.873 | 16.260 | 1.00 | 43.90 | W |
| ATOM | 1803 | OH2 | WAT | W | 84 | 35.821 | −28.944 | 14.638 | 1.00 | 35.73 | W |
| ATOM | 1804 | OH2 | WAT | W | 85 | 40.906 | −36.893 | 20.980 | 1.00 | 35.50 | W |
| ATOM | 1805 | OH2 | WAT | W | 86 | 59.031 | −8.257 | 12.538 | 1.00 | 35.32 | W |
| ATOM | 1806 | OH2 | WAT | W | 87 | 45.069 | −4.274 | 41.958 | 1.00 | 42.19 | W |
| ATOM | 1807 | OH2 | WAT | W | 88 | 33.935 | −26.360 | 8.450 | 1.00 | 46.56 | W |
| ATOM | 1808 | OH2 | WAT | W | 89 | 50.726 | −19.821 | 34.058 | 1.00 | 34.18 | W |
| ATOM | 1809 | OH2 | WAT | W | 90 | 30.250 | −14.642 | 21.689 | 1.00 | 46.63 | W |
| ATOM | 1810 | OH2 | WAT | W | 91 | 43.569 | −20.524 | 5.629 | 1.00 | 41.80 | W |
| ATOM | 1811 | OH2 | WAT | W | 92 | 43.598 | 4.858 | 27.547 | 1.00 | 48.67 | W |
| ATOM | 1812 | OH2 | WAT | W | 93 | 70.776 | −30.681 | 13.045 | 1.00 | 39.65 | W |
| ATOM | 1813 | OH2 | WAT | W | 94 | 61.250 | −9.574 | 23.706 | 1.00 | 53.54 | W |
| ATOM | 1814 | OH2 | WAT | W | 95 | 42.048 | −26.632 | 3.893 | 1.00 | 44.43 | W |
| ATOM | 1815 | OH2 | WAT | W | 96 | 73.449 | −35.614 | 21.545 | 1.00 | 43.76 | W |
| ATOM | 1816 | OH2 | WAT | W | 97 | 50.473 | −31.183 | 24.728 | 1.00 | 35.59 | W |
| ATOM | 1817 | OH2 | WAT | W | 98 | 55.802 | 5.390 | 25.935 | 1.00 | 41.22 | W |
| ATOM | 1818 | OH2 | WAT | W | 99 | 34.348 | .839 | 36.171 | 1.00 | 45.05 | W |
| ATOM | 1819 | OH2 | WAT | W | 100 | 46.884 | −17.753 | 22.952 | 1.00 | 35.80 | W |
| ATOM | 1820 | OH2 | WAT | W | 101 | 26.922 | −14.117 | 27.132 | 1.00 | 46.51 | W |
| ATOM | 1821 | OH2 | WAT | W | 102 | 53.597 | .015 | 13.685 | 1.00 | 46.00 | W |
| ATOM | 1822 | OH2 | WAT | W | 103 | 29.284 | .348 | 31.420 | 1.00 | 47.14 | W |
| ATOM | 1823 | OH2 | WAT | W | 104 | 48.259 | 4.708 | 29.823 | 1.00 | 41.93 | W |
| ATOM | 1824 | OH2 | WAT | W | 105 | 38.149 | −1.183 | 12.378 | 1.00 | 49.01 | W |
| ATOM | 1825 | OH2 | WAY | W | 106 | 49.201 | −17.271 | 4.613 | 1.00 | 45.33 | W |
| ATOM | 1826 | OH2 | WAT | W | 107 | 49.073 | 1.385 | 38.522 | 1.00 | 52.18 | W |
| ATOM | 1827 | OH2 | WAT | W | 108 | 43.631 | −37.270 | 24.443 | 1.00 | 45.09 | W |
| ATOM | 1828 | OH2 | WAT | W | 109 | 29.607 | −21.946 | 27.582 | 1.00 | 54.17 | W |
| ATOM | 1829 | OH2 | WAT | W | 110 | 43.992 | 4.341 | 34.902 | 1.00 | 40.51 | W |
| ATOM | 1830 | OH2 | WAT | W | 111 | 69.856 | −15.066 | 13.446 | 1.00 | 47.79 | W |
| ATOM | 1831 | OH2 | WAT | W | 112 | 42.488 | −17.308 | 40.806 | 1.00 | 48.50 | W |
| ATOM | 1832 | OH2 | WAT | W | 113 | 44.339 | 1.922 | 36.321 | 1.00 | 43.77 | W |
| ATOM | 1833 | OH2 | WAT | W | 114 | 29.531 | −8.002 | 25.167 | 1.00 | 47.17 | W |
| ATOM | 1834 | OH2 | WAT | W | 115 | 50.410 | −27.360 | 32.747 | 1.00 | 38.17 | W |
| ATOM | 1835 | OH2 | WAT | W | 116 | 72.814 | −25.951 | 33.355 | 1.00 | 44.83 | W |
| ATOM | 1836 | OH2 | WAT | W | 117 | 45.342 | −9.204 | 42.273 | 1.00 | 45.61 | W |
| ATOM | 1837 | OH2 | WAT | W | 118 | 68.809 | −26.532 | 9.279 | 1.00 | 52.23 | W |
| ATOM | 1838 | OH2 | WAT | W | 119 | 57.553 | −16.365 | 29.345 | 1.00 | 53.39 | W |
| ATOM | 1839 | OH2 | WAT | W | 120 | 33.819 | −4.277 | 32.940 | 1.00 | 44.22 | W |
| ATOM | 1840 | OH2 | WAT | W | 121 | 41.602 | −28.871 | 9.657 | 1.00 | 52.21 | W |
| ATOM | 1841 | OH2 | WAT | W | 122 | 76.991 | −34.057 | 30.451 | 1.00 | 51.83 | W |
| ATOM | 1842 | OH2 | WAT | W | 123 | 35.454 | −23.777 | 36.483 | 1.00 | 44.51 | W |
| ATOM | 1843 | OH2 | WAT | W | 124 | 35.956 | −3.455 | 13.747 | 1.00 | 20.11 | W |
| ATOM | 1844 | OH2 | WAT | W | 125 | 26.420 | −24.149 | 18.076 | 1.00 | 21.34 | W |
| ATOM | 1845 | OH2 | WAT | W | 126 | 35.334 | −5.667 | 15.906 | 1.00 | 17.94 | W |
| ATOM | 1846 | OH2 | WAT | W | 127 | 51.836 | −17.626 | 32.782 | 1.00 | 29.22 | W |
| ATOM | 1847 | OH2 | WAT | W | 128 | 75.887 | −33.979 | 16.553 | 1.00 | 34.80 | W |
| ATOM | 1848 | OH2 | WAT | W | 129 | 34.342 | −2.331 | 11.862 | 1.00 | 28.03 | W |
| ATOM | 1849 | OH2 | WAT | W | 130 | 36.621 | −1.176 | 16.079 | 1.00 | 24.77 | W |
| ATOM | 1850 | OH2 | WAT | W | 131 | 28.212 | −4.740 | 21.363 | 1.00 | 27.12 | W |
| ATOM | 1851 | OH2 | WAT | W | 132 | 45.780 | −1.666 | 16.693 | 1.00 | 33.94 | W |
| ATOM | 1852 | OH2 | WAT | W | 133 | 61.756 | −15.215 | 13.972 | 1.00 | 36.57 | W |
| ATOM | 1853 | OH2 | WAT | W | 134 | 70.339 | −25.918 | 11.680 | 1.00 | 41.19 | W |
| ATOM | 1854 | OH2 | WAT | W | 135 | 35.992 | −1.863 | 9.266 | 1.00 | 42.97 | W |
| ATOM | 1855 | OH2 | WAT | W | 136 | 50.974 | −34.015 | 23.709 | 1.00 | 36.59 | W |
| ATOM | 1856 | OH2 | WAT | W | 137 | 52.968 | −30.322 | 24.594 | 1.00 | 33.07 | W |
| ATOM | 1857 | OH2 | WAT | W | 138 | 32.457 | −22.711 | 29.325 | 1.00 | 41.34 | W |
| ATOM | 1858 | OH2 | WAT | W | 139 | 52.360 | −18.647 | 22.969 | 1.00 | 40.41 | W |
| ATOM | 1859 | OH2 | WAT | W | 140 | 40.111 | −10.431 | 6.148 | 1.00 | 39.66 | W |
| ATOM | 1860 | OH2 | WAT | W | 141 | 50.498 | −10.197 | 33.090 | 1.00 | 27.16 | W |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 1861 | OH2 | WAT | W | 142 | 41.341 | −6.537 | 8.677 | 1.00 | 38.44 | W |
|------|------|-----|-----|---|-----|--------|--------|-------|------|-------|---|
| ATOM | 1862 | OH2 | WAT | W | 143 | 71.957 | −35.628 | 25.409 | 1.00 | 45.01 | W |
| ATOM | 1863 | OH2 | WAT | W | 144 | 46.276 | 7.530 | 23.751 | 1.00 | 35.30 | W |
| ATOM | 1864 | OH2 | WAT | W | 145 | 52.457 | −16.102 | 24.301 | 1.00 | 35.80 | W |
| ATOM | 1865 | OH2 | WAT | W | 146 | 65.653 | 1.880 | 25.790 | 1.00 | 45.54 | W |
| ATOM | 1866 | OH2 | WAT | W | 147 | 60.922 | 1.944 | 29.217 | 1.00 | 42.43 | W |
| ATOM | 1867 | OH2 | WAT | W | 148 | 33.963 | −31.564 | 17.274 | 1.00 | 42.53 | W |
| ATOM | 1868 | OH2 | WAT | W | 149 | 71.503 | −28.467 | 11.200 | 1.00 | 47.55 | W |
| ATOM | 1869 | OH2 | WAT | W | 150 | 22.889 | −23.504 | 23.317 | 1.00 | 46.29 | W |
| ATOM | 1870 | OH2 | WAT | W | 151 | 61.185 | −24.301 | 7.822 | 1.00 | 48.60 | W |
| ATOM | 1871 | OH2 | WAT | W | 152 | 46.876 | −7.023 | 40.154 | 1.00 | 35.08 | W |
| ATOM | 1872 | OH2 | WAT | W | 153 | 46.438 | 3.775 | 32.997 | 1.00 | 40.75 | W |
| ATOM | 1873 | OH2 | WAT | W | 154 | 64.718 | −32.295 | 25.408 | 1.00 | 42.98 | W |
| ATOM | 1874 | OH2 | WAT | W | 155 | 42.473 | −39.610 | 18.372 | 1.00 | 46.94 | W |
| ATOM | 1875 | OH2 | WAT | W | 156 | 69.222 | −29.469 | 29.868 | 1.00 | 40.57 | W |
| ATOM | 1876 | OH2 | WAT | W | 157 | 34.446 | −16.952 | 21.371 | 1.00 | 38.02 | W |
| ATOM | 1877 | OH2 | WAT | W | 158 | 34.991 | −18.870 | 36.219 | 1.00 | 43.38 | W |
| ATOM | 1878 | OH2 | WAT | W | 159 | 27.403 | −10.163 | 12.857 | 1.00 | 43.36 | W |
| ATOM | 1879 | OH2 | WAT | W | 160 | 50.552 | −2.554 | 15.092 | 1.00 | 43.22 | W |
| ATOM | 1880 | OH2 | WAT | W | 161 | 36.848 | −4.712 | 37.819 | 1.00 | 38.63 | W |
| ATOM | 1881 | OH2 | WAT | W | 162 | 47.421 | −19.832 | 6.445 | 1.00 | 34.37 | W |
| ATOM | 1882 | OH2 | WAT | W | 163 | 52.088 | −13.745 | 37.632 | 1.00 | 38.45 | W |
| ATOM | 1883 | OH2 | WAT | W | 164 | 39.009 | .406 | 41.089 | 1.00 | 45.81 | W |
| ATOM | 1884 | OH2 | WAT | W | 165 | 38.735 | −5.971 | 7.602 | 1.00 | 44.46 | W |
| ATOM | 1885 | OH2 | WAT | W | 166 | 43.315 | −38.052 | 16.613 | 1.00 | 31.70 | W |
| ATOM | 1886 | OH2 | WAT | W | 167 | 28.029 | −15.136 | 30.655 | 1.00 | 46.08 | W |
| ATOM | 1887 | OH2 | WAT | W | 168 | 52.118 | −18.161 | 30.268 | 1.00 | 34.55 | W |
| ATOM | 1888 | OH2 | WAT | W | 169 | 54.611 | −15.578 | 39.069 | 1.00 | 49.12 | W |
| ATOM | 1889 | OH2 | WAT | W | 170 | 47.011 | 1.112 | 36.528 | 1.00 | 39.43 | W |
| ATOM | 1890 | OH2 | WAT | W | 171 | 66.939 | −32.091 | 20.971 | 1.00 | 52.76 | W |
| ATOM | 1891 | OH2 | WAT | W | 172 | 54.817 | −6.405 | 36.064 | 1.00 | 39.35 | W |
| ATOM | 1892 | OH2 | WAT | W | 173 | 35.310 | −3.699 | 36.035 | 1.00 | 43.30 | W |
| ATOM | 1893 | OH2 | WAT | W | 174 | 44.315 | −39.693 | 32.948 | 1.00 | 48.37 | W |
| ATOM | 1894 | OH2 | WAT | W | 175 | 59.742 | −16.330 | 6.340 | 1.00 | 46.29 | W |
| ATOM | 1895 | OH2 | WAT | W | 176 | 39.508 | −19.813 | 37.366 | 1.00 | 48.68 | W |
| ATOM | 1896 | OH2 | WAT | W | 177 | 47.206 | 7.430 | 31.997 | 1.00 | 55.90 | W |
| ATOM | 1897 | OH2 | WAT | W | 178 | 57.228 | 2.950 | 27.978 | 1.00 | 50.55 | W |
| ATOM | 1898 | OH2 | WAT | W | 179 | 71.642 | −18.769 | 10.660 | 1.00 | 44.57 | W |
| ATOM | 1899 | OH2 | WAT | W | 180 | 37.162 | −15.558 | 41.938 | 1.00 | 42.54 | W |
| ATOM | 1900 | OH2 | WAT | W | 181 | 30.882 | −7.180 | 10.669 | 1.00 | 39.77 | W |
| ATOM | 1901 | OH2 | WAT | W | 182 | 37.267 | −36.743 | 34.407 | 1.00 | 47.56 | W |
| ATOM | 1902 | OH2 | WAT | W | 183 | 49.384 | −36.706 | 21.424 | 1.00 | 46.44 | W |
| ATOM | 1903 | OH2 | WAT | W | 184 | 53.237 | −11.013 | 8.153 | 1.00 | 46.36 | W |
| ATOM | 1904 | OH2 | WAT | W | 185 | 70.954 | −24.207 | 35.281 | 1.00 | 48.28 | W |
| ATOM | 1905 | OH2 | WAT | W | 186 | 66.735 | −35.337 | 14.211 | 1.00 | 49.52 | W |
| ATOM | 1906 | OH2 | WAT | W | 187 | 37.554 | −15.247 | 5.842 | 1.00 | 43.58 | W |
| ATOM | 1907 | OH2 | WAT | W | 188 | 54.383 | −18.359 | 5.274 | 1.00 | 40.83 | W |
| ATOM | 1908 | OH2 | WAT | W | 189 | 31.174 | −11.621 | 33.508 | 1.00 | 42.08 | W |
| ATOM | 1909 | OH2 | WAT | W | 190 | 61.773 | −11.468 | 17.554 | 1.00 | 39.47 | W |
| ATOM | 1910 | OH2 | WAT | W | 191 | 50.934 | 2.770 | 33.359 | 1.00 | 50.16 | W |
| ATOM | 1911 | OH2 | WAT | W | 192 | 56.642 | 1.618 | 12.516 | 1.00 | 50.38 | W |
| ATOM | 1912 | OH2 | WAT | W | 193 | 45.142 | −14.488 | 41.340 | 1.00 | 46.57 | W |
| ATOM | 1913 | OH2 | WAT | W | 194 | 50.164 | −11.058 | 6.895 | 1.00 | 44.72 | W |
| ATOM | 1914 | OH2 | WAT | W | 195 | 44.049 | −23.801 | 1.940 | 1.00 | 56.77 | W |
| ATOM | 1915 | OH2 | WAT | W | 196 | 30.026 | −21.121 | 32.514 | 1.00 | 50.64 | W |
| ATOM | 1916 | OH2 | WAT | W | 197 | 79.798 | −34.870 | 27.305 | 1.00 | 50.13 | W |
| ATOM | 1917 | OH2 | WAT | W | 198 | 37.302 | −31.443 | 15.126 | 1.00 | 46.26 | W |
| ATOM | 1918 | OH2 | WAT | W | 199 | 68.876 | −15.087 | 19.694 | 1.00 | 48.70 | W |
| ATOM | 1919 | OH2 | WAT | W | 200 | 65.534 | −6.053 | 23.933 | 1.00 | 56.28 | W |
| ATOM | 1920 | OH2 | WAT | W | 201 | 46.408 | 1.708 | 46.434 | 1.00 | 50.11 | W |
| ATOM | 1921 | OH2 | WAT | W | 202 | 54.541 | −12.954 | 41.868 | 1.00 | 44.25 | W |
| ATOM | 1922 | OH2 | WAT | W | 203 | 38.264 | −34.103 | 25.307 | 1.00 | 44.15 | W |
| ATOM | 1923 | OH2 | WAT | W | 204 | 39.636 | −18.372 | −.362 | 1.00 | 50.52 | W |
| ATOM | 1924 | OH2 | WAT | W | 205 | 55.146 | 6.711 | 14.832 | 1.00 | 45.80 | W |
| ATOM | 1925 | OH2 | WAT | W | 206 | 58.491 | −5.322 | 42.521 | 1.00 | 48.34 | W |
| ATOM | 1926 | OH2 | WAT | W | 207 | 54.006 | −36.570 | 31.956 | 1.00 | 43.54 | W |
| ATOM | 1927 | OH2 | WAT | W | 208 | 36.814 | −20.783 | 1.406 | 1.00 | 47.70 | W |
| ATOM | 1928 | OH2 | WAT | W | 209 | 49.487 | −8.123 | 41.799 | 1.00 | 58.41 | W |
| ATOM | 1929 | OH2 | WAT | W | 210 | 51.485 | .847 | 40.395 | 1.00 | 49.26 | W |
| ATOM | 1930 | OH2 | WAT | W | 211 | 34.265 | −15.199 | 40.327 | 1.00 | 55.47 | W |
| ATOM | 1931 | OH2 | WAT | W | 212 | 26.486 | −14.582 | 34.221 | 1.00 | 50.72 | W |
| ATOM | 1932 | OH2 | WAT | W | 213 | 66.916 | −10.088 | 31.137 | 1.00 | 47.49 | W |
| ATOM | 1933 | OH2 | WAT | W | 214 | 61.880 | −8.393 | 13.804 | 1.00 | 48.18 | W |
| ATOM | 1934 | OH2 | WAT | W | 215 | 52.178 | −17.094 | 27.375 | 1.00 | 45.11 | W |
| ATOM | 1935 | OH2 | WAT | W | 216 | 49.521 | −18.667 | 24.459 | 1.00 | 49.30 | W |

APPENDIX 2-continued

X-RAY DATA COORDINATES FOR CDP-ME SYNTHASE COMPLEXED WITH CTP•Mg$^{2+}$
(SEQ ID NO: 11)

| ATOM | 1936 | OH2 | WAT | W | 217 | 53.886 | −17.906 | 35.573 | 1.00 | 55.93 | W |
|---|---|---|---|---|---|---|---|---|---|---|---|
| ATOM | 1937 | OH2 | WAT | W | 218 | 55.084 | −18.233 | 33.255 | 1.00 | 39.30 | W |
| ATOM | 1938 | OH2 | WAT | W | 219 | 28.371 | −16.056 | 13.349 | 1.00 | 31.78 | W |
| ATOM | 1939 | OH2 | WAT | W | 220 | 32.932 | −14.472 | 37.055 | 1.00 | 42.97 | W |
| ATOM | 1940 | OH2 | WAT | W | 221 | 39.410 | −34.086 | 22.291 | 1.00 | 37.76 | W |
| ATOM | 1941 | OH2 | WAT | W | 222 | 33.275 | −22.371 | 26.097 | 1.00 | 35.53 | W |
| ATOM | 1942 | OH2 | WAT | W | 223 | 26.542 | −20.324 | 17.962 | 1.00 | 32.09 | W |
| ATOM | 1943 | OH2 | WAT | W | 224 | 48.390 | −21.762 | 29.306 | 1.00 | 34.05 | W |
| ATOM | 1944 | OH2 | WAT | W | 225 | 60.310 | −20.076 | 6.547 | 1.00 | 37.28 | W |
| ATOM | 1945 | OH2 | WAT | W | 226 | 43.094 | .669 | 17.220 | 1.00 | 33.70 | W |
| ATOM | 1946 | OH2 | WAT | W | 227 | 73.860 | −35.372 | 31.469 | 1.00 | 37.49 | W |
| ATOM | 1947 | OH2 | WAT | W | 228 | 68.956 | −33.959 | 11.475 | 1.00 | 36.68 | W |
| ATOM | 1948 | OH2 | WAT | W | 229 | 23.816 | −21.242 | 21.882 | 1.00 | 36.45 | W |
| ATOM | 1949 | OH2 | WAT | W | 230 | 27.318 | −15.732 | 17.360 | 1.00 | 38.35 | W |
| ATOM | 1950 | OH2 | WAT | W | 231 | 39.409 | −22.802 | .775 | 1.00 | 36.89 | W |
| ATOM | 1951 | OH2 | WAT | W | 232 | 58.232 | −18.569 | 34.405 | 1.00 | 39.91 | W |
| ATOM | 1952 | OH2 | WAT | W | 233 | 68.355 | −28.762 | 32.730 | 1.00 | 37.69 | W |
| ATOM | 1953 | OH2 | WAT | W | 234 | 55.936 | −37.730 | 30.398 | 1.00 | 39.68 | W |
| ATOM | 1954 | OH2 | WAT | W | 235 | 45.260 | −25.648 | 37.188 | 1.00 | 36.59 | W |
| ATOM | 1955 | OH2 | WAT | W | 236 | 75.374 | −33.981 | 34.034 | 1.00 | 37.73 | W |
| ATOM | 1956 | OH2 | WAT | W | 237 | 52.239 | −34.063 | 32.671 | 1.00 | 37.84 | W |
| ATOM | 1957 | OH2 | WAT | W | 238 | 51.841 | −21.005 | 30.156 | 1.00 | 37.29 | W |
| ATOM | 1958 | OH2 | WAT | W | 239 | 82.007 | −35.370 | 28.582 | 1.00 | 37.20 | W |
| ATOM | 1959 | OH2 | WAT | W | 240 | 63.489 | −10.399 | 34.778 | 1.00 | 38.65 | W |
| ATOM | 1960 | OH2 | WAT | W | 241 | 45.527 | 3.090 | 19.799 | 1.00 | 35.95 | W |
| ATOM | 1961 | OH2 | WAT | W | 242 | 62.245 | −33.868 | 26.786 | 1.00 | 38.85 | W |
| ATOM | 1962 | OH2 | WAT | W | 243 | 52.342 | −32.049 | 35.064 | 1.00 | 40.47 | W |
| ATOM | 1963 | OH2 | WAT | W | 244 | 62.770 | −7.476 | 38.022 | 1.00 | 17.00 | W |
| ATOM | 1964 | OH2 | WAT | W | 245 | 31.655 | −8.160 | 32.543 | 1.00 | 33.60 | W |
| ATOM | 1965 | OH2 | WAT | W | 246 | 50.142 | −9.332 | 30.522 | 1.00 | 28.82 | W |
| ATOM | 1966 | OH2 | WAT | W | 247 | 45.439 | −28.519 | 10.822 | 1.00 | 33.23 | W |
| ATOM | 1967 | OH2 | WAT | W | 248 | 40.072 | −16.759 | 40.869 | 1.00 | 33.87 | W |
| ATOM | 1968 | OH2 | WAT | W | 249 | 52.184 | −16.062 | 36.269 | 1.00 | 37.48 | W |
| ATOM | 1969 | OH2 | WAT | W | 250 | 61.003 | −15.817 | 11.647 | 1.00 | 36.41 | W |
| ATOM | 1970 | OH2 | WAT | W | 251 | 36.495 | −22.153 | 34.743 | 1.00 | 36.46 | W |
| ATOM | 1971 | OH2 | WAT | W | 252 | 76.770 | −34.127 | 18.874 | 1.00 | 34.34 | W |
| ATOM | 1972 | OH2 | WAT | W | 253 | 62.770 | −12.201 | 38.022 | 1.00 | 17.00 | W |
| ATOM | 1973 | OH2 | WAT | W | 254 | 50.484 | −31.854 | 26.997 | 1.00 | 36.81 | W |
| ATOM | 1974 | OH2 | WAT | W | 255 | 58.581 | −12.809 | 18.088 | 1.00 | 39.04 | W |
| ATOM | 1975 | OH2 | WAT | W | 256 | 32.594 | −8.771 | 9.643 | 1.00 | 36.26 | W |
| ATOM | 1976 | OH2 | WAT | W | 257 | 51.336 | −4.634 | 9.213 | 1.00 | 34.53 | W |
| ATOM | 1977 | OH2 | WAT | W | 258 | 35.798 | −7.331 | 37.946 | 1.00 | 37.03 | W |
| ATOM | 1978 | OH2 | WAT | W | 259 | 35.260 | −23.001 | 30.377 | 1.00 | 33.67 | W |
| ATOM | 1979 | OH2 | WAT | W | 260 | 34.896 | −13.902 | 37.589 | 1.00 | 39.31 | W |
| ATOM | 1980 | OH2 | WAT | W | 261 | 42.162 | −40.928 | 20.985 | 1.00 | 37.46 | W |
| ATOM | 1981 | OH2 | WAT | W | 262 | 36.322 | −11.110 | 7.752 | 1.00 | 36.11 | W |
| ATOM | 1982 | OH2 | WAT | W | 263 | 61.892 | −10.371 | 21.398 | 1.00 | 36.91 | W |
| ATOM | 1983 | OH2 | WAT | W | 264 | 47.802 | 2.206 | 34.276 | 1.00 | 36.71 | W |
| ATOM | 1984 | OH2 | WAT | W | 265 | 52.001 | −.402 | 12.062 | 1.00 | 36.46 | W |
| ATOM | 1985 | OH2 | WAT | W | 266 | 40.513 | −23.612 | 36.250 | 1.00 | 37.12 | W |
| ATOM | 1986 | OH2 | WAT | W | 267 | 67.809 | −18.565 | 9.806 | 1.00 | 37.96 | W |
| ATOM | 1987 | OH2 | WAT | W | 268 | 26.113 | −15.588 | 12.746 | 1.00 | 37.09 | W |
| ATOM | 1988 | OH2 | WAT | W | 269 | 61.053 | −12.542 | 21.269 | 1.00 | 37.13 | W |
| ATOM | 1989 | OH2 | WAT | W | 270 | 43.529 | −27.397 | 9.657 | 1.00 | 34.48 | W |
| ATOM | 1990 | OH2 | WAT | W | 271 | 43.736 | −24.233 | 6.927 | 1.00 | 33.17 | W |
| ATOM | 1991 | OH2 | WAT | W | 272 | 42.219 | −2.100 | 11.107 | 1.00 | 39.63 | W |
| ATOM | 1992 | OH2 | WAT | W | 273 | 43.467 | 2.251 | 39.320 | 1.00 | 37.05 | W |
| ATOM | 1993 | OH2 | WAT | W | 274 | 51.766 | −33.764 | 28.769 | 1.00 | 35.16 | W |
| ATOM | 1994 | OH2 | WAT | W | 275 | 29.480 | −13.446 | 29.674 | 1.00 | 38.86 | W |
| ATOM | 1995 | OH2 | WAT | W | 276 | 31.438 | −15.875 | 33.929 | 1.00 | 35.54 | W |
| ATOM | 1996 | OH2 | WAT | W | 277 | 34.840 | 3.875 | 31.200 | 1.00 | 37.50 | W |
| ATOM | 1997 | OH2 | WAT | W | 278 | 45.787 | −14.113 | 39.075 | 1.00 | 40.19 | W |
| ATOM | 1998 | OH2 | WAT | W | 279 | 40.321 | −35.999 | 23.191 | 1.00 | 39.97 | W |
| ATOM | 1999 | OH2 | WAT | W | 280 | 51.237 | −19.654 | 26.273 | 1.00 | 34.90 | W |
| ATOM | 2000 | OH2 | WAT | W | 281 | 54.804 | −.729 | 11.647 | 1.00 | 38.99 | W |
| ATOM | 2001 | OH2 | WAT | W | 282 | 47.778 | −29.403 | 33.616 | 1.00 | 35.73 | W |
| ATOM | 2002 | OH2 | WAT | W | 283 | 66.355 | −33.697 | 24.644 | 1.00 | 37.66 | W |
| ATOM | 2003 | OH2 | WAT | W | 284 | 71.418 | −27.396 | 8.830 | 1.00 | 37.88 | W |
| ATOM | 2004 | OH2 | WAT | W | 285 | 39.188 | −8.324 | 7.787 | 1.00 | 37.51 | W |
| ATOM | 2005 | OH2 | WAT | W | 286 | 27.966 | −22.317 | 19.638 | 1.00 | 31.50 | W |
| ATOM | 2006 | OH2 | WAT | W | 287 | 59.662 | −3.852 | 9.894 | 1.00 | 35.74 | W |
| ATOM | 2007 | OH2 | WAT | W | 288 | 34.463 | −30.800 | 28.613 | 1.00 | 33.15 | W |
| ATOM | 2008 | OH2 | WAT | W | 289 | 45.611 | −39.424 | 19.799 | 1.00 | 39.36 | W |
| ATOM | 2009 | OH2 | WAT | W | 290 | 50.384 | −38.201 | 29.658 | 1.00 | 36.52 | W |
| ATOM | 2010 | OH2 | WAT | W | 291 | 59.847 | 4.646 | 11.852 | 1.00 | 38.17 | W |

APPENDIX 2-continued

X-RAY DATA COORDINATES FOR CDP-ME SYNTHASE COMPLEXED WITH CTP•Mg$^{2+}$
(SEQ ID NO: 11)

| | | | | | | | | | | | |
|---|---|---|---|---|---|---|---|---|---|---|---|
| ATOM | 2011 | OH2 | WAT | W | 292 | 49.189 | 5.518 | 22.494 | 1.00 | 34.19 | W |
| ATOM | 2012 | OH2 | WAT | W | 293 | 46.776 | 4.104 | 39.072 | 1.00 | 38.69 | W |
| ATOM | 2013 | OH2 | WAT | W | 294 | 26.962 | −14.646 | 22.181 | 1.00 | 37.33 | W |
| ATOM | 2014 | OH2 | WAT | W | 295 | 37.661 | −3.844 | 8.058 | 1.00 | 36.35 | W |
| ATOM | 2015 | OH2 | WAT | W | 296 | 46.623 | −30.625 | 9.429 | 1.00 | 38.96 | W |
| ATOM | 2016 | OH2 | WAT | W | 297 | 61.594 | −12.343 | 26.315 | 1.00 | 36.48 | W |
| ATOM | 2017 | OH2 | WAT | W | 298 | 67.747 | −28.627 | 35.305 | 1.00 | 37.90 | W |
| ATOM | 2018 | OH2 | WAT | W | 299 | 33.799 | −2.015 | 36.646 | 1.00 | 36.15 | W |
| ATOM | 2019 | OH2 | WAT | W | 300 | 67.746 | −14.885 | 21.797 | 1.00 | 36.04 | W |
| ATOM | 2020 | OH2 | WAT | W | 301 | 58.854 | 8.524 | 12.900 | 1.00 | 38.09 | W |
| ATOM | 2021 | OH2 | WAT | W | 302 | 32.978 | −3.974 | 8.453 | 1.00 | 33.93 | W |
| ATOM | 2022 | OH2 | WAT | W | 303 | 63.322 | −10.751 | 15.598 | 1.00 | 33.79 | W |
| ATOM | 2023 | OH2 | WAT | W | 304 | 44.768 | 5.928 | 36.747 | 1.00 | 38.29 | W |
| ATOM | 2024 | OH2 | WAT | W | 305 | 49.391 | −36.589 | 23.806 | 1.00 | 37.09 | W |
| ATOM | 2025 | OH2 | WAT | W | 306 | 64.421 | −35.095 | 16.907 | 1.00 | 35.24 | W |
| ATOM | 2026 | OH2 | WAT | W | 307 | 53.513 | 6.511 | 28.897 | 1.00 | 39.31 | W |
| ATOM | 2027 | OH2 | WAT | W | 308 | 68.782 | −5.972 | 28.982 | 1.00 | 38.08 | W |
| ATOM | 2028 | OH2 | WAT | W | 309 | 31.389 | −24.047 | 27.685 | 1.00 | 35.97 | W |
| ATOM | 2029 | OH2 | WAT | W | 310 | 78.419 | −34.694 | 34.315 | 1.00 | 39.67 | W |
| ATOM | 2030 | OH2 | WAT | W | 311 | 38.578 | −6.452 | 40.994 | 1.00 | 37.44 | W |
| ATOM | 2031 | OH2 | WAT | W | 312 | 22.842 | −16.703 | 15.039 | 1.00 | 37.09 | W |
| ATOM | 2032 | OH2 | WAT | W | 313 | 60.802 | −32.616 | 10.210 | 1.00 | 34.91 | W |
| ATOM | 2033 | OH2 | WAT | W | 314 | 57.183 | −16.736 | 35.580 | 1.00 | 33.74 | W |
| ATOM | 2034 | OH2 | WAT | W | 315 | 45.641 | −3.906 | 44.243 | 1.00 | 40.89 | W |
| ATOM | 2035 | OH2 | WAT | W | 316 | 71.745 | −33.932 | 14.736 | 1.00 | 38.44 | W |
| ATOM | 2036 | OH2 | WAT | W | 317 | 55.459 | −34.280 | 32.056 | 1.00 | 39.08 | W |
| ATOM | 2037 | OH2 | WAT | W | 318 | 32.848 | −5.963 | 36.209 | 1.00 | 35.86 | W |
| ATOM | 2038 | OH2 | WAT | W | 319 | 52.516 | −14.147 | 40.227 | 1.00 | 39.85 | W |
| ATOM | 2039 | OH2 | WAT | W | 320 | 73.383 | −35.309 | 16.496 | 1.00 | 35.71 | W |
| ATOM | 2040 | OH2 | WAT | W | 321 | 44.817 | −27.535 | 6.162 | 1.00 | 40.86 | W |
| ATOM | 2041 | OH2 | WAT | W | 322 | 42.999 | −20.760 | 1.675 | 1.00 | 36.03 | W |
| ATOM | 2042 | OH2 | WAT | W | 323 | 57.370 | −7.782 | 42.721 | 1.00 | 37.02 | W |
| ATOM | 2043 | OH2 | WAT | W | 324 | 33.548 | −10.260 | 36.904 | 1.00 | 37.56 | W |
| ATOM | 2044 | OH2 | WAT | W | 325 | 66.504 | −14.765 | 18.547 | 1.00 | 40.28 | W |
| ATOM | 2045 | OH2 | WAT | W | 326 | 64.126 | −15.395 | 18.074 | 1.00 | 35.23 | W |
| ATOM | 2046 | OH2 | WAT | W | 327 | 77.176 | −37.936 | 23.428 | 1.00 | 38.41 | W |
| ATOM | 2047 | OH2 | WAT | W | 328 | 80.622 | −32.273 | 34.010 | 1.00 | 39.04 | W |
| ATOM | 2048 | N1 | CTP | T | 1 | 48.100 | −14.923 | 32.848 | 1.00 | 25.48 | T |
| ATOM | 2049 | C2 | CTP | T | 1 | 46.837 | −15.097 | 33.378 | 1.00 | 26.99 | T |
| ATOM | 2050 | N3 | CTP | T | 1 | 46.607 | −15.831 | 34.480 | 1.00 | 27.82 | T |
| ATOM | 2051 | C4 | CTP | T | 1 | 47.659 | −16.454 | 35.121 | 1.00 | 29.02 | T |
| ATOM | 2052 | C5 | CTP | T | 1 | 48.972 | −16.329 | 34.645 | 1.00 | 27.87 | T |
| ATOM | 2053 | C6 | CTP | T | 1 | 49.140 | −15.556 | 33.504 | 1.00 | 29.45 | T |
| ATOM | 2054 | O2 | CTP | T | 1 | 45.826 | −14.571 | 32.865 | 1.00 | 23.95 | T |
| ATOM | 2055 | N4 | CTP | T | 1 | 47.371 | −17.178 | 36.218 | 1.00 | 26.76 | T |
| ATOM | 2056 | C1* | CTP | T | 1 | 48.318 | −14.103 | 31.612 | 1.00 | 26.60 | T |
| ATOM | 2057 | C2* | CTP | T | 1 | 49.212 | −12.919 | 31.883 | 1.00 | 24.63 | T |
| ATOM | 2058 | O2* | CTP | T | 1 | 48.509 | −11.865 | 32.543 | 1.00 | 26.02 | T |
| ATOM | 2059 | C3* | CTP | T | 1 | 49.729 | −12.600 | 30.509 | 1.00 | 27.12 | T |
| ATOM | 2060 | C4* | CTP | T | 1 | 49.682 | −13.917 | 29.722 | 1.00 | 28.21 | T |
| ATOM | 2061 | O4* | CTP | T | 1 | 49.060 | −14.837 | 30.665 | 1.00 | 26.00 | T |
| ATOM | 2062 | O3* | CTP | T | 1 | 48.907 | −11.720 | 29.762 | 1.00 | 24.59 | T |
| ATOM | 2063 | C5* | CTP | T | 1 | 51.145 | −14.101 | 29.547 | 1.00 | 33.59 | T |
| ATOM | 2064 | O5* | CTP | T | 1 | 51.687 | −15.046 | 30.419 | 1.00 | 36.44 | T |
| ATOM | 2065 | PA | CTP | T | 1 | 53.060 | −14.696 | 31.313 | 1.00 | 38.24 | T |
| ATOM | 2066 | O1A | CTP | T | 1 | 53.690 | −13.420 | 30.710 | 1.00 | 40.22 | T |
| ATOM | 2067 | O2A | CTP | T | 1 | 53.998 | −15.908 | 31.123 | 1.00 | 41.49 | T |
| ATOM | 2068 | O3A | CTP | T | 1 | 52.578 | −14.605 | 32.919 | 1.00 | 42.18 | T |
| ATOM | 2069 | PB | CTP | T | 1 | 52.743 | −13.278 | 33.891 | 1.00 | 35.17 | T |
| ATOM | 2070 | O1B | CTP | T | 1 | 52.149 | −13.768 | 35.226 | 1.00 | 43.39 | T |
| ATOM | 2071 | O2B | CTP | T | 1 | 51.920 | −12.092 | 33.338 | 1.00 | 43.09 | T |
| ATOM | 2072 | O3B | CTP | T | 1 | 54.360 | −12.876 | 34.128 | 1.00 | 33.74 | T |
| ATOM | 2073 | PG | CTP | T | 1 | 55.354 | −13.686 | 35.212 | 1.00 | 28.19 | T |
| ATOM | 2074 | O1G | CTP | T | 1 | 54.735 | −13.510 | 36.647 | 1.00 | 30.67 | T |
| ATOM | 2075 | O2G | CTP | T | 1 | 56.741 | −12.988 | 35.065 | 1.00 | 28.63 | T |
| ATOM | 2076 | O3G | CTP | T | 1 | 55.358 | −15.171 | 34.773 | 1.00 | 28.76 | T |
| ATOM | 2077 | CA + 2 | CA2 | C | 1 | 35.514 | −3.246 | 16.059 | 1.00 | 16.73 | C |
| ATOM | 2078 | MG + 2 | MG2 | M | 1 | 53.667 | −16.446 | 33.965 | 1.00 | 20.91 | M |
| | | | | | END | | | | | | |

APPENDIX 3

X-RAY DATA COORDINATES FOR CDP-ME SYNTHASE COMPLEXED WITH CDP-ME.Mg$^{2+}$ (SEQ ID NO:12)

```
REMARK   coordinates from minimization and B-factor refinement
REMARK   refinement resolution: 90-1.82 A
REMARK   starting r = .2368 free_r = .2626
REMARK   final r = .2214 free_r = .2743
REMARK   rmsd bonds = .008991 rmsd angles = 1.35025
REMARK   B rmsd for bonded mainchain atoms = 3.296 target = 1.5
REMARK   B rmsd for bonded sidechain atoms = 4.641 target = 2.0
REMARK   B rmsd for angle mainchain atoms = 4.298 target = 2.0
REMARK   B rmsd for angle sidechain atoms = 5.838 target = 2.5
REMARK   target = mlf final wa = 2.46162
REMARK   final rweight = .0200 (with wa = 2.46162)
REMARK   md-method = torsion annealing schedule = constant
REMARK   starting temperature = 2000 total md steps = 1 * 100
REMARK   cycles = 2 coordinate steps = 20 B-factor steps = 10
REMARK   sg = C2 a = 129.990 b = 46.764 c = 38.387 alpha = 90 beta = 92.638 gamma = 90
REMARK   topology file 1: CNS_TOPPAR:protein.top
REMARK   topology file 2: CNS_TOPPAR:dna-rna.top
REMARK   topology file 3: CNS_TOPPAR:water.top
REMARK   topology file 4: CNS_TOPPAR:ion.top
REMARK   topology file 5: CNSPAR:prd2.top
REMARK   parameter file 1: CNS_TOPPAR:protein_rep.param
REMARK   parameter file 2: CNS_TOPPAR:dna-rna_rep.param
REMARK   parameter file 3: CNS_TOPPAR:water_rep.param
REMARK   parameter file 4: CNS_TOPPAR:ion.param
REMARK   parameter file 5: CNSPAR:prd2.param
REMARK   molecular structure file: generate.mtf
REMARK   input coordinates: generate.pdb
REMARK   reflection file = ygbp_cdpme03_freer.xpl
REMARK   ncs = none
REMARK   B-correction resolution: 6.0-1.82
REMARK   initial B-factor correction applied to fobs:
REMARK   B11 = 7.881 B22 = -4.981 B33 = -2.899
REMARK   B12 = .000 B13 = 1.914 B23 = .000
REMARK   B-factor correction applied to coordinate array B: .411
REMARK   bulk solvent: density level = .368214 e/A^3, B-factor = 44.6998 A^2
REMARK   reflections with |Fobs|/sigma_F < 0.0 rejected
REMARK   reflections with |Fobs| > 10000 * rms(Fobs) rejected
REMARK   theoretical total number of refl. in resol. range: 20834 (100.0%)
REMARK   number of unobserved reflections (no entry or |F| = 0): 3690 (17.7%)
REMARK   number of reflections rejected: 0 (.0%)
REMARK   total number of reflections used: 17144 (82.3%)
REMARK   number of reflections in working set: 16278 (78.1%)
REMARK   number of reflections in test set: 866 (4.2%)
CRYST1   129.990 46.764 38.387 90.00 92.64 90.00 C 2
REMARK   FILENAME = "refine.pdb"
REMARK   DATE: 5-Apr-01 14:49:24   created by user: richard
REMARK   VERSION:1.0
ATOM     1   CB    THR   A   4   25.657  -16.403  13.519  1.00  45.99  A
ATOM     2   OG1   THR   A   4   25.992  -16.520  14.909  1.00  50.29  A
ATOM     3   CG2   THR   A   4   25.422  -17.805  12.934  1.00  48.97  A
ATOM     4   C     THR   A   4   28.030  -16.608  12.693  1.00  43.82  A
ATOM     5   O     THR   A   4   28.821  -16.686  13.631  1.00  38.41  A
ATOM     6   N     THR   A   4   26.378  -15.298  11.382  1.00  47.34  A
ATOM     7   CA    THR   A   4   26.804  -15.685  12.762  1.00  46.78  A
ATOM     8   N     HIS   A   5   28.189  -17.300  11.570  1.00  42.34  A
ATOM     9   CA    HIS   A   5   29.324  -18.199  11.378  1.00  40.58  A
ATOM    10   CB    HIS   A   5   29.235  -18.845   9.996  1.00  35.11  A
ATOM    11   CG    HIS   A   5   30.545  -19.342   9.473  1.00  41.58  A
ATOM    12   CD2   HIS   A   5   31.190  -19.097   8.307  1.00  44.21  A
ATOM    13   ND1   HIS   A   5   31.354  -20.201  10.185  1.00  47.30  A
ATOM    14   CE1   HIS   A   5   32.442  -20.465   9.482  1.00  47.54  A
ATOM    15   NE2   HIS   A   5   32.367  -19.807   8.339  1.00  52.31  A
ATOM    16   C     HIS   A   5   30.666  -17.485  11.518  1.00  38.26  A
ATOM    17   O     HIS   A   5   31.631  -18.046  12.048  1.00  38.36  A
ATOM    18   N     LEU   A   6   30.731  -16.250  11.036  1.00  33.44  A
ATOM    19   CA    LEU   A   6   31.976  -15.493  11.103  1.00  33.00  A
ATOM    20   CB    LEU   A   6   32.007  -14.428   9.997  1.00  31.48  A
ATOM    21   CG    LEU   A   6   32.091  -14.960   8.559  1.00  36.77  A
ATOM    22   CD1   LEU   A   6   31.946  -13.793   7.562  1.00  41.82  A
ATOM    23   CD2   LEU   A   6   33.416  -15.672   8.352  1.00  34.18  A
ATOM    24   C     LEU   A   6   32.276  -14.839  12.447  1.00  28.86  A
ATOM    25   O     LEU   A   6   33.380  -14.342  12.643  1.00  27.45  A
ATOM    26   N     ASP   A   7   31.312  -14.827  13.366  1.00  29.60  A
ATOM    27   CA    ASP   A   7   31.525  -14.200  14.685  1.00  22.98  A
ATOM    28   CB    ASP   A   7   30.269  -14.293  15.550  1.00  30.56  A
ATOM    29   CG    ASP   A   7   29.205  -13.300  15.138  1.00  41.80  A
```

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 30 | OD1 | ASP | A | 7 | 29.319 | −12.748 | 14.026 | 1.00 | 36.86 | A |
|------|-----|-----|-----|---|----|--------|---------|--------|------|-------|---|
| ATOM | 31 | OD2 | ASP | A | 7 | 28.263 | −13.092 | 15.920 | 1.00 | 42.70 | A |
| ATOM | 32 | C | ASP | A | 7 | 32.649 | −14.891 | 15.433 | 1.00 | 17.00 | A |
| ATOM | 33 | O | ASP | A | 7 | 32.694 | −16.121 | 15.502 | 1.00 | 23.97 | A |
| ATOM | 34 | N | VAL | A | 8 | 33.520 | −14.084 | 16.019 | 1.00 | 22.13 | A |
| ATOM | 35 | CA | VAL | A | 8 | 34.665 | −14.583 | 16.762 | 1.00 | 19.66 | A |
| ATOM | 36 | CB | VAL | A | 8 | 35.983 | −14.193 | 16.043 | 1.00 | 18.02 | A |
| ATOM | 37 | CG1 | VAL | A | 8 | 37.203 | −14.600 | 16.879 | 1.00 | 21.86 | A |
| ATOM | 38 | CG2 | VAL | A | 8 | 36.043 | −14.897 | 14.672 | 1.00 | 29.40 | A |
| ATOM | 39 | C | VAL | A | 8 | 34.683 | −14.027 | 18.168 | 1.00 | 19.90 | A |
| ATOM | 40 | O | VAL | A | 8 | 34.405 | −12.844 | 18.389 | 1.00 | 24.28 | A |
| ATOM | 41 | N | CYS | A | 9 | 34.988 | −14.883 | 19.137 | 1.00 | 19.63 | A |
| ATOM | 42 | CA | CYS | A | 9 | 35.090 | −14.392 | 20.509 | 1.00 | 19.16 | A |
| ATOM | 43 | CB | CYS | A | 9 | 34.306 | −15.266 | 21.496 | 1.00 | 21.92 | A |
| ATOM | 44 | SG | CYS | A | 9 | 34.497 | −14.615 | 23.199 | 1.00 | 29.21 | A |
| ATOM | 45 | C | CYS | A | 9 | 36.576 | −14.442 | 20.841 | 1.00 | 19.88 | A |
| ATOM | 46 | O | CYS | A | 9 | 37.236 | −15.407 | 20.503 | 1.00 | 21.87 | A |
| ATOM | 47 | N | ALA | A | 10 | 37.104 | −13.418 | 21.497 | 1.00 | 18.71 | A |
| ATOM | 48 | CA | ALA | A | 10 | 38.526 | −13.408 | 21.825 | 1.00 | 16.26 | A |
| ATOM | 49 | CB | ALA | A | 10 | 39.148 | −12.071 | 21.408 | 1.00 | 22.53 | A |
| ATOM | 50 | C | ALA | A | 10 | 38.705 | −13.620 | 23.321 | 1.00 | 23.88 | A |
| ATOM | 51 | O | ALA | A | 10 | 37.860 | −13.203 | 24.128 | 1.00 | 22.39 | A |
| ATOM | 52 | N | VAL | A | 11 | 39.789 | −14.302 | 23.677 | 1.00 | 18.67 | A |
| ATOM | 53 | CA | VAL | A | 11 | 40.116 | −14.540 | 25.062 | 1.00 | 15.63 | A |
| ATOM | 54 | CB | VAL | A | 11 | 40.143 | −16.043 | 25.390 | 1.00 | 24.35 | A |
| ATOM | 55 | CG1 | VAL | A | 11 | 40.647 | −16.252 | 26.823 | 1.00 | 22.63 | A |
| ATOM | 56 | CG2 | VAL | A | 11 | 38.744 | −16.628 | 25.237 | 1.00 | 25.61 | A |
| ATOM | 57 | C | VAL | A | 11 | 41.514 | −13.964 | 25.272 | 1.00 | 19.47 | A |
| ATOM | 58 | O | VAL | A | 11 | 42.422 | −14.250 | 24.505 | 1.00 | 21.26 | A |
| ATOM | 59 | N | VAL | A | 12 | 41.677 | −13.118 | 26.287 | 1.00 | 18.88 | A |
| ATOM | 60 | CA | VAL | A | 12 | 42.985 | −12.527 | 26.565 | 1.00 | 18.68 | A |
| ATOM | 61 | CB | VAL | A | 12 | 42.948 | −10.974 | 26.406 | 1.00 | 16.69 | A |
| ATOM | 62 | CG1 | VAL | A | 12 | 44.224 | −10.334 | 26.973 | 1.00 | 18.29 | A |
| ATOM | 63 | CG2 | VAL | A | 12 | 42.763 | −10.619 | 24.953 | 1.00 | 22.46 | A |
| ATOM | 64 | C | VAL | A | 12 | 43.463 | −12.869 | 27.978 | 1.00 | 23.85 | A |
| ATOM | 65 | O | VAL | A | 12 | 42.954 | −12.337 | 28.967 | 1.00 | 24.74 | A |
| ATOM | 66 | N | PRO | A | 13 | 44.435 | −13.791 | 28.088 | 1.00 | 20.81 | A |
| ATOM | 67 | CD | PRO | A | 13 | 44.914 | −14.725 | 27.050 | 1.00 | 14.87 | A |
| ATOM | 68 | CA | PRO | A | 13 | 44.943 | −14.151 | 29.411 | 1.00 | 26.70 | A |
| ATOM | 69 | CB | PRO | A | 13 | 45.742 | −15.440 | 29.144 | 1.00 | 24.55 | A |
| ATOM | 70 | CG | PRO | A | 13 | 46.156 | −15.336 | 27.688 | 1.00 | 19.23 | A |
| ATOM | 71 | C | PRO | A | 13 | 45.807 | −12.987 | 29.908 | 1.00 | 23.46 | A |
| ATOM | 72 | O | PRO | A | 13 | 46.808 | −12.638 | 29.285 | 1.00 | 25.64 | A |
| ATOM | 73 | N | ALA | A | 14 | 45.389 | −12.376 | 31.009 | 1.00 | 24.83 | A |
| ATOM | 74 | CA | ALA | A | 14 | 46.093 | −11.233 | 31.582 | 1.00 | 27.83 | A |
| ATOM | 75 | CB | ALA | A | 14 | 45.403 | −9.947 | 31.157 | 1.00 | 28.84 | A |
| ATOM | 76 | C | ALA | A | 14 | 46.117 | −11.315 | 33.104 | 1.00 | 29.28 | A |
| ATOM | 77 | O | ALA | A | 14 | 46.051 | −10.289 | 33.788 | 1.00 | 29.13 | A |
| ATOM | 78 | N | ALA | A | 15 | 46.213 | −12.531 | 33.625 | 1.00 | 27.61 | A |
| ATOM | 79 | CA | ALA | A | 15 | 46.203 | −12.745 | 35.064 | 1.00 | 34.10 | A |
| ATOM | 80 | CB | ALA | A | 15 | 45.293 | −13.919 | 35.400 | 1.00 | 32.07 | A |
| ATOM | 81 | C | ALA | A | 15 | 47.596 | −12.984 | 35.625 | 1.00 | 37.58 | A |
| ATOM | 82 | O | ALA | A | 15 | 47.744 | −13.290 | 36.803 | 1.00 | 45.94 | A |
| ATOM | 83 | N | GLY | A | 16 | 48.607 | −12.847 | 34.772 | 1.00 | 37.57 | A |
| ATOM | 84 | CA | GLY | A | 16 | 49.973 | −13.043 | 35.208 | 1.00 | 46.44 | A |
| ATOM | 85 | C | GLY | A | 16 | 50.445 | −11.930 | 36.127 | 1.00 | 49.84 | A |
| ATOM | 86 | O | GLY | A | 16 | 50.105 | −10.759 | 35.935 | 1.00 | 47.72 | A |
| ATOM | 87 | N | PHE | A | 17 | 51.218 | −12.306 | 37.142 | 1.00 | 56.23 | A |
| ATOM | 88 | CA | PHE | A | 17 | 51.765 | −11.354 | 38.106 | 1.00 | 62.35 | A |
| ATOM | 89 | CB | PHE | A | 17 | 52.025 | −12.057 | 39.442 | 1.00 | 59.95 | A |
| ATOM | 90 | CG | PHE | A | 17 | 50.803 | −12.701 | 40.034 | 1.00 | 63.20 | A |
| ATOM | 91 | CD1 | PHE | A | 17 | 50.921 | −13.636 | 41.060 | 1.00 | 62.21 | A |
| ATOM | 92 | CD2 | PHE | A | 17 | 49.530 | −12.387 | 39.552 | 1.00 | 61.71 | A |
| ATOM | 93 | CE1 | PHE | A | 17 | 49.796 | −14.253 | 41.597 | 1.00 | 62.78 | A |
| ATOM | 94 | CE2 | PHE | A | 17 | 48.397 | −12.997 | 40.082 | 1.00 | 65.70 | A |
| ATOM | 95 | CZ | PHE | A | 17 | 48.530 | −13.935 | 41.108 | 1.00 | 65.41 | A |
| ATOM | 96 | C | PHE | A | 17 | 53.071 | −10.818 | 37.529 | 1.00 | 64.91 | A |
| ATOM | 97 | O | PHE | A | 17 | 53.606 | −9.805 | 37.989 | 1.00 | 65.52 | A |
| ATOM | 98 | N | GLY | A | 18 | 53.571 | −11.521 | 36.516 | 1.00 | 64.92 | A |
| ATOM | 99 | CA | GLY | A | 18 | 54.796 | −11.129 | 35.848 | 1.00 | 69.16 | A |
| ATOM | 100 | C | GLY | A | 18 | 55.994 | −10.869 | 36.739 | 1.00 | 73.00 | A |
| ATOM | 101 | O | GLY | A | 18 | 56.595 | −9.790 | 36.675 | 1.00 | 73.79 | A |
| ATOM | 102 | N | ARG | A | 19 | 56.356 | −11.840 | 37.574 | 1.00 | 72.63 | A |
| ATOM | 103 | CA | ARG | A | 19 | 57.513 | −11.640 | 38.426 | 1.00 | 72.94 | A |
| ATOM | 104 | CB | ARG | A | 19 | 57.387 | −12.401 | 39.747 | 1.00 | 73.83 | A |
| ATOM | 105 | CG | ARG | A | 19 | 58.378 | −11.895 | 40.778 | 1.00 | 72.01 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 106 | CD  | ARG | A | 19 | 58.020 | −12.315 | 42.187 | 1.00 | 71.92 | A |
|------|-----|-----|-----|---|----|--------|---------|--------|------|-------|---|
| ATOM | 107 | NE  | ARG | A | 19 | 59.105 | −11.986 | 43.110 | 1.00 | 76.20 | A |
| ATOM | 108 | CZ  | ARG | A | 19 | 59.054 | −12.162 | 44.427 | 1.00 | 74.46 | A |
| ATOM | 109 | NH1 | ARG | A | 19 | 57.962 | −12.667 | 44.986 | 1.00 | 71.84 | A |
| ATOM | 110 | NH2 | ARG | A | 19 | 60.097 | −11.831 | 45.182 | 1.00 | 73.96 | A |
| ATOM | 111 | C   | ARG | A | 19 | 58.765 | −12.058 | 37.663 | 1.00 | 75.19 | A |
| ATOM | 112 | O   | ARG | A | 19 | 59.386 | −13.091 | 37.925 | 1.00 | 74.73 | A |
| ATOM | 113 | N   | ARG | A | 20 | 59.080 | −11.215 | 36.685 | 1.00 | 75.66 | A |
| ATOM | 114 | CA  | ARG | A | 20 | 60.226 | −11.314 | 35.791 | 1.00 | 74.89 | A |
| ATOM | 115 | CB  | ARG | A | 20 | 59.969 | −12.314 | 34.655 | 1.00 | 73.64 | A |
| ATOM | 116 | CG  | ARG | A | 20 | 60.304 | −13.756 | 35.019 | 1.00 | 74.15 | A |
| ATOM | 117 | CD  | ARG | A | 20 | 60.081 | −14.695 | 33.849 | 1.00 | 74.85 | A |
| ATOM | 118 | NE  | ARG | A | 20 | 58.669 | −14.758 | 33.471 | 1.00 | 74.80 | A |
| ATOM | 119 | CZ  | ARG | A | 20 | 58.197 | −15.442 | 32.434 | 1.00 | 74.15 | A |
| ATOM | 120 | NH1 | ARG | A | 20 | 59.021 | −16.132 | 31.654 | 1.00 | 73.69 | A |
| ATOM | 121 | NH2 | ARG | A | 20 | 56.897 | −15.436 | 32.178 | 1.00 | 67.39 | A |
| ATOM | 122 | C   | ARG | A | 20 | 60.302 | −9.888  | 35.256 | 1.00 | 75.49 | A |
| ATOM | 123 | O   | ARG | A | 20 | 61.081 | −9.563  | 34.355 | 1.00 | 74.77 | A |
| ATOM | 124 | N   | MET | A | 21 | 59.454 | −9.048  | 35.846 | 1.00 | 75.51 | A |
| ATOM | 125 | CA  | MET | A | 21 | 59.357 | −7.630  | 35.524 | 1.00 | 76.50 | A |
| ATOM | 126 | CB  | MET | A | 21 | 57.891 | −7.219  | 35.345 | 1.00 | 72.76 | A |
| ATOM | 127 | CG  | MET | A | 21 | 57.331 | −7.493  | 33.966 | 1.00 | 74.55 | A |
| ATOM | 128 | SD  | MET | A | 21 | 58.326 | −6.681  | 32.705 | 1.00 | 78.64 | A |
| ATOM | 129 | CE  | MET | A | 21 | 58.264 | −4.965  | 33.269 | 1.00 | 73.09 | A |
| ATOM | 130 | C   | MET | A | 21 | 59.968 | −6.836  | 36.673 | 1.00 | 77.13 | A |
| ATOM | 131 | O   | MET | A | 21 | 60.268 | −5.648  | 36.532 | 1.00 | 78.49 | A |
| ATOM | 132 | N   | ALA | A | 22 | 60.144 | −7.509  | 37.809 | 1.00 | 76.42 | A |
| ATOM | 133 | CA  | ALA | A | 22 | 60.719 | −6.903  | 39.007 | 1.00 | 75.39 | A |
| ATOM | 134 | CB  | ALA | A | 22 | 62.069 | −6.250  | 38.676 | 1.00 | 74.18 | A |
| ATOM | 135 | C   | ALA | A | 22 | 59.780 | −5.877  | 39.642 | 1.00 | 74.55 | A |
| ATOM | 136 | O   | ALA | A | 22 | 59.506 | −5.942  | 40.841 | 1.00 | 75.98 | A |
| ATOM | 137 | N   | THR | A | 23 | 59.290 | −4.934  | 38.840 | 1.00 | 73.51 | A |
| ATOM | 138 | CA  | THR | A | 23 | 58.389 | −3.899  | 39.342 | 1.00 | 75.29 | A |
| ATOM | 139 | CB  | THR | A | 23 | 58.014 | −2.867  | 38.230 | 1.00 | 74.54 | A |
| ATOM | 140 | OG1 | THR | A | 23 | 57.423 | −3.544  | 37.112 | 1.00 | 74.36 | A |
| ATOM | 141 | CG2 | THR | A | 23 | 59.254 | −2.107  | 37.768 | 1.00 | 72.43 | A |
| ATOM | 142 | C   | THR | A | 23 | 57.103 | −4.490  | 39.922 | 1.00 | 75.01 | A |
| ATOM | 143 | O   | THR | A | 23 | 56.609 | −5.519  | 39.456 | 1.00 | 75.20 | A |
| ATOM | 144 | N   | GLU | A | 24 | 56.575 | −3.830  | 40.950 | 1.00 | 72.71 | A |
| ATOM | 145 | CA  | GLU | A | 24 | 55.347 | −4.265  | 41.608 | 1.00 | 70.58 | A |
| ATOM | 146 | CB  | GLU | A | 24 | 55.179 | −3.518  | 42.934 | 1.00 | 70.84 | A |
| ATOM | 147 | CG  | GLU | A | 24 | 54.368 | −4.264  | 43.986 | 1.00 | 72.99 | A |
| ATOM | 148 | CD  | GLU | A | 24 | 54.099 | −3.413  | 45.220 | 1.00 | 73.23 | A |
| ATOM | 149 | OE1 | GLU | A | 24 | 53.198 | −2.548  | 45.160 | 1.00 | 71.07 | A |
| ATOM | 150 | OE2 | GLU | A | 24 | 54.798 | −3.601  | 46.243 | 1.00 | 68.68 | A |
| ATOM | 151 | C   | GLU | A | 24 | 54.152 | −3.978  | 40.689 | 1.00 | 69.02 | A |
| ATOM | 152 | O   | GLU | A | 24 | 53.000 | −4.263  | 41.033 | 1.00 | 65.27 | A |
| ATOM | 153 | N   | CYS | A | 25 | 54.445 | −3.402  | 39.523 | 1.00 | 64.03 | A |
| ATOM | 154 | CA  | CYS | A | 25 | 53.427 | −3.076  | 38.527 | 1.00 | 61.19 | A |
| ATOM | 155 | CB  | CYS | A | 25 | 53.647 | −1.671  | 37.960 | 1.00 | 63.72 | A |
| ATOM | 156 | SG  | CYS | A | 25 | 52.616 | −1.304  | 36.511 | 1.00 | 67.26 | A |
| ATOM | 157 | C   | CYS | A | 25 | 53.466 | −4.074  | 37.379 | 1.00 | 58.70 | A |
| ATOM | 158 | O   | CYS | A | 25 | 54.463 | −4.166  | 36.659 | 1.00 | 56.84 | A |
| ATOM | 159 | N   | PRO | A | 26 | 52.373 | −4.830  | 37.186 | 1.00 | 57.00 | A |
| ATOM | 160 | CD  | PRO | A | 26 | 51.131 | −4.830  | 37.980 | 1.00 | 50.95 | A |
| ATOM | 161 | CA  | PRO | A | 26 | 52.299 | −5.825  | 36.112 | 1.00 | 52.99 | A |
| ATOM | 162 | CB  | PRO | A | 26 | 50.844 | −6.274  | 36.164 | 1.00 | 54.39 | A |
| ATOM | 163 | CG  | PRO | A | 26 | 50.535 | −6.176  | 37.626 | 1.00 | 52.36 | A |
| ATOM | 164 | C   | PRO | A | 26 | 52.689 | −5.259  | 34.756 | 1.00 | 46.91 | A |
| ATOM | 165 | O   | PRO | A | 26 | 52.393 | −4.108  | 34.441 | 1.00 | 48.18 | A |
| ATOM | 166 | N   | LYS | A | 27 | 53.361 | −6.082  | 33.963 | 1.00 | 43.17 | A |
| ATOM | 167 | CA  | LYS | A | 27 | 53.812 | −5.689  | 32.638 | 1.00 | 42.02 | A |
| ATOM | 168 | CB  | LYS | A | 27 | 54.554 | −6.864  | 31.995 | 1.00 | 50.63 | A |
| ATOM | 169 | CG  | LYS | A | 27 | 53.792 | −8.185  | 32.089 | 1.00 | 57.39 | A |
| ATOM | 170 | CD  | LYS | A | 27 | 54.672 | −9.390  | 31.778 | 1.00 | 60.25 | A |
| ATOM | 171 | CE  | LYS | A | 27 | 53.914 | −10.695 | 32.003 | 1.00 | 62.39 | A |
| ATOM | 172 | NZ  | LYS | A | 27 | 54.762 | −11.885 | 31.722 | 1.00 | 66.15 | A |
| ATOM | 173 | C   | LYS | A | 27 | 52.665 | −5.225  | 31.735 | 1.00 | 40.66 | A |
| ATOM | 174 | O   | LYS | A | 27 | 52.813 | −4.256  | 30.981 | 1.00 | 35.61 | A |
| ATOM | 175 | N   | GLN | A | 28 | 51.519 | −5.899  | 31.812 | 1.00 | 34.44 | A |
| ATOM | 176 | CA  | GLN | A | 28 | 50.386 | −5.512  | 30.966 | 1.00 | 37.28 | A |
| ATOM | 177 | CB  | GLN | A | 28 | 49.252 | −6.551  | 31.031 | 1.00 | 41.23 | A |
| ATOM | 178 | CG  | GLN | A | 28 | 48.654 | −6.782  | 32.422 | 1.00 | 49.20 | A |
| ATOM | 179 | CD  | GLN | A | 28 | 49.386 | −7.855  | 33.206 | 1.00 | 49.95 | A |
| ATOM | 180 | OE1 | GLN | A | 28 | 50.617 | −7.875  | 33.259 | 1.00 | 51.37 | A |
| ATOM | 181 | NE2 | GLN | A | 28 | 48.630 | −8.751  | 33.825 | 1.00 | 45.76 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 182 | C | GLN | A | 28 | 49.830 | −4.129 | 31.309 | 1.00 | 42.28 | A |
|---|---|---|---|---|---|---|---|---|---|---|---|
| ATOM | 183 | O | GLN | A | 28 | 49.137 | −3.498 | 30.497 | 1.00 | 37.80 | A |
| ATOM | 184 | N | TYR | A | 29 | 50.140 | −3.647 | 32.508 | 1.00 | 41.29 | A |
| ATOM | 185 | CA | TYR | A | 29 | 49.650 | −2.340 | 32.926 | 1.00 | 42.26 | A |
| ATOM | 186 | CB | TYR | A | 29 | 49.178 | −2.393 | 34.376 | 1.00 | 40.62 | A |
| ATOM | 187 | CG | TYR | A | 29 | 47.887 | −3.158 | 34.544 | 1.00 | 40.31 | A |
| ATOM | 188 | CD1 | TYR | A | 29 | 47.829 | −4.318 | 35.317 | 1.00 | 38.03 | A |
| ATOM | 189 | CE1 | TYR | A | 29 | 46.639 | −5.040 | 35.443 | 1.00 | 34.00 | A |
| ATOM | 190 | CD2 | TYR | A | 29 | 46.722 | −2.733 | 33.903 | 1.00 | 43.65 | A |
| ATOM | 191 | CE2 | TYR | A | 29 | 45.537 | −3.443 | 34.022 | 1.00 | 42.57 | A |
| ATOM | 192 | CZ | TYR | A | 29 | 45.503 | −4.597 | 34.792 | 1.00 | 30.68 | A |
| ATOM | 193 | OH | TYR | A | 29 | 44.323 | −5.304 | 34.887 | 1.00 | 35.99 | A |
| ATOM | 194 | C | TYR | A | 29 | 50.649 | −1.205 | 32.731 | 1.00 | 46.82 | A |
| ATOM | 195 | O | TYR | A | 29 | 50.366 | −.054 | 33.064 | 1.00 | 46.09 | A |
| ATOM | 196 | N | LEU | A | 30 | 51.818 | −1.530 | 32.189 | 1.00 | 45.82 | A |
| ATOM | 197 | CA | LEU | A | 30 | 52.816 | −.513 | 31.906 | 1.00 | 46.62 | A |
| ATOM | 198 | CB | LEU | A | 30 | 54.144 | −1.152 | 31.496 | 1.00 | 48.83 | A |
| ATOM | 199 | CG | LEU | A | 30 | 54.859 | −1.993 | 32.558 | 1.00 | 54.67 | A |
| ATOM | 200 | CD1 | LEU | A | 30 | 56.097 | −2.666 | 31.953 | 1.00 | 54.11 | A |
| ATOM | 201 | CD2 | LEU | A | 30 | 55.242 | −1.103 | 33.729 | 1.00 | 52.34 | A |
| ATOM | 202 | C | LEU | A | 30 | 52.232 | .258 | 30.734 | 1.00 | 49.75 | A |
| ATOM | 203 | O | LEU | A | 30 | 51.361 | −.257 | 30.026 | 1.00 | 48.00 | A |
| ATOM | 204 | N | SER | A | 31 | 52.707 | 1.477 | 30.509 | 1.00 | 47.95 | A |
| ATOM | 205 | CA | SER | A | 31 | 52.166 | 2.274 | 29.417 | 1.00 | 50.26 | A |
| ATOM | 206 | CB | SER | A | 31 | 51.570 | 3.579 | 29.960 | 1.00 | 53.05 | A |
| ATOM | 207 | OG | SER | A | 31 | 50.439 | 3.321 | 30.775 | 1.00 | 54.25 | A |
| ATOM | 208 | C | SER | A | 31 | 53.119 | 2.608 | 28.285 | 1.00 | 48.62 | A |
| ATOM | 209 | O | SER | A | 31 | 54.301 | 2.868 | 28.488 | 1.00 | 45.89 | A |
| ATOM | 210 | N | ILE | A | 32 | 52.567 | 2.596 | 27.081 | 1.00 | 49.08 | A |
| ATOM | 211 | CA | ILE | A | 32 | 53.293 | 2.931 | 25.869 | 1.00 | 45.90 | A |
| ATOM | 212 | CB | ILE | A | 32 | 53.514 | 1.686 | 24.979 | 1.00 | 49.67 | A |
| ATOM | 213 | CG2 | ILE | A | 32 | 54.172 | 2.087 | 23.671 | 1.00 | 49.58 | A |
| ATOM | 214 | CG1 | ILE | A | 32 | 54.401 | .668 | 25.703 | 1.00 | 47.94 | A |
| ATOM | 215 | CD | ILE | A | 32 | 55.822 | 1.130 | 25.940 | 1.00 | 46.89 | A |
| ATOM | 216 | C | ILE | A | 32 | 52.381 | 3.931 | 25.161 | 1.00 | 48.90 | A |
| ATOM | 217 | O | ILE | A | 32 | 51.257 | 3.602 | 24.764 | 1.00 | 39.74 | A |
| ATOM | 218 | N | GLY | A | 33 | 52.856 | 5.164 | 25.020 | 1.00 | 49.17 | A |
| ATOM | 219 | CA | GLY | A | 33 | 52.039 | 6.182 | 24.389 | 1.00 | 43.64 | A |
| ATOM | 220 | C | GLY | A | 33 | 50.933 | 6.535 | 25.359 | 1.00 | 45.95 | A |
| ATOM | 221 | O | GLY | A | 33 | 51.175 | 6.628 | 26.564 | 1.00 | 50.72 | A |
| ATOM | 222 | N | ASN | A | 34 | 49.717 | 6.713 | 24.855 | 1.00 | 47.83 | A |
| ATOM | 223 | CA | ASN | A | 34 | 48.601 | 7.062 | 25.724 | 1.00 | 51.66 | A |
| ATOM | 224 | CB | ASN | A | 34 | 47.711 | 8.128 | 25.052 | 1.00 | 56.21 | A |
| ATOM | 225 | CG | ASN | A | 34 | 46.941 | 7.595 | 23.843 | 1.00 | 57.14 | A |
| ATOM | 226 | OD1 | ASN | A | 34 | 47.517 | 7.285 | 22.805 | 1.00 | 60.54 | A |
| ATOM | 227 | ND2 | ASN | A | 34 | 45.629 | 7.493 | 23.983 | 1.00 | 61.15 | A |
| ATOM | 228 | C | ASN | A | 34 | 47.763 | 5.843 | 26.094 | 1.00 | 50.82 | A |
| ATOM | 229 | O | ASN | A | 34 | 46.545 | 5.947 | 26.239 | 1.00 | 54.75 | A |
| ATOM | 230 | N | GLN | A | 35 | 48.410 | 4.691 | 26.266 | 1.00 | 51.16 | A |
| ATOM | 231 | CA | GLN | A | 35 | 47.683 | 3.463 | 26.597 | 1.00 | 43.73 | A |
| ATOM | 232 | CB | GLN | A | 35 | 47.084 | 2.842 | 25.332 | 1.00 | 47.91 | A |
| ATOM | 233 | CG | GLN | A | 35 | 45.814 | 3.473 | 24.839 | 1.00 | 52.52 | A |
| ATOM | 234 | CD | GLN | A | 35 | 45.162 | 2.646 | 23.756 | 1.00 | 55.94 | A |
| ATOM | 235 | OE1 | GLN | A | 35 | 44.088 | 2.995 | 23.253 | 1.00 | 56.83 | A |
| ATOM | 236 | NE2 | GLN | A | 35 | 45.807 | 1.538 | 23.388 | 1.00 | 47.85 | A |
| ATOM | 237 | C | GLN | A | 35 | 48.495 | 2.380 | 27.289 | 1.00 | 38.15 | A |
| ATOM | 238 | O | GLN | A | 35 | 49.723 | 2.313 | 27.167 | 1.00 | 34.45 | A |
| ATOM | 239 | N | THR | A | 36 | 47.798 | 1.507 | 28.011 | 1.00 | 33.80 | A |
| ATOM | 240 | CA | THR | A | 36 | 48.483 | .409 | 28.672 | 1.00 | 28.77 | A |
| ATOM | 241 | CB | THR | A | 36 | 47.654 | −.172 | 29.850 | 1.00 | 34.00 | A |
| ATOM | 242 | OG1 | THR | A | 36 | 46.418 | −.701 | 29.361 | 1.00 | 31.58 | A |
| ATOM | 243 | CG2 | THR | A | 36 | 47.354 | .922 | 30.882 | 1.00 | 39.71 | A |
| ATOM | 244 | C | THR | A | 36 | 48.730 | −.690 | 27.643 | 1.00 | 29.16 | A |
| ATOM | 245 | O | THR | A | 36 | 48.078 | −.721 | 26.595 | 1.00 | 26.77 | A |
| ATOM | 246 | N | ILE | A | 37 | 49.682 | −1.574 | 27.937 | 1.00 | 29.17 | A |
| ATOM | 247 | CA | ILE | A | 37 | 50.014 | −2.689 | 27.061 | 1.00 | 30.81 | A |
| ATOM | 248 | CB | ILE | A | 37 | 51.107 | −3.581 | 27.700 | 1.00 | 27.58 | A |
| ATOM | 249 | CG2 | ILE | A | 37 | 51.295 | −4.855 | 26.906 | 1.00 | 28.55 | A |
| ATOM | 250 | CG1 | ILE | A | 37 | 52.432 | −2.813 | 27.758 | 1.00 | 39.15 | A |
| ATOM | 251 | CD | ILE | A | 37 | 52.981 | −2.449 | 26.385 | 1.00 | 39.56 | A |
| ATOM | 252 | C | ILE | A | 37 | 48.742 | −3.506 | 26.819 | 1.00 | 27.27 | A |
| ATOM | 253 | O | ILE | A | 37 | 48.453 | −3.904 | 25.680 | 1.00 | 25.35 | A |
| ATOM | 254 | N | LEU | A | 38 | 47.977 | −3.735 | 27.888 | 1.00 | 28.92 | A |
| ATOM | 255 | CA | LEU | A | 38 | 46.714 | −4.483 | 27.793 | 1.00 | 26.13 | A |
| ATOM | 256 | CB | LEU | A | 38 | 45.990 | −4.541 | 29.148 | 1.00 | 28.58 | A |
| ATOM | 257 | CG | LEU | A | 38 | 44.600 | −5.222 | 29.138 | 1.00 | 27.57 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 258 | CD1 | LEU | A | 38 | 44.728 | −6.699 | 28.687 | 1.00 | 24.81 | A |
|------|-----|-----|-----|---|----|--------|--------|--------|------|-------|---|
| ATOM | 259 | CD2 | LEU | A | 38 | 44.004 | −5.162 | 30.552 | 1.00 | 25.59 | A |
| ATOM | 260 | C | LEU | A | 38 | 45.779 | −3.840 | 26.780 | 1.00 | 26.34 | A |
| ATOM | 261 | O | LEU | A | 38 | 45.232 | −4.524 | 25.908 | 1.00 | 29.38 | A |
| ATOM | 262 | N | GLU | A | 39 | 45.602 | −2.523 | 26.879 | 1.00 | 24.93 | A |
| ATOM | 263 | CA | GLU | A | 39 | 44.711 | −1.834 | 25.949 | 1.00 | 23.02 | A |
| ATOM | 264 | CB | GLU | A | 39 | 44.526 | −.371 | 26.364 | 1.00 | 21.65 | A |
| ATOM | 265 | CG | GLU | A | 39 | 43.799 | −.216 | 27.696 | 1.00 | 24.98 | A |
| ATOM | 266 | CD | GLU | A | 39 | 43.944 | 1.191 | 28.275 | 1.00 | 30.75 | A |
| ATOM | 267 | OE1 | GLU | A | 39 | 43.007 | 2.006 | 28.126 | 1.00 | 35.65 | A |
| ATOM | 268 | OE2 | GLU | A | 39 | 45.003 | 1.467 | 28.861 | 1.00 | 31.83 | A |
| ATOM | 269 | C | GLU | A | 39 | 45.196 | −1.938 | 24.499 | 1.00 | 22.79 | A |
| ATOM | 270 | O | GLU | A | 39 | 44.389 | −2.081 | 23.595 | 1.00 | 21.73 | A |
| ATOM | 271 | N | HIS | A | 40 | 46.509 | −1.868 | 24.297 | 1.00 | 22.53 | A |
| ATOM | 272 | CA | HIS | A | 40 | 47.088 | −1.999 | 22.965 | 1.00 | 26.18 | A |
| ATOM | 273 | CB | HIS | A | 40 | 48.613 | −1.872 | 23.043 | 1.00 | 27.87 | A |
| ATOM | 274 | CG | HIS | A | 40 | 49.095 | −.459 | 23.159 | 1.00 | 28.60 | A |
| ATOM | 275 | CD2 | HIS | A | 40 | 49.782 | .172 | 24.140 | 1.00 | 23.74 | A |
| ATOM | 276 | ND1 | HIS | A | 40 | 48.909 | .475 | 22.162 | 1.00 | 34.50 | A |
| ATOM | 277 | CE1 | HIS | A | 40 | 49.463 | 1.618 | 22.522 | 1.00 | 32.98 | A |
| ATOM | 278 | NE2 | HIS | A | 40 | 50.000 | 1.460 | 23.718 | 1.00 | 32.31 | A |
| ATOM | 279 | C | HIS | A | 40 | 46.707 | −3.371 | 22.387 | 1.00 | 22.32 | A |
| ATOM | 280 | O | HIS | A | 40 | 46.211 | −3.465 | 21.267 | 1.00 | 23.85 | A |
| ATOM | 281 | N | SER | A | 41 | 46.933 | −4.424 | 23.170 | 1.00 | 23.42 | A |
| ATOM | 282 | CA | SER | A | 41 | 46.618 | −5.785 | 22.755 | 1.00 | 22.49 | A |
| ATOM | 283 | CB | SER | A | 41 | 47.031 | −6.785 | 23.840 | 1.00 | 24.91 | A |
| ATOM | 284 | OG | SER | A | 41 | 48.430 | −6.745 | 24.042 | 1.00 | 31.40 | A |
| ATOM | 285 | C | SER | A | 41 | 45.141 | −5.969 | 22.422 | 1.00 | 26.91 | A |
| ATOM | 286 | O | SER | A | 41 | 44.784 | −6.518 | 21.369 | 1.00 | 22.29 | A |
| ATOM | 287 | N | VAL | A | 42 | 44.281 | −5.499 | 23.318 | 1.00 | 22.22 | A |
| ATOM | 288 | CA | VAL | A | 42 | 42.841 | −5.610 | 23.120 | 1.00 | 18.27 | A |
| ATOM | 289 | CB | VAL | A | 42 | 42.086 | −5.179 | 24.392 | 1.00 | 20.36 | A |
| ATOM | 290 | CG1 | VAL | A | 42 | 40.569 | −5.169 | 24.121 | 1.00 | 23.44 | A |
| ATOM | 291 | CG2 | VAL | A | 42 | 42.428 | −6.128 | 25.532 | 1.00 | 25.04 | A |
| ATOM | 292 | C | VAL | A | 42 | 42.341 | −4.800 | 21.921 | 1.00 | 24.29 | A |
| ATOM | 293 | O | VAL | A | 42 | 41.494 | −5.269 | 21.162 | 1.00 | 19.73 | A |
| ATOM | 294 | N | HIS | A | 43 | 42.857 | −3.586 | 21.733 | 1.00 | 23.56 | A |
| ATOM | 295 | CA | HIS | A | 43 | 42.417 | −2.796 | 20.585 | 1.00 | 24.18 | A |
| ATOM | 296 | CB | HIS | A | 43 | 42.963 | −1.365 | 20.662 | 1.00 | 33.22 | A |
| ATOM | 297 | CG | HIS | A | 43 | 42.327 | −.542 | 21.740 | 1.00 | 45.05 | A |
| ATOM | 298 | CD2 | HIS | A | 43 | 42.860 | .322 | 22.635 | 1.00 | 45.86 | A |
| ATOM | 299 | ND1 | HIS | A | 43 | 40.970 | −.561 | 21.988 | 1.00 | 46.89 | A |
| ATOM | 300 | CE1 | HIS | A | 43 | 40.695 | .254 | 22.991 | 1.00 | 44.15 | A |
| ATOM | 301 | NE2 | HIS | A | 43 | 41.825 | .803 | 23.403 | 1.00 | 48.24 | A |
| ATOM | 302 | C | HIS | A | 43 | 42.818 | −3.439 | 19.258 | 1.00 | 20.96 | A |
| ATOM | 303 | O | HIS | A | 43 | 42.121 | −3.281 | 18.252 | 1.00 | 23.87 | A |
| ATOM | 304 | N | ALA | A | 44 | 43.912 | −4.192 | 19.255 | 1.00 | 20.69 | A |
| ATOM | 305 | CA | ALA | A | 44 | 44.356 | −4.842 | 18.022 | 1.00 | 24.37 | A |
| ATOM | 306 | CB | ALA | A | 44 | 45.721 | −5.518 | 18.246 | 1.00 | 21.74 | A |
| ATOM | 307 | C | ALA | A | 44 | 43.313 | −5.879 | 17.598 | 1.00 | 23.68 | A |
| ATOM | 308 | O | ALA | A | 44 | 43.028 | −6.045 | 16.413 | 1.00 | 22.13 | A |
| ATOM | 309 | N | LEU | A | 45 | 42.761 | −6.591 | 18.577 | 1.00 | 20.35 | A |
| ATOM | 310 | CA | LEU | A | 45 | 41.734 | −7.592 | 18.292 | 1.00 | 19.40 | A |
| ATOM | 311 | CB | LEU | A | 45 | 41.516 | −8.472 | 19.519 | 1.00 | 22.27 | A |
| ATOM | 312 | CG | LEU | A | 45 | 42.780 | −9.078 | 20.163 | 1.00 | 20.62 | A |
| ATOM | 313 | CD1 | LEU | A | 45 | 42.403 | −9.707 | 21.487 | 1.00 | 17.38 | A |
| ATOM | 314 | CD2 | LEU | A | 45 | 43.421 | −10.084 | 19.247 | 1.00 | 26.24 | A |
| ATOM | 315 | C | LEU | A | 45 | 40.406 | −6.925 | 17.913 | 1.00 | 19.87 | A |
| ATOM | 316 | O | LEU | A | 45 | 39.706 | −7.362 | 16.998 | 1.00 | 19.24 | A |
| ATOM | 317 | N | LEU | A | 46 | 40.056 | −5.870 | 18.638 | 1.00 | 21.01 | A |
| ATOM | 318 | CA | LEU | A | 46 | 38.785 | −5.186 | 18.377 | 1.00 | 25.21 | A |
| ATOM | 319 | CB | LEU | A | 46 | 38.480 | −4.178 | 19.499 | 1.00 | 29.53 | A |
| ATOM | 320 | CG | LEU | A | 46 | 38.044 | −4.724 | 20.881 | 1.00 | 28.23 | A |
| ATOM | 321 | CD1 | LEU | A | 46 | 38.026 | −3.595 | 21.895 | 1.00 | 32.92 | A |
| ATOM | 322 | CD2 | LEU | A | 46 | 36.687 | −5.378 | 20.799 | 1.00 | 26.62 | A |
| ATOM | 323 | C | LEU | A | 46 | 38.772 | −4.483 | 17.018 | 1.00 | 28.20 | A |
| ATOM | 324 | O | LEU | A | 46 | 37.692 | −4.175 | 16.481 | 1.00 | 27.75 | A |
| ATOM | 325 | N | ALA | A | 47 | 39.961 | −4.236 | 16.473 | 1.00 | 29.10 | A |
| ATOM | 326 | CA | ALA | A | 47 | 40.111 | −3.583 | 15.173 | 1.00 | 29.73 | A |
| ATOM | 327 | CB | ALA | A | 47 | 41.587 | −3.266 | 14.907 | 1.00 | 33.23 | A |
| ATOM | 328 | C | ALA | A | 47 | 39.540 | −4.430 | 14.035 | 1.00 | 35.37 | A |
| ATOM | 329 | O | ALA | A | 47 | 39.191 | −3.899 | 12.983 | 1.00 | 32.46 | A |
| ATOM | 330 | N | HIS | A | 48 | 39.442 | −5.744 | 14.233 | 1.00 | 28.63 | A |
| ATOM | 331 | CA | HIS | A | 48 | 38.880 | −6.601 | 13.187 | 1.00 | 29.03 | A |
| ATOM | 332 | CB | HIS | A | 48 | 39.556 | −7.974 | 13.137 | 1.00 | 31.65 | A |
| ATOM | 333 | CG | HIS | A | 48 | 39.175 | −8.767 | 11.926 | 1.00 | 33.48 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 334 | CD2 | HIS | A | 48 | 37.992 | −9.316 | 11.559 | 1.00 | 29.09 | A |
|---|---|---|---|---|---|---|---|---|---|---|---|
| ATOM | 335 | ND1 | HIS | A | 48 | 40.050 | −9.014 | 10.894 | 1.00 | 41.87 | A |
| ATOM | 336 | CE1 | HIS | A | 48 | 39.426 | −9.683 | 9.940 | 1.00 | 34.30 | A |
| ATOM | 337 | NE2 | HIS | A | 48 | 38.177 | −9.878 | 10.318 | 1.00 | 35.40 | A |
| ATOM | 338 | C | HIS | A | 48 | 37.383 | −6.787 | 13.424 | 1.00 | 27.28 | A |
| ATOM | 339 | O | HIS | A | 48 | 36.948 | −7.135 | 14.524 | 1.00 | 22.76 | A |
| ATOM | 340 | N | PRO | A | 49 | 36.571 | −6.553 | 12.380 | 1.00 | 29.00 | A |
| ATOM | 341 | CD | PRO | A | 49 | 37.053 | −6.198 | 11.033 | 1.00 | 28.21 | A |
| ATOM | 342 | CA | PRO | A | 49 | 35.107 | −6.657 | 12.391 | 1.00 | 28.19 | A |
| ATOM | 343 | CB | PRO | A | 49 | 34.734 | −6.471 | 10.921 | 1.00 | 32.09 | A |
| ATOM | 344 | CG | PRO | A | 49 | 35.823 | −5.620 | 10.397 | 1.00 | 32.98 | A |
| ATOM | 345 | C | PRO | A | 49 | 34.536 | −7.956 | 12.934 | 1.00 | 27.93 | A |
| ATOM | 346 | O | PRO | A | 49 | 33.472 | −7.967 | 13.555 | 1.00 | 31.44 | A |
| ATOM | 347 | N | ARG | A | 50 | 35.236 | −9.055 | 12.688 | 1.00 | 24.08 | A |
| ATOM | 348 | CA | ARG | A | 50 | 34.750 | −10.341 | 13.155 | 1.00 | 20.78 | A |
| ATOM | 349 | CB | ARG | A | 50 | 35.516 | −11.476 | 12.477 | 1.00 | 25.42 | A |
| ATOM | 350 | CG | ARG | A | 50 | 35.168 | −11.630 | 11.009 | 1.00 | 26.36 | A |
| ATOM | 351 | CD | ARG | A | 50 | 35.913 | −12.783 | 10.385 | 1.00 | 21.91 | A |
| ATOM | 352 | NE | ARG | A | 50 | 35.555 | −14.056 | 11.000 | 1.00 | 23.38 | A |
| ATOM | 353 | CZ | ARG | A | 50 | 36.150 | −15.214 | 10.729 | 1.00 | 25.64 | A |
| ATOM | 354 | NH1 | ARG | A | 50 | 37.136 | −15.266 | 9.848 | 1.00 | 29.67 | A |
| ATOM | 355 | NH2 | ARG | A | 50 | 35.773 | −16.324 | 11.347 | 1.00 | 26.15 | A |
| ATOM | 356 | C | ARG | A | 50 | 34.787 | −10.545 | 14.661 | 1.00 | 20.63 | A |
| ATOM | 357 | O | ARG | A | 50 | 34.009 | −11.338 | 15.193 | 1.00 | 20.99 | A |
| ATOM | 358 | N | VAL | A | 51 | 35.679 | −9.832 | 15.336 | 1.00 | 21.47 | A |
| ATOM | 359 | CA | VAL | A | 51 | 35.821 | −9.982 | 16.778 | 1.00 | 23.76 | A |
| ATOM | 360 | CB | VAL | A | 51 | 37.194 | −9.499 | 17.251 | 1.00 | 22.80 | A |
| ATOM | 361 | CG1 | VAL | A | 51 | 37.330 | −9.716 | 18.750 | 1.00 | 22.07 | A |
| ATOM | 362 | CG2 | VAL | A | 51 | 38.270 | −10.234 | 16.512 | 1.00 | 24.63 | A |
| ATOM | 363 | C | VAL | A | 51 | 34.726 | −9.199 | 17.466 | 1.00 | 21.48 | A |
| ATOM | 364 | O | VAL | A | 51 | 34.824 | −7.994 | 17.646 | 1.00 | 24.10 | A |
| ATOM | 365 | N | LYS | A | 52 | 33.688 | −9.921 | 17.857 | 1.00 | 19.47 | A |
| ATOM | 366 | CA | LYS | A | 52 | 32.522 | −9.325 | 18.483 | 1.00 | 26.74 | A |
| ATOM | 367 | CB | LYS | A | 52 | 31.296 | −10.194 | 18.192 | 1.00 | 24.55 | A |
| ATOM | 368 | CG | LYS | A | 52 | 31.148 | −10.574 | 16.732 | 1.00 | 31.23 | A |
| ATOM | 369 | CD | LYS | A | 52 | 31.074 | −9.330 | 15.862 | 1.00 | 27.79 | A |
| ATOM | 370 | CE | LYS | A | 52 | 30.950 | −9.685 | 14.388 | 1.00 | 28.49 | A |
| ATOM | 371 | NZ | LYS | A | 52 | 31.024 | −8.462 | 13.559 | 1.00 | 32.39 | A |
| ATOM | 372 | C | LYS | A | 52 | 32.637 | −9.136 | 19.981 | 1.00 | 23.13 | A |
| ATOM | 373 | O | LYS | A | 52 | 32.044 | −8.218 | 20.546 | 1.00 | 23.25 | A |
| ATOM | 374 | N | ARG | A | 53 | 33.419 | −9.995 | 20.618 | 1.00 | 27.50 | A |
| ATOM | 375 | CA | ARG | A | 53 | 33.547 | −9.955 | 22.062 | 1.00 | 27.17 | A |
| ATOM | 376 | CB | ARG | A | 53 | 32.569 | −10.963 | 22.661 | 1.00 | 26.89 | A |
| ATOM | 377 | CG | ARG | A | 53 | 32.494 | −11.022 | 24.167 | 1.00 | 40.61 | A |
| ATOM | 378 | CD | ARG | A | 53 | 31.025 | −11.188 | 24.589 | 1.00 | 48.88 | A |
| ATOM | 379 | NE | ARG | A | 53 | 30.899 | −11.710 | 25.945 | 1.00 | 52.86 | A |
| ATOM | 380 | CZ | ARG | A | 53 | 30.985 | −12.998 | 26.257 | 1.00 | 46.37 | A |
| ATOM | 381 | NH1 | ARG | A | 53 | 31.188 | −13.899 | 25.306 | 1.00 | 47.93 | A |
| ATOM | 382 | NH2 | ARG | A | 53 | 30.873 | −13.384 | 27.522 | 1.00 | 55.68 | A |
| ATOM | 383 | C | ARG | A | 53 | 34.951 | −10.313 | 22.479 | 1.00 | 25.51 | A |
| ATOM | 384 | O | ARG | A | 53 | 35.629 | −11.075 | 21.796 | 1.00 | 24.30 | A |
| ATOM | 385 | N | VAL | A | 54 | 35.391 | −9.733 | 23.584 | 1.00 | 23.87 | A |
| ATOM | 386 | CA | VAL | A | 54 | 36.713 | −10.044 | 24.115 | 1.00 | 23.37 | A |
| ATOM | 387 | CB | VAL | A | 54 | 37.695 | −8.857 | 23.939 | 1.00 | 21.46 | A |
| ATOM | 388 | CG1 | VAL | A | 54 | 38.995 | −9.129 | 24.706 | 1.00 | 22.36 | A |
| ATOM | 389 | CG2 | VAL | A | 54 | 37.984 | −8.631 | 22.462 | 1.00 | 23.74 | A |
| ATOM | 390 | C | VAL | A | 54 | 36.567 | −10.348 | 25.610 | 1.00 | 21.98 | A |
| ATOM | 391 | O | VAL | A | 54 | 36.078 | −9.520 | 26.378 | 1.00 | 24.45 | A |
| ATOM | 392 | N | VAL | A | 55 | 36.989 | −11.545 | 26.009 | 1.00 | 20.32 | A |
| ATOM | 393 | CA | VAL | A | 55 | 36.932 | −11.938 | 27.404 | 1.00 | 23.01 | A |
| ATOM | 394 | CB | VAL | A | 55 | 36.486 | −13.418 | 27.575 | 1.00 | 27.45 | A |
| ATOM | 395 | CG1 | VAL | A | 55 | 36.497 | −13.790 | 29.058 | 1.00 | 25.08 | A |
| ATOM | 396 | CG2 | VAL | A | 55 | 35.068 | −13.614 | 26.998 | 1.00 | 24.70 | A |
| ATOM | 397 | C | VAL | A | 55 | 38.349 | −11.795 | 27.942 | 1.00 | 20.26 | A |
| ATOM | 398 | O | VAL | A | 55 | 39.276 | −12.403 | 27.408 | 1.00 | 21.32 | A |
| ATOM | 399 | N | ILE | A | 56 | 38.514 | −10.967 | 28.967 | 1.00 | 21.16 | A |
| ATOM | 400 | CA | ILE | A | 56 | 39.821 | −10.750 | 29.583 | 1.00 | 17.91 | A |
| ATOM | 401 | CB | ILE | A | 56 | 40.100 | −9.241 | 29.741 | 1.00 | 17.25 | A |
| ATOM | 402 | CG2 | ILE | A | 56 | 41.513 | −9.004 | 30.355 | 1.00 | 22.83 | A |
| ATOM | 403 | CG1 | ILE | A | 56 | 40.017 | −8.568 | 28.367 | 1.00 | 22.48 | A |
| ATOM | 404 | CD | ILE | A | 56 | 40.125 | −7.023 | 28.418 | 1.00 | 20.35 | A |
| ATOM | 405 | C | ILE | A | 56 | 39.868 | −11.425 | 30.961 | 1.00 | 20.20 | A |
| ATOM | 406 | O | ILE | A | 56 | 38.999 | −11.190 | 31.804 | 1.00 | 24.59 | A |
| ATOM | 407 | N | ALA | A | 57 | 40.864 | −12.286 | 31.164 | 1.00 | 21.29 | A |
| ATOM | 408 | CA | ALA | A | 57 | 41.043 | −12.988 | 32.439 | 1.00 | 24.90 | A |
| ATOM | 409 | CB | ALA | A | 57 | 41.502 | −14.424 | 32.204 | 1.00 | 22.96 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 410 | C | ALA | A | 57 | 42.100 | −12.225 | 33.228 | 1.00 | 26.18 | A |
|---|---|---|---|---|---|---|---|---|---|---|---|
| ATOM | 411 | O | ALA | A | 57 | 43.203 | −11.984 | 32.727 | 1.00 | 24.29 | A |
| ATOM | 412 | N | ILE | A | 58 | 41.750 | −11.830 | 34.447 | 1.00 | 26.72 | A |
| ATOM | 413 | CA | ILE | A | 58 | 42.651 | −11.081 | 35.320 | 1.00 | 27.24 | A |
| ATOM | 414 | CB | ILE | A | 58 | 42.106 | −9.666 | 35.613 | 1.00 | 26.58 | A |
| ATOM | 415 | CG2 | ILE | A | 58 | 42.077 | −8.823 | 34.324 | 1.00 | 28.78 | A |
| ATOM | 416 | CG1 | ILE | A | 58 | 40.703 | −9.771 | 36.213 | 1.00 | 27.10 | A |
| ATOM | 417 | CD | ILE | A | 58 | 40.140 | −8.441 | 36.726 | 1.00 | 30.53 | A |
| ATOM | 418 | C | ILE | A | 58 | 42.814 | −11.778 | 36.667 | 1.00 | 31.88 | A |
| ATOM | 419 | O | ILE | A | 58 | 42.094 | −12.735 | 36.983 | 1.00 | 31.48 | A |
| ATOM | 420 | N | SER | A | 59 | 43.761 | −11.289 | 37.461 | 1.00 | 32.09 | A |
| ATOM | 421 | CA | SER | A | 59 | 43.987 | −11.848 | 38.798 | 1.00 | 33.42 | A |
| ATOM | 422 | CB | SER | A | 59 | 45.351 | −11.421 | 39.351 | 1.00 | 41.32 | A |
| ATOM | 423 | OG | SER | A | 59 | 45.428 | −11.706 | 40.754 | 1.00 | 38.99 | A |
| ATOM | 424 | C | SER | A | 59 | 42.900 | −11.365 | 39.757 | 1.00 | 29.69 | A |
| ATOM | 425 | O | SER | A | 59 | 42.459 | −10.228 | 39.679 | 1.00 | 31.54 | A |
| ATOM | 426 | N | PRO | A | 60 | 42.463 | −12.225 | 40.681 | 1.00 | 34.36 | A |
| ATOM | 427 | CD | PRO | A | 60 | 42.859 | −13.633 | 40.849 | 1.00 | 35.71 | A |
| ATOM | 428 | CA | PRO | A | 60 | 41.427 | −11.851 | 41.649 | 1.00 | 38.23 | A |
| ATOM | 429 | CB | PRO | A | 60 | 41.338 | −13.082 | 42.540 | 1.00 | 39.62 | A |
| ATOM | 430 | CG | PRO | A | 60 | 41.691 | −14.195 | 41.587 | 1.00 | 42.51 | A |
| ATOM | 431 | C | PRO | A | 60 | 41.822 | −10.600 | 42.434 | 1.00 | 37.96 | A |
| ATOM | 432 | O | PRO | A | 60 | 40.969 | −9.817 | 42.858 | 1.00 | 38.56 | A |
| ATOM | 433 | N | GLY | A | 61 | 43.125 | −10.415 | 42.616 | 1.00 | 39.00 | A |
| ATOM | 434 | CA | GLY | A | 61 | 43.610 | −9.259 | 43.350 | 1.00 | 45.99 | A |
| ATOM | 435 | C | GLY | A | 61 | 43.915 | −8.077 | 42.449 | 1.00 | 47.20 | A |
| ATOM | 436 | O | GLY | A | 61 | 44.503 | −7.091 | 42.895 | 1.00 | 44.19 | A |
| ATOM | 437 | N | ASP | A | 62 | 43.509 | −8.178 | 41.183 | 1.00 | 45.96 | A |
| ATOM | 438 | CA | ASP | A | 62 | 43.737 | −7.118 | 40.202 | 1.00 | 44.62 | A |
| ATOM | 439 | CB | ASP | A | 62 | 43.538 | −7.655 | 38.779 | 1.00 | 43.13 | A |
| ATOM | 440 | CG | ASP | A | 62 | 43.867 | −6.624 | 37.709 | 1.00 | 48.53 | A |
| ATOM | 441 | OD1 | ASP | A | 62 | 43.666 | −5.413 | 37.954 | 1.00 | 44.68 | A |
| ATOM | 442 | OD2 | ASP | A | 62 | 44.317 | −7.027 | 36.615 | 1.00 | 50.65 | A |
| ATOM | 443 | C | ASP | A | 62 | 42.776 | −5.959 | 40.446 | 1.00 | 45.58 | A |
| ATOM | 444 | O | ASP | A | 62 | 41.557 | −6.105 | 40.338 | 1.00 | 48.49 | A |
| ATOM | 445 | N | SER | A | 63 | 43.332 | −4.799 | 40.766 | 1.00 | 47.96 | A |
| ATOM | 446 | CA | SER | A | 63 | 42.508 | −3.637 | 41.025 | 1.00 | 51.71 | A |
| ATOM | 447 | CB | SER | A | 63 | 42.737 | −3.155 | 42.463 | 1.00 | 50.92 | A |
| ATOM | 448 | OG | SER | A | 63 | 44.106 | −3.246 | 42.824 | 1.00 | 49.99 | A |
| ATOM | 449 | C | SER | A | 63 | 42.729 | −2.495 | 40.034 | 1.00 | 49.41 | A |
| ATOM | 450 | O | SER | A | 63 | 42.064 | −1.463 | 40.123 | 1.00 | 50.09 | A |
| ATOM | 451 | N | ARG | A | 64 | 43.650 | −2.665 | 39.089 | 1.00 | 45.40 | A |
| ATOM | 452 | CA | ARG | A | 64 | 43.871 | −1.599 | 38.122 | 1.00 | 43.93 | A |
| ATOM | 453 | CB | ARG | A | 64 | 45.342 | −1.500 | 37.701 | 1.00 | 46.70 | A |
| ATOM | 454 | CG | ARG | A | 64 | 45.721 | −.046 | 37.395 | 1.00 | 57.12 | A |
| ATOM | 455 | CD | ARG | A | 64 | 46.928 | .146 | 36.479 | 1.00 | 57.01 | A |
| ATOM | 456 | NE | ARG | A | 64 | 46.863 | 1.473 | 35.854 | 1.00 | 58.33 | A |
| ATOM | 457 | CZ | ARG | A | 64 | 47.526 | 1.840 | 34.759 | 1.00 | 62.35 | A |
| ATOM | 458 | NH1 | ARG | A | 64 | 48.329 | .983 | 34.144 | 1.00 | 59.24 | A |
| ATOM | 459 | NH2 | ARG | A | 64 | 47.368 | 3.064 | 34.263 | 1.00 | 57.91 | A |
| ATOM | 460 | C | ARG | A | 64 | 42.994 | −1.742 | 36.878 | 1.00 | 38.62 | A |
| ATOM | 461 | O | ARG | A | 64 | 42.765 | −.766 | 36.168 | 1.00 | 36.54 | A |
| ATOM | 462 | N | PHE | A | 65 | 42.488 | −2.943 | 36.611 | 1.00 | 34.78 | A |
| ATOM | 463 | CA | PHE | A | 65 | 41.639 | −3.126 | 35.438 | 1.00 | 37.30 | A |
| ATOM | 464 | CB | PHE | A | 65 | 41.175 | −4.577 | 35.291 | 1.00 | 39.72 | A |
| ATOM | 465 | CG | PHE | A | 65 | 40.394 | −4.825 | 34.026 | 1.00 | 35.70 | A |
| ATOM | 466 | CD1 | PHE | A | 65 | 41.054 | −5.037 | 32.818 | 1.00 | 32.35 | A |
| ATOM | 467 | CD2 | PHE | A | 65 | 39.001 | −4.799 | 34.031 | 1.00 | 37.72 | A |
| ATOM | 468 | CE1 | PHE | A | 65 | 40.340 | −5.215 | 31.637 | 1.00 | 33.09 | A |
| ATOM | 469 | CE2 | PHE | A | 65 | 38.284 | −4.974 | 32.858 | 1.00 | 43.12 | A |
| ATOM | 470 | CZ | PHE | A | 65 | 38.953 | −5.182 | 31.657 | 1.00 | 40.50 | A |
| ATOM | 471 | C | PHE | A | 65 | 40.404 | −2.243 | 35.492 | 1.00 | 37.84 | A |
| ATOM | 472 | O | PHE | A | 65 | 40.084 | −1.565 | 34.518 | 1.00 | 40.04 | A |
| ATOM | 473 | N | ALA | A | 66 | 39.707 | −2.253 | 36.624 | 1.00 | 39.01 | A |
| ATOM | 474 | CA | ALA | A | 66 | 38.493 | −1.458 | 36.764 | 1.00 | 38.77 | A |
| ATOM | 475 | CB | ALA | A | 66 | 37.841 | −1.728 | 38.115 | 1.00 | 42.87 | A |
| ATOM | 476 | C | ALA | A | 66 | 38.725 | .037 | 36.579 | 1.00 | 39.97 | A |
| ATOM | 477 | O | ALA | A | 66 | 37.774 | .798 | 36.429 | 1.00 | 37.02 | A |
| ATOM | 478 | N | GLN | A | 67 | 39.982 | .469 | 36.582 | 1.00 | 39.65 | A |
| ATOM | 479 | CA | GLN | A | 67 | 40.256 | 1.891 | 36.397 | 1.00 | 45.99 | A |
| ATOM | 480 | CB | GLN | A | 67 | 41.387 | 2.345 | 37.326 | 1.00 | 47.02 | A |
| ATOM | 481 | CG | GLN | A | 67 | 41.128 | 2.039 | 38.800 | 1.00 | 52.64 | A |
| ATOM | 482 | CD | GLN | A | 67 | 39.710 | 2.403 | 39.224 | 1.00 | 54.11 | A |
| ATOM | 483 | OE1 | GLN | A | 67 | 39.268 | 3.541 | 39.045 | 1.00 | 60.55 | A |
| ATOM | 484 | NE2 | GLN | A | 67 | 38.988 | 1.432 | 39.786 | 1.00 | 52.40 | A |
| ATOM | 485 | C | GLN | A | 67 | 40.601 | 2.228 | 34.944 | 1.00 | 47.66 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 486 | O | GLN | A | 67 | 40.991 | 3.352 | 34.637 | 1.00 | 45.96 | A |
|---|---|---|---|---|---|---|---|---|---|---|---|
| ATOM | 487 | N | LEU | A | 68 | 40.464 | 1.252 | 34.051 | 1.00 | 46.35 | A |
| ATOM | 488 | CA | LEU | A | 68 | 40.751 | 1.482 | 32.635 | 1.00 | 47.73 | A |
| ATOM | 489 | CB | LEU | A | 68 | 41.533 | .297 | 32.050 | 1.00 | 43.82 | A |
| ATOM | 490 | CG | LEU | A | 68 | 42.913 | .016 | 32.644 | 1.00 | 38.71 | A |
| ATOM | 491 | CD1 | LEU | A | 68 | 43.422 | −1.326 | 32.145 | 1.00 | 41.50 | A |
| ATOM | 492 | CD2 | LEU | A | 68 | 43.874 | 1.140 | 32.290 | 1.00 | 40.32 | A |
| ATOM | 493 | C | LEU | A | 68 | 39.446 | 1.670 | 31.855 | 1.00 | 44.97 | A |
| ATOM | 494 | O | LEU | A | 68 | 38.391 | 1.183 | 32.264 | 1.00 | 44.55 | A |
| ATOM | 495 | N | PRO | A | 69 | 39.502 | 2.392 | 30.724 | 1.00 | 48.13 | A |
| ATOM | 496 | CD | PRO | A | 69 | 40.634 | 3.228 | 30.287 | 1.00 | 46.43 | A |
| ATOM | 497 | CA | PRO | A | 69 | 38.316 | 2.633 | 29.888 | 1.00 | 50.32 | A |
| ATOM | 498 | CB | PRO | A | 69 | 38.867 | 3.491 | 28.753 | 1.00 | 46.96 | A |
| ATOM | 499 | CG | PRO | A | 69 | 39.953 | 4.266 | 29.424 | 1.00 | 48.61 | A |
| ATOM | 500 | C | PRO | A | 69 | 37.692 | 1.331 | 29.371 | 1.00 | 50.50 | A |
| ATOM | 501 | O | PRO | A | 69 | 36.498 | 1.271 | 29.055 | 1.00 | 54.51 | A |
| ATOM | 502 | N | LEU | A | 70 | 38.513 | .291 | 29.279 | 1.00 | 48.11 | A |
| ATOM | 503 | CA | LEU | A | 70 | 38.058 | −1.009 | 28.798 | 1.00 | 46.44 | A |
| ATOM | 504 | CB | LEU | A | 70 | 39.246 | −1.958 | 28.656 | 1.00 | 46.67 | A |
| ATOM | 505 | CG | LEU | A | 70 | 40.286 | −1.624 | 27.595 | 1.00 | 46.22 | A |
| ATOM | 506 | CD1 | LEU | A | 70 | 41.386 | −2.679 | 27.659 | 1.00 | 53.95 | A |
| ATOM | 507 | CD2 | LEU | A | 70 | 39.646 | −1.611 | 26.213 | 1.00 | 47.43 | A |
| ATOM | 508 | C | LEU | A | 70 | 37.043 | −1.641 | 29.742 | 1.00 | 47.63 | A |
| ATOM | 509 | O | LEU | A | 70 | 36.203 | −2.448 | 29.328 | 1.00 | 44.03 | A |
| ATOM | 510 | N | ALA | A | 71 | 37.147 | −1.282 | 31.017 | 1.00 | 43.51 | A |
| ATOM | 511 | CA | ALA | A | 71 | 36.262 | −1.806 | 32.048 | 1.00 | 44.73 | A |
| ATOM | 512 | CB | ALA | A | 71 | 36.551 | −1.102 | 33.383 | 1.00 | 46.97 | A |
| ATOM | 513 | C | ALA | A | 71 | 34.780 | −1.672 | 31.699 | 1.00 | 43.18 | A |
| ATOM | 514 | O | ALA | A | 71 | 33.987 | −2.563 | 32.010 | 1.00 | 43.61 | A |
| ATOM | 515 | N | ASN | A | 72 | 34.415 | −.572 | 31.045 | 1.00 | 39.33 | A |
| ATOM | 516 | CA | ASN | A | 72 | 33.020 | −.310 | 30.682 | 1.00 | 41.21 | A |
| ATOM | 517 | CB | ASN | A | 72 | 32.657 | 1.127 | 31.078 | 1.00 | 48.12 | A |
| ATOM | 518 | CG | ASN | A | 72 | 32.538 | 1.311 | 32.581 | 1.00 | 53.17 | A |
| ATOM | 519 | OD1 | ASN | A | 72 | 32.752 | 2.410 | 33.102 | 1.00 | 60.98 | A |
| ATOM | 520 | ND2 | ASN | A | 72 | 32.182 | .240 | 33.287 | 1.00 | 53.98 | A |
| ATOM | 521 | C | ASN | A | 72 | 32.653 | −.525 | 29.209 | 1.00 | 34.56 | A |
| ATOM | 522 | O | ASN | A | 72 | 31.555 | −.160 | 28.781 | 1.00 | 33.75 | A |
| ATOM | 523 | N | HIS | A | 73 | 33.565 | −1.118 | 28.451 | 1.00 | 33.12 | A |
| ATOM | 524 | CA | HIS | A | 73 | 33.376 | −1.376 | 27.025 | 1.00 | 28.82 | A |
| ATOM | 525 | CB | HIS | A | 73 | 34.719 | −1.812 | 26.428 | 1.00 | 24.68 | A |
| ATOM | 526 | CG | HIS | A | 73 | 34.742 | −1.828 | 24.936 | 1.00 | 23.50 | A |
| ATOM | 527 | CD2 | HIS | A | 73 | 34.066 | −2.590 | 24.043 | 1.00 | 20.40 | A |
| ATOM | 528 | ND1 | HIS | A | 73 | 35.527 | −.971 | 24.194 | 1.00 | 26.71 | A |
| ATOM | 529 | CE1 | HIS | A | 73 | 35.333 | −1.204 | 22.909 | 1.00 | 18.95 | A |
| ATOM | 530 | NE2 | HIS | A | 73 | 34.451 | −2.182 | 22.791 | 1.00 | 29.15 | A |
| ATOM | 531 | C | HIS | A | 73 | 32.302 | −2.444 | 26.790 | 1.00 | 23.21 | A |
| ATOM | 532 | O | HIS | A | 73 | 32.364 | −3.531 | 27.353 | 1.00 | 23.04 | A |
| ATOM | 533 | N | PRO | A | 74 | 31.295 | −2.145 | 25.949 | 1.00 | 25.87 | A |
| ATOM | 534 | CD | PRO | A | 74 | 31.163 | −.929 | 25.130 | 1.00 | 21.86 | A |
| ATOM | 535 | CA | PRO | A | 74 | 30.222 | −3.110 | 25.672 | 1.00 | 25.59 | A |
| ATOM | 536 | CB | PRO | A | 74 | 29.261 | −2.329 | 24.763 | 1.00 | 29.21 | A |
| ATOM | 537 | CG | PRO | A | 74 | 30.134 | −1.338 | 24.069 | 1.00 | 27.34 | A |
| ATOM | 538 | C | PRO | A | 74 | 30.641 | −4.465 | 25.071 | 1.00 | 25.90 | A |
| ATOM | 539 | O | PRO | A | 74 | 29.904 | −5.445 | 25.164 | 1.00 | 22.37 | A |
| ATOM | 540 | N | GLN | A | 75 | 31.825 | −4.533 | 24.476 | 1.00 | 20.86 | A |
| ATOM | 541 | CA | GLN | A | 75 | 32.269 | −5.785 | 23.882 | 1.00 | 24.40 | A |
| ATOM | 542 | CB | GLN | A | 75 | 32.978 | −5.513 | 22.546 | 1.00 | 21.14 | A |
| ATOM | 543 | CG | GLN | A | 75 | 32.071 | −4.896 | 21.490 | 1.00 | 19.80 | A |
| ATOM | 544 | CD | GLN | A | 75 | 32.774 | −4.628 | 20.179 | 1.00 | 23.19 | A |
| ATOM | 545 | OE1 | GLN | A | 75 | 33.333 | −3.564 | 19.976 | 1.00 | 24.50 | A |
| ATOM | 546 | NE2 | GLN | A | 75 | 32.753 | −5.602 | 19.287 | 1.00 | 31.14 | A |
| ATOM | 547 | C | GLN | A | 75 | 33.193 | −6.546 | 24.816 | 1.00 | 21.67 | A |
| ATOM | 548 | O | GLN | A | 75 | 33.602 | −7.665 | 24.514 | 1.00 | 27.60 | A |
| ATOM | 549 | N | ILE | A | 76 | 33.500 | −5.951 | 25.963 | 1.00 | 23.36 | A |
| ATOM | 550 | CA | ILE | A | 76 | 34.414 | −6.598 | 26.908 | 1.00 | 30.20 | A |
| ATOM | 551 | CB | ILE | A | 76 | 35.479 | −5.601 | 27.416 | 1.00 | 27.04 | A |
| ATOM | 552 | CG2 | ILE | A | 76 | 36.504 | −6.319 | 28.292 | 1.00 | 24.98 | A |
| ATOM | 553 | CG1 | ILE | A | 76 | 36.189 | −4.951 | 26.224 | 1.00 | 33.88 | A |
| ATOM | 554 | CD | ILE | A | 76 | 36.766 | −5.922 | 25.251 | 1.00 | 44.83 | A |
| ATOM | 555 | C | ILE | A | 76 | 33.777 | −7.256 | 28.129 | 1.00 | 32.32 | A |
| ATOM | 556 | O | ILE | A | 76 | 32.922 | −6.669 | 28.789 | 1.00 | 30.27 | A |
| ATOM | 557 | N | THR | A | 77 | 34.201 | −8.487 | 28.402 | 1.00 | 29.84 | A |
| ATOM | 558 | CA | THR | A | 77 | 33.747 | −9.243 | 29.566 | 1.00 | 33.65 | A |
| ATOM | 559 | CB | THR | A | 77 | 33.072 | −10.575 | 29.165 | 1.00 | 31.54 | A |
| ATOM | 560 | OG1 | THR | A | 77 | 31.836 | −10.299 | 28.493 | 1.00 | 37.01 | A |
| ATOM | 561 | CG2 | THR | A | 77 | 32.793 | −11.434 | 30.391 | 1.00 | 40.33 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 562 | C | THR | A | 77 | 34.999 | −9.562 | 30.389 | 1.00 | 29.66 | A |
|---|---|---|---|---|---|---|---|---|---|---|---|
| ATOM | 563 | O | THR | A | 77 | 36.053 | −9.870 | 29.827 | 1.00 | 26.78 | A |
| ATOM | 564 | N | VAL | A | 78 | 34.894 | −9.462 | 31.710 | 1.00 | 28.20 | A |
| ATOM | 565 | CA | VAL | A | 78 | 36.026 | −9.748 | 32.589 | 1.00 | 32.24 | A |
| ATOM | 566 | CB | VAL | A | 78 | 36.381 | −8.500 | 33.460 | 1.00 | 37.97 | A |
| ATOM | 567 | CG1 | VAL | A | 78 | 35.172 | −8.068 | 34.269 | 1.00 | 46.27 | A |
| ATOM | 568 | CG2 | VAL | A | 78 | 37.546 | −8.814 | 34.386 | 1.00 | 40.25 | A |
| ATOM | 569 | C | VAL | A | 78 | 35.753 | −10.946 | 33.504 | 1.00 | 36.17 | A |
| ATOM | 570 | O | VAL | A | 78 | 34.666 | −11.063 | 34.067 | 1.00 | 37.86 | A |
| ATOM | 571 | N | VAL | A | 79 | 36.728 | −11.855 | 33.613 | 1.00 | 33.28 | A |
| ATOM | 572 | CA | VAL | A | 79 | 36.616 | −13.030 | 34.491 | 1.00 | 32.17 | A |
| ATOM | 573 | CB | VAL | A | 79 | 36.325 | −14.335 | 33.703 | 1.00 | 31.78 | A |
| ATOM | 574 | CG1 | VAL | A | 79 | 35.010 | −14.186 | 32.892 | 1.00 | 29.67 | A |
| ATOM | 575 | CG2 | VAL | A | 79 | 37.497 | −14.668 | 32.779 | 1.00 | 33.24 | A |
| ATOM | 576 | C | VAL | A | 79 | 37.937 | −13.209 | 35.242 | 1.00 | 32.36 | A |
| ATOM | 577 | O | VAL | A | 79 | 38.939 | −12.590 | 34.889 | 1.00 | 30.86 | A |
| ATOM | 578 | N | ASP | A | 80 | 37.960 | −14.045 | 36.276 | 1.00 | 36.84 | A |
| ATOM | 579 | CA | ASP | A | 80 | 39.211 | −14.251 | 36.994 | 1.00 | 36.68 | A |
| ATOM | 580 | CB | ASP | A | 80 | 38.962 | −14.630 | 38.455 | 1.00 | 46.47 | A |
| ATOM | 581 | CG | ASP | A | 80 | 38.352 | −13.495 | 39.260 | 1.00 | 49.17 | A |
| ATOM | 582 | OD1 | ASP | A | 80 | 38.764 | −12.327 | 39.080 | 1.00 | 48.56 | A |
| ATOM | 583 | OD2 | ASP | A | 80 | 37.462 | −13.778 | 40.087 | 1.00 | 56.98 | A |
| ATOM | 584 | C | ASP | A | 80 | 40.038 | −15.337 | 36.332 | 1.00 | 30.30 | A |
| ATOM | 585 | O | ASP | A | 80 | 39.503 | −16.341 | 35.862 | 1.00 | 35.11 | A |
| ATOM | 586 | N | GLY | A | 81 | 41.347 | −15.130 | 36.286 | 1.00 | 30.07 | A |
| ATOM | 587 | CA | GLY | A | 81 | 42.236 | −16.121 | 35.696 | 1.00 | 35.52 | A |
| ATOM | 588 | C | GLY | A | 81 | 42.631 | −17.182 | 36.718 | 1.00 | 39.60 | A |
| ATOM | 589 | O | GLY | A | 81 | 42.069 | −17.212 | 37.814 | 1.00 | 40.21 | A |
| ATOM | 590 | N | GLY | A | 82 | 43.586 | −18.044 | 36.363 | 1.00 | 38.16 | A |
| ATOM | 591 | CA | GLY | A | 82 | 44.032 | −19.109 | 37.261 | 1.00 | 37.54 | A |
| ATOM | 592 | C | GLY | A | 82 | 45.517 | −19.109 | 37.591 | 1.00 | 36.16 | A |
| ATOM | 593 | O | GLY | A | 82 | 46.210 | −18.140 | 37.307 | 1.00 | 35.33 | A |
| ATOM | 594 | N | ASP | A | 83 | 46.022 | −20.204 | 38.162 | 1.00 | 36.60 | A |
| ATOM | 595 | CA | ASP | A | 83 | 47.427 | −20.270 | 38.549 | 1.00 | 40.12 | A |
| ATOM | 596 | CB | ASP | A | 83 | 47.718 | −21.564 | 39.312 | 1.00 | 47.09 | A |
| ATOM | 597 | CG | ASP | A | 83 | 46.806 | −21.751 | 40.510 | 1.00 | 48.31 | A |
| ATOM | 598 | OD1 | ASP | A | 83 | 46.399 | −20.726 | 41.105 | 1.00 | 47.48 | A |
| ATOM | 599 | OD2 | ASP | A | 83 | 46.512 | −22.920 | 40.860 | 1.00 | 55.48 | A |
| ATOM | 600 | C | ASP | A | 83 | 48.409 | −20.142 | 37.403 | 1.00 | 41.27 | A |
| ATOM | 601 | O | ASP | A | 83 | 49.411 | −19.439 | 37.516 | 1.00 | 44.03 | A |
| ATOM | 602 | N | GLU | A | 84 | 48.137 | −20.841 | 36.308 | 1.00 | 37.31 | A |
| ATOM | 603 | CA | GLU | A | 84 | 49.007 | −20.787 | 35.143 | 1.00 | 33.84 | A |
| ATOM | 604 | CB | GLU | A | 84 | 49.513 | −22.189 | 34.798 | 1.00 | 29.93 | A |
| ATOM | 605 | CG | GLU | A | 84 | 50.406 | −22.809 | 35.862 | 1.00 | 42.85 | A |
| ATOM | 606 | CD | GLU | A | 84 | 51.674 | −22.010 | 36.073 | 1.00 | 50.91 | A |
| ATOM | 607 | OE1 | GLU | A | 84 | 52.415 | −21.798 | 35.092 | 1.00 | 52.77 | A |
| ATOM | 608 | OE2 | GLU | A | 84 | 51.936 | −21.589 | 37.218 | 1.00 | 61.59 | A |
| ATOM | 609 | C | GLU | A | 84 | 48.235 | −20.203 | 33.961 | 1.00 | 36.91 | A |
| ATOM | 610 | O | GLU | A | 84 | 47.004 | −20.041 | 34.014 | 1.00 | 29.78 | A |
| ATOM | 611 | N | ARG | A | 85 | 48.956 | −19.892 | 32.889 | 1.00 | 33.20 | A |
| ATOM | 612 | CA | ARG | A | 85 | 48.320 | −19.311 | 31.701 | 1.00 | 35.71 | A |
| ATOM | 613 | CB | ARG | A | 85 | 49.354 | −19.112 | 30.587 | 1.00 | 30.05 | A |
| ATOM | 614 | CG | ARG | A | 85 | 48.795 | −18.460 | 29.314 | 1.00 | 27.03 | A |
| ATOM | 615 | CD | ARG | A | 85 | 49.903 | −18.248 | 28.281 | 1.00 | 23.61 | A |
| ATOM | 616 | NE | ARG | A | 85 | 49.388 | −17.637 | 27.050 | 1.00 | 25.32 | A |
| ATOM | 617 | CZ | ARG | A | 85 | 48.692 | −18.293 | 26.130 | 1.00 | 24.50 | A |
| ATOM | 618 | NH1 | ARG | A | 85 | 48.437 | −19.583 | 26.300 | 1.00 | 22.31 | A |
| ATOM | 619 | NH2 | ARG | A | 85 | 48.238 | −17.662 | 25.054 | 1.00 | 27.83 | A |
| ATOM | 620 | C | ARG | A | 85 | 47.183 | −20.195 | 31.194 | 1.00 | 35.28 | A |
| ATOM | 621 | O | ARG | A | 85 | 46.085 | −19.711 | 30.936 | 1.00 | 34.51 | A |
| ATOM | 622 | N | ALA | A | 86 | 47.454 | −21.491 | 31.051 | 1.00 | 31.83 | A |
| ATOM | 623 | CA | ALA | A | 86 | 46.440 | −22.417 | 30.564 | 1.00 | 27.37 | A |
| ATOM | 624 | CB | ALA | A | 86 | 47.002 | −23.844 | 30.518 | 1.00 | 25.12 | A |
| ATOM | 625 | C | ALA | A | 86 | 45.148 | −22.362 | 31.391 | 1.00 | 25.65 | A |
| ATOM | 626 | O | ALA | A | 86 | 44.057 | −22.536 | 30.845 | 1.00 | 31.22 | A |
| ATOM | 627 | N | ASP | A | 87 | 45.264 | −22.107 | 32.694 | 1.00 | 28.65 | A |
| ATOM | 628 | CA | ASP | A | 87 | 44.091 | −22.024 | 33.564 | 1.00 | 30.05 | A |
| ATOM | 629 | CB | ASP | A | 87 | 44.494 | −22.051 | 35.052 | 1.00 | 32.92 | A |
| ATOM | 630 | CG | ASP | A | 87 | 45.321 | −23.271 | 35.422 | 1.00 | 38.45 | A |
| ATOM | 631 | OD1 | ASP | A | 87 | 44.826 | −24.407 | 35.251 | 1.00 | 39.62 | A |
| ATOM | 632 | OD2 | ASP | A | 87 | 46.471 | −23.086 | 35.882 | 1.00 | 33.03 | A |
| ATOM | 633 | C | ASP | A | 87 | 43.322 | −20.731 | 33.285 | 1.00 | 27.42 | A |
| ATOM | 634 | O | ASP | A | 87 | 42.086 | −20.718 | 33.238 | 1.00 | 26.57 | A |
| ATOM | 635 | N | SER | A | 88 | 44.045 | −19.635 | 33.109 | 1.00 | 29.80 | A |
| ATOM | 636 | CA | SER | A | 88 | 43.383 | −18.363 | 32.831 | 1.00 | 29.86 | A |
| ATOM | 637 | CB | SER | A | 88 | 44.410 | −17.231 | 32.816 | 1.00 | 31.10 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 638 | OG | SER | A | 88 | 45.118 | −17.166 | 34.050 | 1.00 | 38.96 | A |
|---|---|---|---|---|---|---|---|---|---|---|---|
| ATOM | 639 | C | SER | A | 88 | 42.665 | −18.450 | 31.479 | 1.00 | 28.97 | A |
| ATOM | 640 | O | SER | A | 88 | 41.549 | −17.953 | 31.325 | 1.00 | 22.94 | A |
| ATOM | 641 | N | VAL | A | 89 | 43.308 | −19.093 | 30.511 | 1.00 | 25.19 | A |
| ATOM | 642 | CA | VAL | A | 89 | 42.724 | −19.241 | 29.180 | 1.00 | 27.04 | A |
| ATOM | 643 | CB | VAL | A | 89 | 43.758 | −19.868 | 28.199 | 1.00 | 24.62 | A |
| ATOM | 644 | CG1 | VAL | A | 89 | 43.084 | −20.263 | 26.878 | 1.00 | 24.12 | A |
| ATOM | 645 | CG2 | VAL | A | 89 | 44.898 | −18.857 | 27.942 | 1.00 | 19.91 | A |
| ATOM | 646 | C | VAL | A | 89 | 41.448 | −20.082 | 29.231 | 1.00 | 30.57 | A |
| ATOM | 647 | O | VAL | A | 89 | 40.453 | −19.783 | 28.551 | 1.00 | 26.11 | A |
| ATOM | 648 | N | LEU | A | 90 | 41.473 | −21.130 | 30.051 | 1.00 | 33.66 | A |
| ATOM | 649 | CA | LEU | A | 90 | 40.309 | −22.000 | 30.199 | 1.00 | 30.39 | A |
| ATOM | 650 | CB | LEU | A | 90 | 40.657 | −23.215 | 31.075 | 1.00 | 31.24 | A |
| ATOM | 651 | CG | LEU | A | 90 | 40.039 | −24.562 | 30.683 | 1.00 | 37.85 | A |
| ATOM | 652 | CD1 | LEU | A | 90 | 39.968 | −25.458 | 31.926 | 1.00 | 37.27 | A |
| ATOM | 653 | CD2 | LEU | A | 90 | 38.665 | −24.386 | 30.094 | 1.00 | 44.28 | A |
| ATOM | 654 | C | LEU | A | 90 | 39.121 | −21.243 | 30.806 | 1.00 | 28.41 | A |
| ATOM | 655 | O | LEU | A | 90 | 37.979 | −21.405 | 30.369 | 1.00 | 31.48 | A |
| ATOM | 656 | N | ALA | A | 91 | 39.390 | −20.403 | 31.802 | 1.00 | 30.15 | A |
| ATOM | 657 | CA | ALA | A | 91 | 38.336 | −19.633 | 32.452 | 1.00 | 26.73 | A |
| ATOM | 658 | CB | ALA | A | 91 | 38.902 | −18.897 | 33.664 | 1.00 | 28.58 | A |
| ATOM | 659 | C | ALA | A | 91 | 37.739 | −18.643 | 31.457 | 1.00 | 32.09 | A |
| ATOM | 660 | O | ALA | A | 91 | 36.542 | −18.363 | 31.491 | 1.00 | 32.74 | A |
| ATOM | 661 | N | GLY | A | 92 | 38.585 | −18.099 | 30.584 | 1.00 | 29.47 | A |
| ATOM | 662 | CA | GLY | A | 92 | 38.091 | −17.178 | 29.568 | 1.00 | 20.98 | A |
| ATOM | 663 | C | GLY | A | 92 | 37.202 | −17.901 | 28.560 | 1.00 | 24.16 | A |
| ATOM | 664 | O | GLY | A | 92 | 36.165 | −17.372 | 28.108 | 1.00 | 29.29 | A |
| ATOM | 665 | N | LEU | A | 93 | 37.603 | −19.117 | 28.196 | 1.00 | 25.01 | A |
| ATOM | 666 | CA | LEU | A | 93 | 36.842 | −19.929 | 27.241 | 1.00 | 26.69 | A |
| ATOM | 667 | CB | LEU | A | 93 | 37.565 | −21.245 | 26.933 | 1.00 | 29.62 | A |
| ATOM | 668 | CG | LEU | A | 93 | 38.832 | −21.210 | 26.082 | 1.00 | 33.50 | A |
| ATOM | 669 | CD1 | LEU | A | 93 | 39.368 | −22.635 | 25.968 | 1.00 | 28.72 | A |
| ATOM | 670 | CD2 | LEU | A | 93 | 38.537 | −20.632 | 24.704 | 1.00 | 24.48 | A |
| ATOM | 671 | C | LEU | A | 93 | 35.441 | −20.264 | 27.744 | 1.00 | 34.31 | A |
| ATOM | 672 | O | LEU | A | 93 | 34.492 | −20.349 | 26.960 | 1.00 | 36.53 | A |
| ATOM | 673 | N | LYS | A | 94 | 35.308 | −20.447 | 29.050 | 1.00 | 36.53 | A |
| ATOM | 674 | CA | LYS | A | 94 | 34.014 | −20.790 | 29.620 | 1.00 | 40.92 | A |
| ATOM | 675 | CB | LYS | A | 94 | 34.191 | −21.251 | 31.069 | 1.00 | 41.10 | A |
| ATOM | 676 | CG | LYS | A | 94 | 34.965 | −22.555 | 31.156 | 1.00 | 40.25 | A |
| ATOM | 677 | CD | LYS | A | 94 | 35.070 | −23.078 | 32.575 | 1.00 | 47.86 | A |
| ATOM | 678 | CE | LYS | A | 94 | 35.818 | −24.403 | 32.602 | 1.00 | 45.88 | A |
| ATOM | 679 | NZ | LYS | A | 94 | 36.170 | −24.814 | 33.987 | 1.00 | 47.89 | A |
| ATOM | 680 | C | LYS | A | 94 | 33.000 | −19.662 | 29.523 | 1.00 | 41.14 | A |
| ATOM | 681 | O | LYS | A | 94 | 31.795 | −19.890 | 29.648 | 1.00 | 35.75 | A |
| ATOM | 682 | N | ALA | A | 95 | 33.482 | −18.449 | 29.274 | 1.00 | 38.84 | A |
| ATOM | 683 | CA | ALA | A | 95 | 32.598 | −17.305 | 29.137 | 1.00 | 38.03 | A |
| ATOM | 684 | CB | ALA | A | 95 | 33.051 | −16.195 | 30.063 | 1.00 | 31.00 | A |
| ATOM | 685 | C | ALA | A | 95 | 32.575 | −16.802 | 27.689 | 1.00 | 37.80 | A |
| ATOM | 686 | O | ALA | A | 95 | 32.087 | −15.707 | 27.417 | 1.00 | 34.89 | A |
| ATOM | 687 | N | ALA | A | 96 | 33.097 | −17.611 | 26.770 | 1.00 | 37.52 | A |
| ATOM | 688 | CA | ALA | A | 96 | 33.170 | −17.252 | 25.350 | 1.00 | 43.22 | A |
| ATOM | 689 | CB | ALA | A | 96 | 33.999 | −18.296 | 24.587 | 1.00 | 37.72 | A |
| ATOM | 690 | C | ALA | A | 96 | 31.817 | −17.083 | 24.677 | 1.00 | 46.74 | A |
| ATOM | 691 | O | ALA | A | 96 | 31.656 | −16.238 | 23.794 | 1.00 | 51.56 | A |
| ATOM | 692 | N | GLY | A | 97 | 30.853 | −17.900 | 25.091 | 1.00 | 47.52 | A |
| ATOM | 693 | CA | GLY | A | 97 | 29.520 | −17.825 | 24.527 | 1.00 | 43.87 | A |
| ATOM | 694 | C | GLY | A | 97 | 29.230 | −18.928 | 23.530 | 1.00 | 43.13 | A |
| ATOM | 695 | O | GLY | A | 97 | 29.623 | −20.084 | 23.717 | 1.00 | 45.18 | A |
| ATOM | 696 | N | ASP | A | 98 | 28.540 | −18.572 | 22.454 | 1.00 | 44.45 | A |
| ATOM | 697 | CA | ASP | A | 98 | 28.200 | −19.541 | 21.426 | 1.00 | 39.02 | A |
| ATOM | 698 | CB | ASP | A | 98 | 26.727 | −19.389 | 21.014 | 1.00 | 49.37 | A |
| ATOM | 699 | CG | ASP | A | 98 | 25.771 | −19.804 | 22.112 | 1.00 | 58.89 | A |
| ATOM | 700 | OD1 | ASP | A | 98 | 25.760 | −21.003 | 22.472 | 1.00 | 65.50 | A |
| ATOM | 701 | OD2 | ASP | A | 98 | 25.031 | −18.933 | 22.619 | 1.00 | 65.41 | A |
| ATOM | 702 | C | ASP | A | 98 | 29.088 | −19.374 | 20.207 | 1.00 | 36.49 | A |
| ATOM | 703 | O | ASP | A | 98 | 28.898 | −20.058 | 19.204 | 1.00 | 34.10 | A |
| ATOM | 704 | N | ALA | A | 99 | 30.039 | −18.449 | 20.279 | 1.00 | 31.01 | A |
| ATOM | 705 | CA | ALA | A | 99 | 30.964 | −18.229 | 19.164 | 1.00 | 36.13 | A |
| ATOM | 706 | CB | ALA | A | 99 | 32.129 | −17.317 | 19.610 | 1.00 | 36.52 | A |
| ATOM | 707 | C | ALA | A | 99 | 31.509 | −19.581 | 18.693 | 1.00 | 28.33 | A |
| ATOM | 708 | O | ALA | A | 99 | 31.834 | −20.435 | 19.511 | 1.00 | 27.94 | A |
| ATOM | 709 | N | GLN | A | 100 | 31.605 | −19.771 | 17.382 | 1.00 | 18.99 | A |
| ATOM | 710 | CA | GLN | A | 100 | 32.108 | −21.023 | 16.827 | 1.00 | 22.75 | A |
| ATOM | 711 | CB | GLN | A | 100 | 31.647 | −21.186 | 15.374 | 1.00 | 19.92 | A |
| ATOM | 712 | CG | GLN | A | 100 | 30.134 | −21.531 | 15.224 | 1.00 | 28.75 | A |
| ATOM | 713 | CD | GLN | A | 100 | 29.586 | −21.377 | 13.797 | 1.00 | 26.62 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 714 | OE1 | GLN | A | 100 | 30.268 | −21.644 | 12.812 | 1.00 | 30.00 | A |
|---|---|---|---|---|---|---|---|---|---|---|---|
| ATOM | 715 | NE2 | GLN | A | 100 | 28.331 | −20.962 | 13.697 | 1.00 | 35.35 | A |
| ATOM | 716 | C | GLN | A | 100 | 33.626 | −21.109 | 16.881 | 1.00 | 23.35 | A |
| ATOM | 717 | O | GLN | A | 100 | 34.195 | −22.193 | 17.040 | 1.00 | 22.70 | A |
| ATOM | 718 | N | TRP | A | 101 | 34.264 | −19.956 | 16.741 | 1.00 | 23.27 | A |
| ATOM | 719 | CA | TRP | A | 101 | 35.705 | −19.876 | 16.749 | 1.00 | 15.64 | A |
| ATOM | 720 | CB | TRP | A | 101 | 36.196 | −19.441 | 15.365 | 1.00 | 22.35 | A |
| ATOM | 721 | CG | TRP | A | 101 | 36.138 | −20.513 | 14.327 | 1.00 | 24.23 | A |
| ATOM | 722 | CD2 | TRP | A | 101 | 37.249 | −21.271 | 13.844 | 1.00 | 27.32 | A |
| ATOM | 723 | CE2 | TRP | A | 101 | 36.745 | −22.181 | 12.886 | 1.00 | 28.01 | A |
| ATOM | 724 | CE3 | TRP | A | 101 | 38.628 | −21.269 | 14.131 | 1.00 | 24.94 | A |
| ATOM | 725 | CD1 | TRP | A | 101 | 35.029 | −20.973 | 13.660 | 1.00 | 25.04 | A |
| ATOM | 726 | NE1 | TRP | A | 101 | 35.394 | −21.978 | 12.791 | 1.00 | 25.95 | A |
| ATOM | 727 | CZ2 | TRP | A | 101 | 37.572 | −23.080 | 12.211 | 1.00 | 23.73 | A |
| ATOM | 728 | CZ3 | TRP | A | 101 | 39.450 | −22.161 | 13.458 | 1.00 | 27.04 | A |
| ATOM | 729 | CH2 | TRP | A | 101 | 38.913 | −23.060 | 12.508 | 1.00 | 25.03 | A |
| ATOM | 730 | C | TRP | A | 101 | 36.222 | −18.901 | 17.820 | 1.00 | 21.75 | A |
| ATOM | 731 | O | TRP | A | 101 | 35.608 | −17.866 | 18.081 | 1.00 | 23.21 | A |
| ATOM | 732 | N | VAL | A | 102 | 37.356 | −19.229 | 18.434 | 1.00 | 21.20 | A |
| ATOM | 733 | CA | VAL | A | 102 | 37.899 | −18.360 | 19.468 | 1.00 | 20.90 | A |
| ATOM | 734 | CB | VAL | A | 102 | 37.822 | −19.048 | 20.865 | 1.00 | 24.10 | A |
| ATOM | 735 | CG1 | VAL | A | 102 | 38.660 | −20.327 | 20.867 | 1.00 | 20.39 | A |
| ATOM | 736 | CG2 | VAL | A | 102 | 38.289 | −18.084 | 21.948 | 1.00 | 25.04 | A |
| ATOM | 737 | C | VAL | A | 102 | 39.323 | −17.962 | 19.134 | 1.00 | 18.89 | A |
| ATOM | 738 | O | VAL | A | 102 | 40.086 | −18.727 | 18.540 | 1.00 | 21.86 | A |
| ATOM | 739 | N | LEU | A | 103 | 39.655 | −16.734 | 19.505 | 1.00 | 19.38 | A |
| ATOM | 740 | CA | LEU | A | 103 | 40.974 | −16.172 | 19.257 | 1.00 | 23.93 | A |
| ATOM | 741 | CB | LEU | A | 103 | 40.804 | −14.807 | 18.592 | 1.00 | 22.17 | A |
| ATOM | 742 | CG | LEU | A | 103 | 41.959 | −14.186 | 17.825 | 1.00 | 37.54 | A |
| ATOM | 743 | CD1 | LEU | A | 103 | 42.251 | −14.993 | 16.546 | 1.00 | 27.30 | A |
| ATOM | 744 | CD2 | LEU | A | 103 | 41.599 | −12.749 | 17.489 | 1.00 | 40.17 | A |
| ATOM | 745 | C | LEU | A | 103 | 41.584 | −15.986 | 20.639 | 1.00 | 17.92 | A |
| ATOM | 746 | O | LEU | A | 103 | 40.967 | −15.355 | 21.482 | 1.00 | 22.00 | A |
| ATOM | 747 | N | VAL | A | 104 | 42.770 | −16.544 | 20.887 | 1.00 | 18.56 | A |
| ATOM | 748 | CA | VAL | A | 104 | 43.399 | −16.379 | 22.207 | 1.00 | 19.29 | A |
| ATOM | 749 | CB | VAL | A | 104 | 43.759 | −17.743 | 22.856 | 1.00 | 18.67 | A |
| ATOM | 750 | CG1 | VAL | A | 104 | 44.339 | −17.506 | 24.261 | 1.00 | 20.13 | A |
| ATOM | 751 | CG2 | VAL | A | 104 | 42.494 | −18.617 | 22.936 | 1.00 | 14.94 | A |
| ATOM | 752 | C | VAL | A | 104 | 44.666 | −15.589 | 21.978 | 1.00 | 20.36 | A |
| ATOM | 753 | O | VAL | A | 104 | 45.512 | −15.986 | 21.178 | 1.00 | 17.88 | A |
| ATOM | 754 | N | HIS | A | 105 | 44.785 | −14.457 | 22.656 | 1.00 | 19.74 | A |
| ATOM | 755 | CA | HIS | A | 105 | 45.937 | −13.597 | 22.447 | 1.00 | 19.79 | A |
| ATOM | 756 | CB | HIS | A | 105 | 45.489 | −12.413 | 21.556 | 1.00 | 17.21 | A |
| ATOM | 757 | CG | HIS | A | 105 | 46.578 | −11.448 | 21.221 | 1.00 | 16.62 | A |
| ATOM | 758 | CD2 | HIS | A | 105 | 46.671 | −10.111 | 21.426 | 1.00 | 18.79 | A |
| ATOM | 759 | ND1 | HIS | A | 105 | 47.754 | −11.827 | 20.615 | 1.00 | 17.54 | A |
| ATOM | 760 | CE1 | HIS | A | 105 | 48.532 | −10.769 | 20.470 | 1.00 | 18.17 | A |
| ATOM | 761 | NE2 | HIS | A | 105 | 47.898 | −9.714 | 20.958 | 1.00 | 21.82 | A |
| ATOM | 762 | C | HIS | A | 105 | 46.531 | −13.109 | 23.775 | 1.00 | 16.42 | A |
| ATOM | 763 | O | HIS | A | 105 | 45.828 | −12.588 | 24.652 | 1.00 | 16.02 | A |
| ATOM | 764 | N | ASP | A | 106 | 47.843 | −13.267 | 23.937 | 1.00 | 17.10 | A |
| ATOM | 765 | CA | ASP | A | 106 | 48.510 | −12.794 | 25.156 | 1.00 | 19.32 | A |
| ATOM | 766 | CB | ASP | A | 106 | 50.039 | −13.001 | 25.105 | 1.00 | 18.74 | A |
| ATOM | 767 | CG | ASP | A | 106 | 50.450 | −14.462 | 25.086 | 1.00 | 24.98 | A |
| ATOM | 768 | OD1 | ASP | A | 106 | 49.737 | −15.298 | 25.673 | 1.00 | 24.55 | A |
| ATOM | 769 | OD2 | ASP | A | 106 | 51.506 | −14.764 | 24.487 | 1.00 | 23.72 | A |
| ATOM | 770 | C | ASP | A | 106 | 48.306 | −11.295 | 25.384 | 1.00 | 23.60 | A |
| ATOM | 771 | O | ASP | A | 106 | 48.451 | −10.476 | 24.456 | 1.00 | 20.97 | A |
| ATOM | 772 | N | ALA | A | 107 | 47.973 | −10.908 | 26.612 | 1.00 | 17.70 | A |
| ATOM | 773 | CA | ALA | A | 107 | 47.805 | −9.476 | 26.887 | 1.00 | 20.48 | A |
| ATOM | 774 | CB | ALA | A | 107 | 47.376 | −9.284 | 28.308 | 1.00 | 21.67 | A |
| ATOM | 775 | C | ALA | A | 107 | 49.143 | −8.754 | 26.652 | 1.00 | 28.20 | A |
| ATOM | 776 | O | ALA | A | 107 | 49.184 | −7.579 | 26.274 | 1.00 | 22.84 | A |
| ATOM | 777 | N | ALA | A | 108 | 50.230 | −9.495 | 26.847 | 1.00 | 26.69 | A |
| ATOM | 778 | CA | ALA | A | 108 | 51.596 | −8.973 | 26.729 | 1.00 | 29.71 | A |
| ATOM | 779 | CB | ALA | A | 108 | 52.511 | −9.828 | 27.571 | 1.00 | 30.45 | A |
| ATOM | 780 | C | ALA | A | 108 | 52.191 | −8.815 | 25.326 | 1.00 | 32.03 | A |
| ATOM | 781 | O | ALA | A | 108 | 53.392 | −8.537 | 25.178 | 1.00 | 25.61 | A |
| ATOM | 782 | N | ARG | A | 109 | 51.377 | −9.017 | 24.297 | 1.00 | 28.09 | A |
| ATOM | 783 | CA | ARG | A | 109 | 51.850 | −8.860 | 22.928 | 1.00 | 21.72 | A |
| ATOM | 784 | CB | ARG | A | 109 | 51.667 | −10.160 | 22.139 | 1.00 | 23.48 | A |
| ATOM | 785 | CG | ARG | A | 109 | 52.630 | −11.283 | 22.511 | 1.00 | 26.58 | A |
| ATOM | 786 | CD | ARG | A | 109 | 52.364 | −12.493 | 21.627 | 1.00 | 21.06 | A |
| ATOM | 787 | NE | ARG | A | 109 | 53.134 | −13.677 | 22.028 | 1.00 | 27.47 | A |
| ATOM | 788 | CZ | ARG | A | 109 | 54.420 | −13.874 | 21.755 | 1.00 | 26.76 | A |
| ATOM | 789 | NH1 | ARG | A | 109 | 55.115 | −12.965 | 21.071 | 1.00 | 30.79 | A |

APPENDIX 3-continued

X-RAY DATA COORDINATES FOR CDP-ME SYNTHASE COMPLEXED WITH CDP-ME.Mg$^{2+}$(SEQ ID NO:12)

| ATOM | 790 | NH2 | ARG | A | 109 | 55.014 | −14.988 | 22.158 | 1.00 | 31.54 | A |
|---|---|---|---|---|---|---|---|---|---|---|---|
| ATOM | 791 | C | ARG | A | 109 | 51.056 | −7.730 | 22.288 | 1.00 | 21.53 | A |
| ATOM | 792 | O | ARG | A | 109 | 50.129 | −7.971 | 21.529 | 1.00 | 24.06 | A |
| ATOM | 793 | N | PRO | A | 110 | 51.432 | −6.470 | 22.573 | 1.00 | 25.30 | A |
| ATOM | 794 | CD | PRO | A | 110 | 52.499 | −6.067 | 23.509 | 1.00 | 28.30 | A |
| ATOM | 795 | CA | PRO | A | 110 | 50.742 | −5.295 | 22.039 | 1.00 | 25.40 | A |
| ATOM | 796 | CB | PRO | A | 110 | 51.072 | −4.223 | 23.067 | 1.00 | 28.00 | A |
| ATOM | 797 | CG | PRO | A | 110 | 52.512 | −4.546 | 23.382 | 1.00 | 33.07 | A |
| ATOM | 798 | C | PRO | A | 110 | 51.104 | −4.844 | 20.635 | 1.00 | 24.93 | A |
| ATOM | 799 | O | PRO | A | 110 | 50.488 | −3.915 | 20.126 | 1.00 | 31.54 | A |
| ATOM | 800 | N | CYS | A | 111 | 52.056 | −5.507 | 19.990 | 1.00 | 23.29 | A |
| ATOM | 801 | CA | CYS | A | 111 | 52.476 | −5.059 | 18.672 | 1.00 | 29.21 | A |
| ATOM | 802 | CB | CYS | A | 111 | 54.015 | −5.148 | 18.569 | 1.00 | 23.05 | A |
| ATOM | 803 | SG | CYS | A | 111 | 54.829 | −4.140 | 19.846 | 1.00 | 36.29 | A |
| ATOM | 804 | C | CYS | A | 111 | 51.816 | −5.742 | 17.482 | 1.00 | 32.48 | A |
| ATOM | 805 | O | CYS | A | 111 | 52.276 | −5.587 | 16.353 | 1.00 | 30.99 | A |
| ATOM | 806 | N | LEU | A | 112 | 50.731 | −6.473 | 17.735 | 1.00 | 25.40 | A |
| ATOM | 807 | CA | LEU | A | 112 | 50.005 | −7.178 | 16.690 | 1.00 | 23.18 | A |
| ATOM | 808 | CB | LEU | A | 112 | 48.801 | −7.911 | 17.295 | 1.00 | 20.02 | A |
| ATOM | 809 | CG | LEU | A | 112 | 47.864 | −8.609 | 16.305 | 1.00 | 24.91 | A |
| ATOM | 810 | CD1 | LEU | A | 112 | 48.608 | −9.742 | 15.593 | 1.00 | 27.53 | A |
| ATOM | 811 | CD2 | LEU | A | 112 | 46.657 | −9.163 | 17.068 | 1.00 | 23.60 | A |
| ATOM | 812 | C | LEU | A | 112 | 49.513 | −6.274 | 15.564 | 1.00 | 24.34 | A |
| ATOM | 813 | O | LEU | A | 112 | 48.836 | −5.278 | 15.821 | 1.00 | 28.28 | A |
| ATOM | 814 | N | HIS | A | 113 | 49.829 | −6.642 | 14.325 | 1.00 | 26.98 | A |
| ATOM | 815 | CA | HIS | A | 113 | 49.405 | −5.887 | 13.140 | 1.00 | 31.14 | A |
| ATOM | 816 | CB | HIS | A | 113 | 50.502 | −5.876 | 12.061 | 1.00 | 32.41 | A |
| ATOM | 817 | CG | HIS | A | 113 | 51.625 | −4.932 | 12.349 | 1.00 | 37.39 | A |
| ATOM | 818 | CD2 | HIS | A | 113 | 52.197 | −4.553 | 13.516 | 1.00 | 38.82 | A |
| ATOM | 819 | ND1 | HIS | A | 113 | 52.302 | −4.262 | 11.353 | 1.00 | 41.80 | A |
| ATOM | 820 | CE1 | HIS | A | 113 | 53.242 | −3.507 | 11.897 | 1.00 | 48.05 | A |
| ATOM | 821 | NE2 | HIS | A | 113 | 53.201 | −3.666 | 13.209 | 1.00 | 43.59 | A |
| ATOM | 822 | C | HIS | A | 113 | 48.142 | −6.487 | 12.537 | 1.00 | 26.49 | A |
| ATOM | 823 | O | HIS | A | 113 | 47.926 | −7.700 | 12.601 | 1.00 | 23.11 | A |
| ATOM | 824 | N | GLN | A | 114 | 47.311 | −5.639 | 11.933 | 1.00 | 22.66 | A |
| ATOM | 825 | CA | GLN | A | 114 | 46.066 | −6.109 | 11.334 | 1.00 | 24.25 | A |
| ATOM | 826 | CB | GLN | A | 114 | 45.232 | −4.906 | 10.853 | 1.00 | 25.32 | A |
| ATOM | 827 | CG | GLN | A | 114 | 44.741 | −4.041 | 12.006 | 1.00 | 25.37 | A |
| ATOM | 828 | CD | GLN | A | 114 | 43.858 | −4.843 | 12.972 | 1.00 | 23.76 | A |
| ATOM | 829 | OE1 | GLN | A | 114 | 42.784 | −5.345 | 12.603 | 1.00 | 24.75 | A |
| ATOM | 830 | NE2 | GLN | A | 114 | 44.328 | −4.988 | 14.207 | 1.00 | 23.83 | A |
| ATOM | 831 | C | GLN | A | 114 | 46.227 | −7.114 | 10.192 | 1.00 | 21.45 | A |
| ATOM | 832 | O | GLN | A | 114 | 45.401 | −8.003 | 10.041 | 1.00 | 25.80 | A |
| ATOM | 833 | N | ASP | A | 115 | 47.275 | −6.985 | 9.388 | 1.00 | 23.01 | A |
| ATOM | 834 | CA | ASP | A | 115 | 47.437 | −7.923 | 8.286 | 1.00 | 24.77 | A |
| ATOM | 835 | CB | ASP | A | 115 | 48.562 | −7.478 | 7.339 | 1.00 | 28.75 | A |
| ATOM | 836 | CG | ASP | A | 115 | 49.896 | −7.327 | 8.036 | 1.00 | 37.85 | A |
| ATOM | 837 | OD1 | ASP | A | 115 | 49.951 | −7.323 | 9.291 | 1.00 | 46.17 | A |
| ATOM | 838 | OD2 | ASP | A | 115 | 50.899 | −7.194 | 7.314 | 1.00 | 46.05 | A |
| ATOM | 839 | C | ASP | A | 115 | 47.692 | −9.328 | 8.796 | 1.00 | 20.79 | A |
| ATOM | 840 | O | ASP | A | 115 | 47.152 | −10.280 | 8.256 | 1.00 | 24.47 | A |
| ATOM | 841 | N | ASP | A | 116 | 48.502 | −9.451 | 9.846 | 1.00 | 22.82 | A |
| ATOM | 842 | CA | ASP | A | 116 | 48.784 | −10.758 | 10.419 | 1.00 | 22.69 | A |
| ATOM | 843 | CB | ASP | A | 116 | 49.807 | −10.660 | 11.552 | 1.00 | 24.90 | A |
| ATOM | 844 | CG | ASP | A | 116 | 51.238 | −10.628 | 11.045 | 1.00 | 23.96 | A |
| ATOM | 845 | OD1 | ASP | A | 116 | 51.428 | −10.821 | 9.832 | 1.00 | 31.59 | A |
| ATOM | 846 | OD2 | ASP | A | 116 | 52.158 | −10.430 | 11.865 | 1.00 | 26.58 | A |
| ATOM | 847 | C | ASP | A | 116 | 47.483 | −11.317 | 10.968 | 1.00 | 21.60 | A |
| ATOM | 848 | O | ASP | A | 116 | 47.171 | −12.468 | 10.739 | 1.00 | 20.34 | A |
| ATOM | 849 | N | LEU | A | 117 | 46.735 | −10.487 | 11.690 | 1.00 | 23.95 | A |
| ATOM | 850 | CA | LEU | A | 117 | 45.468 | −10.917 | 12.269 | 1.00 | 22.01 | A |
| ATOM | 851 | CB | LEU | A | 117 | 44.850 | −9.783 | 13.084 | 1.00 | 20.85 | A |
| ATOM | 852 | CG | LEU | A | 117 | 43.479 | −10.068 | 13.713 | 1.00 | 18.62 | A |
| ATOM | 853 | CD1 | LEU | A | 117 | 43.495 | −11.377 | 14.508 | 1.00 | 22.76 | A |
| ATOM | 854 | CD2 | LEU | A | 117 | 43.132 | −8.889 | 14.600 | 1.00 | 22.77 | A |
| ATOM | 855 | C | LEU | A | 117 | 44.467 | −11.406 | 11.221 | 1.00 | 20.47 | A |
| ATOM | 856 | O | LEU | A | 117 | 43.850 | −12.478 | 11.378 | 1.00 | 22.04 | A |
| ATOM | 857 | N | ALA | A | 118 | 44.291 | −10.624 | 10.159 | 1.00 | 21.07 | A |
| ATOM | 858 | CA | ALA | A | 118 | 43.363 | −11.009 | 9.100 | 1.00 | 24.78 | A |
| ATOM | 859 | CB | ALA | A | 118 | 43.244 | −9.887 | 8.048 | 1.00 | 23.53 | A |
| ATOM | 860 | C | ALA | A | 118 | 43.802 | −12.317 | 8.441 | 1.00 | 23.04 | A |
| ATOM | 861 | O | ALA | A | 118 | 42.958 | −13.151 | 8.115 | 1.00 | 26.43 | A |
| ATOM | 862 | N | ARG | A | 119 | 45.102 | −12.519 | 8.246 | 1.00 | 27.95 | A |
| ATOM | 863 | CA | ARG | A | 119 | 45.533 | −13.760 | 7.616 | 1.00 | 29.19 | A |
| ATOM | 864 | CB | ARG | A | 119 | 47.024 | −13.709 | 7.237 | 1.00 | 30.71 | A |
| ATOM | 865 | CG | ARG | A | 119 | 47.278 | −13.113 | 5.845 | 1.00 | 36.65 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 866 | CD | ARG | A | 119 | 48.737 | −13.242 | 5.375 | 1.00 | 34.57 | A |
|---|---|---|---|---|---|---|---|---|---|---|---|
| ATOM | 867 | NE | ARG | A | 119 | 49.659 | −12.656 | 6.332 | 1.00 | 40.01 | A |
| ATOM | 868 | CZ | ARG | A | 119 | 50.588 | −13.339 | 6.991 | 1.00 | 41.63 | A |
| ATOM | 869 | NH1 | ARG | A | 119 | 50.732 | −14.646 | 6.788 | 1.00 | 45.99 | A |
| ATOM | 870 | NH2 | ARG | A | 119 | 51.349 | −12.715 | 7.878 | 1.00 | 37.56 | A |
| ATOM | 871 | C | ARG | A | 119 | 45.242 | −14.962 | 8.506 | 1.00 | 28.69 | A |
| ATOM | 872 | O | ARG | A | 119 | 44.893 | −16.031 | 8.012 | 1.00 | 26.98 | A |
| ATOM | 873 | N | LEU | A | 120 | 45.382 | −14.787 | 9.816 | 1.00 | 26.20 | A |
| ATOM | 874 | CA | LEU | A | 120 | 45.090 | −15.864 | 10.766 | 1.00 | 23.00 | A |
| ATOM | 875 | CB | LEU | A | 120 | 45.503 | −15.450 | 12.180 | 1.00 | 18.65 | A |
| ATOM | 876 | CG | LEU | A | 120 | 45.296 | −16.530 | 13.263 | 1.00 | 24.57 | A |
| ATOM | 877 | CD1 | LEU | A | 120 | 46.285 | −17.670 | 13.008 | 1.00 | 24.89 | A |
| ATOM | 878 | CD2 | LEU | A | 120 | 45.497 | −15.962 | 14.663 | 1.00 | 19.06 | A |
| ATOM | 879 | C | LEU | A | 120 | 43.597 | −16.198 | 10.785 | 1.00 | 22.34 | A |
| ATOM | 880 | O | LEU | A | 120 | 43.196 | −17.371 | 10.832 | 1.00 | 22.65 | A |
| ATOM | 881 | N | LEU | A | 121 | 42.773 | −15.156 | 10.779 | 1.00 | 20.79 | A |
| ATOM | 882 | CA | LEU | A | 121 | 41.338 | −15.333 | 10.816 | 1.00 | 19.64 | A |
| ATOM | 883 | CB | LEU | A | 121 | 40.651 | −13.967 | 10.982 | 1.00 | 17.53 | A |
| ATOM | 884 | CG | LEU | A | 121 | 40.695 | −13.410 | 12.401 | 1.00 | 32.93 | A |
| ATOM | 885 | CD1 | LEU | A | 121 | 40.194 | −11.969 | 12.442 | 1.00 | 26.55 | A |
| ATOM | 886 | CD2 | LEU | A | 121 | 39.848 | −14.292 | 13.293 | 1.00 | 28.08 | A |
| ATOM | 887 | C | LEU | A | 121 | 40.802 | −16.063 | 9.586 | 1.00 | 22.73 | A |
| ATOM | 888 | O | LEU | A | 121 | 39.760 | −16.715 | 9.651 | 1.00 | 20.18 | A |
| ATOM | 889 | N | ALA | A | 122 | 41.513 | −15.963 | 8.469 | 1.00 | 22.06 | A |
| ATOM | 890 | CA | ALA | A | 122 | 41.068 | −16.626 | 7.247 | 1.00 | 28.96 | A |
| ATOM | 891 | CB | ALA | A | 122 | 41.977 | −16.256 | 6.085 | 1.00 | 34.80 | A |
| ATOM | 892 | C | ALA | A | 122 | 41.029 | −18.140 | 7.418 | 1.00 | 33.12 | A |
| ATOM | 893 | O | ALA | A | 122 | 40.282 | −18.833 | 6.716 | 1.00 | 31.70 | A |
| ATOM | 894 | N | LEU | A | 123 | 41.813 | −18.657 | 8.367 | 1.00 | 27.58 | A |
| ATOM | 895 | CA | LEU | A | 123 | 41.855 | −20.106 | 8.612 | 1.00 | 29.07 | A |
| ATOM | 896 | CB | LEU | A | 123 | 42.783 | −20.434 | 9.789 | 1.00 | 29.67 | A |
| ATOM | 897 | CG | LEU | A | 123 | 44.279 | −20.218 | 9.566 | 1.00 | 32.03 | A |
| ATOM | 898 | CD1 | LEU | A | 123 | 45.039 | −20.698 | 10.807 | 1.00 | 32.57 | A |
| ATOM | 899 | CD2 | LEU | A | 123 | 44.741 | −21.000 | 8.334 | 1.00 | 36.08 | A |
| ATOM | 900 | C | LEU | A | 123 | 40.497 | −20.779 | 8.864 | 1.00 | 30.01 | A |
| ATOM | 901 | O | LEU | A | 123 | 40.328 | −21.975 | 8.596 | 1.00 | 26.68 | A |
| ATOM | 902 | N | SER | A | 124 | 39.530 | −20.028 | 9.379 | 1.00 | 27.40 | A |
| ATOM | 903 | CA | SER | A | 124 | 38.220 | −20.609 | 9.651 | 1.00 | 25.54 | A |
| ATOM | 904 | CB | SER | A | 124 | 37.334 | −19.624 | 10.419 | 1.00 | 29.50 | A |
| ATOM | 905 | OG | SER | A | 124 | 37.048 | −18.472 | 9.639 | 1.00 | 26.90 | A |
| ATOM | 906 | C | SER | A | 124 | 37.505 | −21.035 | 8.365 | 1.00 | 27.69 | A |
| ATOM | 907 | O | SER | A | 124 | 36.549 | −21.808 | 8.404 | 1.00 | 31.33 | A |
| ATOM | 908 | N | GLU | A | 125 | 37.966 | −20.527 | 7.231 | 1.00 | 33.28 | A |
| ATOM | 909 | CA | GLU | A | 125 | 37.344 | −20.863 | 5.957 | 1.00 | 38.91 | A |
| ATOM | 910 | CB | GLU | A | 125 | 37.070 | −19.585 | 5.160 | 1.00 | 37.88 | A |
| ATOM | 911 | CG | GLU | A | 125 | 36.360 | −18.520 | 5.986 | 1.00 | 42.24 | A |
| ATOM | 912 | CD | GLU | A | 125 | 35.156 | −19.084 | 6.731 | 1.00 | 43.92 | A |
| ATOM | 913 | OE1 | GLU | A | 125 | 35.048 | −18.867 | 7.959 | 1.00 | 35.48 | A |
| ATOM | 914 | OE2 | GLU | A | 125 | 34.315 | −19.750 | 6.089 | 1.00 | 49.24 | A |
| ATOM | 915 | C | GLU | A | 125 | 38.215 | −21.811 | 5.143 | 1.00 | 44.07 | A |
| ATOM | 916 | O | GLU | A | 125 | 37.932 | −22.081 | 3.978 | 1.00 | 53.04 | A |
| ATOM | 917 | N | THR | A | 126 | 39.277 | −22.321 | 5.750 | 1.00 | 43.05 | A |
| ATOM | 918 | CA | THR | A | 126 | 40.157 | −23.234 | 5.039 | 1.00 | 45.62 | A |
| ATOM | 919 | CB | THR | A | 126 | 41.361 | −22.482 | 4.415 | 1.00 | 43.90 | A |
| ATOM | 920 | OG1 | THR | A | 126 | 42.176 | −21.917 | 5.453 | 1.00 | 45.54 | A |
| ATOM | 921 | CG2 | THR | A | 126 | 40.875 | −21.364 | 3.503 | 1.00 | 44.96 | A |
| ATOM | 922 | C | THR | A | 126 | 40.682 | −24.328 | 5.955 | 1.00 | 48.52 | A |
| ATOM | 923 | O | THR | A | 126 | 41.397 | −25.224 | 5.507 | 1.00 | 49.07 | A |
| ATOM | 924 | N | SER | A | 127 | 40.317 | −24.257 | 7.233 | 1.00 | 45.05 | A |
| ATOM | 925 | CA | SER | A | 127 | 40.776 | −25.228 | 8.217 | 1.00 | 45.95 | A |
| ATOM | 926 | CB | SER | A | 127 | 41.895 | −24.629 | 9.080 | 1.00 | 44.81 | A |
| ATOM | 927 | OG | SER | A | 127 | 42.250 | −25.515 | 10.131 | 1.00 | 49.63 | A |
| ATOM | 928 | C | SER | A | 127 | 39.670 | −25.717 | 9.131 | 1.00 | 44.97 | A |
| ATOM | 929 | O | SER | A | 127 | 38.686 | −25.020 | 9.380 | 1.00 | 47.08 | A |
| ATOM | 930 | N | ARG | A | 128 | 39.855 | −26.933 | 9.626 | 1.00 | 43.89 | A |
| ATOM | 931 | CA | ARG | A | 128 | 38.918 | −27.567 | 10.533 | 1.00 | 42.93 | A |
| ATOM | 932 | CB | ARG | A | 128 | 38.604 | −28.990 | 10.042 | 1.00 | 51.95 | A |
| ATOM | 933 | CG | ARG | A | 128 | 37.366 | −29.115 | 9.154 | 1.00 | 54.74 | A |
| ATOM | 934 | CD | ARG | A | 128 | 36.093 | −29.168 | 10.004 | 1.00 | 60.19 | A |
| ATOM | 935 | NE | ARG | A | 128 | 34.879 | −29.330 | 9.207 | 1.00 | 62.65 | A |
| ATOM | 936 | CZ | ARG | A | 128 | 34.401 | −28.412 | 8.368 | 1.00 | 68.49 | A |
| ATOM | 937 | NH1 | ARG | A | 128 | 35.035 | −27.257 | 8.212 | 1.00 | 67.91 | A |
| ATOM | 938 | NH2 | ARG | A | 128 | 33.284 | −28.647 | 7.688 | 1.00 | 67.50 | A |
| ATOM | 939 | C | ARG | A | 128 | 39.517 | −27.627 | 11.941 | 1.00 | 42.19 | A |
| ATOM | 940 | O | ARG | A | 128 | 38.809 | −27.880 | 12.919 | 1.00 | 44.76 | A |
| ATOM | 941 | N | THR | A | 129 | 40.820 | −27.399 | 12.052 | 1.00 | 41.39 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 942 | CA | THR | A | 129 | 41.450 | −27.465 | 13.361 | 1.00 | 40.78 | A |
|---|---|---|---|---|---|---|---|---|---|---|---|
| ATOM | 943 | CB | THR | A | 129 | 42.582 | −28.510 | 13.390 | 1.00 | 42.20 | A |
| ATOM | 944 | OG1 | THR | A | 129 | 43.617 | −28.133 | 12.475 | 1.00 | 50.78 | A |
| ATOM | 945 | CG2 | THR | A | 129 | 42.038 | −29.872 | 13.003 | 1.00 | 40.95 | A |
| ATOM | 946 | C | THR | A | 129 | 41.987 | −26.126 | 13.826 | 1.00 | 34.67 | A |
| ATOM | 947 | O | THR | A | 129 | 42.095 | −25.884 | 15.022 | 1.00 | 43.67 | A |
| ATOM | 948 | N | GLY | A | 130 | 42.312 | −25.250 | 12.888 | 1.00 | 27.96 | A |
| ATOM | 949 | CA | GLY | A | 130 | 42.816 | −23.945 | 13.277 | 1.00 | 25.79 | A |
| ATOM | 950 | C | GLY | A | 130 | 44.315 | −23.800 | 13.112 | 1.00 | 26.64 | A |
| ATOM | 951 | O | GLY | A | 130 | 44.957 | −24.641 | 12.489 | 1.00 | 23.28 | A |
| ATOM | 952 | N | GLY | A | 131 | 44.872 | −22.727 | 13.664 | 1.00 | 24.45 | A |
| ATOM | 953 | CA | GLY | A | 131 | 46.311 | −22.504 | 13.550 | 1.00 | 20.41 | A |
| ATOM | 954 | C | GLY | A | 131 | 46.781 | −21.350 | 14.417 | 1.00 | 20.76 | A |
| ATOM | 955 | O | GLY | A | 131 | 46.020 | −20.813 | 15.226 | 1.00 | 21.17 | A |
| ATOM | 956 | N | ILE | A | 132 | 48.045 | −20.971 | 14.244 | 1.00 | 21.83 | A |
| ATOM | 957 | CA | ILE | A | 132 | 48.640 | −19.893 | 15.024 | 1.00 | 20.95 | A |
| ATOM | 958 | CB | ILE | A | 132 | 49.471 | −20.449 | 16.226 | 1.00 | 20.47 | A |
| ATOM | 959 | CG2 | ILE | A | 132 | 48.697 | −21.537 | 16.941 | 1.00 | 17.28 | A |
| ATOM | 960 | CG1 | ILE | A | 132 | 50.786 | −21.066 | 15.717 | 1.00 | 21.17 | A |
| ATOM | 961 | CD | ILE | A | 132 | 51.801 | −21.349 | 16.845 | 1.00 | 21.54 | A |
| ATOM | 962 | C | ILE | A | 132 | 49.591 | −19.028 | 14.197 | 1.00 | 17.76 | A |
| ATOM | 963 | O | ILE | A | 132 | 50.073 | −19.453 | 13.151 | 1.00 | 23.88 | A |
| ATOM | 964 | N | LEU | A | 133 | 49.848 | −17.816 | 14.685 | 1.00 | 21.08 | A |
| ATOM | 965 | CA | LEU | A | 133 | 50.792 | −16.913 | 14.050 | 1.00 | 24.05 | A |
| ATOM | 966 | CB | LEU | A | 133 | 50.607 | −15.488 | 14.564 | 1.00 | 21.48 | A |
| ATOM | 967 | CG | LEU | A | 133 | 49.440 | −14.759 | 13.896 | 1.00 | 23.30 | A |
| ATOM | 968 | CD1 | LEU | A | 133 | 49.384 | −13.275 | 14.336 | 1.00 | 25.14 | A |
| ATOM | 969 | CD2 | LEU | A | 133 | 49.634 | −14.843 | 12.358 | 1.00 | 25.37 | A |
| ATOM | 970 | C | LEU | A | 133 | 52.118 | −17.478 | 14.523 | 1.00 | 25.59 | A |
| ATOM | 971 | O | LEU | A | 133 | 52.216 | −17.977 | 15.649 | 1.00 | 20.11 | A |
| ATOM | 972 | N | ALA | A | 134 | 53.140 | −17.402 | 13.677 | 1.00 | 23.59 | A |
| ATOM | 973 | CA | ALA | A | 134 | 54.438 | −17.963 | 14.030 | 1.00 | 25.45 | A |
| ATOM | 974 | CB | ALA | A | 134 | 54.424 | −19.500 | 13.784 | 1.00 | 23.71 | A |
| ATOM | 975 | C | ALA | A | 134 | 55.575 | −17.325 | 13.242 | 1.00 | 27.73 | A |
| ATOM | 976 | O | ALA | A | 134 | 55.365 | −16.848 | 12.124 | 1.00 | 24.04 | A |
| ATOM | 977 | N | ALA | A | 135 | 56.778 | −17.339 | 13.814 | 1.00 | 23.49 | A |
| ATOM | 978 | CA | ALA | A | 135 | 57.940 | −16.755 | 13.132 | 1.00 | 25.63 | A |
| ATOM | 979 | CB | ALA | A | 135 | 58.421 | −15.478 | 13.869 | 1.00 | 23.16 | A |
| ATOM | 980 | C | ALA | A | 135 | 59.072 | −17.768 | 13.033 | 1.00 | 28.82 | A |
| ATOM | 981 | O | ALA | A | 135 | 59.425 | −18.420 | 14.013 | 1.00 | 28.05 | A |
| ATOM | 982 | N | PRO | A | 136 | 59.663 | −17.906 | 11.838 | 1.00 | 34.33 | A |
| ATOM | 983 | CD | PRO | A | 136 | 59.348 | −17.142 | 10.618 | 1.00 | 29.79 | A |
| ATOM | 984 | CA | PRO | A | 136 | 60.768 | −18.847 | 11.603 | 1.00 | 31.03 | A |
| ATOM | 985 | CB | PRO | A | 136 | 61.129 | −18.594 | 10.141 | 1.00 | 34.78 | A |
| ATOM | 986 | CG | PRO | A | 136 | 59.851 | −18.048 | 9.546 | 1.00 | 32.53 | A |
| ATOM | 987 | C | PRO | A | 136 | 61.973 | −18.611 | 12.518 | 1.00 | 26.42 | A |
| ATOM | 988 | O | PRO | A | 136 | 62.317 | −17.471 | 12.810 | 1.00 | 23.61 | A |
| ATOM | 989 | N | VAL | A | 137 | 62.629 | −19.684 | 12.955 | 1.00 | 25.72 | A |
| ATOM | 990 | CA | VAL | A | 137 | 63.804 | −19.563 | 13.816 | 1.00 | 23.16 | A |
| ATOM | 991 | CB | VAL | A | 137 | 64.093 | −20.908 | 14.554 | 1.00 | 24.83 | A |
| ATOM | 992 | CG1 | VAL | A | 137 | 65.507 | −20.897 | 15.190 | 1.00 | 23.13 | A |
| ATOM | 993 | CG2 | VAL | A | 137 | 63.052 | −21.108 | 15.676 | 1.00 | 24.16 | A |
| ATOM | 994 | C | VAL | A | 137 | 64.996 | −19.161 | 12.940 | 1.00 | 27.04 | A |
| ATOM | 995 | O | VAL | A | 137 | 65.161 | −19.683 | 11.836 | 1.00 | 30.50 | A |
| ATOM | 996 | N | ARG | A | 138 | 65.803 | −18.223 | 13.432 | 1.00 | 27.80 | A |
| ATOM | 997 | CA | ARG | A | 138 | 66.971 | −17.728 | 12.711 | 1.00 | 31.83 | A |
| ATOM | 998 | CB | ARG | A | 138 | 66.970 | −16.201 | 12.681 | 1.00 | 34.01 | A |
| ATOM | 999 | CG | ARG | A | 138 | 65.773 | −15.562 | 12.000 | 1.00 | 45.82 | A |
| ATOM | 1000 | CD | ARG | A | 138 | 65.929 | −14.040 | 12.029 | 1.00 | 51.85 | A |
| ATOM | 1001 | NE | ARG | A | 138 | 64.853 | −13.351 | 11.321 | 1.00 | 60.52 | A |
| ATOM | 1002 | CZ | ARG | A | 138 | 64.933 | −12.099 | 10.882 | 1.00 | 59.91 | A |
| ATOM | 1003 | NH1 | ARG | A | 138 | 66.046 | −11.398 | 11.082 | 1.00 | 51.33 | A |
| ATOM | 1004 | NH2 | ARG | A | 138 | 63.904 | −11.558 | 10.239 | 1.00 | 56.45 | A |
| ATOM | 1005 | C | ARG | A | 138 | 68.318 | −18.196 | 13.269 | 1.00 | 31.64 | A |
| ATOM | 1006 | O | ARG | A | 138 | 69.192 | −18.599 | 12.510 | 1.00 | 33.64 | A |
| ATOM | 1007 | N | ASP | A | 139 | 68.498 | −18.136 | 14.582 | 1.00 | 27.62 | A |
| ATOM | 1008 | CA | ASP | A | 139 | 69.766 | −18.562 | 15.157 | 1.00 | 27.35 | A |
| ATOM | 1009 | CB | ASP | A | 139 | 69.933 | −18.050 | 16.585 | 1.00 | 31.60 | A |
| ATOM | 1010 | CG | ASP | A | 139 | 70.006 | −16.554 | 16.667 | 1.00 | 27.85 | A |
| ATOM | 1011 | OD1 | ASP | A | 139 | 70.589 | −15.936 | 15.751 | 1.00 | 30.40 | A |
| ATOM | 1012 | OD2 | ASP | A | 139 | 69.488 | −16.012 | 17.671 | 1.00 | 35.49 | A |
| ATOM | 1013 | C | ASP | A | 139 | 69.892 | −20.068 | 15.217 | 1.00 | 25.50 | A |
| ATOM | 1014 | O | ASP | A | 139 | 68.904 | −20.797 | 15.131 | 1.00 | 25.21 | A |
| ATOM | 1015 | N | THR | A | 140 | 71.124 | −20.531 | 15.384 | 1.00 | 24.74 | A |
| ATOM | 1016 | CA | THR | A | 140 | 71.357 | −21.960 | 15.535 | 1.00 | 25.72 | A |
| ATOM | 1017 | CB | THR | A | 140 | 72.876 | −22.279 | 15.523 | 1.00 | 19.91 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 1018 | OG1 | THR | A | 140 | 73.375 | −22.103 | 14.197 | 1.00 | 28.24 | A |
|---|---|---|---|---|---|---|---|---|---|---|---|
| ATOM | 1019 | CG2 | THR | A | 140 | 73.155 | −23.710 | 15.961 | 1.00 | 20.51 | A |
| ATOM | 1020 | C | THR | A | 140 | 70.779 | −22.208 | 16.930 | 1.00 | 25.65 | A |
| ATOM | 1021 | O | THR | A | 140 | 70.972 | −21.392 | 17.824 | 1.00 | 24.08 | A |
| ATOM | 1022 | N | MET | A | 141 | 70.070 | −23.314 | 17.125 | 1.00 | 23.51 | A |
| ATOM | 1023 | CA | MET | A | 141 | 69.502 | −23.614 | 18.426 | 1.00 | 22.08 | A |
| ATOM | 1024 | CB | MET | A | 141 | 68.016 | −24.018 | 18.288 | 1.00 | 19.77 | A |
| ATOM | 1025 | CG | MET | A | 141 | 66.989 | −22.902 | 18.021 | 1.00 | 30.65 | A |
| ATOM | 1026 | SD | MET | A | 141 | 66.965 | −21.538 | 19.189 | 1.00 | 18.93 | A |
| ATOM | 1027 | CE | MET | A | 141 | 67.771 | −20.517 | 18.219 | 1.00 | 23.08 | A |
| ATOM | 1028 | C | MET | A | 141 | 70.290 | −24.746 | 19.090 | 1.00 | 28.16 | A |
| ATOM | 1029 | O | MET | A | 141 | 70.800 | −25.643 | 18.413 | 1.00 | 28.96 | A |
| ATOM | 1030 | N | LYS | A | 142 | 70.407 | −24.681 | 20.419 | 1.00 | 23.59 | A |
| ATOM | 1031 | CA | LYS | A | 142 | 71.124 | −25.698 | 21.186 | 1.00 | 25.71 | A |
| ATOM | 1032 | CB | LYS | A | 142 | 72.390 | −25.115 | 21.821 | 1.00 | 25.60 | A |
| ATOM | 1033 | CG | LYS | A | 142 | 73.367 | −24.457 | 20.872 | 1.00 | 30.53 | A |
| ATOM | 1034 | CD | LYS | A | 142 | 73.906 | −25.424 | 19.831 | 1.00 | 25.24 | A |
| ATOM | 1035 | CE | LYS | A | 142 | 74.976 | −24.730 | 18.994 | 1.00 | 29.76 | A |
| ATOM | 1036 | NZ | LYS | A | 142 | 75.561 | −25.590 | 17.933 | 1.00 | 21.43 | A |
| ATOM | 1037 | C | LYS | A | 142 | 70.287 | −26.269 | 22.329 | 1.00 | 26.37 | A |
| ATOM | 1038 | O | LYS | A | 142 | 69.632 | −25.525 | 23.070 | 1.00 | 26.20 | A |
| ATOM | 1039 | N | ARG | A | 143 | 70.339 | −27.588 | 22.490 | 1.00 | 27.82 | A |
| ATOM | 1040 | CA | ARG | A | 143 | 69.646 | −28.259 | 23.579 | 1.00 | 30.30 | A |
| ATOM | 1041 | CB | ARG | A | 143 | 69.094 | −29.612 | 23.110 | 1.00 | 30.18 | A |
| ATOM | 1042 | CG | ARG | A | 143 | 68.646 | −30.519 | 24.239 | 1.00 | 35.06 | A |
| ATOM | 1043 | CD | ARG | A | 143 | 67.373 | −29.999 | 24.867 | 1.00 | 29.87 | A |
| ATOM | 1044 | NE | ARG | A | 143 | 66.283 | −29.964 | 23.895 | 1.00 | 29.44 | A |
| ATOM | 1045 | CZ | ARG | A | 143 | 65.186 | −29.228 | 24.045 | 1.00 | 24.15 | A |
| ATOM | 1046 | NH1 | ARG | A | 143 | 65.041 | −28.473 | 25.128 | 1.00 | 24.69 | A |
| ATOM | 1047 | NH2 | ARG | A | 143 | 64.244 | −29.251 | 23.119 | 1.00 | 25.98 | A |
| ATOM | 1048 | C | ARG | A | 143 | 70.706 | −28.486 | 24.670 | 1.00 | 30.42 | A |
| ATOM | 1049 | O | ARG | A | 143 | 71.766 | −29.064 | 24.407 | 1.00 | 28.79 | A |
| ATOM | 1050 | N | ALA | A | 144 | 70.432 | −28.019 | 25.883 | 1.00 | 26.70 | A |
| ATOM | 1051 | CA | ALA | A | 144 | 71.360 | −28.182 | 26.995 | 1.00 | 32.38 | A |
| ATOM | 1052 | CB | ALA | A | 144 | 71.086 | −27.125 | 28.056 | 1.00 | 31.20 | A |
| ATOM | 1053 | C | ALA | A | 144 | 71.226 | −29.564 | 27.618 | 1.00 | 37.80 | A |
| ATOM | 1054 | O | ALA | A | 144 | 70.181 | −30.208 | 27.500 | 1.00 | 30.99 | A |
| ATOM | 1055 | N | GLU | A | 145 | 72.287 | −30.010 | 28.281 | 1.00 | 33.68 | A |
| ATOM | 1056 | CA | GLU | A | 145 | 72.267 | −31.299 | 28.956 | 1.00 | 33.78 | A |
| ATOM | 1057 | CB | GLU | A | 145 | 73.681 | −31.746 | 29.315 | 1.00 | 39.72 | A |
| ATOM | 1058 | CG | GLU | A | 145 | 74.519 | −32.054 | 28.088 | 1.00 | 36.69 | A |
| ATOM | 1059 | CD | GLU | A | 145 | 75.874 | −32.660 | 28.419 | 1.00 | 50.16 | A |
| ATOM | 1060 | OE1 | GLU | A | 145 | 76.564 | −32.141 | 29.329 | 1.00 | 44.36 | A |
| ATOM | 1061 | OE2 | GLU | A | 145 | 76.257 | −33.654 | 27.761 | 1.00 | 48.24 | A |
| ATOM | 1062 | C | GLU | A | 145 | 71.416 | −31.131 | 30.201 | 1.00 | 41.12 | A |
| ATOM | 1063 | O | GLU | A | 145 | 71.443 | −30.072 | 30.841 | 1.00 | 33.17 | A |
| ATOM | 1064 | N | PRO | A | 146 | 70.643 | −32.175 | 30.554 | 1.00 | 42.14 | A |
| ATOM | 1065 | CD | PRO | A | 146 | 70.796 | −33.533 | 29.998 | 1.00 | 44.90 | A |
| ATOM | 1066 | CA | PRO | A | 146 | 69.750 | −32.202 | 31.712 | 1.00 | 48.22 | A |
| ATOM | 1067 | CB | PRO | A | 146 | 69.701 | −33.682 | 32.066 | 1.00 | 45.99 | A |
| ATOM | 1068 | CG | PRO | A | 146 | 69.694 | −34.308 | 30.708 | 1.00 | 48.46 | A |
| ATOM | 1069 | C | PRO | A | 146 | 70.161 | −31.328 | 32.882 | 1.00 | 49.31 | A |
| ATOM | 1070 | O | PRO | A | 146 | 69.526 | −30.313 | 33.155 | 1.00 | 55.93 | A |
| ATOM | 1071 | N | GLY | A | 147 | 71.227 | −31.705 | 33.571 | 1.00 | 49.59 | A |
| ATOM | 1072 | CA | GLY | A | 147 | 71.635 | −30.915 | 34.715 | 1.00 | 58.44 | A |
| ATOM | 1073 | C | GLY | A | 147 | 72.964 | −30.225 | 34.529 | 1.00 | 60.62 | A |
| ATOM | 1074 | O | GLY | A | 147 | 73.829 | −30.295 | 35.403 | 1.00 | 64.08 | A |
| ATOM | 1075 | N | LYS | A | 148 | 73.129 | −29.548 | 33.400 | 1.00 | 54.83 | A |
| ATOM | 1076 | CA | LYS | A | 148 | 74.381 | −28.869 | 33.121 | 1.00 | 54.32 | A |
| ATOM | 1077 | CB | LYS | A | 148 | 75.412 | −29.892 | 32.626 | 1.00 | 58.05 | A |
| ATOM | 1078 | CG | LYS | A | 148 | 75.897 | −30.848 | 33.726 | 1.00 | 61.10 | A |
| ATOM | 1079 | CD | LYS | A | 148 | 76.162 | −32.259 | 33.205 | 1.00 | 64.34 | A |
| ATOM | 1080 | CE | LYS | A | 148 | 76.558 | −33.201 | 34.339 | 1.00 | 62.92 | A |
| ATOM | 1081 | NZ | LYS | A | 148 | 76.784 | −34.601 | 33.874 | 1.00 | 64.16 | A |
| ATOM | 1082 | C | LYS | A | 148 | 74.195 | −27.743 | 32.108 | 1.00 | 53.05 | A |
| ATOM | 1083 | O | LYS | A | 148 | 73.197 | −27.696 | 31.388 | 1.00 | 54.61 | A |
| ATOM | 1084 | N | ASN | A | 149 | 75.143 | −26.817 | 32.070 | 1.00 | 48.31 | A |
| ATOM | 1085 | CA | ASN | A | 149 | 75.047 | −25.712 | 31.136 | 1.00 | 47.84 | A |
| ATOM | 1086 | CB | ASN | A | 149 | 75.366 | −24.391 | 31.837 | 1.00 | 48.75 | A |
| ATOM | 1087 | CG | ASN | A | 149 | 74.133 | −23.520 | 32.024 | 1.00 | 54.19 | A |
| ATOM | 1088 | OD1 | ASN | A | 149 | 74.231 | −22.380 | 32.466 | 1.00 | 65.56 | A |
| ATOM | 1089 | ND2 | ASN | A | 149 | 72.964 | −24.057 | 31.684 | 1.00 | 50.82 | A |
| ATOM | 1090 | C | ASN | A | 149 | 75.993 | −25.947 | 29.972 | 1.00 | 44.48 | A |
| ATOM | 1091 | O | ASN | A | 149 | 76.721 | −25.056 | 29.551 | 1.00 | 50.18 | A |
| ATOM | 1092 | N | ALA | A | 150 | 75.977 | −27.174 | 29.473 | 1.00 | 41.41 | A |
| ATOM | 1093 | CA | ALA | A | 150 | 76.800 | −27.573 | 28.355 | 1.00 | 36.46 | A |

APPENDIX 3-continued

X-RAY DATA COORDINATES FOR CDP-ME SYNTHASE
COMPLEXED WITH CDP-ME.Mg²⁺(SEQ ID NO:12)

| ATOM | 1094 | CB  | ALA | A | 150 | 77.733 | −28.694 | 28.776 | 1.00 | 39.25 | A |
|------|------|-----|-----|---|-----|--------|---------|--------|------|-------|---|
| ATOM | 1095 | C   | ALA | A | 150 | 75.863 | −28.042 | 27.243 | 1.00 | 32.20 | A |
| ATOM | 1096 | O   | ALA | A | 150 | 74.743 | −28.495 | 27.495 | 1.00 | 35.67 | A |
| ATOM | 1097 | N   | ILE | A | 151 | 76.326 | −27.929 | 26.009 | 1.00 | 29.49 | A |
| ATOM | 1098 | CA  | ILE | A | 151 | 75.537 | −28.333 | 24.863 | 1.00 | 28.87 | A |
| ATOM | 1099 | CB  | ILE | A | 151 | 76.115 | −27.730 | 23.589 | 1.00 | 27.43 | A |
| ATOM | 1100 | CG2 | ILE | A | 151 | 75.277 | −28.143 | 22.385 | 1.00 | 26.12 | A |
| ATOM | 1101 | CG1 | ILE | A | 151 | 76.160 | −26.198 | 23.727 | 1.00 | 25.51 | A |
| ATOM | 1102 | CD  | ILE | A | 151 | 76.771 | −25.523 | 22.531 | 1.00 | 24.00 | A |
| ATOM | 1103 | C   | ILE | A | 151 | 75.445 | −29.843 | 24.663 | 1.00 | 26.67 | A |
| ATOM | 1104 | O   | ILE | A | 151 | 76.464 | −30.532 | 24.582 | 1.00 | 28.74 | A |
| ATOM | 1105 | N   | ALA | A | 152 | 74.221 | −30.353 | 24.593 | 1.00 | 25.35 | A |
| ATOM | 1106 | CA  | ALA | A | 152 | 73.999 | −31.777 | 24.349 | 1.00 | 27.34 | A |
| ATOM | 1107 | CB  | ALA | A | 152 | 72.581 | −32.169 | 24.759 | 1.00 | 31.23 | A |
| ATOM | 1108 | C   | ALA | A | 152 | 74.176 | −31.987 | 22.855 | 1.00 | 26.66 | A |
| ATOM | 1109 | O   | ALA | A | 152 | 75.011 | −32.780 | 22.423 | 1.00 | 28.64 | A |
| ATOM | 1110 | N   | HIS | A | 153 | 73.359 | −31.273 | 22.080 | 1.00 | 25.29 | A |
| ATOM | 1111 | CA  | HIS | A | 153 | 73.397 | −31.313 | 20.622 | 1.00 | 29.62 | A |
| ATOM | 1112 | CB  | HIS | A | 153 | 72.727 | −32.585 | 20.081 | 1.00 | 32.35 | A |
| ATOM | 1113 | CG  | HIS | A | 153 | 71.321 | −32.769 | 20.554 | 1.00 | 36.67 | A |
| ATOM | 1114 | CD2 | HIS | A | 153 | 70.146 | −32.311 | 20.062 | 1.00 | 33.31 | A |
| ATOM | 1115 | ND1 | HIS | A | 153 | 71.014 | −33.426 | 21.728 | 1.00 | 36.91 | A |
| ATOM | 1116 | CE1 | HIS | A | 153 | 69.713 | −33.355 | 21.941 | 1.00 | 38.35 | A |
| ATOM | 1117 | NE2 | HIS | A | 153 | 69.162 | −32.682 | 20.946 | 1.00 | 37.49 | A |
| ATOM | 1118 | C   | HIS | A | 153 | 72.676 | −30.094 | 20.038 | 1.00 | 24.65 | A |
| ATOM | 1119 | O   | HIS | A | 153 | 72.005 | −29.343 | 20.748 | 1.00 | 27.25 | A |
| ATOM | 1120 | N   | THR | A | 154 | 72.834 | −29.900 | 18.735 | 1.00 | 27.29 | A |
| ATOM | 1121 | CA  | THR | A | 154 | 72.204 | −28.798 | 18.047 | 1.00 | 27.85 | A |
| ATOM | 1122 | CB  | THR | A | 154 | 72.983 | −28.443 | 16.773 | 1.00 | 23.93 | A |
| ATOM | 1123 | OG1 | THR | A | 154 | 74.177 | −27.747 | 17.134 | 1.00 | 24.26 | A |
| ATOM | 1124 | CG2 | THR | A | 154 | 72.163 | −27.588 | 15.842 | 1.00 | 24.63 | A |
| ATOM | 1125 | C   | THR | A | 154 | 70.795 | −29.202 | 17.656 | 1.00 | 22.25 | A |
| ATOM | 1126 | O   | THR | A | 154 | 70.558 | −30.353 | 17.297 | 1.00 | 24.48 | A |
| ATOM | 1127 | N   | VAL | A | 155 | 69.866 | −28.260 | 17.749 | 1.00 | 22.22 | A |
| ATOM | 1128 | CA  | VAL | A | 155 | 68.481 | −28.522 | 17.361 | 1.00 | 28.08 | A |
| ATOM | 1129 | CB  | VAL | A | 155 | 67.489 | −27.906 | 18.373 | 1.00 | 30.09 | A |
| ATOM | 1130 | CG1 | VAL | A | 155 | 66.046 | −28.191 | 17.935 | 1.00 | 27.84 | A |
| ATOM | 1131 | CG2 | VAL | A | 155 | 67.738 | −28.486 | 19.746 | 1.00 | 33.47 | A |
| ATOM | 1132 | C   | VAL | A | 155 | 68.305 | −27.871 | 15.997 | 1.00 | 25.10 | A |
| ATOM | 1133 | O   | VAL | A | 155 | 68.446 | −26.661 | 15.873 | 1.00 | 26.47 | A |
| ATOM | 1134 | N   | ASP | A | 156 | 67.980 | −28.665 | 14.981 | 1.00 | 25.79 | A |
| ATOM | 1135 | CA  | ASP | A | 156 | 67.824 | −28.143 | 13.616 | 1.00 | 30.12 | A |
| ATOM | 1136 | CB  | ASP | A | 156 | 67.407 | −29.286 | 12.672 | 1.00 | 34.60 | A |
| ATOM | 1137 | CG  | ASP | A | 156 | 67.442 | −28.881 | 11.210 | 1.00 | 36.20 | A |
| ATOM | 1138 | OD1 | ASP | A | 156 | 67.863 | −27.737 | 10.930 | 1.00 | 36.63 | A |
| ATOM | 1139 | OD2 | ASP | A | 156 | 67.055 | −29.703 | 10.345 | 1.00 | 43.11 | A |
| ATOM | 1140 | C   | ASP | A | 156 | 66.843 | −26.965 | 13.509 | 1.00 | 25.62 | A |
| ATOM | 1141 | O   | ASP | A | 156 | 65.664 | −27.111 | 13.794 | 1.00 | 27.19 | A |
| ATOM | 1142 | N   | ARG | A | 157 | 67.350 | −25.801 | 13.106 | 1.00 | 28.06 | A |
| ATOM | 1143 | CA  | ARG | A | 157 | 66.518 | −24.595 | 12.995 | 1.00 | 30.65 | A |
| ATOM | 1144 | CB  | ARG | A | 157 | 67.392 | −23.334 | 12.920 | 1.00 | 35.87 | A |
| ATOM | 1145 | CG  | ARG | A | 157 | 68.297 | −23.270 | 11.703 | 1.00 | 31.98 | A |
| ATOM | 1146 | CD  | ARG | A | 157 | 69.134 | −22.009 | 11.701 | 1.00 | 32.68 | A |
| ATOM | 1147 | NE  | ARG | A | 157 | 70.160 | −22.038 | 10.662 | 1.00 | 34.98 | A |
| ATOM | 1148 | CZ  | ARG | A | 157 | 71.187 | −21.197 | 10.604 | 1.00 | 40.01 | A |
| ATOM | 1149 | NH1 | ARG | A | 157 | 71.321 | −20.257 | 11.535 | 1.00 | 30.29 | A |
| ATOM | 1150 | NH2 | ARG | A | 157 | 72.082 | −21.304 | 9.624  | 1.00 | 31.13 | A |
| ATOM | 1151 | C   | ARG | A | 157 | 65.587 | −24.632 | 11.791 | 1.00 | 34.05 | A |
| ATOM | 1152 | O   | ARG | A | 157 | 64.653 | −23.826 | 11.683 | 1.00 | 30.56 | A |
| ATOM | 1153 | N   | ASN | A | 158 | 65.861 | −25.551 | 10.872 | 1.00 | 36.16 | A |
| ATOM | 1154 | CA  | ASN | A | 158 | 65.025 | −25.689 | 9.690  | 1.00 | 38.54 | A |
| ATOM | 1155 | CB  | ASN | A | 158 | 65.744 | −26.533 | 8.618  | 1.00 | 41.88 | A |
| ATOM | 1156 | CG  | ASN | A | 158 | 67.038 | −25.876 | 8.112  | 1.00 | 53.99 | A |
| ATOM | 1157 | OD1 | ASN | A | 158 | 67.030 | −24.747 | 7.599  | 1.00 | 51.76 | A |
| ATOM | 1158 | ND2 | ASN | A | 158 | 68.155 | −26.587 | 8.255  | 1.00 | 53.26 | A |
| ATOM | 1159 | C   | ASN | A | 158 | 63.728 | −26.354 | 10.144 | 1.00 | 32.84 | A |
| ATOM | 1160 | O   | ASN | A | 158 | 63.758 | −27.370 | 10.834 | 1.00 | 30.73 | A |
| ATOM | 1161 | N   | GLY | A | 159 | 62.594 | −25.750 | 9.782  | 1.00 | 33.23 | A |
| ATOM | 1162 | CA  | GLY | A | 159 | 61.295 | −26.282 | 10.164 | 1.00 | 31.87 | A |
| ATOM | 1163 | C   | GLY | A | 159 | 60.939 | −25.965 | 11.612 | 1.00 | 28.76 | A |
| ATOM | 1164 | O   | GLY | A | 159 | 59.938 | −26.439 | 12.136 | 1.00 | 29.41 | A |
| ATOM | 1165 | N   | LEU | A | 160 | 61.769 | −25.158 | 12.264 | 1.00 | 28.69 | A |
| ATOM | 1166 | CA  | LEU | A | 160 | 61.524 | −24.795 | 13.649 | 1.00 | 23.98 | A |
| ATOM | 1167 | CB  | LEU | A | 160 | 62.838 | −24.809 | 14.435 | 1.00 | 26.54 | A |
| ATOM | 1168 | CG  | LEU | A | 160 | 62.706 | −24.798 | 15.957 | 1.00 | 24.94 | A |
| ATOM | 1169 | CD1 | LEU | A | 160 | 62.018 | −26.065 | 16.457 | 1.00 | 29.00 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 1170 | CD2 | LEU | A | 160 | 64.083 | −24.693 | 16.566 | 1.00 | 28.96 | A |
|------|------|-----|-----|---|-----|--------|---------|--------|------|-------|---|
| ATOM | 1171 | C | LEU | A | 160 | 60.897 | −23.400 | 13.684 | 1.00 | 27.29 | A |
| ATOM | 1172 | O | LEU | A | 160 | 61.370 | −22.482 | 13.010 | 1.00 | 23.82 | A |
| ATOM | 1173 | N | TRP | A | 161 | 59.832 | −23.248 | 14.467 | 1.00 | 23.84 | A |
| ATOM | 1174 | CA | TRP | A | 161 | 59.124 | −21.968 | 14.551 | 1.00 | 20.56 | A |
| ATOM | 1175 | CB | TRP | A | 161 | 57.748 | −22.070 | 13.872 | 1.00 | 20.57 | A |
| ATOM | 1176 | CG | TRP | A | 161 | 57.796 | −22.329 | 12.396 | 1.00 | 27.92 | A |
| ATOM | 1177 | CD2 | TRP | A | 161 | 57.439 | −21.415 | 11.357 | 1.00 | 25.22 | A |
| ATOM | 1178 | CE2 | TRP | A | 161 | 57.601 | −22.095 | 10.125 | 1.00 | 29.23 | A |
| ATOM | 1179 | CE3 | TRP | A | 161 | 56.980 | −20.089 | 11.341 | 1.00 | 25.62 | A |
| ATOM | 1180 | CD1 | TRP | A | 161 | 58.167 | −23.493 | 11.774 | 1.00 | 28.31 | A |
| ATOM | 1181 | NE1 | TRP | A | 161 | 58.054 | −23.360 | 10.413 | 1.00 | 30.05 | A |
| ATOM | 1182 | CZ2 | TRP | A | 161 | 57.337 | −21.494 | 8.892 | 1.00 | 29.35 | A |
| ATOM | 1183 | CZ3 | TRP | A | 161 | 56.714 | −19.488 | 10.112 | 1.00 | 35.71 | A |
| ATOM | 1184 | CH2 | TRP | A | 161 | 56.890 | −20.198 | 8.902 | 1.00 | 34.04 | A |
| ATOM | 1185 | C | TRP | A | 161 | 58.893 | −21.473 | 15.965 | 1.00 | 23.31 | A |
| ATOM | 1186 | O | TRP | A | 161 | 58.779 | −22.250 | 16.927 | 1.00 | 25.66 | A |
| ATOM | 1187 | N | HIS | A | 162 | 58.841 | −20.149 | 16.058 | 1.00 | 27.90 | A |
| ATOM | 1188 | CA | HIS | A | 162 | 58.535 | −19.433 | 17.283 | 1.00 | 23.36 | A |
| ATOM | 1189 | CB | HIS | A | 162 | 59.014 | −17.981 | 17.203 | 1.00 | 22.62 | A |
| ATOM | 1190 | CG | HIS | A | 162 | 60.473 | −17.783 | 17.465 | 1.00 | 23.65 | A |
| ATOM | 1191 | CD2 | HIS | A | 162 | 61.517 | −17.631 | 16.616 | 1.00 | 29.38 | A |
| ATOM | 1192 | ND1 | HIS | A | 162 | 60.980 | −17.631 | 18.735 | 1.00 | 29.50 | A |
| ATOM | 1193 | CE1 | HIS | A | 162 | 62.277 | −17.388 | 18.659 | 1.00 | 31.62 | A |
| ATOM | 1194 | NE2 | HIS | A | 162 | 62.630 | −17.383 | 17.386 | 1.00 | 22.48 | A |
| ATOM | 1195 | C | HIS | A | 162 | 57.006 | −19.362 | 17.294 | 1.00 | 25.86 | A |
| ATOM | 1196 | O | HIS | A | 162 | 56.422 | −18.812 | 16.369 | 1.00 | 24.70 | A |
| ATOM | 1197 | N | ALA | A | 163 | 56.352 | −19.912 | 18.306 | 1.00 | 26.24 | A |
| ATOM | 1198 | CA | ALA | A | 163 | 54.904 | −19.800 | 18.341 | 1.00 | 24.70 | A |
| ATOM | 1199 | CB | ALA | A | 163 | 54.310 | −20.898 | 19.212 | 1.00 | 20.38 | A |
| ATOM | 1200 | C | ALA | A | 163 | 54.574 | −18.411 | 18.913 | 1.00 | 20.12 | A |
| ATOM | 1201 | O | ALA | A | 163 | 55.160 | −17.979 | 19.919 | 1.00 | 19.24 | A |
| ATOM | 1202 | N | LEU | A | 164 | 53.658 | −17.704 | 18.263 | 1.00 | 16.87 | A |
| ATOM | 1203 | CA | LEU | A | 164 | 53.252 | −16.387 | 18.727 | 1.00 | 21.64 | A |
| ATOM | 1204 | CB | LEU | A | 164 | 53.516 | −15.358 | 17.628 | 1.00 | 22.15 | A |
| ATOM | 1205 | CG | LEU | A | 164 | 54.945 | −15.331 | 17.060 | 1.00 | 28.58 | A |
| ATOM | 1206 | CD1 | LEU | A | 164 | 55.004 | −14.419 | 15.851 | 1.00 | 26.97 | A |
| ATOM | 1207 | CD2 | LEU | A | 164 | 55.930 | −14.853 | 18.132 | 1.00 | 20.89 | A |
| ATOM | 1208 | C | LEU | A | 164 | 51.744 | −16.475 | 18.991 | 1.00 | 20.46 | A |
| ATOM | 1209 | O | LEU | A | 164 | 51.180 | −17.563 | 19.031 | 1.00 | 20.16 | A |
| ATOM | 1210 | N | THR | A | 165 | 51.097 | −15.335 | 19.183 | 1.00 | 17.73 | A |
| ATOM | 1211 | CA | THR | A | 165 | 49.643 | −15.314 | 19.347 | 1.00 | 18.75 | A |
| ATOM | 1212 | CB | THR | A | 165 | 49.146 | −15.226 | 20.847 | 1.00 | 16.44 | A |
| ATOM | 1213 | OG1 | THR | A | 165 | 49.411 | −13.931 | 21.370 | 1.00 | 18.30 | A |
| ATOM | 1214 | CG2 | THR | A | 165 | 49.813 | −16.295 | 21.731 | 1.00 | 19.63 | A |
| ATOM | 1215 | C | THR | A | 165 | 49.218 | −14.074 | 18.578 | 1.00 | 18.15 | A |
| ATOM | 1216 | O | THR | A | 165 | 50.025 | −13.171 | 18.344 | 1.00 | 21.96 | A |
| ATOM | 1217 | N | PRO | A | 166 | 47.933 | −13.987 | 18.227 | 1.00 | 18.69 | A |
| ATOM | 1218 | CD | PRO | A | 166 | 47.384 | −12.825 | 17.515 | 1.00 | 18.60 | A |
| ATOM | 1219 | CA | PRO | A | 166 | 46.884 | −14.967 | 18.512 | 1.00 | 18.06 | A |
| ATOM | 1220 | CB | PRO | A | 166 | 45.607 | −14.312 | 17.951 | 1.00 | 18.16 | A |
| ATOM | 1221 | CG | PRO | A | 166 | 45.922 | −12.879 | 17.929 | 1.00 | 19.78 | A |
| ATOM | 1222 | C | PRO | A | 166 | 47.021 | −16.378 | 17.963 | 1.00 | 21.86 | A |
| ATOM | 1223 | O | PRO | A | 166 | 47.753 | −16.656 | 17.014 | 1.00 | 17.92 | A |
| ATOM | 1224 | N | GLN | A | 167 | 46.228 | −17.243 | 18.580 | 1.00 | 19.50 | A |
| ATOM | 1225 | CA | GLN | A | 167 | 46.095 | −18.648 | 18.237 | 1.00 | 18.36 | A |
| ATOM | 1226 | CB | GLN | A | 167 | 46.644 | −19.508 | 19.377 | 1.00 | 16.46 | A |
| ATOM | 1227 | CG | GLN | A | 167 | 48.132 | −19.176 | 19.601 | 1.00 | 15.32 | A |
| ATOM | 1228 | CD | GLN | A | 167 | 48.952 | −20.346 | 20.175 | 1.00 | 21.79 | A |
| ATOM | 1229 | OE1 | GLN | A | 167 | 48.398 | −21.377 | 20.587 | 1.00 | 20.55 | A |
| ATOM | 1230 | NE2 | GLN | A | 167 | 50.285 | −20.181 | 20.201 | 1.00 | 20.06 | A |
| ATOM | 1231 | C | GLN | A | 167 | 44.582 | −18.767 | 18.047 | 1.00 | 24.49 | A |
| ATOM | 1232 | O | GLN | A | 167 | 43.813 | −18.398 | 18.929 | 1.00 | 21.28 | A |
| ATOM | 1233 | N | PHE | A | 168 | 44.177 | −19.277 | 16.885 | 1.00 | 21.99 | A |
| ATOM | 1234 | CA | PHE | A | 168 | 42.766 | −19.341 | 16.481 | 1.00 | 21.35 | A |
| ATOM | 1235 | CB | PHE | A | 168 | 42.687 | −18.572 | 15.151 | 1.00 | 17.98 | A |
| ATOM | 1236 | CG | PHE | A | 168 | 41.290 | −18.240 | 14.693 | 1.00 | 17.59 | A |
| ATOM | 1237 | CD1 | PHE | A | 168 | 40.375 | −17.698 | 15.584 | 1.00 | 20.08 | A |
| ATOM | 1238 | CD2 | PHE | A | 168 | 40.919 | −18.392 | 13.358 | 1.00 | 24.64 | A |
| ATOM | 1239 | CE1 | PHE | A | 168 | 39.100 | −17.297 | 15.155 | 1.00 | 16.26 | A |
| ATOM | 1240 | CE2 | PHE | A | 168 | 39.634 | −17.995 | 12.912 | 1.00 | 18.20 | A |
| ATOM | 1241 | CZ | PHE | A | 168 | 38.733 | −17.447 | 13.819 | 1.00 | 25.36 | A |
| ATOM | 1242 | C | PHE | A | 168 | 42.247 | −20.777 | 16.335 | 1.00 | 20.20 | A |
| ATOM | 1243 | O | PHE | A | 168 | 42.785 | −21.537 | 15.528 | 1.00 | 22.22 | A |
| ATOM | 1244 | N | PHE | A | 169 | 41.219 | −21.143 | 17.098 | 1.00 | 20.89 | A |
| ATOM | 1245 | CA | PHE | A | 169 | 40.696 | −22.514 | 17.040 | 1.00 | 20.61 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 1246 | CB | PHE | A | 169 | 41.331 | −23.372 | 18.147 | 1.00 | 22.37 | A |
|---|---|---|---|---|---|---|---|---|---|---|---|
| ATOM | 1247 | CG | PHE | A | 169 | 42.818 | −23.508 | 18.036 | 1.00 | 21.21 | A |
| ATOM | 1248 | CD1 | PHE | A | 169 | 43.663 | −22.754 | 18.847 | 1.00 | 25.39 | A |
| ATOM | 1249 | CD2 | PHE | A | 169 | 43.371 | −24.382 | 17.117 | 1.00 | 24.72 | A |
| ATOM | 1250 | CE1 | PHE | A | 169 | 45.059 | −22.871 | 18.742 | 1.00 | 24.15 | A |
| ATOM | 1251 | CE2 | PHE | A | 169 | 44.747 | −24.510 | 17.000 | 1.00 | 29.52 | A |
| ATOM | 1252 | CZ | PHE | A | 169 | 45.594 | −23.751 | 17.814 | 1.00 | 24.47 | A |
| ATOM | 1253 | C | PHE | A | 169 | 39.199 | −22.596 | 17.222 | 1.00 | 20.32 | A |
| ATOM | 1254 | O | PHE | A | 169 | 38.574 | −21.651 | 17.682 | 1.00 | 20.19 | A |
| ATOM | 1255 | N | PRO | A | 170 | 38.602 | −23.742 | 16.850 | 1.00 | 25.60 | A |
| ATOM | 1256 | CD | PRO | A | 170 | 39.166 | −24.827 | 16.024 | 1.00 | 21.64 | A |
| ATOM | 1257 | CA | PRO | A | 170 | 37.156 | −23.897 | 17.031 | 1.00 | 22.96 | A |
| ATOM | 1258 | CB | PRO | A | 170 | 36.868 | −25.292 | 16.456 | 1.00 | 19.67 | A |
| ATOM | 1259 | CG | PRO | A | 170 | 37.909 | −25.446 | 15.369 | 1.00 | 25.84 | A |
| ATOM | 1260 | C | PRO | A | 170 | 37.019 | −23.851 | 18.557 | 1.00 | 23.02 | A |
| ATOM | 1261 | O | PRO | A | 170 | 37.823 | −24.455 | 19.270 | 1.00 | 20.61 | A |
| ATOM | 1262 | N | ARG | A | 171 | 36.013 | −23.135 | 19.046 | 1.00 | 19.58 | A |
| ATOM | 1263 | CA | ARG | A | 171 | 35.795 | −22.939 | 20.479 | 1.00 | 27.75 | A |
| ATOM | 1264 | CB | ARG | A | 171 | 34.553 | −22.067 | 20.679 | 1.00 | 31.50 | A |
| ATOM | 1265 | CG | ARG | A | 171 | 34.529 | −21.272 | 21.967 | 1.00 | 33.72 | A |
| ATOM | 1266 | CD | ARG | A | 171 | 33.110 | −21.075 | 22.502 | 1.00 | 46.03 | A |
| ATOM | 1267 | NE | ARG | A | 171 | 32.620 | −22.300 | 23.125 | 1.00 | 45.83 | A |
| ATOM | 1268 | CZ | ARG | A | 171 | 31.709 | −23.103 | 22.593 | 1.00 | 40.61 | A |
| ATOM | 1269 | NH1 | ARG | A | 171 | 31.167 | −22.810 | 21.422 | 1.00 | 47.16 | A |
| ATOM | 1270 | NH2 | ARG | A | 171 | 31.368 | −24.222 | 23.216 | 1.00 | 48.85 | A |
| ATOM | 1271 | C | ARG | A | 171 | 35.672 | −24.181 | 21.367 | 1.00 | 21.21 | A |
| ATOM | 1272 | O | ARG | A | 171 | 36.435 | −24.371 | 22.325 | 1.00 | 26.16 | A |
| ATOM | 1273 | N | GLU | A | 172 | 34.694 | −25.027 | 21.064 | 1.00 | 21.99 | A |
| ATOM | 1274 | CA | GLU | A | 172 | 34.489 | −26.226 | 21.877 | 1.00 | 23.36 | A |
| ATOM | 1275 | CB | GLU | A | 172 | 33.154 | −26.903 | 21.491 | 1.00 | 30.61 | A |
| ATOM | 1276 | CG | GLU | A | 172 | 32.513 | −27.736 | 22.624 | 1.00 | 34.68 | A |
| ATOM | 1277 | CD | GLU | A | 172 | 31.185 | −28.391 | 22.213 | 1.00 | 44.59 | A |
| ATOM | 1278 | OE1 | GLU | A | 172 | 31.191 | −29.590 | 21.840 | 1.00 | 38.35 | A |
| ATOM | 1279 | OE2 | GLU | A | 172 | 30.139 | −27.698 | 22.256 | 1.00 | 38.39 | A |
| ATOM | 1280 | C | GLU | A | 172 | 35.661 | −27.216 | 21.783 | 1.00 | 23.87 | A |
| ATOM | 1281 | O | GLU | A | 172 | 36.039 | −27.831 | 22.784 | 1.00 | 25.07 | A |
| ATOM | 1282 | N | LEU | A | 173 | 36.246 | −27.362 | 20.596 | 1.00 | 22.72 | A |
| ATOM | 1283 | CA | LEU | A | 173 | 37.383 | −28.256 | 20.432 | 1.00 | 24.14 | A |
| ATOM | 1284 | CB | LEU | A | 173 | 37.858 | −28.276 | 18.964 | 1.00 | 26.48 | A |
| ATOM | 1285 | CG | LEU | A | 173 | 39.029 | −29.209 | 18.636 | 1.00 | 26.96 | A |
| ATOM | 1286 | CD1 | LEU | A | 173 | 38.695 | −30.618 | 19.100 | 1.00 | 31.40 | A |
| ATOM | 1287 | CD2 | LEU | A | 173 | 39.317 | −29.206 | 17.141 | 1.00 | 23.02 | A |
| ATOM | 1288 | C | LEU | A | 173 | 38.518 | −27.786 | 21.350 | 1.00 | 22.61 | A |
| ATOM | 1289 | O | LEU | A | 173 | 39.086 | −28.581 | 22.120 | 1.00 | 25.96 | A |
| ATOM | 1290 | N | LEU | A | 174 | 38.843 | −26.498 | 21.290 | 1.00 | 22.40 | A |
| ATOM | 1291 | CA | LEU | A | 174 | 39.913 | −25.963 | 22.142 | 1.00 | 23.75 | A |
| ATOM | 1292 | CB | LEU | A | 174 | 40.124 | −24.456 | 21.868 | 1.00 | 20.05 | A |
| ATOM | 1293 | CG | LEU | A | 174 | 41.183 | −23.786 | 22.750 | 1.00 | 28.30 | A |
| ATOM | 1294 | CD1 | LEU | A | 174 | 42.520 | −24.541 | 22.588 | 1.00 | 29.73 | A |
| ATOM | 1295 | CD2 | LEU | A | 174 | 41.349 | −22.299 | 22.379 | 1.00 | 22.03 | A |
| ATOM | 1296 | C | LEU | A | 174 | 39.547 | −26.178 | 23.611 | 1.00 | 23.44 | A |
| ATOM | 1297 | O | LEU | A | 174 | 40.363 | −26.635 | 24.411 | 1.00 | 24.58 | A |
| ATOM | 1298 | N | HIS | A | 175 | 38.313 | −25.840 | 23.961 | 1.00 | 25.20 | A |
| ATOM | 1299 | CA | HIS | A | 175 | 37.852 | −26.001 | 25.331 | 1.00 | 27.11 | A |
| ATOM | 1300 | CB | HIS | A | 175 | 36.381 | −25.610 | 25.427 | 1.00 | 32.98 | A |
| ATOM | 1301 | CG | HIS | A | 175 | 35.760 | −25.918 | 26.752 | 1.00 | 38.21 | A |
| ATOM | 1302 | CD2 | HIS | A | 175 | 35.470 | −25.119 | 27.805 | 1.00 | 37.72 | A |
| ATOM | 1303 | ND1 | HIS | A | 175 | 35.388 | −27.193 | 27.121 | 1.00 | 36.09 | A |
| ATOM | 1304 | CE1 | HIS | A | 175 | 34.899 | −27.166 | 28.348 | 1.00 | 36.63 | A |
| ATOM | 1305 | NE2 | HIS | A | 175 | 34.939 | −25.920 | 28.786 | 1.00 | 37.11 | A |
| ATOM | 1306 | C | HIS | A | 175 | 38.039 | −27.433 | 25.845 | 1.00 | 23.87 | A |
| ATOM | 1307 | O | HIS | A | 175 | 38.566 | −27.658 | 26.944 | 1.00 | 26.85 | A |
| ATOM | 1308 | N | ASP | A | 176 | 37.605 | −28.401 | 25.047 | 1.00 | 27.06 | A |
| ATOM | 1309 | CA | ASP | A | 176 | 37.708 | −29.799 | 25.426 | 1.00 | 28.12 | A |
| ATOM | 1310 | CB | ASP | A | 176 | 36.839 | −30.663 | 24.501 | 1.00 | 28.42 | A |
| ATOM | 1311 | CG | ASP | A | 176 | 35.352 | −30.343 | 24.629 | 1.00 | 33.87 | A |
| ATOM | 1312 | OD1 | ASP | A | 176 | 34.951 | −29.712 | 25.634 | 1.00 | 31.79 | A |
| ATOM | 1313 | OD2 | ASP | A | 176 | 34.577 | −30.732 | 23.734 | 1.00 | 31.04 | A |
| ATOM | 1314 | C | ASP | A | 176 | 39.130 | −30.338 | 25.460 | 1.00 | 31.20 | A |
| ATOM | 1315 | O | ASP | A | 176 | 39.488 | −31.103 | 26.365 | 1.00 | 29.68 | A |
| ATOM | 1316 | N | CYS | A | 177 | 39.950 | −29.947 | 24.487 | 1.00 | 24.43 | A |
| ATOM | 1317 | CA | CYS | A | 177 | 41.336 | −30.411 | 24.463 | 1.00 | 24.37 | A |
| ATOM | 1318 | CB | CYS | A | 177 | 41.997 | −30.028 | 23.136 | 1.00 | 26.45 | A |
| ATOM | 1319 | SG | CYS | A | 177 | 41.321 | −30.860 | 21.704 | 1.00 | 31.85 | A |
| ATOM | 1320 | C | CYS | A | 177 | 42.123 | −29.825 | 25.641 | 1.00 | 29.28 | A |
| ATOM | 1321 | O | CYS | A | 177 | 42.929 | −30.516 | 26.272 | 1.00 | 24.42 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 1322 | N   | LEU | A | 178 | 41.876 | −28.553 | 25.954 | 1.00 | 27.82 | A |
|------|------|-----|-----|---|-----|--------|---------|--------|------|-------|---|
| ATOM | 1323 | CA  | LEU | A | 178 | 42.578 | −27.933 | 27.068 | 1.00 | 29.15 | A |
| ATOM | 1324 | CB  | LEU | A | 178 | 42.313 | −26.425 | 27.096 | 1.00 | 24.68 | A |
| ATOM | 1325 | CG  | LEU | A | 178 | 43.103 | −25.587 | 28.103 | 1.00 | 28.29 | A |
| ATOM | 1326 | CD1 | LEU | A | 178 | 44.609 | −25.729 | 27.858 | 1.00 | 24.01 | A |
| ATOM | 1327 | CD2 | LEU | A | 178 | 42.670 | −24.142 | 27.986 | 1.00 | 31.36 | A |
| ATOM | 1328 | C   | LEU | A | 178 | 42.148 | −28.583 | 28.390 | 1.00 | 33.36 | A |
| ATOM | 1329 | O   | LEU | A | 178 | 42.983 | −28.896 | 29.234 | 1.00 | 27.27 | A |
| ATOM | 1330 | N   | THR | A | 179 | 40.848 | −28.808 | 28.561 | 1.00 | 35.46 | A |
| ATOM | 1331 | CA  | THR | A | 179 | 40.348 | −29.428 | 29.777 | 1.00 | 32.88 | A |
| ATOM | 1332 | CB  | THR | A | 179 | 38.818 | −29.603 | 29.743 | 1.00 | 36.98 | A |
| ATOM | 1333 | OG1 | THR | A | 179 | 38.197 | −28.319 | 29.682 | 1.00 | 32.55 | A |
| ATOM | 1334 | CG2 | THR | A | 179 | 38.332 | −30.345 | 30.991 | 1.00 | 33.89 | A |
| ATOM | 1335 | C   | THR | A | 179 | 40.968 | −30.808 | 29.942 | 1.00 | 31.51 | A |
| ATOM | 1336 | O   | THR | A | 179 | 41.447 | −31.158 | 31.020 | 1.00 | 34.69 | A |
| ATOM | 1337 | N   | ARG | A | 180 | 40.952 | −31.594 | 28.872 | 1.00 | 27.44 | A |
| ATOM | 1338 | CA  | ARG | A | 180 | 41.511 | −32.944 | 28.925 | 1.00 | 32.63 | A |
| ATOM | 1339 | CB  | ARG | A | 180 | 41.259 | −33.676 | 27.591 | 1.00 | 38.39 | A |
| ATOM | 1340 | CG  | ARG | A | 180 | 41.797 | −35.111 | 27.498 | 1.00 | 38.63 | A |
| ATOM | 1341 | CD  | ARG | A | 180 | 41.378 | −35.747 | 26.163 | 1.00 | 48.42 | A |
| ATOM | 1342 | NE  | ARG | A | 180 | 42.468 | −36.442 | 25.473 | 1.00 | 52.71 | A |
| ATOM | 1343 | CZ  | ARG | A | 180 | 42.484 | −36.704 | 24.162 | 1.00 | 57.37 | A |
| ATOM | 1344 | NH1 | ARG | A | 180 | 41.469 | −36.330 | 23.393 | 1.00 | 58.81 | A |
| ATOM | 1345 | NH2 | ARG | A | 180 | 43.520 | −37.333 | 23.612 | 1.00 | 57.50 | A |
| ATOM | 1346 | C   | ARG | A | 180 | 43.007 | −32.932 | 29.265 | 1.00 | 36.27 | A |
| ATOM | 1347 | O   | ARG | A | 180 | 43.453 | −33.665 | 30.161 | 1.00 | 34.74 | A |
| ATOM | 1348 | N   | ALA | A | 181 | 43.779 | −32.089 | 28.576 | 1.00 | 27.46 | A |
| ATOM | 1349 | CA  | ALA | A | 181 | 45.216 | −32.022 | 28.828 | 1.00 | 34.07 | A |
| ATOM | 1350 | CB  | ALA | A | 181 | 45.886 | −31.032 | 27.874 | 1.00 | 30.80 | A |
| ATOM | 1351 | C   | ALA | A | 181 | 45.507 | −31.638 | 30.274 | 1.00 | 38.88 | A |
| ATOM | 1352 | O   | ALA | A | 181 | 46.304 | −32.294 | 30.954 | 1.00 | 37.81 | A |
| ATOM | 1353 | N   | LEU | A | 182 | 44.863 | −30.574 | 30.740 | 1.00 | 33.28 | A |
| ATOM | 1354 | CA  | LEU | A | 182 | 45.056 | −30.119 | 32.109 | 1.00 | 37.15 | A |
| ATOM | 1355 | CB  | LEU | A | 182 | 44.258 | −28.835 | 32.366 | 1.00 | 35.37 | A |
| ATOM | 1356 | CG  | LEU | A | 182 | 44.836 | −27.580 | 31.684 | 1.00 | 37.20 | A |
| ATOM | 1357 | CD1 | LEU | A | 182 | 43.861 | −26.409 | 31.829 | 1.00 | 38.56 | A |
| ATOM | 1358 | CD2 | LEU | A | 182 | 46.188 | −27.235 | 32.302 | 1.00 | 42.55 | A |
| ATOM | 1359 | C   | LEU | A | 182 | 44.654 | −31.200 | 33.118 | 1.00 | 43.30 | A |
| ATOM | 1360 | O   | LEU | A | 182 | 45.323 | −31.379 | 34.129 | 1.00 | 40.78 | A |
| ATOM | 1361 | N   | ASN | A | 183 | 43.565 | −31.915 | 32.842 | 1.00 | 42.67 | A |
| ATOM | 1362 | CA  | ASN | A | 183 | 43.117 | −32.981 | 33.734 | 1.00 | 45.95 | A |
| ATOM | 1363 | CB  | ASN | A | 183 | 41.773 | −33.552 | 33.271 | 1.00 | 42.58 | A |
| ATOM | 1364 | CG  | ASN | A | 183 | 40.584 | −32.730 | 33.754 | 1.00 | 43.14 | A |
| ATOM | 1365 | OD1 | ASN | A | 183 | 39.444 | −33.005 | 33.390 | 1.00 | 46.52 | A |
| ATOM | 1366 | ND2 | ASN | A | 183 | 40.846 | −31.726 | 34.584 | 1.00 | 47.13 | A |
| ATOM | 1367 | C   | ASN | A | 183 | 44.148 | −34.107 | 33.791 | 1.00 | 47.24 | A |
| ATOM | 1368 | O   | ASN | A | 183 | 44.375 | −34.701 | 34.844 | 1.00 | 46.63 | A |
| ATOM | 1369 | N   | GLU | A | 184 | 44.770 | −34.393 | 32.654 | 1.00 | 46.16 | A |
| ATOM | 1370 | CA  | GLU | A | 184 | 45.772 | −35.442 | 32.575 | 1.00 | 43.60 | A |
| ATOM | 1371 | CB  | GLU | A | 184 | 45.720 | −36.090 | 31.186 | 1.00 | 38.52 | A |
| ATOM | 1372 | CG  | GLU | A | 184 | 44.554 | −37.069 | 31.022 | 1.00 | 30.01 | A |
| ATOM | 1373 | CD  | GLU | A | 184 | 44.204 | −37.374 | 29.565 | 1.00 | 39.87 | A |
| ATOM | 1374 | OE1 | GLU | A | 184 | 45.109 | −37.348 | 28.704 | 1.00 | 43.83 | A |
| ATOM | 1375 | OE2 | GLU | A | 184 | 43.018 | −37.662 | 29.280 | 1.00 | 40.89 | A |
| ATOM | 1376 | C   | GLU | A | 184 | 47.172 | −34.914 | 32.902 | 1.00 | 44.99 | A |
| ATOM | 1377 | O   | GLU | A | 184 | 48.183 | −35.565 | 32.629 | 1.00 | 44.80 | A |
| ATOM | 1378 | N   | GLY | A | 185 | 47.211 | −33.725 | 33.500 | 1.00 | 45.32 | A |
| ATOM | 1379 | CA  | GLY | A | 185 | 48.463 | −33.102 | 33.899 | 1.00 | 46.40 | A |
| ATOM | 1380 | C   | GLY | A | 185 | 49.537 | −32.950 | 32.843 | 1.00 | 46.00 | A |
| ATOM | 1381 | O   | GLY | A | 185 | 50.714 | −33.179 | 33.121 | 1.00 | 49.53 | A |
| ATOM | 1382 | N   | ALA | A | 186 | 49.152 | −32.555 | 31.635 | 1.00 | 42.61 | A |
| ATOM | 1383 | CA  | ALA | A | 186 | 50.123 | −32.379 | 30.562 | 1.00 | 42.07 | A |
| ATOM | 1384 | CB  | ALA | A | 186 | 49.463 | −32.648 | 29.214 | 1.00 | 47.06 | A |
| ATOM | 1385 | C   | ALA | A | 186 | 50.720 | −30.969 | 30.589 | 1.00 | 40.77 | A |
| ATOM | 1386 | O   | ALA | A | 186 | 50.160 | −30.062 | 31.204 | 1.00 | 40.17 | A |
| ATOM | 1387 | N   | THR | A | 187 | 51.860 | −30.797 | 29.925 | 1.00 | 40.52 | A |
| ATOM | 1388 | CA  | THR | A | 187 | 52.537 | −29.501 | 29.854 | 1.00 | 43.28 | A |
| ATOM | 1389 | CB  | THR | A | 187 | 54.032 | −29.668 | 29.529 | 1.00 | 43.23 | A |
| ATOM | 1390 | OG1 | THR | A | 187 | 54.640 | −30.555 | 30.479 | 1.00 | 48.91 | A |
| ATOM | 1391 | CG2 | THR | A | 187 | 54.733 | −28.326 | 29.581 | 1.00 | 36.64 | A |
| ATOM | 1392 | C   | THR | A | 187 | 51.908 | −28.683 | 28.730 | 1.00 | 36.95 | A |
| ATOM | 1393 | O   | THR | A | 187 | 52.054 | −29.030 | 27.559 | 1.00 | 38.01 | A |
| ATOM | 1394 | N   | ILE | A | 188 | 51.233 | −27.595 | 29.081 | 1.00 | 38.12 | A |
| ATOM | 1395 | CA  | ILE | A | 188 | 50.557 | −26.763 | 28.084 | 1.00 | 33.23 | A |
| ATOM | 1396 | CB  | ILE | A | 188 | 49.039 | −26.808 | 28.317 | 1.00 | 31.44 | A |
| ATOM | 1397 | CG2 | ILE | A | 188 | 48.297 | −26.085 | 27.197 | 1.00 | 30.91 | A |

APPENDIX 3-continued

X-RAY DATA COORDINATES FOR CDP-ME SYNTHASE COMPLEXED WITH CDP-ME.Mg$^{2+}$(SEQ ID NO:12)

| ATOM | 1398 | CG1 | ILE | A | 188 | 48.581 | −28.260 | 28.354 | 1.00 | 35.10 | A |
|---|---|---|---|---|---|---|---|---|---|---|---|
| ATOM | 1399 | CD | ILE | A | 188 | 47.399 | −28.462 | 29.274 | 1.00 | 46.06 | A |
| ATOM | 1400 | C | ILE | A | 188 | 51.016 | −25.312 | 28.135 | 1.00 | 30.03 | A |
| ATOM | 1401 | O | ILE | A | 188 | 50.564 | −24.550 | 28.984 | 1.00 | 33.74 | A |
| ATOM | 1402 | N | THR | A | 189 | 51.893 | −24.923 | 27.212 | 1.00 | 27.65 | A |
| ATOM | 1403 | CA | THR | A | 189 | 52.401 | −23.555 | 27.189 | 1.00 | 24.61 | A |
| ATOM | 1404 | CB | THR | A | 189 | 53.911 | −23.528 | 26.905 | 1.00 | 20.05 | A |
| ATOM | 1405 | OG1 | THR | A | 189 | 54.168 | −24.149 | 25.642 | 1.00 | 23.58 | A |
| ATOM | 1406 | CG2 | THR | A | 189 | 54.665 | −24.276 | 27.998 | 1.00 | 24.86 | A |
| ATOM | 1407 | C | THR | A | 189 | 51.691 | −22.632 | 26.212 | 1.00 | 26.56 | A |
| ATOM | 1408 | O | THR | A | 189 | 51.950 | −21.424 | 26.172 | 1.00 | 25.97 | A |
| ATOM | 1409 | N | ASP | A | 190 | 50.826 | −23.205 | 25.388 | 1.00 | 23.70 | A |
| ATOM | 1410 | CA | ASP | A | 190 | 50.015 | −22.401 | 24.486 | 1.00 | 28.06 | A |
| ATOM | 1411 | CB | ASP | A | 190 | 50.824 | −21.868 | 23.284 | 1.00 | 22.09 | A |
| ATOM | 1412 | CG | ASP | A | 190 | 51.194 | −22.919 | 22.275 | 1.00 | 24.30 | A |
| ATOM | 1413 | OD1 | ASP | A | 190 | 50.987 | −24.131 | 22.509 | 1.00 | 24.69 | A |
| ATOM | 1414 | OD2 | ASP | A | 190 | 51.707 | −22.508 | 21.200 | 1.00 | 21.73 | A |
| ATOM | 1415 | C | ASP | A | 190 | 48.787 | −23.221 | 24.099 | 1.00 | 23.26 | A |
| ATOM | 1416 | O | ASP | A | 190 | 48.623 | −24.344 | 24.582 | 1.00 | 21.66 | A |
| ATOM | 1417 | N | GLU | A | 191 | 47.896 | −22.653 | 23.297 | 1.00 | 23.73 | A |
| ATOM | 1418 | CA | GLU | A | 191 | 46.672 | −23.363 | 22.920 | 1.00 | 22.24 | A |
| ATOM | 1419 | CB | GLU | A | 191 | 45.630 | −22.385 | 22.375 | 1.00 | 23.88 | A |
| ATOM | 1420 | CG | GLU | A | 191 | 45.059 | −21.457 | 23.435 | 1.00 | 22.31 | A |
| ATOM | 1421 | CD | GLU | A | 191 | 46.152 | −20.616 | 24.129 | 1.00 | 26.32 | A |
| ATOM | 1422 | OE1 | GLU | A | 191 | 46.870 | −19.860 | 23.437 | 1.00 | 23.45 | A |
| ATOM | 1423 | OE2 | GLU | A | 191 | 46.266 | −20.711 | 25.355 | 1.00 | 27.07 | A |
| ATOM | 1424 | C | GLU | A | 191 | 46.923 | −24.440 | 21.893 | 1.00 | 21.29 | A |
| ATOM | 1425 | O | GLU | A | 191 | 46.234 | −25.468 | 21.870 | 1.00 | 23.52 | A |
| ATOM | 1426 | N | ALA | A | 192 | 47.906 | −24.198 | 21.034 | 1.00 | 23.27 | A |
| ATOM | 1427 | CA | ALA | A | 192 | 48.242 | −25.173 | 20.019 | 1.00 | 21.56 | A |
| ATOM | 1428 | CB | ALA | A | 192 | 49.380 | −24.672 | 19.153 | 1.00 | 26.07 | A |
| ATOM | 1429 | C | ALA | A | 192 | 48.639 | −26.468 | 20.715 | 1.00 | 26.60 | A |
| ATOM | 1430 | O | ALA | A | 192 | 48.306 | −27.562 | 20.245 | 1.00 | 24.52 | A |
| ATOM | 1431 | N | SER | A | 193 | 49.321 | −26.334 | 21.854 | 1.00 | 21.47 | A |
| ATOM | 1432 | CA | SER | A | 193 | 49.764 | −27.505 | 22.614 | 1.00 | 21.96 | A |
| ATOM | 1433 | CB | SER | A | 193 | 50.577 | −27.098 | 23.853 | 1.00 | 21.25 | A |
| ATOM | 1434 | OG | SER | A | 193 | 51.806 | −26.534 | 23.455 | 1.00 | 35.21 | A |
| ATOM | 1435 | C | SER | A | 193 | 48.623 | −28.413 | 23.035 | 1.00 | 24.96 | A |
| ATOM | 1436 | O | SER | A | 193 | 48.801 | −29.635 | 23.099 | 1.00 | 26.33 | A |
| ATOM | 1437 | N | ALA | A | 194 | 47.459 | −27.833 | 23.320 | 1.00 | 23.72 | A |
| ATOM | 1438 | CA | ALA | A | 194 | 46.296 | −28.629 | 23.713 | 1.00 | 24.70 | A |
| ATOM | 1439 | CB | ALA | A | 194 | 45.201 | −27.736 | 24.319 | 1.00 | 22.78 | A |
| ATOM | 1440 | C | ALA | A | 194 | 45.766 | −29.396 | 22.506 | 1.00 | 27.04 | A |
| ATOM | 1441 | O | ALA | A | 194 | 45.469 | −30.587 | 22.626 | 1.00 | 31.64 | A |
| ATOM | 1442 | N | LEU | A | 195 | 45.648 | −28.753 | 21.343 | 1.00 | 23.86 | A |
| ATOM | 1443 | CA | LEU | A | 195 | 45.189 | −29.507 | 20.184 | 1.00 | 26.36 | A |
| ATOM | 1444 | CB | LEU | A | 195 | 45.068 | −28.643 | 18.926 | 1.00 | 26.34 | A |
| ATOM | 1445 | CG | LEU | A | 195 | 43.775 | −27.832 | 18.766 | 1.00 | 32.93 | A |
| ATOM | 1446 | CD1 | LEU | A | 195 | 42.598 | −28.765 | 18.505 | 1.00 | 36.27 | A |
| ATOM | 1447 | CD2 | LEU | A | 195 | 43.552 | −27.015 | 20.019 | 1.00 | 25.88 | A |
| ATOM | 1448 | C | LEU | A | 195 | 46.184 | −30.619 | 19.903 | 1.00 | 32.46 | A |
| ATOM | 1449 | O | LEU | A | 195 | 45.798 | −31.726 | 19.539 | 1.00 | 29.89 | A |
| ATOM | 1450 | N | GLU | A | 196 | 47.469 | −30.335 | 20.089 | 1.00 | 25.64 | A |
| ATOM | 1451 | CA | GLU | A | 196 | 48.494 | −31.340 | 19.816 | 1.00 | 26.61 | A |
| ATOM | 1452 | CB | GLU | A | 196 | 49.878 | −30.716 | 20.010 | 1.00 | 29.48 | A |
| ATOM | 1453 | CG | GLU | A | 196 | 50.276 | −29.743 | 18.902 | 1.00 | 23.90 | A |
| ATOM | 1454 | CD | GLU | A | 196 | 51.340 | −28.773 | 19.348 | 1.00 | 19.56 | A |
| ATOM | 1455 | OE1 | GLU | A | 196 | 52.289 | −29.226 | 20.016 | 1.00 | 27.52 | A |
| ATOM | 1456 | OE2 | GLU | A | 196 | 51.224 | −27.570 | 19.019 | 1.00 | 26.47 | A |
| ATOM | 1457 | C | GLU | A | 196 | 48.341 | −32.565 | 20.704 | 1.00 | 28.89 | A |
| ATOM | 1458 | O | GLU | A | 196 | 48.459 | −33.699 | 20.244 | 1.00 | 32.12 | A |
| ATOM | 1459 | N | TYR | A | 197 | 48.075 | −32.324 | 21.978 | 1.00 | 26.74 | A |
| ATOM | 1460 | CA | TYR | A | 197 | 47.909 | −33.398 | 22.941 | 1.00 | 36.58 | A |
| ATOM | 1461 | CB | TYR | A | 197 | 47.641 | −32.798 | 24.325 | 1.00 | 25.07 | A |
| ATOM | 1462 | CG | TYR | A | 197 | 47.626 | −33.811 | 25.434 | 1.00 | 39.30 | A |
| ATOM | 1463 | CD1 | TYR | A | 197 | 48.762 | −34.560 | 25.725 | 1.00 | 41.22 | A |
| ATOM | 1464 | CE1 | TYR | A | 197 | 48.750 | −35.526 | 26.719 | 1.00 | 49.25 | A |
| ATOM | 1465 | CD2 | TYR | A | 197 | 46.469 | −34.047 | 26.174 | 1.00 | 41.12 | A |
| ATOM | 1466 | CE2 | TYR | A | 197 | 46.441 | −35.012 | 27.174 | 1.00 | 41.42 | A |
| ATOM | 1467 | CZ | TYR | A | 197 | 47.583 | −35.752 | 27.442 | 1.00 | 49.85 | A |
| ATOM | 1468 | OH | TYR | A | 197 | 47.553 | −36.736 | 28.414 | 1.00 | 52.93 | A |
| ATOM | 1469 | C | TYR | A | 197 | 46.761 | −34.338 | 22.535 | 1.00 | 42.35 | A |
| ATOM | 1470 | O | TYR | A | 197 | 46.794 | −35.543 | 22.803 | 1.00 | 42.54 | A |
| ATOM | 1471 | N | CYS | A | 198 | 45.757 | −33.780 | 21.870 | 1.00 | 41.70 | A |
| ATOM | 1472 | CA | CYS | A | 198 | 44.604 | −34.559 | 21.460 | 1.00 | 39.46 | A |
| ATOM | 1473 | CB | CYS | A | 198 | 43.344 | −33.705 | 21.589 | 1.00 | 40.51 | A |

APPENDIX 3-continued

X-RAY DATA COORDINATES FOR CDP-ME SYNTHASE COMPLEXED WITH CDP-ME.Mg$^{2+}$ (SEQ ID NO:12)

| | | | | | | | | | | | |
|---|---|---|---|---|---|---|---|---|---|---|---|
| ATOM | 1474 | SG | CYS | A | 198 | 43.039 | −33.268 | 23.338 | 1.00 | 50.71 | A |
| ATOM | 1475 | C | CYS | A | 198 | 44.741 | −35.142 | 20.069 | 1.00 | 37.98 | A |
| ATOM | 1476 | O | CYS | A | 198 | 43.773 | −35.635 | 19.487 | 1.00 | 41.21 | A |
| ATOM | 1477 | N | GLY | A | 199 | 45.953 | −35.065 | 19.534 | 1.00 | 34.97 | A |
| ATOM | 1478 | CA | GLY | A | 199 | 46.226 | −35.638 | 18.228 | 1.00 | 29.64 | A |
| ATOM | 1479 | C | GLY | A | 199 | 46.136 | −34.786 | 16.989 | 1.00 | 34.39 | A |
| ATOM | 1480 | O | GLY | A | 199 | 46.313 | −35.312 | 15.889 | 1.00 | 30.26 | A |
| ATOM | 1481 | N | PHE | A | 200 | 45.861 | −33.491 | 17.138 | 1.00 | 29.22 | A |
| ATOM | 1482 | CA | PHE | A | 200 | 45.757 | −32.615 | 15.976 | 1.00 | 33.43 | A |
| ATOM | 1483 | CB | PHE | A | 200 | 44.645 | −31.577 | 16.181 | 1.00 | 30.59 | A |
| ATOM | 1484 | CG | PHE | A | 200 | 43.309 | −32.184 | 16.543 | 1.00 | 34.93 | A |
| ATOM | 1485 | CD1 | PHE | A | 200 | 42.961 | −32.403 | 17.876 | 1.00 | 37.37 | A |
| ATOM | 1486 | CD2 | PHE | A | 200 | 42.412 | −32.557 | 15.549 | 1.00 | 39.78 | A |
| ATOM | 1487 | CE1 | PHE | A | 200 | 41.738 | −32.984 | 18.210 | 1.00 | 36.62 | A |
| ATOM | 1488 | CE2 | PHE | A | 200 | 41.186 | −33.139 | 15.872 | 1.00 | 40.74 | A |
| ATOM | 1489 | CZ | PHE | A | 200 | 40.852 | −33.351 | 17.203 | 1.00 | 33.30 | A |
| ATOM | 1490 | C | PHE | A | 200 | 47.071 | −31.905 | 15.666 | 1.00 | 36.21 | A |
| ATOM | 1491 | O | PHE | A | 200 | 48.003 | −31.904 | 16.470 | 1.00 | 33.02 | A |
| ATOM | 1492 | N | HIS | A | 201 | 47.122 | −31.291 | 14.490 | 1.00 | 38.02 | A |
| ATOM | 1493 | CA | HIS | A | 201 | 48.303 | −30.583 | 14.024 | 1.00 | 35.10 | A |
| ATOM | 1494 | CB | HIS | A | 201 | 49.028 | −31.458 | 12.996 | 1.00 | 37.66 | A |
| ATOM | 1495 | CG | HIS | A | 201 | 49.460 | −32.783 | 13.547 | 1.00 | 36.76 | A |
| ATOM | 1496 | CD2 | HIS | A | 201 | 50.671 | −33.217 | 13.967 | 1.00 | 36.43 | A |
| ATOM | 1497 | ND1 | HIS | A | 201 | 48.577 | −33.812 | 13.798 | 1.00 | 40.22 | A |
| ATOM | 1498 | CE1 | HIS | A | 201 | 49.226 | −34.822 | 14.351 | 1.00 | 32.04 | A |
| ATOM | 1499 | NE2 | HIS | A | 201 | 50.498 | −34.486 | 14.465 | 1.00 | 43.81 | A |
| ATOM | 1500 | C | HIS | A | 201 | 47.910 | −29.232 | 13.413 | 1.00 | 35.64 | A |
| ATOM | 1501 | O | HIS | A | 201 | 47.678 | −29.133 | 12.195 | 1.00 | 32.21 | A |
| ATOM | 1502 | N | PRO | A | 202 | 47.834 | −28.174 | 14.252 | 1.00 | 31.52 | A |
| ATOM | 1503 | CD | PRO | A | 202 | 47.952 | −28.211 | 15.721 | 1.00 | 24.33 | A |
| ATOM | 1504 | CA | PRO | A | 202 | 47.461 | −26.828 | 13.804 | 1.00 | 28.33 | A |
| ATOM | 1505 | CB | PRO | A | 202 | 47.494 | −26.008 | 15.088 | 1.00 | 25.14 | A |
| ATOM | 1506 | CG | PRO | A | 202 | 47.134 | −27.016 | 16.129 | 1.00 | 25.77 | A |
| ATOM | 1507 | C | PRO | A | 202 | 48.340 | −26.242 | 12.723 | 1.00 | 28.77 | A |
| ATOM | 1508 | O | PRO | A | 202 | 49.514 | −26.582 | 12.614 | 1.00 | 28.13 | A |
| ATOM | 1509 | N | GLN | A | 203 | 47.750 | −25.354 | 11.930 | 1.00 | 26.19 | A |
| ATOM | 1510 | CA | GLN | A | 203 | 48.441 | −24.694 | 10.835 | 1.00 | 28.01 | A |
| ATOM | 1511 | CB | GLN | A | 203 | 47.395 | −24.123 | 9.868 | 1.00 | 33.27 | A |
| ATOM | 1512 | CG | GLN | A | 203 | 47.563 | −24.515 | 8.396 | 1.00 | 43.96 | A |
| ATOM | 1513 | CD | GLN | A | 203 | 47.902 | −25.993 | 8.198 | 1.00 | 48.25 | A |
| ATOM | 1514 | OE1 | GLN | A | 203 | 47.216 | −26.884 | 8.709 | 1.00 | 48.41 | A |
| ATOM | 1515 | NE2 | GLN | A | 203 | 48.969 | −26.255 | 7.445 | 1.00 | 56.65 | A |
| ATOM | 1516 | C | GLN | A | 203 | 49.358 | −23.586 | 11.353 | 1.00 | 27.73 | A |
| ATOM | 1517 | O | GLN | A | 203 | 49.095 | −22.978 | 12.391 | 1.00 | 24.02 | A |
| ATOM | 1518 | N | LEU | A | 204 | 50.451 | −23.350 | 10.633 | 1.00 | 29.08 | A |
| ATOM | 1519 | CA | LEU | A | 204 | 51.412 | −22.312 | 10.984 | 1.00 | 27.46 | A |
| ATOM | 1520 | CB | LEU | A | 204 | 52.845 | −22.865 | 10.906 | 1.00 | 32.07 | A |
| ATOM | 1521 | CG | LEU | A | 204 | 53.306 | −23.825 | 12.013 | 1.00 | 30.57 | A |
| ATOM | 1522 | CD1 | LEU | A | 204 | 54.559 | −24.571 | 11.565 | 1.00 | 33.73 | A |
| ATOM | 1523 | CD2 | LEU | A | 204 | 53.579 | −23.068 | 13.271 | 1.00 | 25.87 | A |
| ATOM | 1524 | C | LEU | A | 204 | 51.252 | −21.148 | 10.009 | 1.00 | 28.09 | A |
| ATOM | 1525 | O | LEU | A | 204 | 51.411 | −21.317 | 8.804 | 1.00 | 29.63 | A |
| ATOM | 1526 | N | VAL | A | 205 | 50.903 | −19.979 | 10.531 | 1.00 | 26.87 | A |
| ATOM | 1527 | CA | VAL | A | 205 | 50.732 | −18.785 | 9.709 | 1.00 | 25.63 | A |
| ATOM | 1528 | CB | VAL | A | 205 | 49.362 | −18.117 | 9.941 | 1.00 | 28.90 | A |
| ATOM | 1529 | CG1 | VAL | A | 205 | 49.269 | −16.823 | 9.127 | 1.00 | 35.28 | A |
| ATOM | 1530 | CG2 | VAL | A | 205 | 48.253 | −19.056 | 9.530 | 1.00 | 24.69 | A |
| ATOM | 1531 | C | VAL | A | 205 | 51.823 | −17.797 | 10.072 | 1.00 | 23.72 | A |
| ATOM | 1532 | O | VAL | A | 205 | 51.844 | −17.256 | 11.179 | 1.00 | 27.68 | A |
| ATOM | 1533 | N | GLU | A | 206 | 52.728 | −17.561 | 9.126 | 1.00 | 26.74 | A |
| ATOM | 1534 | CA | GLU | A | 206 | 53.855 | −16.678 | 9.367 | 1.00 | 25.64 | A |
| ATOM | 1535 | CB | GLU | A | 206 | 54.816 | −16.689 | 8.170 | 1.00 | 27.77 | A |
| ATOM | 1536 | CG | GLU | A | 206 | 56.135 | −16.029 | 8.506 | 1.00 | 29.82 | A |
| ATOM | 1537 | CD | GLU | A | 206 | 57.209 | −16.218 | 7.450 | 1.00 | 32.28 | A |
| ATOM | 1538 | OE1 | GLU | A | 206 | 57.076 | −17.123 | 6.598 | 1.00 | 41.46 | A |
| ATOM | 1539 | OE2 | GLU | A | 206 | 58.195 | −15.460 | 7.500 | 1.00 | 38.20 | A |
| ATOM | 1540 | C | GLU | A | 206 | 53.410 | −15.267 | 9.657 | 1.00 | 26.76 | A |
| ATOM | 1541 | O | GLU | A | 206 | 52.614 | −14.701 | 8.922 | 1.00 | 30.35 | A |
| ATOM | 1542 | N | GLY | A | 207 | 53.905 | −14.710 | 10.759 | 1.00 | 22.65 | A |
| ATOM | 1543 | CA | GLY | A | 207 | 53.547 | −13.349 | 11.110 | 1.00 | 28.88 | A |
| ATOM | 1544 | C | GLY | A | 207 | 54.823 | −12.580 | 11.332 | 1.00 | 26.30 | A |
| ATOM | 1545 | O | GLY | A | 207 | 55.901 | −13.167 | 11.271 | 1.00 | 33.22 | A |
| ATOM | 1546 | N | ARG | A | 208 | 54.719 | −11.283 | 11.586 | 1.00 | 28.30 | A |
| ATOM | 1547 | CA | ARG | A | 208 | 55.896 | −10.468 | 11.825 | 1.00 | 26.20 | A |
| ATOM | 1548 | CB | ARG | A | 208 | 55.510 | −8.989 | 11.863 | 1.00 | 27.69 | A |
| ATOM | 1549 | CG | ARG | A | 208 | 54.576 | −8.520 | 10.767 | 1.00 | 31.85 | A |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 1550 | CD | ARG | A | 208 | 53.963 | −7.181 | 11.169 | 1.00 | 30.58 | A |
|------|------|------|-----|---|-----|--------|--------|--------|------|-------|---|
| ATOM | 1551 | NE | ARG | A | 208 | 55.003 | −6.193 | 11.486 | 1.00 | 36.20 | A |
| ATOM | 1552 | CZ | ARG | A | 208 | 55.603 | −5.425 | 10.581 | 1.00 | 42.15 | A |
| ATOM | 1553 | NH1 | ARG | A | 208 | 55.259 | −5.528 | 9.301 | 1.00 | 45.96 | A |
| ATOM | 1554 | NH2 | ARG | A | 208 | 56.540 | −4.561 | 10.955 | 1.00 | 40.62 | A |
| ATOM | 1555 | C | ARG | A | 208 | 56.536 | −10.845 | 13.163 | 1.00 | 32.96 | A |
| ATOM | 1556 | O | ARG | A | 208 | 55.835 | −11.118 | 14.152 | 1.00 | 28.29 | A |
| ATOM | 1557 | N | ALA | A | 209 | 57.868 | −10.831 | 13.188 | 1.00 | 27.58 | A |
| ATOM | 1558 | CA | ALA | A | 209 | 58.637 | −11.162 | 14.383 | 1.00 | 31.10 | A |
| ATOM | 1559 | CB | ALA | A | 209 | 60.074 | −11.538 | 14.002 | 1.00 | 31.86 | A |
| ATOM | 1560 | C | ALA | A | 209 | 58.652 | −9.998 | 15.361 | 1.00 | 29.50 | A |
| ATOM | 1561 | O | ALA | A | 209 | 59.119 | −10.140 | 16.497 | 1.00 | 30.70 | A |
| ATOM | 1562 | N | ASP | A | 210 | 58.155 | −8.841 | 14.938 | 1.00 | 25.17 | A |
| ATOM | 1563 | CA | ASP | A | 210 | 58.113 | −7.702 | 15.857 | 1.00 | 30.72 | A |
| ATOM | 1564 | CB | ASP | A | 210 | 58.128 | −6.369 | 15.080 | 1.00 | 30.47 | A |
| ATOM | 1565 | CG | ASP | A | 210 | 56.811 | −6.052 | 14.389 | 1.00 | 39.40 | A |
| ATOM | 1566 | OD1 | ASP | A | 210 | 56.204 | −6.946 | 13.776 | 1.00 | 34.28 | A |
| ATOM | 1567 | OD2 | ASP | A | 210 | 56.388 | −4.875 | 14.451 | 1.00 | 50.59 | A |
| ATOM | 1568 | C | ASP | A | 210 | 56.892 | −7.805 | 16.795 | 1.00 | 25.97 | A |
| ATOM | 1569 | O | ASP | A | 210 | 56.662 | −6.950 | 17.649 | 1.00 | 25.64 | A |
| ATOM | 1570 | N | ASN | A | 211 | 56.134 | −8.879 | 16.632 | 1.00 | 24.15 | A |
| ATOM | 1571 | CA | ASN | A | 211 | 54.967 | −9.151 | 17.471 | 1.00 | 26.21 | A |
| ATOM | 1572 | CB | ASN | A | 211 | 54.018 | −10.075 | 16.714 | 1.00 | 25.38 | A |
| ATOM | 1573 | CG | ASN | A | 211 | 52.789 | −10.483 | 17.526 | 1.00 | 26.91 | A |
| ATOM | 1574 | OD1 | ASN | A | 211 | 52.443 | −9.856 | 18.519 | 1.00 | 27.63 | A |
| ATOM | 1575 | ND2 | ASN | A | 211 | 52.118 | −11.547 | 17.079 | 1.00 | 22.69 | A |
| ATOM | 1576 | C | ASN | A | 211 | 55.533 | −9.841 | 18.717 | 1.00 | 32.24 | A |
| ATOM | 1577 | O | ASN | A | 211 | 55.288 | −11.028 | 18.960 | 1.00 | 31.21 | A |
| ATOM | 1578 | N | ILE | A | 212 | 56.294 | −9.086 | 19.505 | 1.00 | 28.92 | A |
| ATOM | 1579 | CA | ILE | A | 212 | 56.937 | −9.639 | 20.682 | 1.00 | 32.34 | A |
| ATOM | 1580 | CB | ILE | A | 212 | 58.262 | −8.882 | 21.004 | 1.00 | 42.77 | A |
| ATOM | 1581 | CG2 | ILE | A | 212 | 59.118 | −8.757 | 19.752 | 1.00 | 38.38 | A |
| ATOM | 1582 | CG1 | ILE | A | 212 | 57.955 | −7.498 | 21.587 | 1.00 | 34.48 | A |
| ATOM | 1583 | CD | ILE | A | 212 | 57.329 | −6.554 | 20.615 | 1.00 | 44.22 | A |
| ATOM | 1584 | C | ILE | A | 212 | 56.096 | −9.666 | 21.950 | 1.00 | 35.03 | A |
| ATOM | 1585 | O | ILE | A | 212 | 55.056 | −9.018 | 22.042 | 1.00 | 35.44 | A |
| ATOM | 1586 | N | LYS | A | 213 | 56.580 | −10.427 | 22.925 | 1.00 | 26.32 | A |
| ATOM | 1587 | CA | LYS | A | 213 | 55.931 | −10.568 | 24.222 | 1.00 | 28.76 | A |
| ATOM | 1588 | CB | LYS | A | 213 | 55.879 | −12.045 | 24.628 | 1.00 | 34.04 | A |
| ATOM | 1589 | CG | LYS | A | 213 | 55.150 | −12.298 | 25.943 | 1.00 | 38.37 | A |
| ATOM | 1590 | CD | LYS | A | 213 | 55.058 | −13.789 | 26.283 | 1.00 | 36.08 | A |
| ATOM | 1591 | CE | LYS | A | 213 | 56.381 | −14.330 | 26.833 | 1.00 | 38.22 | A |
| ATOM | 1592 | NZ | LYS | A | 213 | 57.058 | −15.228 | 25.858 | 1.00 | 42.03 | A |
| ATOM | 1593 | C | LYS | A | 213 | 56.737 | −9.780 | 25.255 | 1.00 | 35.01 | A |
| ATOM | 1594 | O | LYS | A | 213 | 57.947 | −9.972 | 25.380 | 1.00 | 32.48 | A |
| ATOM | 1595 | N | VAL | A | 214 | 56.070 | −8.883 | 25.976 | 1.00 | 29.53 | A |
| ATOM | 1596 | CA | VAL | A | 214 | 56.726 | −8.072 | 26.999 | 1.00 | 38.83 | A |
| ATOM | 1597 | CB | VAL | A | 214 | 56.016 | −6.712 | 27.172 | 1.00 | 39.03 | A |
| ATOM | 1598 | CG1 | VAL | A | 214 | 56.717 | −5.891 | 28.273 | 1.00 | 39.43 | A |
| ATOM | 1599 | CG2 | VAL | A | 214 | 56.039 | −5.949 | 25.849 | 1.00 | 35.04 | A |
| ATOM | 1600 | C | VAL | A | 214 | 56.709 | −8.806 | 28.334 | 1.00 | 42.88 | A |
| ATOM | 1601 | O | VAL | A | 214 | 55.665 | −8.913 | 28.972 | 1.00 | 40.58 | A |
| ATOM | 1602 | N | THR | A | 215 | 57.864 | −9.309 | 28.758 | 1.00 | 46.63 | A |
| ATOM | 1603 | CA | THR | A | 215 | 57.942 | −10.044 | 30.016 | 1.00 | 50.56 | A |
| ATOM | 1604 | CB | THR | A | 215 | 58.288 | −11.525 | 29.780 | 1.00 | 53.56 | A |
| ATOM | 1605 | OG1 | THR | A | 215 | 57.581 | −12.011 | 28.631 | 1.00 | 50.16 | A |
| ATOM | 1606 | CG2 | THR | A | 215 | 57.888 | −12.349 | 30.994 | 1.00 | 54.02 | A |
| ATOM | 1607 | C | THR | A | 215 | 59.004 | −9.464 | 30.937 | 1.00 | 56.61 | A |
| ATOM | 1608 | O | THR | A | 215 | 58.834 | −9.419 | 32.158 | 1.00 | 53.65 | A |
| ATOM | 1609 | N | ARG | A | 216 | 60.101 | −9.020 | 30.332 | 1.00 | 55.86 | A |
| ATOM | 1610 | CA | ARG | A | 216 | 61.222 | −8.450 | 31.064 | 1.00 | 55.27 | A |
| ATOM | 1611 | CB | ARG | A | 216 | 62.541 | −8.938 | 30.457 | 1.00 | 53.61 | A |
| ATOM | 1612 | CG | ARG | A | 216 | 63.407 | −9.722 | 31.411 | 1.00 | 62.74 | A |
| ATOM | 1613 | CD | ARG | A | 216 | 63.419 | −11.202 | 31.078 | 1.00 | 61.82 | A |
| ATOM | 1614 | NE | ARG | A | 216 | 62.088 | −11.802 | 31.095 | 1.00 | 61.33 | A |
| ATOM | 1615 | CZ | ARG | A | 216 | 61.866 | −13.104 | 30.953 | 1.00 | 67.39 | A |
| ATOM | 1616 | NH1 | ARG | A | 216 | 62.891 | −13.933 | 30.790 | 1.00 | 62.86 | A |
| ATOM | 1617 | NH2 | ARG | A | 216 | 60.628 | −13.575 | 30.966 | 1.00 | 68.72 | A |
| ATOM | 1618 | C | ARG | A | 216 | 61.185 | −6.928 | 31.036 | 1.00 | 56.05 | A |
| ATOM | 1619 | O | ARG | A | 216 | 60.529 | −6.330 | 30.187 | 1.00 | 56.49 | A |
| ATOM | 1620 | N | PRO | A | 217 | 61.901 | −6.279 | 31.970 | 1.00 | 57.08 | A |
| ATOM | 1621 | CD | PRO | A | 217 | 62.666 | −6.880 | 33.079 | 1.00 | 54.70 | A |
| ATOM | 1622 | CA | PRO | A | 217 | 61.942 | −4.813 | 32.041 | 1.00 | 54.45 | A |
| ATOM | 1623 | CB | PRO | A | 217 | 62.961 | −4.552 | 33.151 | 1.00 | 56.69 | A |
| ATOM | 1624 | CG | PRO | A | 217 | 62.778 | −5.727 | 34.054 | 1.00 | 56.67 | A |
| ATOM | 1625 | C | PRO | A | 217 | 62.346 | −4.151 | 30.720 | 1.00 | 50.89 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 1626 | O | PRO | A | 217 | 61.714 | −3.189 | 30.284 | 1.00 | 51.43 | A |
|---|---|---|---|---|---|---|---|---|---|---|---|
| ATOM | 1627 | N | GLU | A | 218 | 63.394 | −4.672 | 30.087 | 1.00 | 50.91 | A |
| ATOM | 1628 | CA | GLU | A | 218 | 63.868 | −4.108 | 28.826 | 1.00 | 53.84 | A |
| ATOM | 1629 | CB | GLU | A | 218 | 65.211 | −4.735 | 28.418 | 1.00 | 58.08 | A |
| ATOM | 1630 | CG | GLU | A | 218 | 65.854 | −4.068 | 27.190 | 1.00 | 64.79 | A |
| ATOM | 1631 | CD | GLU | A | 218 | 66.975 | −4.901 | 26.557 | 1.00 | 72.12 | A |
| ATOM | 1632 | OE1 | GLU | A | 218 | 66.755 | −6.113 | 26.326 | 1.00 | 71.16 | A |
| ATOM | 1633 | OE2 | GLU | A | 218 | 68.065 | −4.345 | 26.275 | 1.00 | 67.83 | A |
| ATOM | 1634 | C | GLU | A | 218 | 62.865 | −4.287 | 27.690 | 1.00 | 49.59 | A |
| ATOM | 1635 | O | GLU | A | 218 | 62.864 | −3.513 | 26.733 | 1.00 | 50.18 | A |
| ATOM | 1636 | N | ASP | A | 219 | 62.010 | −5.299 | 27.790 | 1.00 | 45.70 | A |
| ATOM | 1637 | CA | ASP | A | 219 | 61.028 | −5.540 | 26.736 | 1.00 | 45.36 | A |
| ATOM | 1638 | CB | ASP | A | 219 | 60.144 | −6.751 | 27.066 | 1.00 | 43.64 | A |
| ATOM | 1639 | CG | ASP | A | 219 | 60.920 | −8.043 | 27.109 | 1.00 | 45.39 | A |
| ATOM | 1640 | OD1 | ASP | A | 219 | 61.961 | −8.127 | 26.416 | 1.00 | 49.21 | A |
| ATOM | 1641 | OD2 | ASP | A | 219 | 60.489 | −8.982 | 27.823 | 1.00 | 36.59 | A |
| ATOM | 1642 | C | ASP | A | 219 | 60.151 | −4.321 | 26.514 | 1.00 | 42.03 | A |
| ATOM | 1643 | O | ASP | A | 219 | 59.735 | −4.048 | 25.392 | 1.00 | 41.73 | A |
| ATOM | 1644 | N | LEU | A | 220 | 59.870 | −3.588 | 27.585 | 1.00 | 43.58 | A |
| ATOM | 1645 | CA | LEU | A | 220 | 59.032 | −2.400 | 27.483 | 1.00 | 40.64 | A |
| ATOM | 1646 | CB | LEU | A | 220 | 58.957 | −1.685 | 28.830 | 1.00 | 45.60 | A |
| ATOM | 1647 | CG | LEU | A | 220 | 58.270 | −.315 | 28.833 | 1.00 | 48.05 | A |
| ATOM | 1648 | CD1 | LEU | A | 220 | 56.755 | −.467 | 28.706 | 1.00 | 46.41 | A |
| ATOM | 1649 | CD2 | LEU | A | 220 | 58.622 | .411 | 30.135 | 1.00 | 53.44 | A |
| ATOM | 1650 | C | LEU | A | 220 | 59.582 | −1.436 | 26.453 | 1.00 | 40.17 | A |
| ATOM | 1651 | O | LEU | A | 220 | 58.885 | −1.042 | 25.524 | 1.00 | 34.63 | A |
| ATOM | 1652 | N | ALA | A | 221 | 60.839 | −1.044 | 26.640 | 1.00 | 42.34 | A |
| ATOM | 1653 | CA | ALA | A | 221 | 61.493 | −.106 | 25.733 | 1.00 | 45.60 | A |
| ATOM | 1654 | CB | ALA | A | 221 | 62.961 | .078 | 26.136 | 1.00 | 45.74 | A |
| ATOM | 1655 | C | ALA | A | 221 | 61.398 | −.589 | 24.293 | 1.00 | 41.75 | A |
| ATOM | 1656 | O | ALA | A | 221 | 61.035 | .175 | 23.396 | 1.00 | 36.25 | A |
| ATOM | 1657 | N | LEU | A | 222 | 61.717 | −1.864 | 24.081 | 1.00 | 39.59 | A |
| ATOM | 1658 | CA | LEU | A | 222 | 61.660 | −2.456 | 22.747 | 1.00 | 38.28 | A |
| ATOM | 1659 | CB | LEU | A | 222 | 62.132 | −3.916 | 22.798 | 1.00 | 39.70 | A |
| ATOM | 1660 | CG | LEU | A | 222 | 62.087 | −4.707 | 21.487 | 1.00 | 39.68 | A |
| ATOM | 1661 | CD1 | LEU | A | 222 | 63.047 | −4.099 | 20.489 | 1.00 | 43.78 | A |
| ATOM | 1662 | CD2 | LEU | A | 222 | 62.437 | −6.150 | 21.745 | 1.00 | 40.10 | A |
| ATOM | 1663 | C | LEU | A | 222 | 60.247 | −2.389 | 22.162 | 1.00 | 42.22 | A |
| ATOM | 1664 | O | LEU | A | 222 | 60.068 | −2.057 | 20.987 | 1.00 | 43.92 | A |
| ATOM | 1665 | N | ALA | A | 223 | 59.241 | −2.713 | 22.970 | 1.00 | 41.63 | A |
| ATOM | 1666 | CA | ALA | A | 223 | 57.862 | −2.674 | 22.482 | 1.00 | 44.91 | A |
| ATOM | 1667 | CB | ALA | A | 223 | 56.901 | −3.134 | 23.572 | 1.00 | 40.65 | A |
| ATOM | 1668 | C | ALA | A | 223 | 57.525 | −1.255 | 22.030 | 1.00 | 42.30 | A |
| ATOM | 1669 | O | ALA | A | 223 | 56.879 | −1.059 | 20.999 | 1.00 | 40.78 | A |
| ATOM | 1670 | N | GLU | A | 224 | 57.970 | −.266 | 22.800 | 1.00 | 43.74 | A |
| ATOM | 1671 | CA | GLU | A | 224 | 57.719 | 1.125 | 22.441 | 1.00 | 46.16 | A |
| ATOM | 1672 | CB | GLU | A | 224 | 58.304 | 2.071 | 23.484 | 1.00 | 44.87 | A |
| ATOM | 1673 | CG | GLU | A | 224 | 58.311 | 3.513 | 23.017 | 1.00 | 55.07 | A |
| ATOM | 1674 | CD | GLU | A | 224 | 58.260 | 4.512 | 24.153 | 1.00 | 57.49 | A |
| ATOM | 1675 | OE1 | GLU | A | 224 | 59.249 | 4.601 | 24.922 | 1.00 | 51.86 | A |
| ATOM | 1676 | OE2 | GLU | A | 224 | 57.217 | 5.205 | 24.271 | 1.00 | 60.96 | A |
| ATOM | 1677 | C | GLU | A | 224 | 58.326 | 1.440 | 21.076 | 1.00 | 47.29 | A |
| ATOM | 1678 | O | GLU | A | 224 | 57.695 | 2.085 | 20.237 | 1.00 | 47.20 | A |
| ATOM | 1679 | N | PHE | A | 225 | 59.555 | .977 | 20.869 | 1.00 | 50.18 | A |
| ATOM | 1680 | CA | PHE | A | 225 | 60.268 | 1.177 | 19.614 | 1.00 | 47.05 | A |
| ATOM | 1681 | CB | PHE | A | 225 | 61.597 | .415 | 19.642 | 1.00 | 48.91 | A |
| ATOM | 1682 | CG | PHE | A | 225 | 62.339 | .431 | 18.331 | 1.00 | 49.43 | A |
| ATOM | 1683 | CD1 | PHE | A | 225 | 62.994 | 1.581 | 17.897 | 1.00 | 51.99 | A |
| ATOM | 1684 | CD2 | PHE | A | 225 | 62.374 | −.705 | 17.523 | 1.00 | 49.62 | A |
| ATOM | 1685 | CE1 | PHE | A | 225 | 63.673 | 1.602 | 16.673 | 1.00 | 44.11 | A |
| ATOM | 1686 | CE2 | PHE | A | 225 | 63.047 | −.699 | 16.299 | 1.00 | 43.16 | A |
| ATOM | 1687 | CZ | PHE | A | 225 | 63.698 | .456 | 15.872 | 1.00 | 48.09 | A |
| ATOM | 1688 | C | PHE | A | 225 | 59.429 | .673 | 18.450 | 1.00 | 47.63 | A |
| ATOM | 1689 | O | PHE | A | 225 | 59.208 | 1.389 | 17.477 | 1.00 | 48.88 | A |
| ATOM | 1690 | N | TYR | A | 226 | 58.966 | −.567 | 18.551 | 1.00 | 49.30 | A |
| ATOM | 1691 | CA | TYR | A | 226 | 58.165 | −1.166 | 17.490 | 1.00 | 48.89 | A |
| ATOM | 1692 | CB | TYR | A | 226 | 57.886 | −2.637 | 17.813 | 1.00 | 50.20 | A |
| ATOM | 1693 | CG | TYR | A | 226 | 59.064 | −3.556 | 17.585 | 1.00 | 44.80 | A |
| ATOM | 1694 | CD1 | TYR | A | 226 | 59.369 | −4.564 | 18.499 | 1.00 | 46.11 | A |
| ATOM | 1695 | CE1 | TYR | A | 226 | 60.435 | −5.435 | 18.279 | 1.00 | 47.03 | A |
| ATOM | 1696 | CD2 | TYR | A | 226 | 59.858 | −3.440 | 16.440 | 1.00 | 43.72 | A |
| ATOM | 1697 | CE2 | TYR | A | 226 | 60.927 | −4.308 | 16.209 | 1.00 | 43.50 | A |
| ATOM | 1698 | CZ | TYR | A | 226 | 61.209 | −5.302 | 17.132 | 1.00 | 43.61 | A |
| ATOM | 1699 | OH | TYR | A | 226 | 62.261 | −6.165 | 16.917 | 1.00 | 44.48 | A |
| ATOM | 1700 | C | TYR | A | 226 | 56.856 | −.439 | 17.228 | 1.00 | 49.19 | A |
| ATOM | 1701 | O | TYR | A | 226 | 56.389 | −.388 | 16.088 | 1.00 | 46.23 | A |

APPENDIX 3-continued

X-RAY DATA COORDINATES FOR CDP-ME SYNTHASE
COMPLEXED WITH CDP-ME.Mg$^{2+}$ (SEQ ID NO:12)

| ATOM | 1702 | N | LEU | A | 227 | 56.262 | .123 | 18.276 | 1.00 | 51.04 | A |
|---|---|---|---|---|---|---|---|---|---|---|---|
| ATOM | 1703 | CA | LEU | A | 227 | 54.995 | .846 | 18.135 | 1.00 | 55.54 | A |
| ATOM | 1704 | CB | LEU | A | 227 | 54.249 | .877 | 19.476 | 1.00 | 57.70 | A |
| ATOM | 1705 | CG | LEU | A | 227 | 53.603 | −.419 | 19.977 | 1.00 | 55.63 | A |
| ATOM | 1706 | CD1 | LEU | A | 227 | 53.114 | −.236 | 21.409 | 1.00 | 53.74 | A |
| ATOM | 1707 | CD2 | LEU | A | 227 | 52.452 | −.799 | 19.058 | 1.00 | 54.22 | A |
| ATOM | 1708 | C | LEU | A | 227 | 55.226 | 2.274 | 17.656 | 1.00 | 53.48 | A |
| ATOM | 1709 | O | LEU | A | 227 | 54.300 | 3.075 | 17.607 | 1.00 | 55.24 | A |
| ATOM | 1710 | N | THR | A | 228 | 56.463 | 2.578 | 17.283 | 1.00 | 55.39 | A |
| ATOM | 1711 | CA | THR | A | 228 | 56.823 | 3.923 | 16.841 | 1.00 | 55.53 | A |
| ATOM | 1712 | CB | THR | A | 228 | 58.049 | 4.411 | 17.654 | 1.00 | 55.92 | A |
| ATOM | 1713 | OG1 | THR | A | 228 | 57.748 | 4.315 | 19.052 | 1.00 | 57.68 | A |
| ATOM | 1714 | CG2 | THR | A | 228 | 58.395 | 5.855 | 17.330 | 1.00 | 52.13 | A |
| ATOM | 1715 | C | THR | A | 228 | 57.106 | 4.065 | 15.334 | 1.00 | 55.95 | A |
| ATOM | 1716 | OT1 | THR | A | 228 | 57.397 | 3.046 | 14.671 | 1.00 | 53.29 | A |
| ATOM | 1717 | OXT | THR | A | 228 | 57.039 | 5.213 | 14.832 | 1.00 | 55.13 | A |
| ATOM | 1718 | OH2 | WAT | W | 1 | 53.847 | −7.444 | 15.008 | 1.00 | 28.25 | W |
| ATOM | 1719 | OH2 | WAT | W | 2 | 47.027 | −3.691 | 14.794 | 1.00 | 27.00 | W |
| ATOM | 1720 | OH2 | WAT | W | 3 | 45.444 | −9.337 | 36.235 | 1.00 | 30.05 | W |
| ATOM | 1721 | OH2 | WAT | W | 4 | 33.922 | .643 | 18.800 | 1.00 | 46.44 | W |
| ATOM | 1722 | OH2 | WAT | W | 5 | 29.022 | .031 | 27.797 | 1.00 | 33.48 | W |
| ATOM | 1723 | OH2 | WAT | W | 6 | 49.115 | −3.454 | 18.135 | 1.00 | 34.94 | W |
| ATOM | 1724 | OH2 | WAT | W | 7 | 42.749 | −7.436 | 10.961 | 1.00 | 28.12 | W |
| ATOM | 1725 | OH2 | WAT | W | 8 | 48.242 | −2.786 | 11.852 | 1.00 | 33.73 | W |
| ATOM | 1726 | OH2 | WAT | W | 9 | 38.166 | −13.364 | 7.759 | 1.00 | 26.24 | W |
| ATOM | 1727 | OH2 | WAT | W | 10 | 70.200 | −13.434 | 18.230 | 1.00 | 27.23 | W |
| ATOM | 1728 | OH2 | WAT | W | 11 | 32.460 | −8.229 | 32.731 | 1.00 | 45.56 | W |
| ATOM | 1729 | OH2 | WAT | W | 12 | 59.016 | −11.798 | 22.216 | 1.00 | 32.91 | W |
| ATOM | 1730 | OH2 | WAT | W | 13 | 60.995 | −13.831 | 10.396 | 1.00 | 46.99 | W |
| ATOM | 1731 | OH2 | WAT | W | 14 | 49.286 | −34.083 | 17.618 | 1.00 | 30.47 | W |
| ATOM | 1732 | OH2 | WAT | W | 15 | 33.791 | −17.472 | 13.391 | 1.00 | 32.71 | W |
| ATOM | 1733 | OH2 | WAT | W | 16 | 30.947 | −5.854 | 12.464 | 1.00 | 38.93 | W |
| ATOM | 1734 | OH2 | WAT | W | 17 | 46.728 | −1.736 | 18.777 | 1.00 | 38.92 | W |
| ATOM | 1735 | OH2 | WAT | W | 18 | 28.006 | −21.025 | 27.775 | 1.00 | 48.34 | W |
| ATOM | 1736 | OH2 | WAT | W | 19 | 58.466 | −13.965 | 10.078 | 1.00 | 39.44 | W |
| ATOM | 1737 | OH2 | WAT | W | 20 | 41.247 | −6.716 | 8.377 | 1.00 | 45.81 | W |
| ATOM | 1738 | OH2 | WAT | W | 21 | 58.906 | −13.109 | 17.325 | 1.00 | 42.74 | W |
| ATOM | 1739 | OH2 | WAT | W | 22 | 69.328 | −24.424 | 14.872 | 1.00 | 51.19 | W |
| ATOM | 1740 | OH2 | WAT | W | 23 | 26.850 | −10.998 | 14.095 | 1.00 | 50.74 | W |
| ATOM | 1741 | OH2 | WAT | W | 24 | 46.592 | −22.926 | 26.823 | 1.00 | 33.88 | W |
| ATOM | 1742 | OH2 | WAT | W | 25 | 69.780 | −25.888 | 10.403 | 1.00 | 57.17 | W |
| ATOM | 1743 | OH2 | WAT | W | 26 | 45.111 | −26.028 | 37.762 | 1.00 | 46.34 | W |
| ATOM | 1744 | OH2 | WAT | W | 27 | 60.710 | −15.221 | 6.454 | 1.00 | 49.35 | W |
| ATOM | 1745 | OH2 | WAT | W | 28 | 68.617 | −14.221 | 14.947 | 1.00 | 39.32 | W |
| ATOM | 1746 | OH2 | WAT | W | 29 | 35.082 | −5.686 | 16.665 | 1.00 | 30.26 | W |
| ATOM | 1747 | OH2 | WAT | W | 30 | 32.135 | −23.281 | 28.156 | 1.00 | 71.05 | W |
| ATOM | 1748 | OH2 | WAT | W | 31 | 33.020 | −14.898 | 35.681 | 1.00 | 38.98 | W |
| ATOM | 1749 | OH2 | WAT | W | 32 | 44.423 | 2.273 | 36.015 | 1.00 | 53.68 | W |
| ATOM | 1750 | OH2 | WAT | W | 33 | 33.459 | −11.487 | 36.757 | 1.00 | 52.78 | W |
| ATOM | 1751 | OH2 | WAT | W | 34 | 36.437 | −16.867 | 36.394 | 1.00 | 54.25 | W |
| ATOM | 1752 | OH2 | WAT | W | 35 | 49.491 | −37.974 | 15.120 | 1.00 | 75.95 | W |
| ATOM | 1753 | OH2 | WAT | W | 36 | 59.826 | −17.334 | 5.348 | 1.00 | 58.58 | W |
| ATOM | 1754 | OH2 | WAT | W | 37 | 34.090 | −31.163 | 18.062 | 1.00 | 45.16 | W |
| ATOM | 1755 | OH2 | WAT | W | 38 | 31.474 | −26.269 | 26.034 | 1.00 | 47.13 | W |
| ATOM | 1756 | OH2 | WAT | W | 39 | 33.485 | −25.607 | 34.333 | 1.00 | 61.09 | W |
| ATOM | 1757 | OH2 | WAT | W | 40 | 41.501 | −3.527 | 10.668 | 1.00 | 43.25 | W |
| ATOM | 1758 | OH2 | WAT | W | 41 | 58.424 | 7.398 | 25.955 | 1.00 | 52.89 | W |
| ATOM | 1759 | OH2 | WAT | W | 42 | 45.178 | −31.571 | 12.324 | 1.00 | 40.69 | W |
| ATOM | 1760 | OH2 | WAT | W | 43 | 40.434 | −12.172 | 7.724 | 1.00 | 37.51 | W |
| ATOM | 1761 | OH2 | WAT | W | 44 | 36.432 | −27.375 | 31.518 | 1.00 | 45.12 | W |
| ATOM | 1762 | OH2 | WAT | W | 45 | 38.394 | −36.117 | 34.325 | 1.00 | 61.82 | W |
| ATOM | 1763 | OH2 | WAT | W | 46 | 63.449 | −32.687 | 24.761 | 1.00 | 50.76 | W |
| ATOM | 1764 | OH2 | WAT | W | 47 | 53.209 | −31.426 | 21.007 | 1.00 | 30.89 | W |
| ATOM | 1765 | OH2 | WAT | W | 48 | 57.450 | −25.595 | 24.104 | 1.00 | 56.01 | W |
| ATOM | 1766 | OH2 | WAT | W | 49 | 38.837 | −33.859 | 23.542 | 1.00 | 57.69 | W |
| ATOM | 1767 | OH2 | WAT | W | 50 | 51.023 | −26.542 | 32.249 | 1.00 | 62.14 | W |
| ATOM | 1768 | OH2 | WAT | W | 51 | 30.280 | −22.322 | 25.792 | 1.00 | 69.26 | W |
| ATOM | 1769 | OH2 | WAT | W | 52 | 64.004 | −21.598 | 10.616 | 1.00 | 33.97 | W |
| ATOM | 1770 | OH2 | WAT | W | 53 | 40.490 | 1.862 | 25.889 | 1.00 | 64.76 | W |
| ATOM | 1771 | OH2 | WAT | W | 54 | 52.502 | −21.666 | 31.069 | 1.00 | 39.06 | W |
| ATOM | 1772 | OH2 | WAT | W | 55 | 70.054 | −27.529 | 31.630 | 1.00 | 46.25 | W |
| ATOM | 1773 | OH2 | WAT | W | 56 | 59.563 | −7.794 | 12.066 | 1.00 | 39.75 | W |
| ATOM | 1774 | OH2 | WAT | W | 57 | 51.756 | −18.437 | 36.423 | 1.00 | 50.57 | W |
| ATOM | 1775 | OH2 | WAT | W | 58 | 67.957 | −29.464 | 28.996 | 1.00 | 38.73 | W |
| ATOM | 1776 | OH2 | WAT | W | 59 | 53.377 | −27.213 | 25.693 | 1.00 | 33.12 | W |
| ATOM | 1777 | OH2 | WAT | W | 60 | 35.027 | −17.956 | 33.841 | 1.00 | 47.36 | W |

APPENDIX 3-continued

X-RAY DATA COORDINATES FOR CDP-ME SYNTHASE
COMPLEXED WITH CDP-ME.Mg$^{2+}$(SEQ ID NO:12)

| ATOM | 1778 | OH2 | WAT | W | 61 | 34.699 | .015 | 36.542 | 1.00 | 54.16 | W |
|---|---|---|---|---|---|---|---|---|---|---|---|
| ATOM | 1779 | OH2 | WAT | W | 62 | 49.063 | −21.870 | 27.908 | 1.00 | 29.93 | W |
| ATOM | 1780 | OH2 | WAT | W | 63 | 43.825 | 5.170 | 28.220 | 1.00 | 46.89 | W |
| ATOM | 1781 | OH2 | WAT | W | 64 | 33.220 | −24.741 | 18.208 | 1.00 | 26.03 | W |
| ATOM | 1782 | OH2 | WAT | W | 65 | 69.838 | −24.974 | 30.604 | 1.00 | 38.88 | W |
| ATOM | 1783 | OH2 | WAT | W | 66 | 64.094 | −14.214 | 18.283 | 1.00 | 55.93 | W |
| ATOM | 1784 | OH2 | WAT | W | 67 | 53.048 | −12.059 | 14.317 | 1.00 | 24.60 | W |
| ATOM | 1785 | OH2 | WAT | W | 68 | 66.367 | −31.832 | 21.573 | 1.00 | 37.27 | W |
| ATOM | 1786 | OH2 | WAT | W | 69 | 34.520 | −27.015 | 18.111 | 1.00 | 27.09 | W |
| ATOM | 1787 | OH2 | WAT | W | 70 | 36.890 | −.419 | 16.622 | 1.00 | 57.10 | W |
| ATOM | 1788 | OH2 | WAT | W | 71 | 52.781 | −34.086 | 20.553 | 1.00 | 38.70 | W |
| ATOM | 1789 | OH2 | WAT | W | 72 | 53.288 | −1.345 | 9.327 | 1.00 | 55.98 | W |
| ATOM | 1790 | OH2 | WAT | W | 73 | 34.173 | −12.450 | 5.882 | 1.00 | 48.44 | W |
| ATOM | 1791 | OH2 | WAT | W | 74 | 30.528 | −17.942 | 15.418 | 1.00 | 34.06 | W |
| ATOM | 1792 | OH2 | WAT | W | 75 | 42.189 | 1.121 | 18.812 | 1.00 | 44.27 | W |
| ATOM | 1793 | OH2 | WAT | W | 76 | 43.424 | −.609 | 12.645 | 1.00 | 40.00 | W |
| ATOM | 1794 | OH2 | WAT | W | 77 | 51.611 | −4.183 | 8.587 | 1.00 | 44.46 | W |
| ATOM | 1795 | OH2 | WAT | W | 78 | 42.365 | −24.866 | 35.053 | 1.00 | 41.89 | W |
| ATOM | 1796 | OH2 | WAT | W | 79 | 52.460 | −18.464 | 6.314 | 1.00 | 42.10 | W |
| ATOM | 1797 | OH2 | WAT | W | 80 | 29.549 | −8.429 | 24.951 | 1.00 | 49.93 | W |
| ATOM | 1798 | OH2 | WAT | W | 81 | 45.708 | −20.606 | 43.804 | 1.00 | 50.97 | W |
| ATOM | 1799 | OH2 | WAT | W | 82 | 48.759 | −4.126 | 9.313 | 1.00 | 38.92 | W |
| ATOM | 1800 | OH2 | WAT | W | 83 | 69.186 | −32.976 | 14.262 | 1.00 | 47.91 | W |
| ATOM | 1801 | OH2 | WAT | W | 84 | 45.989 | −18.009 | 6.140 | 1.00 | 40.93 | W |
| ATOM | 1802 | OH2 | WAT | W | 85 | 56.927 | −26.566 | 26.449 | 1.00 | 59.64 | W |
| ATOM | 1803 | OH2 | WAT | W | 86 | 36.811 | −32.057 | 33.335 | 1.00 | 45.03 | W |
| ATOM | 1804 | OH2 | WAT | W | 87 | 29.983 | −15.853 | 36.792 | 1.00 | 51.41 | W |
| ATOM | 1805 | OH2 | WAT | W | 88 | 27.309 | −2.621 | 27.741 | 1.00 | 40.84 | W |
| ATOM | 1806 | OH2 | WAT | W | 89 | 51.895 | −19.984 | 33.020 | 1.00 | 34.45 | W |
| ATOM | 1807 | OH2 | WAT | W | 90 | 43.526 | −19.558 | 5.099 | 1.00 | 54.75 | W |
| ATOM | 1808 | OH2 | WAT | W | 91 | 49.330 | −29.216 | 33.581 | 1.00 | 52.42 | W |
| ATOM | 1809 | OH2 | WAT | W | 92 | 46.912 | −4.742 | 39.215 | 1.00 | 58.61 | W |
| ATOM | 1810 | OH2 | WAT | W | 93 | 59.739 | −18.695 | 32.277 | 1.00 | 52.62 | W |
| ATOM | 1811 | OH2 | WAT | W | 94 | 47.594 | −39.154 | 17.313 | 1.00 | 62.20 | W |
| ATOM | 1812 | OH2 | WAT | W | 95 | 55.288 | 6.323 | 26.048 | 1.00 | 63.96 | W |
| ATOM | 1813 | OH2 | WAT | W | 96 | 43.413 | −35.485 | 13.897 | 1.00 | 54.83 | W |
| ATOM | 1814 | OH2 | WAT | W | 97 | 36.760 | −10.358 | 37.741 | 1.00 | 42.77 | W |
| ATOM | 1815 | OH2 | WAT | W | 98 | 37.400 | −5.550 | 37.108 | 1.00 | 48.75 | W |
| ATOM | 1816 | OH2 | WAT | W | 100 | 32.447 | −17.305 | 33.447 | 1.00 | 56.24 | W |
| ATOM | 1817 | OH2 | WAT | W | 102 | 72.661 | −35.327 | 22.942 | 1.00 | 47.31 | W |
| ATOM | 1818 | OH2 | WAT | W | 103 | 33.696 | −26.412 | 31.300 | 1.00 | 64.91 | W |
| ATOM | 1819 | OH2 | WAT | W | 104 | 45.761 | −40.125 | 19.803 | 1.00 | 62.37 | W |
| ATOM | 1820 | OH2 | WAT | W | 111 | 43.033 | −36.570 | 16.978 | 1.00 | 60.28 | W |
| ATOM | 1821 | N1 | PRD | | 1 | 48.972 | −15.320 | 32.129 | 1.00 | 28.74 | |
| ATOM | 1822 | C2 | PRD | | 1 | 47.711 | −15.455 | 32.800 | 1.00 | 29.39 | |
| ATOM | 1823 | N3 | PRD | | 1 | 47.604 | −16.211 | 33.929 | 1.00 | 32.53 | |
| ATOM | 1824 | C4 | PRD | | 1 | 48.759 | −16.883 | 34.469 | 1.00 | 38.68 | |
| ATOM | 1825 | C5 | PRD | | 1 | 50.037 | −16.794 | 33.854 | 1.00 | 37.19 | |
| ATOM | 1826 | C6 | PRD | | 1 | 50.086 | −16.008 | 32.703 | 1.00 | 36.55 | |
| ATOM | 1827 | O2 | PRD | | 1 | 46.649 | −14.916 | 32.422 | 1.00 | 26.35 | |
| ATOM | 1828 | N4 | PRD | | 1 | 48.591 | −17.609 | 35.589 | 1.00 | 40.89 | |
| ATOM | 1829 | C1* | PRD | | 1 | 49.134 | −14.495 | 30.891 | 1.00 | 24.92 | |
| ATOM | 1830 | C2* | PRD | | 1 | 50.055 | −13.319 | 31.132 | 1.00 | 22.59 | |
| ATOM | 1831 | O2* | PRD | | 1 | 49.351 | −12.350 | 31.855 | 1.00 | 27.79 | |
| ATOM | 1832 | C3* | PRD | | 1 | 50.529 | −12.941 | 29.743 | 1.00 | 31.02 | |
| ATOM | 1833 | C4* | PRD | | 1 | 50.336 | −14.252 | 28.943 | 1.00 | 25.94 | |
| ATOM | 1834 | O4* | PRD | | 1 | 49.735 | −15.210 | 29.845 | 1.00 | 25.94 | |
| ATOM | 1835 | O3* | PRD | | 1 | 49.677 | −11.980 | 29.080 | 1.00 | 28.50 | |
| ATOM | 1836 | C5* | PRD | | 1 | 51.739 | −14.679 | 28.527 | 1.00 | 24.84 | |
| ATOM | 1837 | O5* | PRD | | 1 | 52.433 | −15.082 | 29.674 | 1.00 | 33.73 | |
| ATOM | 1838 | PA | PRD | | 1 | 54.056 | −15.077 | 29.828 | 1.00 | 34.41 | |
| ATOM | 1839 | O1A | PRD | | 1 | 54.488 | −13.616 | 29.398 | 1.00 | 36.75 | |
| ATOM | 1840 | O2A | PRD | | 1 | 54.497 | −16.134 | 28.879 | 1.00 | 36.37 | |
| ATOM | 1841 | O3A | PRD | | 1 | 54.346 | −15.458 | 31.470 | 1.00 | 41.01 | |
| ATOM | 1842 | PB | PRD | | 1 | 54.585 | −17.612 | 28.672 | 1.00 | 32.13 | |
| ATOM | 1843 | O1B | PRD | | 1 | 53.337 | −18.265 | 29.179 | 1.00 | 38.59 | |
| ATOM | 1844 | O2B | PRD | | 1 | 55.839 | −18.087 | 29.434 | 1.00 | 31.11 | |
| ATOM | 1845 | O3B | PRD | | 1 | 54.687 | −18.200 | 27.300 | 1.00 | 39.60 | |
| ATOM | 1846 | C1M | PRD | | 1 | 53.636 | −17.827 | 26.427 | 1.00 | 28.82 | |
| ATOM | 1847 | C2M | PRD | | 1 | 54.008 | −18.440 | 25.091 | 1.00 | 24.91 | |
| ATOM | 1848 | O2M | PRD | | 1 | 53.969 | −19.941 | 25.302 | 1.00 | 20.93 | |
| ATOM | 1849 | C3M | PRD | | 1 | 53.045 | −18.056 | 23.911 | 1.00 | 27.33 | |
| ATOM | 1850 | O3M | PRD | | 1 | 53.182 | −16.597 | 23.532 | 1.00 | 25.46 | |
| ATOM | 1851 | C5M | PRD | | 1 | 51.561 | −18.347 | 24.271 | 1.00 | 22.50 | |

APPENDIX 3-continued

X-RAY DATA COORDINATES FOR CDP-ME SYNTHASE COMPLEXED WITH CDP-ME.Mg$^{2+}$ (SEQ ID NO:12)

| ATOM | 1852 C4M | PRD | 1 | 53.514 | −18.842 | 22.709 | 1.00 | 26.78 |
|---|---|---|---|---|---|---|---|---|
| ATOM | 1853 O4M | PRD | 1 | 54.967 | −18.442 | 22.335 | 1.00 | 25.55 |
| ATOM | 1854 MG + 2 | MG2 | 1 | 54.167 | −17.365 | 33.325 | 1.00 | 63.74 |
| END | | | | | | | | |

The invention claimed is:

1. A method of screening for compounds that inhibit the non-mevalonate isoprenoid biosynthesis pathway, said method comprising:
 a) employing the three-dimensional structural coordinates of 4-diphosphocytidyl-2-C-methylerythritol (CDP-ME) synthase according to any one of Appendices 1-3 to determine the points of interaction between said CDP-ME synthase and a substrate or a substrate mimic;
 b) selecting compound(s) which have similar points of interaction with said CDP-ME synthase as the substrate or substrate mimics as determined in (a), wherein said compounds are selected by docking a three-dimensional representation of a candidate compound structure with a three-dimensional representation of CDP-ME synthase employed in (a); and
 c) assaying the activity of said CDP-ME synthase in the presence and absence of the selected compound in (b) to determine if said compound(s) is an inhibitor.

2. A method of screening for compounds that inhibit the non-mevalonate isoprenoid biosynthesis pathway, said method comprising:
 a) screening for compound(s) having points of interaction with a three-dimensional representation of a crystalline form of 4-diphosphocytidyl-2-C-methylerythritol (CPD-ME) synthase according to any one of Appendices 1-3, wherein compounds with similar points of interaction are selected based on similar interactions between CPD-ME synthase and the three-dimensional representation of a substrate or substrate mimic therefor according to any one of Appendices 1-3; and
 b) assaying the activity of said CDP-ME synthase in the presence and absence of the selected compound in (a) to determine if said compound(s) is an inhibitor.

3. A method according to claim 1, wherein said three-dimensional structural coordinates of CDP-ME synthase according to Appendices 1-3 are determined from a crystalline form of CDP-ME synthase, wherein said crystals form in the presence or absence of a substrate or substrate mimic in a monoclinic space group C2 with unit cell dimensions selected from the group consisting of about a=130 Å, b=47 Å, c=38 Å and β=94°; a=130.3 Å b=47.3 Å, c=38.1 Å and β=94.2°; a=130 Å, b=46.8 Å, c=38.4 Å and β=92.6°; and a=130.3 Å, b=47.3 Å, c=38.1 Å and β=94.2°.

4. A method according to claim 3 wherein said crystalline form of 4-diphosphocytidyl-2-C-methylerythritol synthase further comprises a known inhibitor of said synthase.

5. A method according to claim 3 wherein the crystals have a monoclinic space group C2 with unit cell dimensions of about: a=130 Å, b=47 Å, c=38 Å and β=94°.

6. A method according to claim 3 wherein the crystals have a monoclinic space group C2 with unit cell dimensions: a=130.3 Å b=47.3 Å, c=38.1 Å and β=94.2°.

7. A method according to claim 3 wherein the crystals have a monoclinic space group C2 with unit cell dimensions: a=130 Å, b=46.8 Å, c=38.4 Å and β=92.6°.

8. A method according to claim 3 wherein the crystals have a monoclinic space group C2 with unit cell dimensions: a=130.3 Å, b=47.3 Å, c=38.1 Å and β=94.2°.

* * * * *